(12) United States Patent
Hirano et al.

(10) Patent No.: US 9,188,862 B2
(45) Date of Patent: Nov. 17, 2015

(54) ACTINIC RAY-SENSITIVE OR RADIATION-SENSITIVE RESIN COMPOSITION, AND, ACTINIC RAY-SENSITIVE OR RADIATION-SENSITIVE FILM AND PATTERN FORMING METHOD, EACH USING THE SAME

(71) Applicant: FUJIFILM Corporation, Minato-ku, Tokyo (JP)

(72) Inventors: Shuji Hirano, Haibara-gun (JP); Hiroo Takizawa, Haibara-gun (JP); Hideaki Tsubaki, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/303,090

(22) Filed: Jun. 12, 2014

(65) Prior Publication Data

US 2014/0295332 A1  Oct. 2, 2014

Related U.S. Application Data

(63) Continuation of application No. PCT/JP2012/084249, filed on Dec. 18, 2012.

(30) Foreign Application Priority Data

Dec. 28, 2011 (JP) ................................. 2011-288314
Nov. 14, 2012 (JP) ................................. 2012-250461

(51) Int. Cl.

| G03F 7/039 | (2006.01) |
|---|---|
| G03F 7/20 | (2006.01) |
| G03F 7/038 | (2006.01) |
| C07D 233/06 | (2006.01) |
| C07D 233/56 | (2006.01) |
| C07D 235/22 | (2006.01) |
| C08F 12/22 | (2006.01) |
| C07D 295/22 | (2006.01) |
| C08F 220/10 | (2006.01) |
| G03F 7/004 | (2006.01) |
| G03F 7/11 | (2006.01) |
| C08F 220/18 | (2006.01) |
| C08F 12/20 | (2006.01) |
| C08F 12/30 | (2006.01) |
| C08F 212/14 | (2006.01) |
| C07D 401/12 | (2006.01) |
| C07C 313/06 | (2006.01) |
| C07C 313/24 | (2006.01) |
| C07D 267/00 | (2006.01) |
| G03F 7/32 | (2006.01) |

(52) U.S. Cl.
CPC ............ *G03F 7/0388* (2013.01); *C07D 233/06* (2013.01); *C07D 233/56* (2013.01); *C07D 235/22* (2013.01); *C07D 295/22* (2013.01); *C08F 12/20* (2013.01); *C08F 12/22* (2013.01); *C08F 12/30* (2013.01); *C08F 212/14* (2013.01); *C08F 220/10* (2013.01); *C08F 220/18* (2013.01); *G03F 7/004* (2013.01); *G03F 7/0045* (2013.01); *G03F 7/0046* (2013.01); *G03F 7/039* (2013.01); *G03F 7/0392* (2013.01); *G03F 7/0397* (2013.01); *G03F 7/11* (2013.01); *G03F 7/2041* (2013.01); *C07C 313/06* (2013.01); *C07C 313/24* (2013.01); *C07D 267/00* (2013.01); *C07D 401/12* (2013.01); *G03F 7/322* (2013.01); *G03F 7/325* (2013.01)

(58) Field of Classification Search
CPC ..... G03F 7/0045; G03F 7/039; G03F 7/0392; G03F 7/0397; G03F 7/20; G03F 7/2002; G03F 7/32; G03F 7/325
USPC ........................................ 430/270.1, 326, 434
See application file for complete search history.

(56) References Cited

U.S. PATENT DOCUMENTS

| 4,842,986 A * | 6/1989 | Matsuda et al. ............... 430/170 |
|---|---|---|
| 5,198,326 A * | 3/1993 | Hashimoto et al. ........... 430/296 |
| 5,413,896 A * | 5/1995 | Kajita et al. ................... 430/192 |
| 8,592,540 B2 | 11/2013 | Mori et al. |
| 2003/0117842 A1* | 6/2003 | Hanzawa et al. ......... 365/185.02 |
| 2003/0143824 A1* | 7/2003 | Endo et al. ..................... 438/552 |
| 2006/0166135 A1* | 7/2006 | Wada .......................... 430/270.1 |
| 2008/0187860 A1* | 8/2008 | Tsubaki et al. ............. 430/270.1 |
| 2009/0081590 A1* | 3/2009 | Shimbori .................... 430/287.1 |
| 2010/0055608 A1* | 3/2010 | Ohashi et al. .............. 430/270.1 |
| 2011/0129765 A1* | 6/2011 | Tanaka et al. ..................... 430/5 |
| 2011/0129777 A1 | 6/2011 | Hatakeyama et al. |

FOREIGN PATENT DOCUMENTS

| JP | 61-167945 | * | 7/1986 |
|---|---|---|---|
| JP | 63-149637 | * | 6/1988 |
| JP | 10-274853 | * | 10/1998 |
| JP | 2943379 B2 | | 8/1999 |
| JP | 2001-166476 A | | 6/2001 |
| JP | 2001-215689 A | | 8/2001 |
| JP | 2003-43677 A | | 2/2003 |
| JP | 2010150367 A | | 7/2010 |
| JP | 2011-138111 A | | 7/2011 |

OTHER PUBLICATIONS

Machine translation of the abstract of JP 61-167945, published on Jul. 29, 1986.*

(Continued)

*Primary Examiner* — Anca Eoff
(74) *Attorney, Agent, or Firm* — Sughrue Mion, PLLC

(57) ABSTRACT

An actinic ray-sensitive or radiation-sensitive resin composition, which is excellent in sensitivity, resolution, a pattern profile and a depth of focus (DOF), and, an actinic ray-sensitive or radiation-sensitive film and a pattern forming method, each using the same, are provided. The actinic ray-sensitive or radiation-sensitive resin composition includes a nitrogen-containing compound and a resin (Ab) capable of varying a polarity or an alkali solubility thereof by the action of an acid.

18 Claims, No Drawings

(56) References Cited

OTHER PUBLICATIONS

Machine translation of JP 10-274853, published on Oct. 13, 1998.*
English translation of JP 61-167945, published on Jul. 29, 1986.*
Machine translation of the abstract of JP 63-149637, published on Jun. 22, 1988.*
International Search Report for PCT/JP2012/084249 dated Jan. 29, 2013, 4 pages.
Written Opinion for PCT/JP2012/084249 dated Jan. 29, 2013, 4 pages.
Notice of Reasons for Rejection, mailed Sep. 2, 2014, issued in corresponding JP Application No. 2012-250461, 6 pages in English and Japanese.
Office Action dated Apr. 1, 2015, issued by the Korean Intellectual Property Office in counterpart Korean Patent Application No. 10-2014-7014704.
Office Action dated Jul. 27, 2015, issued by the Korean Intellectual Property Office in corresponding Korean Application No. 10-2014-7014704.

* cited by examiner

US 9,188,862 B2

ACTINIC RAY-SENSITIVE OR RADIATION-SENSITIVE RESIN COMPOSITION, AND, ACTINIC RAY-SENSITIVE OR RADIATION-SENSITIVE FILM AND PATTERN FORMING METHOD, EACH USING THE SAME

CROSS-REFERENCE TO RELATED APPLICATIONS

This application is a Continuation of PCT International Application No. PCT/JP2012/084249 filed on Dec. 18, 2012, which claims priority under 35 U.S.C. §119(a) to Japanese Patent Application No. 2011-288314 filed on Dec. 28, 2011 and Japanese Patent Application No. 2012-250461 filed on Nov. 14, 2012. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition, and, an actinic ray-sensitive or radiation-sensitive film and a pattern forming method, each using the same. Specifically, the present invention relates to an actinic ray-sensitive or radiation-sensitive resin composition which is suitable for use in an ultramicrolithography process applicable to a process for manufacturing a super-LSI or a high-capacity microchip, a process for fabricating a nanoimprint mold, a process for producing a high-density information recording medium, and the like, and other photofabrication processes, and, an actinic ray-sensitive or radiation-sensitive film and a pattern forming method, each using the same.

2. Description of the Related Art

In the production process for semiconductor devices such as ICs and LSIs, it is a practice in the related art to perform microfabrication by lithography using a photoresist composition. Recently, the formation of an ultrafine pattern in the submicron region or quarter-micron region has been demanded in accordance with the realization of high integration for integrated circuits. Accordingly, the trend of exposure wavelength toward a short wavelength, for example, from g rays to i rays, and further to KrF excimer laser light has been seen. At present, an exposure device using an ArF excimer laser having a wavelength of 193 nm has been developed. Further, a so-called immersion method has been developed, in which the space between a projection lens and a sample is filled with a liquid having a high refractive index (hereinafter referred to also as a "liquid for immersion liquid"). Furthermore, lithography using an electron beam, X rays, EUV, or the like in addition to excimer laser has been also developed. Thus, a chemical amplification type resist composition having excellent resolution in effective response to various types of radiation has been developed (see, for example, JP2003-43677A, JP2001-166476A, and JP2001-215689A).

Electron beam lithography has been recognized as a pattern forming technique of the next generation or the generation after the next, and a resist having high sensitivity as well as high resolution has been demanded. However, various types of difficulty are caused during practical use in an ultrafine region with a size of 0.25 μm or less, and thus, there is room for further improvement of a pattern profile and a depth of focus (DOF).

SUMMARY OF THE INVENTION

It is an object of the present invention to provide an actinic ray-sensitive or radiation-sensitive resin composition, which is excellent in sensitivity, resolution, a pattern profile and a depth of focus (DOF), an actinic ray-sensitive or radiation-sensitive film using the same, and a pattern forming method.

In one embodiment, the present invention is as follows.

[1] An actinic ray-sensitive or radiation-sensitive resin composition including: a nitrogen-containing compound, and a resin (Ab) capable of varying a polarity thereof by the action of an acid, wherein the nitrogen-containing compound is a compound having at least one amino group formed by bonding one or two hydrogen atoms to a nitrogen atom, and at least one hydrogen atom of the one or two hydrogen atoms is substituted by an —S—$R_3$ group(s) or an —S(O)$R_3$ group(s) (wherein $R_3$ represents a substituent).

[2] An actinic ray-sensitive or radiation-sensitive resin composition including: a nitrogen-containing compound, and a resin (Ab) capable of varying an alkali solubility thereof by the action of an acid, wherein the nitrogen-containing compound is a compound having at least one amino group formed by bonding one or two hydrogen atoms to a nitrogen atom, and at least one hydrogen atom of the one or two hydrogen atoms is substituted by an —S—$R_3$ group(s) or an —S(O)$R_3$ group(s) (wherein $R_3$ represents a substituent).

[3] The composition as described in [1] or [2], wherein the nitrogen-containing compound is represented by either the general formula (N1) or (N2).

[Chem. 1]

In the general formulae (N1) and (N2),
$R_1$ and $R_2$ each independently represent a hydrogen atom or a substituent, provided that a case where $R_1$ and $R_2$ are hydrogen atoms at the same time is excluded. Further, $R_1$ and $R_2$ may be bonded to each other to form a ring together with a nitrogen atom in the formula.
$R_3$ represents a substituent.

[4] The composition as described in [3], wherein $R_1$ and $R_2$ in the general formula (N1) and (N2) are bonded to each other to form a ring together with a nitrogen atom in the formula.

[5] The composition as described in any one of [1] to [4], wherein the substituent represented by $R_3$ is a group containing an acid-decomposable group.

[6] The composition as described in any one of [1] to [5], further including a compound capable of generating an acid by irradiation with actinic rays or radiation.

[7] The composition as described in any one of [1] to [6], wherein the resin (Ab) contains a repeating unit (B) including a structural portion capable of generating an acid by irradiation with actinic rays or radiation.

[8] The composition as described in any one of [1] to [7], further including a resin (Aa) containing at least any one of fluorine atoms and silicon atoms.

[9] The composition as described in any one of [1] to [8], wherein the resin (Ab) contains at least one kind of repeating unit represented by the general formula (A)

[Chem. 2]

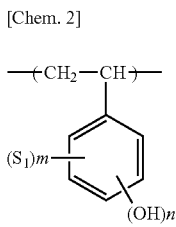

(A)

In the general formula (A), n represents an integer of 1 to 5 and m represents an integer of 0 to 4, satisfying the relationship of 1≤m+n≤5

$S_1$ represents a substituent. In the case where m is 2 or more, a plurality of $S_1$'s may be the same as or different from each other.

[10] The composition as described in [9], wherein the resin (Ab) at least contains a repeating unit represented by the following formula as the repeating unit represented by the general formula (A).

[Chem. 3]

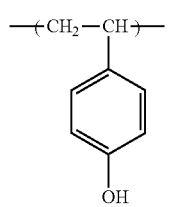

[11] The composition as described in any one of [1] to [10], wherein the resin (Ab) contains at least one kind of the repeating units represented by the general formulae (A1) and (A2).

[Chem. 2]

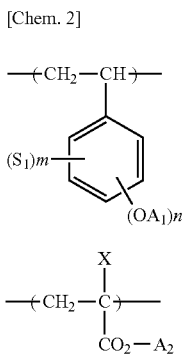

(A1)

(A2)

In the general formula (A1), n represents an integer of 1 to 5 and m represents an integer of 0 to 4, satisfying the relationship of 1≤m+n≤5.

$S_1$ represents a substituent, and in the case where m is 2 or more, a plurality of $S_1$'s may be the same as or different from each other.

$A_1$ represents a hydrogen atom or a group capable of leaving by the action of an acid. However, at least one $A_1$ represents a group capable of leaving by the action of an acid. In the case of n≥2, a plurality of $A_1$'s may be the same or different from each other.

In the general formula (A2),

X represents a hydrogen atom, an alkyl group, a hydroxyl group, an alkoxy group, a halogen atom, a cyano group, a nitro group, an acyl group, an acyloxy group, a cycloalkyl group, a cycloalkyloxy group, an aryl group, a carboxy group, an alkyloxycarbonyl group, an alkylcarbonyloxy group, or an aralkyl group.

$A_2$ represents a group capable of leaving by the action of an acid.

[12] The composition as described in any one of [1] to [11], wherein the weight average molecular weight of the resin (Ab) is in a range of 1,000 to 200,000.

[13] The composition as described in any one of [1] to [11], wherein the weight average molecular weight of the resin (Ab) is in a range of 1,000 to 100,000.

[14] The composition as described in any one of [1] to [11], wherein the weight average molecular weight of the resin (Ab) is in a range of 1,000 to 50,000.

[15] The composition as described in any one of [1] to [11], wherein the weight average molecular weight of the resin (Ab) is in a range of 1,000 to 25,000.

[16] The composition as described in any one of [1] to [15], further including a basic compound (excluding a nitrogen-containing compound).

[17] The composition as described in [16], wherein the basic compound is a compound having a functional group with proton accepting properties, and generating a compound capable of decomposing under irradiation with actinic rays or radiation to decrease or lose the proton accepting properties or to be converted from proton accepting properties to acidity.

[18] The composition as described in any one of [1] to [17], further including a surfactant.

[19] The composition as described in any one of [1] to [18], further including a solvent.

[20] The composition as described in [19], wherein the solvent contains propylene glycol monomethyl ether acetate.

[21] The composition as described in [20], wherein the solvent further contains propylene glycol monomethyl ether.

[22] The composition as described in any one of [1] to [21], which is used for EUV exposure.

[23] The composition as described in any one of [1] to [21], which is used for KrF excimer laser, electron beam, or X ray exposure.

[24] An actinic ray-sensitive or radiation-sensitive film formed using the composition as described in any one of [1] to [23].

[25] A pattern forming method including a step of forming a film using the composition as described in any one of [1] to [23]; a step of exposing the formed film; and a step of developing the exposed film.

[26] The pattern forming method as described in [25], wherein exposure is carried out using EUV.

[27] A semiconductor device produced by performing the steps including the pattern forming method as described in [25] or [26].

Effects of the Invention

By the present invention, it is possible to provide an actinic ray-sensitive or radiation-sensitive resin composition, which is excellent in sensitivity, resolution, and DOF, and is capable of forming a pattern having a good profile, actinic ray-sensitive or radiation-sensitive film using the same, and a pattern forming method.

DESCRIPTION OF THE PREFERRED EMBODIMENTS

Hereinbelow, the present invention will be described in detail.

Further, when a group and an atomic group are described without specifying whether substituted or unsubstituted, a group includes both a group and an atomic group, each having no substituent, and a group and an atomic group, each having a substituent. For example, the "alkyl group" which is described without specifying whether substituted or unsubstituted includes not only an alkyl group having no substituent (unsubstituted alkyl group) but also an alkyl group having a substituent (substituted alkyl group).

In addition, the "actinic rays" or "radiation" as used herein refers to, for example, a bright line spectrum of a mercury lamp, far ultraviolet rays typified by an excimer laser, extreme-ultraviolet (EUV) rays, X rays, or an electron beam (EB). Further, the "light" in the present invention means actinic rays or radiation.

Furthermore, unless otherwise specifically indicated, the "exposure" as used herein includes not only exposure to a mercury lamp, far ultraviolet rays typified by an excimer laser, X rays, EUV light, or the like, but also lithography with a particle beam such as an electron beam and an ion beam.

The actinic ray-sensitive or radiation-sensitive resin composition according to the present invention includes (1) a nitrogen-containing compound and (2) a resin (Ab) capable of varying an alkali solubility thereof by the action of an acid as essential components. Hereinafter, the respective components will be described.

(1) Nitrogen-Containing Compound

The composition according to the present invention contains a nitrogen-containing compound. The nitrogen-containing compound is a compound having at least one amino group formed by bonding one or two hydrogen atoms to a nitrogen atom (which may be hereinafter referred to an "amino compound (a)" in some cases), and at least one hydrogen atom of the one or two hydrogen atoms is substituted by an —S—$R_3$ group(s) or an —S(O)$R_3$ group(s) (wherein $R_3$ represents a substituent) (which may be hereinafter referred to "the nitrogen-containing compound of the present invention", or the like). Here, the substituent represented by $R_3$ has the same definition as the substituent as $R_3$ in the general formulae (N1) and (N2) as described later.

Since this nitrogen-containing compound of the present invention has lower basicity than common basic compounds, the uniformity in component distribution in the film in the steps of coating and film formation is improved. Further, the N—S bonds are cleaved by an acid generated from an acid generator during exposure and a part or all of the basic compound of the present invention changes into a compound with high basicity (for example, a compound having a structure represented by the general formula (N0) as described later), and performs functions of inhibition of acid diffusion or the like. Therefore, it is thought that by incorporating the nitrogen-containing compound into the composition of the present invention, the pattern profile becomes rectangular, thereby leading to improvement of sensitivity and resolution.

In the nitrogen-containing compound of the present invention, in the case where the amino compound (a) has two or more amino groups and two or more —S—$R_3$ groups or —S(O)$R_3$ groups, each of the —S—$R_3$ groups or the —S(O)$R_3$ groups may be bonded to the same or different nitrogen atoms.

The nitrogen-containing compound of the present invention is represented by, for example, either the following general formula (N1) or (N2) In one embodiment, the composition according to the present invention more preferably contains a nitrogen-containing compound represented by the general formula (N1).

[Chem. 5]

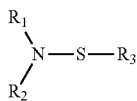
(N1)

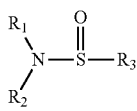
(N2)

In the general formulae (N1) and (N2), $R_1$ and $R_2$ each independently represent a hydrogen atom or a substituent, provided that a case where $R_1$ and $R_2$ are hydrogen atoms at the same time is excluded. Further, $R_1$ and $R_2$ may be bonded to each other to form a ring.

$R_3$ represents a substituent.

Further, the nitrogen-containing compound may be a compound having a plurality of structures represented by the general formula (N1) or (N2). For example, the compound may be a compound having a structure where at least one of $R_1$ to $R_3$ in the compound represented by the general formula (N1) is bonded to at least one of $R_1$ to $R_3$ in another compound represented by the general formula (N1) through a single bond or a divalent connecting group.

Examples of the substituents represented by $R_1$, $R_2$ and $R_3$ include an alkyl group, a cycloalkyl group, an alkoxy group, an acyl group, an acyloxy group, a halogen atom, a cyano group, a silicon atom-containing organic group, an aryl group, an aryloxy group, an aralkyl group, an aralkyloxy group, a hydroxy group, a nitro group, a sulfonylamino group, an alkylthio group, an arylthio group, and an aralkylthio group.

As the alkyl group represented by $R_1$, $R_2$ and $R_3$, for example, an alkyl group having 1 to 20 carbon atoms is preferred, and specific examples thereof include a methyl group, an ethyl group, a propyl group, an isopropyl group, an n-butyl group, an isobutyl group, a t-butyl group, a pentyl group, and a hexyl group. The alkyl group may contain an oxygen atom or a sulfur atom in the alkyl chain. Further, the alkyl group may further contain a substituent. Examples of the preferred substituent which the alkyl group may further contain include a halogen atom, an alkoxy group, a cycloalkyl group, a hydroxyl group, a nitro group, an alkoxycarbonyl group, an acyl group, an acyloxy group, an acylamino group, a sulfonylamino group, an alkylthio group, an arylthio group, an aralkylthio group, a thiophenecarbonyloxy group, a thiophenemethylcarbonyloxy group, and heterocyclic residues such as a pyrrolidone residue, and preferably substituents having 12 or less carbon atoms.

As the cycloalkyl group represented by $R_1$, $R_2$, and $R_3$, for example, a cycloalkyl group having 3 to 10 carbon atoms is preferred, and specific examples thereof include a cyclobutyl group, a cyclopentyl group, a cyclohexyl group, a norbornyl group, and an adamantyl group. The cycloalkyl group may further contain a substituent. Examples of the preferred substituent which the cycloalkyl group may further contain include an alkyl group, in addition to the substituents which the alkyl groups as $R_1$, $R_2$ and $R_3$ as described above may have.

As the alkoxy group represented by $R_1$, $R_2$ and $R_3$, for example, an alkoxy group having 1 to 10 carbon atoms is preferred, and specific examples thereof include a methoxy group, an ethoxy group, a propoxy group, and a butoxy group.

The alkoxy group may further contain a substituent and examples of the substituent include the substituents which the alkyl group as $R_1$, $R_2$ and $R_3$ as described above may have.

As the acyl group represented by $R_1$, $R_2$ and $R_3$, for example, an acyl group having 2 to 10 carbon atoms is preferred, and specific examples thereof include an acetyl group, a propionyl group, a butyryl group, and an isobutyryl group. The acyl group may further contain a substituent and examples of the substituent include the substituents which the alkyl group as $R_1$, $R_2$ and $R_3$ as described above may have.

As the acyloxy group represented by $R_1$, $R_2$ and $R_3$, for example, an acyloxy group having 2 to 10 carbon atoms is preferred. Examples of the acyl group in the acyloxy group include the same specific examples of the acyl group as described above, and examples of the substituents which the acyloxy group may have are also the same.

As the aryl group represented by $R_1$, $R_2$ and $R_3$, for example, an aryl group having 6 to 10 carbon atoms is preferred, and specific examples thereof include a phenyl group, a xylyl group, a tolyl group, a cumenyl group, a naphthyl group, and an anthracenyl group. The aryl group may further contain a substituent and examples of the substituent include the same groups as the substituents which the alkyl group or cycloalkyl group as $R_1$, $R_2$ and $R_3$ as described above may have.

As the aryloxy group and the arylthio group represented by $R_1$, $R_2$ and $R_3$, for example, an aryloxy group and an arylthio group having 2 to 10 carbon atoms are preferred. Examples of the aryl group in the aryloxy group and the arylthio group include the same specific examples of the aryl group as described above, and examples of the substituents which the aryloxy group and the arylthio group may have are also the same.

As the aralkyl group represented by $R_1$, $R_2$ and $R_3$, for example, an aralkyl group having 7 to 15 carbon atoms is preferred, and specific examples thereof include a benzyl group. This group may further contain a substituent and examples of the substituent include the same groups as the substituents which the alkyl group or cycloalkyl group as $R_1$, $R_2$ and $R_3$ as described above may have.

As the aralkyloxy group and the aralkylthio group represented by $R_1$, $R_2$ and $R_3$, for example, an aralkyloxy group and an aralkylthio group, each having 7 to 15 carbon atoms, are preferable. Examples of the aralkyl group in the aralkyloxy group and the aralkylthio group include the same specific examples of the aralkyl group as described above, and examples of the substituents which the aralkyl group may have are also the same.

As the alkylthio group represented by $R_1$, $R_2$ and $R_3$, for example, those having 1 to 10 carbon atoms are preferred. Examples of the alkyl group in the alkylthio group include the same specific examples of the alkyl group as described above, and examples of the substituents which the alkylthio group may have are also the same.

In one embodiment of the present invention, the nitrogen-containing compound preferably contains a hydroxyl group and/or —$(C_2H_4)O$— in any one of $R_1$, $R_2$ and $R_3$ of the general formula (N1) or (N2), and more preferably contains a hydroxyl group and/or —$(C_2H_4)O$— in at least one of $R_1$ and $R_2$.

Furthermore, in another embodiment of the present invention, for the nitrogen-containing compound, $R_3$ of the general formula (N1) or (N2) is preferably an alkyl group or an aryl group.

In addition, in still another embodiment of the present invention, for the nitrogen-containing compound, $R_3$ of the general formula (N1) or (N2) is preferably a group containing an acid-decomposable group. Here, the acid-decomposable group has the same definition as the acid-decomposable group which the resin (Ab) may have as described later, and includes the same specific examples.

Furthermore, in still another embodiment of the present invention, for the nitrogen-containing compound, $R_1$ and $R_2$ of the general formula (N1) or (N2) are preferably bonded to each other to form a ring together with a nitrogen atom in the formula. The nitrogen-containing heterocycle formed by $R_1$—N—$R_2$ may further contain nitrogen atoms or oxygen atoms, in addition to the nitrogen atoms in the formula. The nitrogen-containing heterocycle formed by $R_1$—N—$R_2$ is preferably a nitrogen-containing aromatic heterocycle, more preferably imidazoline or imidazole, and particularly preferably imidazole.

The nitrogen-containing compound of the present invention, containing the compound represented by the general formula (N1) or (N2), is a compound having at least one amino group formed by bonding one or two hydrogen atoms to a nitrogen atom, and at least one hydrogen atom of the one or two hydrogen atoms is substituted by an —S—$R_3$ group(s) or an —S(O)$R_3$ group(s), as described above.

Here, the "amino group" includes an amino group bonded to a carbonyl group or a sulfonyl group, but in one embodiment of the present invention, the amino group is preferably not bonded to a carbonyl group or a sulfonyl group.

The amino compound (a) preferably has one or more structures represented by, for example, the following general formula (N0).

[Chem. 6]

(N0)

($R_1$ and $R_2$ in the formula have the same definitions as $R_1$ and $R_2$ in the general formula (N1) and (N2)).

Examples of the amino compound (a) having one or more structures represented by the general formula (N0) include a compound having one structure represented by the general formula (N0) and having an amino group not bonded to a carbonyl group or a sulfonyl group (hereinafter referred to as an "amino compound (a1)"), a compound having two structures represented by the general formula (N0) and having an amino group not bonded to a carbonyl group or a sulfonyl group (hereinafter referred to as an "amino compound (a2)"), a compound having three structures represented by the general formula (N0) and having an amino group not bonded to a carbonyl group or a sulfonyl group (hereinafter referred to as an "amino compound (a3)"), an amide group-containing compound, and a urea compound. Here, embodiments of the amino compound (a2) include a compound having a structure in which at least one of $R_1$ and $R_3$ in the amino group represented by the general formula (N0) is bonded to at least one of $R_1$ and $R_3$ in the alkyl group represented by the general formula (N0) through a single bond or a polyvalent connecting group, and a compound in which a heterocycle having an N—H bond has an amino group as a substituent (adenine and the like).

In the present invention, it is preferable that at least one kind of the amino compound (a1), the amino compound (a2), and the amino compound (a3) be used, it is more preferred that at least one kind of the amino compound (a1) and the amino compound (a2) be used, and it is particularly preferable that at least one kind of the amino compound (a1) be used.

Examples of the amino compound (a1) include monoalkylamines such as n-hexylamine, n-heptylamine, n-octylamine, n-nonylamine, n-decylamine, and cyclohexylamine; dialkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; aromatic amines such as aniline, N-methylaniline, 2-methylaniline, 3-methylaniline, 4-methylaniline, 4-nitroaniline, diphenylamine, 1-naphthylamine, 2-(4-aminophenyl)-2-(3-hydroxyphenyl)propane, and 2-(4-aminophenyl)-2-(4-hydroxyphenyl)propane; alkanolamines such as ethanolamine and diethanolamine; and 1-adamantylamine and N-methyl-1-adamantylamine, and further examples of the nitrogen-containing heterocycle include imidazoles such as imidazole, benzimidazole, 2-methylimidazole, 4-methylimidazole, 2-phenylimidazole, 4-phenylimidazole, 2-phenyl-4-methylimidazole, 2-methyl-4-phenylimidazole, 2-methylbenzimidazole, and 2-phenylbenzimidazole, indole, pyrrole, pyrazole, guanine, purine, pyrrolidine, piperidine, morpholine, and piperazine.

Examples of the amino compound (a2) include ethylenediamine, tetramethylenediamine, hexamethylenediamine, 1,7-diaminoheptane, 1,8-diaminooctane, 1,9-diaminononane, 1,10-diaminodecane, 1,12-diaminododecane, 4,4'-diaminodiphenylmethane, 4,4'-diaminodiphenyl ether, 4,4'-diaminobenzophenone, 2,2-bis(4-aminophenyl)propane, 2-(3-aminophenyl)-2-(4-aminophenyl)propane, 1,4-bis[1-(4-aminophenyl)-1-methylethyl]benzene, 1,3-bis[1-(4-aminophenyl)-1-methylethyl]benzene, and adenine. Examples of the amino compound (a3) include polymers such as 4,4'-diaminodiphenylamine, polyallylamine, and polymetharylamine.

Examples of the amide group-containing compound include formamide, N-methylformamide, acetamide, N-methylacetamide, propionamide, benzamide, pyrrolidone, and N-methylbenzenesulfonamide. Examples of the urea compound include urea, methylurea, 1,1-dimethylurea, 1,3-dimethylurea, 1,3-diphenylurea, and tri-n-butylthiourea.

Specific examples of the amino compound (a) and specific examples of the sulfur atom-containing protective group (an —S—$R_3$ group or an —S(O)$R_3$ group) are shown below.

(Examples of Amino Compound (a))

[Chem. 7]

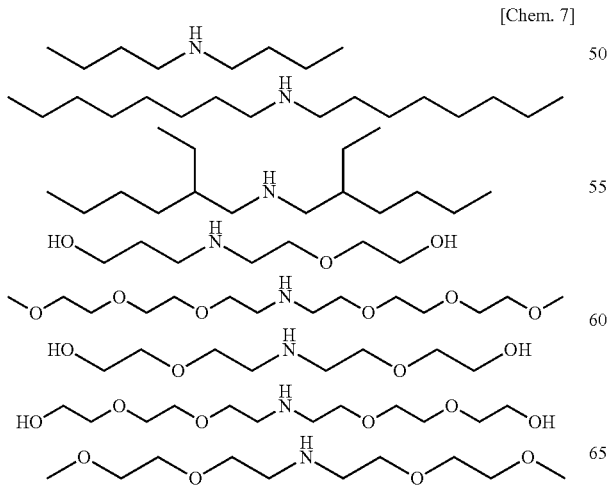

[Chem. 8]

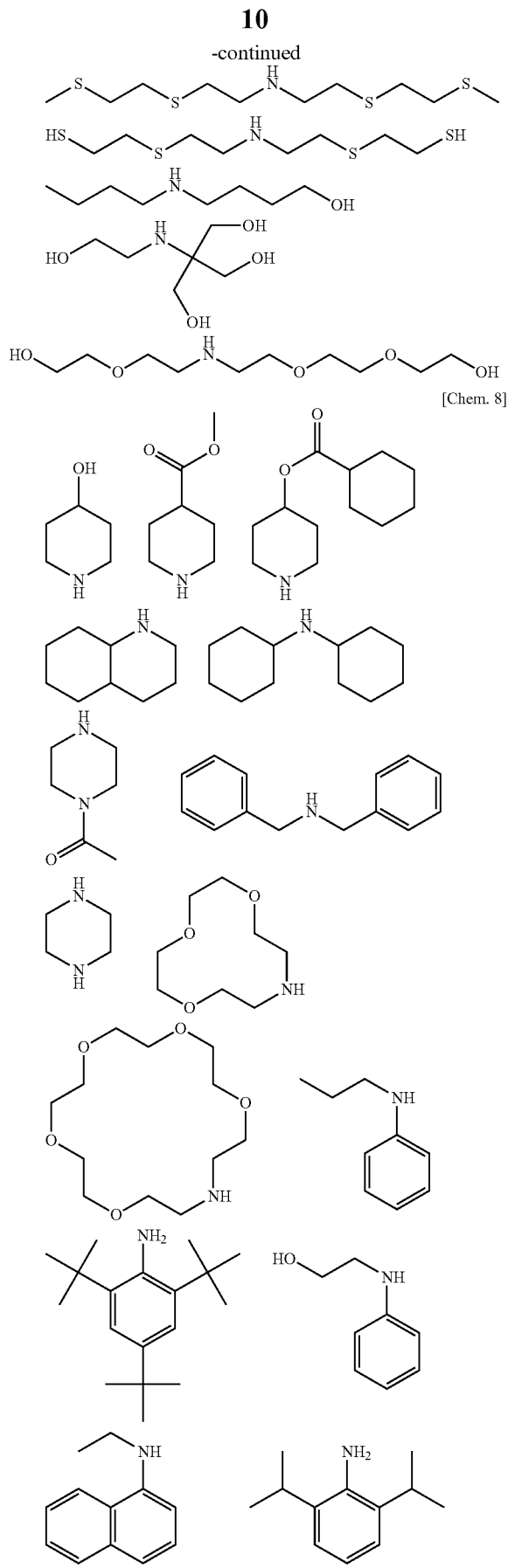

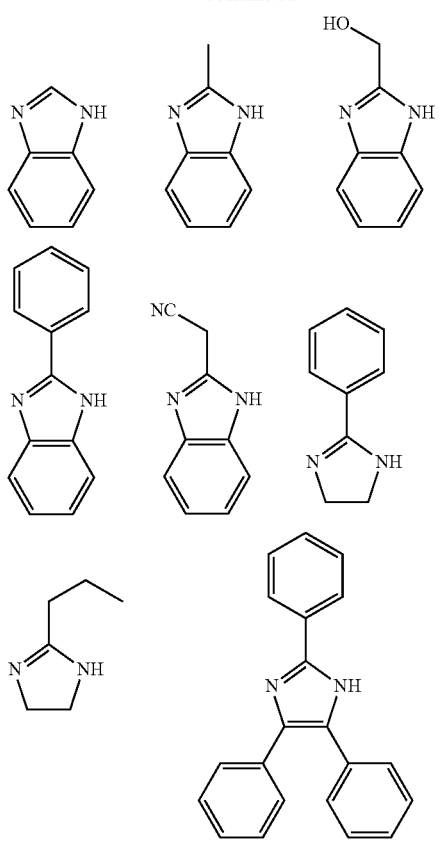
(Examples of Protective Group Containing Sulfur Atom)
[Chem. 9]
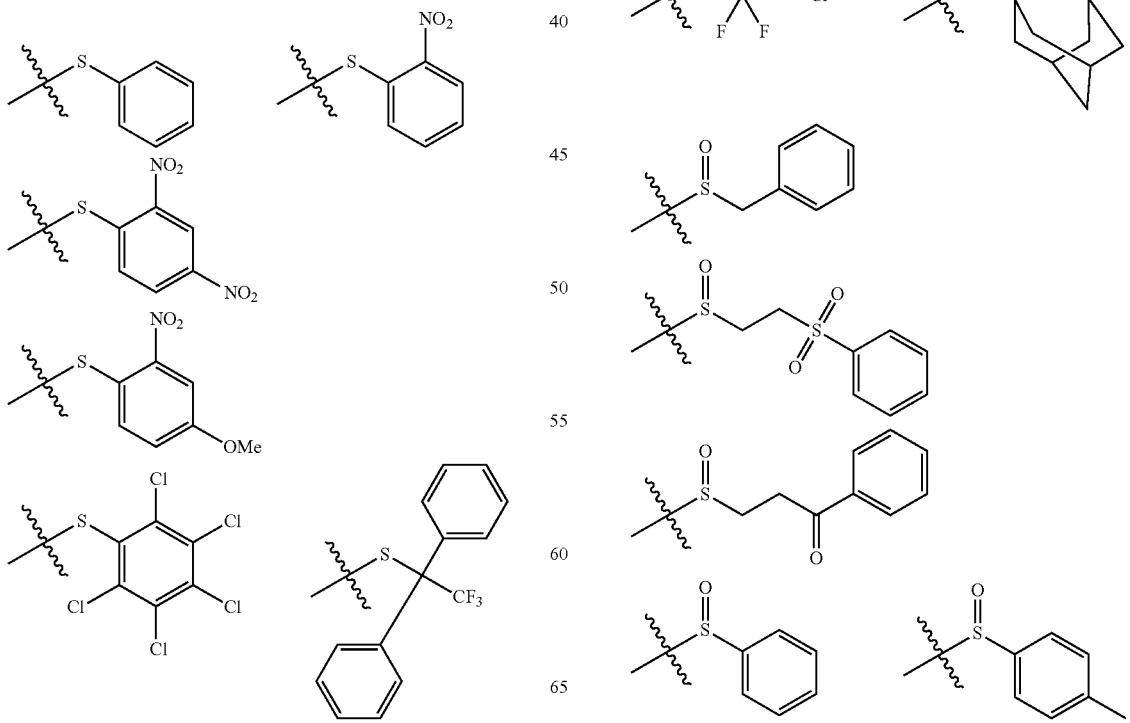

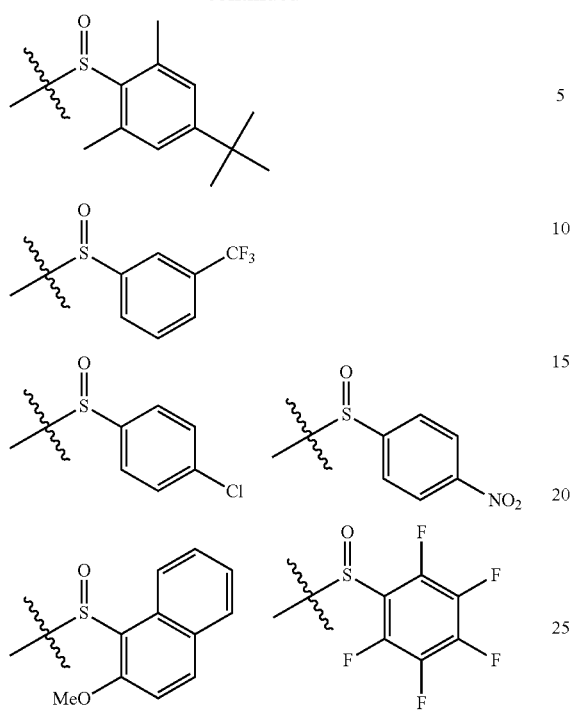
Specific examples of the nitrogen-containing compound of the present invention are shown below, but the present invention is not limited thereto.
[Chem. 10]
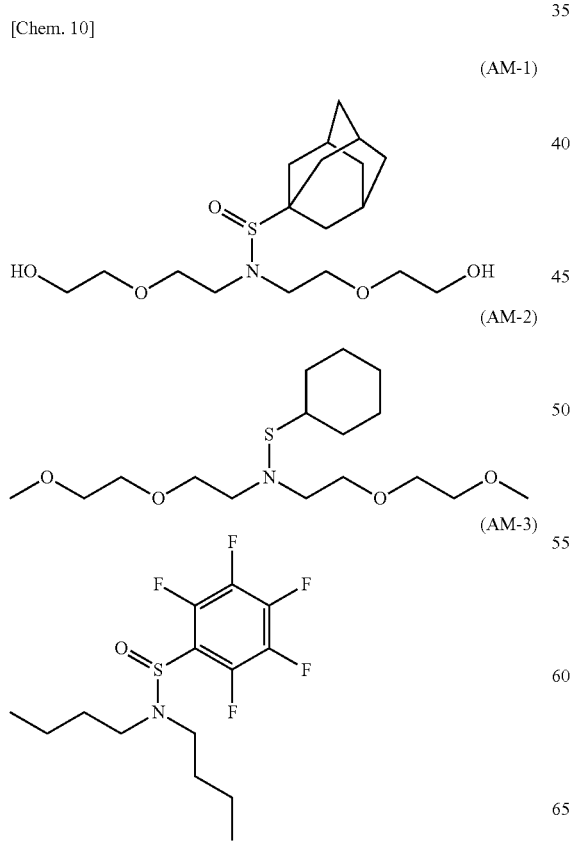
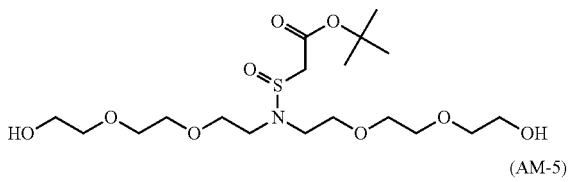
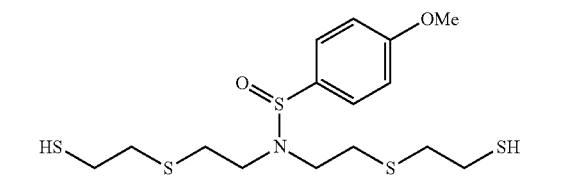
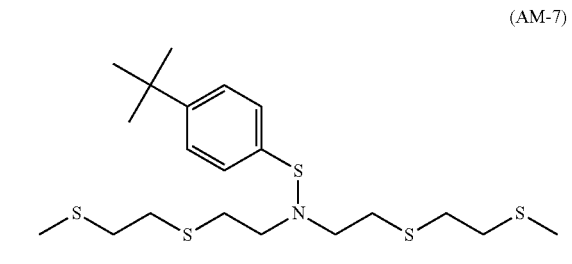
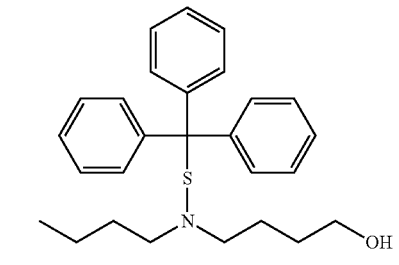
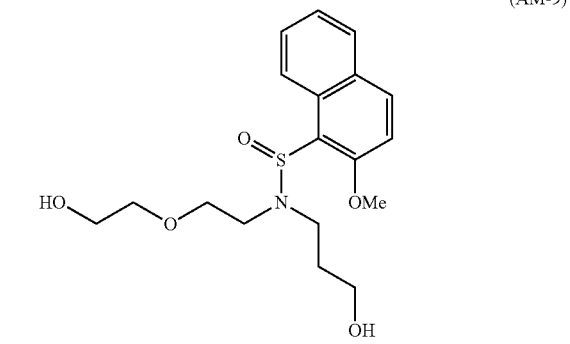
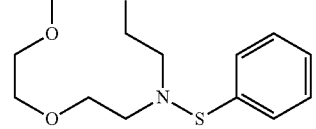

(AM-11)
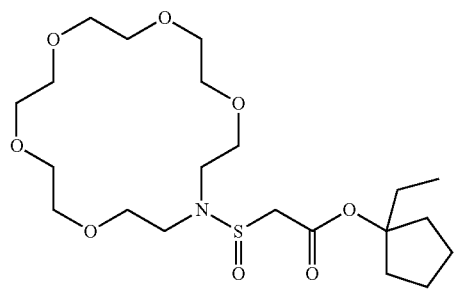
[Chem. 11]
(AM-12)
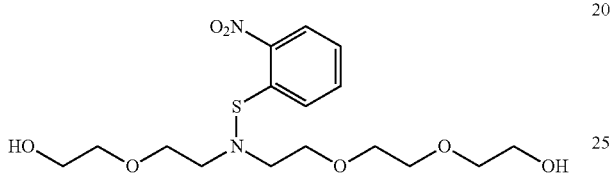
(AM-13)
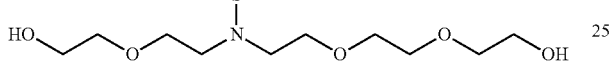
(AM-14)
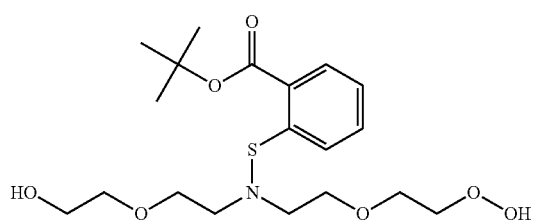
(AM-15)
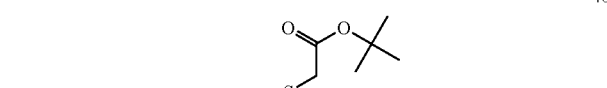
(AM-16)
(AM-17)
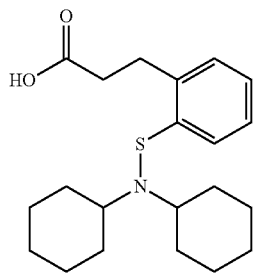
(AM-18)
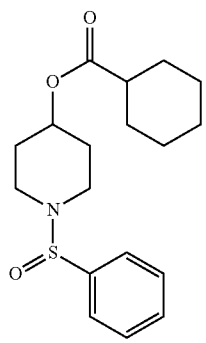
(AM-19)
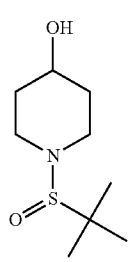
(AM-20)
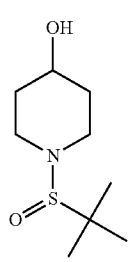
[Chem. 12]
(AM-21)
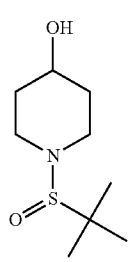

(AM-22)
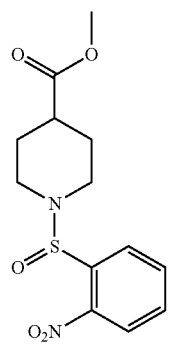
(AM-23)
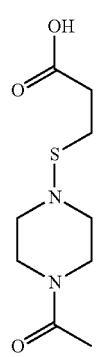
(AM-24)
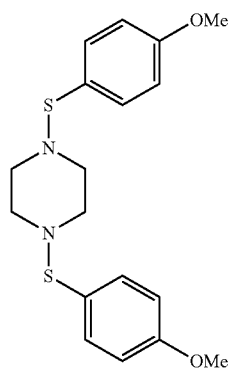
(AM-25)
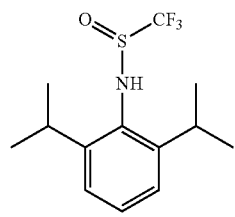
(AM-26)
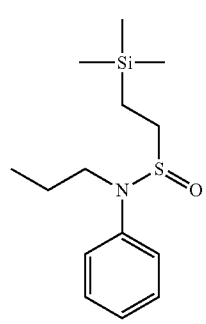
(AM-27)
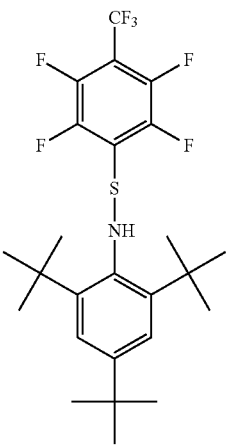
(AM-28)
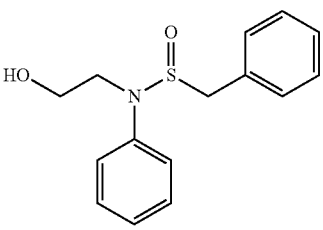
(AM-29)
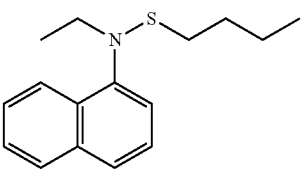
[Chem. 13]
(AM-30)
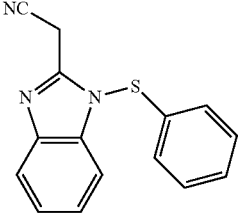
(AM-31)
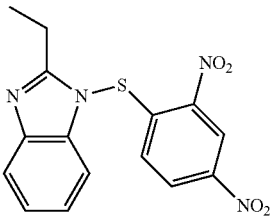
(AM-32)
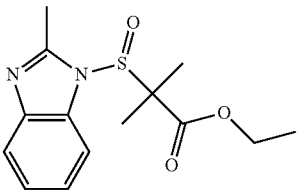

(AM-33)

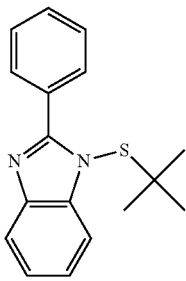

(AM-34)

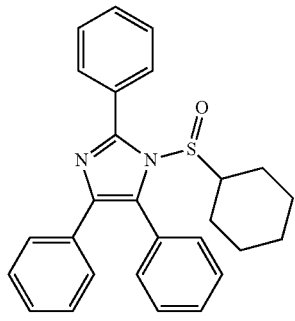

(AM-35)

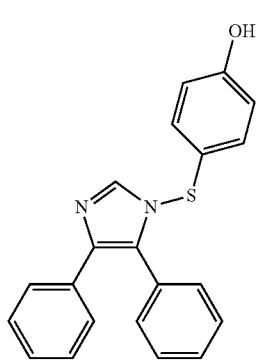

(AM-36)

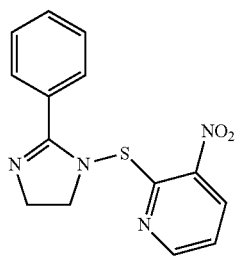

(AM-37)

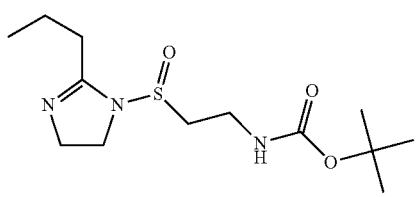

(AM-38)

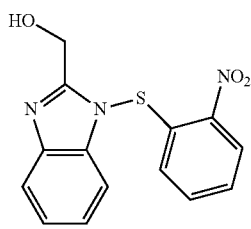

(AM-39)

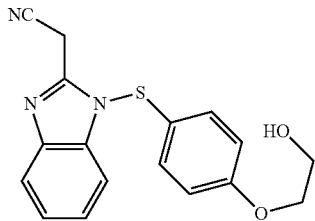

(AM-40)

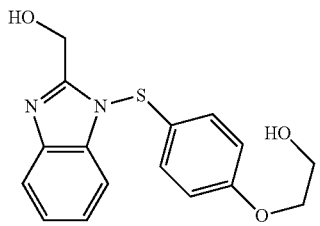

(AM-41)

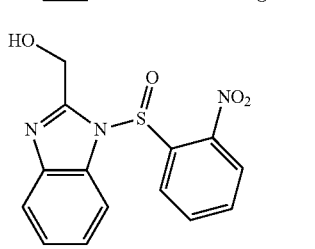

The molecular weight of the nitrogen-containing compound is preferably 2,000 or less, more preferably 1,000 or less, still more preferably 750 or less, and most preferably 500 or less.

The nitrogen-containing compound as described above may be used alone or in combination of two or more kinds thereof.

The content of the nitrogen-containing compound of the present invention is preferably 0.001 to 20% by mass, more preferably 0.001 to 10% by mass, and particularly preferably 0.01 to 5% by mass, based on the total solid contents of the composition.

The method for preparing the nitrogen-containing compound of the present invention is not particularly limited, and can be appropriately chosen according to a desired compound. However, examples thereof include a method in which a nitrogen-containing compound having an N—H bond is reacted with a sulfanyl halide (a compound having an —S—X group (wherein X is a halogen atom)) or a sulfinyl halide (a compound having an —S(=O)—X group (wherein X is a halogen atom)) under a basic condition to incorporate N—S and N—SO bonds.

(2) Resin (Ab) Capable of Varying A Polarity Thereof by Action of Acid

The composition according to the present invention contains a resin (Ab) capable of varying a polarity thereof by the action of an acid.

The resin (Ab) is a resin capable of varying a polarity thereof by the action of an acid, and specifically, has an increased solubility in an alkali developer or a decreased solubility in a developer having an organic solvent as a main component, by the action of an acid.

The resin (Ab) preferably has a repeating unit having an acid-decomposable group Examples of the acid-decomposable group include groups in which a hydrogen atom of an alkali-soluble group is protected with a group capable of leaving by the action of an acid, such as a carboxyl group, a phenolic hydroxyl group, a sulfonic acid group, and a thiol group.

Examples of the group capable of leaving by the action of an acid include —C($R_{36}$)($R_{37}$)($R_{38}$), —C($R_{36}$)($R_{37}$)($OR_{39}$), —C(=O)—O—C($R_{36}$)($R_{37}$)($R_{38}$), —C($R_{01}$)($R_{02}$)($OR_{39}$), and —C($R_{01}$)($R_{02}$)—C(=O)—O—C($R_{36}$)($R_{37}$)($R_{38}$).

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring. $R_{01}$ to $R_{02}$ each independently represent a hydrogen atom, an alkyl group, a cycloalkyl group, an aryl group, an aralkyl group, or an alkenyl group.

In one embodiment, the resin (Ab) preferably contains a repeating unit represented by the following general formula (AI) as a repeating unit having an acid-decomposable group.

[Chem. 14]

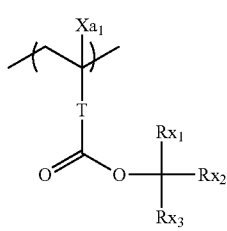

(AI)

In the general formula (AI), $Xa_1$ represents a hydrogen atom, a methyl group which may have a substituent, or a group represented by —$CH_2$—$R_9$. $R_9$ represents a hydroxyl group or a monovalent organic group. Examples of the monovalent organic group include an alkyl group having 5 or less carbon atoms and an acyl group having 5 or less carbon atoms. Among these, an alkyl group having 3 or less carbon atoms is preferred, and a methyl group is more preferred. $Xa_1$ is preferably a hydrogen atom, a methyl group, a trifluoromethyl group, or a hydroxymethyl group.

T represents a single bond or a divalent connecting group.

$Rx_1$ to $Rx_3$ each independently represent an alkyl group (linear or branched) or a cycloalkyl group (monocyclic or polycyclic).

At least two members out of $Rx_1$ to $Rx_3$ may be bonded to each other to form a cycloalkyl group (monocyclic or polycyclic).

Examples of the divalent connecting group of T include an alkylene group, a —COO-Rt- group, and a —O-Rt- group. In the formulae, Rt represents an alkylene group or a cycloalkylene group.

T is preferably a single bond or a —COO-Rt- group. Rt is preferably an alkylene group having 1 to 5 carbon atoms, and more preferably a —$CH_2$— group, a —($CH_2$)$_2$— group, or a —($CH_2$)$_3$— group.

The alkyl group of $Rx_1$ to $Rx_3$ is preferably an alkyl group having 1 to 4 carbon atoms, such as a methyl group, an ethyl group, an n-propyl group, an isopropyl group, an n-butyl group, an isobutyl group, and a t-butyl group.

The cycloalkyl group of $R_{x1}$ to $R_{x3}$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group.

The cycloalkyl group formed by the bonding of at least two members out of $R_{x1}$ to $R_{x3}$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group.

An embodiment where $R_{x1}$ is a methyl group or an ethyl group, and $R_{x2}$ and $R_{x3}$ are bonded to each other to form the above-described cycloalkyl group is preferable.

The respective groups above may have a substituent, and examples of the substituent include an alkyl group (having 1 to 4 carbon atoms), a halogen atom, a hydroxyl group, an alkoxy group (having 1 to 4 carbon atoms), a carboxyl group and an alkoxycarbonyl group (having 2 to 6 carbon atoms), and the number of carbon atoms is preferably 8 or less.

In another embodiment, the resin (Ab) preferably contains at least one kind of repeating units represented by the following general formulae (A1) and (A2).

[Chem. 15]

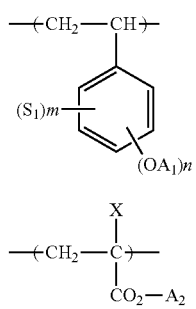

(A1)

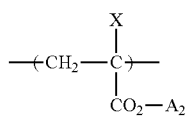

(A2)

In the general formula (A1), n represents an integer of 1 to 5 and m represents an integer of 0 to 4, satisfying the relationship of 1≤m+n≤5.

$S_1$ represents a substituent (except for a hydrogen atom), and in the case where m is 2 or more, a plurality of $S_1$'s may be the same as or different from each other.

$A_1$ represents a hydrogen atom or a group capable of leaving by the action of an acid, provided that at least one $A_1$ represents a group capable of leaving by the action of an acid. In the case of n≥2, a plurality of $A_1$'s may be the same as or different from each other.

In the general formula (A2),

X represents a hydrogen atom, an alkyl group, a hydroxyl group, an alkoxy group, a halogen atom, a cyano group, a nitro group, an acyl group, an acyloxy group, a cycloalkyl group, a cycloalkyloxy group, an aryl group, a carboxy group, an alkyloxycarbonyl group, an alkylcarbonyloxy group, or an aralkyl group.

$A_2$ represents a group capable of leaving by the action of an acid

First, the repeating unit represented by the general formula (A1) will be described.

n represents an integer of 1 to 5, as described above, preferably 1 or 2, and particularly preferably 1.

m represents an integer of 0 to 4, satisfying the relationship of 1≤m≤5, as described above, preferably 0 to 2, more preferably 0 or 1, and particularly preferably 0.

$S_1$ represents a substituent (except for a hydrogen atom), as described above. Examples of the substituent include the same substituents as described with respect to $S_1$ in the general formula (A) as described later.

$A_1$ represents a hydrogen atom or a group capable of leaving by the action of an acid, as described above, and at least one of $A_1$ is a group capable of leaving by the action of an acid.

Examples of the group capable of leaving by the action of an acid include tertiary alkyl groups such as a t-butyl group and a t-amyl group, a t-butoxycarbonyl group, a t-butoxycarbonylmethyl group, and an acetal group represented by formula —C($L_1$)($L_2$)-O—$Z_2$.

Hereinbelow, the acetal group represented by formula —C($L_1$)($L_2$)-O—$Z_2$ will be described. In the formula, $L_1$ and $L_2$ each independently represent a hydrogen atom, an alkyl group, a cycloalkyl group, or an aralkyl group. $Z_2$ represents an alkyl group, a cycloalkyl group, or an aralkyl group. Further, $Z_2$ and $L_1$ may be bonded to each other to form a 5- or 6-membered ring.

The alkyl group may be a linear alkyl group or a branched alkyl group.

As the linear alkyl group, one having 1 to 30 carbon atoms is preferred, and one having 1 to 20 carbon atoms is more preferred. Examples of the linear alkyl group include a methyl group, an ethyl group, an n-propyl group, an n-butyl group, a sec-butyl group, a t-butyl group, an n-pentyl group, an n-hexyl group, an n-heptyl group, an n-octyl group, an n-nonyl group, and an n-decanyl group.

As the branched alkyl group, one having 3 to 30 carbon atoms is preferred, and one having 3 to 20 carbon atoms is more preferred. Examples of the branched alkyl group include an i-propyl group, an i-butyl group, a t-butyl group, an i-pentyl group, a t-pentyl group, an i-hexyl group, at hexyl group, an i-heptyl group, a t-heptyl group, an i-octyl group, a t-octyl group, an i-nonyl group, and a t-decanoyl group.

These alkyl groups may further have a substituent. Examples of the substituent include a hydroxyl group; halogen atoms such as fluorine, chlorine, bromine and iodine atoms; a nitro group; a cyano group; an amide group; a sulfonamide group; alkyl groups such as a methyl group, an ethyl group, a propyl group, an isopropyl group, an n-butyl group, a sec-butyl group, a hexyl group, a 2-ethylhexyl group, an octyl group, and a dodecyl group; alkoxy groups such as a methoxy group, an ethoxy group, a hydroxyethoxy group, a propoxy group, a hydroxypropoxy group and a butoxy group; alkoxycarbonyl groups such as a methoxycarbonyl group and an ethoxycarbonyl group; acyl groups such as a formyl group, an acetyl group, and a benzoyl group; acyloxy groups such as an acetoxy group and a butyryloxy group, and a carboxy group.

As the alkyl group, an ethyl group, an isopropyl group, an isobutyl group, a cyclohexylethyl group, a phenylmethyl group, or a phenylethyl group is particularly preferable.

The cycloalkyl group may be monocyclic or polycyclic, and in the case where the cycloalkyl group is polycyclic, it may be a crosslinked cycloalkyl group. That is, in this case, the cycloalkyl group may have a bridged structure. Further, parts of carbon atoms in the cycloalkyl group may be substituted with heteroatoms such as an oxygen atom.

The monocyclic cycloalkyl group is preferably a cycloalkyl group having 3 to 8 carbon atoms. Examples of the cycloalkyl group include a cyclopropyl group, a cyclopentyl group, a cyclohexyl group, a cyclobutyl group, and a cyclooctyl group.

Examples of the polycyclic cycloalkyl group include groups having a bicyclo structure, a tricyclo structure, or a tetracyclo structure. As the polycyclic cycloalkyl group, one having 6 to 20 carbon atoms is preferable. Examples of such cycloalkyl group include an adamantyl group, a norbornyl group, an isobornyl group, a camphanyl group, a dicyclopentyl group, an α-pinanyl group, a tricyclodecanyl group, a tetracyclododecyl group, and an androstanyl group.

Examples of the aralkyl group in $L_1$, $L_2$ and $Z_2$ include those having 7 to 15 carbon atoms, such as a benzyl group and a phenethyl group.

These aralkyl groups may further have a substituent. Preferred examples of the substituent include an alkoxy group, a hydroxyl group, a halogen atom, a nitro group, an acyl group, an acylamino group, a sulfonylamino group, an alkylthio group, an arylthio group and an aralkylthio group. Examples of the aralkyl group having a substituent include an alkoxybenzyl group, a hydroxybenzyl group and a phenylthiophenethyl group. Further, the number of carbon atoms of the substituent which the aralkyl group may have is preferably 12 or less.

Examples of the 5- or 6-membered ring in which $Z_2$ and $L_1$ are bonded to each other include a tetrahydropyran ring and a tetrahydrofuran ring. Among these, a tetrahydropyran ring is particularly preferred.

$Z_2$ is preferably a linear or branched alkyl group. Through this, the effect of the present invention becomes more apparent.

Specific examples of the repeating unit represented by the general formula (A1) are shown below, but the present invention is not limited thereto.

[Chem. 16]

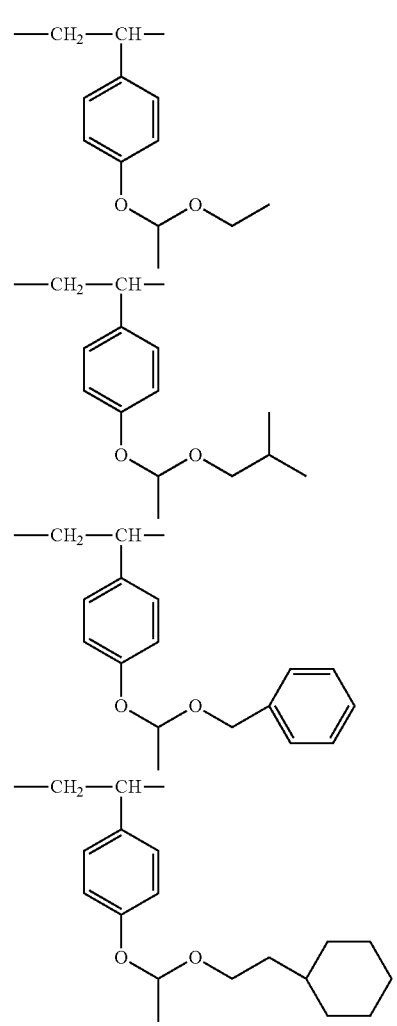

-continued
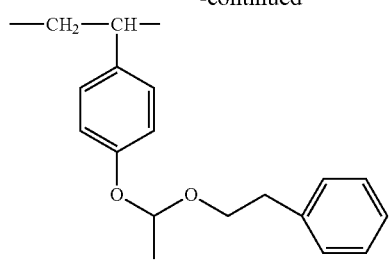
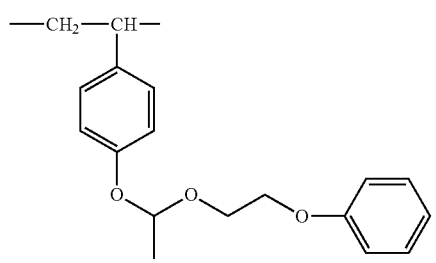
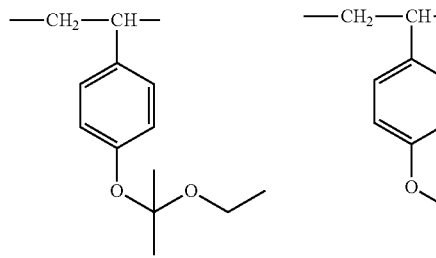
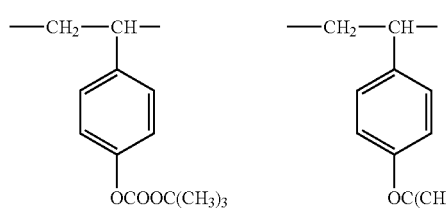
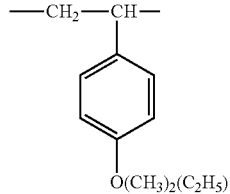
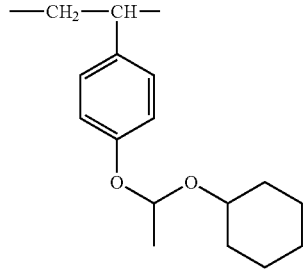
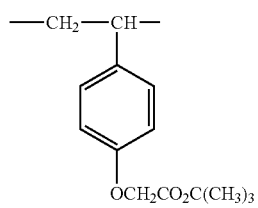
-continued
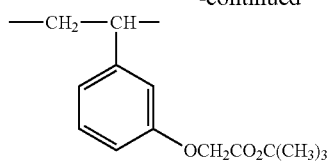
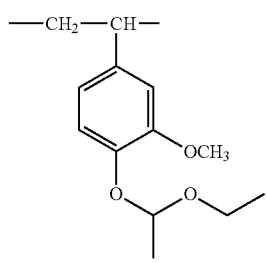
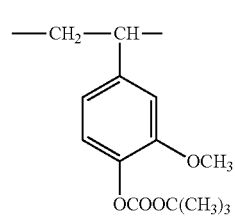
[Chem. 17]
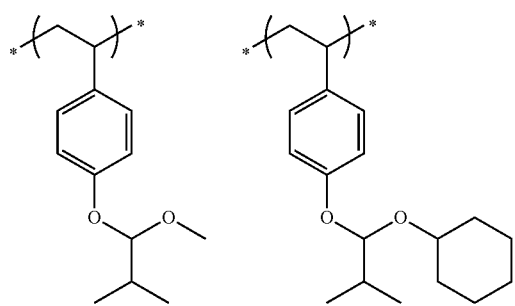
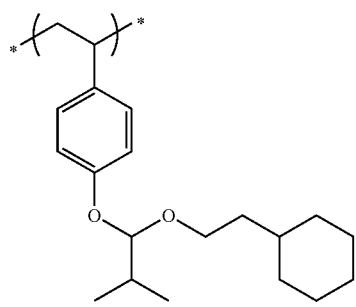
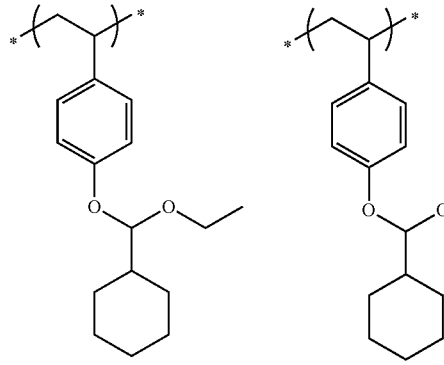

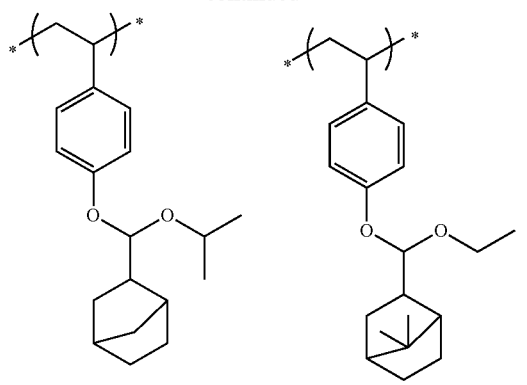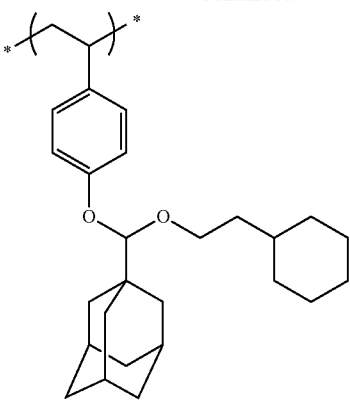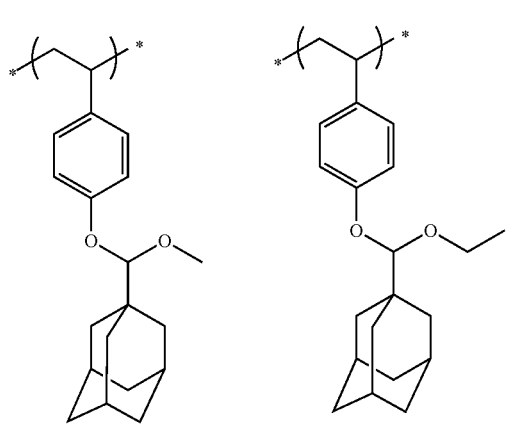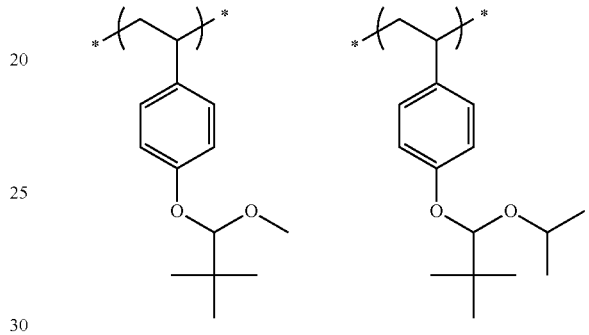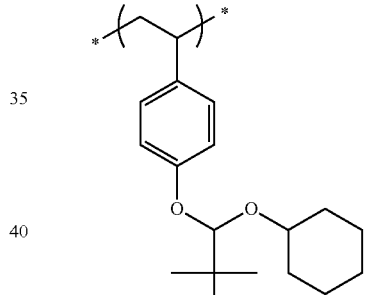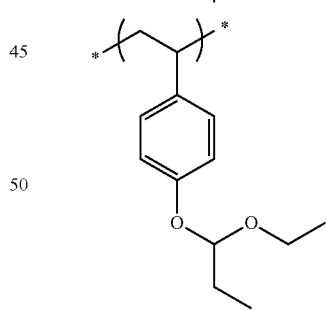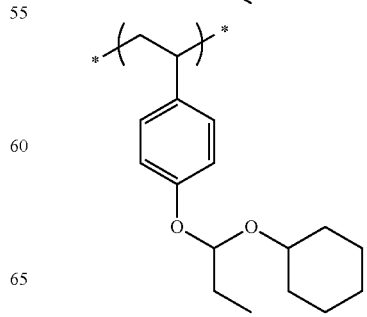

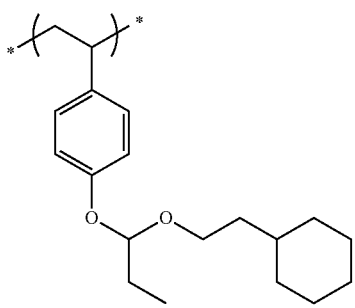
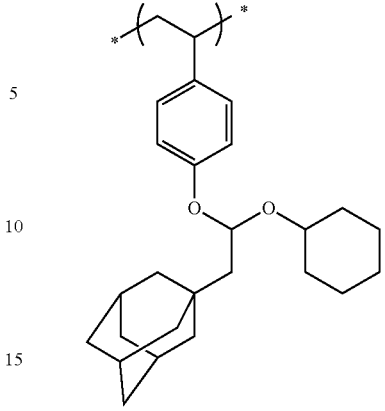
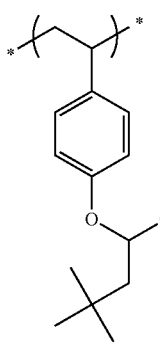
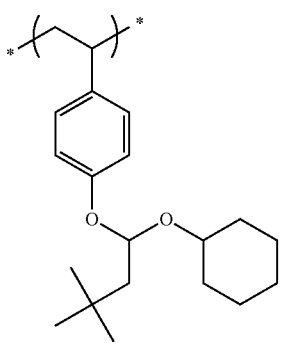
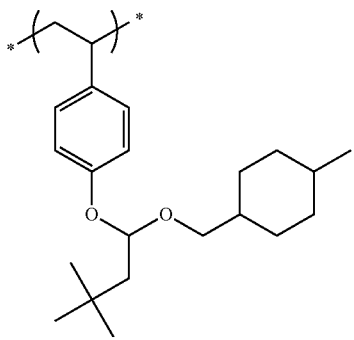
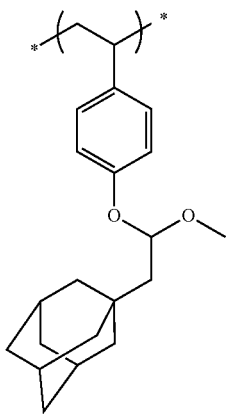
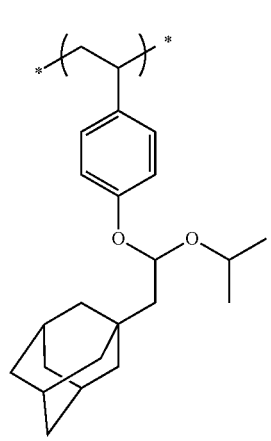

Next, the repeating unit represented by the general formula (A2) will be described.

X represents a hydrogen atom, an alkyl group, a hydroxyl group, an alkoxy group, a halogen atom, a cyano group, a nitro group, an acyl group, an acyloxy group, a cycloalkyl group, a cycloalkyloxy group, an aryl group, a carboxy group, an alkyloxycarbonyl group, an alkylcarbonyloxy group, or an aralkyl group, as described above.

The alkyl group as X may have a substituent and may be either linear or branched. The linear alkyl group is preferably an alkyl group having 1 to 30 carbon atoms, more preferably 1 to 20 carbon atoms, and examples thereof include a methyl group, an ethyl group, an n-propyl group, an n-butyl group, a sec-butyl group, a t-butyl group, an n-pentyl group, an n-hexyl group, an n-heptyl group, an n-octyl group, an n-nonyl group, and an n-decanyl group. The branched alkyl group is preferably an alkyl group having 3 to 30 carbon atoms, and more preferably an alkyl group having 3 to 20 carbon atoms, and examples thereof include an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group, and a t-decanoyl group.

The alkoxy group as X may have a substituent, and it is, for example, an alkoxy group having 1 to 8 carbon atoms, examples of which include a methoxy group, an ethoxy group, a propoxy group, a butoxy group, a pentyloxy group, a hexyloxy group, and a cyclohexyloxy group.

Examples of the halogen atom as X include a fluorine atom, a chlorine atom, a bromine atom and an iodine atom, and a fluorine atom is preferable.

The acyl group as X may have a substituent, and it is, for example, an acyl group having 2 to 8 carbon atoms, specific examples of which preferably include a formyl group, an acetyl group, a propanoyl group, a butanoyl group, a pivaloyl group and a benzoyl group.

The acyloxy group as X may have a substituent, and it is, for example, an acyloxy groups having 2 to 8 carbon atoms, examples of which include an acetoxy group, a propionyloxy group, a butylyloxy group, a valeryloxy group, a pivaloyloxy group, a hexanoyloxy group, an octanoyloxy group, and a benzoyloxy group.

The cycloalkyl group as X may have a substituent and may be monocyclic or polycyclic, and in the case of polycyclic, the cycloalkyl group may be a crosslinked cycloalkyl group. That is, in this case, the cycloalkyl group may have a bridged structure. The monocyclic cycloalkyl group is preferably a cycloalkyl group having 3 to 8 carbon atoms, and examples thereof include a cyclopropyl group, a cyclopentyl group, a cyclohexyl group, a cyclobutyl group, and a cyclooctyl group. The polycyclic cycloalkyl group includes a group having a bicyclo structure, a tricyclo structure, a tetracyclo structure, and the like and having 5 or more carbon atoms, and a cycloalkyl group having 6 to 20 carbon atoms is preferable. Examples thereof include an adamantyl group, a norbornyl group, an isobornyl group, a camphanyl group, a dicyclopentyl group, an α-pinanyl group, a tricyclodecanyl group, a tetracyclododecyl group, and an androstanyl group. Further, a part of carbon atoms in the cycloalkyl group may be substituted with a heteroatom such as an oxygen atom.

The aryl group as X may have a substituent, and is preferably an aryl group having 6 to 14 carbon atoms. Examples thereof include a phenyl group, a xylyl group, a tolyl group, a cumenyl group, a naphthyl group, and an anthracenyl group.

The alkyloxycarbonyl group as X may have a substituent, and is preferably an alkyloxycarbonyl group having 2 to 8 carbon atoms. Examples thereof include a methoxycarbonyl group, an ethoxycarbonyl group, and a propoxycarbonyl group.

The alkylcarbonyloxy group as X may have a substituent, and is preferably an alkylcarbonyloxy group having 2 to 8 carbon atoms. Examples thereof include a methylcarbonyloxy group and an ethylcarbonyloxy group.

The aralkyl group as X may have a substituent, and is preferably an aralkyl group having 7 to 16 carbon atoms. Examples thereof include a benzyl group.

Examples of the substituent which the alkyl group, the alkoxy group, the acyl group, the cycloalkyl group, the aryl group, the alkyloxycarbonyl group, the alkylcarbonyloxy group, or the aralkyl group as X may further have include a hydroxyl group, a fluorine atom, a chlorine atom, a bromine atom, an iodine atom, an alkyl group, a hydroxyl group, an alkoxy group, a halogen atom, a cyano group, a nitro group, an acyl group, an acyloxy group, a cycloalkyl group, an aryl group, a carboxyl group, an alkyloxycarbonyl group, an alkylcarbonyloxy group, and an aralkyl group.

$A_2$ represents a group capable of leaving by the action of an acid, as described above. That is, the repeating unit represented by the general formula (A2) is provided with a group represented by "—COOA$_2$" as the acid-decomposable group. Examples of $A_2$ include the same groups as described with respect to $A_1$ in the general formula (A1) above.

$A_2$ is preferably a hydrocarbon group (preferably having 20 or less carbon atoms, and more preferably having 4 to 12 carbon atoms), and more preferably a t-butyl group, a t-amyl group, or a hydrocarbon group having an alicyclic structure (for example, an alicyclic group itself, and a group having the alkyl group substituted with an alicyclic group).

$A_2$ is preferably a tertiary alkyl group or a tertiary cycloalkyl group.

The alicyclic structure may be monocyclic or polycyclic, and specific examples thereof include groups having a monocyclo structure, a bicyclo structure, a tricyclo structure, and a tetracyclo structure, each having 5 or more carbon atoms. The number of carbon atoms is preferably 6 to 30, and particularly preferably 7 to 25. The hydrocarbon group having the alicyclic structure may have a substituent.

Examples of the alicyclic structure are shown below.

[Chem. 18]

 (1)

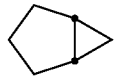 (2)

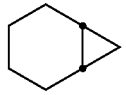 (3)

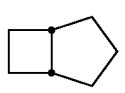 (4)

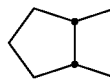 (5)

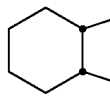 (6)

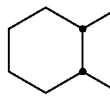 (7)

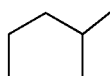 (8)

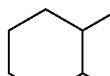 (9)

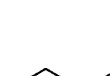 (10)

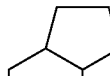 (11)

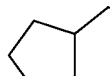 (12)

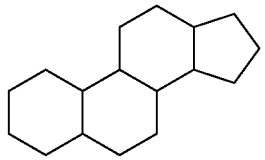 (13)

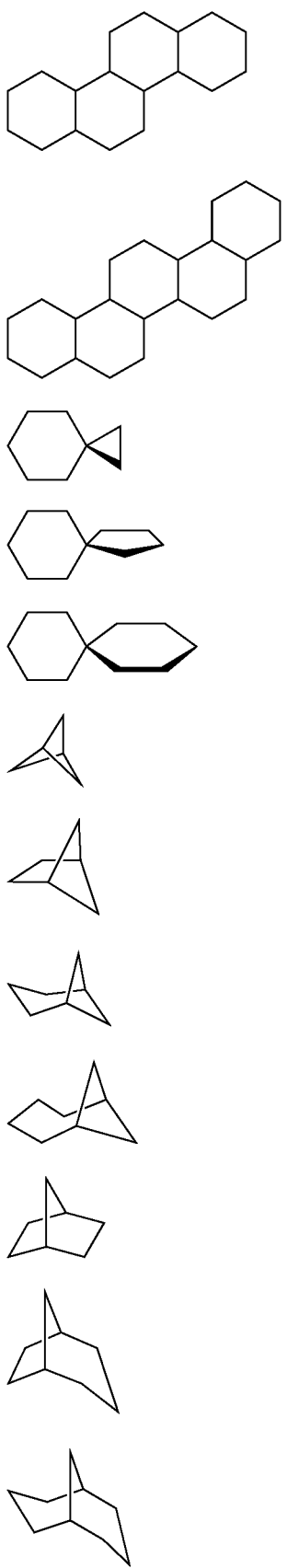
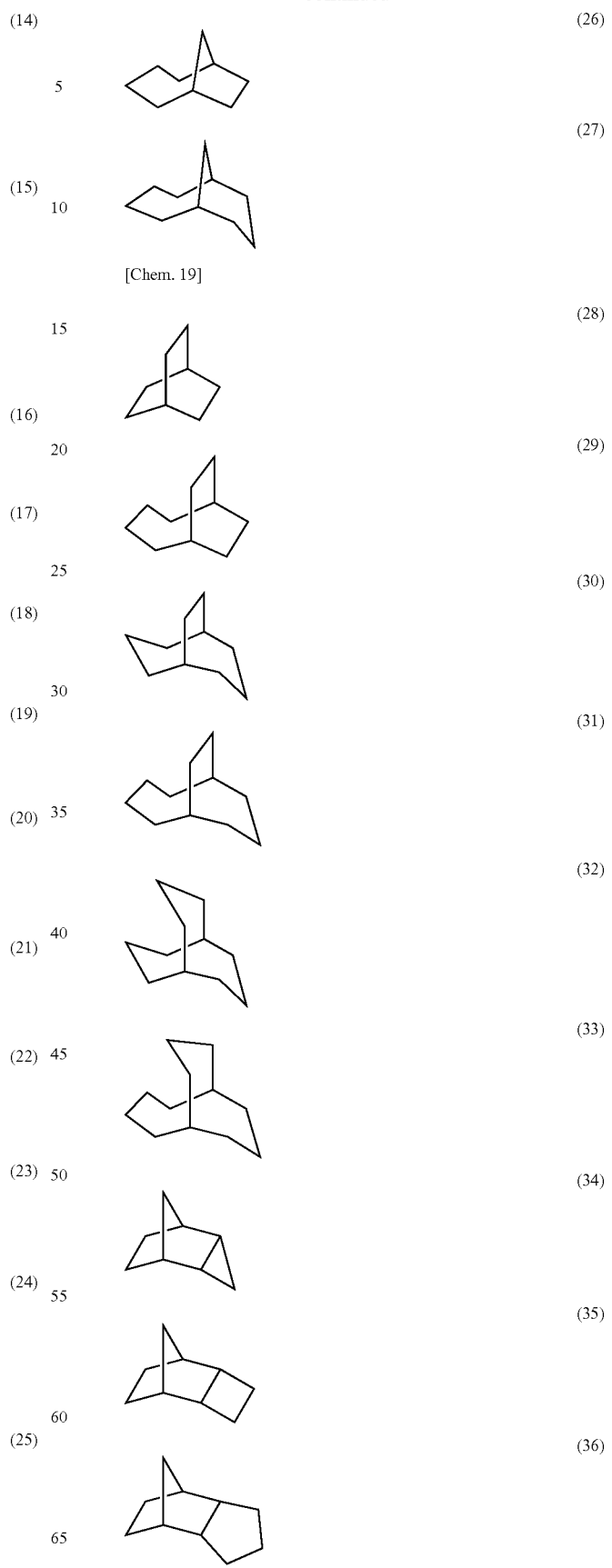
[Chem. 19]

-continued

(37) 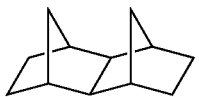

(38) 

(39) 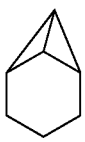

(40) 

(41) 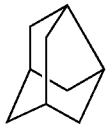

(42) 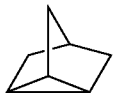

(43) 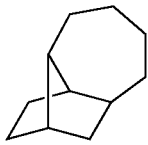

(44) 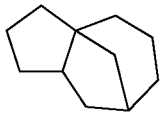

(45) 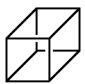

(46) 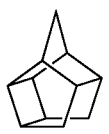

(47) 

(48) 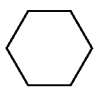

(49) 

-continued

(50) 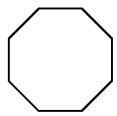

In the present invention, among these alicyclic structures, preferred examples of the groups, as denoted in terms of the monovalent alicyclic group, include an adamantyl group, a noradamantyl group, a decalin residue, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group, and more preferred examples thereof include an adamantyl group, a decalin residue, a norbornyl group, a cedrol group, a cyclohexyl group, a cycloheptyl group, a cyclooctyl group, a cyclodecanyl group and a cyclododecanyl group.

Examples of the substituent which the alicyclic ring in these structures may have include an alkyl group, a halogen atom, a hydroxyl group, an alkoxy group, a carboxyl group, and an alkoxycarbonyl group. The alkyl group is preferably a lower alkyl group such as a methyl group, an ethyl group, a propyl group, an isopropyl group and a butyl group, and more preferably a methyl group, an ethyl group, a propyl group or an isopropyl group. The alkoxy group includes an alkoxy group having 1 to 4 carbon atoms, such as a methoxy group, an ethoxy group, a propoxy group and a butoxy group. The alkyl group and the alkoxy group each may further have a substituent, and examples of the substituent which the alkyl group and alkoxy group may further have include a hydroxyl group, a halogen atom and an alkoxy group.

The acid-decomposable group having an alicyclic structure is preferably a group represented by any one of the following formulae (pI) to (pV):

[Chem. 20]

(pI) 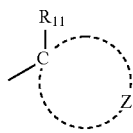

(pII) 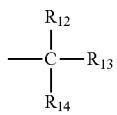

(pIII) 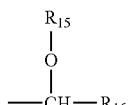

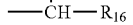

(pIV) 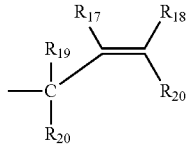

-continued

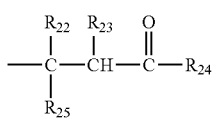 (pV)

[Chem. 22]

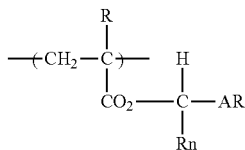 (A3)

In the general formulae (pI) to (pV), $R_{11}$ represents a methyl group, an ethyl group, an n-propyl group, an isopropyl group, an n-butyl group, an isobutyl group or a sec-butyl group, and Z represents an atomic group necessary for forming an alicyclic hydrocarbon group together with the carbon atom.

$R_{12}$ to $R_{16}$ each independently represent a linear or branched alkyl group having 1 to 4 carbon atoms or an alicyclic hydrocarbon group, provided that at least one of $R_{12}$ to $R_{14}$ or either one of $R_{15}$ and $R_{16}$ represents an alicyclic hydrocarbon group.

$R_{17}$ to $R_{21}$ each independently represent a hydrogen atom, a linear or branched alkyl group having 1 to 4 carbon atoms or an alicyclic hydrocarbon group, provided that at least one of $R_{17}$ to $R_{21}$ represents an alicyclic hydrocarbon group. Further, either one of $R_{19}$ and $R_{21}$ represents a linear or branched alkyl group having 1 to 4 carbon atoms or an alicyclic hydrocarbon group.

$R_{22}$ to $R_{25}$ each independently represent a hydrogen atom, a linear or branched alkyl group having 1 to 4 carbon atoms or an alicyclic hydrocarbon group, provided that at least one of $R_{22}$ to $R_{25}$ represents an alicyclic hydrocarbon group. Further, $R_{23}$ and $R_{24}$ may be bonded to each other to form a ring.

In the general formulae (pI) to (pV), the alkyl group of $R_{12}$ to $R_{25}$ is a linear or branched alkyl group having from 1 to 4 carbon atoms, which may be substituted or unsubstituted, and examples of the alkyl group include a methyl group, an ethyl group, an n-propyl group, an isopropyl group, an n-butyl group, an isobutyl group, a sec-butyl group and a t-butyl group.

Furthermore, examples of the substituent which the alkyl group may further have include an alkoxy group having 1 to 4 carbon atoms, a halogen atom (a fluorine atom, a chlorine atom, a bromine atom, and an iodine atom), an acyl group, an acyloxy group, a cyano group, a hydroxyl group, a carboxy group, an alkoxycarbonyl group and a nitro group.

Examples of the alicyclic hydrocarbon group in $R_{11}$ to $R_{25}$ and the alicyclic hydrocarbon group formed by Z together with the carbon atom include the same groups mentioned above as the alicyclic structure.

In one embodiment, the repeating unit represented by the general formula (A2) is preferably a repeating unit represented by the following formula.

[Chem. 21]

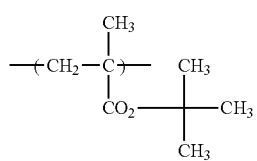

Furthermore, in another embodiment, the repeating unit represented by the general formula (A2) is preferably a repeating unit represented by the general formula (A3) shown below:

In the general formula (A3),

AR represents an aryl group.

Rn represents an alkyl group, a cycloalkyl group, or an aryl group. Rn and AR may be bonded to each other to form a non-aromatic ring.

R represents a hydrogen atom, an alkyl group, a cycloalkyl group, a halogen atom, a cyano group, or an alkyloxycarbonyl group.

The repeating unit represented by the general formula (A3) will be described in detail.

AR represents an aryl group as described above. As the aryl group of AR, those having 6 to 20 carbon atoms, such as a phenyl group, a naphthyl group, an anthryl group, or a fluorene group are preferred, and those having 6 to 15 carbon atoms are more preferred.

In the case where AR is a naphthyl group, an anthryl group, or a fluorene group, the bonding site between AR and the carbon atom to which Rn is bonded is not particularly limited. For example, when AR is a naphthyl group, the carbon atom may be bonded to the α-position or the β-position of the naphthyl group, or when AR is an anthryl group, the carbon atom may be bonded to the 1-position, the 2-position or the 9-position of the anthryl group.

The aryl group as AR each may have one or more substituents. Specific examples of the substituent include a linear or branched alky group having 1 to 20 carbon atoms, such as a methyl group, an ethyl group, a propyl group, an isopropyl group, an n-butyl group, an isobutyl group, a t-butyl group, a pentyl group, a hexyl group, an octyl group, and a dodecyl group, an alkoxy group containing such an alkyl group moiety, a cycloalkyl group such as cyclopentyl group and cyclohexyl group, a cycloalkoxy group containing such a cycloalkyl group moiety, a hydroxyl group, a halogen atom, an aryl group, a cyano group, a nitro group, an acyl group, an acyloxy group, an acylamino group, a sulfonylamino group, an alkylthio group, an arylthio group, an aralkylthio group, a thiophenecarbonyloxy group, a thiophenemethylcarbonyloxy group, and a heterocyclic residue such as a pyrrolidone residue. The substituent is preferably a linear or branched alkyl group having 1 to 5 carbon atoms or an alkoxy group containing such an alkyl group moiety, and more preferably a paramethyl group or a paramethoxy group.

In the case where the aryl group as AR has a plurality of substituents, at least two members out of the plurality of substituents may be bonded to each other to form a ring. The ring is preferably a 5- to 8-membered ring, more preferably a 5- or 6-membered ring. The ring may be also a heterocycle containing a heteroatom such as an oxygen atom, a nitrogen atom and a sulfur atom in the ring members.

Furthermore, this ring may have a substituent. Examples of the substituent are the same as those described later for the further substituent which Rn may have.

Moreover, in view of the roughness performance, the repeating unit represented by the general formula (A3) preferably contains two or more aromatic rings. Usually, the number of aromatic rings contained in the repeating unit is preferably 5 or less, and more preferably 3 or less.

In addition, in view of the roughness performance, in the repeating unit represented by the general formula (A3), AR preferably contains two or more aromatic rings, and AR is more preferably a naphthyl group or a biphenyl group. Usually, the number of the aromatic rings contained in AR is preferably 5 or less, and more preferably 3 or less.

As described above, Rn represents an alkyl group, a cycloalkyl group or an aryl group.

The alkyl group of Rn may be a linear alkyl group or a branched alkyl group. The alkyl group is preferably an alkyl group having 1 to 20 carbon atoms, such as a methyl group, an ethyl group, a propyl group, an isopropyl group, an n-butyl group, an isobutyl group, a t-butyl group, a pentyl group, a hexyl group, a cyclohexyl group, an octyl group, and a dodecyl group. The alkyl group of Rn is preferably an alkyl group having 1 to 5 carbon atoms, and more preferably an alkyl group having 1 to 3 carbon atoms.

Examples of the cycloalkyl group of Rn include a cycloalkyl group having 3 to 15 carbon atoms, such as a cyclopentyl group and a cyclohexyl group.

The aryl group of Rn is preferably, for example, an aryl group having 6 to 14 carbon atoms, such as a phenyl group, a xylyl group, a tolyl group, a cumenyl group, a naphthyl group and an anthryl group.

Each of the alkyl group, the cycloalkyl group, and the aryl group as Rn may further have a substituent. Examples of the substituent include an alkoxy group, a hydroxyl group, a halogen atom, a nitro group, an acyl group, an acyloxy group, an acylamino group, a sulfonylamino group, dialkylamino group, an alkylthio group, an arylthio group, an aralkylthio group, a thiophenecarbonyloxy group, a thiophenemethylcarbonyloxy group, and heterocyclic residues such as a pyrrolidone residue. Among these, an alkoxy group, a hydroxyl group, a halogen atom, a nitro group, an acyl group, an acyloxy group, an acylamino group, and a sulfonylamino group are particularly preferred.

As described above, R represents a hydrogen atom, an alkyl group, a cycloalkyl group, a halogen atom, a cyano group or an alkyloxycarbonyl group.

Examples of the alkyl group and the cycloalkyl group of R are the same as those described above for Rn. Each of these alkyl groups and cycloalkyl groups may have a substituent. Examples of this substituent are the same as those described above for Rn.

In the case where R is an alkyl group or a cycloalkyl group having a substituent, particularly preferred examples of R include a trifluoromethyl group, an alkyloxycarbonyl methyl group, an alkylcarbonyloxymethyl group, a hydroxymethyl group and an alkoxymethyl group.

The halogen atom of R includes a fluorine atom, a chlorine atom, a bromine atom and an iodine atom, and among these, the fluorine atom is particularly preferable.

As the alkyl group moiety contained in the alkyloxycarbonyl group of R, for example, the configuration described above as the alkyl group of R may be employed.

Rn and AR are preferably bonded to each other to form a non-aromatic ring and in this case, particularly the roughness performance can be more improved.

The non-aromatic ring which may be formed by the mutual bonding of Rn and AR is preferably a 5- to 8-membered ring, and more preferably a 5- or 6-membered ring.

The non-aromatic ring may be an aliphatic ring or a heterocycle containing a heteroatom such as an oxygen atom, a nitrogen atom and a sulfur atom, as a ring member.

The non-aromatic ring may have a substituent. Examples of the substituent are the same as those described above with respect to the further substituent which Rn may have.

Specific examples of the monomer corresponding to the repeating unit represented by the general formula (A2) and specific examples of the repeating units are illustrated below, but the present invention is not limited thereto.

[Chem. 23]

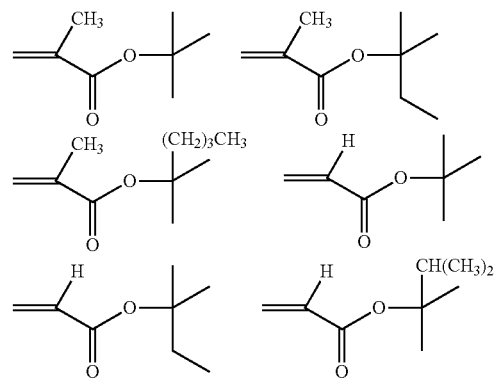

[Chem. 24]

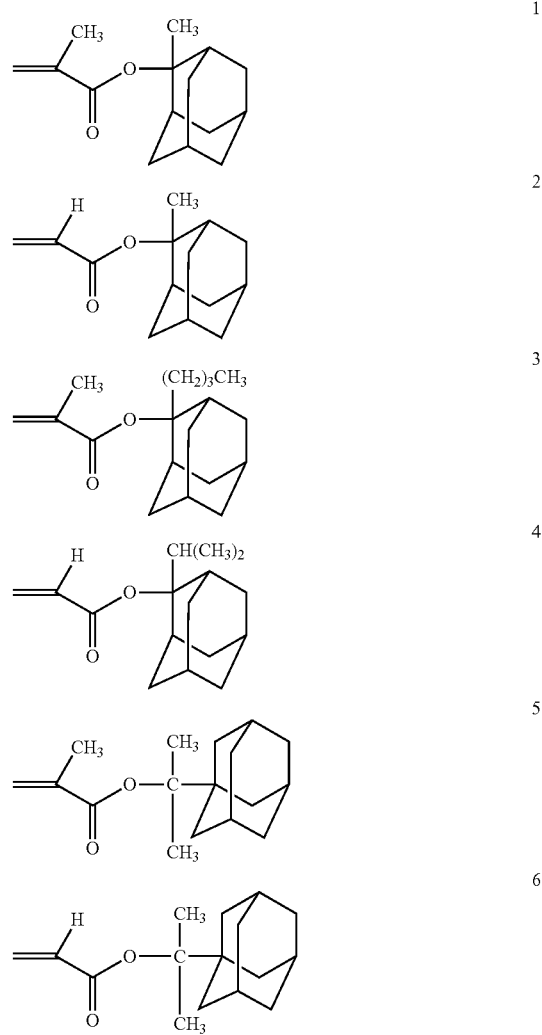

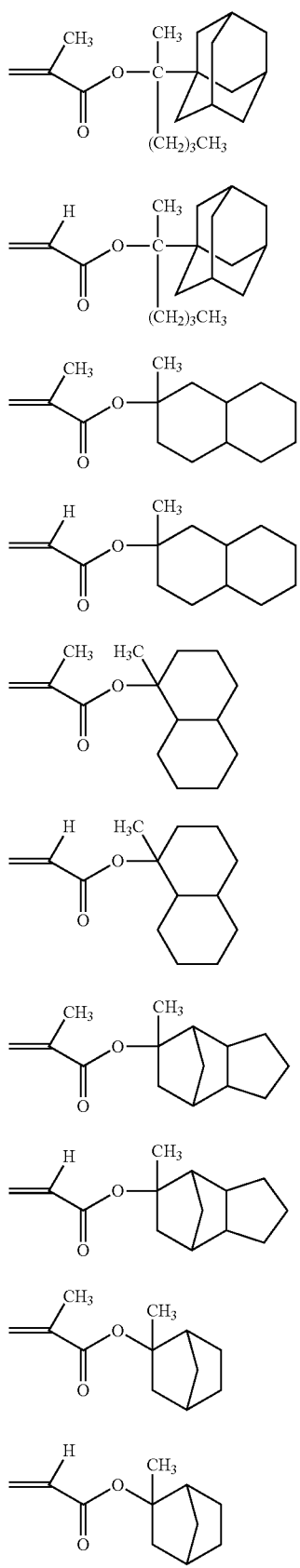
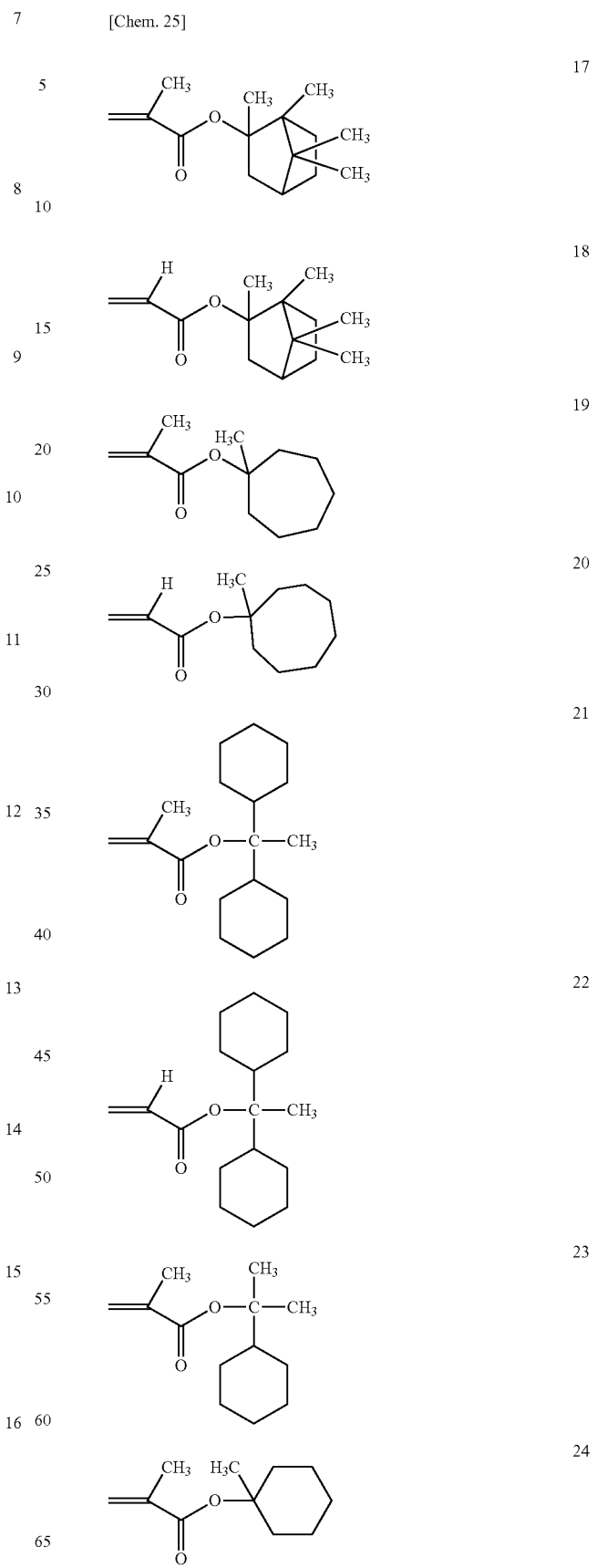
[Chem. 25]

-continued
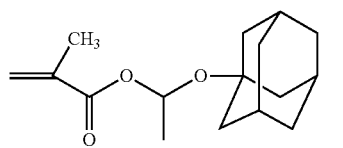
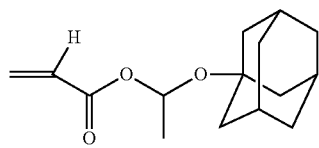
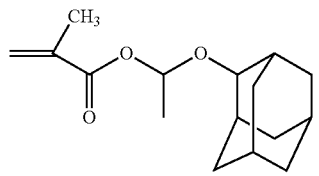
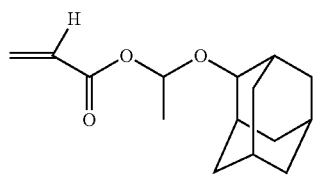
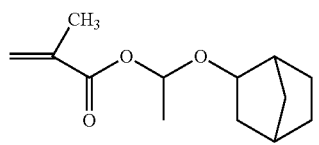
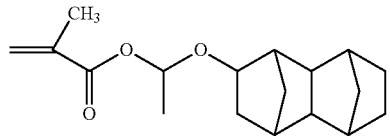
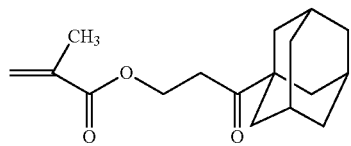
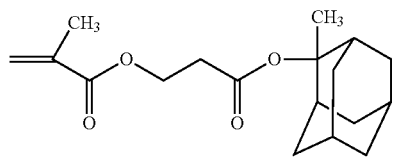
[Chem. 26]
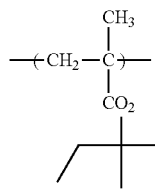 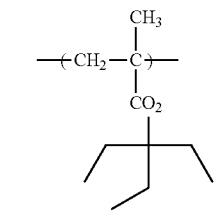
-continued
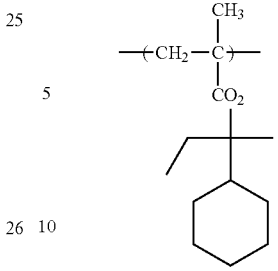 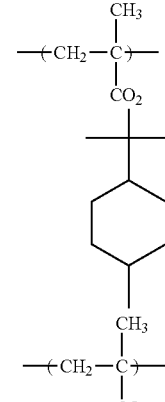
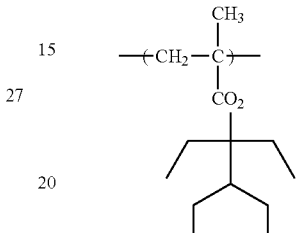
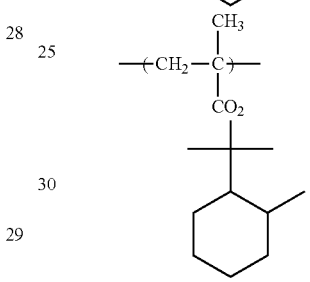 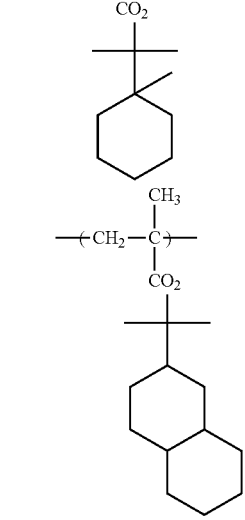
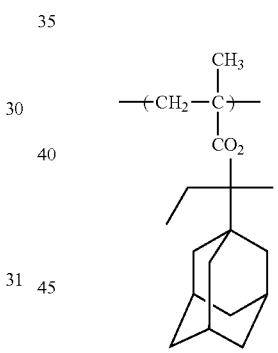
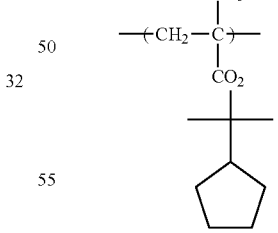 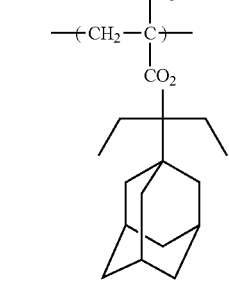
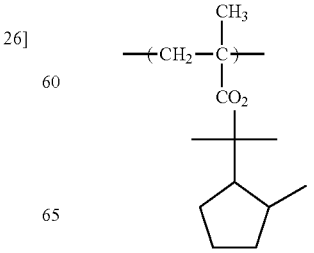 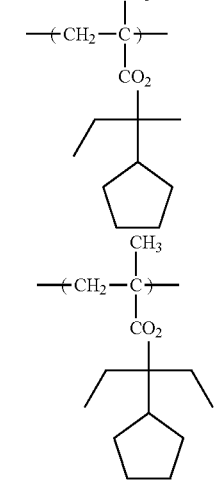

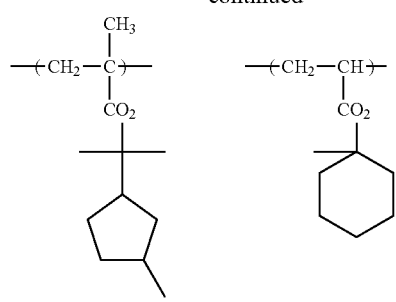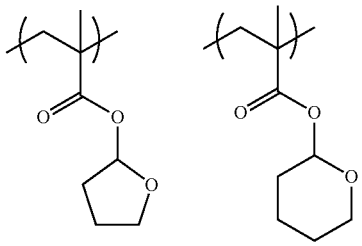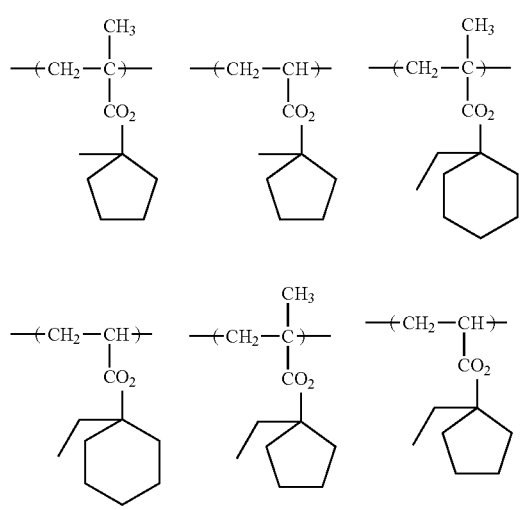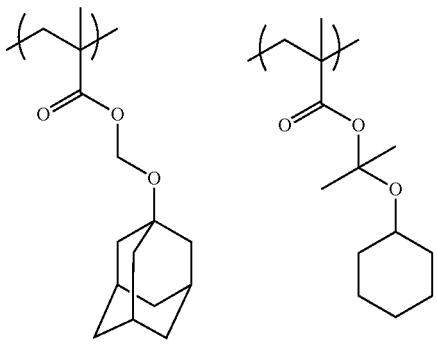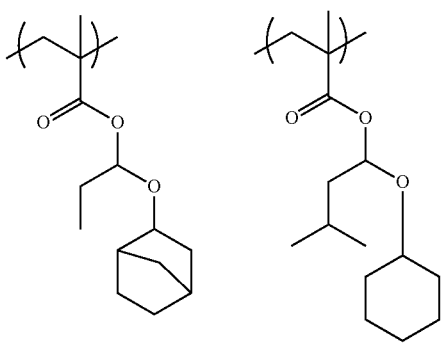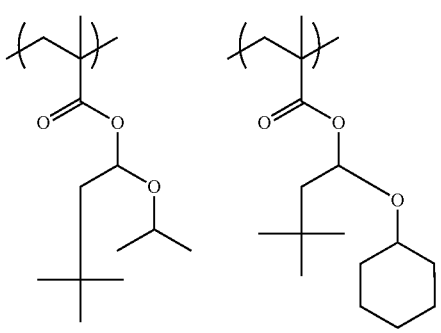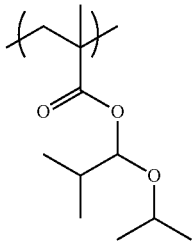

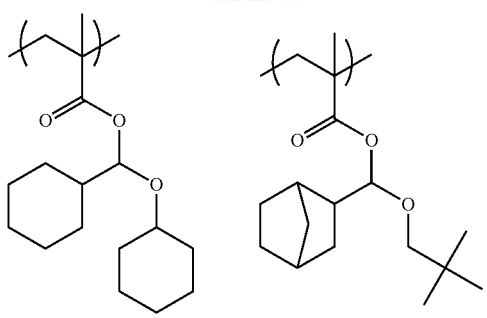
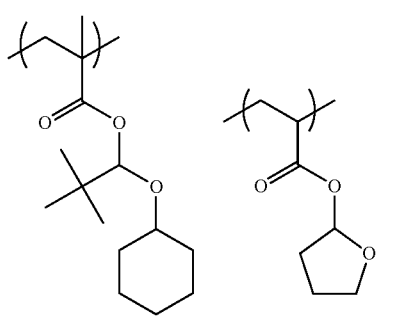
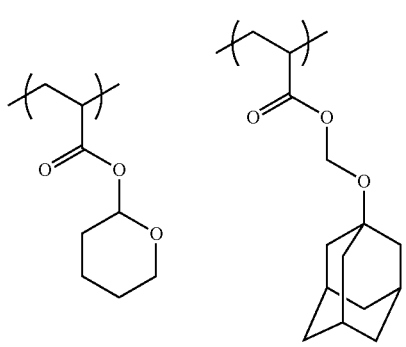
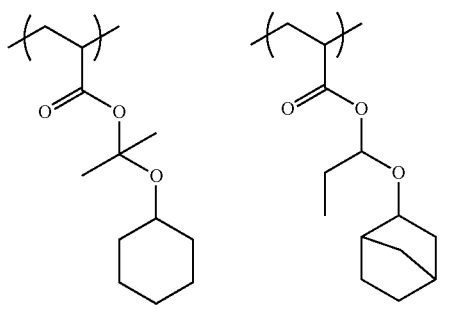
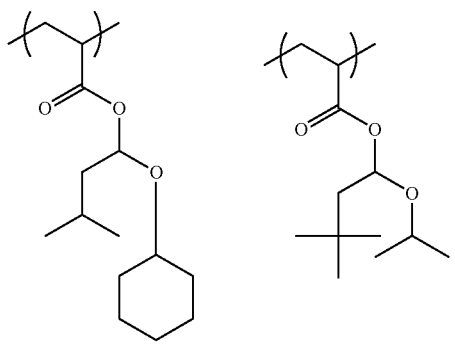
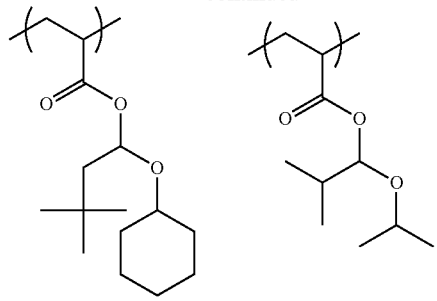
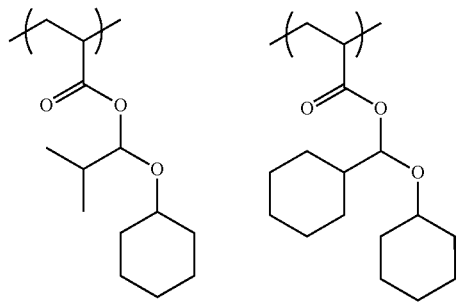
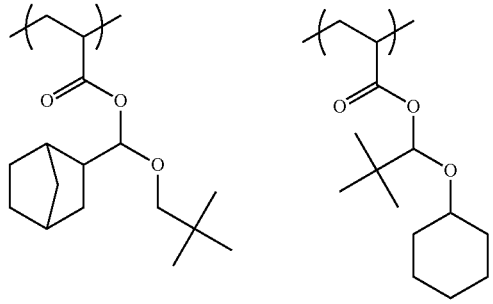
Specific examples of the repeating unit represented by the general formula (A3) are illustrated below, but the present invention is not limited thereto.
[Chem. 28]
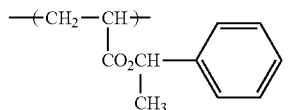
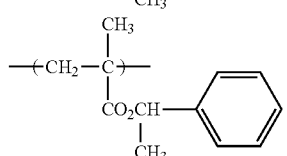
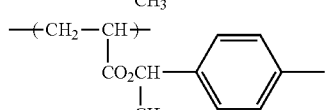
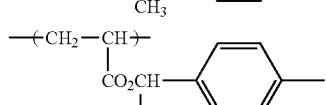
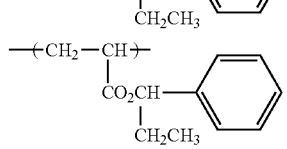

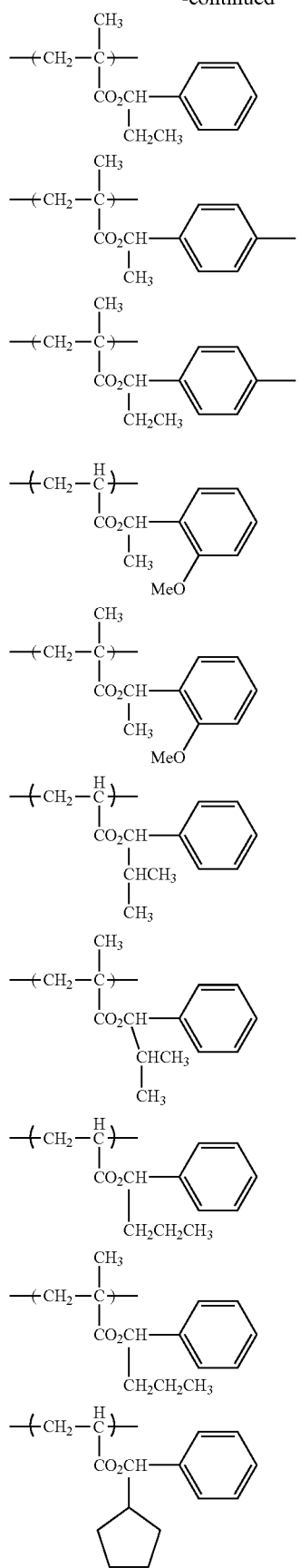
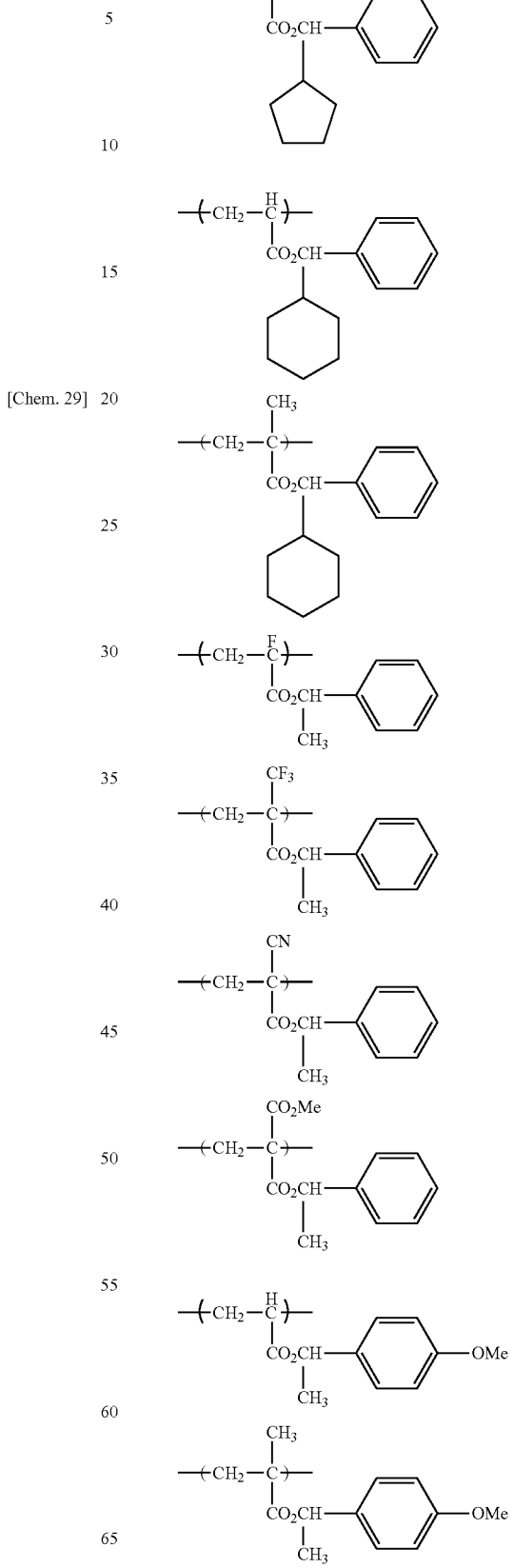

-continued
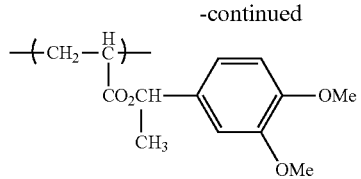
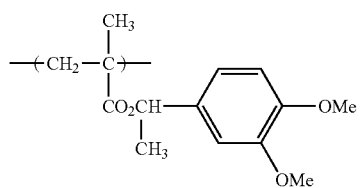
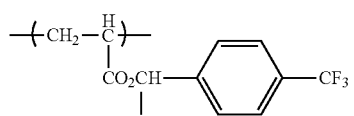
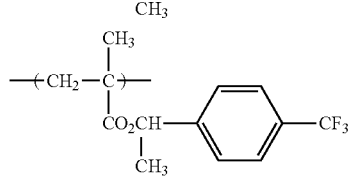
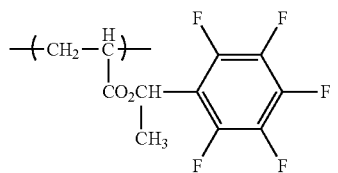
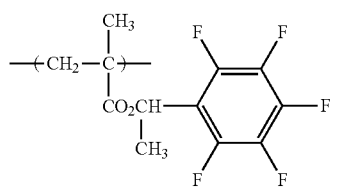
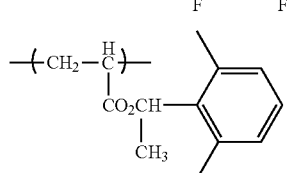
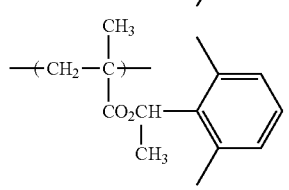
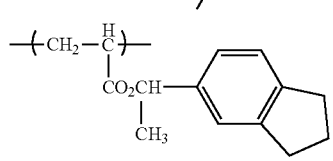
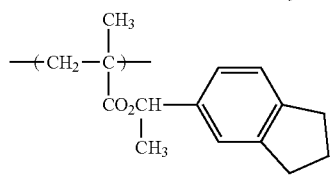
-continued

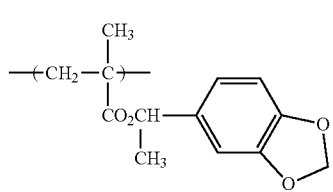
[Chem. 31]
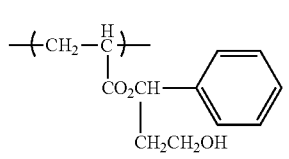
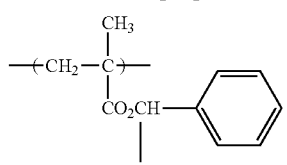
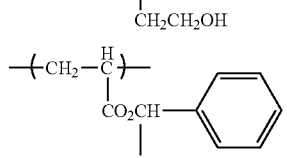
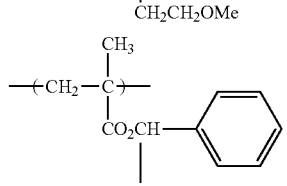

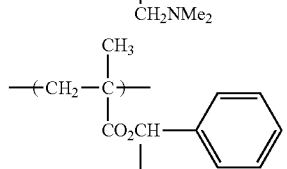

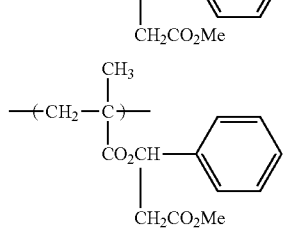

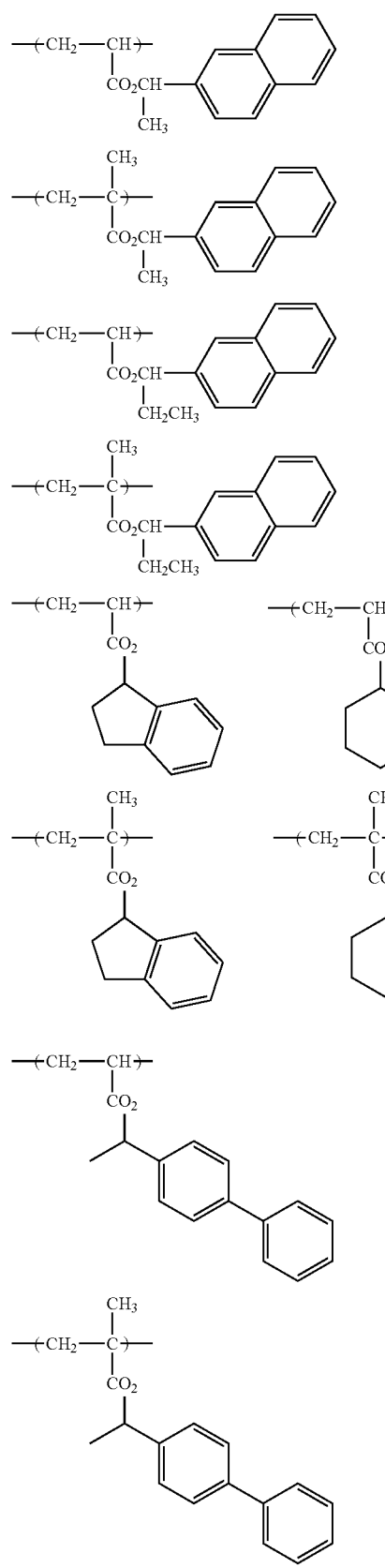
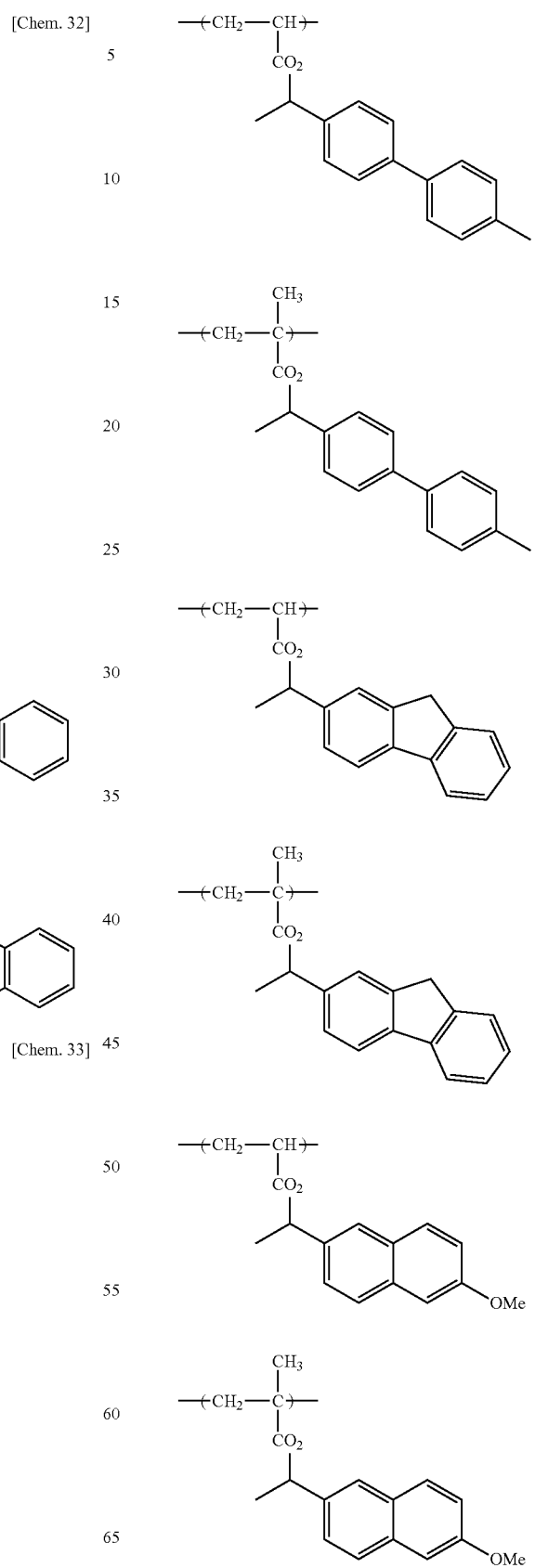

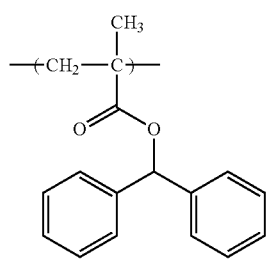
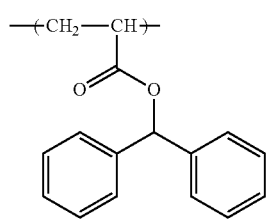
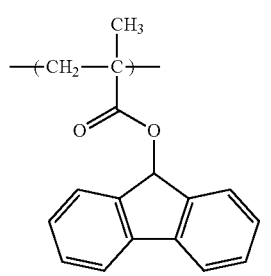
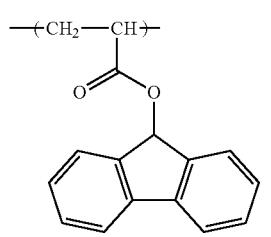
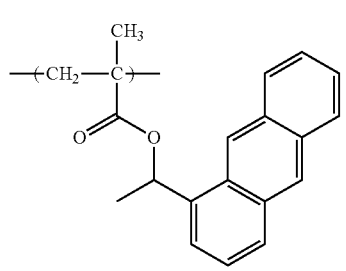
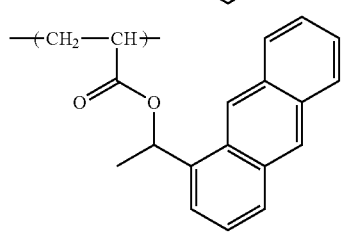
[Chem. 34]
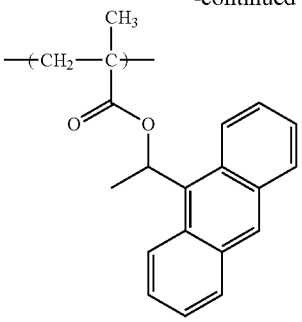
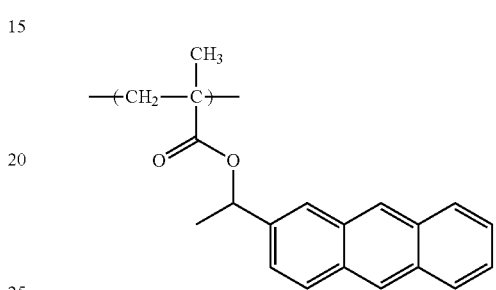
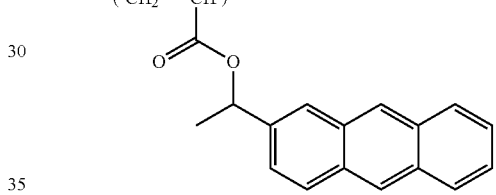
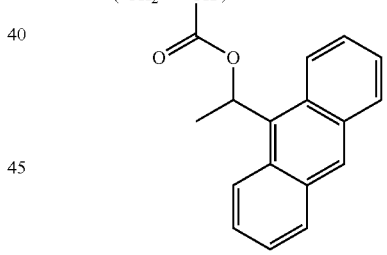
[Chem. 35]
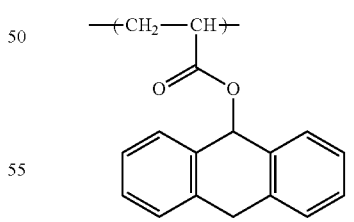
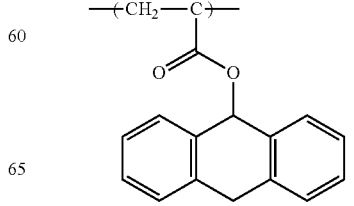

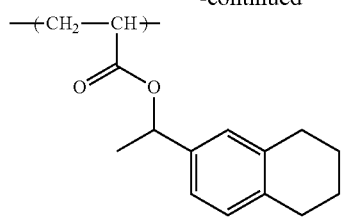
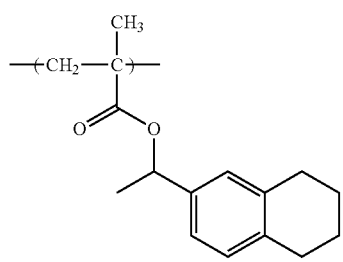
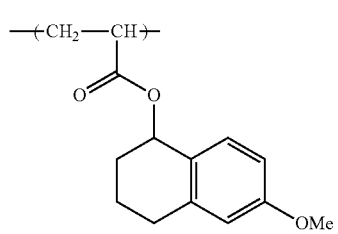
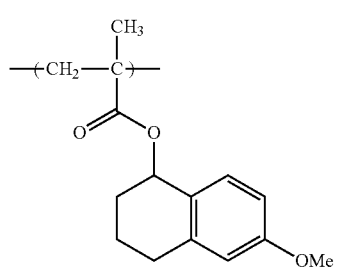
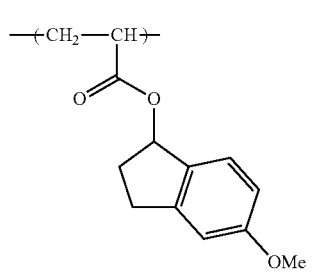
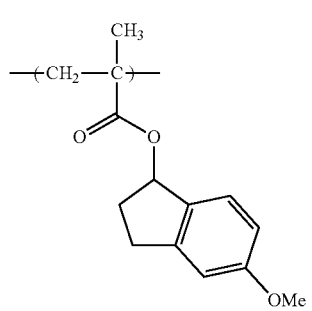
Among these, the repeating units shown below are preferred.
[Chem. 36]
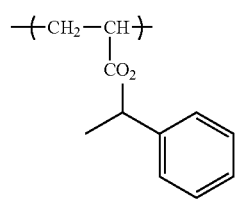
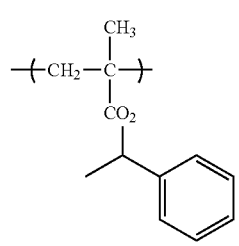
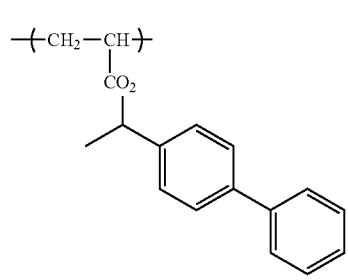
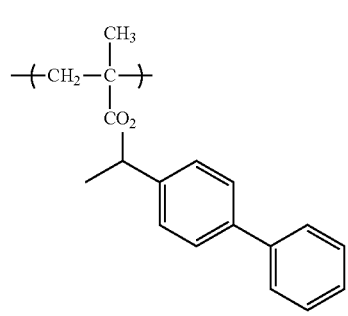
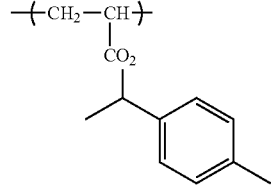
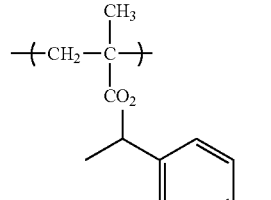
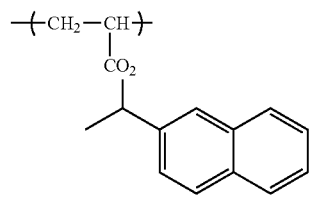

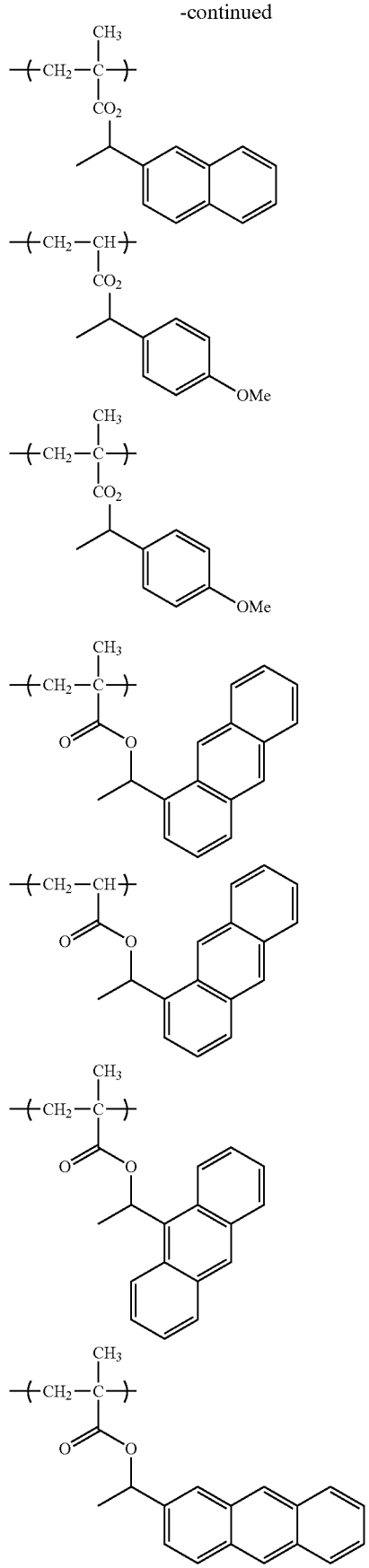
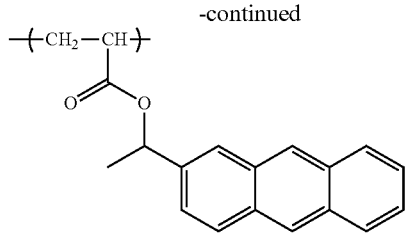
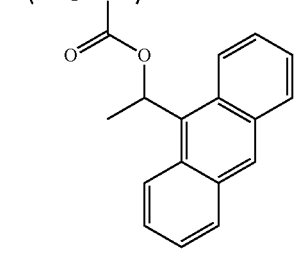
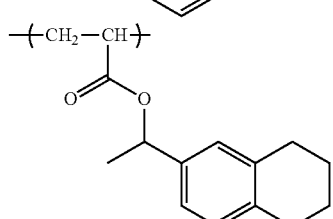
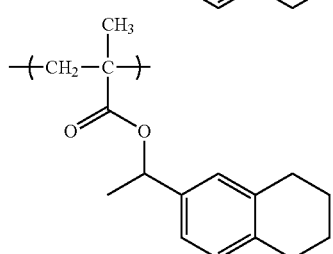
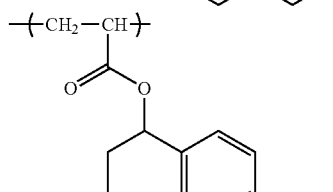
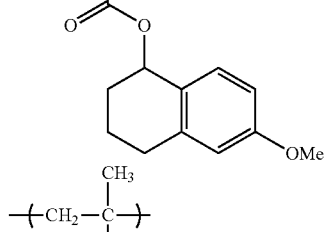

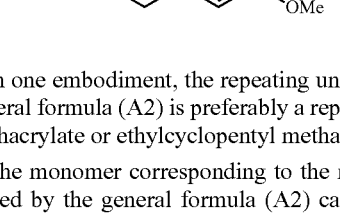

[Chem. 37]

In one embodiment, the repeating unit represented by the general formula (A2) is preferably a repeating unit of t-butyl methacrylate or ethylcyclopentyl methacrylate.

The monomer corresponding to the repeating unit represented by the general formula (A2) can be synthesized by esterifying a (meth)acrylic acid chloride and an alcohol compound in a solvent such as THF, acetone, and methylene chloride, in the presence of a basic catalyst such as triethylamine, pyridine and DBU. A commercially available product may also be used.

The resin (Ab) may further contain a repeating unit represented by the following general formula (A5).

[Chem. 38]

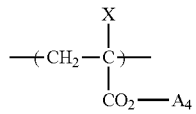
(A5)

In the formula (A5),

X represents a hydrogen atom, an alkyl group, a hydroxyl group, an alkoxy group, a halogen atom, a cyano group, a nitro group, an acyl group, an acyloxy group, a cycloalkyl group, an aryl group, a carboxyl group, an alkyloxycarbonyl group, an alkylcarbonyloxy group, or an aralkyl group, which is the same as X in the general formula (A2b).

$A_4$ represents a hydrocarbon group incapable of leaving by the action of an acid.

In the general formula (A5), examples of the hydrocarbon group incapable of leaving by the action of an acid of $A_4$ include hydrocarbon groups other than the above-described acid-decomposable groups, for example, an alkyl group not leaving by the action of an acid (preferably having 1 to 15 carbon atoms), a cycloalkyl group incapable of leaving by the action of an acid (preferably having 3 to 15 carbon atoms), and an aryl group incapable of leaving by the action of an acid (preferably having 6 to 15 carbon atoms).

The hydrocarbon group incapable of leaving by the action of an acid of $A_4$ may be further substituted with a hydroxyl group, an alkyl group, a cycloalkyl group, an aryl group, or the like.

It is also preferable for the resin (Ab) to further have a repeating unit represented by the general formula (A6).

[Chem. 39]

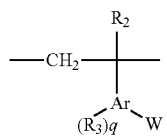
(A6)

In the general formula (A6), $R_2$ represents a hydrogen atom, a methyl group, a cyano group, a halogen atom, or a perfluoro group having 1 to 4 carbon atoms.

$R_3$ represents a hydrogen atom, an alkyl group, a cycloalkyl group, a halogen atom, an aryl group, an alkoxy group, or an acyl group.

q represents an integer of 0 to 4.

Ar represents a (q+2)-valent aromatic ring.

W represents a group incapable of decomposing by the action of an acid, or a hydrogen atom.

The aromatic ring represented by Ar is preferably a benzene ring, a naphthalene ring, or an anthracene ring, and more preferably a benzene ring.

W represents a group incapable of decomposing under the action of an acid (also referred to as an "acid-stable group"), examples thereof include groups other than the above-described acid-decomposable groups, and specific examples thereof include a halogen atom, an alkyl group, a cycloalkyl group, an alkenyl group, an aryl group, an acyl group, an alkylamide group, an arylamidomethyl group, and an arylamide group. The acid-stable group is preferably an acyl group or an alkylamide group, more preferably an acyl group, an alkylcarbonyloxy group, an alkyloxy group, a cycloalkyloxy group, or an aryloxy group.

In the acid-stable group of W, the alkyl group is preferably one having 1 to 4 carbon atoms, such as a methyl group, an ethyl group, a propyl group, an n-butyl group, a sec-butyl group, and a t-butyl group; the cycloalkyl group is preferably one having 3 to 10 carbon atoms, such as a cyclopropyl group, a cyclobutyl group, a cyclohexyl group, and an adamantyl group; the alkenyl group is preferably one having 2 to 4 carbon atoms, such as a vinyl group, a propenyl group, an allyl group, and a butenyl group; the alkenyl group is preferably one having 2 to 4 carbon atoms, such as a vinyl group, a propenyl group, an allyl group, and a butenyl group; and the aryl group is preferably one having 6 to 14 carbon atoms, such as a phenyl group, a xylyl group, a tolyl group, a cumenyl group, a naphthyl group, and an anthracenyl group. W may be at any position of the benzene ring, but is preferably at the meta- or para-position of the styrene skeleton, and particularly preferably at the para position. arylamidemethyl Specific examples of the repeating unit represented by the general formula (A6) are shown below, but the present invention is not limited thereto.

[Chem. 40]

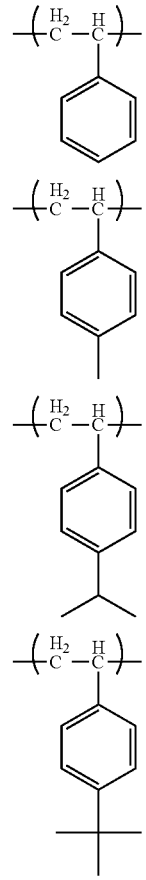

63
-continued
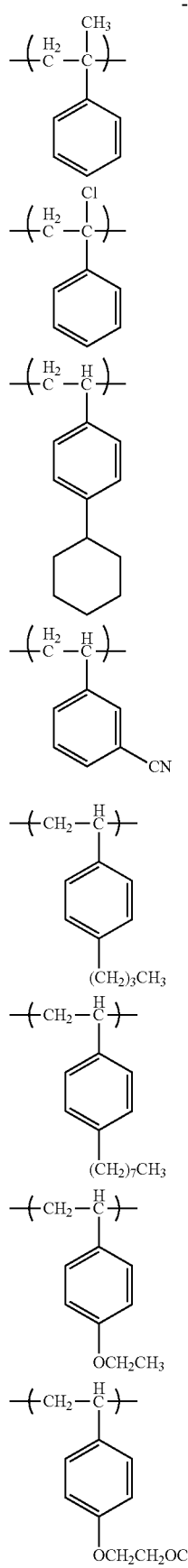
64
-continued
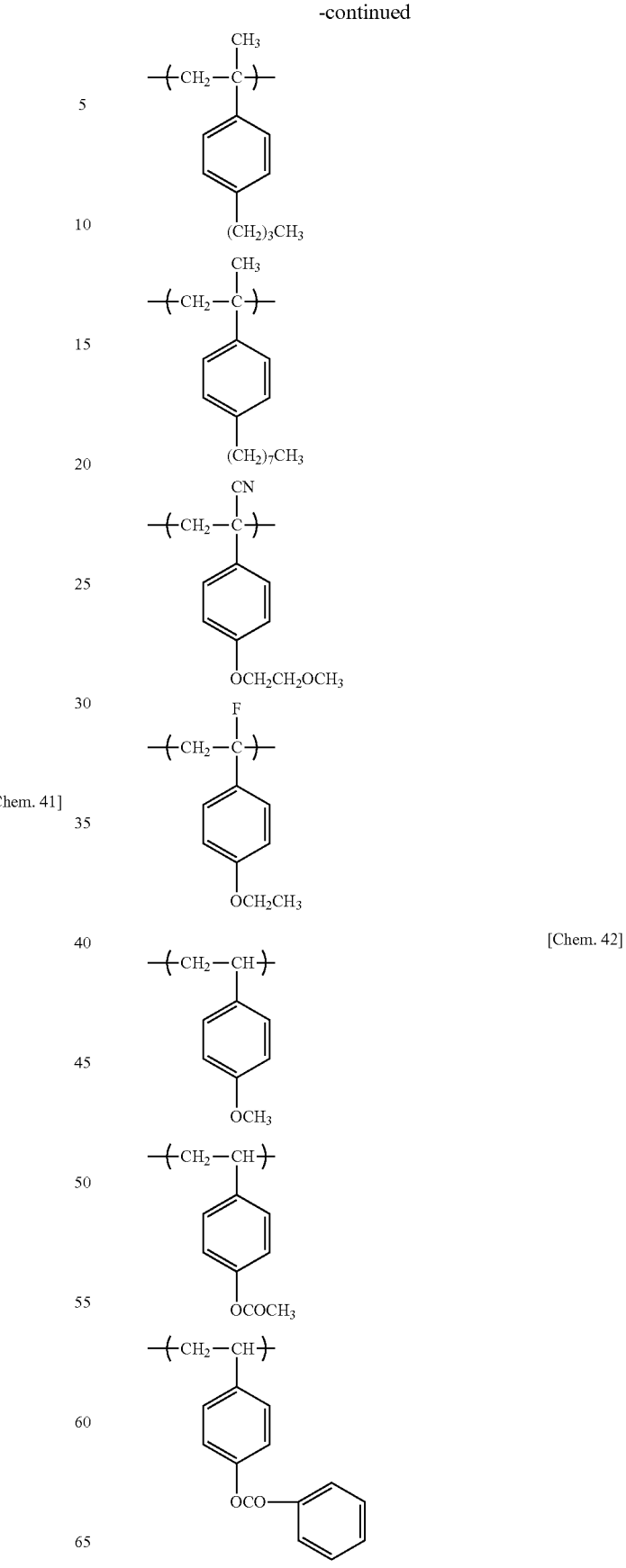
[Chem. 41]
[Chem. 42]

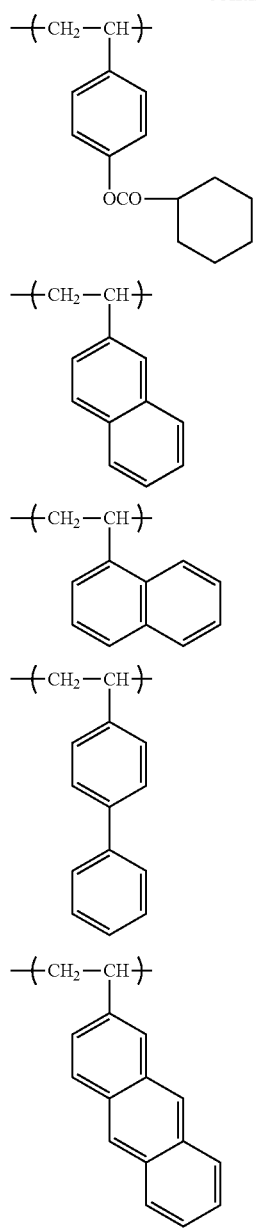
It is also preferable that the resin (Ab) further have a repeating unit including a (meth)acrylic acid derivative incapable of decomposing by the action of an acid. Specific examples thereof are shown below, but the present invention is not limited thereto.
[Chem. 43]
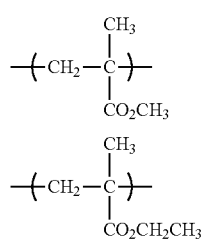
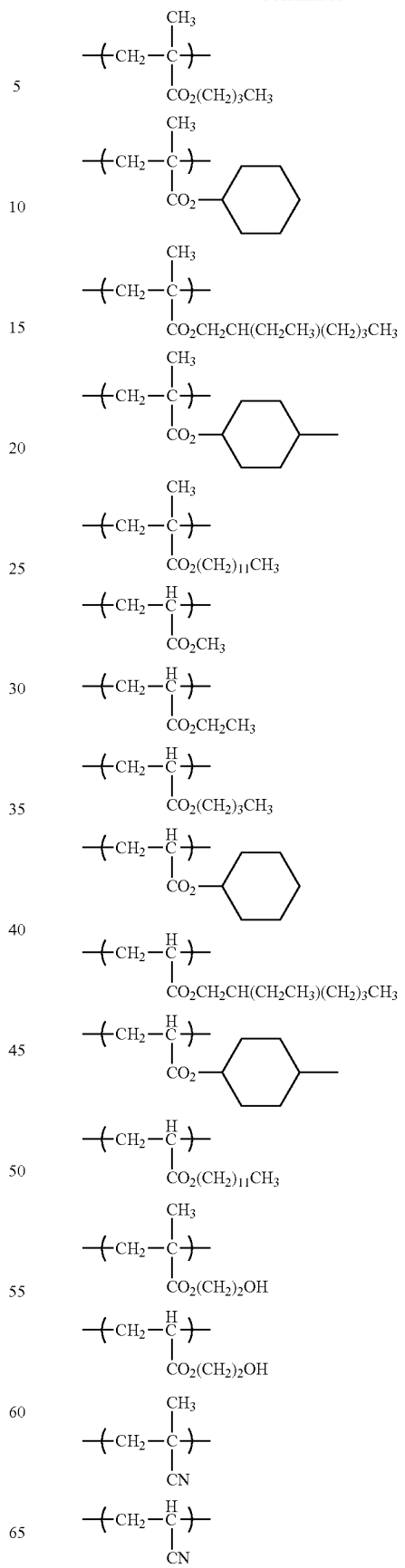

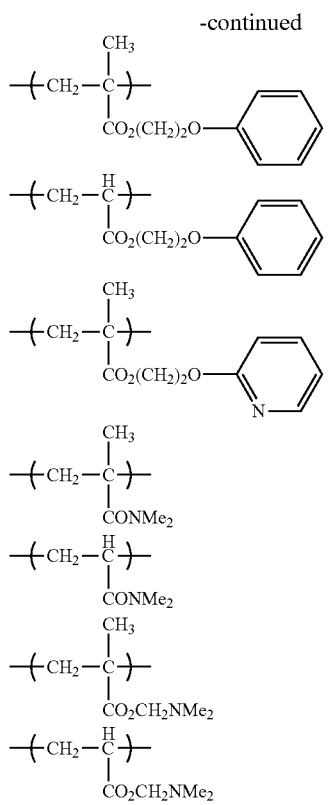

The content of the repeating units having the acid-decomposable groups in the resin (Ab) is preferably from 5 to 95% by mole, more preferably from 10 to 60% by mole, and particularly preferably 15 to 50% by mole, based on all the repeating units.

The content of repeating unit represented by the general formula (A1) in the resin (Ab) is preferably from 0 to 90% by mole, more preferably from 10 to 70% by mole, and particularly preferably from 20 to 50% by mole, based on all the repeating units.

The content of repeating unit represented by the general formula (A2) in the resin (Ab) is preferably from 0 to 90% by mole, more preferably from 5 to 75% by mole, and particularly preferably from 10 to 60% by mole, based on all the repeating units.

The content of repeating unit represented by the general formula (A3) in the resin (Ab) is preferably from 0 to 90% by mole, more preferably from 5 to 75% by mole, and particularly preferably from 10 to 60% by mole, based on all the repeating units.

The content of repeating unit represented by the general formula (A5) in the resin (Ab) is preferably from 0 to 50% by mole, more preferably from 0 to 40% by mole, and particularly preferably from 0 to 30% by mole, based on all the repeating units.

The resin (Ab) may further contain a repeating unit represented by the following general formula (A6), which is preferable from the viewpoints of enhancing the film quality and suppressing the film loss in the unexposed area. The content of repeating unit represented by the general formula (A6) in the resin (Ab) is preferably from 0 to 50% by mole, more preferably from 0 to 40% by mole, and particularly preferably from 0 to 30% by mole, based on all the repeating units.

Furthermore, the resin (Ab) may be copolymerized with other appropriate polymerizable monomers to incorporate an alkali-soluble group, for example, a phenolic hydroxyl group or a carboxyl group for the purpose of maintaining good developability with an alkali developer, or may be copolymerized with other appropriate hydrophobic polymerizable monomers such as alkyl acrylate and alkyl methacrylate for the purpose of enhancing the film quality.

The monomer corresponding to the repeating unit represented by the general formula (A2) can be synthesized by esterifying a (meth)acrylic acid chloride and an alcohol compound in a solvent such as THF, acetone, and methylene chloride, in the presence of a basic catalyst such as triethylamine, pyridine, and DBU. Further, a commercially available product may also be used.

The monomer corresponding to the repeating unit represented by the general formula (A1) may be synthesized by acetalizing a hydroxy-substituted styrene monomer and a vinyl ether compound in a solvent such as THF and methylene chloride, in the presence of an acidic catalyst such as p-toluenesulfonic acid and pyridine p-toluenesulfonate, or by effecting t-Boc protection using t-butyl dicarboxylate in the presence of a basic catalyst such as triethylamine, pyridine and DBU. A commercially available product may also be used.

In one embodiment, the resin (Ab) preferably contains a repeating unit represented by the following general formula (A).

[Chem. 44]

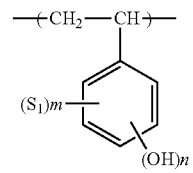

(A)

Here, n represents an integer of 1 to 5 and m represents an integer of 0 to 4, satisfying the relationship of $1 \leq m+n \leq 5$. n is preferably 1 or 2, and more preferably 1. m is preferably 0 to 2, more preferably 0 or 1, and particularly preferably 0.

$S_1$ represents a substituent. In the case where m is 2 or more, a plurality of $S_1$'s may be the same as or different from each other.

Examples of the substituent represented by $S_1$ include an alkyl group, an alkoxy group, an acyl group, an acyloxy group, an aryl group, an aryloxy group, an aralkyl group, an aralkyloxy group, a hydroxy group, a halogen atom, a cyano group, a nitro group, a sulfonylamino group, an alkylthio group, an arylthio group, and an aralkylthio group.

For example, the alkyl group or the cycloalkyl group is preferably a linear or branched alkyl group or a cycloalkyl group, each having 1 to 20 carbon atoms, such as a methyl group, an ethyl group, a propyl group, an isopropyl group, an n-butyl group, an isobutyl group, a t-butyl group, a pentyl group, a cyclopentyl group, a hexyl group, a cyclohexyl group, an octyl group, and a dodecyl group. These groups may further have a substituent.

Preferred examples of the substituent which these groups each may further have include an alkyl group, an alkoxy group, a hydroxyl group, a halogen atom, a nitro group, an acyl group, an acyloxy group, an acylamino group, a sulfonylamino group, an alkylthio group, an arylthio group, an aralkylthio group, a thiophenecarbonyloxy group, a thiophenemethylcarbonyloxy group, and heterocyclic residues such as a pyrrolidone residue. The substituent is preferably a substituent having 12 or less carbon atoms.

Examples of the alkyl group having a substituent include a cyclohexylethyl group, an alkylcarbonyloxymethyl group, an alkylcarbonyloxyethyl group, a cycloalkylcarbonyloxymethyl group, a cycloalkylcarbonyloxyethyl group, an arylcarbonyloxyethyl group, an aralkylcarbonyloxyethyl group, an alkyloxymethyl group, a cycloalkyloxymethyl group, an aryloxymethyl group, an aralkyloxymethyl group, an alkyloxyethyl group, a cycloalkyloxyethyl group, an aryloxyethyl group, an aralkyloxyethyl group, an alkylthiomethyl group, a cycloalkylthiomethyl group, an arylthiomethyl group, an aralkylthiomethyl group, an alkylthioethyl group, a cycloalkylthioethyl group, an arylthioethyl group, and an aralkylthioethyl group.

The alkyl group or the cycloalkyl group in these groups is not particularly limited, and may further have the above-described substituent such as an alkyl group, a cycloalkyl group, and an alkoxy group.

Examples of the alkylcarbonyloxyethyl group and the cycloalkylcarbonyloxyethyl group include a cyclohexylcarbonyloxyethyl group, a t-butylcyclohexylcarbonyloxyethyl group, and an n-butylcyclohexylcarbonyloxyethyl group.

The aryl group is also not particularly limited, but generally includes an aryl group having 6 to 14 carbon atoms, such as a phenyl group, a xylyl group, a tolyl group, a cumenyl group, a naphthyl group, and an anthracenyl group, and may further have the above-described substituent such as an alkyl group, a cycloalkyl group, and an alkoxy group.

Examples of the aryloxyethyl group include a phenyloxyethyl group and a cyclohexylphenyloxyethyl group. These groups each may further have a substituent.

The aralkyl is also not particularly limited but examples thereof include a benzyl group.

Examples of the aralkylcarbonyloxyethyl group include a benzylcarbonyloxyethyl group. These groups each may further have a substituent.

Examples of the repeating unit represented by the general formula (A) include the following.

[Chem. 45]

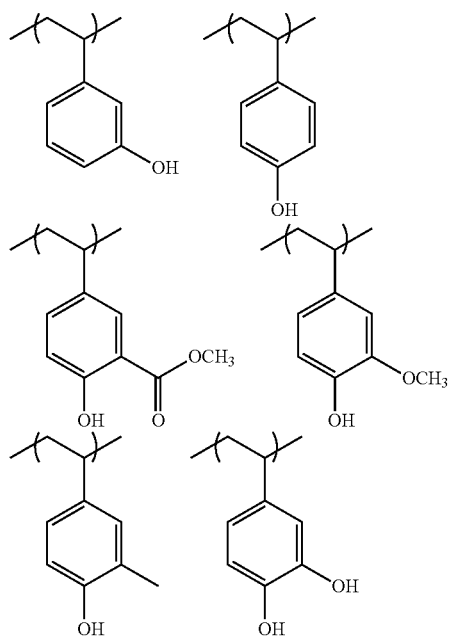

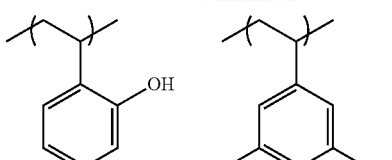

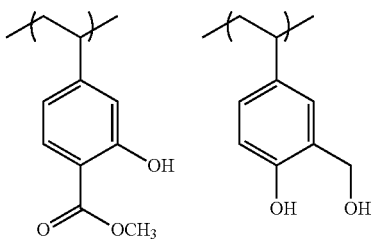

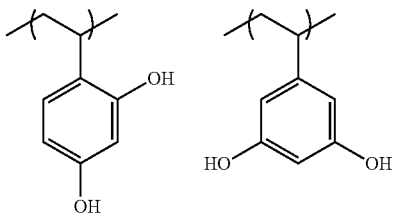

In one embodiment, the resin (Ab) preferably at least contains a repeating unit represented by the following formula as the repeating unit represented by the general formula (A).

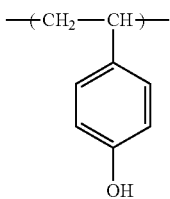

[Chem. 46]

The content of repeating unit represented by the general formula (A) in the resin (Ab) is preferably from 0 to 90% by mole, more preferably from 5 to 80% by mole, still more preferably from 10 to 70% by mole, and particularly preferably from 20 to 60% by mole, based on all the repeating units in the resin (Ab).

It is also preferable that the resin (Ab) have repeating units represented by the following general formulae. In the following general formulae, j represents an integer of 0 to 3, preferably an integer of 0 to 2, and more preferably 0 or 1.

[Chem. 47]
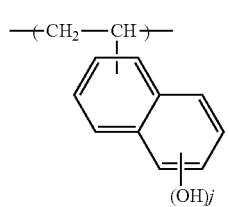 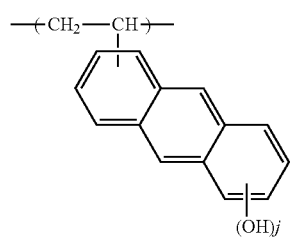 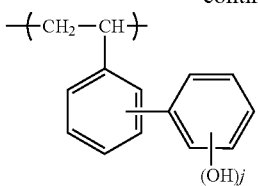
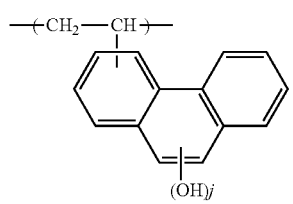 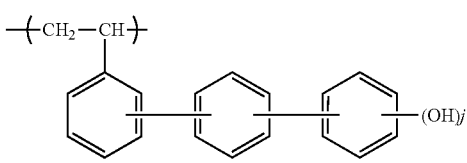
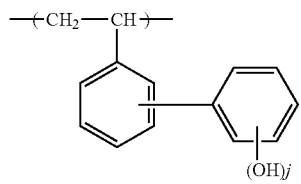 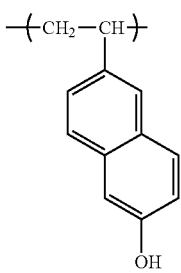
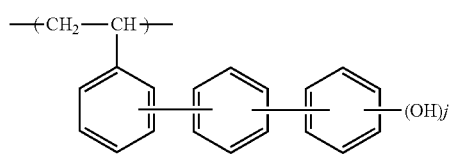 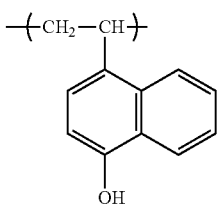
Specific examples of the repeating units represented by these general formulae are shown below.
[Chem. 48]
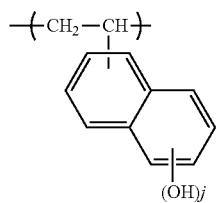 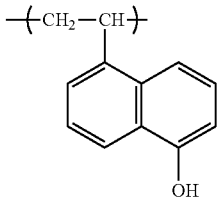
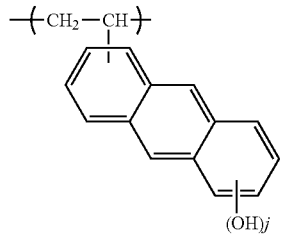 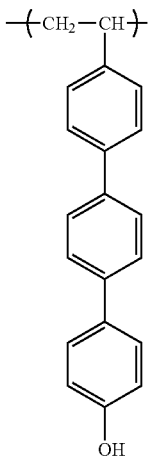
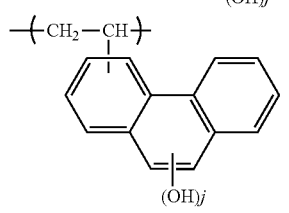

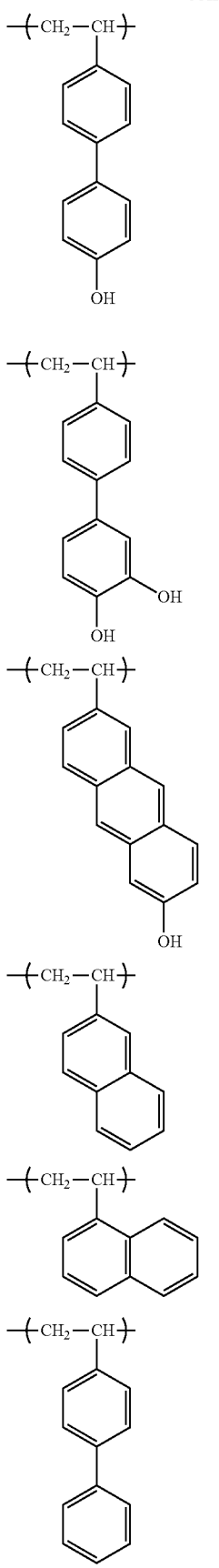

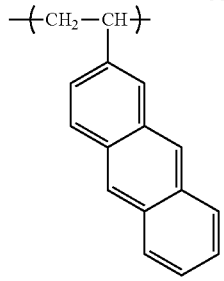

In one embodiment, the resin (Ab) may contain a repeating unit (B) including a structural moiety capable of decomposing by irradiation with actinic rays or radiation to generate an acid (hereinafter referred to as an "acid-generating repeating unit (B)" or a "repeating unit (B)").

The structural moiety may be, for example, a structural moiety capable of decomposing by irradiation with actinic rays or radiation to generate an acid anion in the repeating unit (B), or a structural moiety capable of discharging an acid anion to generate a cation structure in the repeating unit (B).

Furthermore, this structural moiety is preferably, for example, an ionic structural moiety including a sulfonium salt structure or an iodonium salt structure.

This structural moiety may be, for example, a structural moiety such as a structural moiety represented by A in the general formulae (B1), (B2), and (B3) shown below.

In one embodiment, it is preferable that the repeating unit (B) be at least one selected from the group consisting of repeating units of the following general formulae (B1), (B2) and (B3). Among these, the repeating unit represented by the following general formula (B1) or (B3) is more preferred, and the repeating unit represented by the following general formula (B1) is particularly preferred.

[Chem. 49]

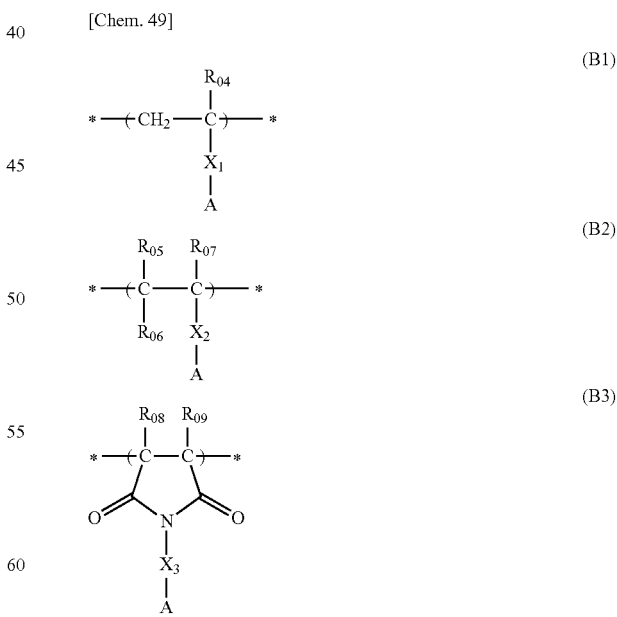

In the general formulae (B1), (B2) and (B3),

A represents a structural moiety capable of decomposing by irradiation with actinic rays or radiation to generate an acid anion.

$R_{04}$, $R_{05}$ and $R_{07}$ to $R_{09}$ each independently represent a hydrogen atom, an alkyl group, a cycloalkyl group, a halogen atom, a cyano group, or an alkoxycarbonyl group.

$R_{06}$ represents a cyano group, a carboxyl group, —CO—$OR_{25}$ or —CO—$N(R_{26})(R_{27})$, wherein $R_{25}$ represents an alkyl group, a cycloalkyl group, an alkenyl group, a cycloalkenyl group, an aryl group or an aralkyl group, and $R_{26}$ and $R_{27}$ each independently represent a hydrogen atom, an alkyl group, a cycloalkyl group, an alkenyl group, a cycloalkenyl group, an aryl group or an aralkyl group, provided that $R_{26}$ and $R_{27}$ may be bonded to each other to form a ring together with the N atom.

$X_1$, $X_2$ and $X_3$ each independently represent a single bond, an arylene group, an alkylene group, a cycloalkylene group, —O—, —$SO_2$—, —CO—, —$N(R_{33})$—, or a divalent connecting group formed by a combination of two or more of these, wherein $R_{33}$ represents a hydrogen atom, an alkyl group, a cycloalkyl group, an alkenyl group, a cycloalkenyl group, an aryl group, or an aralkyl group.

The alkyl group of $R_{04}$, $R_{05}$ and $R_{07}$ to $R_{09}$ is preferably one having 20 or less carbon atoms, and more preferably one having 8 or less carbon atoms. Examples of the alkyl group include a methyl group, an ethyl group, a propyl group, an isopropyl group, an n-butyl group, a sec-butyl group, a hexyl group, a 2-ethylhexyl group, an octyl group, and a dodecyl group. Further, these alkyl groups may further have a substituent.

The cycloalkyl group of $R_{04}$, $R_{05}$ and $R_{07}$ to $R_{09}$ may be monocyclic or polycyclic. This cycloalkyl group is preferably one having 3 to 8 carbon atoms. Examples of the cycloalkyl group include a cyclopropyl group, a cyclopentyl group or a cyclohexyl group.

Examples of the halogen atom of $R_{04}$, $R_{05}$ and $R_{07}$ to $R_{09}$ include a fluorine atom, a chlorine atom, a bromine atom, and an iodine atom. Among these, a fluorine atom is particularly preferred.

The alkyl group contained in the alkoxycarbonyl group of $R_{04}$, $R_{05}$ and $R_{07}$ to $R_{09}$ is preferably, for example, any of those set forth above as the alkyl group of $R_{04}$, $R_{05}$ and $R_{07}$ to $R_{09}$.

The alkyl groups of $R_{25}$ to $R_{27}$ and $R_{33}$ are preferably, for example, those set forth above as being of $R_{04}$, $R_{05}$ and $R_{07}$ to $R_{09}$.

The cycloalkyl groups of $R_{25}$ to $R_{27}$ and $R_{33}$ are preferably, for example, those set forth above as being of $R_{04}$, $R_{05}$ and $R_{07}$ to $R_{09}$.

The alkenyl group of $R_{25}$ to $R_{27}$ and $R_{33}$ is preferably one having 2 to 6 carbon atoms. Examples of the alkenyl group include a vinyl group, a propenyl group, an allyl group, a butenyl group, a pentenyl group, and a hexenyl group.

The cycloalkenyl group of $R_{25}$ to $R_{27}$ and $R_{33}$ is preferably one having 3 to 6 carbon atoms. Examples of the cycloalkenyl group include a cyclohexenyl group.

The aryl group of $R_{25}$ to $R_{27}$ and $R_{33}$ may be a monocyclic aromatic group or a polycyclic aromatic group. This aryl group is preferably one having 6 to 14 carbon atoms. A substituent may further be introduced in the aryl group. Further, the aryl groups may be bonded to each other to form multiple rings. Examples of the aryl group $R_{25}$ to $R_{27}$ and $R_{33}$ include a phenyl group, a tolyl group, a chlorophenyl group, a methoxyphenyl group, and a naphthyl group.

The aralkyl group of $R_{25}$ to $R_{27}$ and $R_{33}$ is preferably one having 7 to 15 carbon atoms. A substituent may further be introduced in this aralkyl group. Examples of the aralkyl group of $R_{25}$ to $R_{27}$ and $R_{33}$ include a benzyl group, a phenethyl group, and a cumyl group.

The ring formed by the mutual bonding of $R_{26}$ and $R_{27}$ together with the nitrogen atom is preferably a 5- to 8-membered ring. Specific examples thereof include pyrrolidine, piperidine, and piperazine.

The arylene group of $X_1$ to $X_3$ is preferably one having 6 to 14 carbon atoms. Examples of this arylene group include a phenylene group, a tolylene group, and a naphthylene group. These arylene groups may further have a substituent.

The alkylene group of $X_1$ to $X_3$ is preferably one having 1 to 8 carbon atoms. Examples of this alkylene group include a methylene group, an ethylene group, a propylene group, a butylene group, a hexylene group, and an octylene group. These alkylene groups may further have a substituent.

The cycloalkylene group of $X_1$ to $X_3$ is preferably one having 5 to 8 carbon atoms. Examples of this cycloalkylene group include a cyclopentylene group and a cyclohexylene group. These cycloalkylene groups may further have a substituent.

Preferred examples of the substituents that can be introduced in the individual groups in the general formulae (B1) to (B3) include a hydroxyl group; a halogen atom (fluorine, chlorine, bromine, or iodine); a nitro group; a cyano group; an amido group; a sulfonamido group; any of the alkyl groups mentioned above as $R_{04}$, $R_{05}$ and $R_{07}$ to $R_{09}$; an alkoxy group, such as a methoxy group, an ethoxy group, a hydroxyethoxy group, a propoxy group, a hydroxypropoxy group, and a butoxy group; an alkoxycarbonyl group, such as a methoxycarbonyl group and an ethoxycarbonyl group; an acyl group, such as a formyl group, an acetyl group, and a benzoyl group; an acyloxy group, such as an acetoxy group and a butyryloxy group; and a carboxyl group. These substituents preferably have 8 or less carbon atoms.

A represents a structural moiety capable of decomposing by irradiation with actinic rays or radiation to generate an acid anion, and specific examples thereof include a photoinitiator for photocationic polymerization, a photoinitiator for photoradical polymerization, a photo-achromatic agent and photodiscoloring agent for dyes, structural moieties contained in generally known compounds that generate an acid by light, employed in microresists or the like.

Furthermore, A is preferably an ionic structural moiety with a sulfonium salt structure or an iodonium salt structure. In particular, A is preferably any of the groups represented by the following general formulae (ZI) and (ZII).

[Chem. 50]

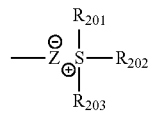

ZI

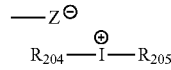

ZII

In the general formula (ZI), $R_{201}$, $R_{202}$ and $R_{203}$ each independently represent an organic group.

The number of carbon atoms of each of the organic groups as $R_{201}$, $R_{202}$ and $R_{203}$ is generally in the range of 1 to 30, preferably 1 to 20. Two members of $R_{201}$ to $R_{203}$ may be bonded to each other to form a ring structure, and the ring within the same may contain an oxygen atom, a sulfur atom, an ester bond, an amido bond, or a carbonyl group. Examples of the group formed by bonding of two members out of $R_{201}$ to $R_{203}$ include an alkylene group such as a butylene group and a pentylene group.

$Z^-$ represents the acid anion generated by the decomposition by irradiation with actinic rays or radiation. $Z^-$ is preferably a nonnucleophilic anion. Examples of the nonnucleophilic anion include a sulfonate anion, a carboxylate anion, a sulfonylimido anion, a bis(alkylsulfonyl)imido anion, and a tris(alkylsulfonyl)methyl anion.

Furthermore, the nonnucleophilic anion means an anion whose capability of inducing a nucleophilic reaction is extremely low. By using the nucleophilic anion, any temporal decomposition by intramolecular nucleophilic reaction can be inhibited. This would realize an enhancement of the temporal stability of the resin and the composition.

Examples of the organic groups of $R_{201}$, $R_{202}$ and $R_{203}$ include corresponding groups represented by (ZI-1), (ZI-2) and (ZI-3).

More preferred examples of the group represented by the general formula (ZI) include the (ZI-1), (ZI-2), (ZI-3) and (ZI-4) groups as described below.

The (ZI-1) groups are groups of the general formula (ZI), wherein at least one of $R_{201}$ to $R_{203}$ is an aryl group, that is, a group containing an arylsulfonium as a cation.

All of the $R_{201}$ to $R_{203}$ may be aryl groups. It is also appropriate that $R_{201}$ to $R_{203}$ are partially an aryl group and the remaining groups are an alkyl group or a cycloalkyl group.

Examples of the (ZI-1) group include a group corresponding to each of triarylsulfonium, diarylalkylsulfonium, aryldialkylsulfonium, diarylcycloalkylsulfonium, and aryldicycloalkyl sulfonium.

The aryl group of arylsulfonium is preferably a phenyl group or a naphthyl group, more preferably a phenyl group. The aryl group may be one having a heterocyclic structure containing a heteroatom such as an oxygen atom, a nitrogen atom, and a sulfur atom. Examples of the heterocyclic structure include pyrrole, furan, thiophene, indole, benzofuran, and benzothiophene. When the arylsulfonium has two or more aryl groups, these aryl groups may be the same as or different from each other.

The alkyl group or cycloalkyl group contained in the arylsulfonium according to necessity is preferably a linear or branched alkyl group having 1 to 15 carbon atoms or a cycloalkyl group having 3 to 15 carbon atoms. Examples of the alkyl group or cycloalkyl group include a methyl group, an ethyl group, a propyl group, an n-butyl group, a sec-butyl group, a t-butyl group, a cyclopropyl group, a cyclobutyl group, and a cyclohexyl group.

The aryl group, alkyl group or a cycloalkyl group represented by $R_{201}$ to $R_{203}$ may have as its substituent an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a halogen atom, a hydroxyl group, or a phenylthio group.

Preferred examples of the substituents are a linear or branched alkyl group having 1 to 12 carbon atoms, a cycloalkyl group having 3 to 12 carbon atoms, and a linear, branched, or cyclic alkoxy group having 1 to 12 carbon atoms. More preferred examples of the substituents include an alkyl group having 1 to 4 carbon atoms and an alkoxy group having 1 to 4 carbon atoms. The substituents may be contained in any one of the three $R_{201}$ to $R_{203}$, or alternatively may be contained in two or more of $R_{201}$ to $R_{203}$. Further, in the case where $R_{201}$ to $R_{203}$ represent phenyl groups, the substituent is preferably substituted at the p-position of the phenyl group.

Next, the (ZI-2) group will be described.

The (ZI-2) group is the group of the general formula (ZI), wherein $R_{201}$ to $R_{203}$ each independently represent an organic group having no aromatic ring. Here, the aromatic ring also includes a heterocycle having a heteroatom.

The organic group having no aromatic ring as $R_{201}$ to $R_{203}$ generally has 1 to 30 carbon atoms, and preferably 1 to 20 carbon atoms.

$R_{201}$ to $R_{203}$ each independently preferably represent an alkyl group, a cycloalkyl group, an allyl group, or a vinyl group, still more preferably a linear or branched 2-oxoalkyl group, a 2-oxocycloalkyl group, or an alkoxycarbonylmethyl group, and particularly preferably a linear or branched 2-oxoalkyl group.

Preferable examples of the alkyl group and the cycloalkyl group of $R_{201}$ to $R_{203}$ include a linear or branched alkyl group having 1 to 10 carbon atoms (for example, a methyl group, an ethyl group, a propyl group, a butyl group, and a pentyl group), and a cycloalkyl group having 3 to 10 carbon atoms (a cyclopentyl group, a cyclohexyl group, and a norbornyl group). More preferred examples of the alkyl group include a 2-oxoalkyl group and an alkoxycarbonylmethyl group. Still more preferred examples of the cycloalkyl group include a 2-oxocycloalkyl group.

The 2-oxoalkyl group may be linear or branched. Preferred examples of the 2-oxoalkyl group include a group having $>C=O$ at the 2-position of the above-described alkyl group. Preferred examples of the 2-oxocycloalkyl group include a group having $>C=O$ at the 2-position of the above-described cycloalkyl group.

Examples of the alkoxy group in the alkoxycarbonylmethyl group preferably include an alkoxy group having 1 to 5 carbon atoms (for example, a methoxy group, an ethoxy group, a propoxy group, a butoxy group, and a pentoxy group).

$R_{201}$ to $R_{203}$ may be further substituted with a halogen atom, an alkoxyl group (for example, having 1 to 5 carbon atoms), a hydroxyl group, a cyano group, or a nitro group.

Next, the (ZI-3) group will be described.

The (ZI-3) group is a group represented by the following general formula (ZI-3) which has a phenacylsulfonium salt structure.

[Chem. 51]

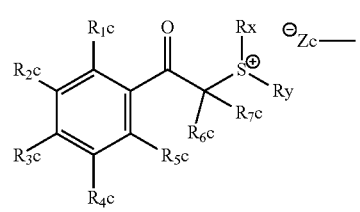

ZI-3

In the general formula (ZI-3), $R_{1c}$ to $R_{5c}$ each independently represent a hydrogen atom, an alkyl group, a cycloalkyl group, an alkoxy group, or a halogen atom.

$R_{6c}$ and $R_{7c}$ each independently represent a hydrogen atom, an alkyl group, or a cycloalkyl group.

$R_x$ and $R_y$ each independently represent an alkyl group, a cycloalkyl group, an allyl group or a vinyl group.

Any two or more members out of $R_{1c}$ to $R_{5c}$, and $R_{6c}$ and $R_{7c}$, and $R_x$ and $R_y$ may be bonded to each other to form a ring structure. This ring structure may contain an oxygen atom, a sulfur atom, an ester bond and/or an amido bond. Examples of the group formed by the mutual bonding of the groups include a butylene group and a pentylene group.

$Z_c^-$ represents a nonnucleophilic anion, and examples thereof include the same nonnucleophilic anions as $Z^-$ of the general formula (ZI).

With respect to particular structures of the cation moieties of the general formula (ZI-3), reference may be made to the structures of the cation moieties of acid generators set forth by way of example in paragraphs 0047 and 0048 of JP2004-233661A and set forth by way of example in paragraphs 0040 to 0046 of JP2003-35948A.

Next, the (ZI-4) group will be described.

The (ZI-4) group is a group represented by the general formula (ZI-4) below. This group is effective in the suppression of outgassing.

[Chem. 52]

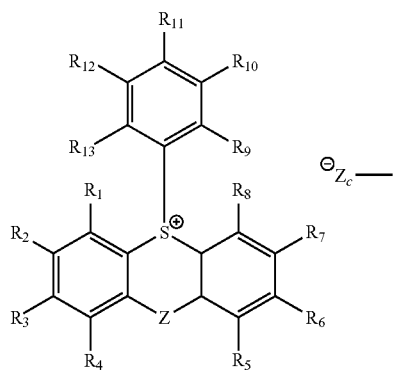

ZI-4

In the general formula (ZI-4), $R_1$ to $R_{13}$ each independently represent a hydrogen atom or a substituent.

Preferably, at least one of $R_1$ to $R_{13}$ is a substituent containing an alcoholic hydroxyl group. Further, the "alcoholic hydroxyl group" as used herein refers to a hydroxyl group bonded to a carbon atom of an alkyl group.

Z represents a single bond or a divalent connecting group.

$Z_c^-$ represents a nonnucleophilic anion. Examples thereof include the same nonnucleophilic anions as $Z^-$ in the general formula (ZI).

In the case where $R_1$ to $R_{13}$ represent substituents containing an alcoholic hydroxyl group, $R_1$ to $R_{13}$ preferably represent the groups represented by —(WY), wherein Y represents a hydroxyl-substituted alkyl group and W represents a single bond or a divalent connecting group.

Preferred examples of the alkyl group represented by Y include an ethyl group, a propyl group and an isopropyl group. Particularly preferably, Y contains a structure represented by —$CH_2CH_2OH$.

The divalent connecting group represented by W is not particularly limited, but it is preferably a single bond, or a divalent group as obtained by substituting with a single bond any hydrogen atom of a group selected from among an alkoxy group, an acyloxy group, an acylamino group, an alkyl- or arylsulfonylamino group, an alkylthio group, an alkylsulfonyl group, an acyl group, an alkoxycarbonyl group and a carbamoyl group. More preferably, W is a single bond, or a divalent group as obtained by substituting with a single bond any hydrogen atom of a group selected from among an acyloxy group, an alkylsulfonyl group, an acyl group and an alkoxycarbonyl group.

In the case where $R_1$ to $R_{13}$ represent substituents containing an alcoholic hydroxyl group, the number of carbon atoms contained in each of the substituents is preferably from 2 to 10, more preferably from 2 to 6, and still more preferably from 2 to 4.

Each of the substituents containing an alcoholic hydroxyl group as $R_1$ to $R_{13}$ may have two or more alcoholic hydroxyl groups. The number of the alcoholic hydroxyl groups contained in each of the substituents containing an alcoholic hydroxyl group as $R_1$ to $R_{13}$ is from 1 to 6, preferably from 1 to 3, and more preferably 1.

The number of the alcoholic hydroxyl groups contained in the (ZI-4) group as the total of those of $R_1$ to $R_{13}$ is from 1 to 10, preferably from 1 to 6, and more preferably from 1 to 3.

In the case where $R_1$ to $R_{13}$ do not contain any alcoholic hydroxyl group, examples of $R_1$ to $R_{13}$ include a hydrogen atom, a halogen atom, an alkyl group, a cycloalkyl group, an alkenyl group, a cycloalkenyl group, an alkynyl group, an aryl group, heterocycle group, a cyano group, a nitro group, a carboxy group, an alkoxy group, an aryloxy group, silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an aryl- or heterocyclic azo group, an imido group, a phosphino group, a phosphinyl group, a phosphinyloxy group, a phosphinylamino group, a phosphono group, a silyl group, a hydrazino group, a ureido group, a boronic acid group (—$B(OH)_2$), a phosphato group (—$OPO(OH)_2$), a sulfato group (—$OSO_3H$), and other known substituents.

In the case where $R_1$ to $R_{13}$ contain no alcoholic hydroxyl group, each of $R_1$ to $R_{13}$ is preferably a hydrogen atom, a halogen atom, an alkyl group, a cycloalkyl group, a cyano group, an alkoxy group, an acyloxy group, an acylamino group, an aminocarbonylamino group, an alkoxycarbonylamino group, an alkyl- or aryl-sulfonylamino group, an alkylthio group, a sulfamoyl group, an alkyl- or aryl-sulfonyl group, an alkoxycarbonyl group or a carbamoyl group.

In the case where $R_1$ to $R_{13}$ contain no alcoholic hydroxyl group, each of $R_1$ to $R_{13}$ is more preferably a hydrogen atom, an alkyl group, a cycloalkyl group, a halogen atom or an alkoxy group.

Two adjacent members out of $R_1$ to $R_{13}$ may be bonded to each other to form a ring structure. This ring structure includes an aromatic or non-aromatic hydrocarbon ring and a heterocycle. These ring structures may be further combined with each other to form a condensed ring.

The (ZI-4) group preferably has a structure where at least one of $R_1$ to $R_{13}$ contains an alcoholic hydroxyl group, more preferably a structure where at least one of $R_9$ to $R_{13}$ contains an alcoholic hydroxyl group.

Z represents, as described above, a single bond or a divalent connecting group. Examples of the divalent connecting group include an alkylene group, an arylene group, a carbonyl group, a sulfonyl group, a carbonyloxy group, a carbonylamino group, a sulfonylamido group, an ether bond, a thioether bond, an amino group, a disulfide group, an acyl group, an alkylsulfonyl group, —CH=CH—, an aminocarbonylamino group and an aminosulfonylamino group.

The divalent connecting group may have a substituent. Examples of the substituent thereof include the same substituents enumerated above with respect to $R_1$ to $R_{13}$.

Preferably, Z is a single bond, an ether bond or a thioether bond, and particularly preferably a single bond.

Now, the general formula (ZII) will be described.

In the general formula (ZII), $R_{204}$ and $R_{205}$ each independently represent an aryl group, an alkyl group or a cycloalkyl group.

Specific examples and preferred forms of the aryl group, the alkyl group and the cycloalkyl group of $R_{204}$ and $R_{205}$ are the same groups as set forth above with respect to $R_{201}$ to $R_{203}$ in the above-described compounds (ZI-1).

The aryl group, alkyl group and cycloalkyl group of $R_{204}$ and $R_{205}$ may further have substituents. The substituents are also the same groups as set forth above with respect to $R_{201}$ to $R_{203}$ of the above compounds (ZI-1).

$Z^-$ represents an acid anion generated by the decomposition by irradiation with actinic rays or radiation, preferably a nonnucleophilic anion. Examples thereof include the same groups as $Z^-$ of the general formula (ZI).

Preferred examples of A also include groups represented by the following general formulae (ZCI) and (ZCII).

[Chem. 53]

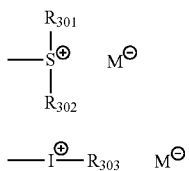

In the general formulae (ZCI) and (ZCII), $R_{301}$ and $R_{302}$ each independently represent an organic group. This organic group generally has 1 to 30 carbon atoms, and preferably 1 to 20 carbon atoms. $R_{301}$ and $R_{302}$ may be bonded to each other to form a ring structure. With respect to the ring structure, at least one selected from among an oxygen atom, a sulfur atom, an ester bond, an amido bond and a carbonyl group may be contained in the ring. Examples of the group formed by the mutual bonding of $R_{301}$ and $R_{302}$ include alkylene groups such as a butylene group and a pentylene group.

Examples of the organic groups of $R_{301}$ and $R_{302}$ include the aryl groups, alkyl groups and cycloalkyl groups set forth above as examples of $R_{201}$ to $R_{203}$ of the general formula (ZI).

M represents an atomic group capable of forming an acid with the addition of a proton. In particular, the structures represented by any of the general formulae AN1 to AN3 to be described hereinafter may be mentioned. Among these, the structure represented by the general formula AN1 is particularly preferred.

$R_{303}$ represents an organic group. The organic group as $R_{303}$ has generally 1 to 30 carbon atoms, and preferably 1 to 20 carbon atoms. Specific examples of the organic groups as $R_{303}$ include the aryl groups, alkyl groups, cycloalkyl groups, and the like as set forth above as the specific examples of $R_{204}$ and $R_{205}$ in the general formula (ZII).

Moreover, examples of the structural portion capable of generating an acid by irradiation with actinic rays or radiation include the structural moiety destined for a sulfonic acid precursor that is introduced in each of the following photo-acid generators. Examples of the photo-acid generators include the following compounds (1) to (3).

(1) Compounds photolyzed to generate a sulfonic acid whose representative is an iminosulfonate or the like, as described in M. Tunooka et al., Polymer Preprints Japan, 35(8); G. Berner et al., J. Rad. Curing, 13(4); W. J. Mijs et al., Coating Technol., 55(697), 45 (1983); H. Adachi et al., Polymer Preprints Japan, 37(3); EP0199,672B, EP84515B, EP199,672B, EP044,115B, and EP0101,122B; U.S. Pat. No. 618,564B, U.S. Pat. No. 4,371,605B and U.S. Pat. No. 4,431,774B; JP1989-18143A (JP-S64-18143A), JP1990-245756A (JP-H02-245756A), and JP1992-365048A (JP-H04-365048A); etc.

(2) Disulfone compounds as described in JP1986-166544A (JP-S61-166544A), etc.

(3) Compounds capable of generating an acid, as described in V. N. R. Pillai, Synthesis, (1), 1 (1980); A. Abad et al., Tetrahedron Lett., (47) 4555 (1971); D. H. R. Barton et al., J. Chem. Soc., (C), 329 (1970); U.S. Pat. No. 3,779,778B; EP126,712B; etc.

It is preferable for the repeating unit (B) to contain a structural moiety that is converted to an acid anion upon irradiation with actinic rays or radiation. For example, it is preferable for A in the general formulae (B1) to (B3) to represent a structural moiety that is converted to an acid anion upon irradiation with actinic rays or radiation.

That is, it is more preferred for the repeating unit (B) to have a structure that generates an acid anion upon irradiation with actinic rays or radiation in a side chain of the resin. When this structure is employed, the diffusion of generated acid anions can be inhibited to enhance the resolution, roughness characteristic, or the like.

It is preferable for each of the moiety —$X_1$-A in the general formula (B1), the moiety —$X_2$-A in the general formula (B2) and the moiety —$X_3$-A in the general formula (B3) to be represented by any one of the following general formulae (L1), (L2) and (L3).

—$X_{11}$-$L_{11}$-$X_{12}$—$Ar_1$—$X_{13}$-$L_{12}$-$Z_1$ (L1)

—$Ar_2$—$X_{21}$-$L_{21}$-$X_{22}$-$L_{22}$-$Z_2$ (L2)

—$X_{31}$-$L_{31}$-$X_{32}$-$L_{32}$-$Z_3$ (L3)

First, the moieties represented by the general formula (L1) will be described.

$X_{11}$ represents —O—, —S—, —CO—, —$SO_2$—, —NR— (wherein R represents a hydrogen atom or an alkyl group), a divalent nitrogen-containing non-aromatic heterocyclic group, or a group formed by combination thereof.

$X_{12}$ and $X_{13}$ each independently represent a single bond, —O—, —S—, —CO—, —$SO_2$—, —NR— (wherein R represents a hydrogen atom or an alkyl group), a divalent nitrogen-containing non-aromatic heterocyclic group, or a group formed by combination thereof.

The alkyl group of R may be linear or branched. Further, the alkyl group of R may further have a substituent. The alkyl group preferably has 20 or less carbon atoms, more preferably 8 or less carbon atoms, and still more preferably 3 or less carbon atoms. Examples of such an alkyl group include a methyl group, an ethyl group, a propyl group and an isopropyl group. R is particularly preferably a hydrogen atom, a methyl group or an ethyl group.

Incidentally, the divalent nitrogen-containing non-aromatic heterocyclic group preferably means a 3- to 8-membered non-aromatic heterocyclic group having at least one nitrogen atom.

$X_{11}$ is more preferably —O—, —CO—, —NR— (wherein R represents a hydrogen atom or an alkyl group) or a group formed by combination thereof, and particularly preferably —COO— or —CONR— (wherein R represents a hydrogen atom or an alkyl group).

$L_{11}$ represents an alkylene group, an alkenylene group, a divalent aliphatic hydrocarbon ring group, or a group formed by a combination of two or more of these, provided that in the group formed by a combination, two or more groups combined together may be the same as or different from each other and may be connected to each other through O—, —S—, —CO—, —SO$_2$—, —NR— (wherein R represents a hydrogen atom or an alkyl group), a divalent nitrogen-containing non-aromatic heterocyclic group, a divalent aromatic ring group, or a group formed by combination thereof.

The alkylene group of $L_{11}$ may be in the form of a linear or branched chain. This alkylene group preferably has 1 to 8 carbon atoms, more preferably 1 to 6 carbon atoms, and still more preferably 1 to 4 carbon atoms.

Examples of the alkenylene group of $L_{11}$ include a group having a double bond at an arbitrary position of the above-described alkylene group.

The divalent aliphatic hydrocarbon ring group of $L_{11}$ may be monocyclic or polycyclic. This divalent aliphatic hydrocarbon ring group preferably has 5 to 12 carbon atoms, more preferably 6 to 10 carbon atoms.

The divalent aromatic ring group as a connecting group may be an arylene group or a heteroarylene group. This aromatic ring group preferably has 6 to 14 carbon atoms. The aromatic ring group may further have a substituent.

Incidentally, —NR— and the divalent nitrogen-containing non-aromatic heterocyclic group as the connecting group are the same respective groups as set forth above in $X_{11}$.

$L_{11}$ is particularly preferably an alkylene group, a divalent aliphatic hydrocarbon ring group, or a group formed by combining an alkylene group and a divalent aliphatic hydrocarbon ring group through —OCO—, —O— or —CONH— (for example, -alkylene group-O-alkylene group-, -alkylene group-OCO-alkylene group-, or -divalent aliphatic hydrocarbon ring group-O-alkylene group-, or -alkylene group-CONH-alkylene group-).

Specific examples of —NR— and the divalent nitrogen-containing non-aromatic heterocyclic group in $X_{12}$ and $X_{13}$ are the same specific examples as the respective groups in $X_{11}$ described above, and preferred examples are also the same.

$X_{12}$ is preferably a single bond, —S—, —O—, —CO—, —SO$_2$— or a group formed by a combination thereof, and more preferably a single bond, —S—, —OCO—, or —OSO$_2$—.

$X_{13}$ is preferably —O—, —CO—, —SO$_2$— or a group formed by a combination thereof, and particularly preferably —OSO$_2$—.

$Ar_1$ represents a divalent aromatic ring group. The divalent aromatic ring group may be an arylene group or a heteroarylene group. This divalent aromatic ring group may further have a substituent. Examples of the substituent include an alkyl group, an alkoxy group and an aryl group.

$Ar_1$ is particularly preferably an arylene group having 6 to 18 carbon atoms, which may have a substituent, or an aralkylene group formed by combining an arylene group having 6 to 18 carbon atoms and an alkylene group having 1 to 4 carbon atoms, and more preferably a phenylene group, a naphthylene group, a biphenylene group, or a phenylene group substituted with a phenyl group.

$L_{12}$ represents an alkylene group, an alkenylene group, a divalent aliphatic hydrocarbon ring group, a divalent aromatic ring group, or a group formed by a combination of two or more thereof, and in these groups, hydrogen atoms partially or entirely substituted with a substituent selected from a fluorine atom, an alkyl fluoride group, a nitro group and a cyano group. In the group formed by a combination, two or more groups combined may be the same as or different from each other. Further, these groups may be connected through —O—, —S—, —CO—, —SO$_2$—, —NR— (R is a hydrogen atom or an alkyl group), a divalent nitrogen-containing non-aromatic heterocyclic group, a divalent aromatic ring group, or a group formed by a combination thereof.

$L_{12}$ is more preferably an alkylene group or divalent aromatic ring group with hydrogen atoms being partially or entirely substituted with a fluorine atom or an alkyl fluoride group (more preferably a perfluoroalkyl group), or a group formed by a combination thereof, and particularly preferably an alkylene group or divalent aromatic ring group with hydrogen atoms being partially or entirely substituted with a fluorine atom. $L_{12}$ is particularly preferably an alkylene group or divalent aromatic ring group where from 30 to 100% by number of hydrogen atoms are substituted with a fluorine atom.

The alkylene group of $L_{12}$ may be linear or branched. This alkylene group preferably has 1 to 6 carbon atoms, and more preferably 1 to 4 carbon atoms.

Examples of the alkenylene group of $L_{12}$ include a group formed by introduction of a double bond in an arbitrary position of the above alkylene group.

The divalent aliphatic hydrocarbon ring group of $L_{12}$ may be monocyclic or polycyclic. The divalent aliphatic hydrocarbon ring group is preferably one having 3 to 17 carbon atoms.

Examples of the divalent aromatic ring group as $L_{12}$ include the same groups as set forth above as the connecting group in $L_{11}$.

Further, specific examples of —NR— and the divalent nitrogen-containing non-aromatic heterocyclic group as the connecting group in $L_{12}$ include the same groups as set forth above in $X_{11}$, and preferred examples are also the same.

$Z_1$ represents a moiety leading to a sulfonic acid group by irradiation with actinic rays or radiation, and specific examples thereof include a structure represented by formula (ZI).

Next, the moieties represented by the general formula (L2) will be described.

$Ar_2$ represents a divalent aromatic ring group. The divalent aromatic ring group may be an arylene group or a heteroarylene group. This divalent aromatic ring group preferably has 6 to 18 carbon atoms. The divalent aromatic ring group may further have a substituent.

$X_{21}$ represents —O—, —S—, —CO—, —SO$_2$—, —NR— (wherein R represents a hydrogen atom or an alkyl group), a divalent nitrogen containing non-aromatic heterocyclic group, or a group formed by combination thereof.

Examples of the —NR— and the divalent nitrogen containing non-aromatic heterocyclic group in $X_{21}$ include the same groups as set forth above with respect to $X_{11}$.

$X_{21}$ is more preferably —O—, —S—, —CO—, —SO$_2$— or a group formed by combination thereof, and particularly preferably —O—, —OCO— or —OSO$_2$—.

$X_{22}$ represents a single bond, —O—, —S—, —CO—, —SO$_2$—, —NR— (wherein R represents a hydrogen atom or an alkyl group), a divalent nitrogen containing non-aromatic heterocyclic group, or a group formed by combination thereof. Examples of the —NR— and the divalent nitrogen containing non-aromatic heterocyclic group in $X_{22}$ include the same groups as set forth above with respect to $X_{11}$.

$X_{22}$ is more preferably —O—, —S—, —CO—, —SO$_2$— or a group formed by combination thereof, and particularly preferably —O—, —OCO—, or —OSO$_2$—.

$L_{21}$ represents a single bond, an alkylene group, an alkenylene group, a divalent aliphatic hydrocarbon ring group, a divalent aromatic ring group, or a group formed by a combination of two or more of these. In the group formed by a combination, two or more groups combined together may be the same as to or different from each other. Further, these groups may be connected to each other through —O—, —S—, —CO—, —SO$_2$—, —NR— (wherein R represents a hydrogen atom or an alkyl group), a divalent nitrogen containing non-aromatic heterocyclic group, a divalent aromatic ring group, or a group formed by combination thereof.

Examples of the alkylene group, the alkenylene group and the divalent aliphatic hydrocarbon ring group of $L_{21}$ include the same groups as set forth above with respect to the respective group in $L_{11}$.

The divalent aromatic ring group of $L_{21}$ may be an arylene group or a heteroarylene group. This divalent aromatic ring group preferably has 6 to 14 carbon atoms.

Examples of the —NR— and the divalent nitrogen-containing non-aromatic heterocyclic group of $L_{21}$ include the same groups as set forth above with respect to $X_{11}$.

$L_{21}$ is particularly preferably a single bond, an alkylene group, a divalent aliphatic hydrocarbon ring group, a divalent aromatic ring group, or a group formed by a combination of two or more thereof (for example, -alkylene group-divalent aromatic ring group- or -divalent aliphatic hydrocarbon ring group-alkylene group-), or a group formed by combining two or more of these groups through a connecting group such as —OCO—, —COO—, —O— and —S— (for example, -alkylene group-OCO-divalent aromatic ring group-, -alkylene group-5-divalent aromatic ring group-, or -alkylene group-O-alkylene group-divalent aromatic ring group).

$L_{22}$ represents an alkylene group, an alkenylene group, a divalent aliphatic hydrocarbon ring group, a divalent aromatic ring group, or a group formed by a combination of two or more thereof, and in these groups, hydrogen atoms may be partially or entirely substituted with a substituent selected from a fluorine atom, an alkyl fluoride group, a nitro group and a cyano group. In the group formed by a combination, two or more groups combined may be the same as or different from each other. Further, these groups may be connected through —O—, —S—, —CO—, —SO$_2$—, —NR— (wherein R is a hydrogen atom or an alkyl group), a divalent nitrogen-containing non-aromatic heterocyclic group, a divalent aromatic ring group, or a group formed by a combination thereof.

$L_{22}$ is preferably an alkylene group or divalent aromatic ring group with hydrogen atoms being partially or entirely substituted with a fluorine atom or an alkyl fluoride group (more preferably a perfluoroalkyl group), or a group formed by a combination thereof, and particularly preferably an alkylene group or divalent aromatic ring group with hydrogen atoms being partially or entirely substituted with a fluorine atom.

Specific examples of the alkylene group, the alkenylene group, the aliphatic hydrocarbon ring group, the divalent aromatic ring group and a group formed by a combination of two or more thereof, represented by $L_{22}$, include the same groups as exemplified above as $L_{12}$ in the general formula (L1).

Furthermore, specific examples of —NR— and the divalent nitrogen-containing non-aromatic heterocyclic group as the connecting group in $L_{22}$ include the same specific examples as the respective groups in $X_{11}$, and preferred examples are also the same.

$Z_2$ represents a moiety that is converted to a sulfonic acid group upon irradiation with actinic rays or radiation. Specific examples of the moieties of $Z_2$ include the same groups as set forth above with respect to $Z_1$.

Next, the moiety represented by the general formula (L3) will be described.

$X_{31}$ and $X_{32}$ each independently represent a single bond, —O—, —S—, —CO—, —SO$_2$—, —NR— (wherein R represents a hydrogen atom or an alkyl group), a divalent nitrogen-containing non-aromatic heterocyclic group, or a group formed by combination thereof.

Examples of the —NR— and the divalent nitrogen-containing non-aromatic heterocyclic group in each of $X_{22}$ and $X_{32}$ include the same groups as set forth above with respect to $X_{11}$.

$X_{31}$ is more preferably a single bond, —O—, —CO—, —NR— (wherein R represents a hydrogen atom or an alkyl group) or a group formed by combination thereof. $X_{22}$ is particularly preferably a single bond, —COO—, or —CONR— (wherein R represents a hydrogen atom or an alkyl group).

$X_{32}$ is preferably —O—, —S—, —CO—, —SO$_2$—, a divalent nitrogen-containing non-aromatic heterocyclic group, or a group formed by combination thereof. $X_{32}$ is particularly preferably —O—, —OCO—, or —OSO$_2$—.

$L_{31}$ represents a single bond, an alkylene group, an alkenylene group, a divalent aliphatic hydrocarbon ring group, a divalent aromatic ring group, or a group formed by a combination of two or more thereof. In the group formed by a combination, two or more groups combined together may be the same as to or different from each other. Further, these groups may be connected to each other through —O—, —S—, —CO—, —SO$_2$—, —NR— (wherein R represents a hydrogen atom or an alkyl group), a divalent nitrogen-containing non-aromatic heterocyclic group, a divalent aromatic ring group, or a group formed by combination thereof.

Examples of the alkylene group, the alkenylene group, the divalent aliphatic hydrocarbon ring group, and the divalent aromatic ring group of $L_{31}$ include the same groups as set forth above with respect to $L_{21}$.

Specific examples of the —NR— and the divalent nitrogen-containing non-aromatic heterocyclic group as a connecting group in $L_{31}$ include the same specific examples as the respective groups described above in $X_{11}$. Preferred examples are also the same.

$L_{32}$ represents an alkylene group, an alkenylene group, a divalent aliphatic hydrocarbon ring group, a divalent aromatic ring group, or a group formed by a combination of two or more of these. In the group formed by a combination, two or more groups combined together may be the same as to or different from each other. Further, these groups may be connected to each other through —O—, —S—, —CO—, —SO$_2$—, —NR— (wherein R represents a hydrogen atom or an alkyl group), a divalent nitrogen-containing non-aromatic heterocyclic group, a divalent aromatic ring group, or a group formed by combination thereof.

With respect to each of the alkylene group, the alkenylene group, the divalent aliphatic hydrocarbon ring group, the divalent aromatic ring group, or a group formed by a combination of two or more of these, of $L_{32}$, it is preferable for the hydrogen atoms thereof to be partially or entirely substituted with a substituent selected from among a fluorine atom, a fluoroalkyl group, a nitro group, and a cyano group.

$L_{32}$ is more preferably an alkylene group, divalent aromatic ring group, or a group formed by combination thereof with hydrogen atoms being partially or entirely substituted with a fluorine atom or a fluoroalkyl group (more preferably a perfluoroalkyl group), and particularly preferably an alkylene group and divalent aromatic ring group with hydrogen atoms being partially or entirely substituted with a fluorine atom.

Examples of the alkylene group, the alkenylene group, the divalent aliphatic hydrocarbon ring group, the divalent aromatic ring group, and a group formed by a combination of two or more of these, of $L_{32}$, include the same groups as set forth above with respect to $L_{12}$. Specific examples of the —NR— and the divalent nitrogen-containing non-aromatic heterocyclic group as a connecting group, in $L_{32}$, include the same groups as set forth above with respect to $X_{11}$. Preferred examples are also the same.

Furthermore, in the case where $X_{31}$ is a single bond while $L_{31}$ is an aromatic ring group and when $R_{32}$ forms a ring together with the aromatic ring group of $L_{31}$, the alkylene group represented by $R_{32}$ is preferably one having 1 to 8 carbon atoms, more preferably one having 1 to 4 carbon atoms, and still more preferably one having 1 or 2 carbon atoms.

$Z_3$ represents an onium salt that is converted to an imidic acid group or a methide acid group upon irradiation with actinic rays or radiation. It is preferable for the onium salt represented by $Z_3$ to be a sulfonium salt or an iodonium salt. The onium salt preferably has a structure represented by the following general formula (ZIII) or (ZIV).

[Chem. 54]

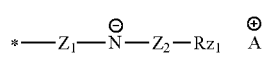
(ZIII)

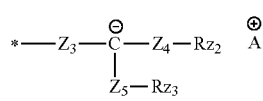
(ZIV)

In the general formulae (ZIII) and (ZIV), $Z_1$, $Z_2$, $Z_3$, $Z_4$ and $Z_5$ each independently represent —CO— or —SO$_2$—, and preferably —SO$_2$—.

$Rz_1$, $Rz_2$ and $Rz_3$ each independently represent an alkyl group, a monovalent aliphatic hydrocarbon ring group, an aryl group, or an aralkyl group. Forms of these groups having the hydrogen atoms thereof partially or entirely being substituted with a fluorine atom or a fluoroalkyl group (more preferably a perfluoroalkyl group) are more preferred.

The alkyl group of $Rz_1$, $Rz_2$ and $Rz_3$ may be linear or branched. This alkyl group preferably has 1 to 8 carbon atoms, more preferably 1 to 6 carbon atoms, and still more preferably 1 to 4 carbon atoms.

The monovalent aliphatic hydrocarbon ring group of $Rz_1$, $Rz_2$ and $Rz_3$ preferably has 3 to 10 carbon atoms, and more preferably 3 to 6 carbon atoms.

The aryl group of $Rz_1$, $Rz_2$ and $Rz_3$ preferably has 6 to 18 carbon atoms, and more preferably 6 to 10 carbon atoms. This aryl group is particularly preferably a phenyl group.

Preferred examples of the aralkyl group of $Rz_1$, $Rz_2$ and $Rz_3$ include those formed by the bonding of the above aryl group to an alkylene group having 1 to 8 carbon atoms. An aralkyl group formed by the bonding of the above aryl group to an alkylene group having 1 to 6 carbon atoms is more preferred. An aralkyl group formed by the bonding of the above aryl group to an alkylene group having 1 to 4 carbon atoms is particularly preferred.

$A^+$ represents a sulfonium cation or an iodonium cation. Preferred examples of $A^+$ include the sulfonium cation structures in the general formula (ZI) and the iodonium cation structures in the general formula (ZII).

Specific examples of the repeating units (B) are shown below, but the scope of the present invention is not limited thereto.

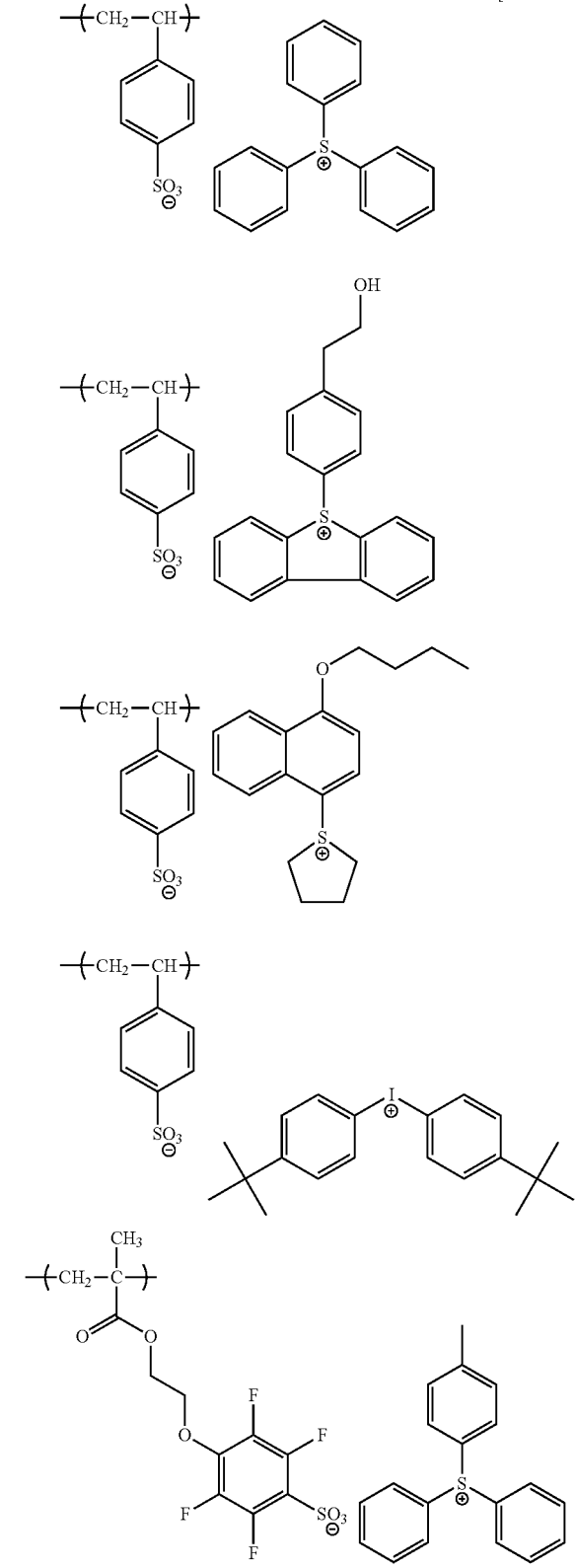

[Chem. 55]

89
-continued
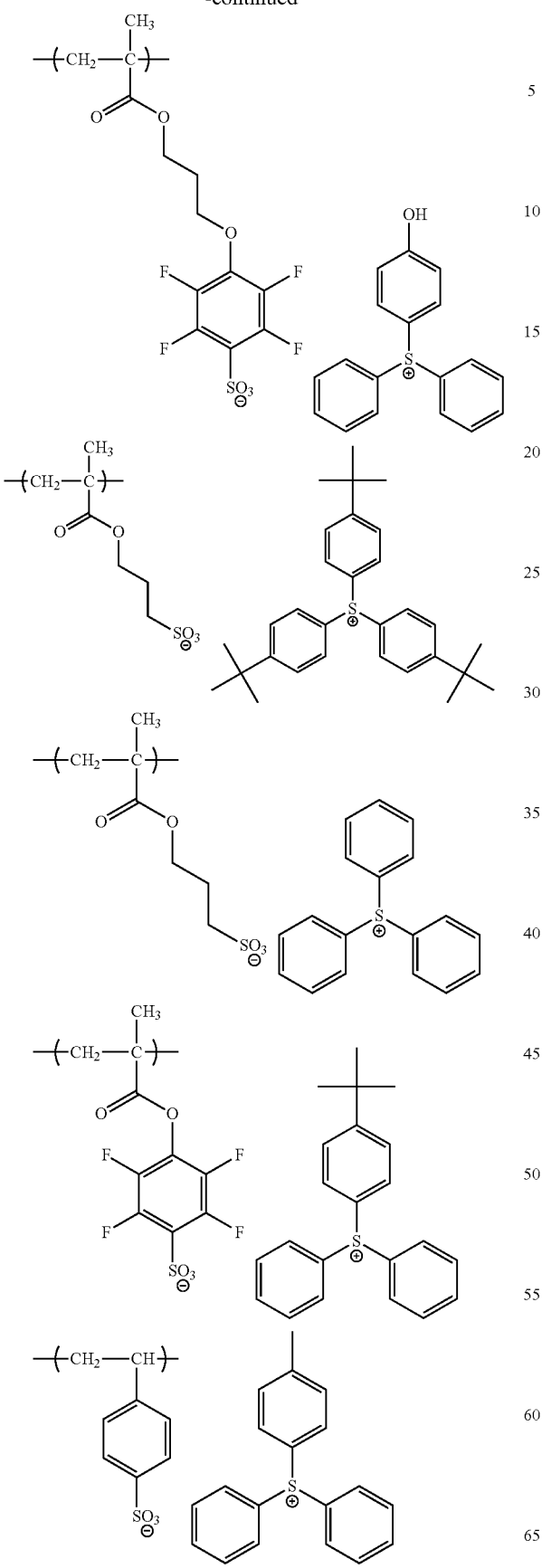
90
-continued
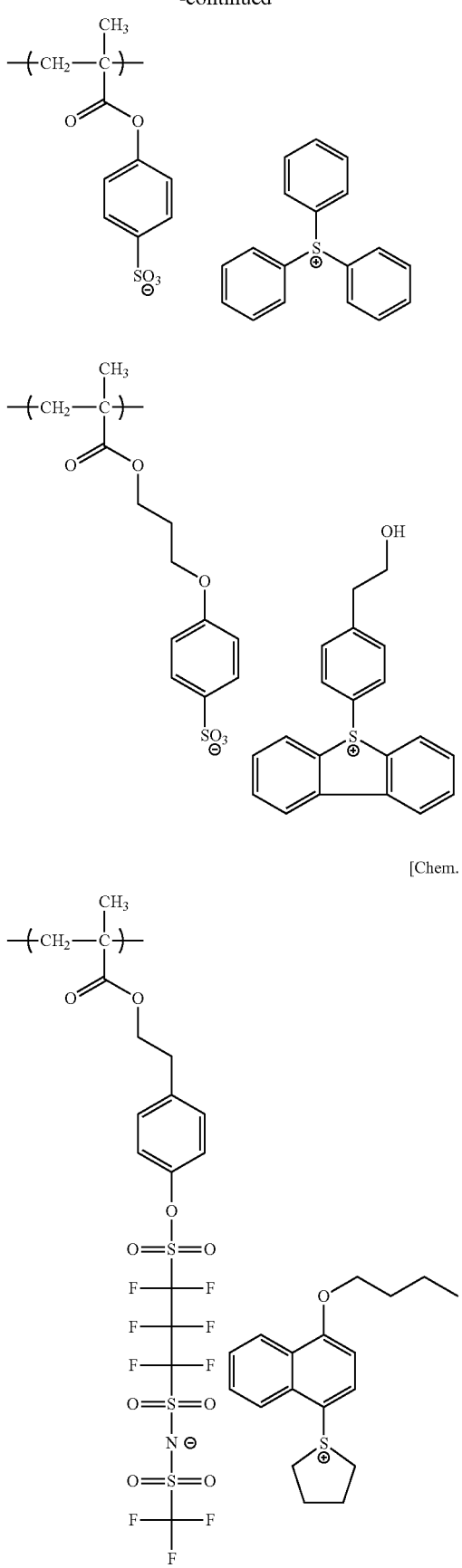
[Chem. 56]

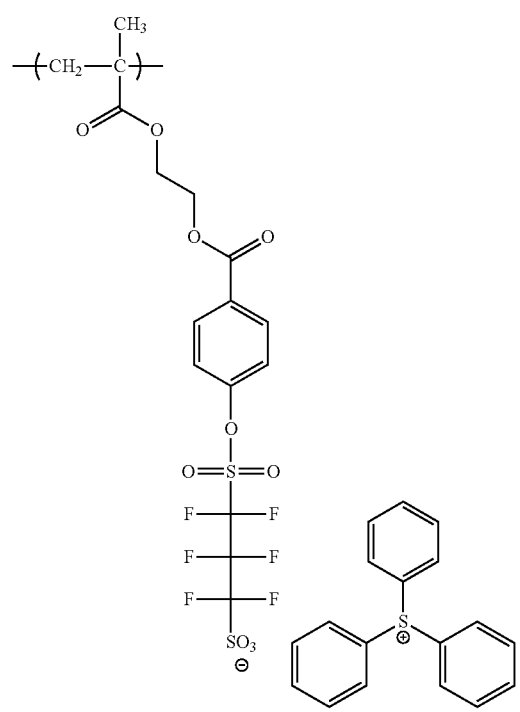
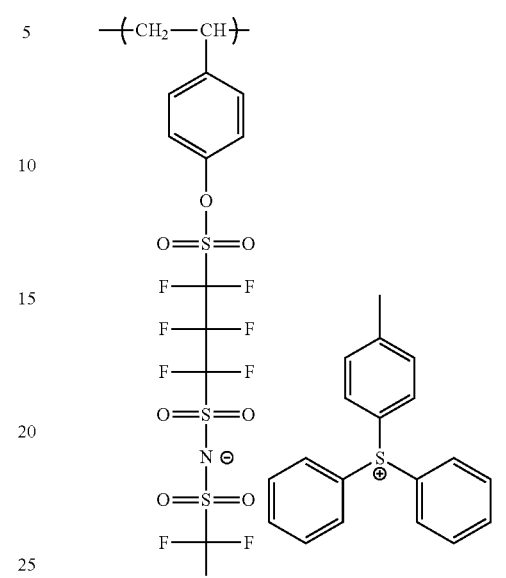
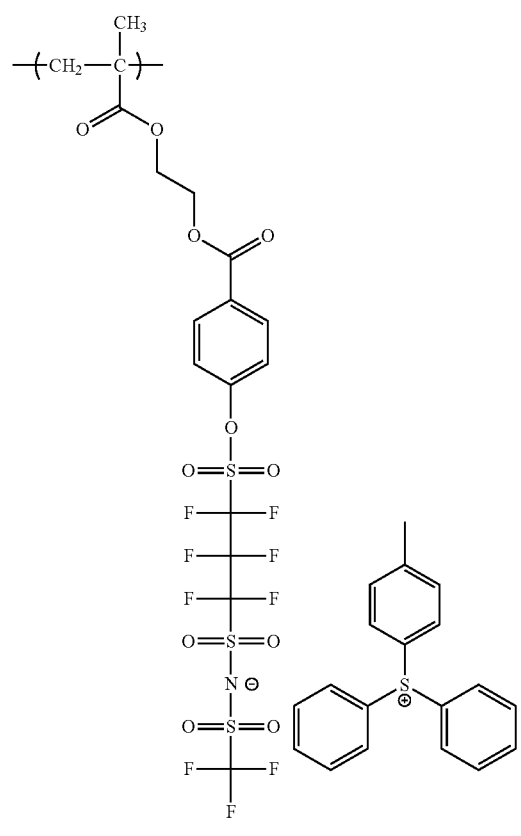
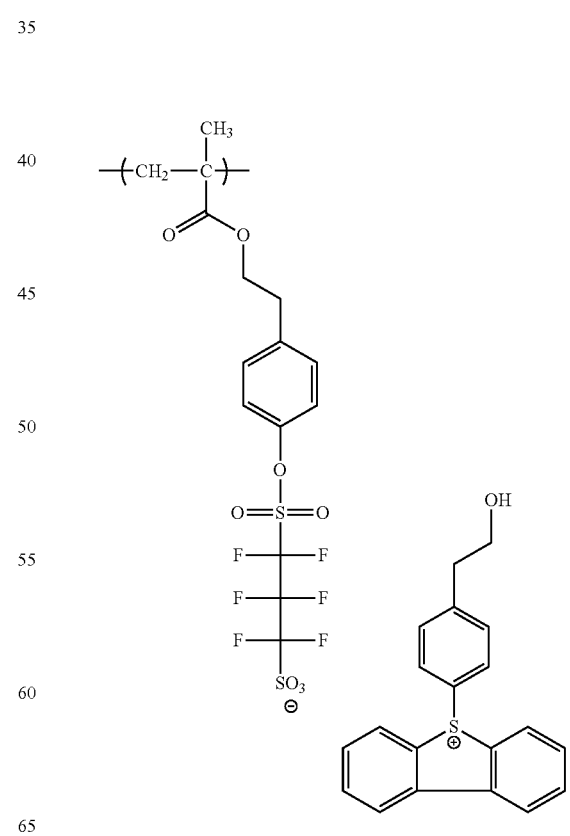

93
-continued
94
-continued
[Chem. 57]
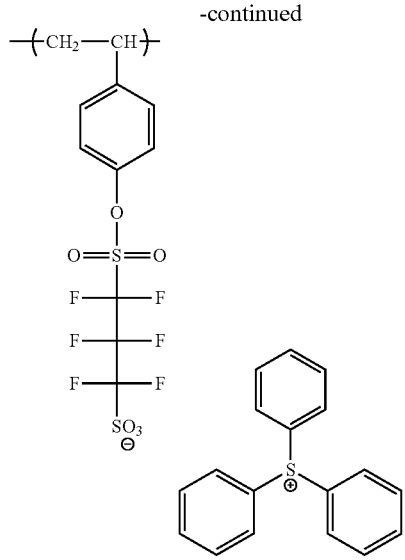
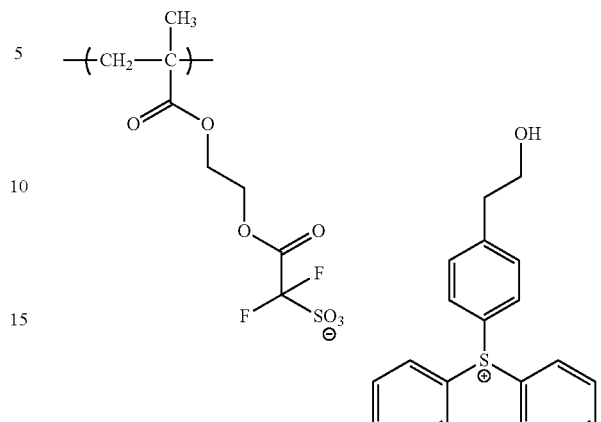
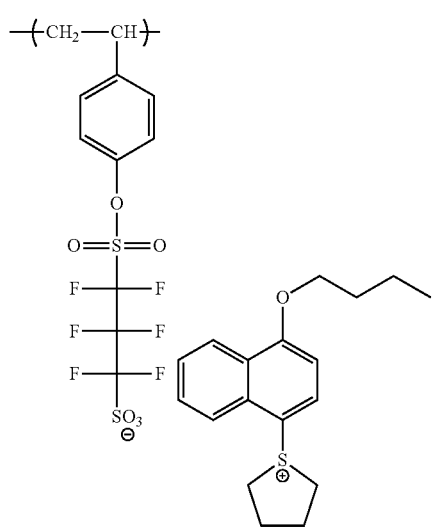
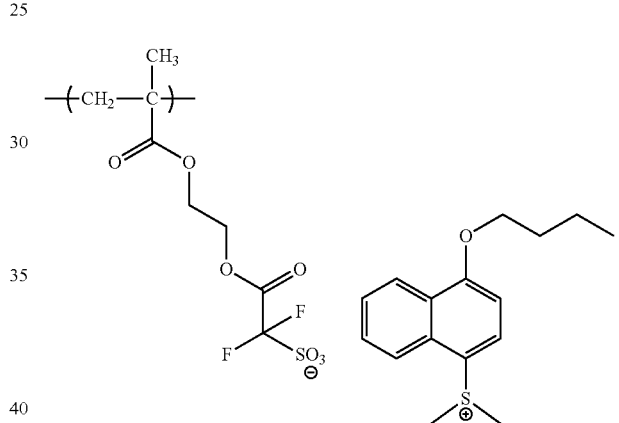
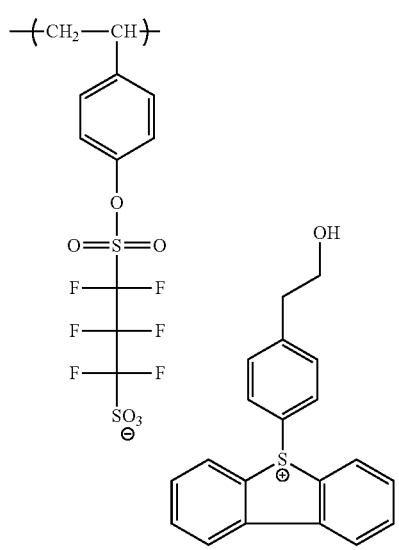
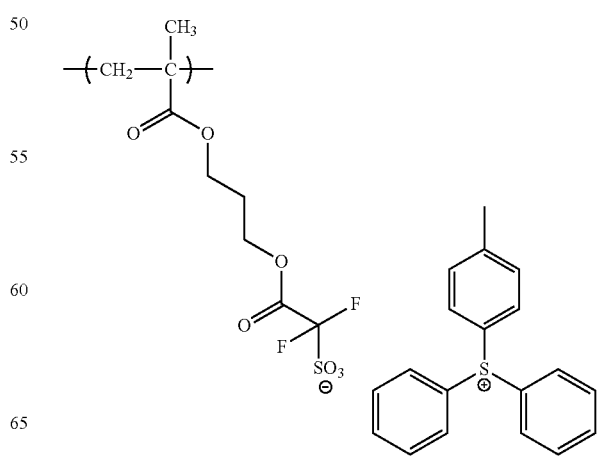

95
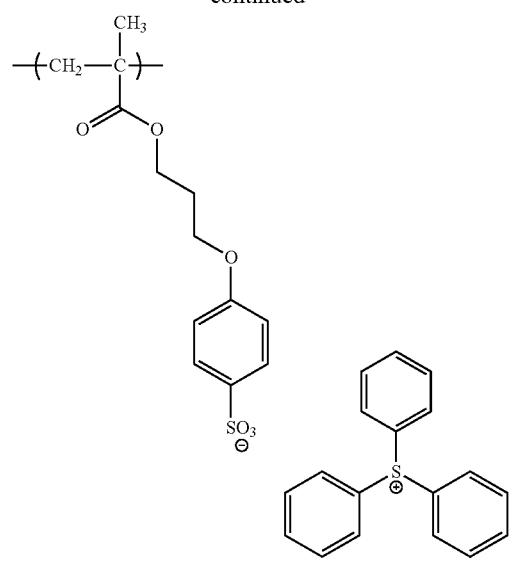
96
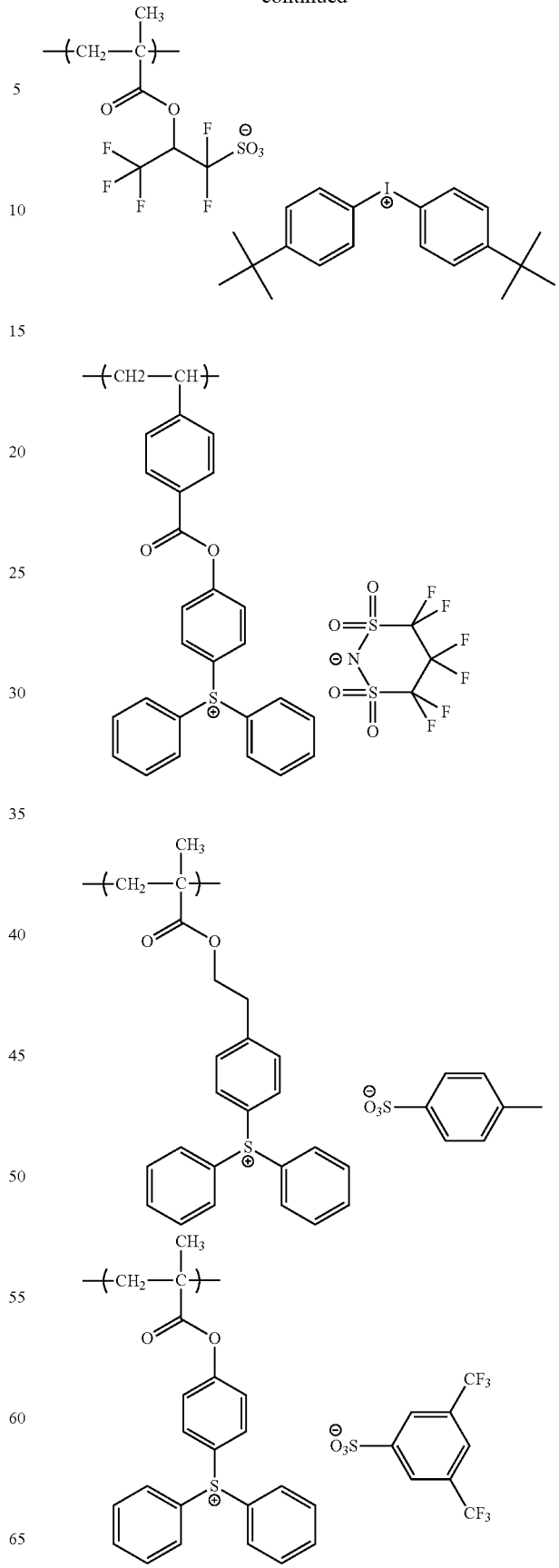

97
-continued
[Chem. 58]
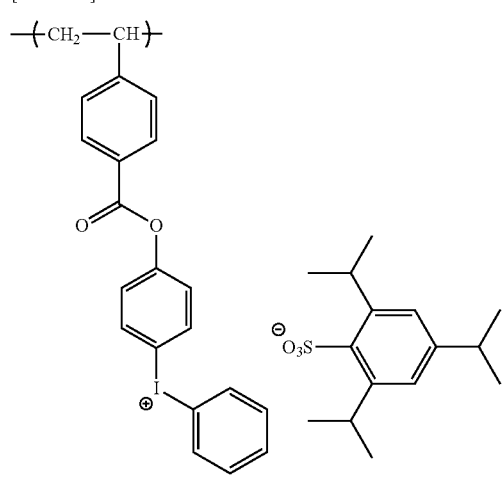
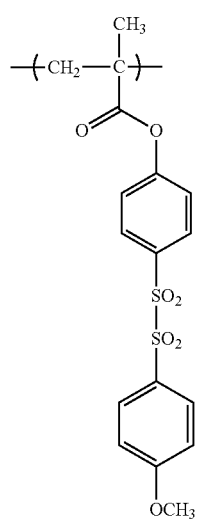
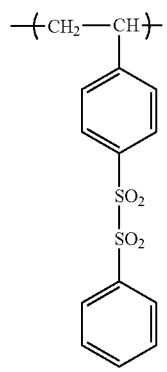
98
-continued
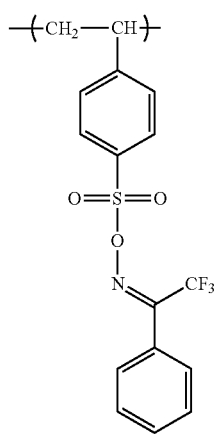
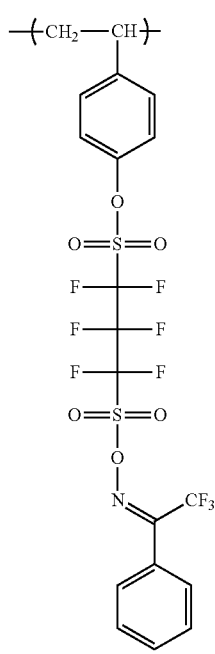
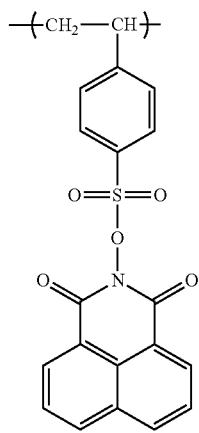

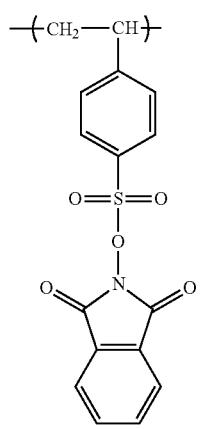
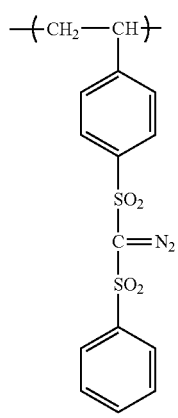
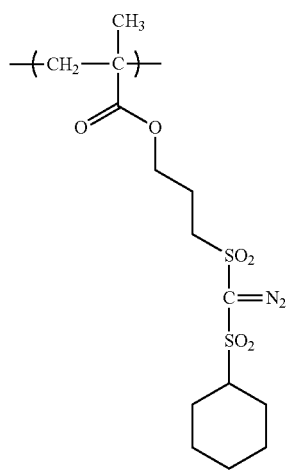
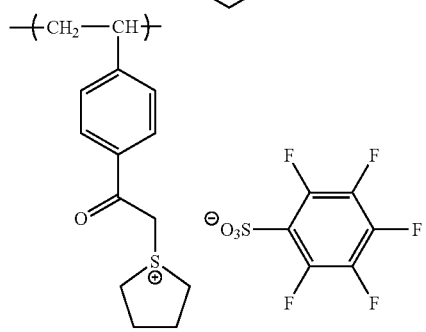
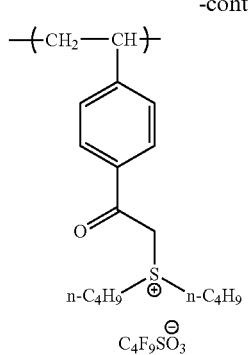
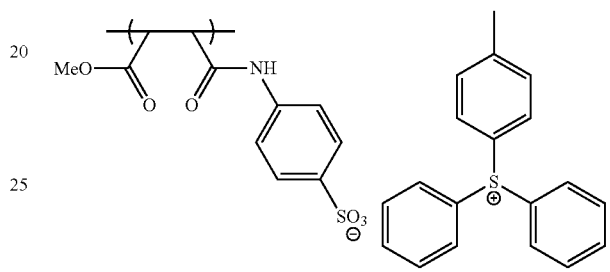
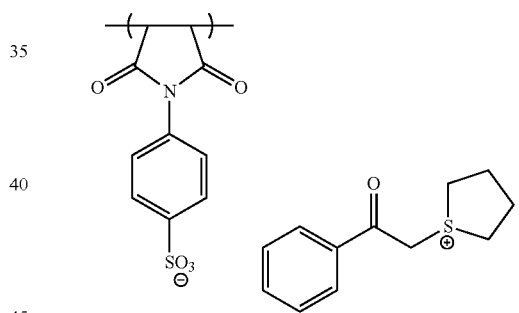
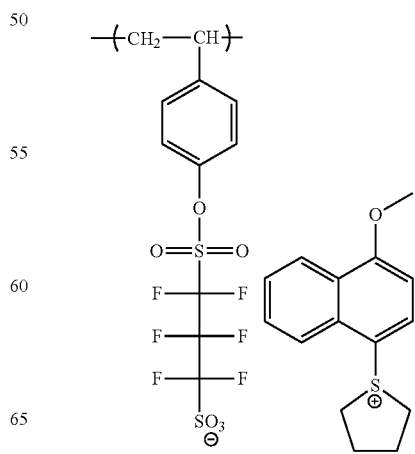

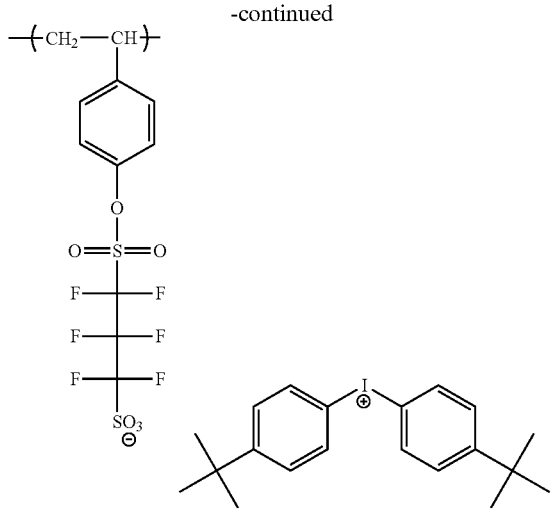

In the case where the resin (Ab) contains the repeating unit (B), the content of the repeating units (B) in the resin (Ab) is preferably from 0.1 to 80% by mole, more preferably from 0.5 to 60% by mole, and still more preferably from 1 to 40% by mole, based on all the repeating units in the resin (Ab).

The weight average molecular weight (Mw) of the resin (Ab) is each preferably in the range of 1,000 to 200,000. In views of the solubilization rate in an alkali and the sensitivity of the resin itself it is preferably 200,000 or less. The dispersity (Mw/Mn) is preferably from 1.0 to 3.0, more preferably from 1.0 to 2.5, and particularly preferably from 1.0 to 2.0.

Among these, the weight average molecular weight (Mw) of the resin is preferably in the range of 1,000 to 200,000, still more preferably in the range of 1,000 to 100,000, particularly preferably in the range of 1,000 to 50,000, and most preferably in the range of 1,000 to 25,000.

Here, the weight average molecular weight is defined as value in terms of polystyrene by means of gel permeation chromatography. Specifically, the weight average molecular weight (Mw) and the number average molecular weight (Mn) of the resin (Ab) may be calculated by using, for example, an HLC-8120 (manufactured by Tosoh Corporation) using TSK gel Multipore HXL-M columns (manufactured by Tosoh Corporation, 7.8 mm ID×30.0 cm) and THF (tetrahydrofuran) as an eluent.

The resin (Ab) having a dispersity of 2.0 or less can be synthesized by carrying out radical polymerization using an azo-based polymerization initiator. More preferably, the resin (Ab) having a dispersity of 1.0 to 1.5 can be synthesized by, for example, living radical polymerization.

The resin (Ab) is preferably polymerized by a known anion polymerization method, a radical polymerization method, or the like.

The anion polymerization method is carried out at a temperature of −100 to 90° C. in an organic solvent, usually under an inert gas atmosphere such as nitrogen and argon, using an alkali metal or an organic alkali metal as a polymerization initiator. Incidentally, in the copolymerization, the monomers can be added sequentially to a reaction system to carry out polymerization, thereby obtaining a block copolymer, or a mixture of the respective monomers can be added to a reaction system to carry out polymerization, thereby obtaining a random copolymer.

Examples of the alkali metal for the polymerization initiator include lithium, sodium, potassium, and cesium, and as an organic alkali metal, alkyl, allyl and aryl compounds of the above alkali metals can be used. Specific examples of the organic alkali metal include ethyl lithium, n-butyl lithium, sec-butyl lithium, tert-butyl lithium, ethylsodium, lithium biphenyl, lithium naphthalene, lithium triphenyl, sodium naphthalene, α-methylstyrene sodium dianions, 1,1-diphenylhexyl lithium, and 1,1-diphenyl-3-methylpentyl lithium.

The radical polymerization method is carried out at a temperature of 50 to 200° C. in an organic solvent, under an inert gas atmosphere such as nitrogen and argon, using a known radical polymerization initiator, for example, azo compounds such as azobisisobutyronitrile and azobisisovaleronitrile, and organic oxides such as benzoyl peroxide, methyl ethyl ketone peroxide, and cumene hydroperoxide, and if necessary, using a known chain transfer agent such as 1-dodecanethiol.

Examples of the organic solvent include aliphatic hydrocarbons such as n-hexane and n-heptane, alicyclic hydrocarbons such as cyclohexane and cyclopentane, aromatic hydrocarbons such as benzene and toluene, ketones such as methyl ethyl ketone and cyclohexanone, polyvalent alcohol derivatives such as propylene glycol monomethyl ether acetate, propylene glycol monomethyl ether, ethylene glycol monobutyl ether acetate, ethylene glycol monobutyl ether, ethylene glycol monoethyl ether acetate, ethylene glycol monoethyl ether, propylene glycol monoethyl ether acetate, and propylene glycol monoethyl ether, ethers such as diethyl ether, tetrahydrofuran, and dioxane, and organic solvents that are usually used in the anion polymerization, such as anisole and hexamethylphosphoramide, and these solvents may be used alone or as a mixed solvent of two or more kinds of the solvents. More preferred examples of the solvent include propylene glycol monomethyl ether acetate, propylene glycol monomethyl ether, and cyclohexanone.

Furthermore, when the positive tone resist of the present invention is exposed to an ArF excimer laser, it is preferable from the viewpoint of transparency to an ArF excimer laser to use a resin having no aromatic ring as the resin (Ab).

A resin suitable for ArF excimer laser exposure (also hereinafter referred to as a resin (A')) will be described below.

Examples of acid-decomposable group contained in the resin (A') include the same groups as set forth in the resin (Ab), and preferred examples of the repeating unit containing an acid-decomposable group include repeating units represented by the general formula (A2).

The content of the repeating units having an acid-decomposable group is preferably from 20 to 50% by mole, and more preferably from 25 to 45% by mole, based on all the repeating units in the resin (A').

The resin (A') is also preferably one having a repeating unit containing at least one kind of group selected from a lactone group, a hydroxyl group, a cyano group, and an alkali-soluble group.

The repeating unit having a lactone group which the resin (A') can have will be described.

As for the lactone group, any group may be used as long as it has a lactone structure, but the lactone structure is preferably a 5- to 7-membered ring lactone structure, and a structure where another ring structure is condensed with a 5- to 7-membered ring lactone structure in the form of forming a bicyclo or spiro structure is preferable. The resin more preferably contains a repeating unit having a lactone structure represented by any one of the following formulae (LC1-1) to (LC1-16). Further, the lactone structure may be bonded directly to the main chain.

Among these lactone structures, (LC1-1), (LC1-4), (LC1-5), (LC1-6), (LC1-13), and (LC1-14) are preferred. By using a specific lactone structure, the line edge roughness and the development defects are improved.

[Chem. 59]
LC1-1 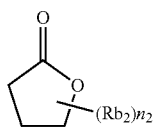
LC1-2 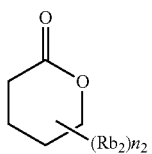
LC1-3 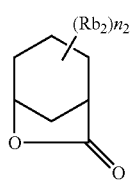
LC1-4 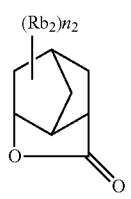
LC1-5 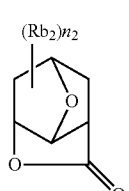
LC1-6 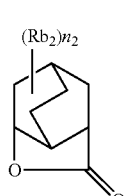
LC1-7 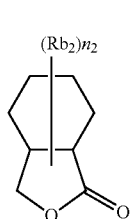
LC1-8 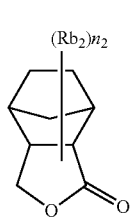
-continued
LC1-9 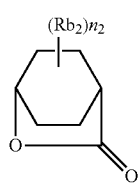
LC1-10 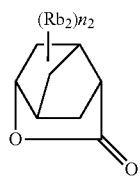
LC1-11 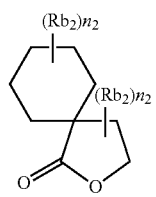
LC1-12 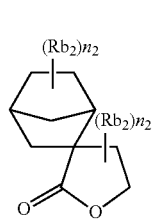
LC1-13 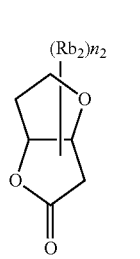
LC1-14 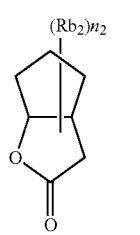
LC1-15 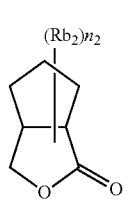

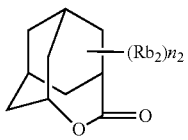
LC1-16

The lactone structural moiety may or may not have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, and an acid-decomposable group. Among these, an alkyl group having 1 to 4 carbon atoms, a cyano group and an acid-decomposable group are more preferred. n2 represents an integer of 0 to 4. When n2 is 2 or more, a plurality of substituents ($Rb_2$) may be the same as or different from each other and the plurality of substituents ($Rb_2$) may be bonded to each other to form a ring.

Examples of the repeating unit having a lactone structure represented by any one of the general formulae (LC1-1) to (LC1-16) include a repeating unit represented by the following general formula (AII).

[Chem. 60]

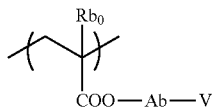
(AII)

In the general formula (AII), $Rb_0$ represents a hydrogen atom, a halogen atom, or an alkyl group having 1 to 4 carbon atoms. Preferred examples of the substituent which the alkyl group of $Rb_0$ may have include a hydroxyl group and a halogen atom. Examples of the halogen atom of $Rb_0$ include a fluorine atom, a chlorine atom, a bromine atom, and an iodine atom. $Rb_0$ is preferably a hydrogen atom, a methyl group, a hydroxymethyl group, or a trifluoromethyl group, and particularly preferably a hydrogen atom or a methyl group.

Ab represents a single bond, an alkylene group, a divalent connecting group having a monocyclic or polycyclic alicyclic hydrocarbon structure, an ether group, an ester group, a carbonyl group, or a divalent connecting group formed by a combination thereof, and preferably, a single bond or a divalent connecting group represented by -$Ab_1$-$CO_2$—.

$Ab_1$ is a linear or branched alkylene group or a monocyclic or polycyclic cycloalkylene group, and preferably a methylene group, an ethylene group, a cyclohexylene group, an adamantylene group, or a norbornylene group.

V represents a group having a structure represented by any of the general formulae (LC1-1) to (LC1-16).

The repeating unit having a lactone group usually has an optical isomer, but any optical isomer may be used. One optical isomer may be used alone or a mixture of a plurality of optical isomers may be used. In the case of mainly using one optical isomer, the optical purity (ee) thereof is preferably 90 or more, and more preferably 95 or more.

The content of the repeating units having a lactone group is preferably from 15 to 60% by mole, more preferably from 20 to 50% by mole, and still more preferably from 30 to 50% by mole, based on all the repeating units in the resin (A').

Specific examples of the repeating unit having a lactone group are shown below, but the present invention is not limited thereto.

[Chem. 61]

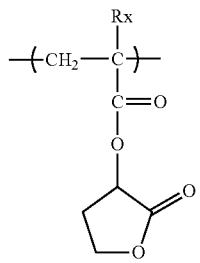

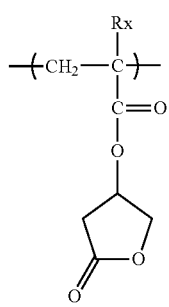

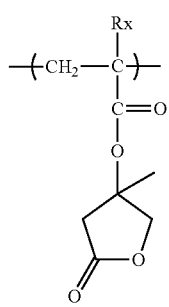

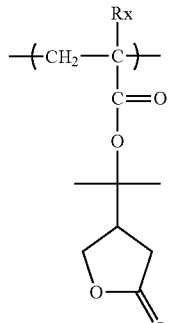

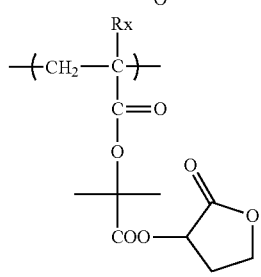

107
-continued
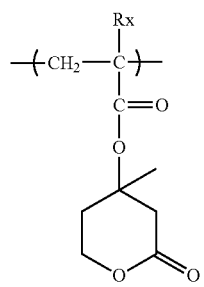
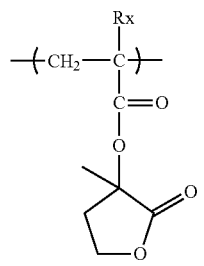
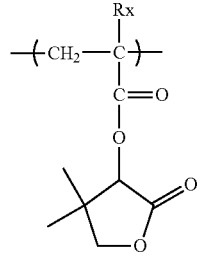
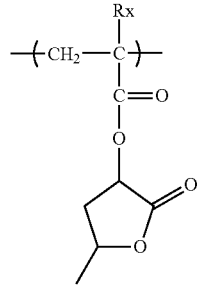
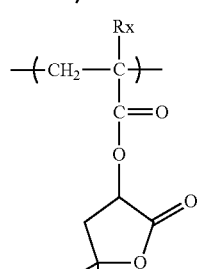
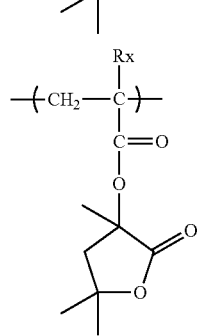
108
-continued
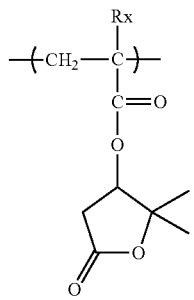
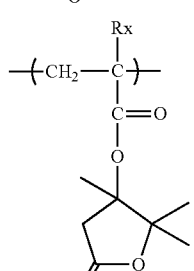
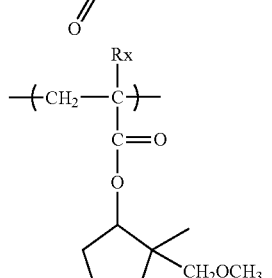
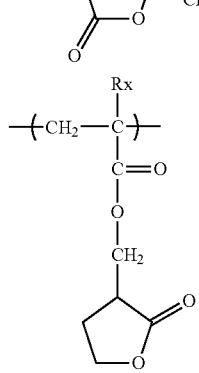
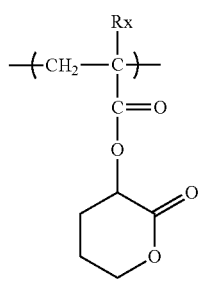
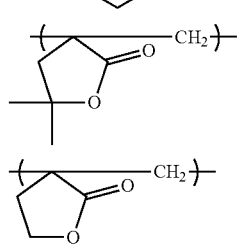

109
-continued
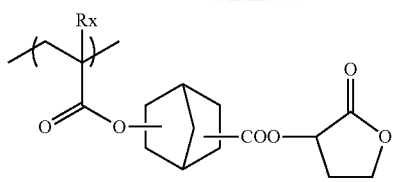
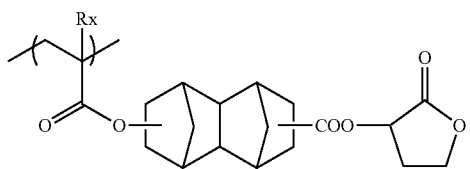
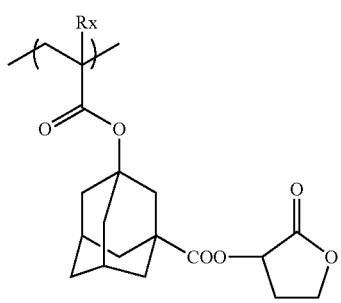
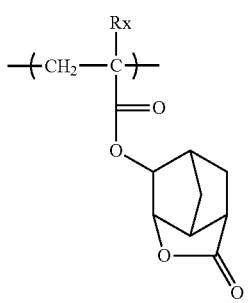
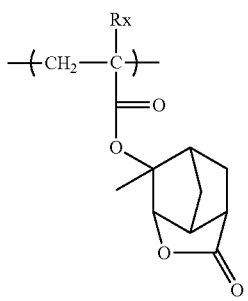
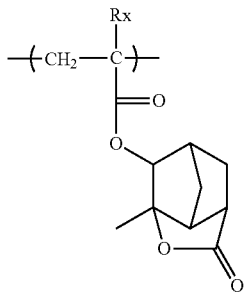
110
-continued
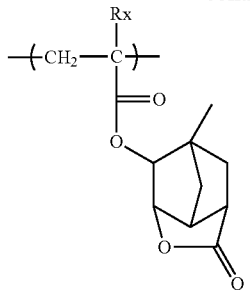
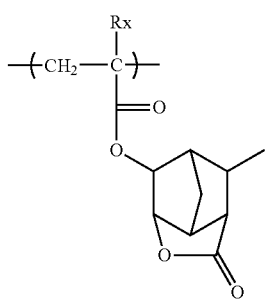
[Chem. 62]
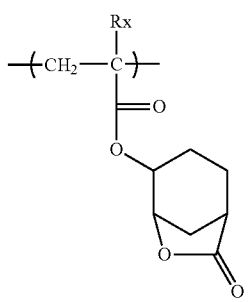
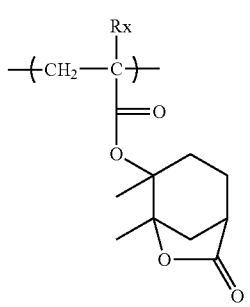
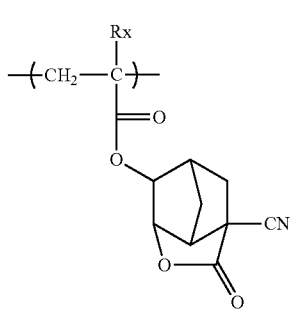

111
-continued
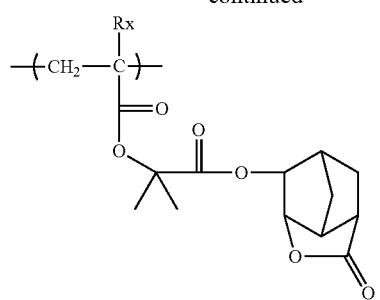
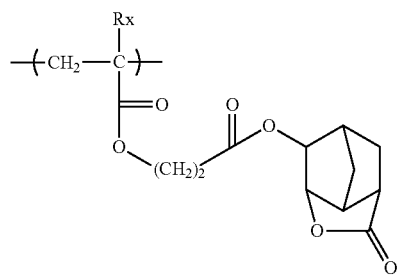
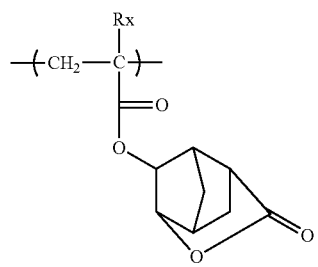
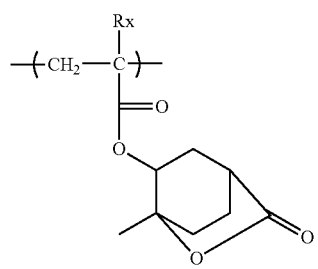
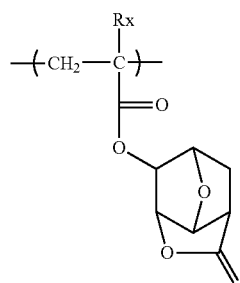
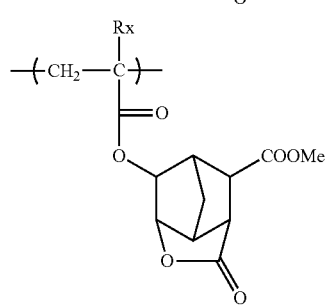
112
-continued
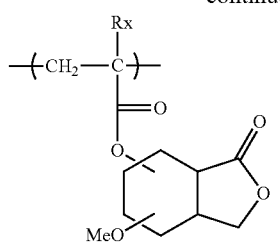
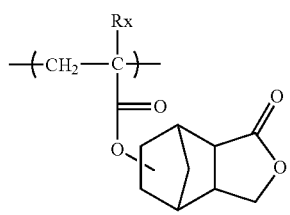
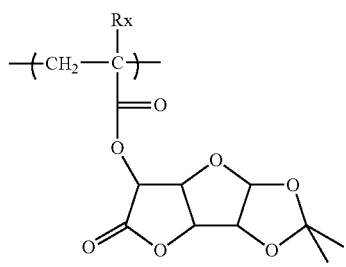
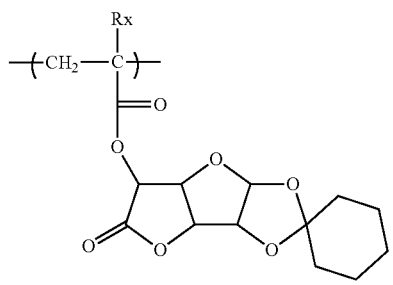
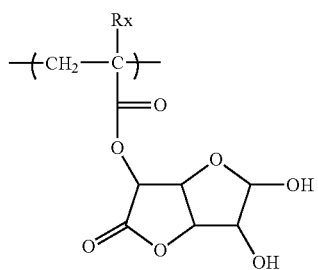
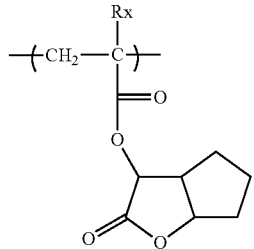

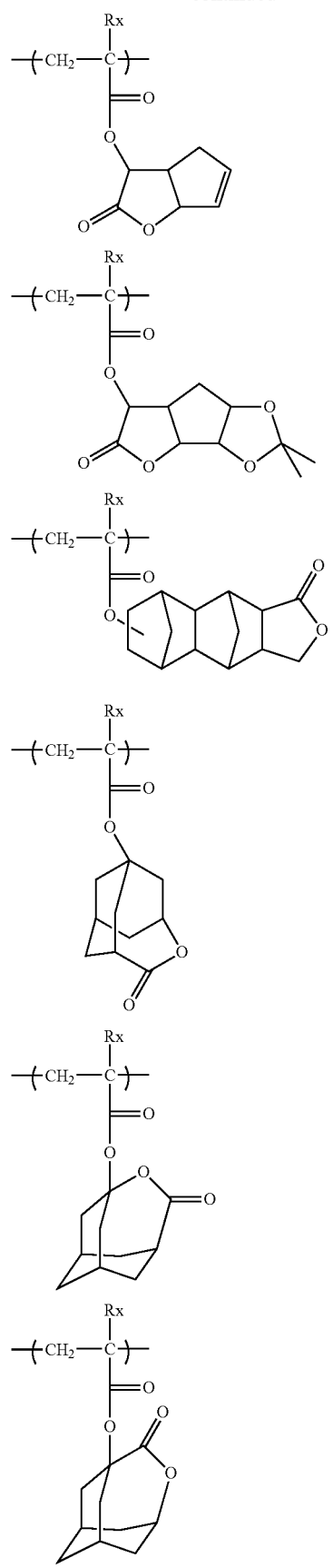
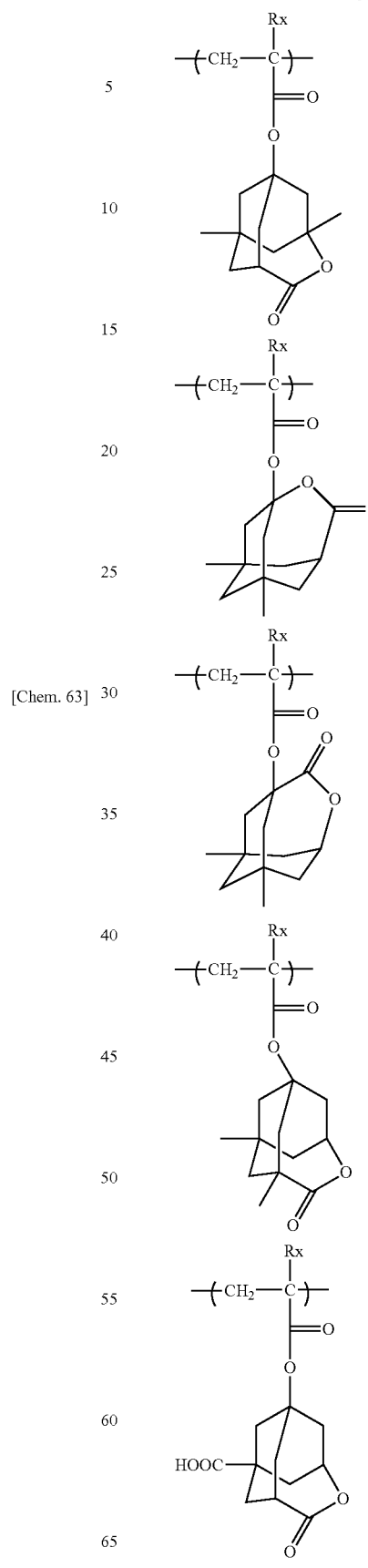

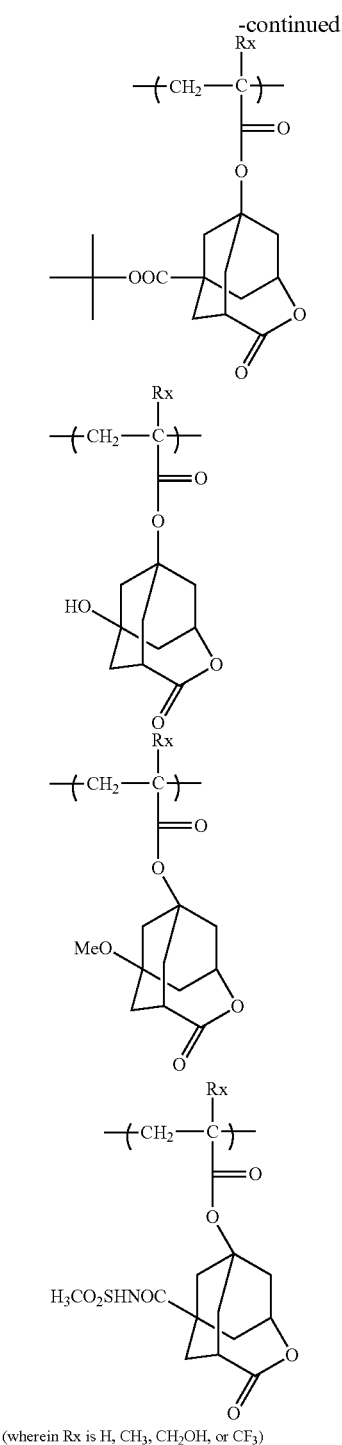

(wherein Rx is H, CH₃, CH₂OH, or CF₃)

The resin (A') preferably has a repeating unit containing a hydroxyl group or a cyano group. This increases the adherence to a substrate and affinity to a developer. The repeating unit having a hydroxyl group or a cyano group is preferably a repeating unit having an alicyclic hydrocarbon structure substituted with a hydroxyl group or a cyano group. The alicyclic hydrocarbon structure in the alicyclic hydrocarbon structure substituted with a hydroxyl group or a cyano group is preferably an adamantyl group, a diadamantyl group, or a norbornane group. Preferred examples of the alicyclic hydrocarbon structures substituted with a hydroxyl group or a cyano group include the partial structures of the following general formulae (VIIa) to (VIId).

[Chem. 64]

(VIIa)
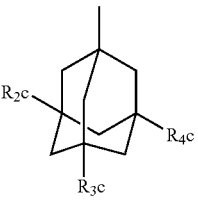

(VIIb)
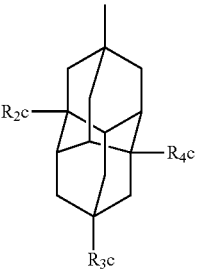

(VIIc)
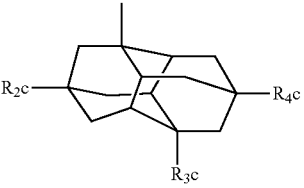

(VIId)
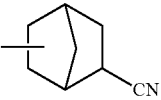

In the general formulae (VIIa) to (VIIc), $R_2c$ to $R_4c$ each independently represent a hydrogen atom, a hydroxyl group, or a cyano group, provided that at least one of $R_2c$ to $R_4c$ represents a hydroxyl group or a cyano group. A structure where one or two members out of $R_2c$ to $R_4c$ are hydroxyl groups with the remaining members being a hydrogen atom is preferred. In the general formula (VIIa), it is more preferable that two members out of $R_2c$ to $R_4c$ be hydroxyl groups and the remaining members be a hydrogen atom.

Examples of the repeating units having partial structures represented by the general formulae (VIIa) to (VIId) include repeating units represented by the following general formulae (AIIa) to (AIId).

[Chem. 65]

(AIIa)
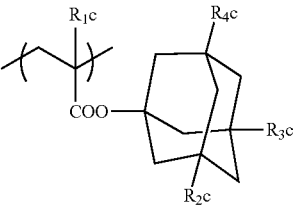

-continued

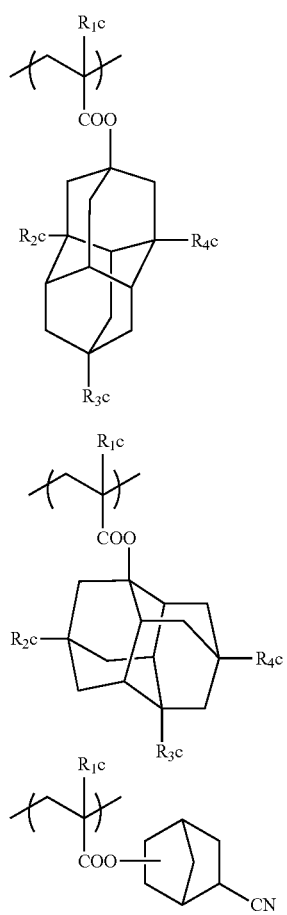

In the general formulae (AIia) to (AIId),

R₁c represents a hydrogen atom, a methyl group, a trifluoromethyl group, or a hydroxymethyl group.

R₂c to R₄c have the same meanings as R₂c to R₄c in the general formulae (VIIa) to (VIIc).

The content of the repeating units having a hydroxyl group or a cyano group is preferably from 5 to 40% by mole, more preferably from 5 to 30% by mole, and still more preferably from 10 to 25% by mole, based on all the repeating units in the resin (A').

Specific examples of the repeating unit having a hydroxyl group or a cyano group are shown below, but the present invention is not limited thereto.

[Chem. 66]

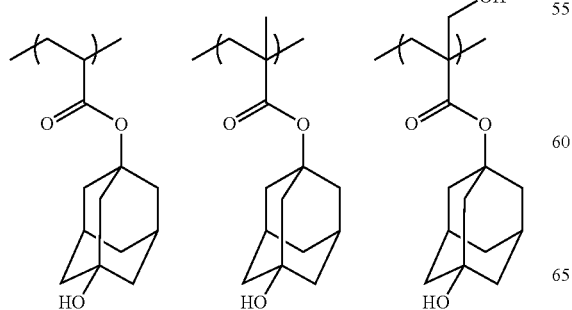

-continued

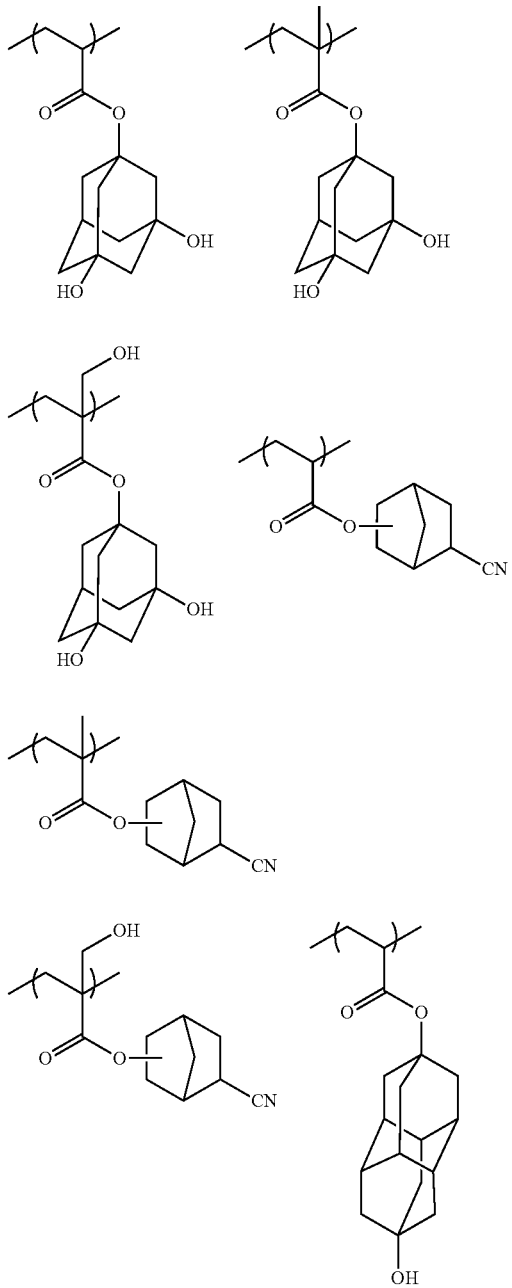

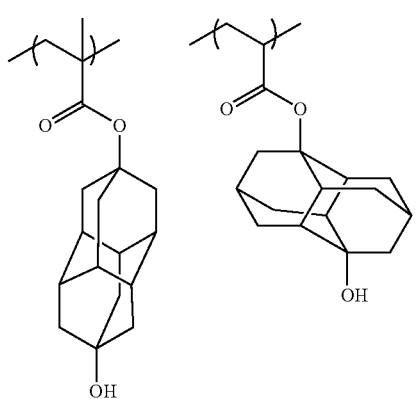

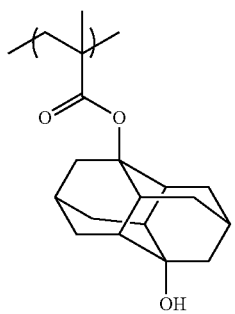

The resin (A') preferably has a repeating unit having an alkali-soluble group. Examples of the alkali-soluble group include a carboxyl group, a sulfonamide group, a sulfonylimide group, a bissulfonylimide group, and an aliphatic alcohol (for example, a hexafluoroisopropanol group) with the α-position being substituted with an electron-withdrawing group, and more preferably has a repeating unit having a carboxyl group. By virtue of containing the repeating units having an alkali-soluble group, the resolution increases in the usage of forming contact holes. As the repeating unit having an alkali-soluble group, a repeating unit in which an alkali-soluble group is directly bonded to the main chain of a resin such as a repeating unit by an acrylic acid or a methacrylic acid, a repeating unit in which an alkali-soluble group is bonded to the main chain of a resin by a connecting group, and a repeating unit in which a polymerization initiator or a chain transfer agent having an alkali-soluble group is used in the polymerization to be introduced into the end of a polymer chain are all preferred, and the connecting group may have a monocyclic or polycyclic hydrocarbon structure. A repeating unit of acrylic acid or methacrylic acid is particularly preferred.

The content of the repeating units having an alkali-soluble group is preferably from 0 to 20% by mole, more preferably from 3 to 15% by mole, and still more preferably from 5 to 10% by mole, based on the entire repeating units in the resin (A').

Specific examples of the repeating unit having an alkali-soluble group are shown below, but the present invention is not limited thereto.

[Chem. 67]

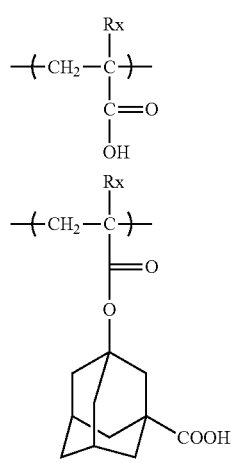

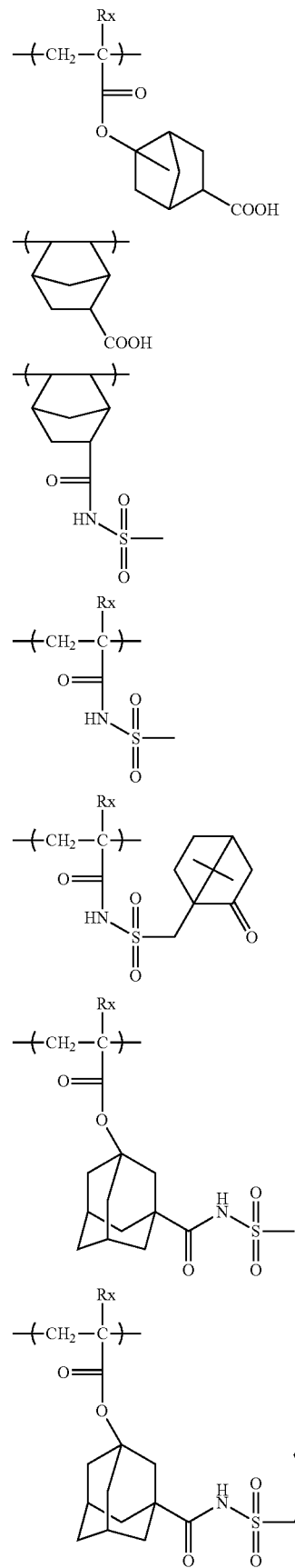

-continued

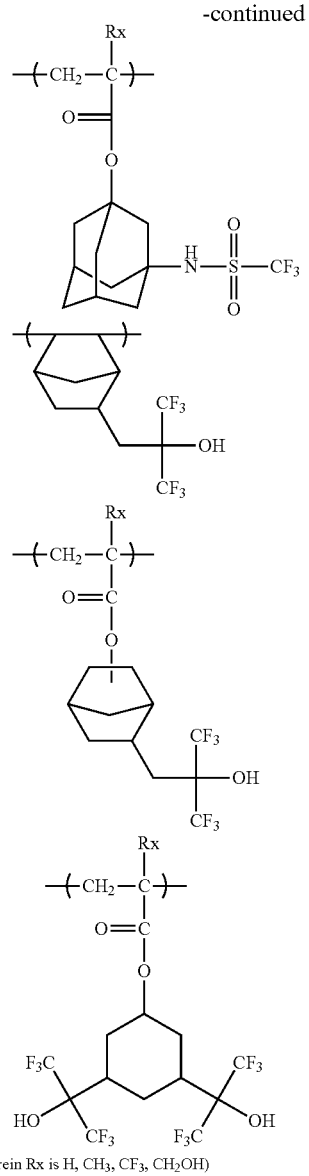

(wherein Rx is H, CH₃, CF₃, CH₂OH)

The resin (A') may further have an alicyclic hydrocarbon structure and may have a repeating unit which does not show acid-decomposability. This can reduce the elution of low molecular components from a resist film to a liquid for immersion liquid upon immersion liquid exposure. Examples of the repeating unit include repeating units of 1-adamantyl (meth)acrylate, diamantyl (meth)acrylate, tricyclodecanyl (meth)acrylate, or cyclohexyl (meth)acrylate.

The resin (A') may contain, in addition to the above-described repeating structural units, various repeating structural units for the purpose of controlling the dry etching resistance, suitability for a standard developer, adherence to a substrate, a resist profile, and properties generally required of a resist, such as resolution, heat resistance, and sensitivity.

Examples of such a repeating structural unit include, but are not limited to, repeating structural units corresponding to the monomers described below.

The performance required for the resin (A'), particularly
(1) solubility in a coating solvent,
(2) a film-forming property (glass transition point),
(3) alkaline developability,
(4) film loss (selection of a hydrophilic, hydrophobic, or alkali-soluble group),
(5) adherence of an unexposed area to a substrate,
(6) dry etching resistance,
and the like, can be subtly controlled.

The resin (A') can be synthesized according to an ordinary method (for example, radical polymerization). Examples of the general synthesis method include a batch polymerization method in which a monomer species and an initiator are dissolved in a solvent and heated so as to accomplish polymerization and a dropping polymerization method in which a solution of monomer species and initiator is added by dropwise addition to a heated solvent over 1 to 10 hours. The dropping polymerization method is preferred. Examples of the reaction solvent include tetrahydrofuran, 1,4-dioxane, ethers such as diisopropyl ether, ketones such as methyl ethyl ketone and methyl isobutyl ketone, an ester solvent such as ethyl acetate, an amide solvent such as dimethylformamide and dimethylacetamide, and the solvents capable of dissolving the composition of the present invention as described later, such as propylene glycol monomethyl ether acetate, propylene glycol monomethyl ether, and cyclohexanone. The polymerization is more preferably carried out using the same solvent as the solvent used in the positive tone resist composition of the present invention. By this, generation of particles during storage may be inhibited.

The polymerization reaction is preferably carried out in an inert gas atmosphere such as nitrogen or argon. Regarding the polymerization initiator, the polymerization is started using a commercially available radical initiator (an azo-based initiator, a peroxide, and the like). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The initiator is added additionally or dividedly, if desired. After the completion of reaction, the reaction solution is poured into a solvent, and the desired polymer is collected by powder or solid recovery, or other methods. The concentration during the reaction is in the range of 5 to 50% by mass, and preferably 10 to 30% by mass, and the reaction temperature is usually in the range of 10° C. to 150° C., preferably 30° C. to 120° C., and more preferably 60° C. to 100° C.

The weight average molecular weight of the resin (A') is preferably from 1,000 to 200,000, more preferably from 2,000 to 20,000, still more preferably from 3,000 to 15,000, and particularly preferably from 3,000 to 10,000, in terms of a polystyrene by means of a GPC method. When the weight average molecular weight is from 1,000 to 200,000, the deterioration of heat resistance and dry etching resistance, and the deterioration of developability or a film forming property due to an increase in viscosity may be prevented.

The dispersity (molecular weight distribution) is usually in the range of 1 to 3, preferably 1 to 2.6, still more preferably 1 to 2, and particularly preferably 1.4 to 1.7. As the molecular weight distribution is narrower, the resolution and resist profile are better, the side wall of the resist pattern is smoother, and the roughness property is more improved.

The resin (Ab) may be used in combination of two or more kinds thereof.

The addition amount of the resin (Ab) in terms of a total amount is usually from 10 to 99% by mass, preferably from 20 to 99% by mass, and particularly preferably from 30 to 99% by mass, based on the total solid contents of the composition of the present invention.

Specific examples of the resin (Ab) are shown below, but the present invention is not limited thereto.
[Chem. 68]
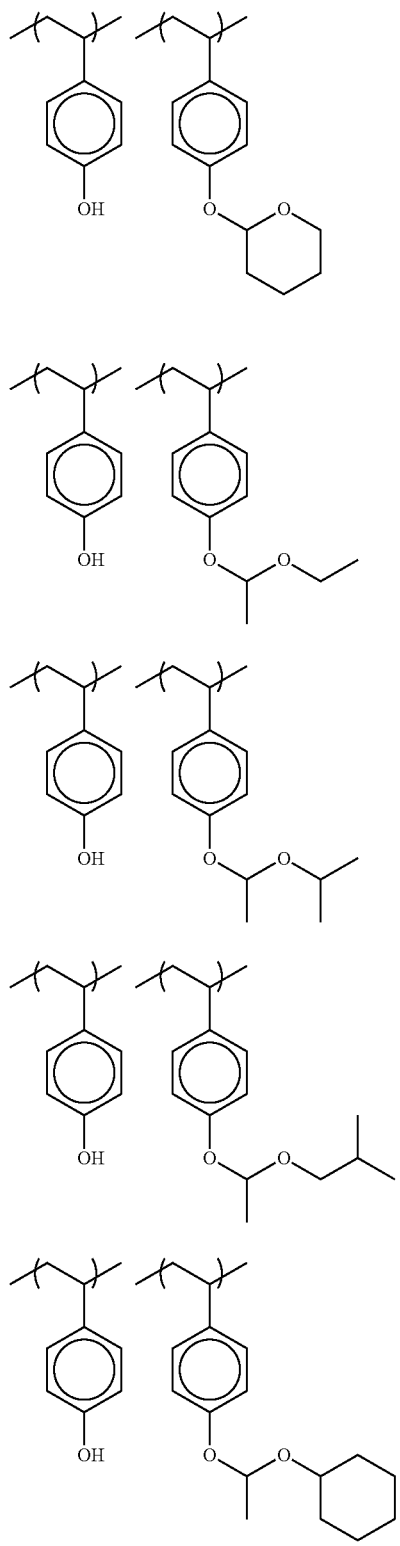

(Ab-11)
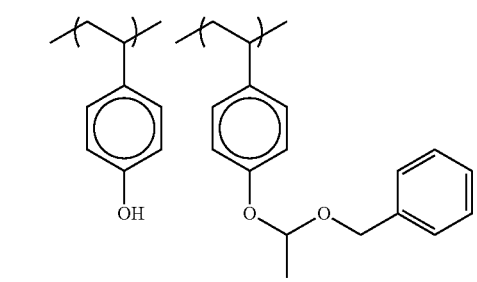
(Ab-12)
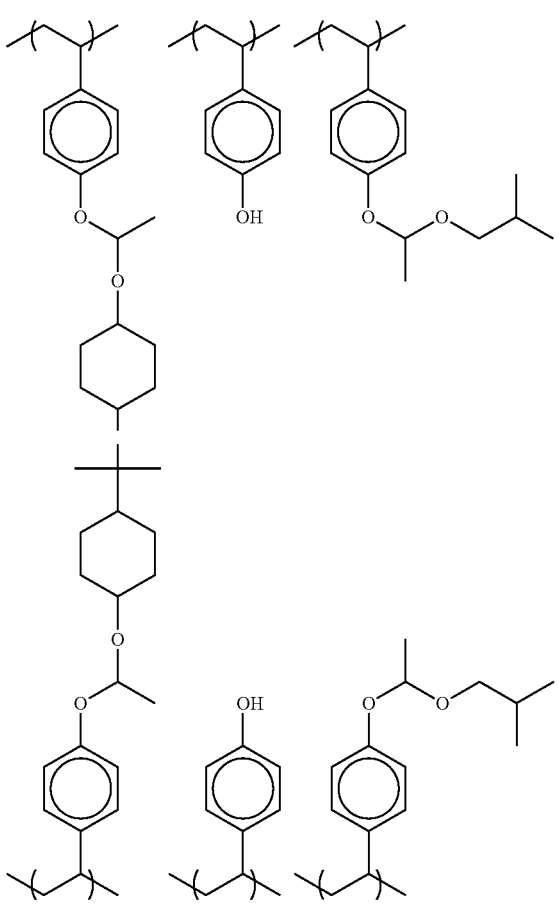
[Chem. 69]
(Ab-13)
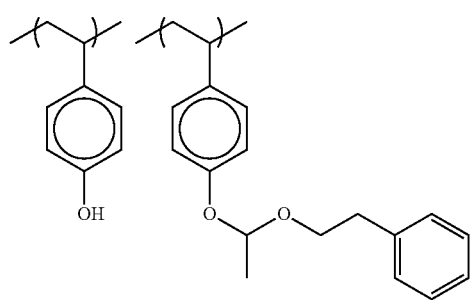
(Ab-14)
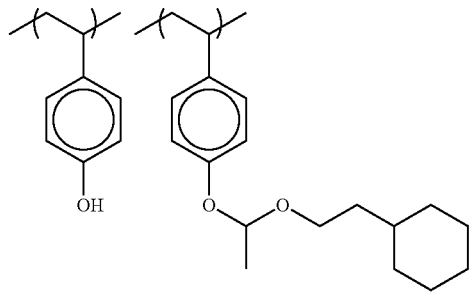
(Ab-15)
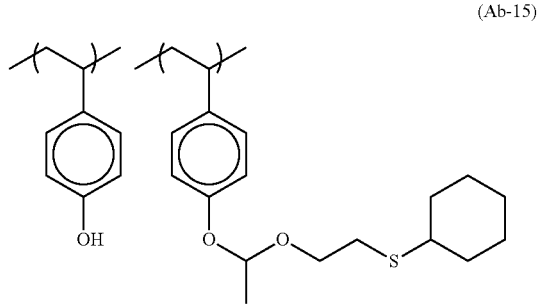
(Ab-16)
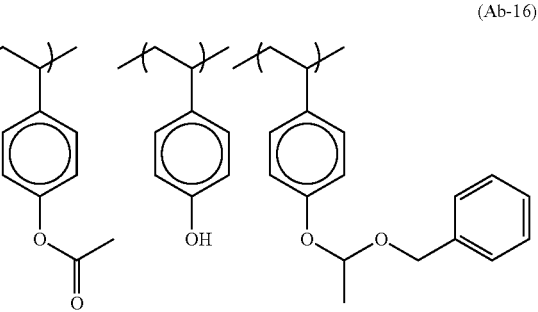
(Ab-17)
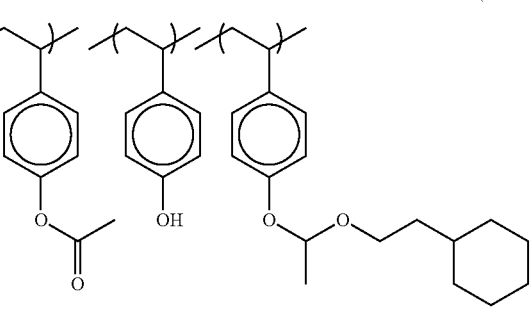
(Ab-18)
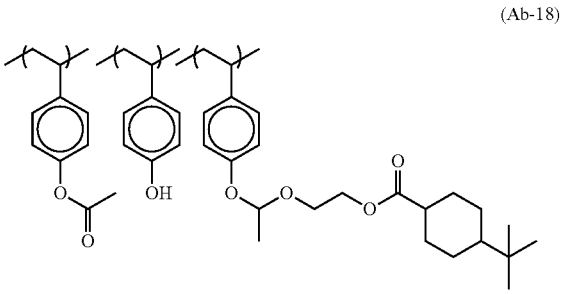

-continued
(Ab-19)
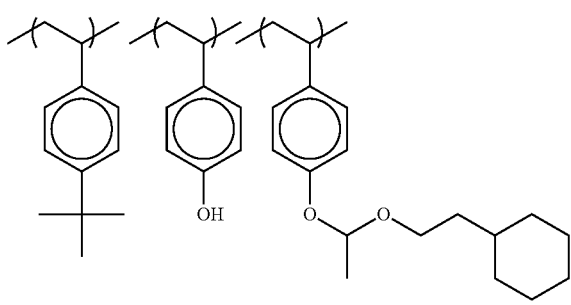
(Ab-20)
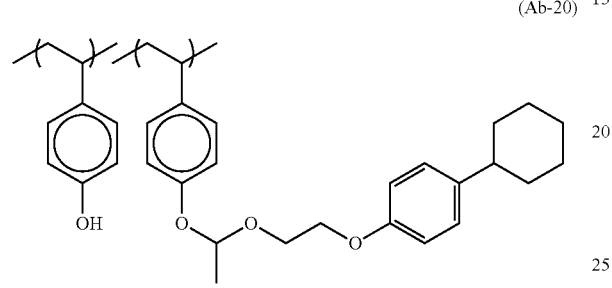
(Ab-21)
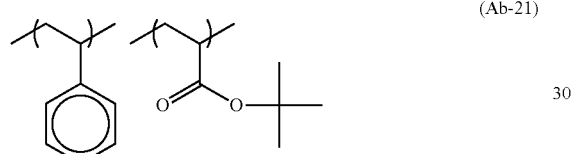
(Ab-22)
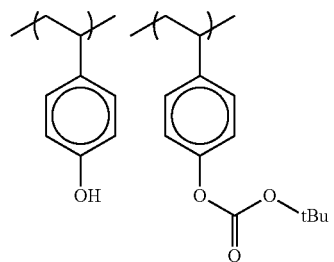
(Ab-23)
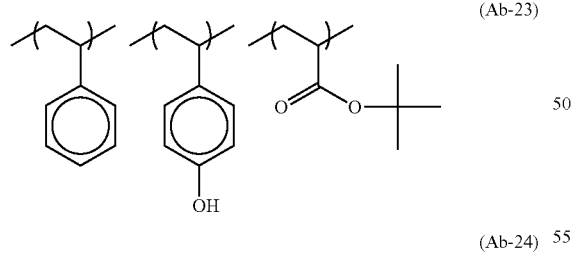
(Ab-24)
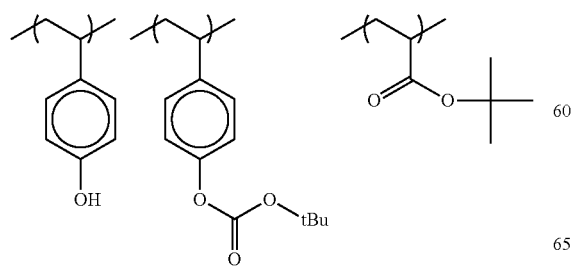
-continued
(Ab-25)
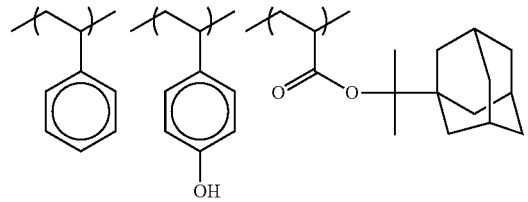
(Ab-26)
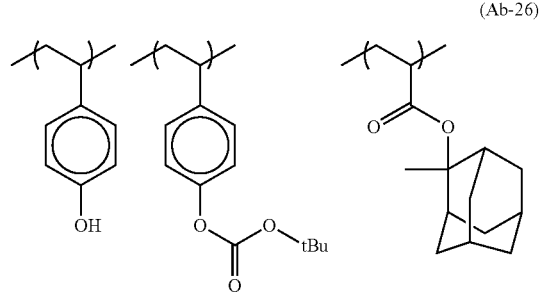
[Chem. 70]
(Ab-27)
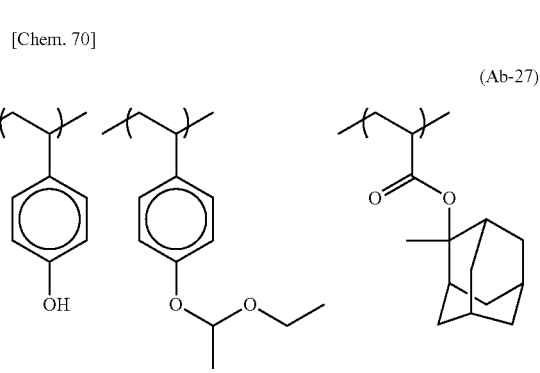
(Ab-28)
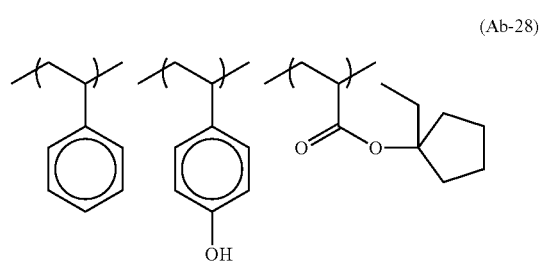
(Ab-29)
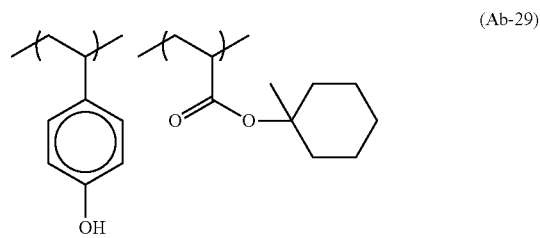

[Chem. 71]
(Ab-30)
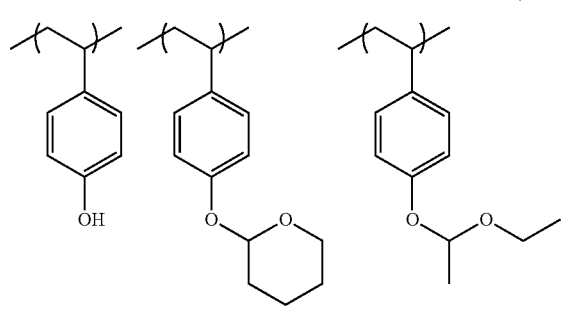
(Ab-35)
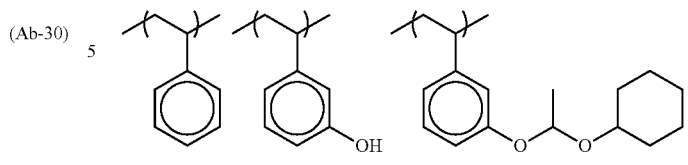
(Ab-36)
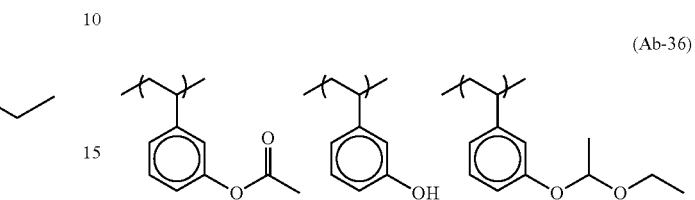
(Ab-31)
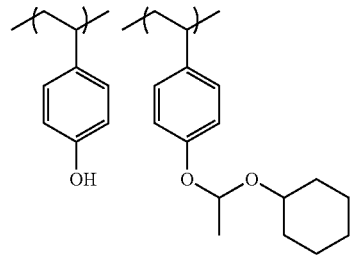 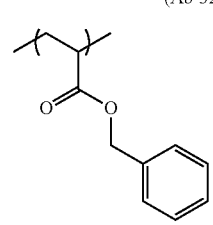
(Ab-37)
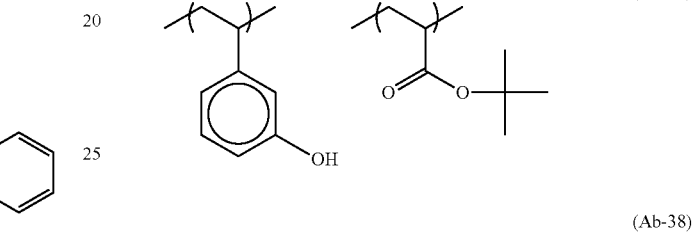
(Ab-32)
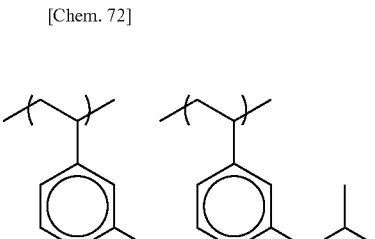
(Ab-38)
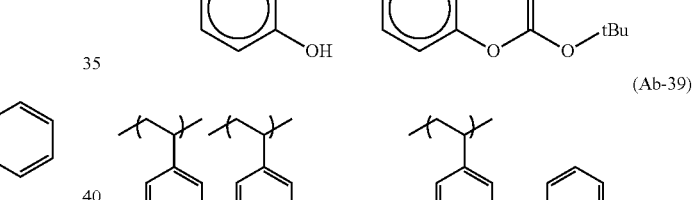
(Ab-39)
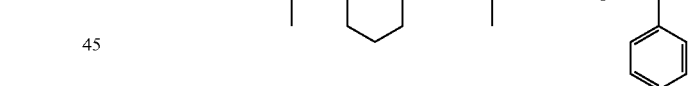
[Chem. 72]
(Ab-33)
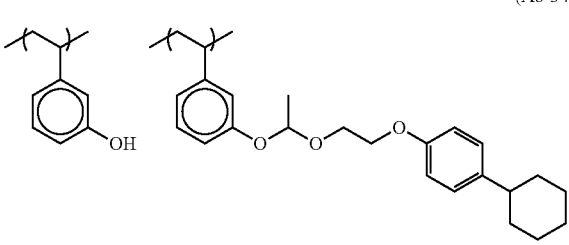
(Ab-40)
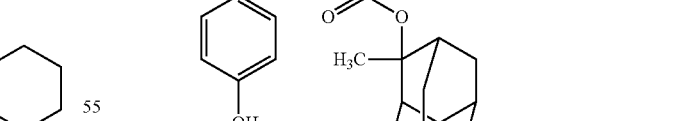
(Ab-34)
(Ab-41)
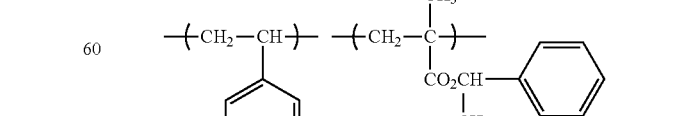

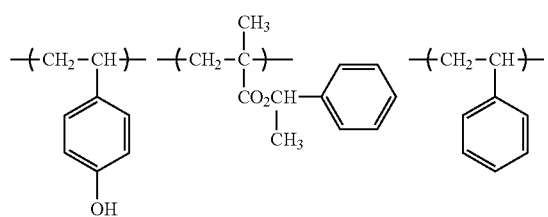

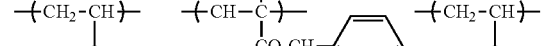

(Ab-55)
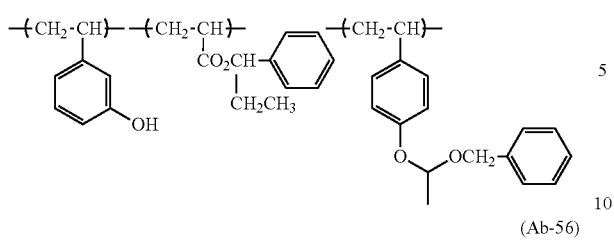
(Ab-56)
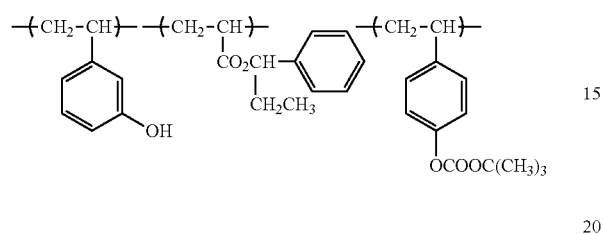
[Chem. 75]
(Ab-57)
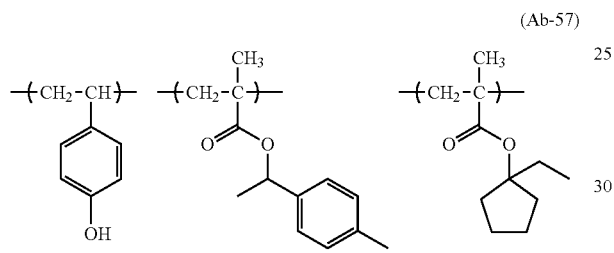
(Ab-58)
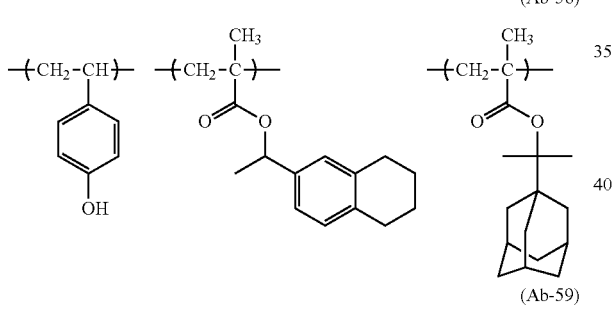
(Ab-59)
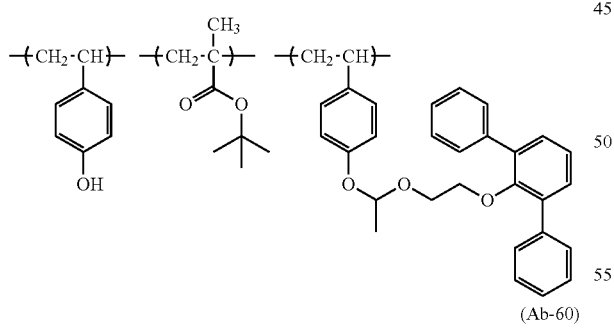
(Ab-60)
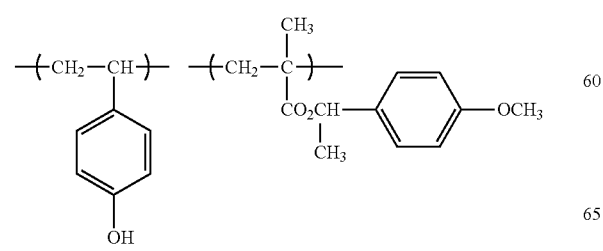
(Ab-61)
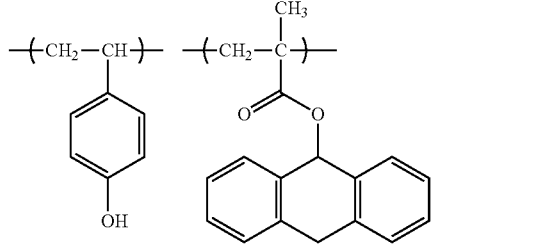
(Ab-62)
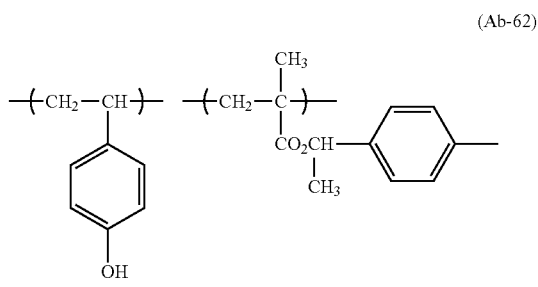
(Ab-63)
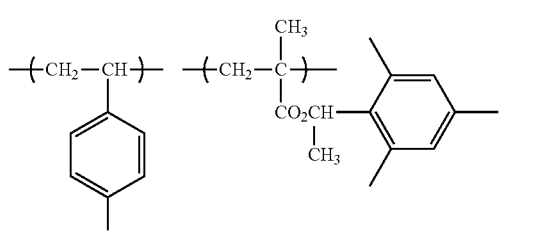
(Ab-64)
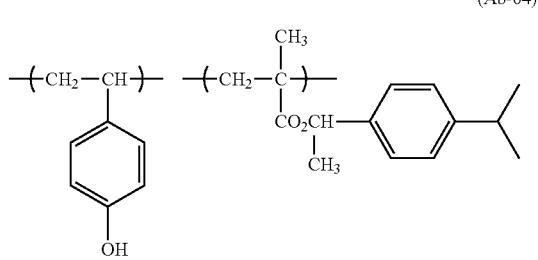
(Ab-65)
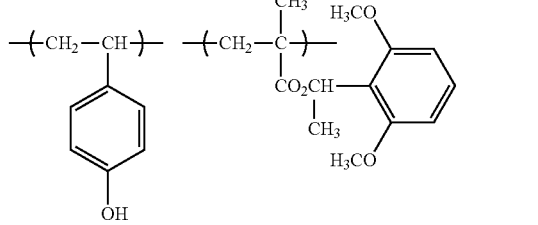
[Chem. 76]
(Ab-66)
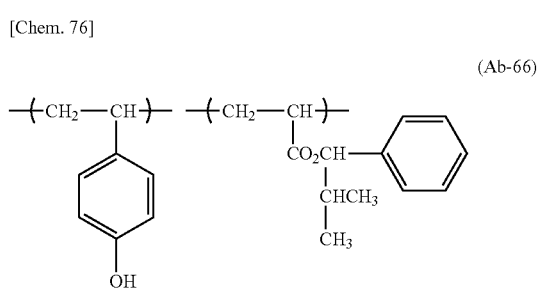

-continued
(Ab-67)
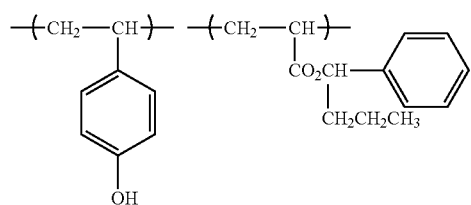
(Ab-68)
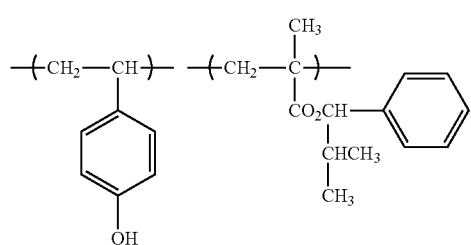
(Ab-69)
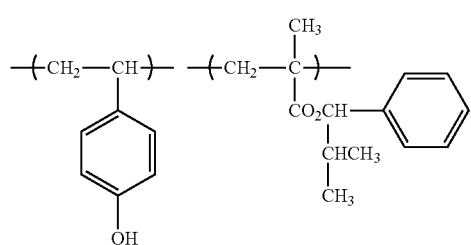
(Ab-70)
(Ab-71)
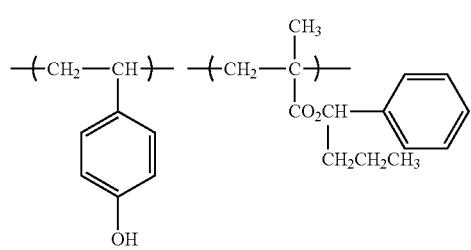
(Ab-72)
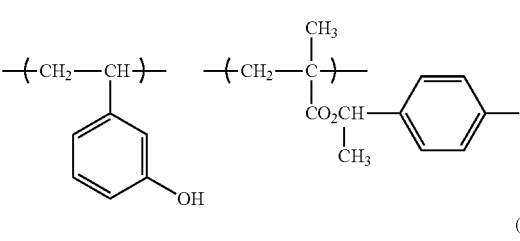
-continued
(Ab-73)
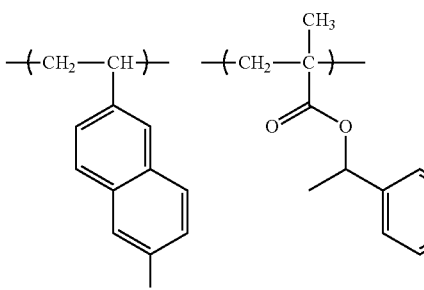
{Chem. 77}
(Ab-74)
(Ab-75)
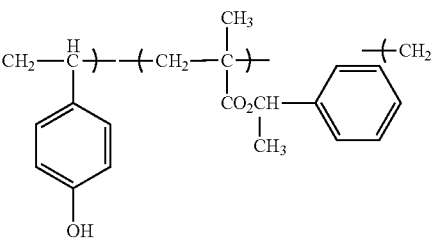
(Ab-76)
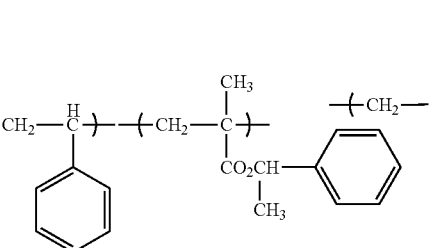
(Ab-77)
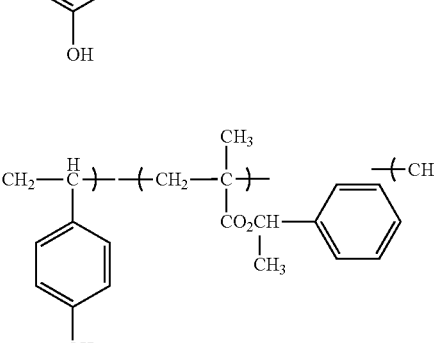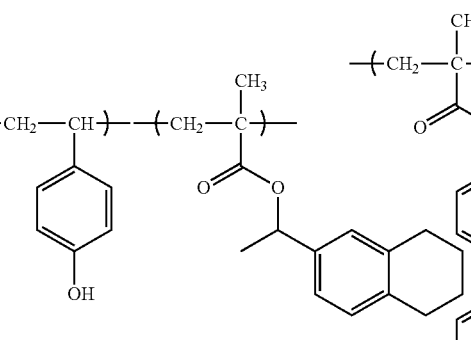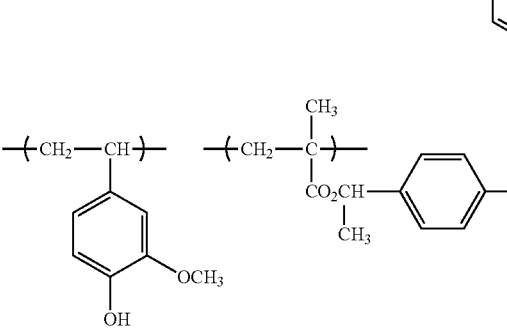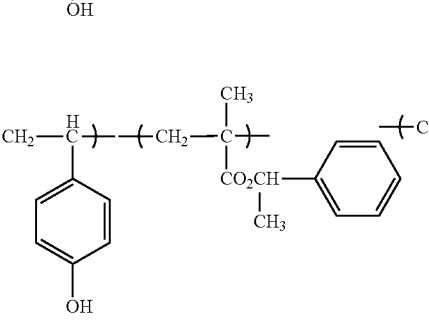

[Chem. 78]
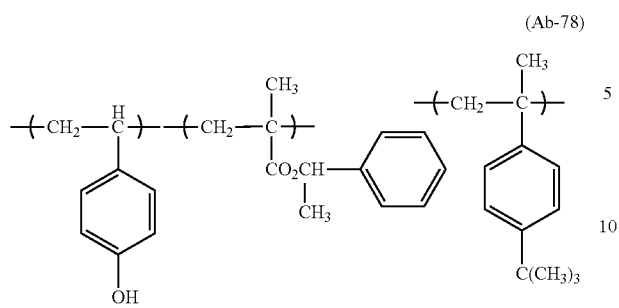
(Ab-78)
(Ab-79)
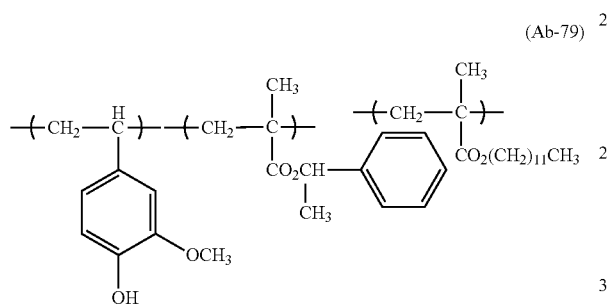
(Ab-80)
(Ab-81)
(Ab-82)
[Chem. 79]
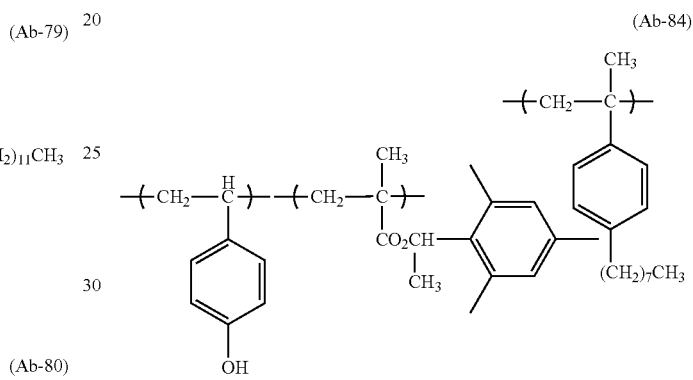
(Ab-83)
(Ab-84)
(Ab-85)
[Chem. 80]
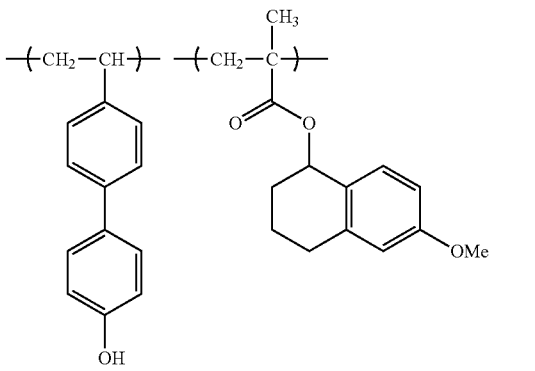
(Ab-86)

(Ab-87)
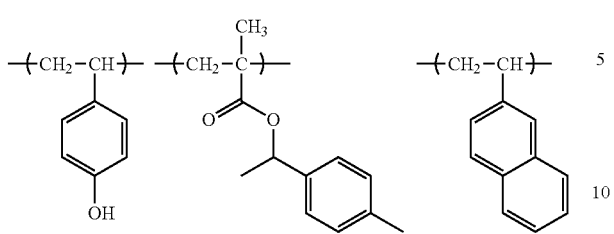
(Ab-88)
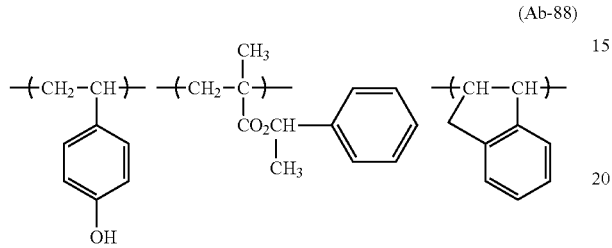
(Ab-89)
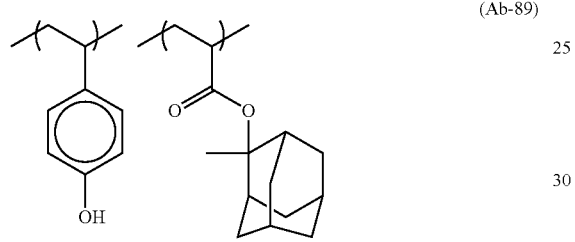
[Chem. 81]
(Ab-90)
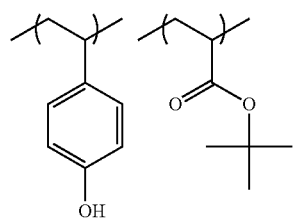
(Ab-91)
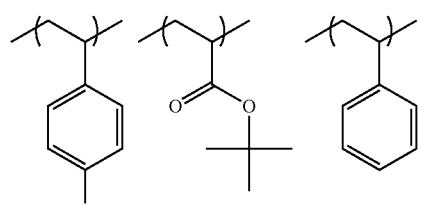
(Ab-92)
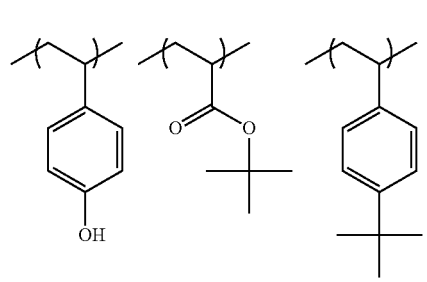
(Ab-93)
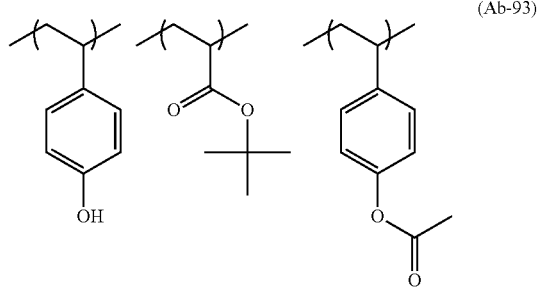
(Ab-94)
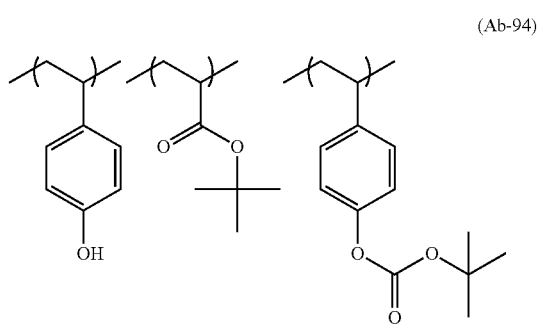
(Ab-95)
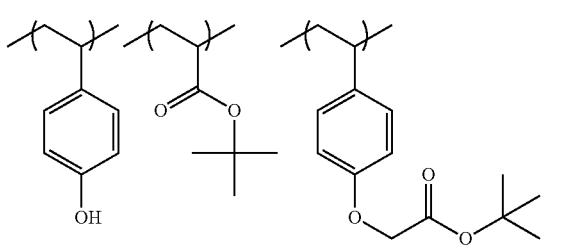
(Ab-96)
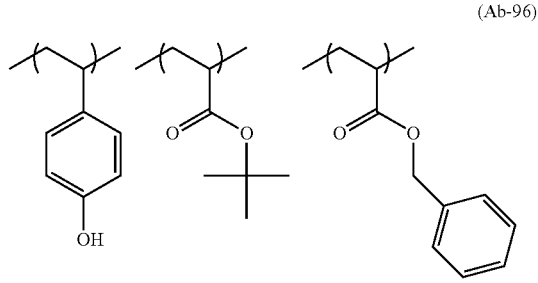
(Ab-97)
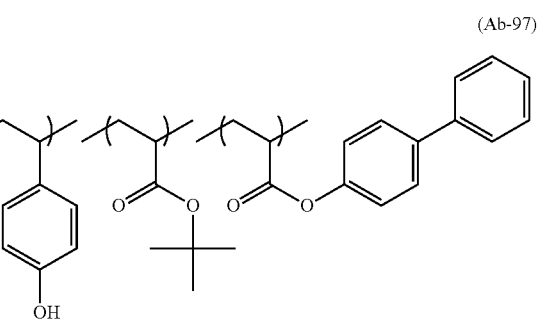

(Ab-98)
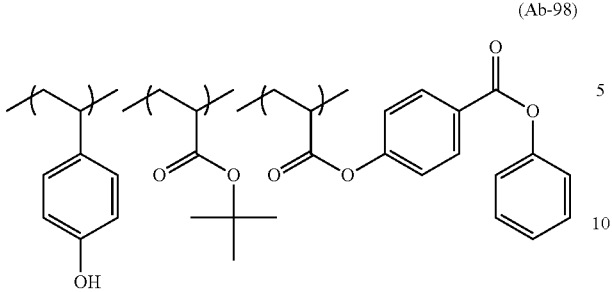
(Ab-103)
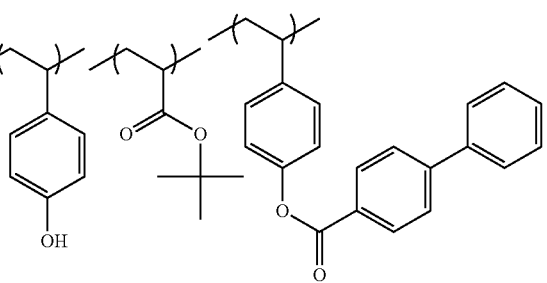
(Ab-99)
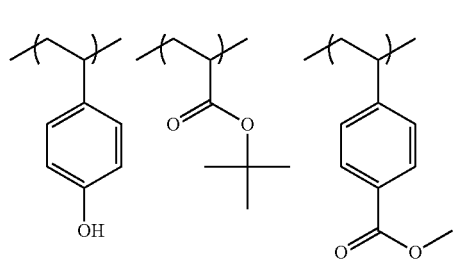
(Ab-104)
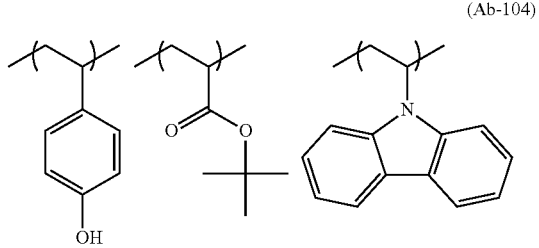
(Ab-100)
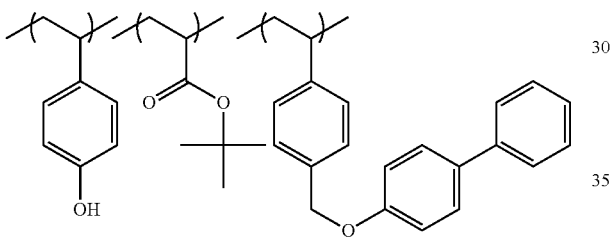
(Ab-105)
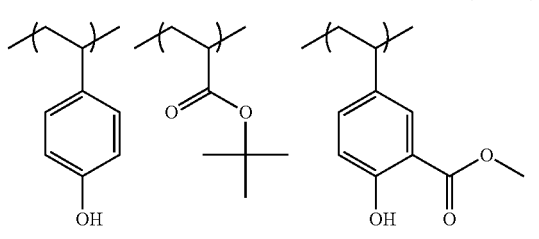
(Ab-101)
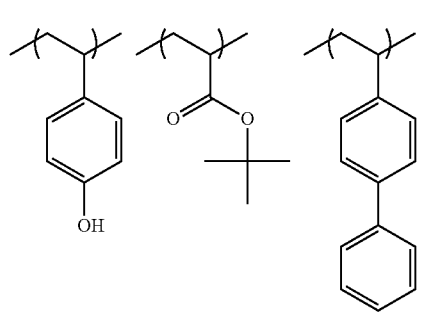
(Ab-106)
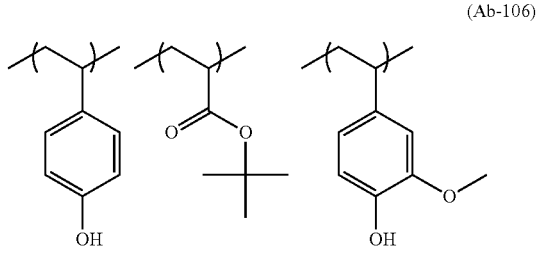
(Ab-102)
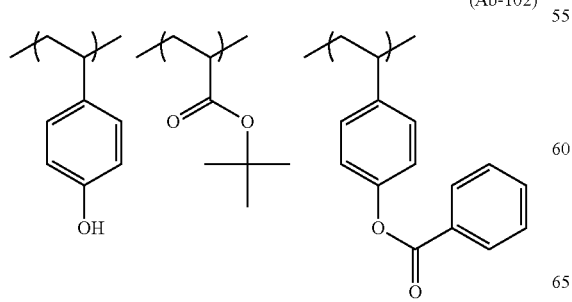
[Chem. 82]
(Ab-107)
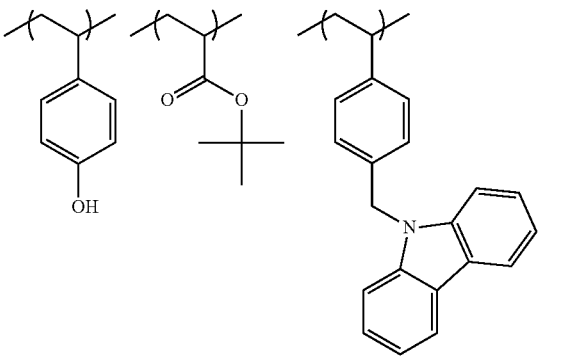

(Ab-108)
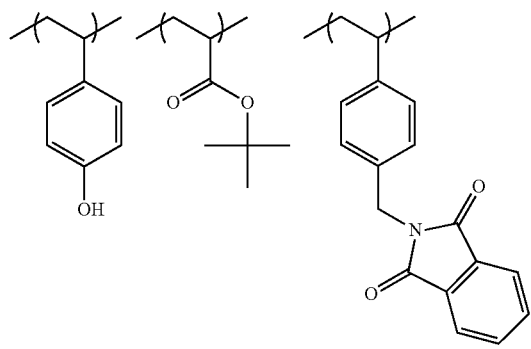
(Ab-109)
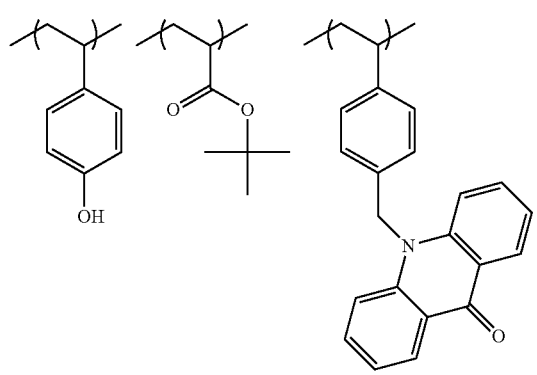
(Ab-110)
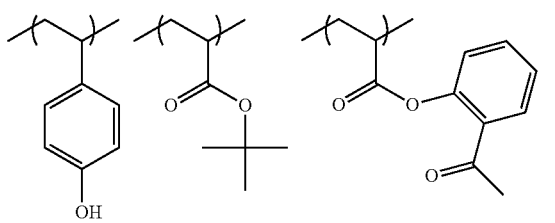
(Ab-111)
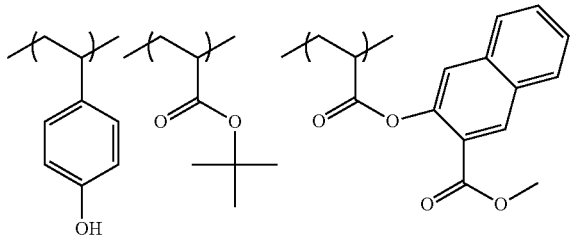
(Ab-112)
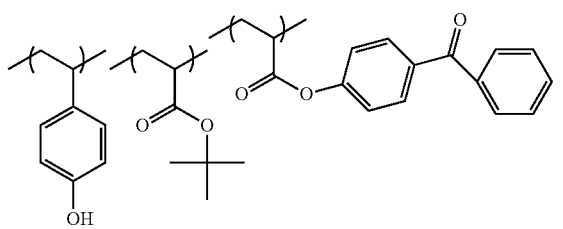
[Chem. 83]
(Ab-113)
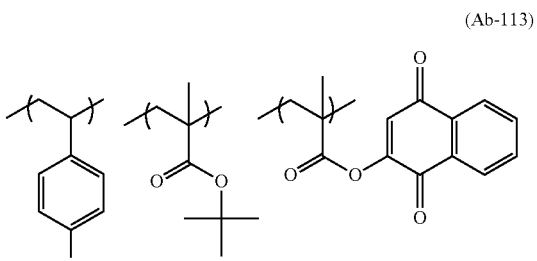
(Ab-114)
(Ab-115)
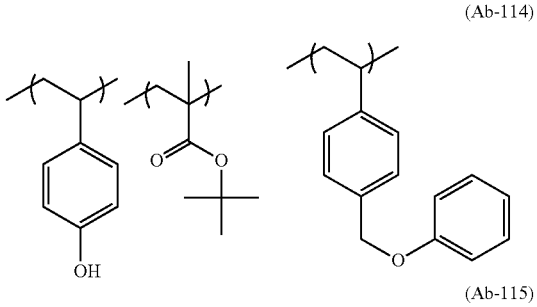
(Ab-116)
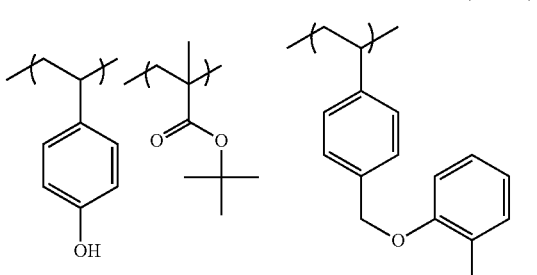
(Ab-117)
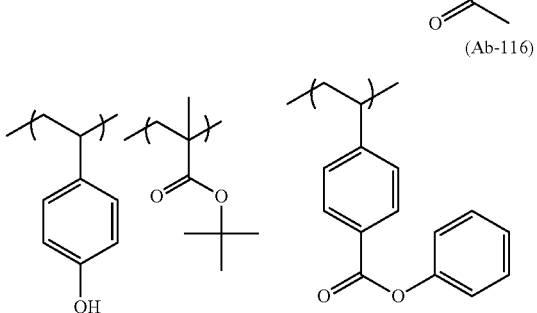
(Ab-118)
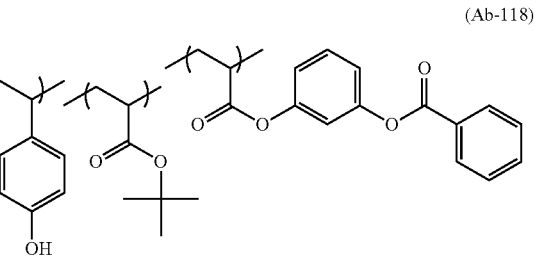

(Ab-119)
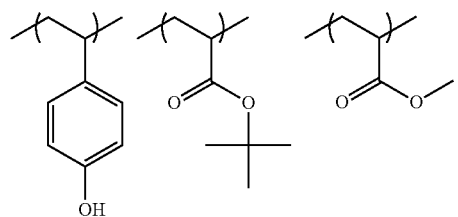
(Ab-120)
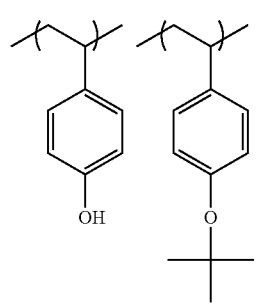
(Ab-121)
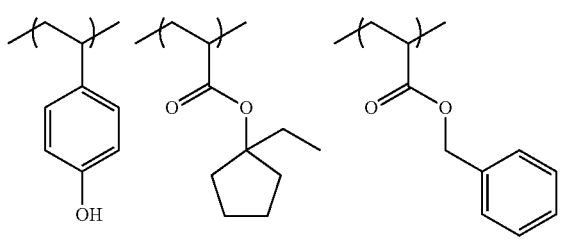
[Chem. 84]
(Ab-122)
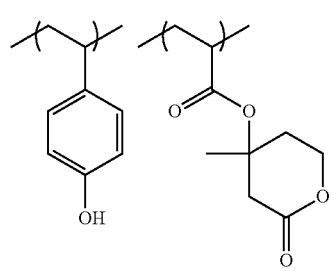
(Ab-123)
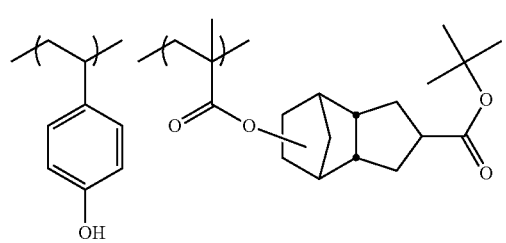
(Ab-124)
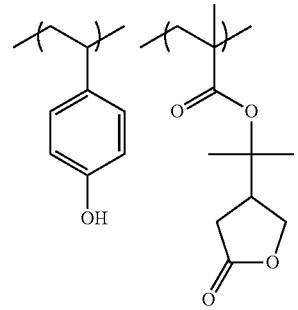
(Ab-125)
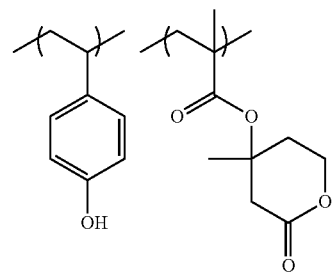
(Ab-126)
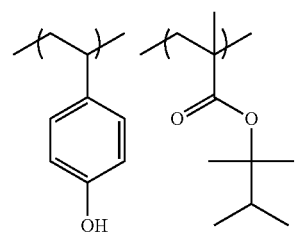
(Ab-127)
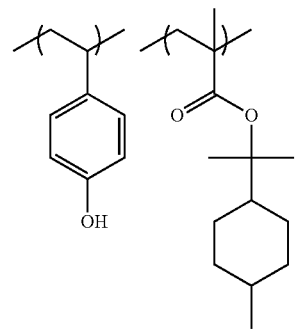
(Ab-128)
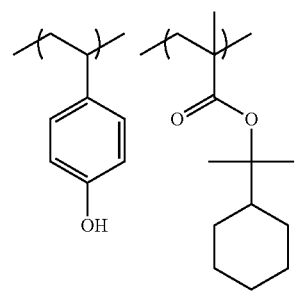

(Ab-129) 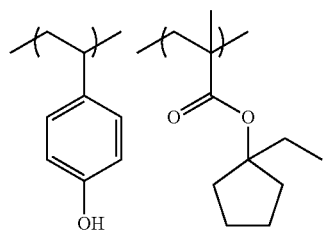
(Ab-130) 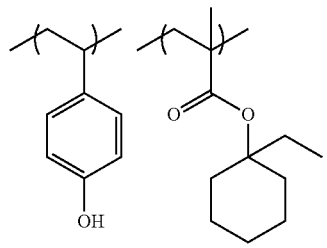
(Ab-131) 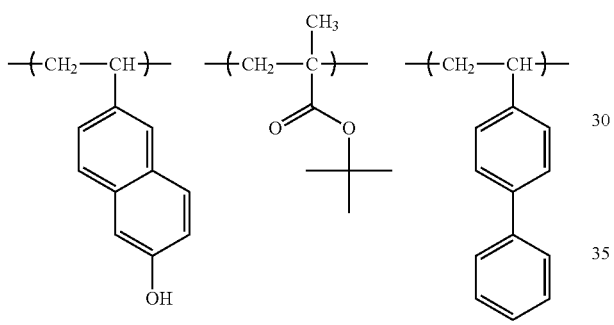
(Ab-132) 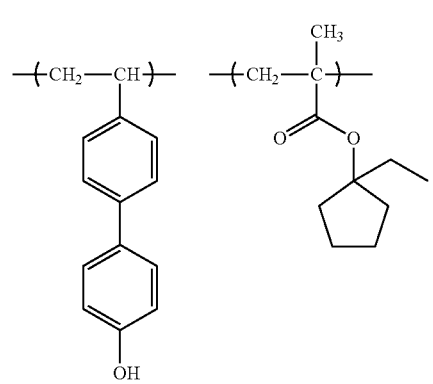
(Ab-133) 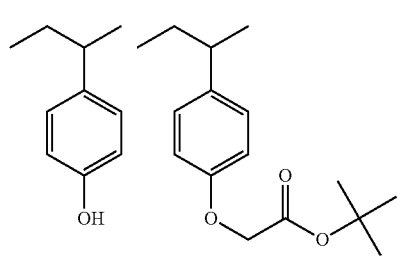
(Ab-134) 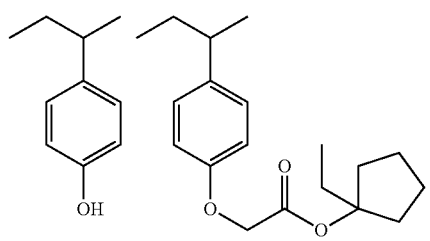
(Ab-135) 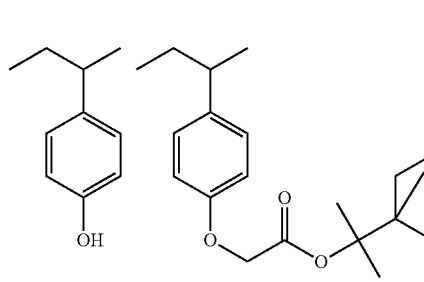
(Ab-136) 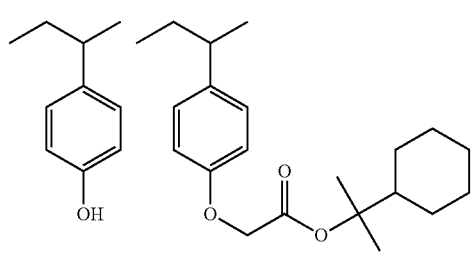
(Ab-137) 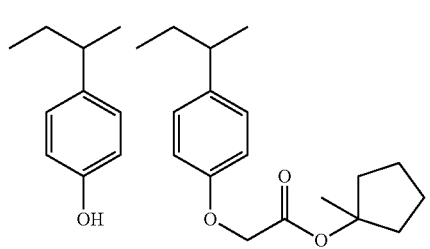
(Ab-138) 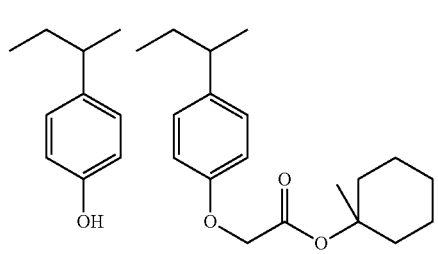

[Chem. 85]
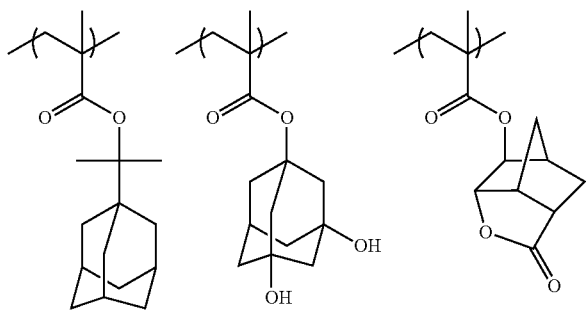
(Ab-139)
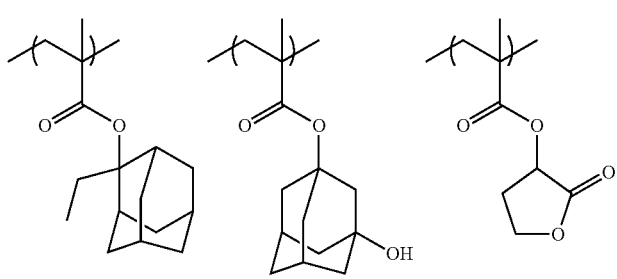
(Ab-140)
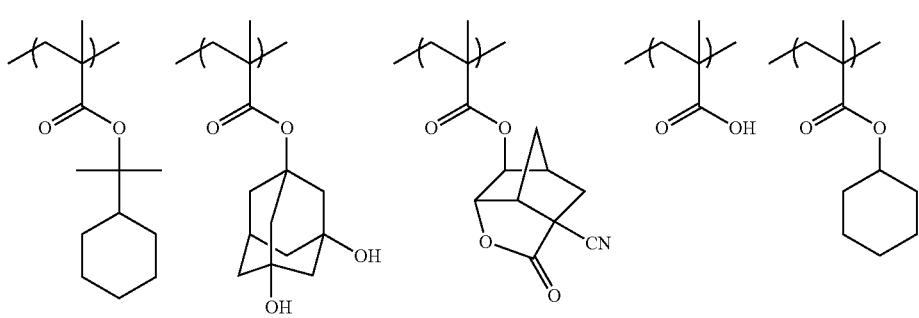
(Ab-141)
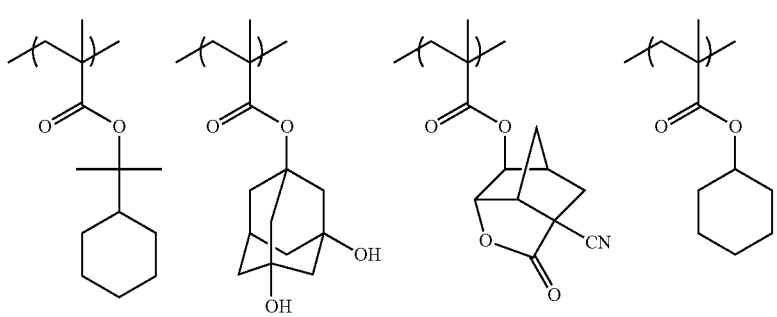
(Ab-142)
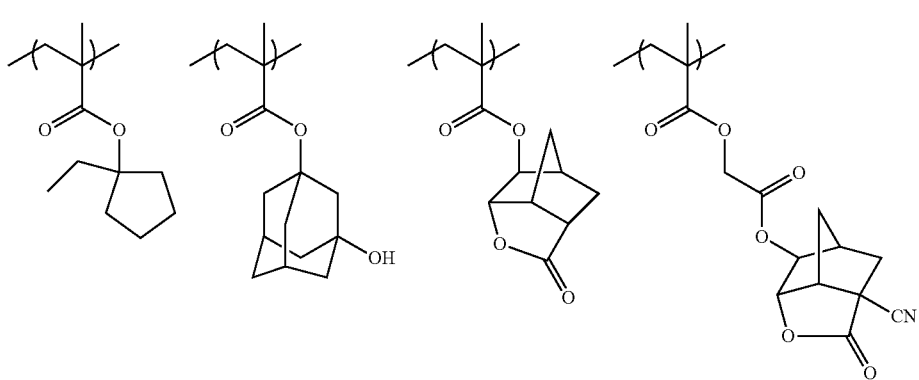
(Ab-143)

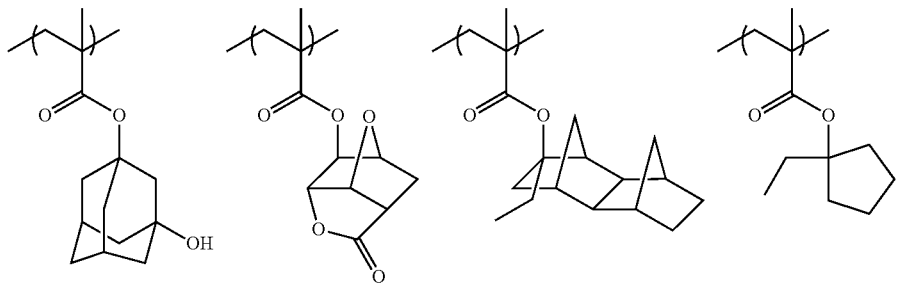
(Ab-144)
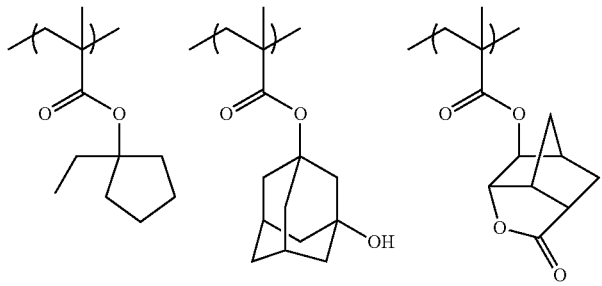
(Ab-145)
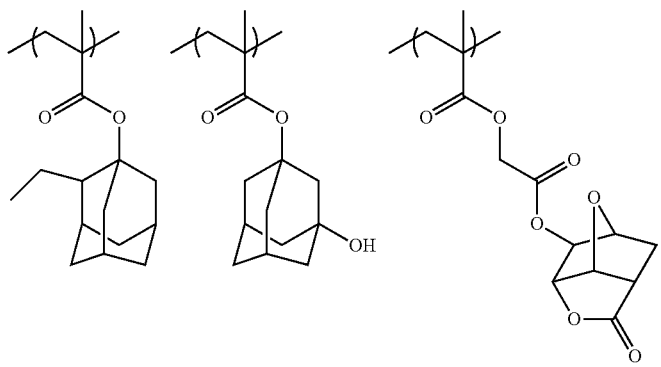
(Ab-146)
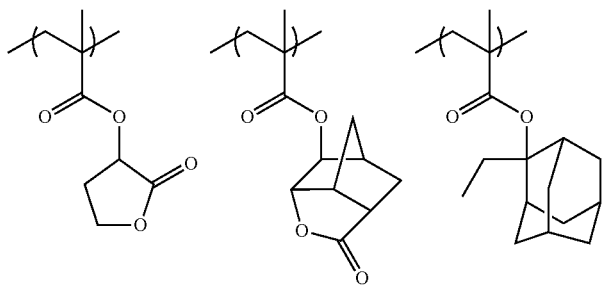
(Ab-147)
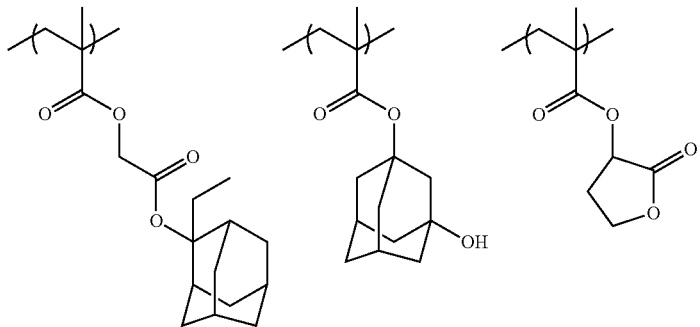
(Ab-148)

[Chem. 86]
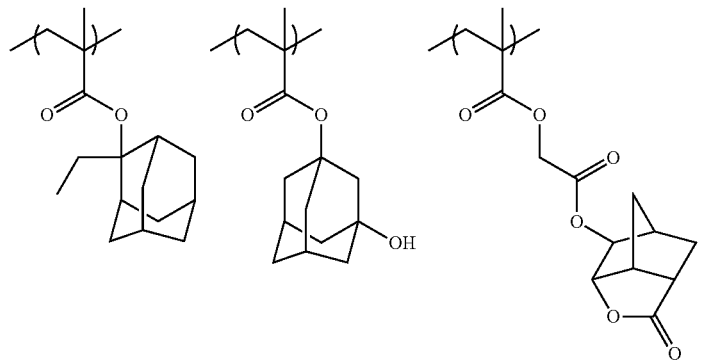
(Ab-149)
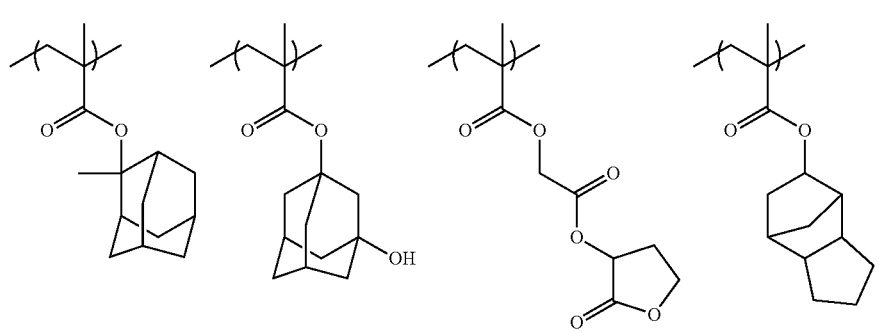
(Ab-150)
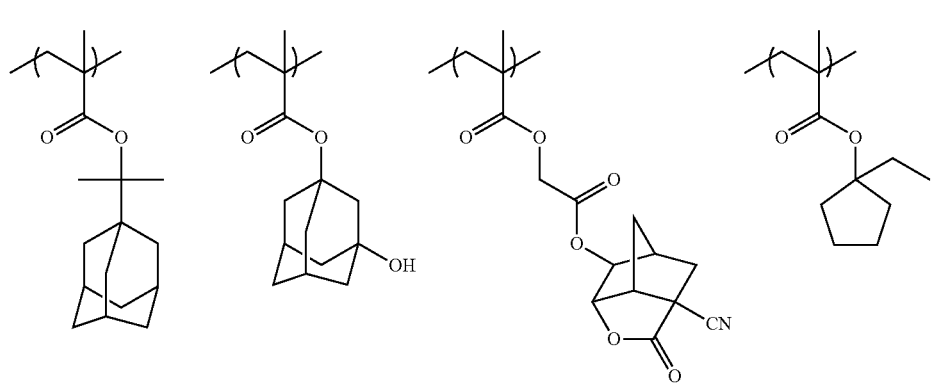
(Ab-151)
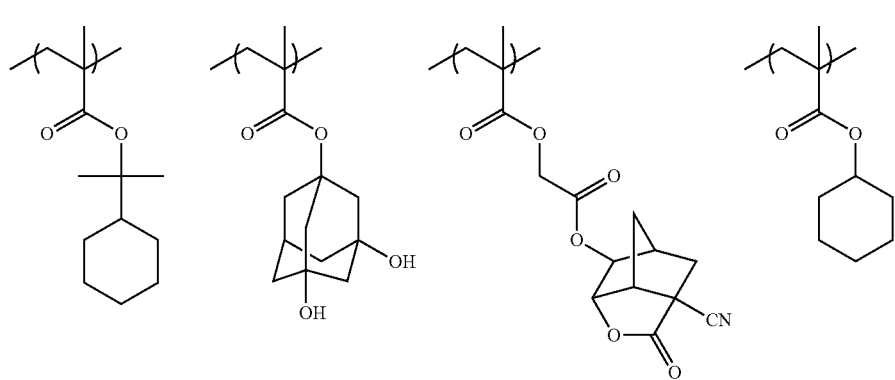
(Ab-152)

-continued
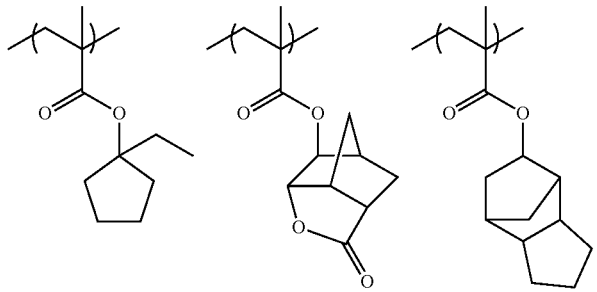
(Ab-153)
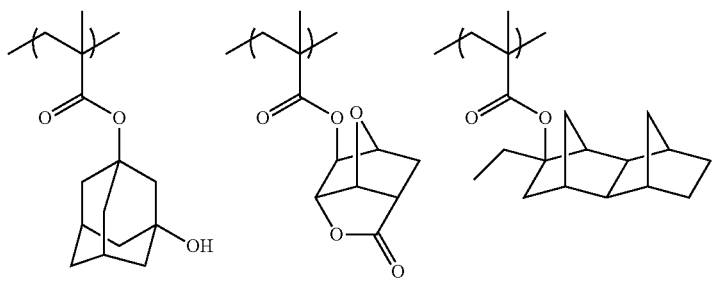
(Ab-154)
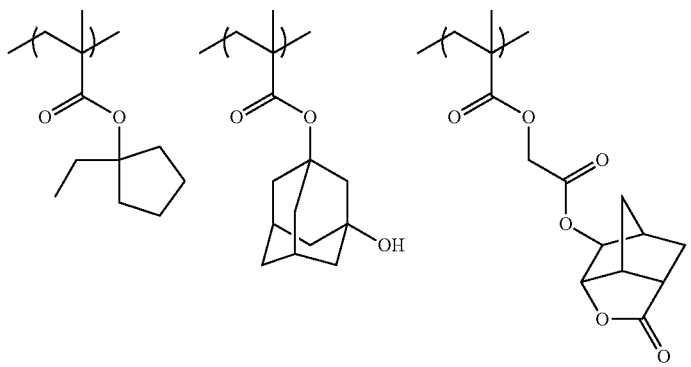
(Ab-155)
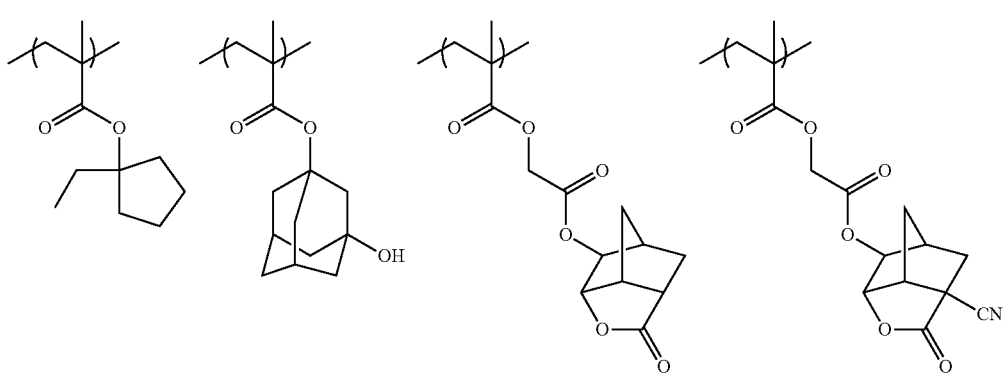
(Ab-156)

[Chem. 87]
(Ab-157)
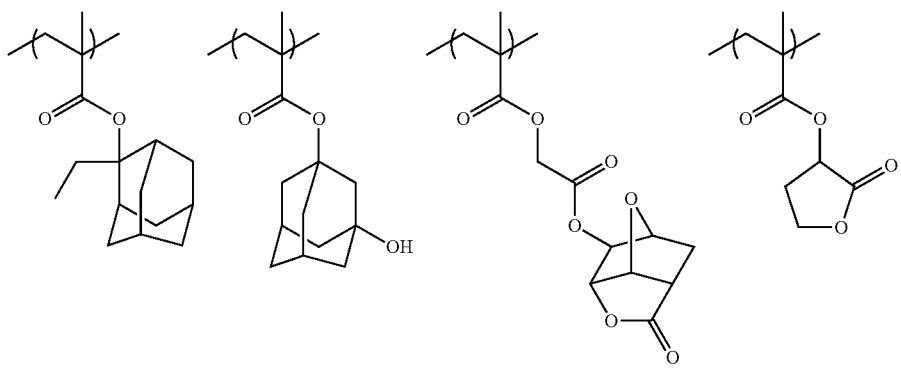
(Ab-158)
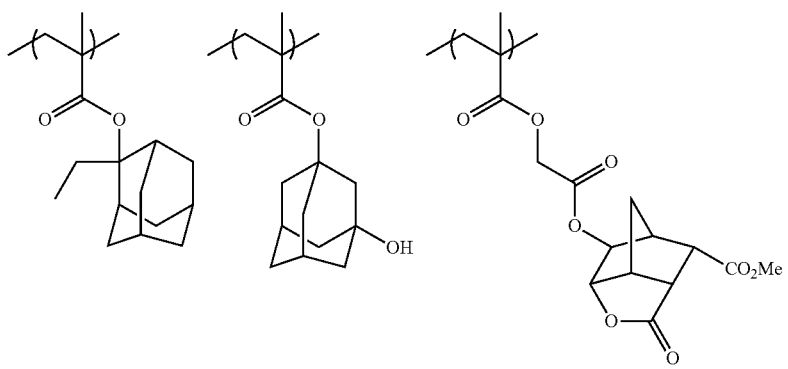
(Ab-159)
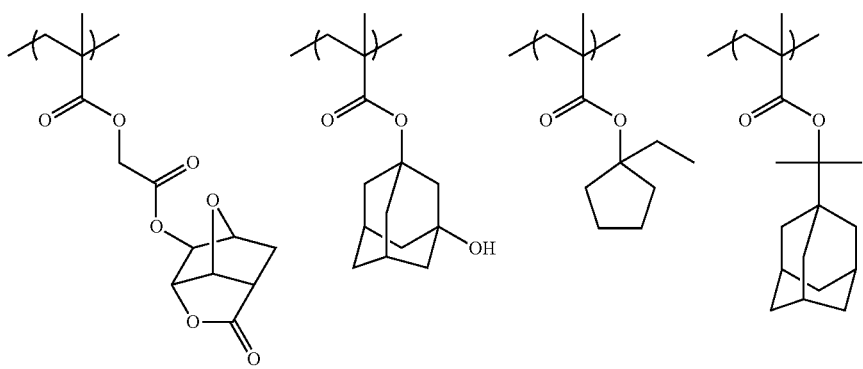
(Ab-160)
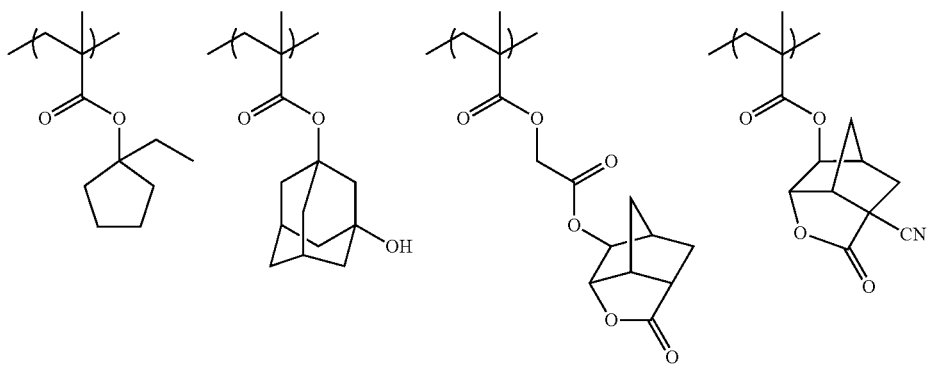

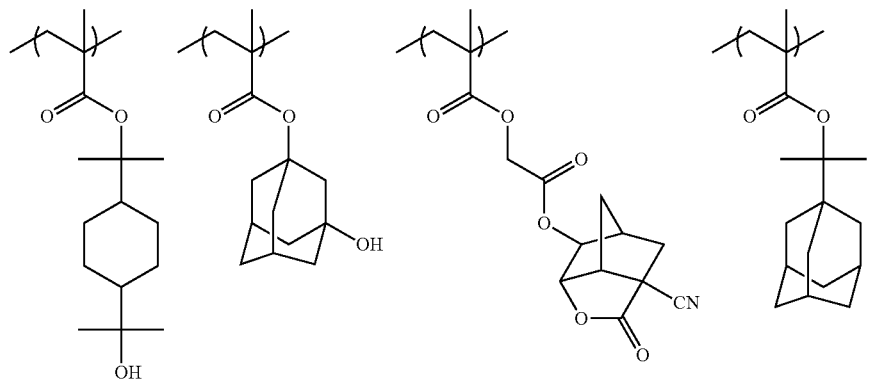
(Ab-161)
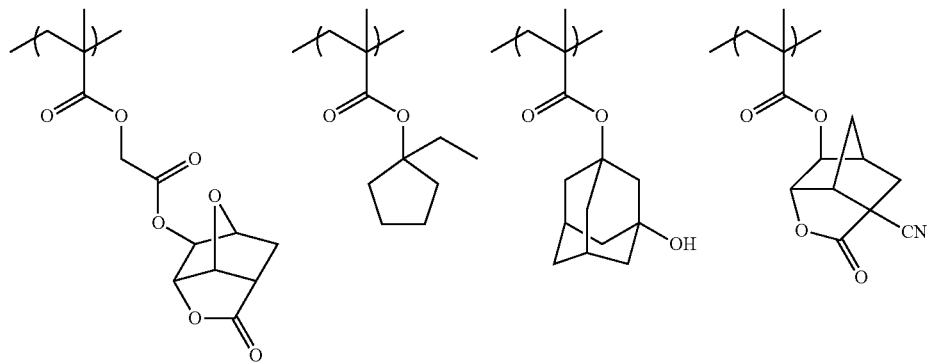
(Ab-162)
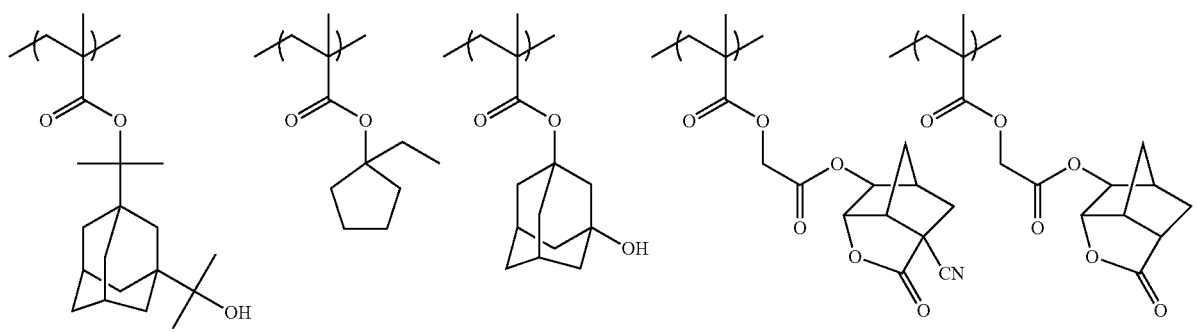
(Ab-163)
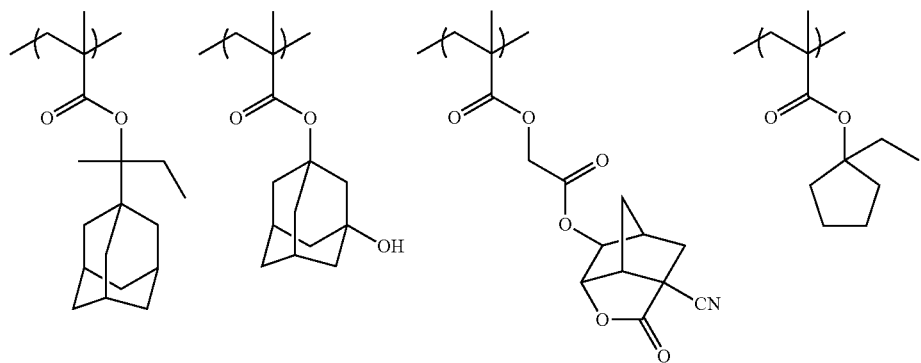
(Ab-164)

[Chem. 88]
(Ab-165)
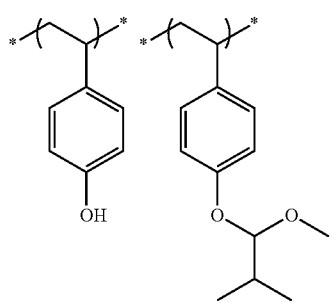
(Ab-166)
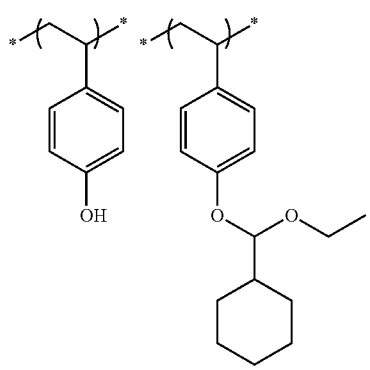
(Ab-167)
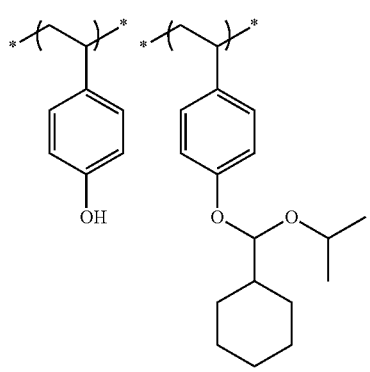
(Ab-168)
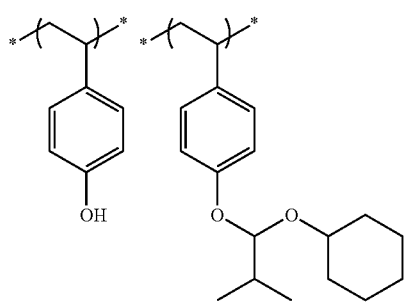
-continued
(Ab-169)
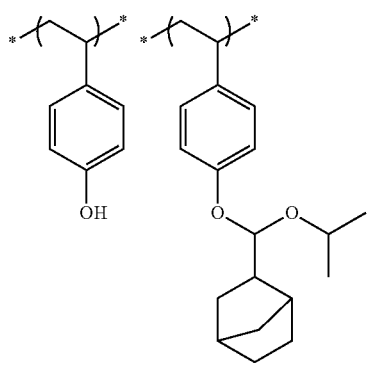
(Ab-170)
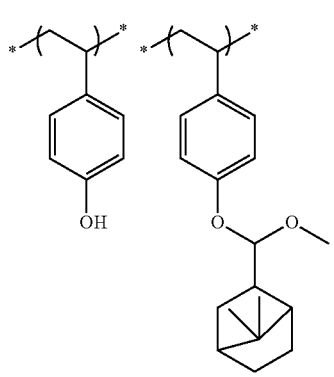
(Ab-171)
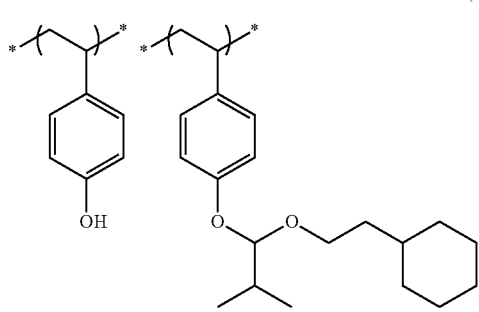
(Ab-172)
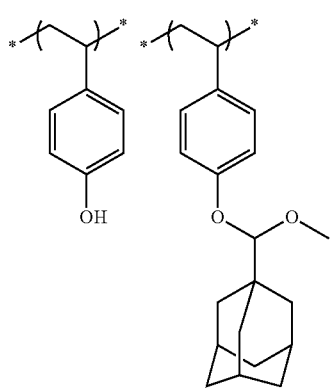

(Ab-173)
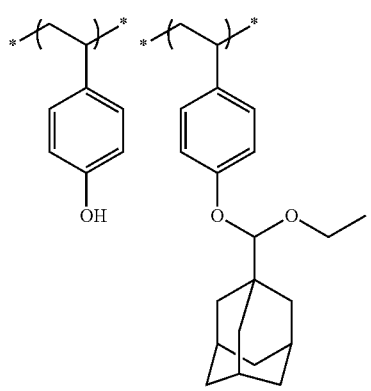
(Ab-174)
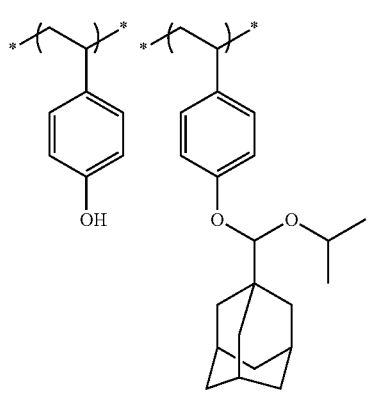
(Ab-175)
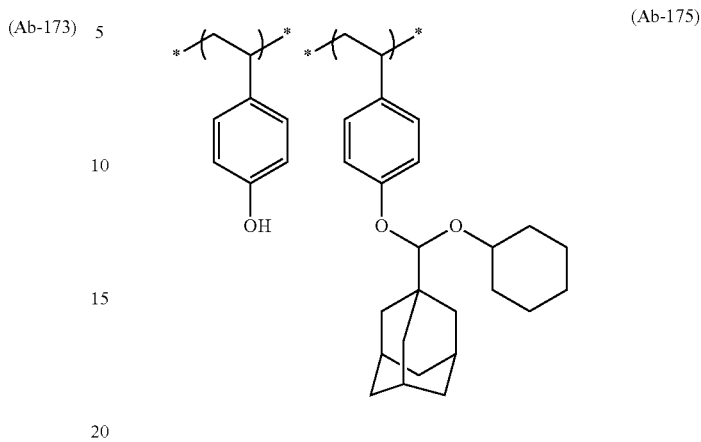
(Ab-176)
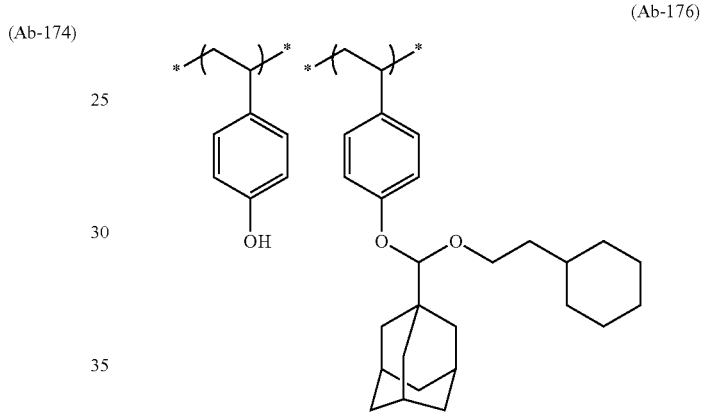
[Chem. 89]
Ab-177
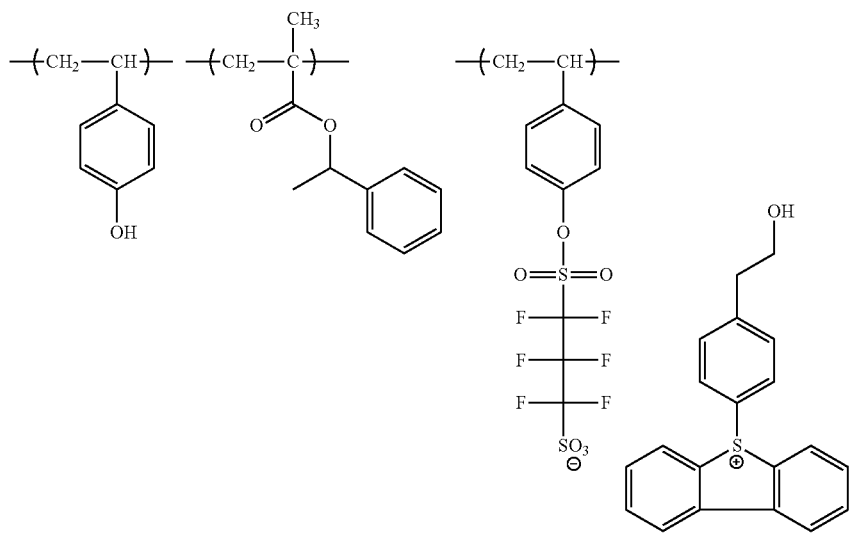

-continued
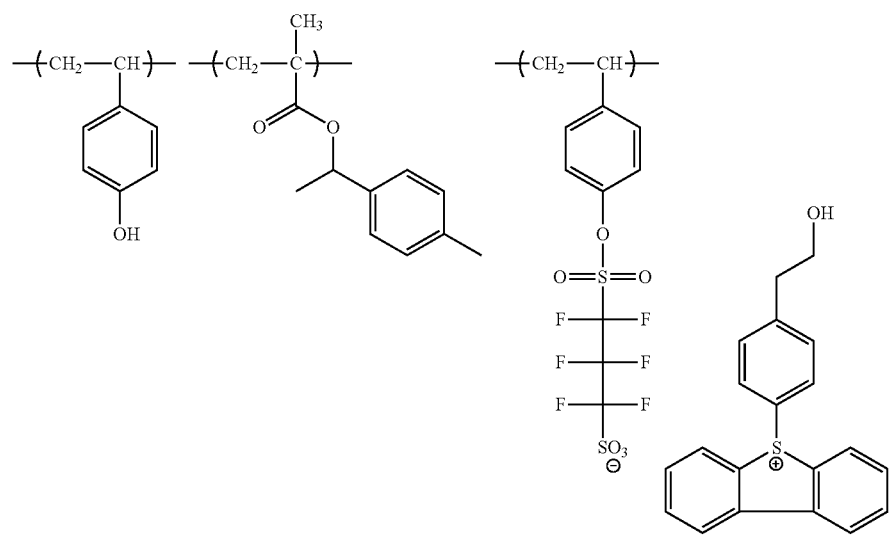
Ab-178
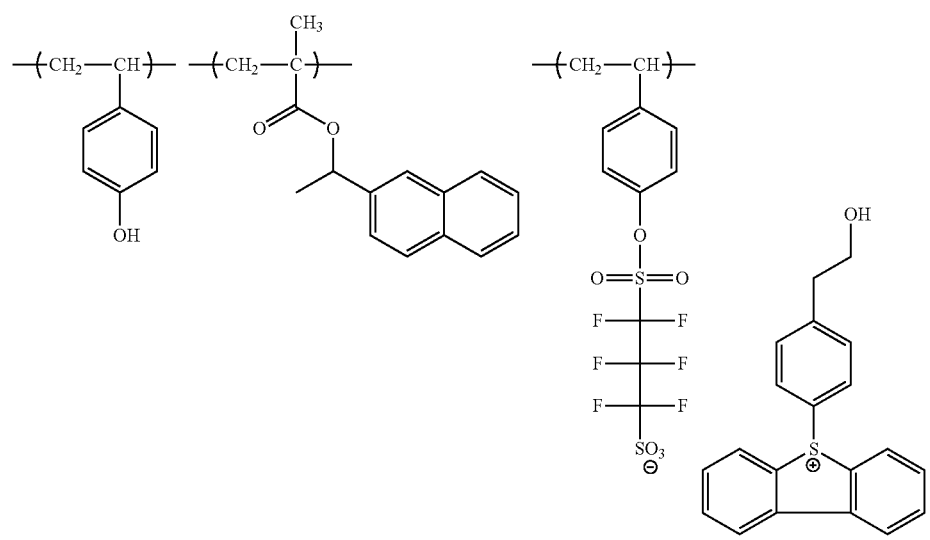
Ab-179
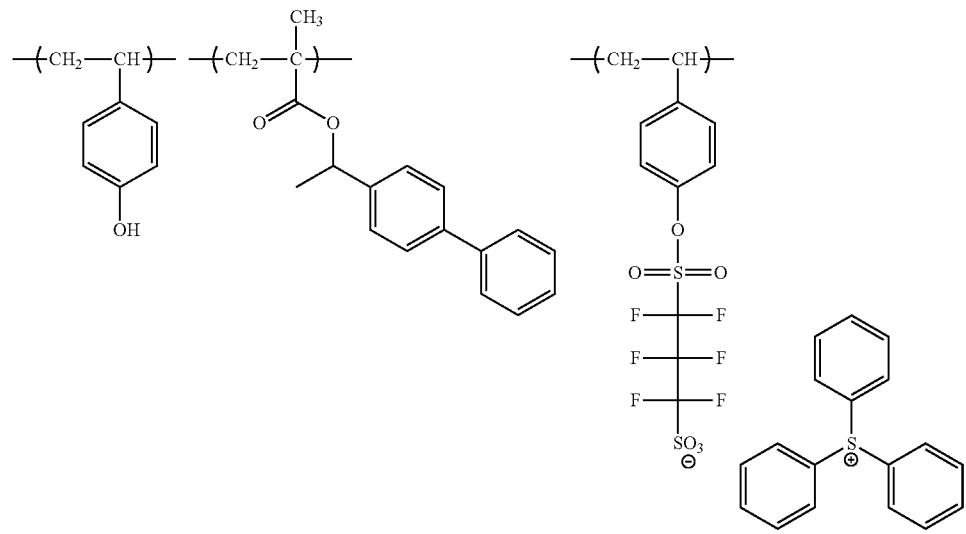
Ab-180

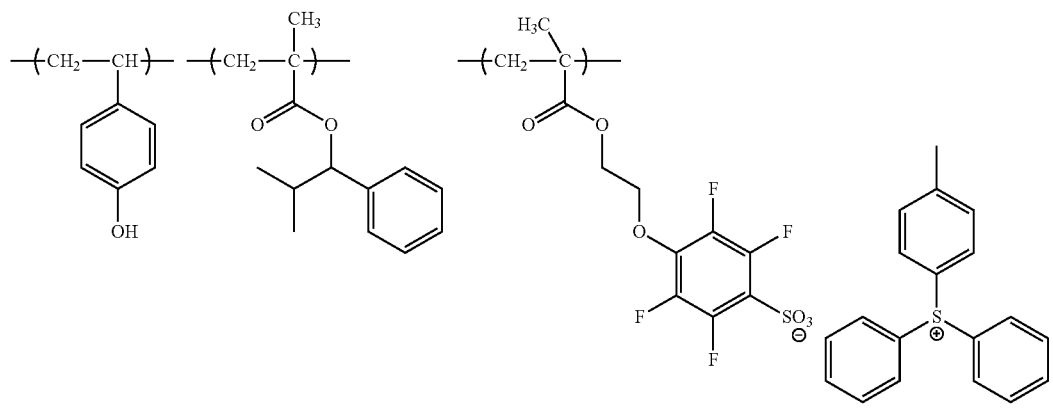
Ab-181
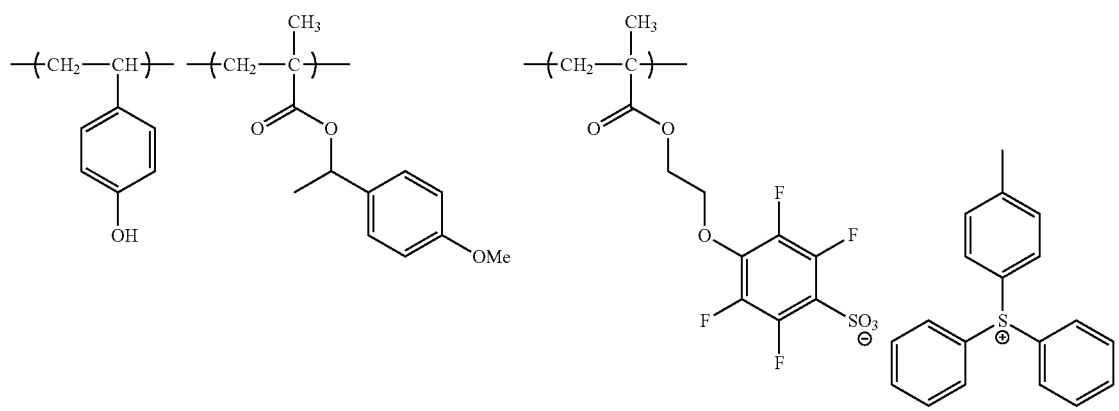
Ab-182
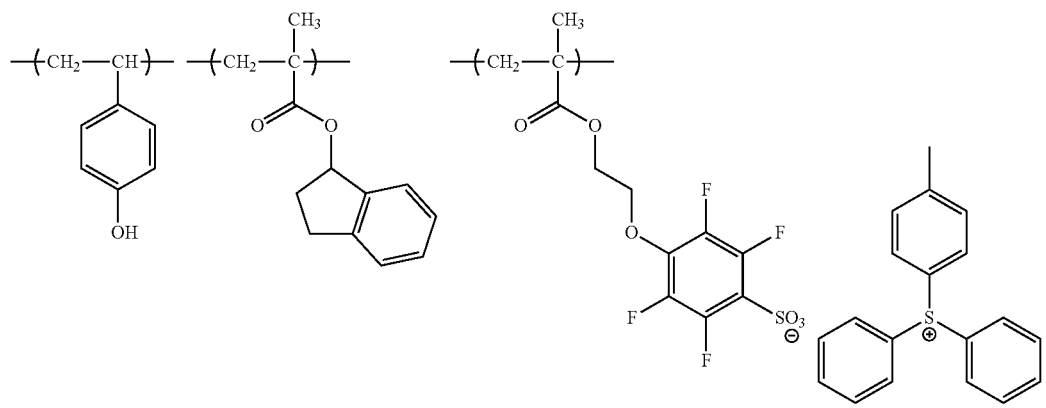
Ab-183

-continued
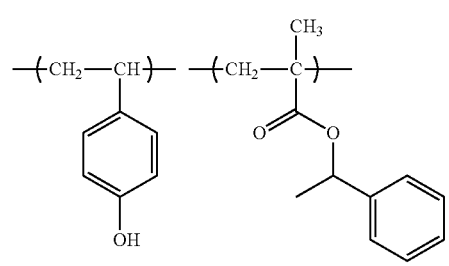
Ab-184
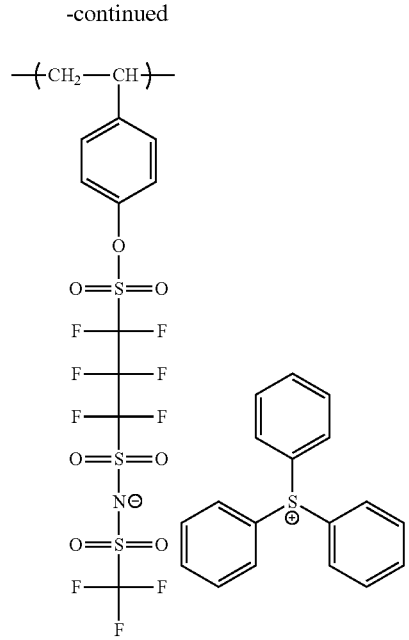
[Chem. 90]
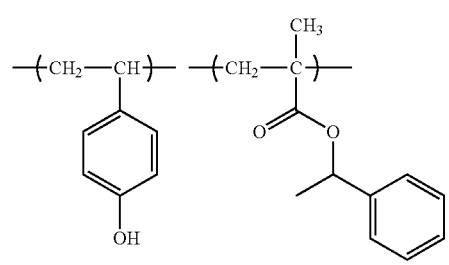
Ab-185
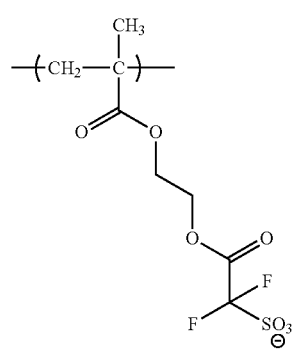
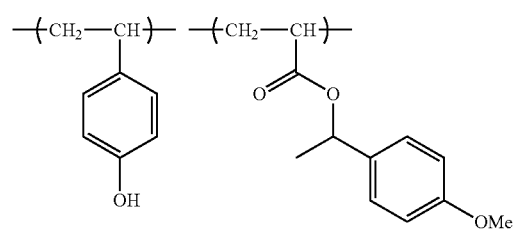
Ab-186
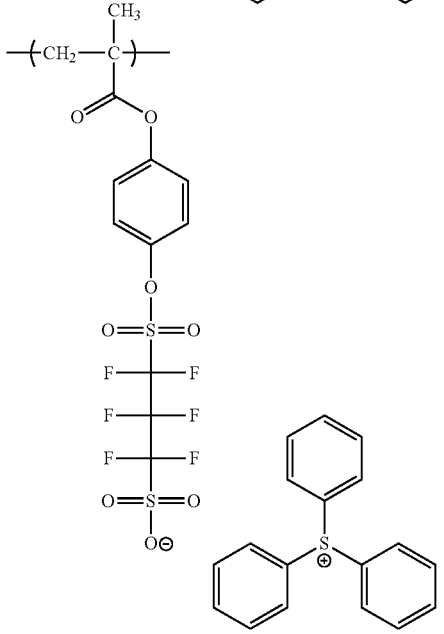

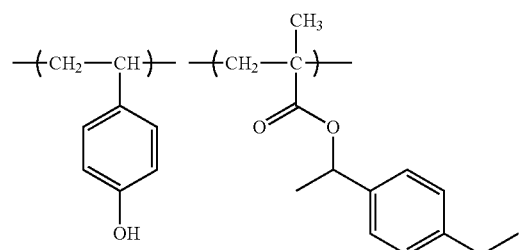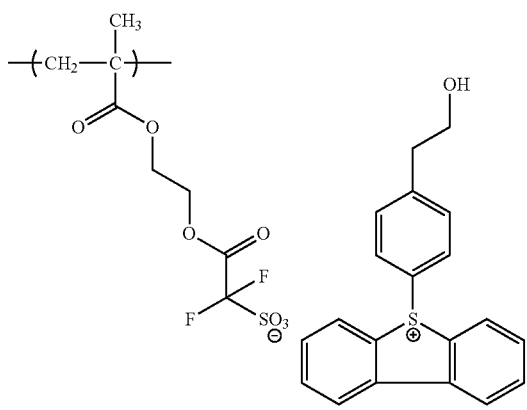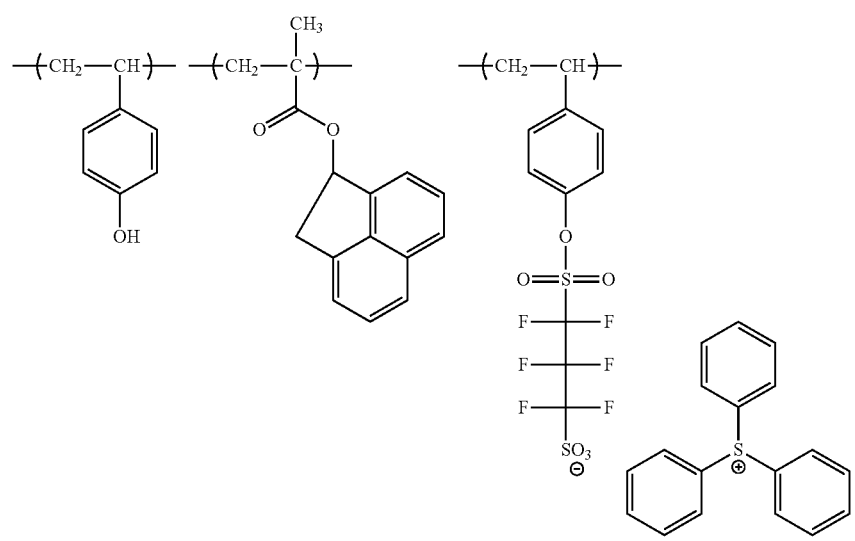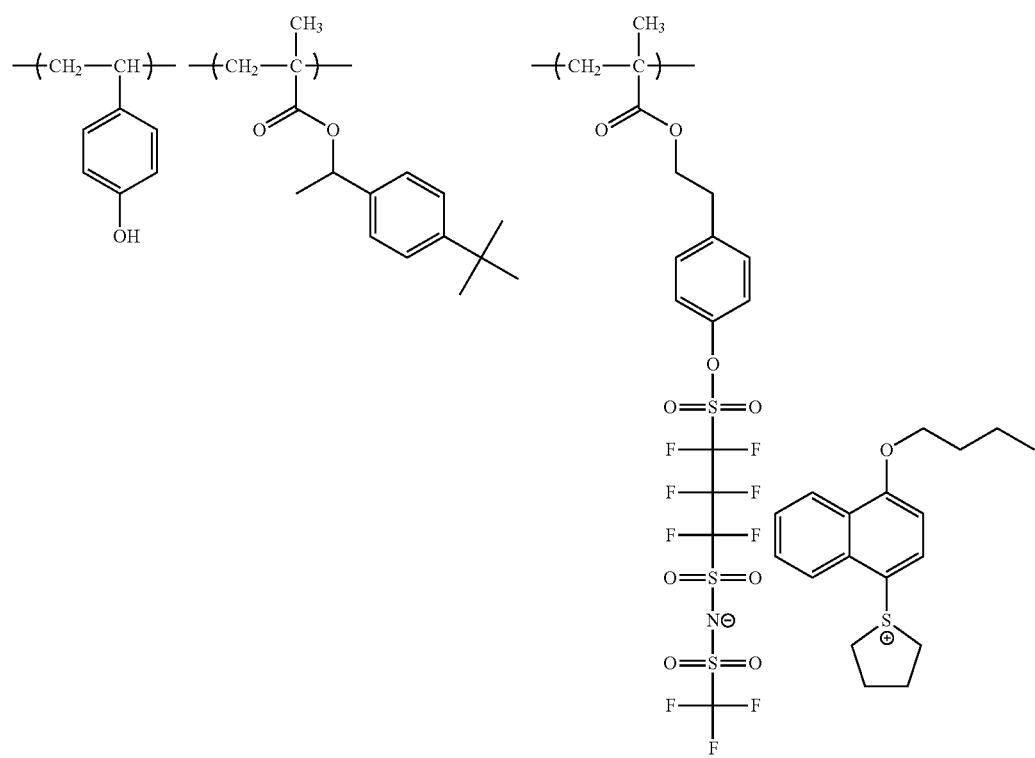

-continued
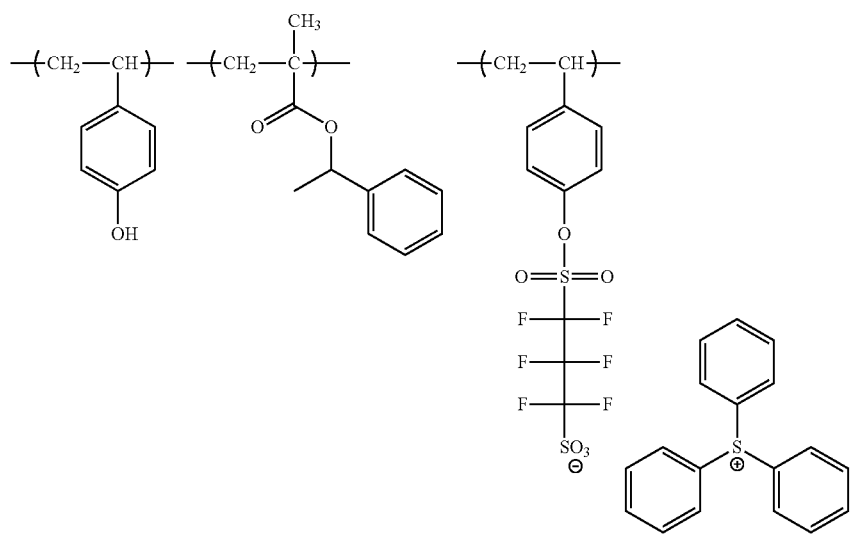
Ab-190
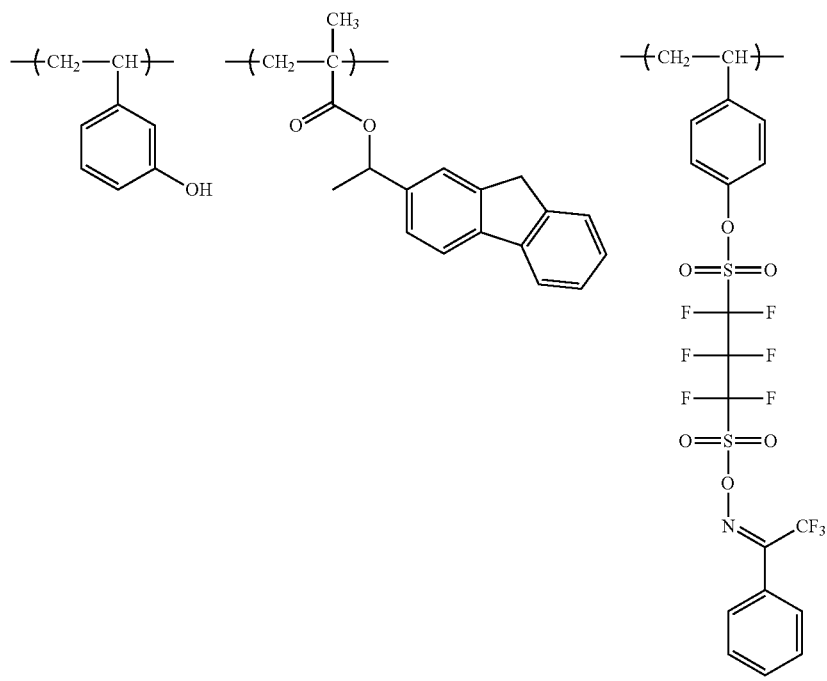
Ab-191
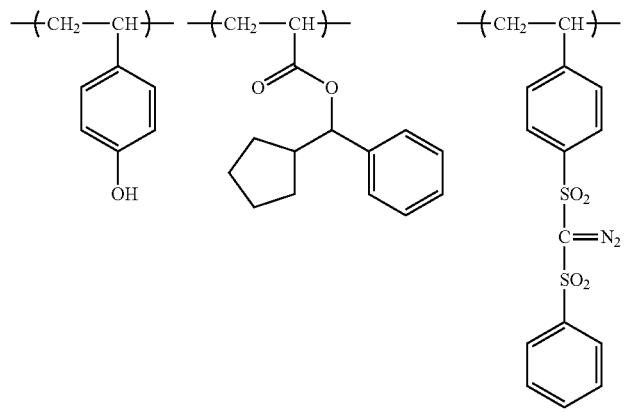
Ab-192

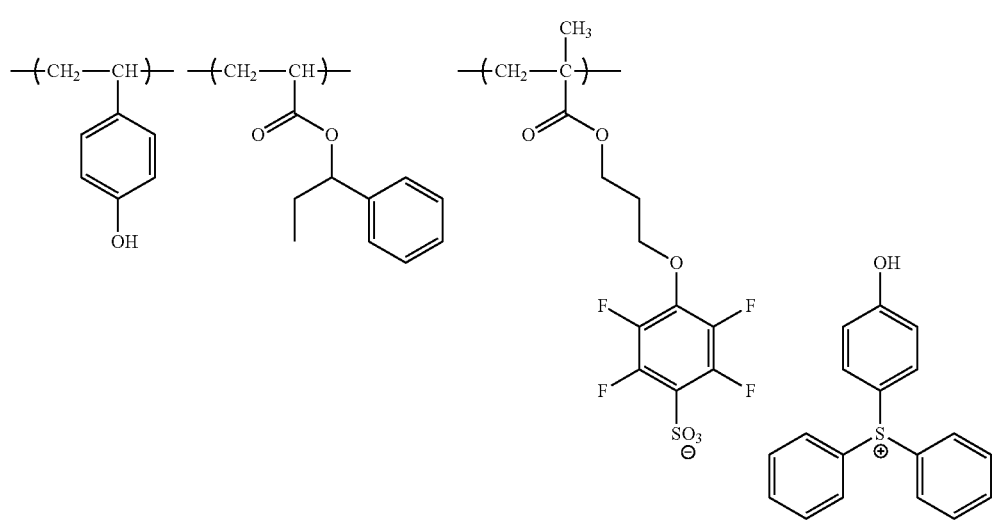
Ab-193
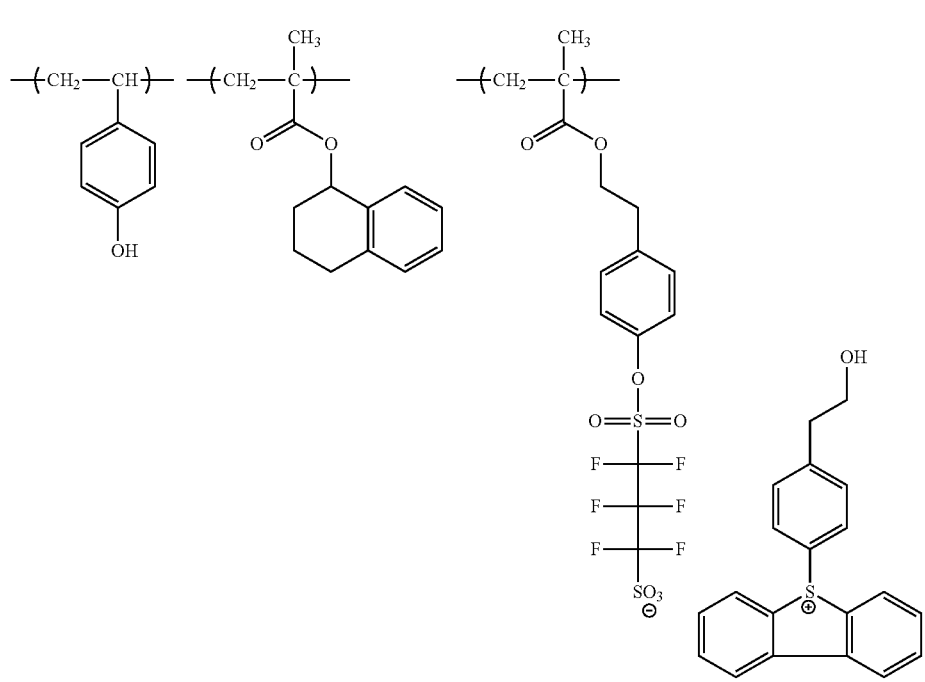
Ab-194

-continued
Ab-195
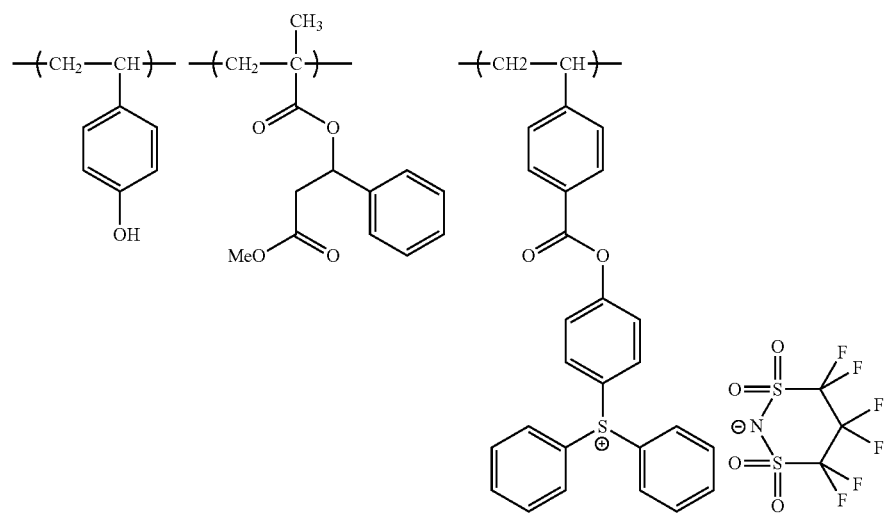
Ab-196
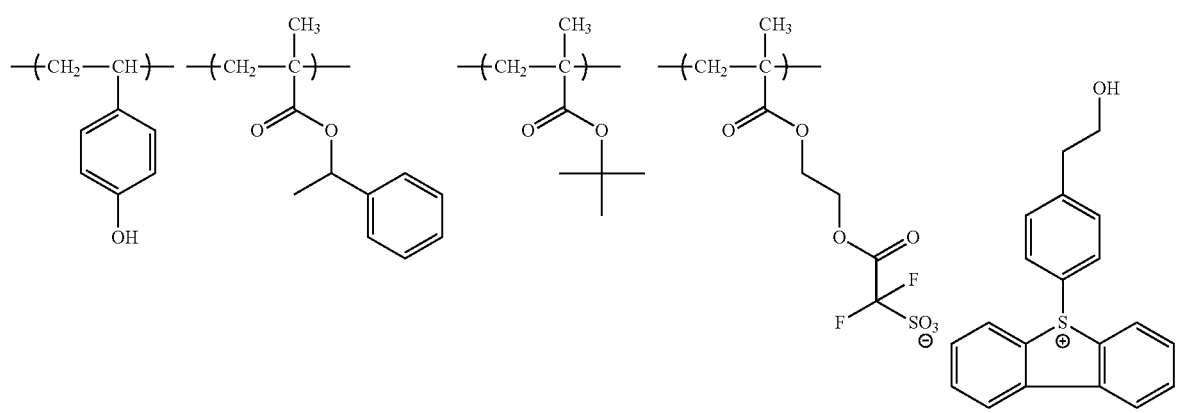
Ab-197
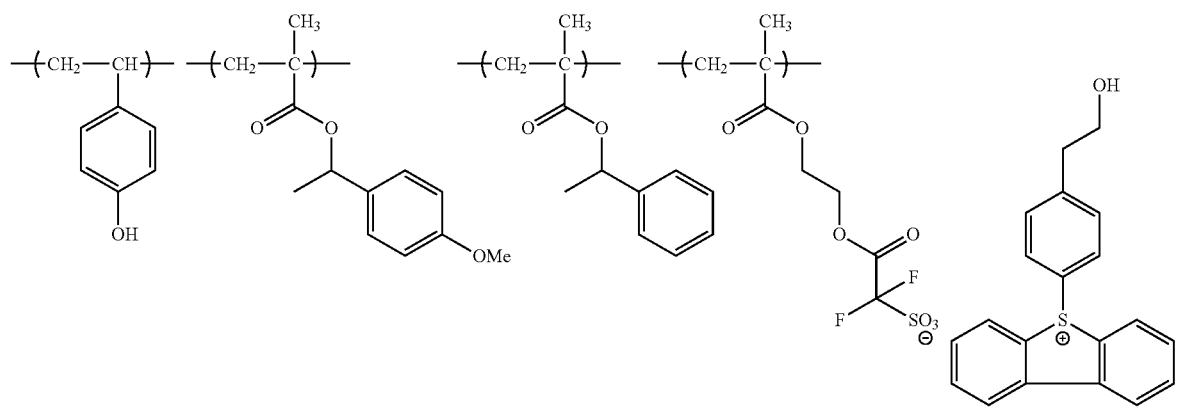

-continued
Ab-198
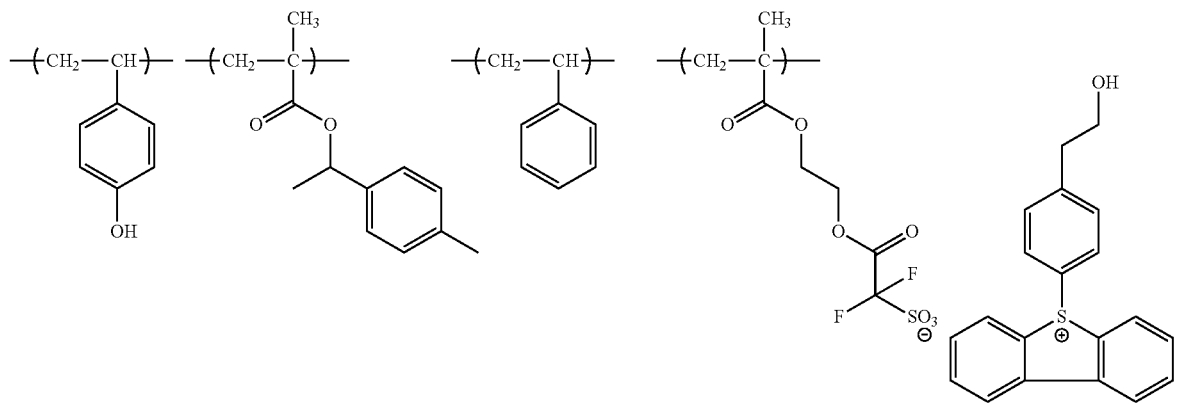
[Chem. 92]
Ab-199
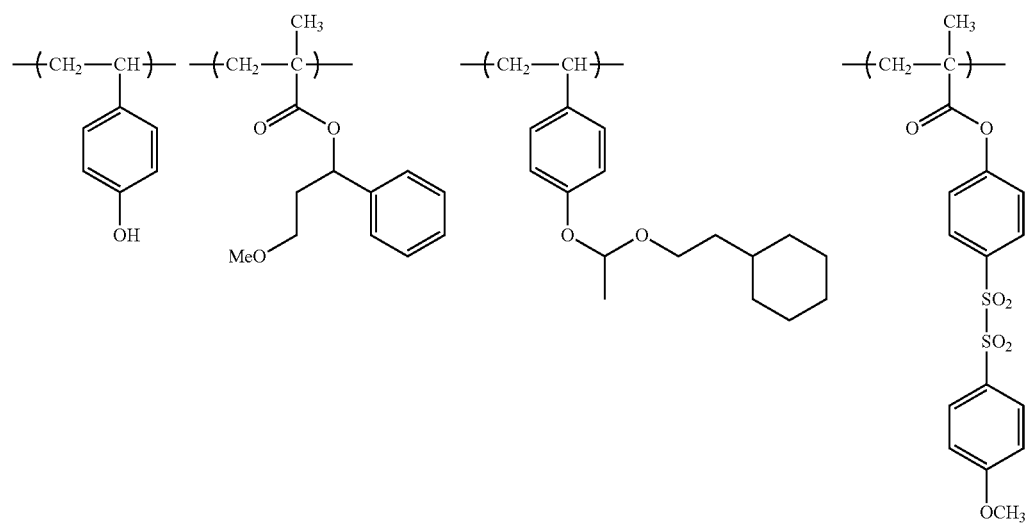
Ab-200
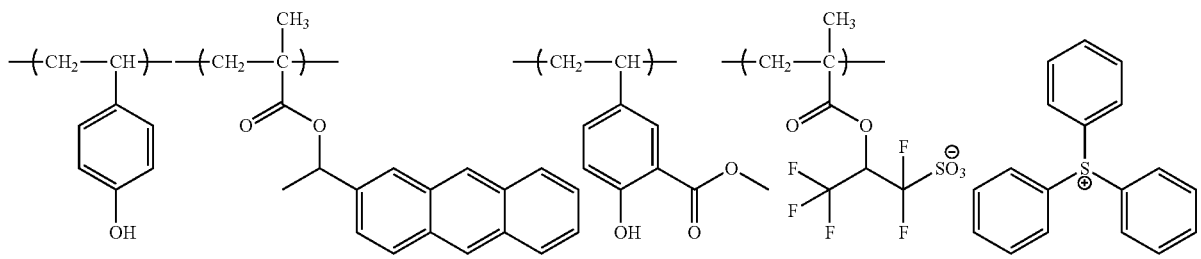

-continued
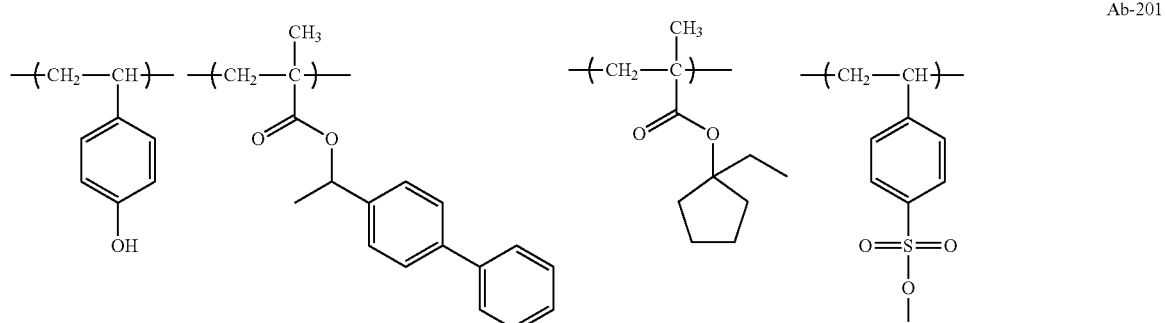
Ab-201
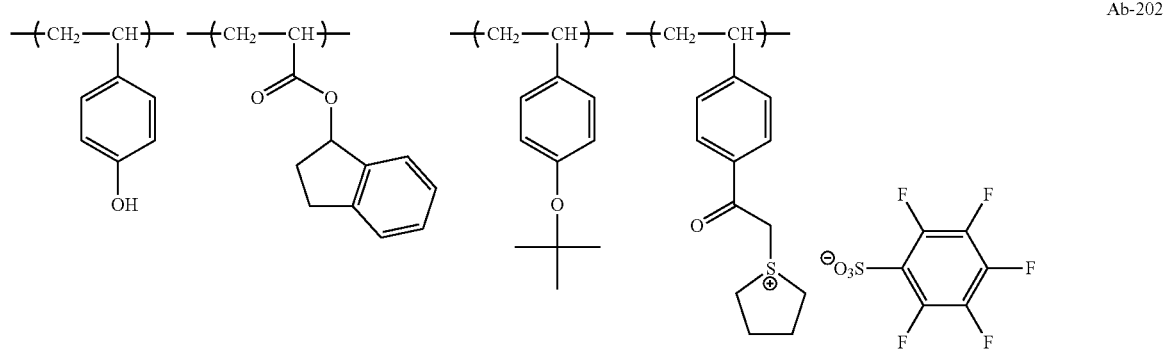
Ab-202
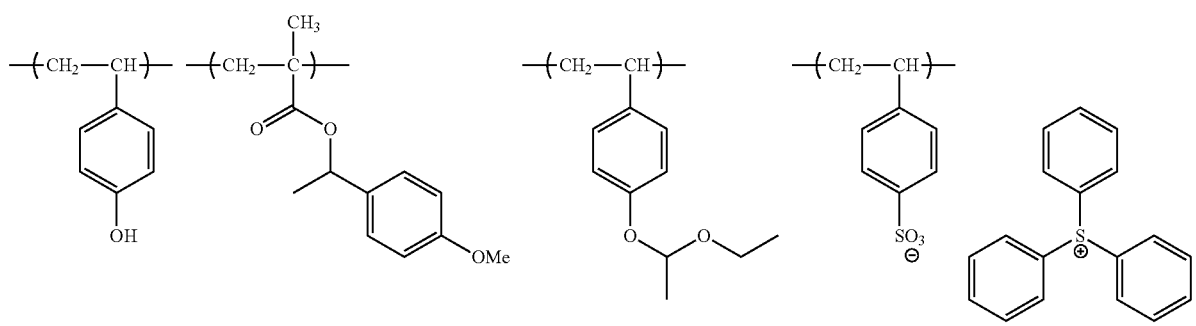
Ab-203
[Chem. 93]
Ab-204
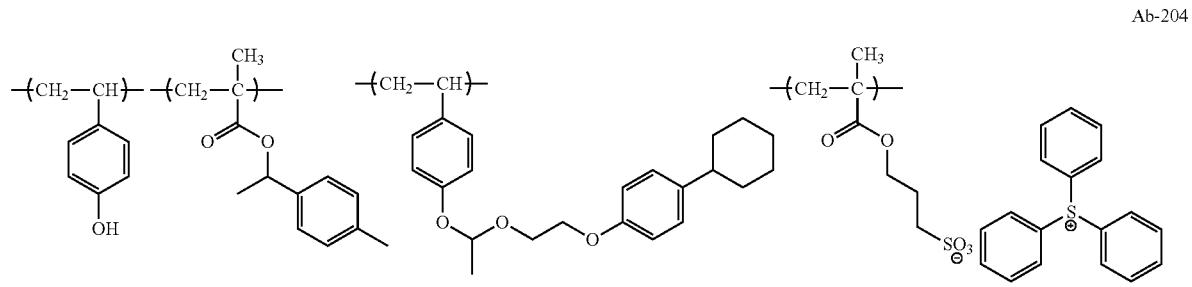

-continued
Ab-205
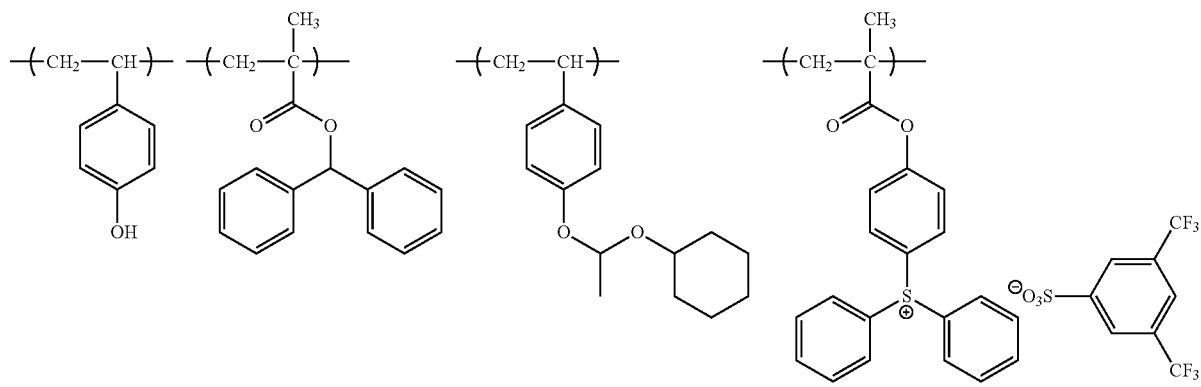
Ab-206
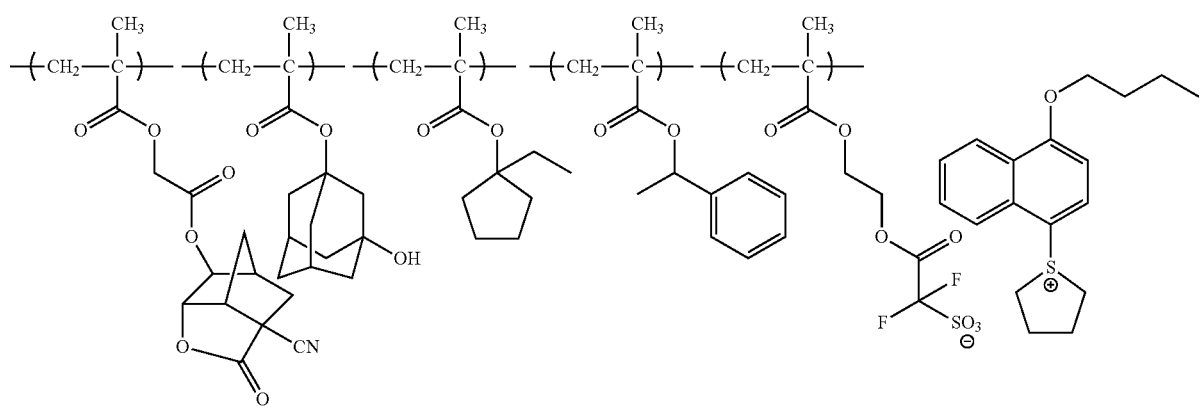
Ab-207
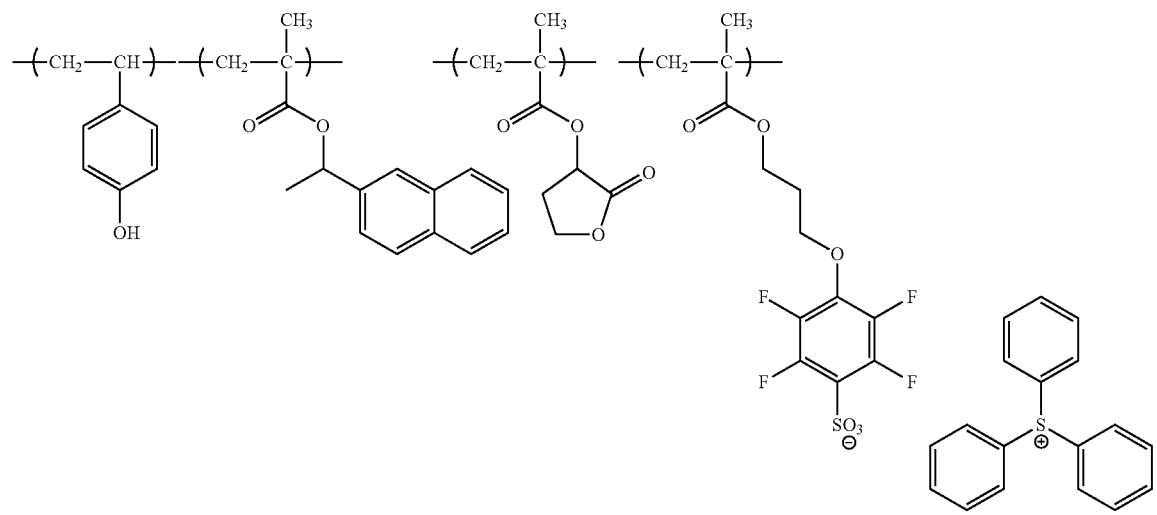

Ab-208
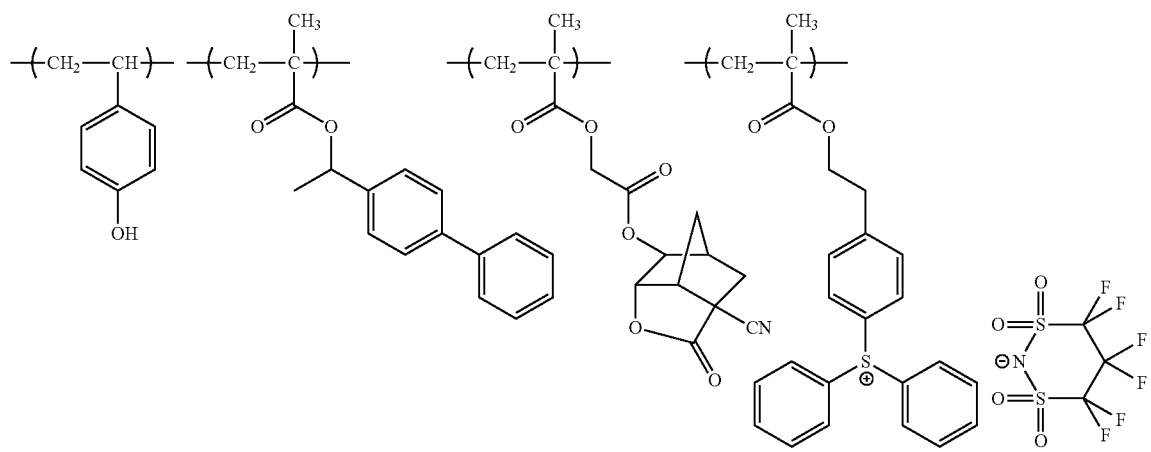
Ab-209
Ab-210

-continued
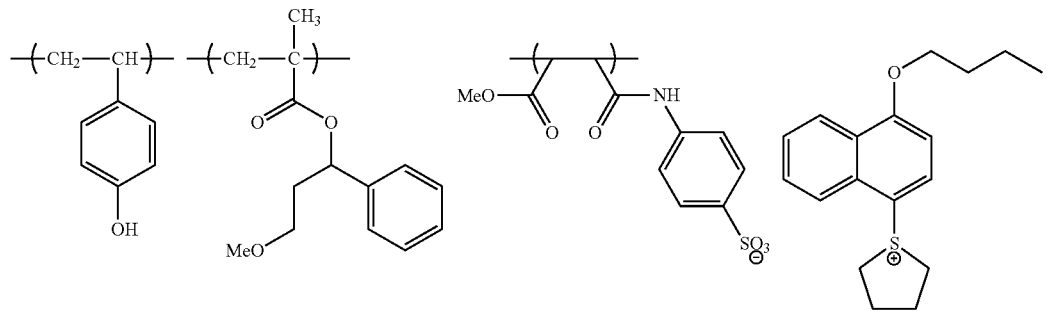
Ab-211
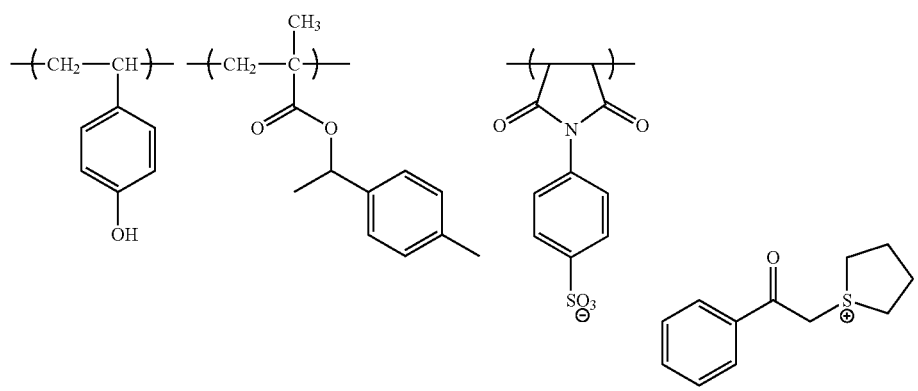
Ab-212
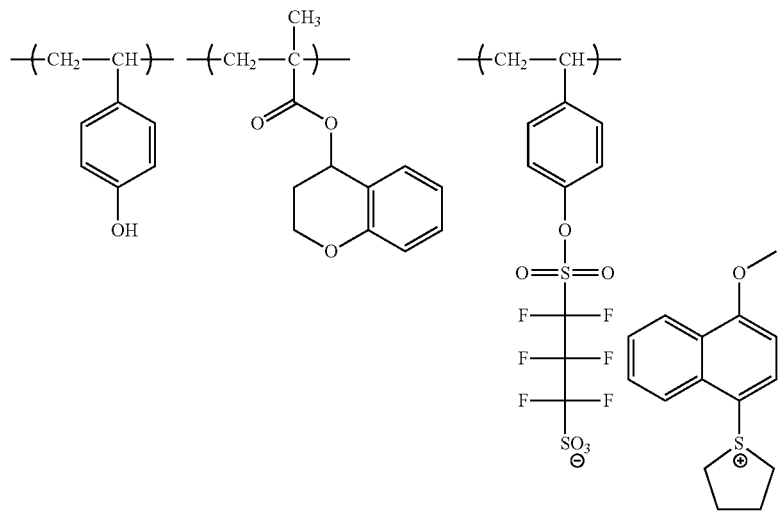
Ab-213

[Chem. 95]
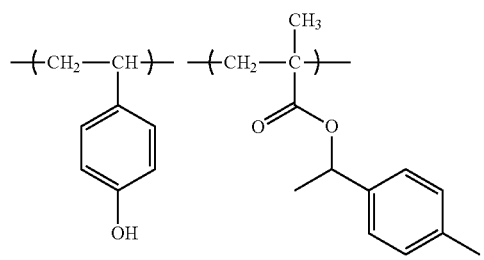
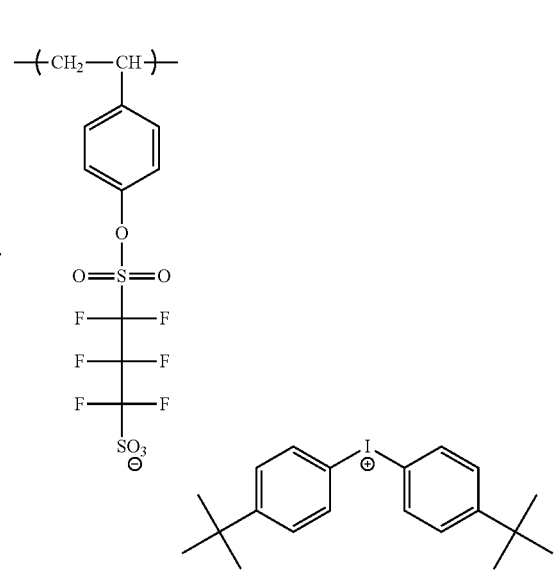
Ab-214
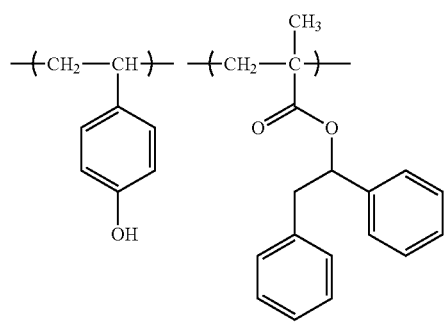
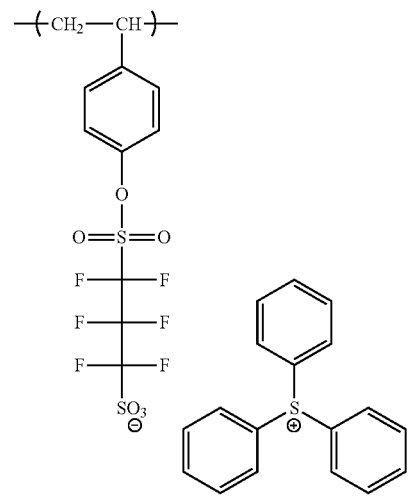
Ab-215
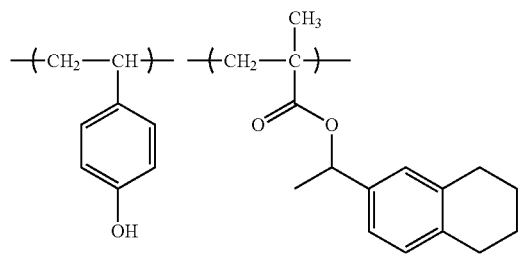
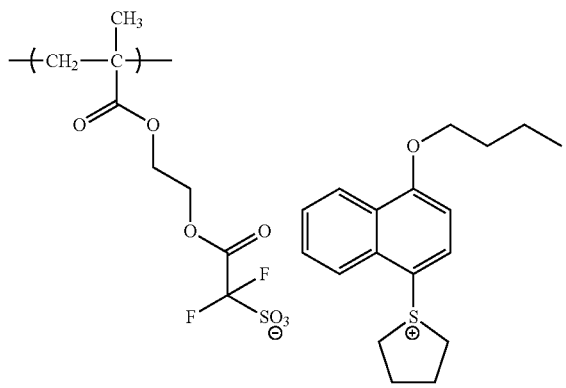
Ab-216

-continued
Ab-217
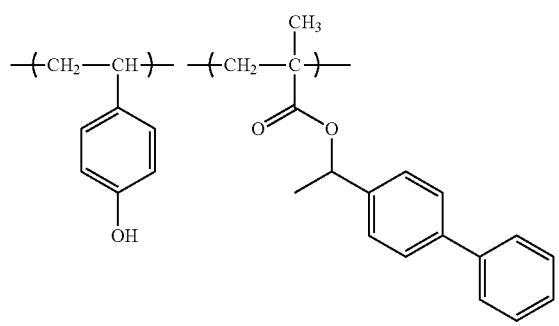
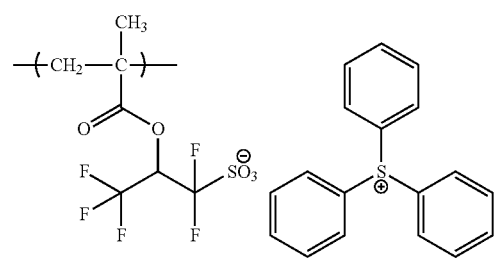
Ab-218
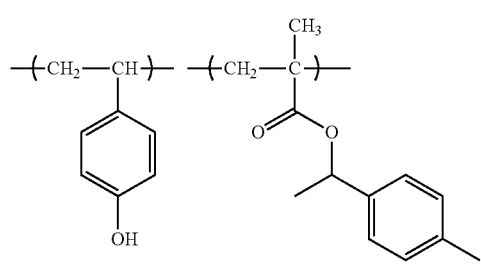
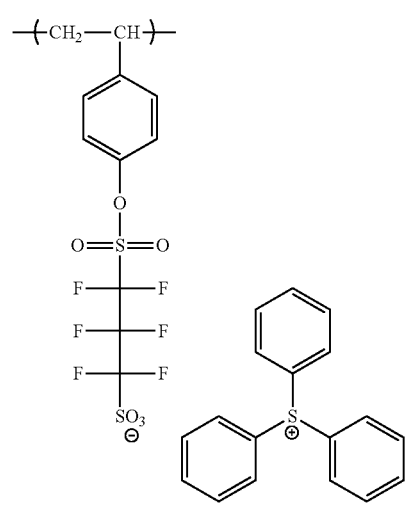
[Chem. 96]
Ab-219
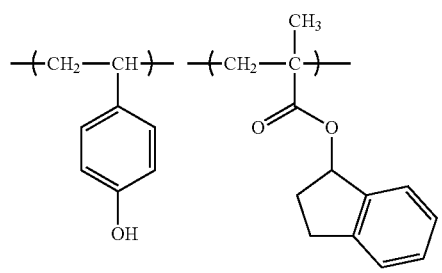
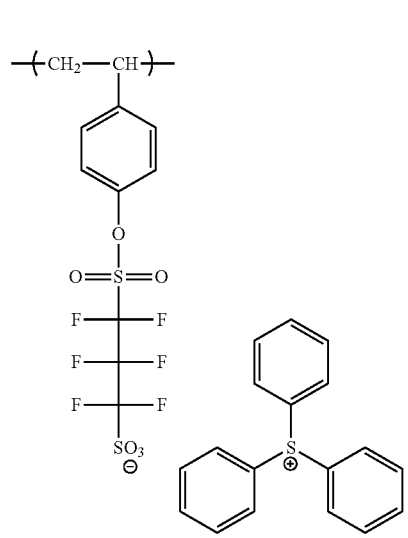

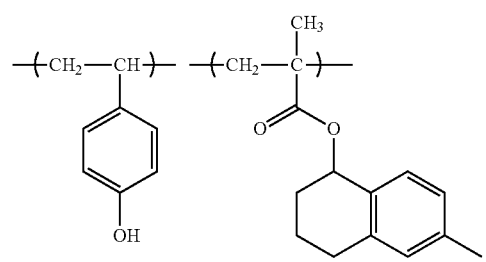 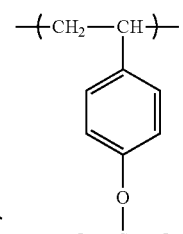 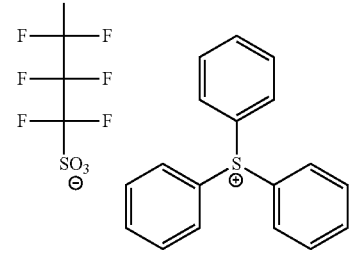
Ab-220
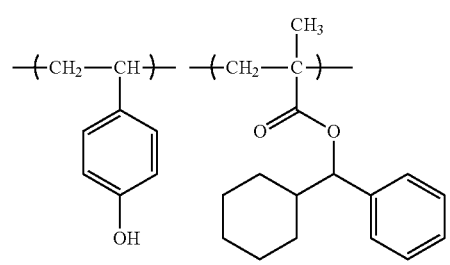 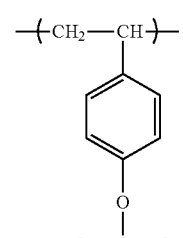 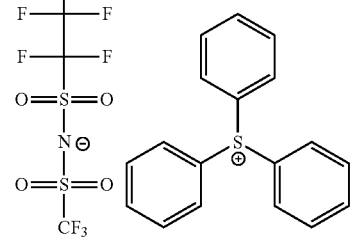
Ab-221

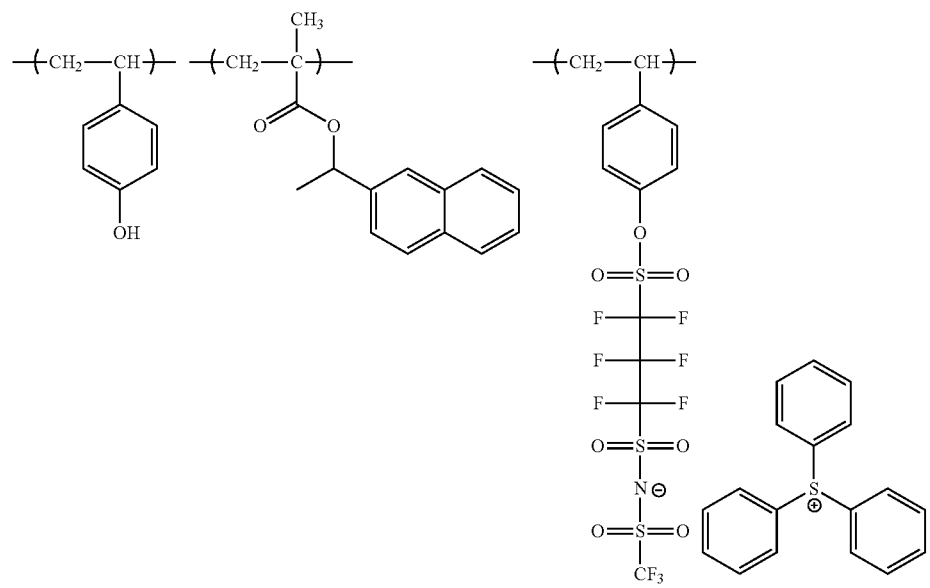
Ab-222
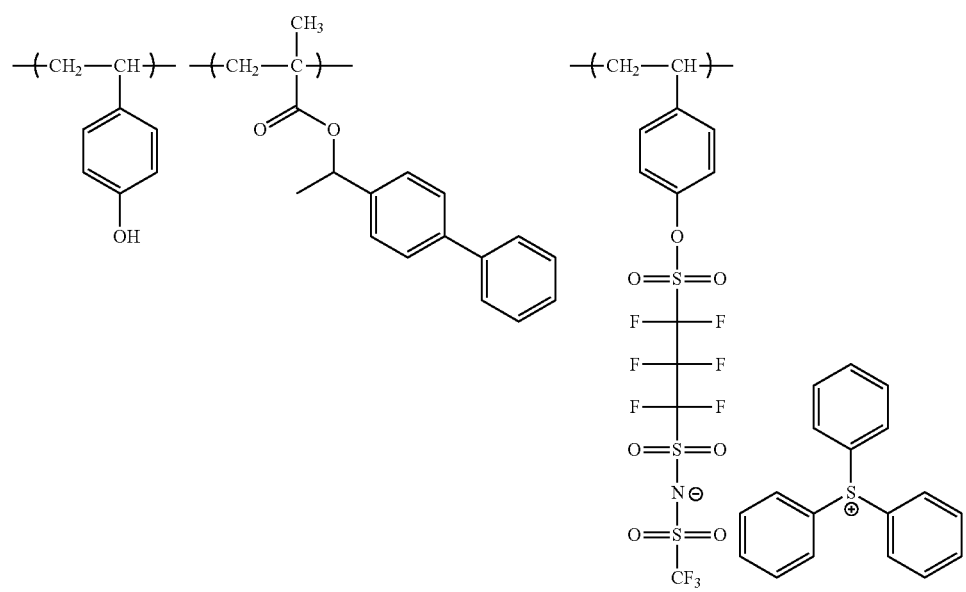
Ab-223

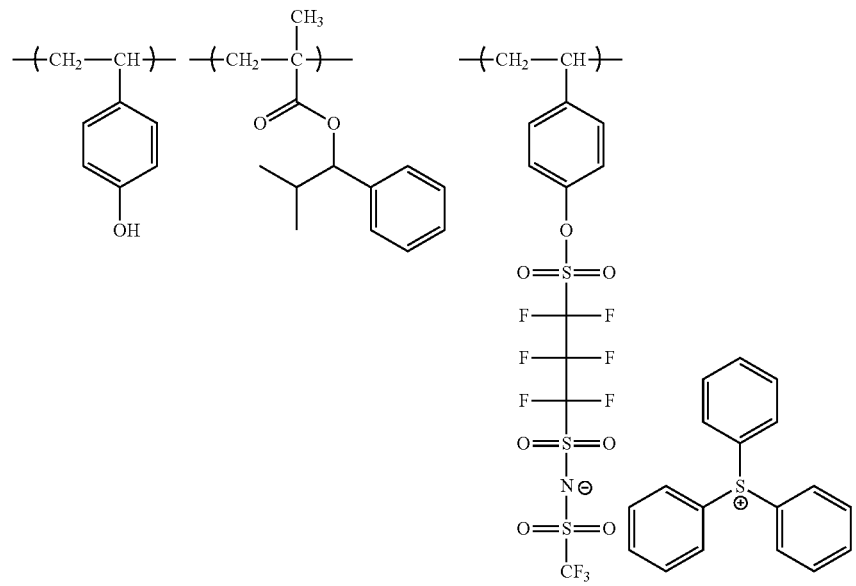
Ab-224
[Chem. 97]
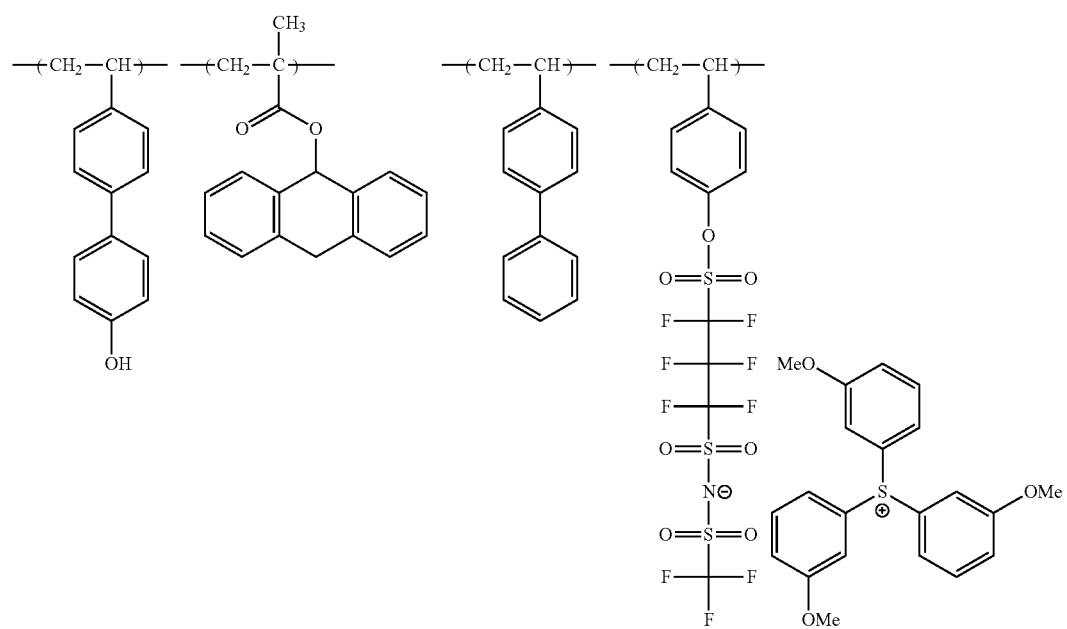
Ab-225

Ab-226
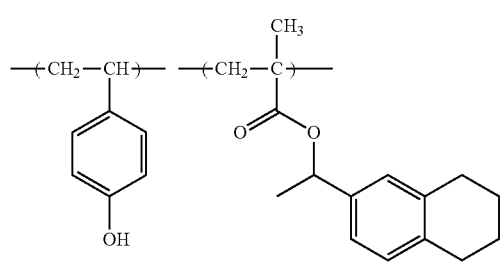
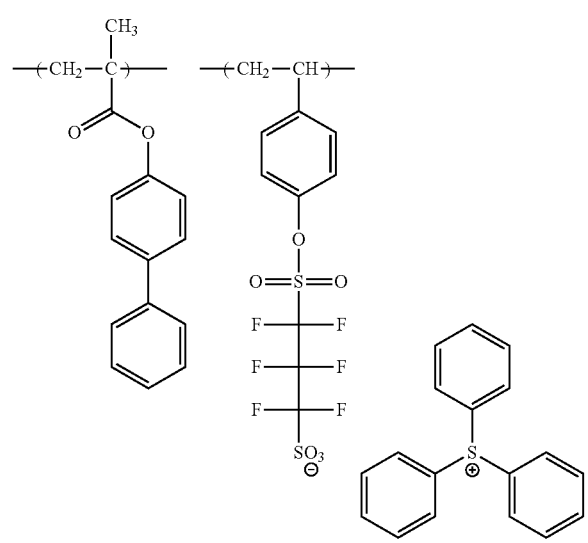
Ab-227
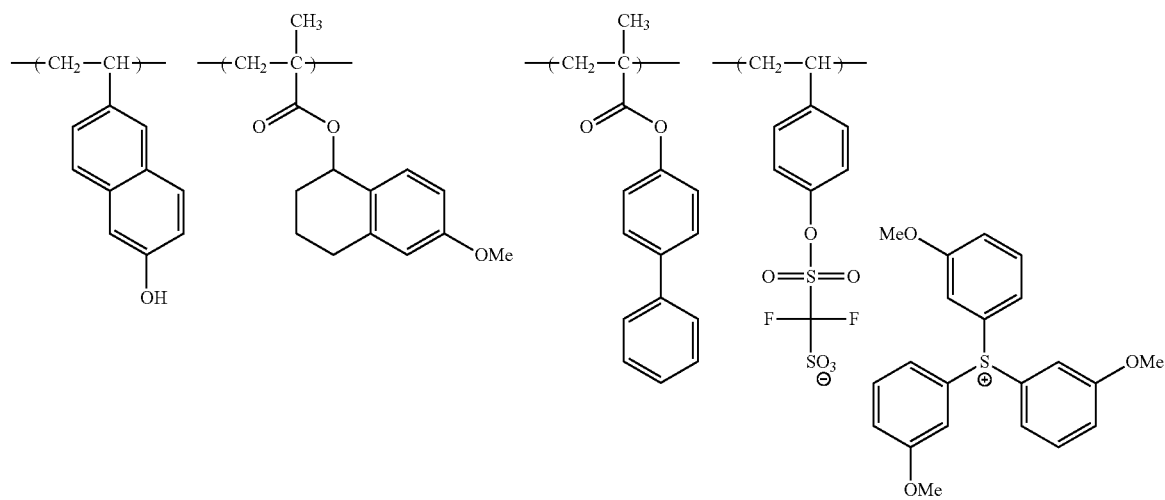
Ab-228
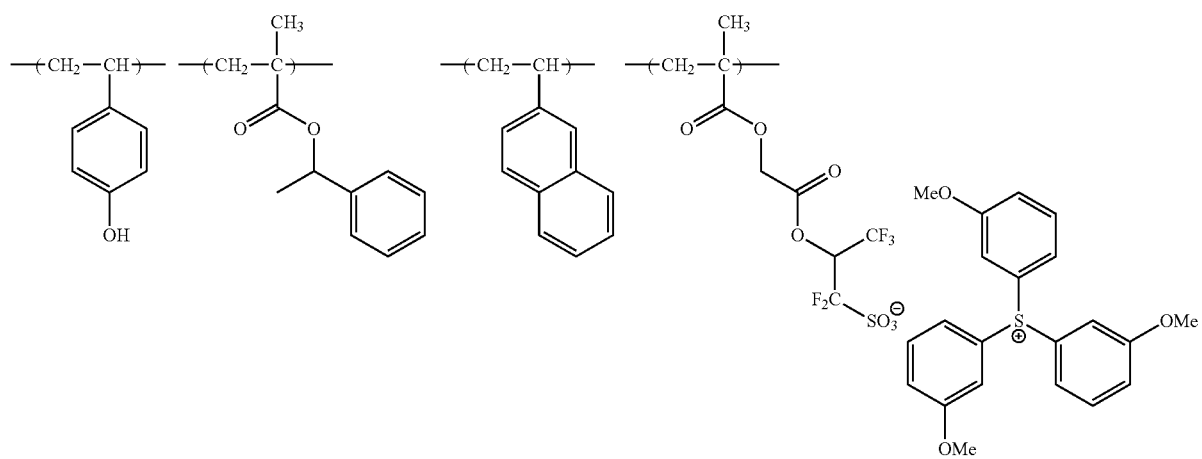

[Chem. 98]
Ab-229
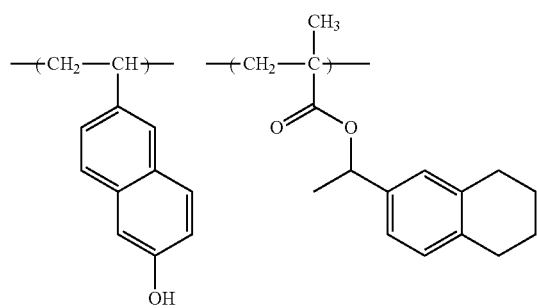
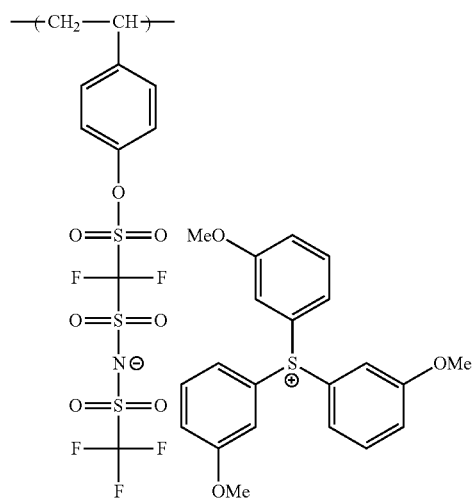
Ab-230
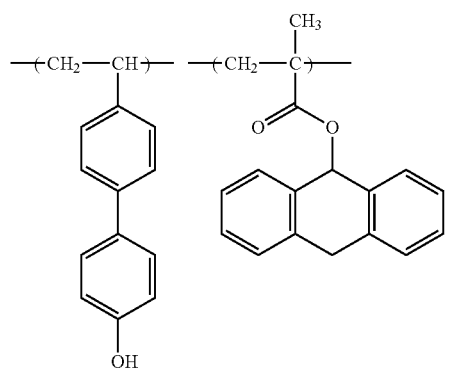
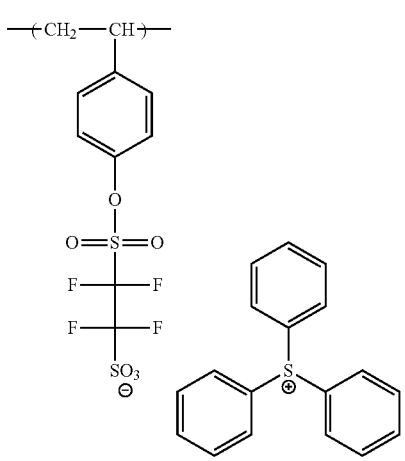
Ab-231
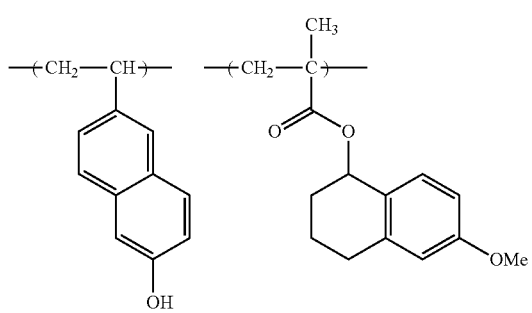
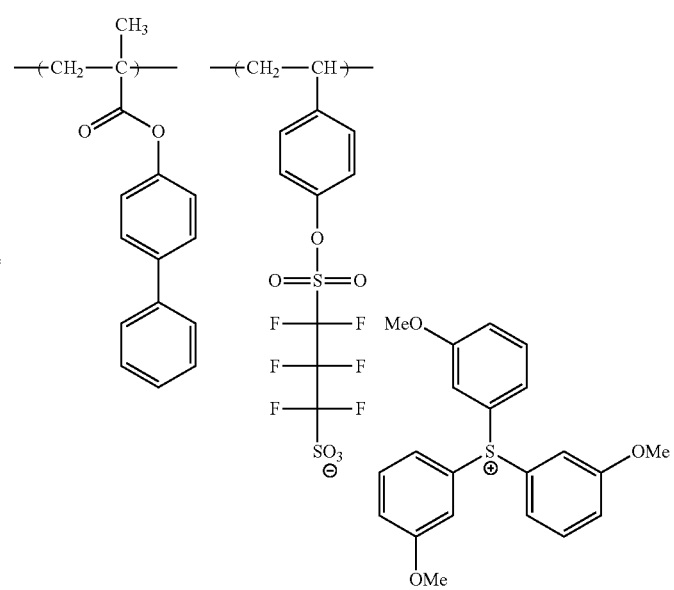

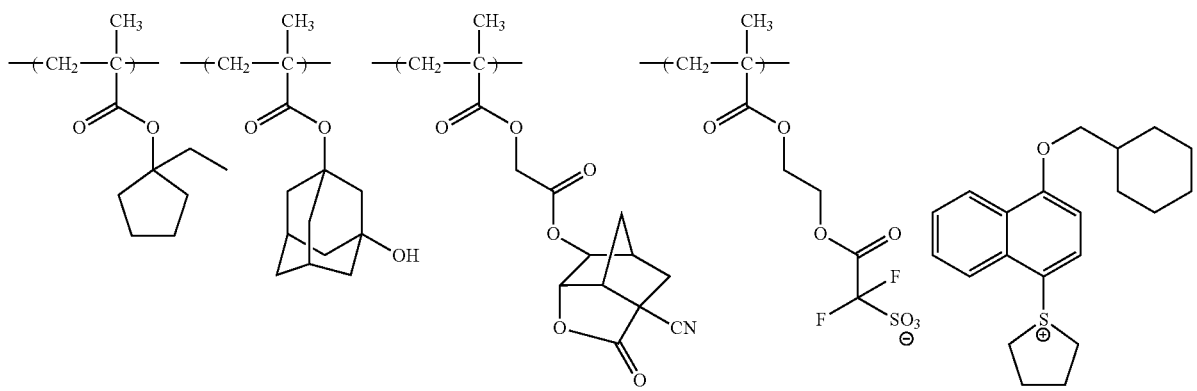
Ab-232
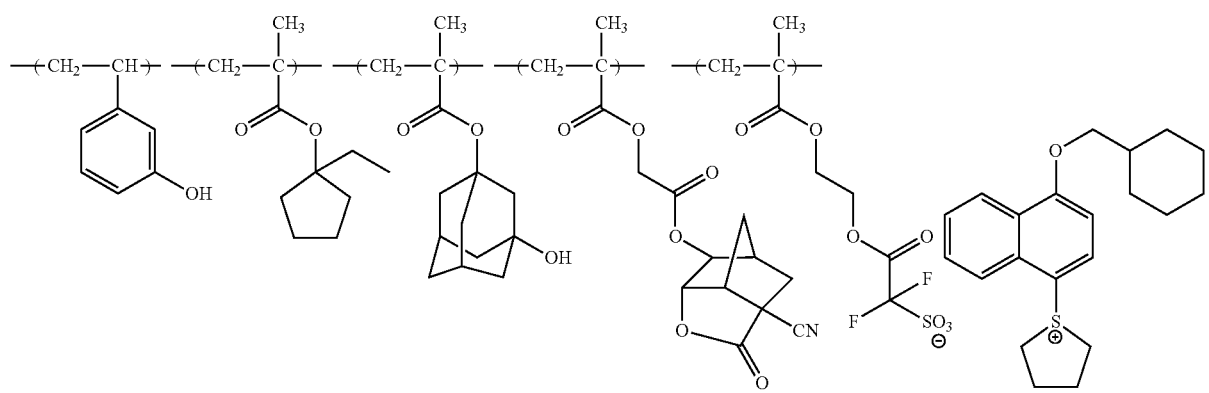
Ab-233
[Chem. 99]
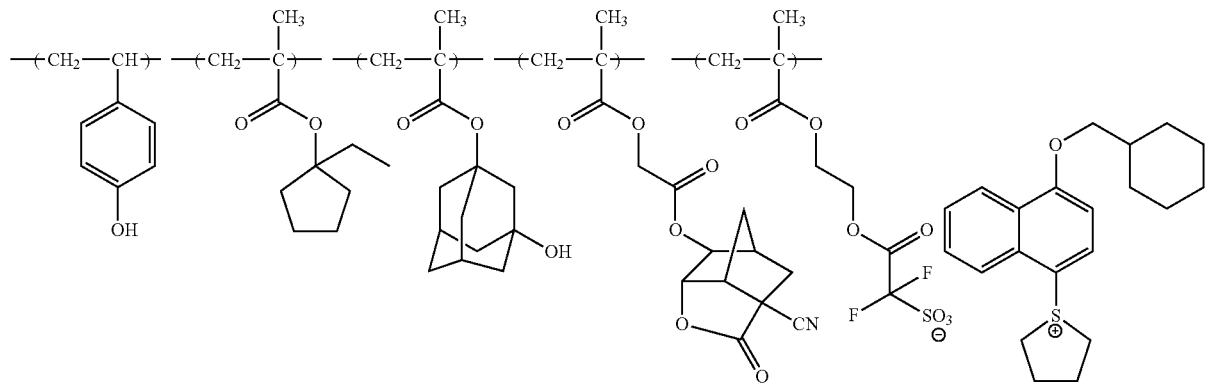
Ab-234

-continued
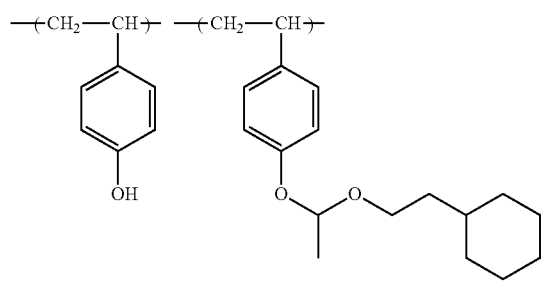 Ab-235
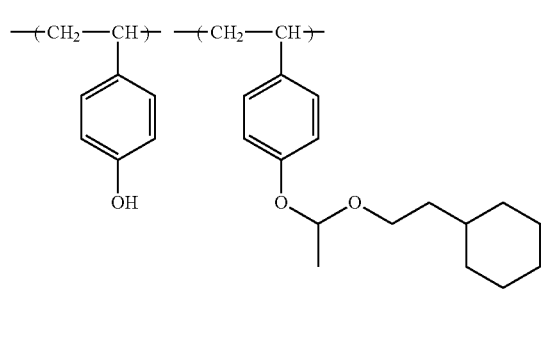 Ab-236
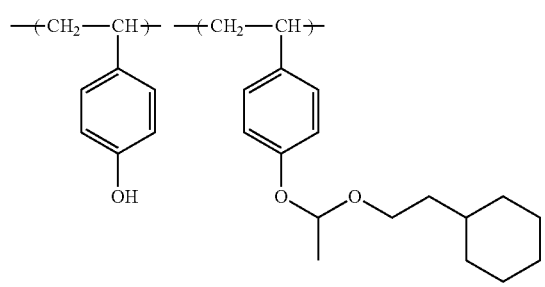 Ab-237
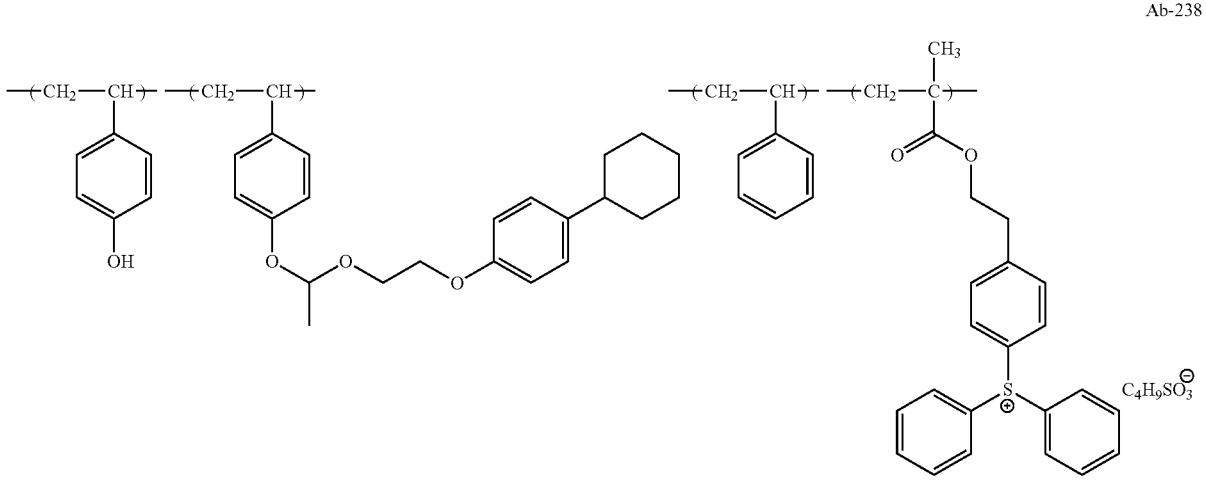 Ab-238

[Chem. 100]
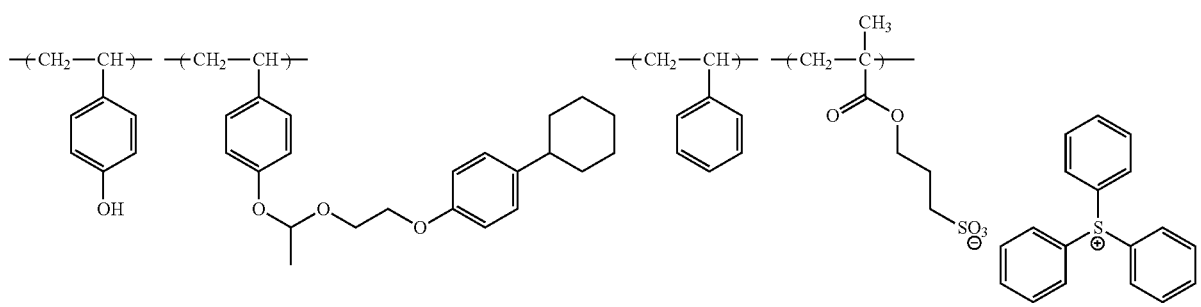
Ab-239
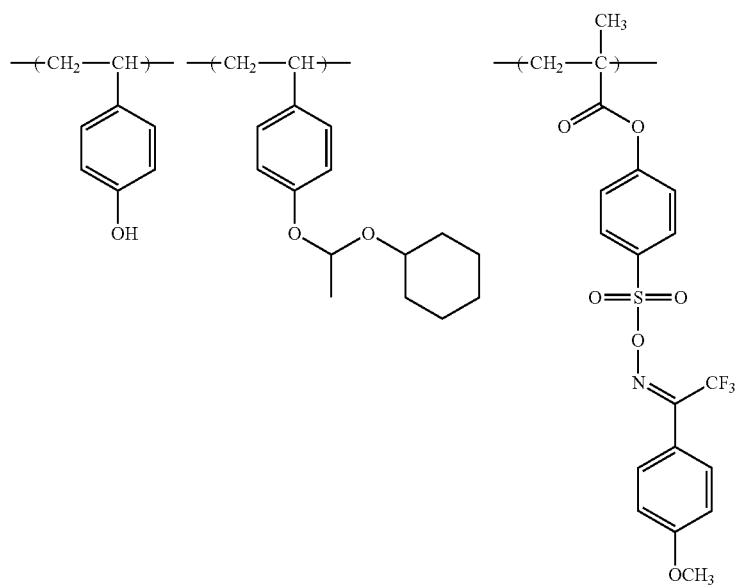
Ab-240
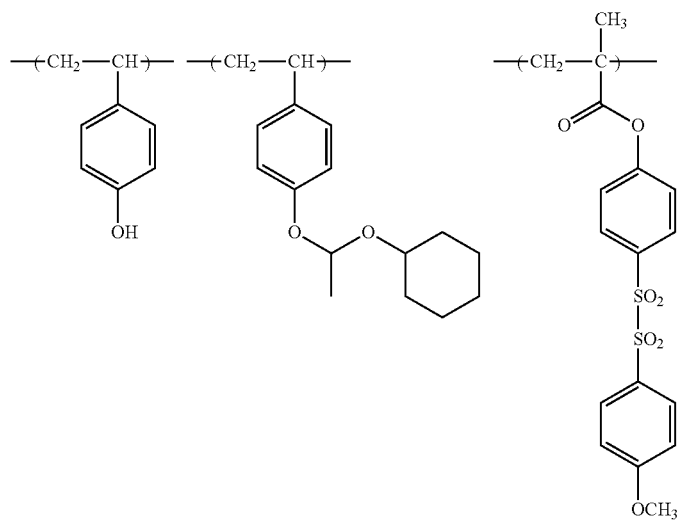
Ab-241

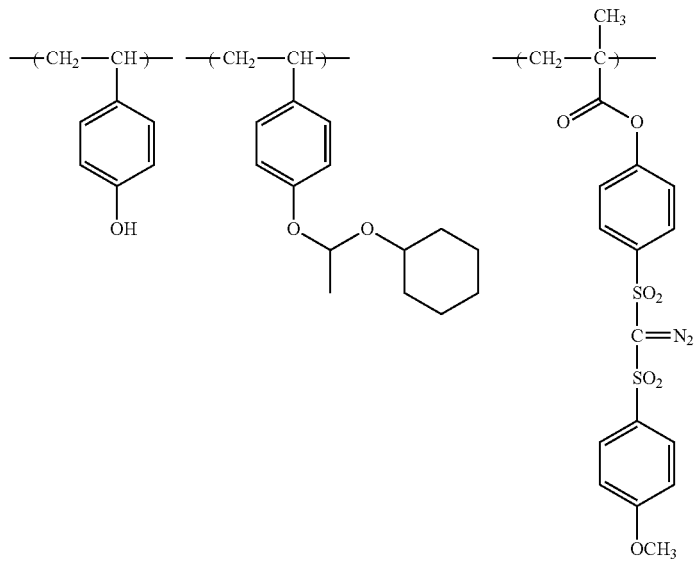
Ab-242
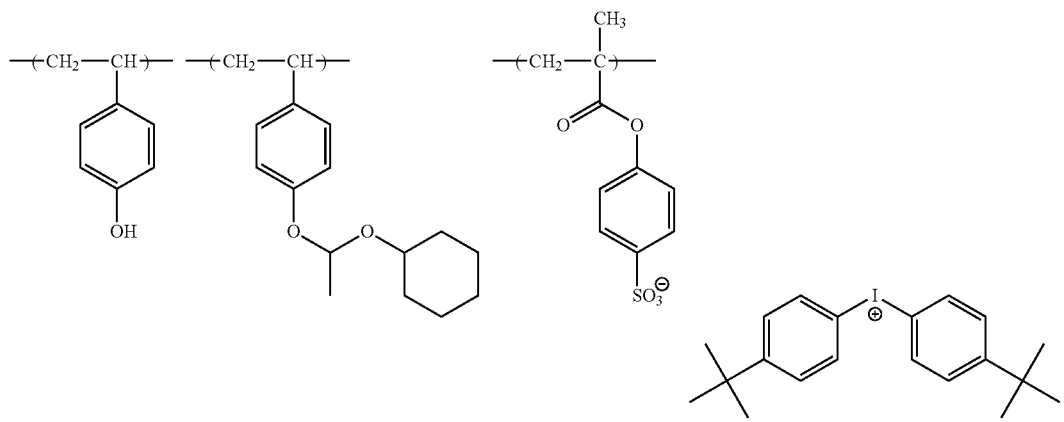
Ab-243
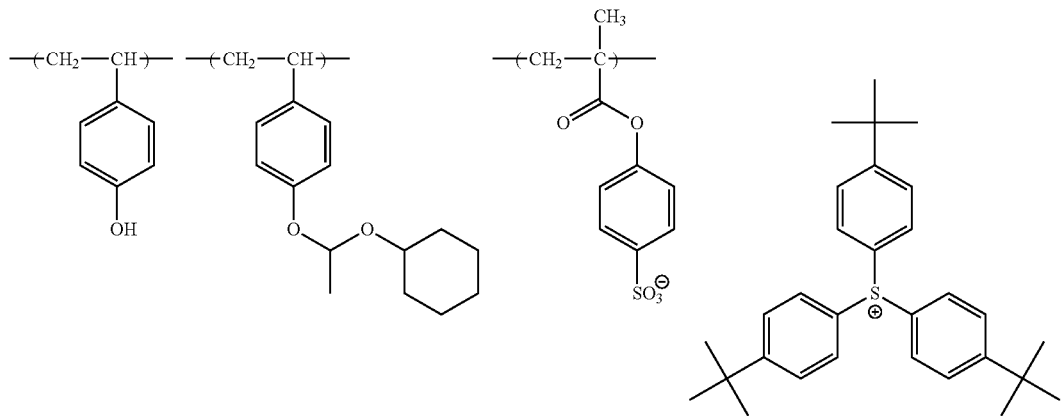
Ab-244

[Chem. 101]
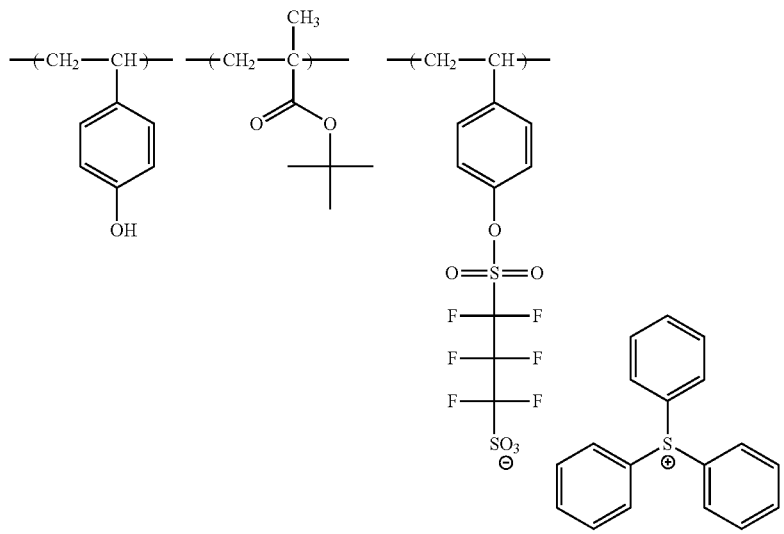
Ab-245
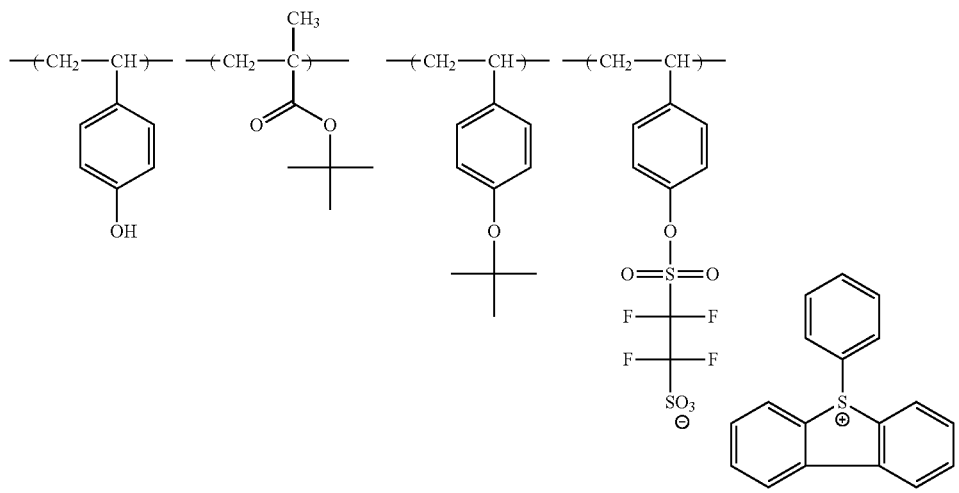
Ab-246
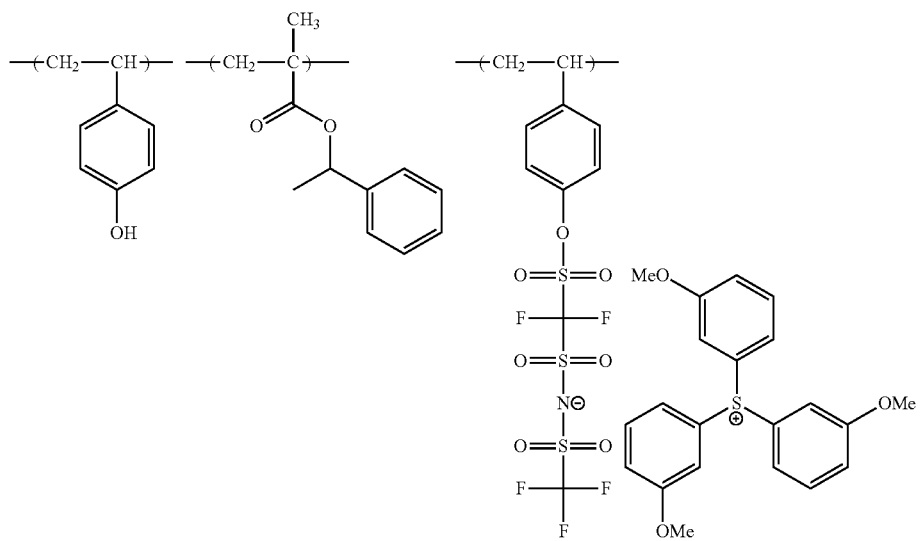
Ab-247

Ab-248
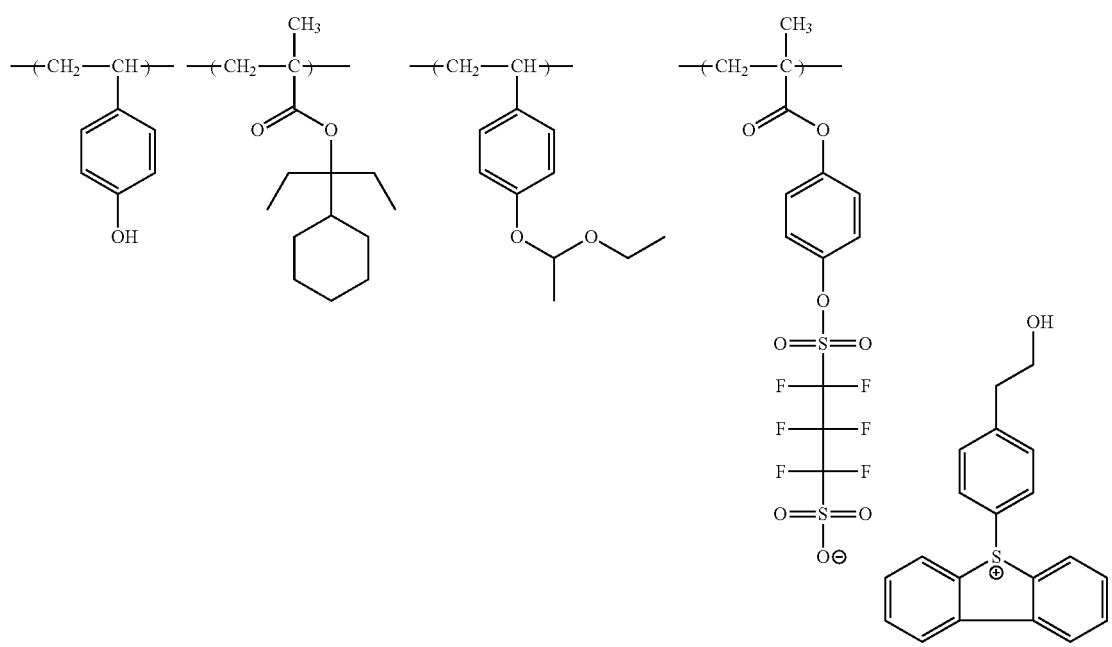
[Chem. 102]
Ab-249
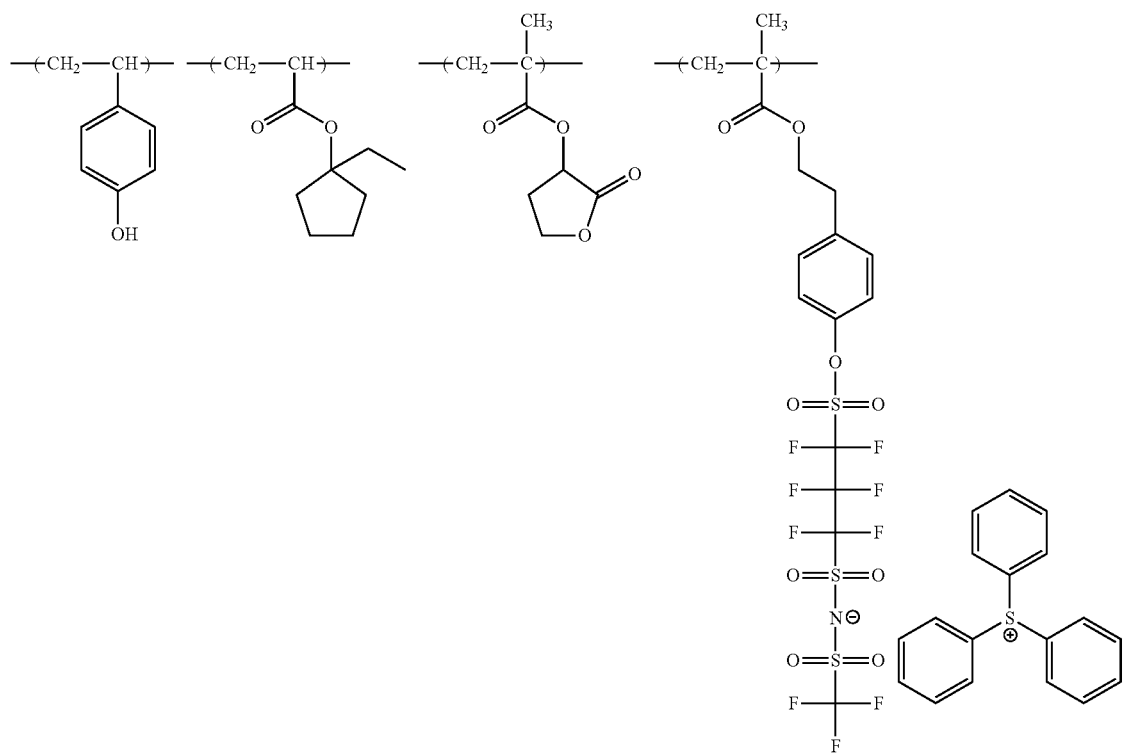

-continued
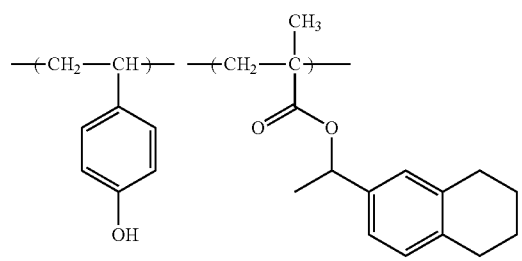
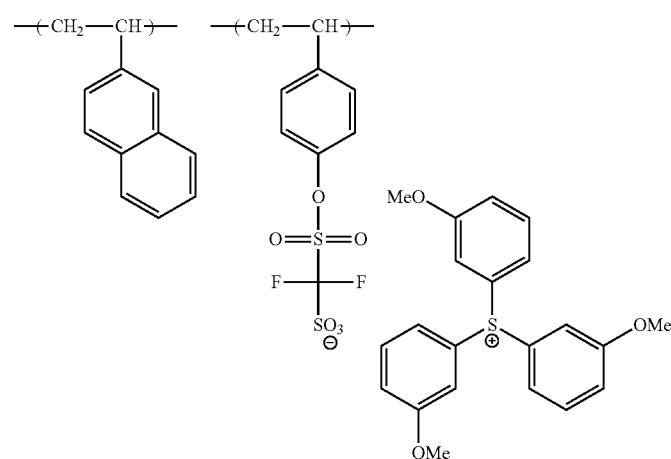
Ab-250
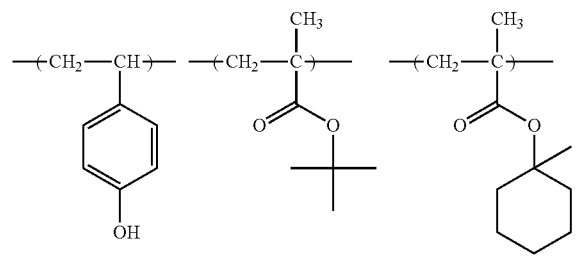
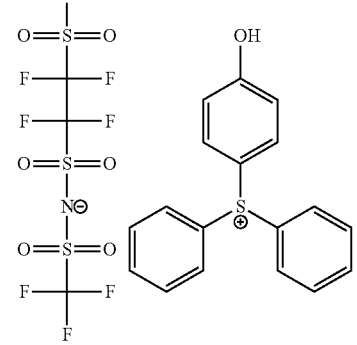
Ab-251
[Chem. 103]
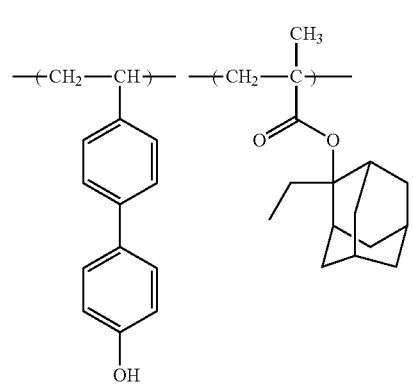
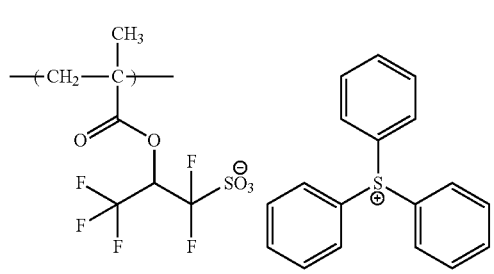
Ab-252

-continued
Ab-253
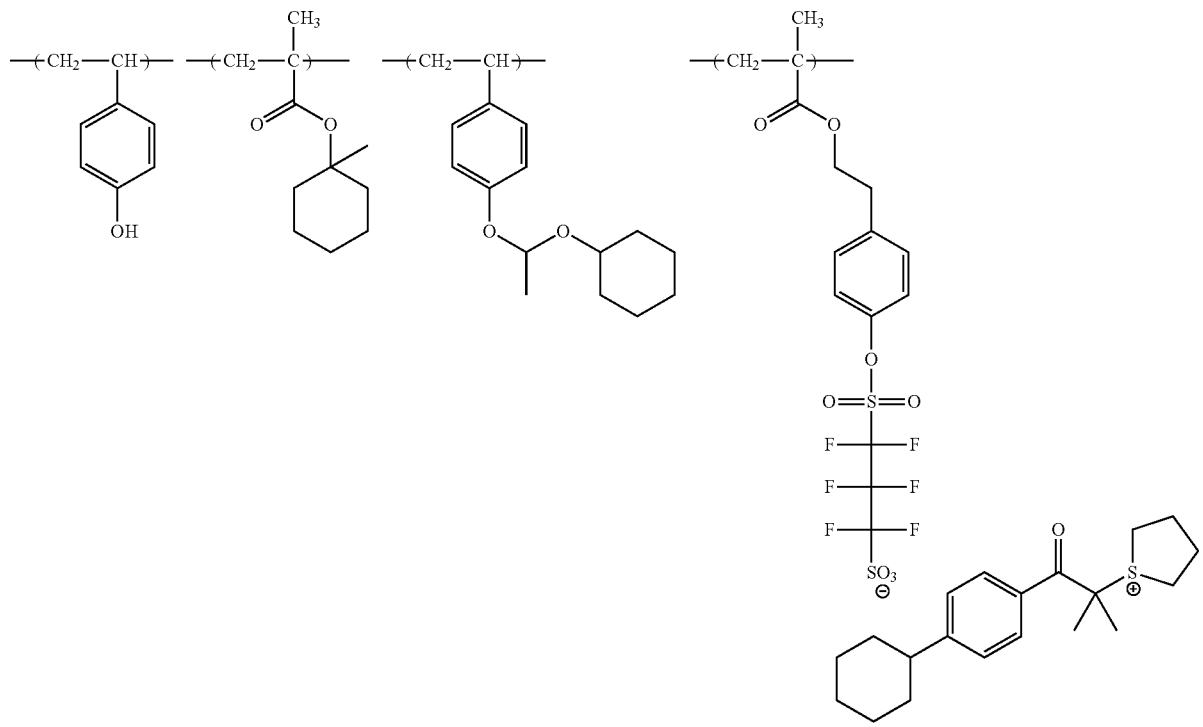
Ab-254
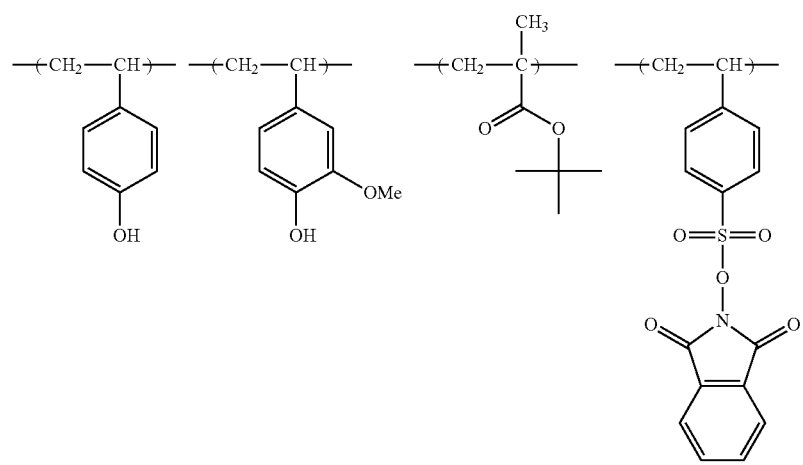
Ab-255
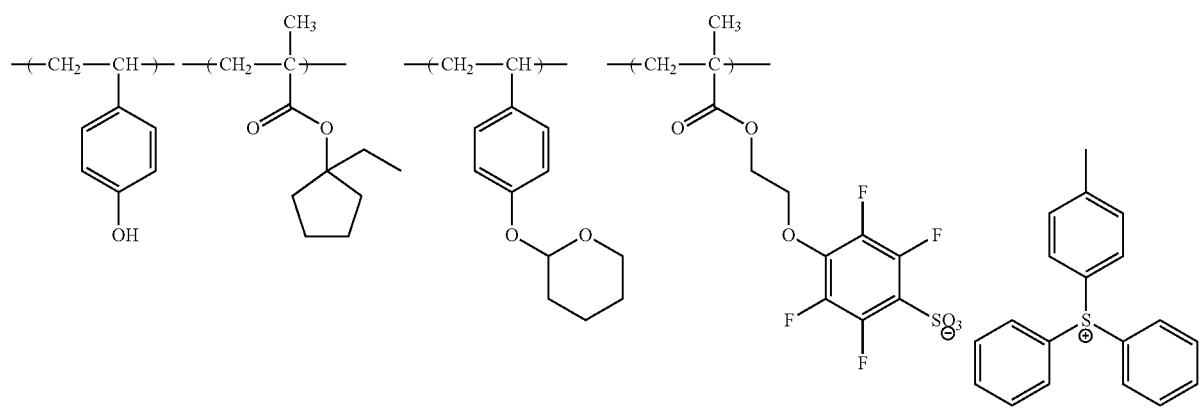

-continued
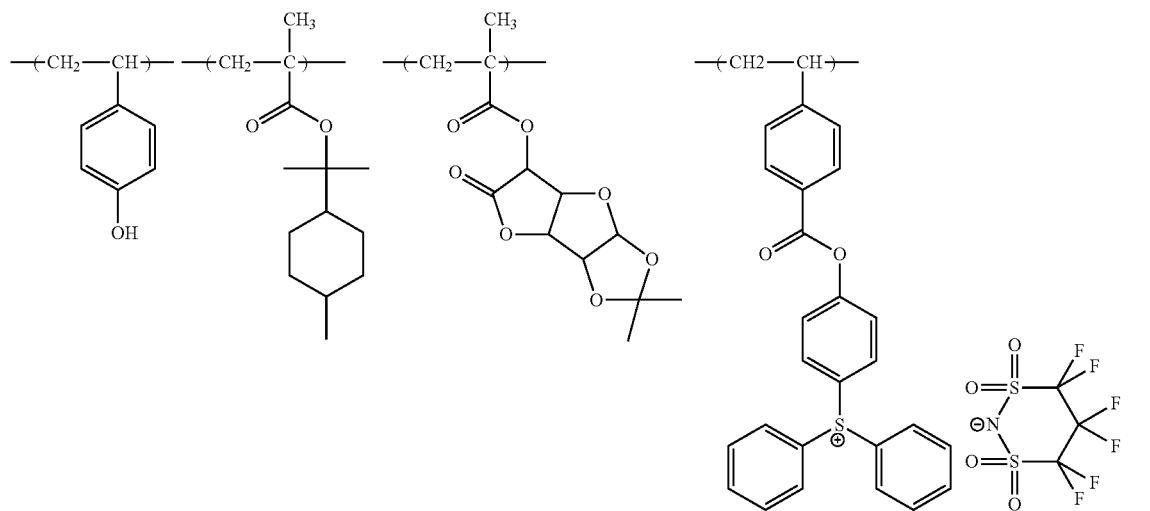
Ab-256
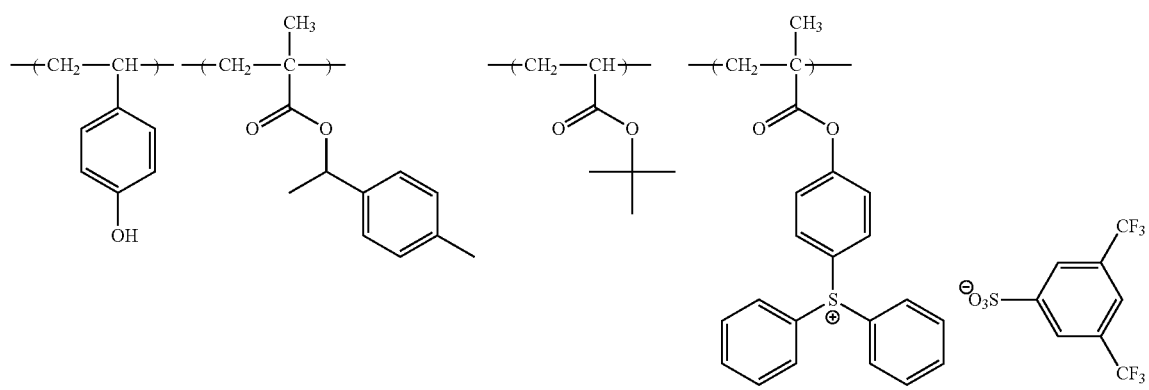
Ab-257
[Chem. 104]
Ab-258
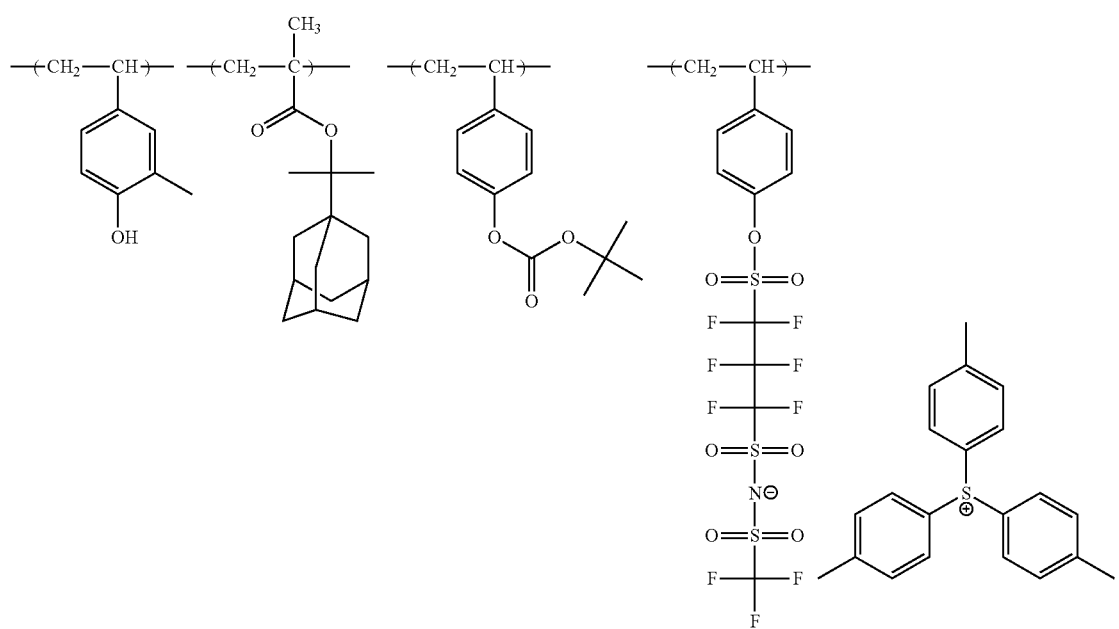

Ab-259
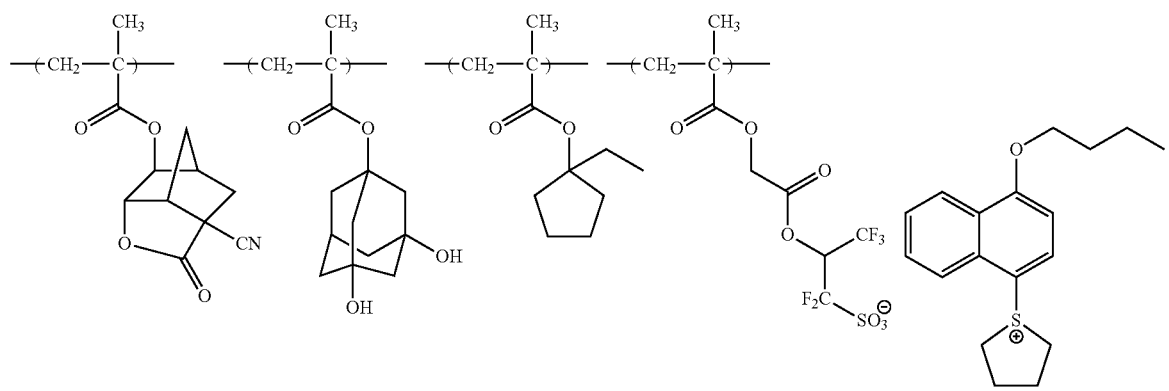
Ab-260
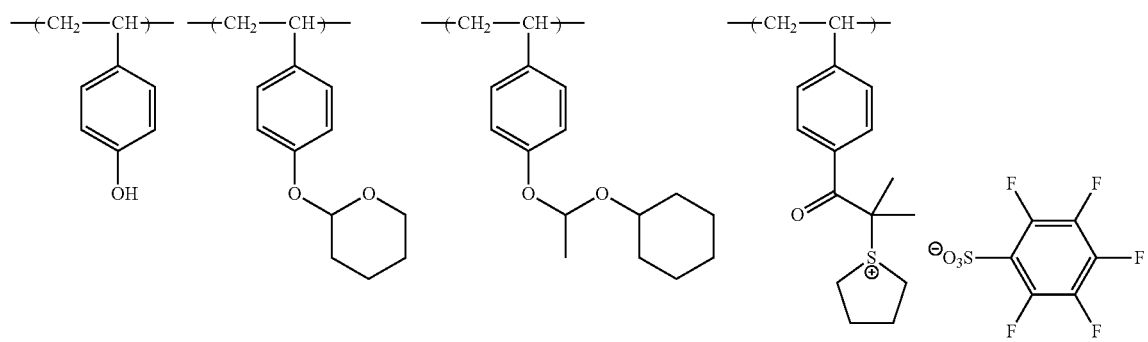
Ab-261
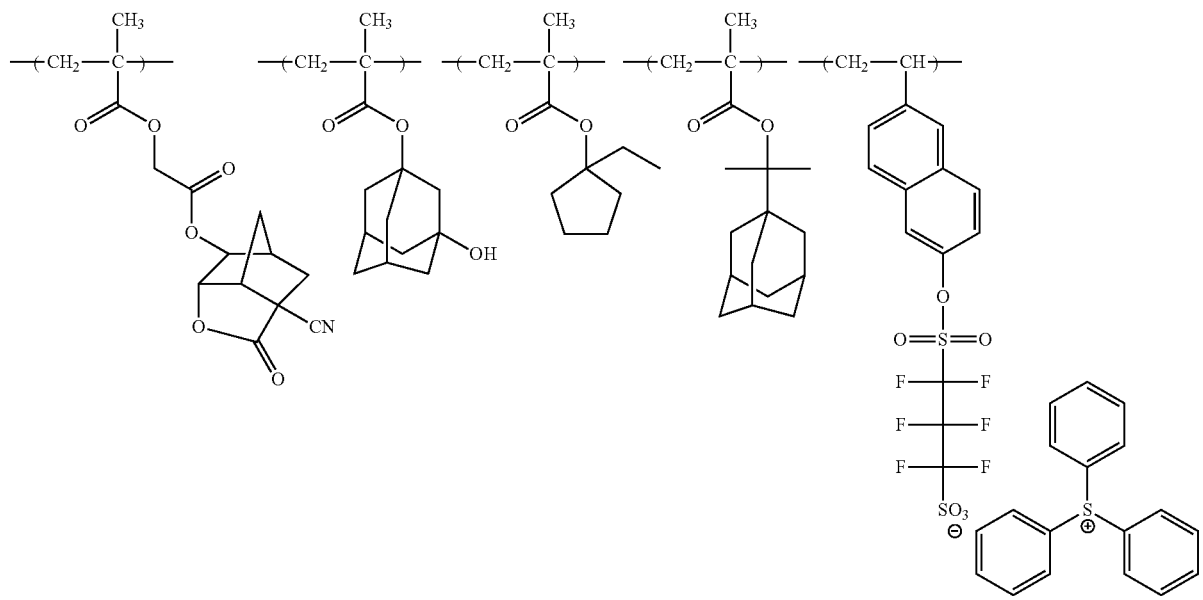

-continued
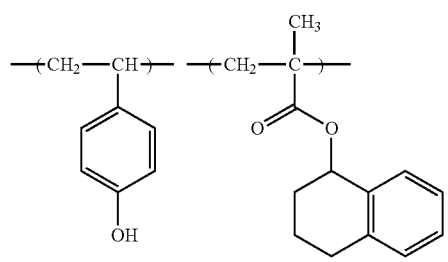
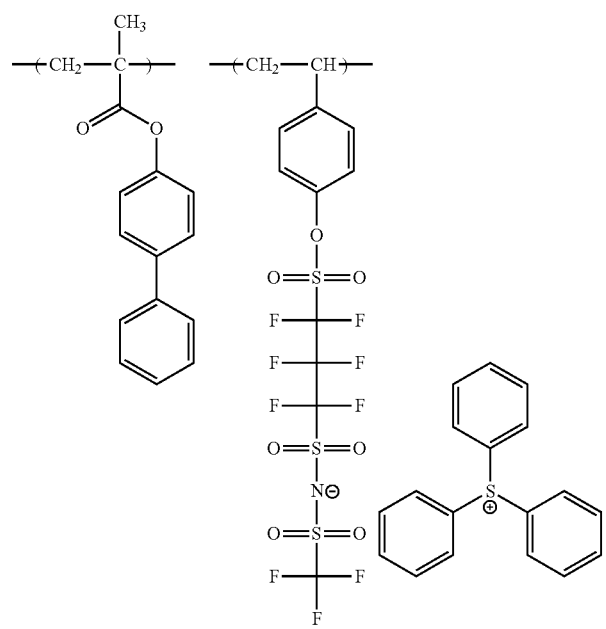
Ab-262
[Chem. 105]
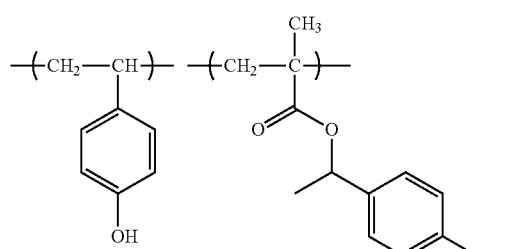
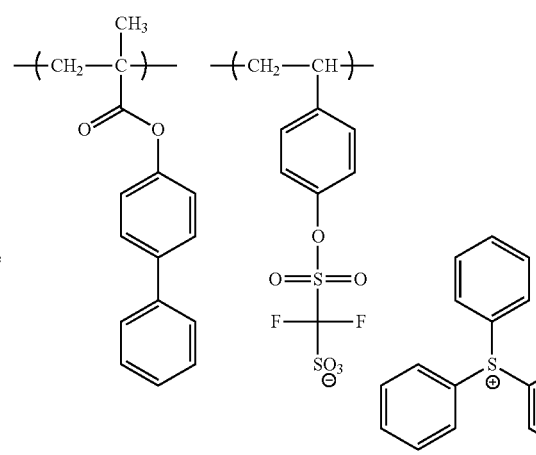
Ab-263
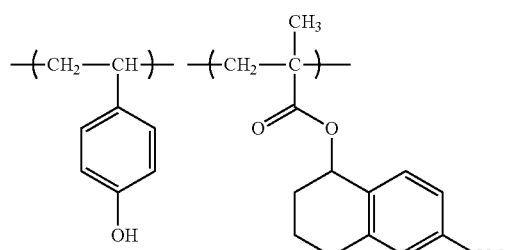
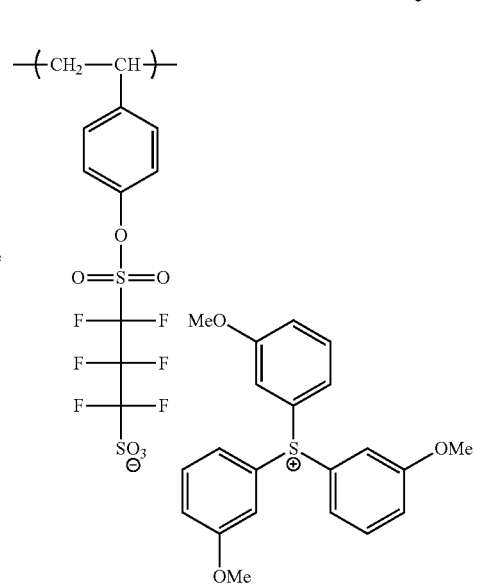
Ab-264

-continued
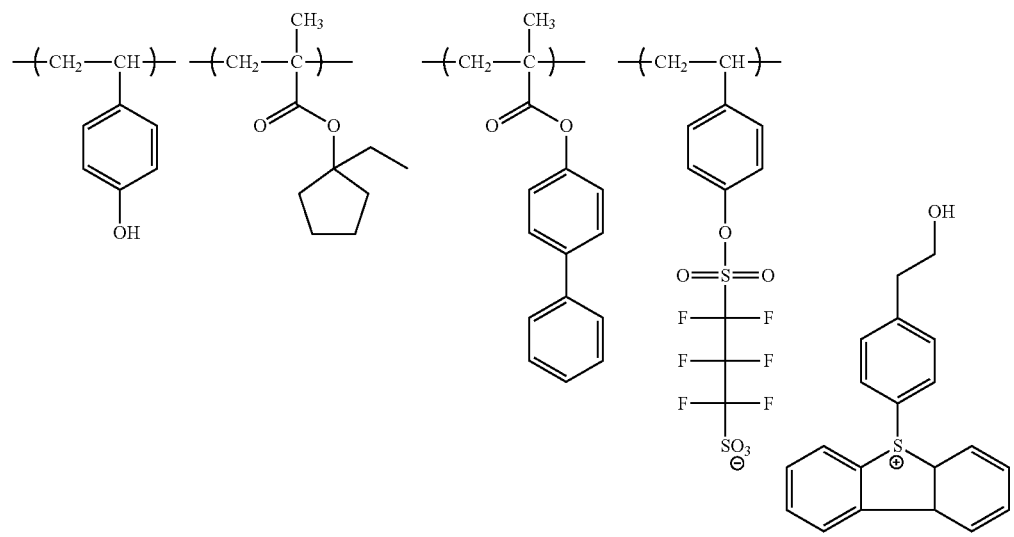
Ab-265
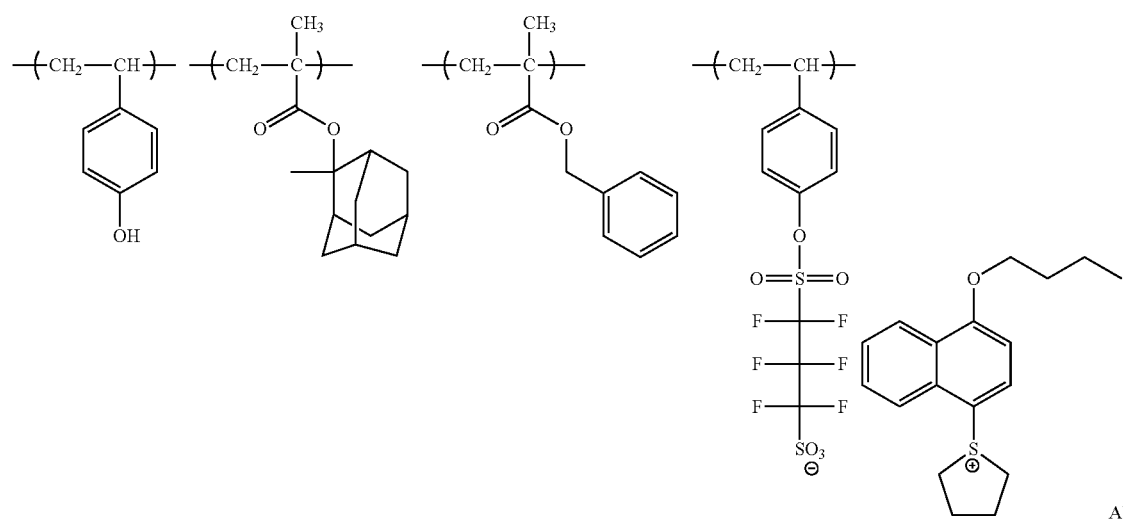
Ab-266
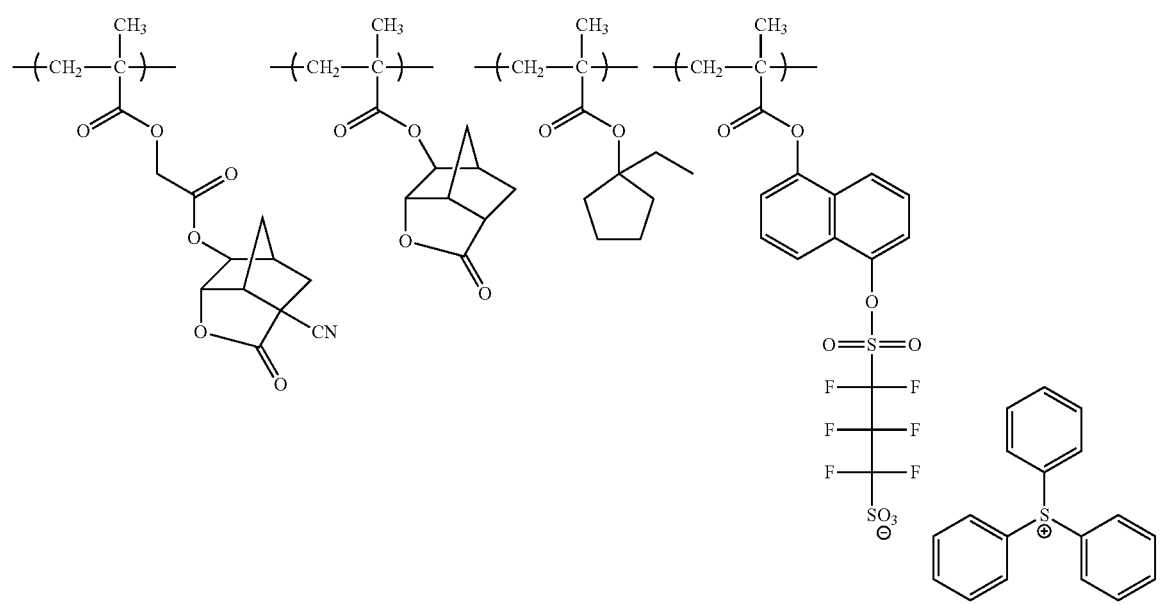
Ab-267

[Chem. 106]
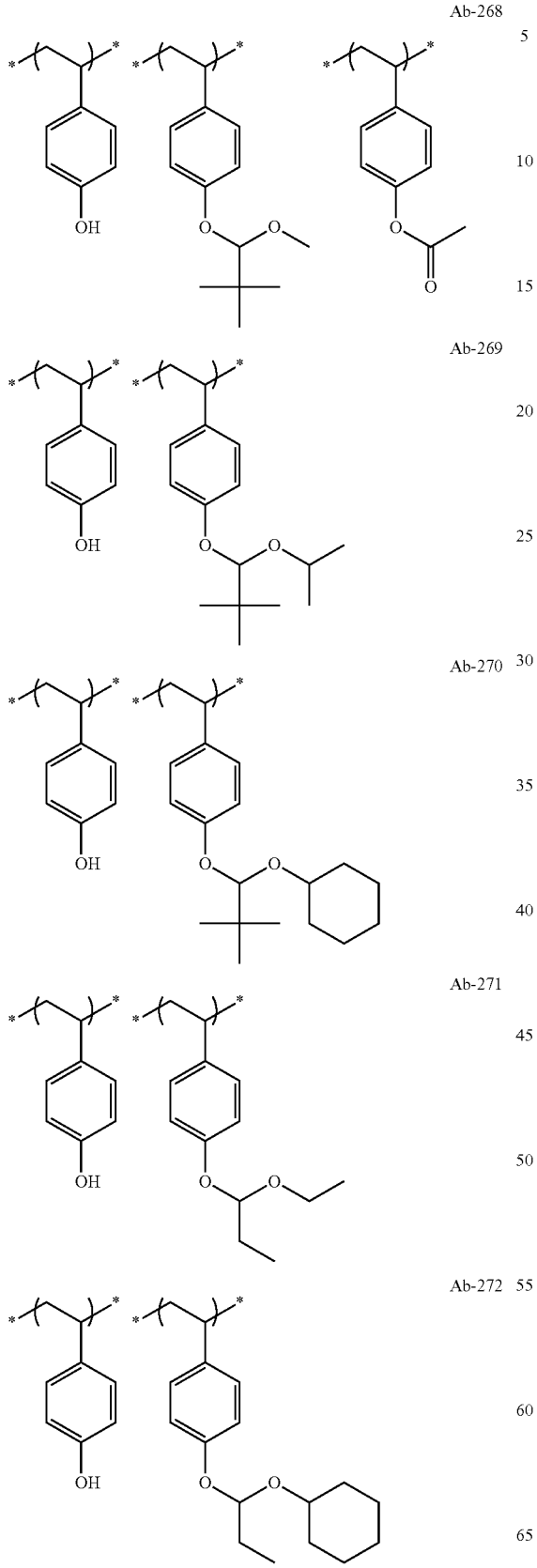
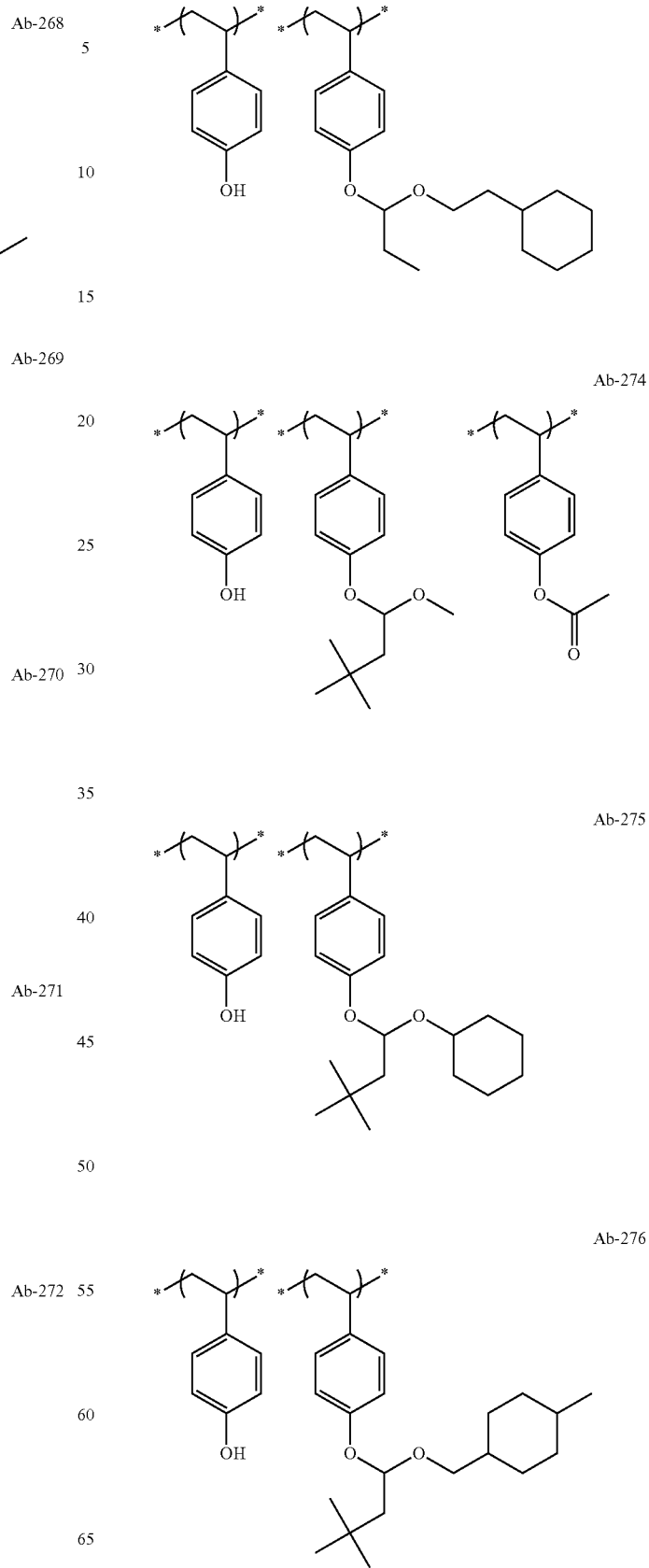

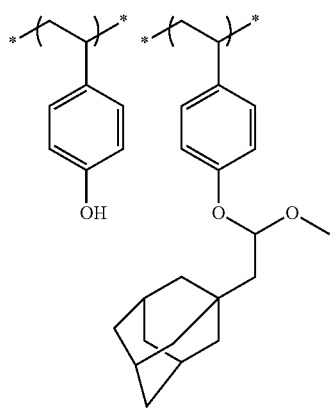

Ab-277

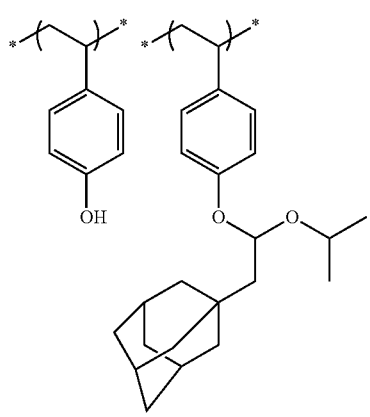

Ab-278

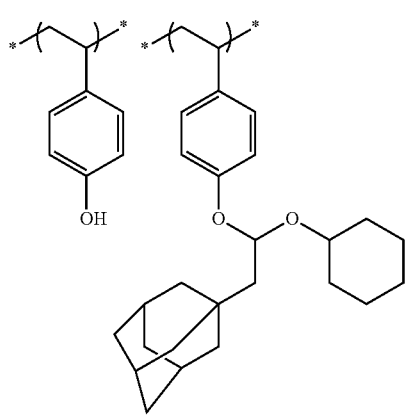

Ab-279

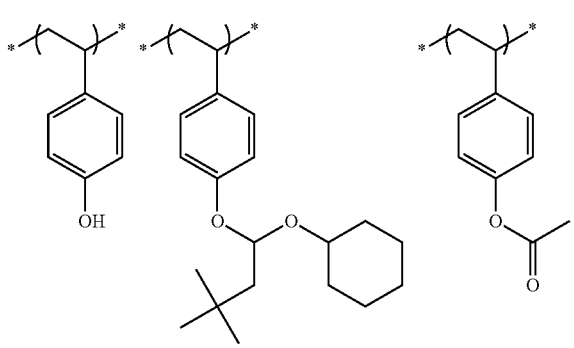

Ab-280

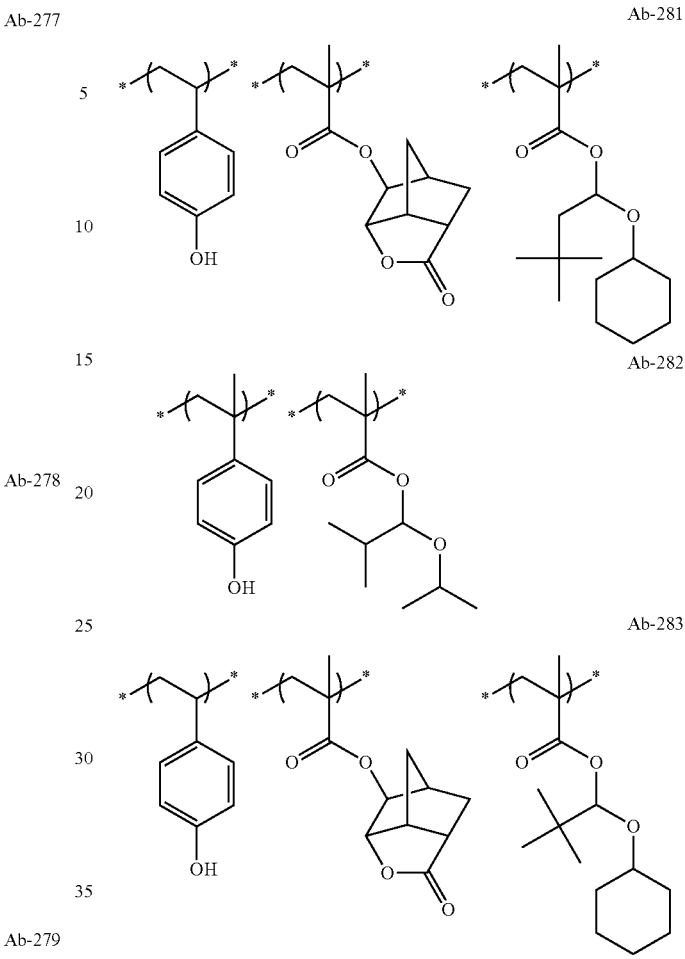

Ab-281

Ab-282

Ab-283

In the case where the resin (Ab) contains no acid-generating repeating unit (B), the content of the fluorine atom-containing repeating unit is preferably 1% by mole or less, and more preferably, the repeating unit contains no fluorine atom. In the case where the resin (Ab) has a repeating unit (B), the repeating unit is a repeating unit other than the repeating unit (B), and the content of the fluorine atom-containing repeating unit is more preferably 1% by mole or less, and most preferably, the repeating unit contains no fluorine atom.

(3) Compound Capable of Generating Acid upon Irradiation with Actinic Rays or Radiation The composition of the present invention may further include a compound capable of generating an acid by irradiation with actinic rays or radiation (also hereinafter referred to a "photo-acid generator").

As such a photo-acid generator, photoinitiators for photo-cation polymerization, photoinitiators for photo-radical polymerization, photodecoloring agents, photo-discoloring agents, known compounds that generate an acid by irradiation with actinic rays or radiation, which are used in microresists, or the like, mixtures thereof may be suitably selected and used. Examples thereof include onium salts such as a sulfonium salt and an iodonium salt, and diazodisulfone compounds such as bis(alkylsulfonyldiazomethane).

Preferred examples of the photo-acid generator include the compounds represented by the following general formulae (ZI), (ZII) and (ZIII).

[Chem. 107]

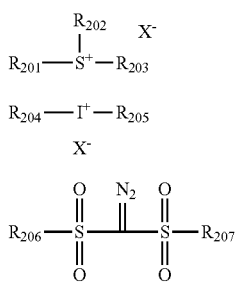

(ZI)
(ZII)
(ZIII)

In the general formula (ZI), $R_{201}$, $R_{202}$ and $R_{203}$ each independently represent an organic group. The number of carbon atoms of the organic group as $R_{201}$, $R_{202}$ and $R_{203}$ is, for example, from 1 to 30, and preferably from 1 to 20.

Two members out of $R_{201}$ to $R_{203}$ may be bonded to each other via a single bond or a connecting group to form a ring structure. In this case, examples of the connecting group include an ether bond, a thioether bond, an ester bond, an amide bond, a carbonyl group, a methylene group, and an ethylene group. Examples of the group formed by combining two members out of $R_{201}$ to $R_{203}$ include alkylene groups such as a butylene group and a pentylene group.

Specific examples of $R_{201}$, $R_{202}$ and $R_{203}$ include the corresponding groups in the compound (ZI-1), (ZI-2), or (ZI-3) as described later.

$X^-$ represents a non-nucleophilic anion. Examples of $X^-$ include a sulfonate anion, a bis(alkylsulfonyl)amide anion, a tris(alkylsulfonyl)methide anion, $BF_4^-$, $PF_6^-$, and $SbF_6^-$. $X^-$ is preferably an organic anion containing a carbon atom. Preferred examples of the organic anions include organic anions represented by the following AN1 to AN3.

[Chem. 108]

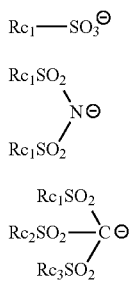

AN1
AN2
AN3

In the formulae AN1 to AN3, $Rc_1$ to $Rc_3$ each independently represent an organic group. Examples of the organic group include an organic group having 1 to 30 carbon atoms, and the organic group is preferably an alkyl group, an aryl group, or a group formed by connecting a plurality of these groups through a connecting group. Examples of the connecting group include a single bond, —O—, —$CO_2$—, —S—, —$SO_3$— and —$SO_2N(Rd_1)$—. Here, $Rd_1$ represents a hydrogen atom or an alkyl group and may form a ring structure together with the alkyl group or aryl group to which $Rd_1$ is bonded.

The organic group of $Rc_1$ to $Rc_3$ may be an alkyl group substituted with a fluorine atom or a fluoroalkyl group at the 1-position, or a phenyl group substituted with a fluorine atom or a fluoroalkyl group. By virtue of having a fluorine atom or a fluoroalkyl group, the acidity of the acid generated upon irradiation with light is increased and in turn, the sensitivity of the actinic ray-sensitive or radiation-sensitive resin composition is enhanced. Incidentally, each of $Rc_1$ to $Rc_3$ may be bonded to another alkyl group, aryl group, or the like to form a ring structure.

Furthermore, preferred examples of $X^-$ include sulfonic acid anions represented by the following general formula (SA1) or (SA2).

[Chem. 109]

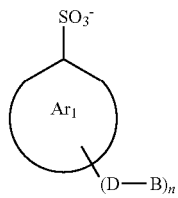

(SA1)

In the formula (SA1), $Ar_1$ represents an aryl group, and may further have a substituent other than a -(D-B) group.

n represents an integer of 1 or more, and n is preferably from 1 to 4, more preferably from 2 to 3, and most preferably 3.

D represents a single bond or a divalent connecting group. This divalent connecting group is an ether group, a thioether group, a carbonyl group, a sulfoxide group, a sulfone group, a sulfonic acid ester group, or an ester group.

B represents a hydrocarbon group.

[Chem. 110]

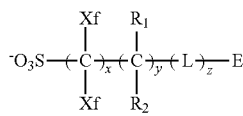

(SA2)

In the formula (SA2),

Xf's each independently represent a fluorine atom, or an alkyl group with at least one hydrogen atom being substituted with at least one fluorine atom.

$R_1$ and $R_2$ each independently represent a hydrogen atom, a fluorine atom, an alkyl group, or an alkyl group with at least one hydrogen atom being substituted with at least one fluorine atom, and in the case where a plurality of $R_1$'s and $R_2$'s are present, they may be the same as or different from each other.

L represents a single bond or a divalent connecting group, and in the case where a plurality of L's are present, they may be the same as or different from each other.

E represents a group having a cyclic structure.

x represents an integer of 1 to 20, y represents an integer of 0 to 10, and z represents an integer of 0 to 10.

First, the sulfonic acid anion represented by the formula (SA1) will be described in detail.

In the formula (SA1), $Ar_1$ is preferably an aromatic ring having 6 to 30 carbon atoms. Specifically, examples of $Ar_1$ include a benzene ring, a naphthalene ring, a pentalene ring, an indene ring, an azulene ring, a heptalene ring, an indecene ring, a perylene ring, a pentacene ring, an acenaphthalene ring, a phenanthrene ring, an anthracene ring, a naphthacene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolidine ring, a quinoline ring, a phthalazine ring, a naphthylidine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring, and a phenazine ring. Among these, from the viewpoints of a balance between the improvement of roughness and the realization of high sensitivity, a benzene ring, a naphthalene ring, and an anthracene ring are preferred, and a benzene ring is more preferred.

In the case where $Ar_1$ further has a substituent other than a -(D-B) group, the substituent may be exemplified as follows. That is, examples of the substituent include halogen atoms such as a fluorine atom, a chlorine atom, a bromine atom and an iodine atom; alkoxy groups such as a methoxy group, an ethoxy group and a tert-butoxy group; aryloxy groups such as a phenoxy group and a p-tolyloxy group; alkylthioxy groups such as a methylthioxy group, an ethylthioxy group and a tert-butylthioxy group; arylthioxy groups such as a phenylthioxy group and a p-tolylthioxy group; alkoxycarbonyl groups such as a methoxycarbonyl group, a butoxycarbonyl group and a phenoxycarbonyl group; acetoxy groups; linear alkyl groups such as a methyl group, an ethyl group, a propyl group, a butyl group, a heptyl group, a hexyl group, a dodecyl group and a 2-ethylhexyl group; branched alkyl groups; alkenyl groups such as a vinyl group, a propenyl group and a hexenyl group; acetylene groups; alkynyl groups such as a propynyl group and a hexynyl group; aryl groups such as a phenyl group and a tolyl group; a hydroxy group; a carboxy group; and a sulfonic acid group. Among these, from the viewpoint of the improvement of roughness, linear alkyl groups and branched alkyl groups are preferred.

In the formula (SA1), D is preferably a single bond, or an ether group or ester group. More preferably, D is a single bond.

In the formula (SA1), B is, for example, an alkyl group, an alkenyl group, an alkynyl group, an aryl group or a cycloalkyl group. B is, preferably, an alkyl group or a cycloalkyl group. The alkyl group, the alkenyl group, the alkynyl group, the aryl group, or the cycloalkyl group as B may have a substituent.

The alkyl group as B is preferably a branched alkyl group. Examples of the branched alkyl group include an isopropyl group, a tert-butyl group, a tert-pentyl group, a neopentyl group, a sec-butyl group, an isobutyl group, an isohexyl group, a 3,3-dimethylpentyl group, and a 2-ethylhexyl group.

The cycloalkyl group as B may be either a monocyclic cycloalkyl group or a polycyclic cycloalkyl group. Examples of the monocyclic cycloalkyl group include a cyclopropyl group, a cyclobutyl group, a cyclopentyl group, a cyclohexyl group, a cycloheptyl group and a cyclooctyl group. Examples of the polycyclic cycloalkyl group include an adamantyl group, a norbornyl group, a bornyl group, a camphenyl group, a decahydronaphthyl group, a tricyclodecanyl group, a tetracyclodecanyl group, a camphoroyl group, a dicyclohexyl group and a pinenyl group.

In the case where the alkyl group, the alkenyl group, the alkynyl group, the aryl group, or the cycloalkyl group as B has a substituent, the substituent may be exemplified as follows. That is, examples of the substituent include halogen atoms such as a fluorine atom, a chlorine atom, a bromine atom and an iodine atom; alkoxy groups such as a methoxy group, an ethoxy group and a tert-butoxy group; aryloxy groups such as a phenoxy group and a p-tolyloxy group; alkylthioxy groups such as a methylthioxy group, an ethylthioxy group and a tert-butylthioxy group; arylthioxy groups such as a phenylthioxy group and a p-tolylthioxy group; alkoxycarbonyl groups such as a methoxycarbonyl group, a butoxycarbonyl group and a phenoxycarbonyl group; acetoxy groups; linear alkyl groups such as a methyl group, an ethyl group, a propyl group, a butyl group, a heptyl group, a hexyl group, a dodecyl group and a 2-ethylhexyl group; branched alkyl groups; cycloalkyl groups such as a cyclohexyl group; alkenyl groups such as a vinyl group, a propenyl group and a hexenyl group; acetylene groups; alkynyl groups such as a propynyl group and a hexynyl group; aryl groups such as a phenyl group and a tolyl group; a hydroxy group; a carboxy group; and a sulfonic acid group. Among these, from the viewpoint of a balance between the improvement of roughness and the realization of high sensitivity, linear alkyl groups and branched alkyl groups are preferred.

Next, the sulfonic acid anion represented by the formula (SA2) will be described in detail.

In the formula (SA2), Xf is a fluorine atom or an alkyl group with at least one hydrogen atom being substituted with at least one fluorine atom. The alkyl group preferably has 1 to 10 carbon atoms, and more preferably 1 to 4 carbon atoms. Further, the alkyl group substituted with fluorine atoms is preferably a perfluoroalkyl group.

Xf is preferably a fluorine atom or a perfluoroalkyl group having 1 to 4 carbon atoms. Specifically, Xf is preferably a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, or $CH_2CH_2C_4F_9$. Among these, a fluorine atom or $CF_3$ is preferred, and a fluorine atom is most preferred.

In the formula (SA2), each of $R_1$ and $R_2$ is a group selected from a hydrogen atom, a fluorine atom, an alkyl group, and an alkyl group with at least one hydrogen atom being substituted with at least one fluorine atom. The alkyl group which may be substituted with fluorine atom(s) preferably has 1 to 4 carbon atoms. Further, the alkyl group which may be substituted with fluorine atom(s) is particularly preferably a perfluoroalkyl group having 1 to 4 carbon atoms. Specific examples thereof include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$, and among these, $CF_3$ is preferred.

In the formula (SA2), x is preferably from 1 to 8, and more preferably from 1 to 4. y is preferably from 0 to 4, and more preferably 0. z is preferably from 0 to 8, and more preferably from 0 to 4.

In the formula (SA2), L represents a single bond or a divalent connecting group. Examples of the divalent connecting group include —COO—, —OCO—, —CO—, —O—, —S—, —SO—, —SO$_2$—, an alkylene group, a cycloalkylene group, and an alkenylene group. Among these, —COO—, —OCO—, —CO—, —O—, —S—, —SO— or —SO$_2$— is preferred, and —COO—, —OCO— or —SO$_2$— is more preferred.

In the formula (SA2), E represents a group having a ring structure. Examples of E include a cyclic aliphatic group, an aryl group, and a group having a heterocyclic structure.

The cyclic aliphatic group as E may have a monocyclic structure or a polycyclic structure. As the cyclic aliphatic group having a monocyclic structure, monocyclic cycloalkyl groups such as a cyclopentyl group, a cyclohexyl group and a cyclooctyl group are preferred. As the cyclic aliphatic group having a polycyclic structure, polycyclic cycloalkyl groups such as a norbornyl group, a tricyclodecanyl group, a tetracyclodecanyl group, a tetracyclododecanyl group and an adamantyl group are preferred. Particularly, in the case where a cyclic aliphatic group having a structure with a high volume, such as a 6 or more-membered ring is employed as E, the diffusion in the film at the step of PEB (post-exposure heating), and thus, the resolution and EL (exposure latitude) can be further improved.

The aryl group as E is, for example, a benzene ring, a naphthalene ring, a phenanthrene ring, or an anthracene ring.

The group having a heterocyclic structure as E may or may not have aromatic properties. As the heteroatom contained in the group, a nitrogen atom or an oxygen atom is preferred. Specific examples of the heterocyclic structure include a furan ring, a thiophene ring, a benzofuran ring, a benzothiophene ring, a dibenzofuran ring, a dibenzothiophene ring, a pyridine ring, a piperidine ring and a morpholine ring. Among these, a furan ring, a thiophene ring, a pyridine ring, a piperidine ring, and a morpholine ring are preferred.

E may have a substituent. Examples of the substituent include alkyl groups (being linear, branched, or cyclic, and preferably having 1 to 12 carbon atoms), aryl groups (preferably having 6 to 14 carbon atoms), a hydroxy group, an alkoxy group, an ester group, an amide group, a urethane group, a ureido group, a thioether group, a sulfonamide group and a sulfonic acid ester group.

Examples of the sulfonic acid anion represented by the general formula (SA1) or (SA2) include the following.

[Chem. 111]

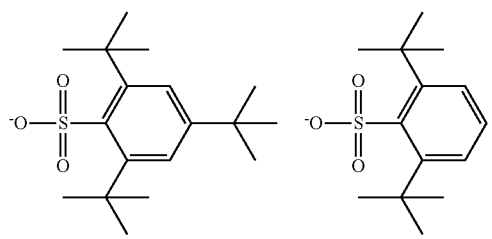

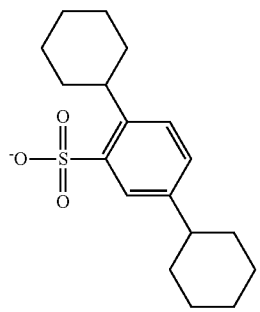

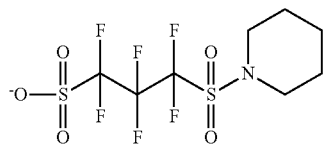

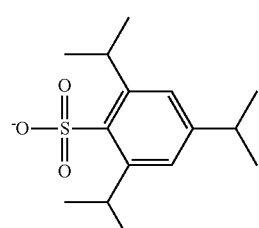

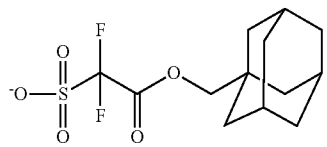

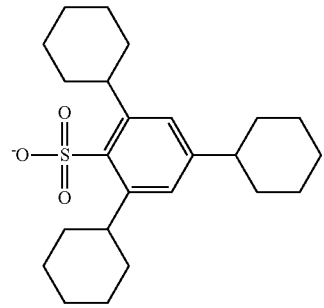

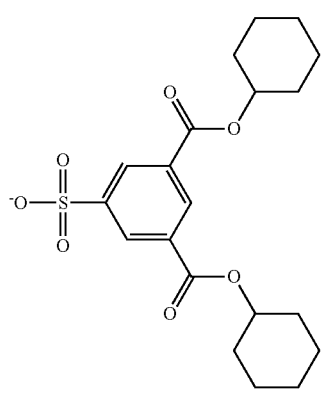

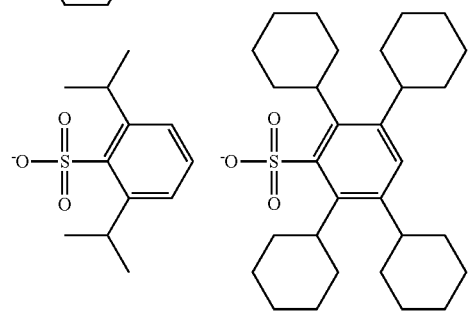

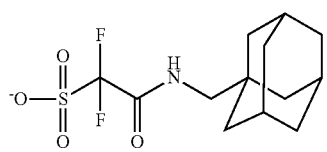

-continued
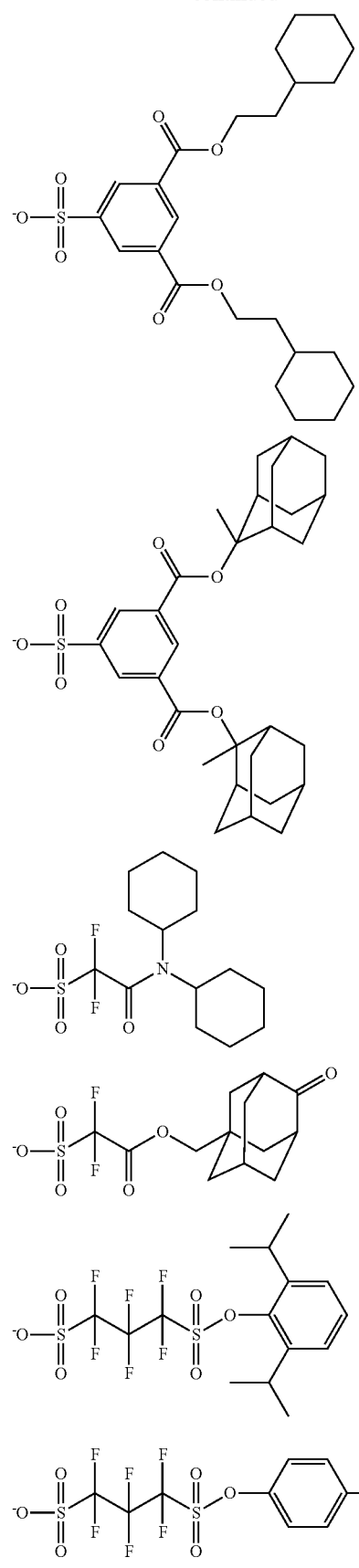
-continued
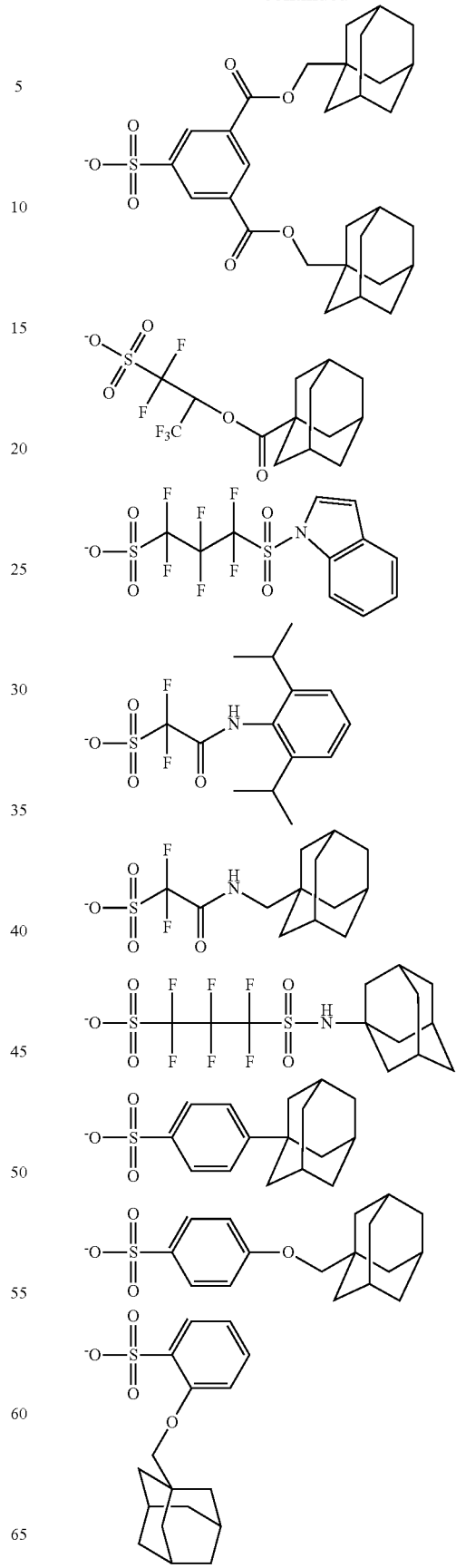

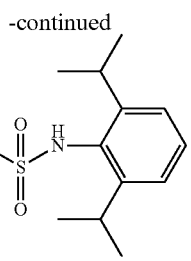

As the photo-acid generator, a compound having a plurality of structures represented by the general formula (ZI) may be also used. For example, the compound may be a compound having a structure where at least one of $R_{201}$ to $R_{203}$ in a compound represented by the general formula (ZI) is bonded to at least one of $R_{201}$ to $R_{203}$ of another compound represented by the general formula (ZI).

More preferred examples of the (ZI) component include the compounds (ZI-1) to (ZI-4) as described below.

For the compound (ZI-1), at least one of $R_{201}$ to $R_{203}$ in the general formula (ZI) is an aryl group. That is, the compound (ZI-1) is an arylsulfonium compound, that is, a compound having arylsulfonium as a cation.

For the compound (ZI-1), all of $R_{201}$ to $R_{203}$ may be aryl groups, or parts of $R_{201}$ to $R_{203}$ may be aryl groups with the remaining groups being alkyl groups. Further, in the case where the compound (ZI-1) has a plurality of aryl groups, these aryl groups may be the same as or different from each other.

Examples of the compound (ZI-1) include a triarylsulfonium compound, a diarylalkylsulfonium compound and an aryldialkylsulfonium compound.

As the aryl group in the compound (ZI-1), a phenyl group, a naphthyl group, or a heteroaryl group such as an indole residue and a pyrrole residue is preferred, and a phenyl group, a naphthyl group, or an indole residue is particularly preferred.

The alkyl group which is contained, if desired, in the compound (ZI-1) is preferably a linear, branched, or cyclic alkyl group having 1 to 15 carbon atoms, and examples thereof include a methyl group, an ethyl group, a propyl group, an n-butyl group, a sec-butyl group, a t-butyl group, a cyclopropyl group, a cyclobutyl group and a cyclohexyl group.

These aryl groups and alkyl groups may have substituents. Examples of the substituents include an alkyl group (preferably having 1 to 15 carbon atoms), an aryl group (preferably having 6 to 14 carbon atoms), an alkoxy group (preferably having 1 to 15 carbon atoms), a halogen atom, a hydroxyl group, and a phenylthio group.

Preferred examples of the substituent include a linear, branched, or cyclic alkyl group having 1 to 12 carbon atoms, and a linear, branched, or cyclic alkoxy group having 1 to 12 carbon atoms. Particularly preferred examples of the substituent include an alkyl group having 1 to 6 carbon atoms and an alkoxy group having 1 to 6 carbon atoms. The substituent may be substituted on any one of three members $R_{201}$ to $R_{203}$ or may be substituted on all of these members. In the case where $R_{201}$ to $R_{203}$ are a phenyl group, the substituent is preferably substituted at the p-position of the aryl group.

Furthermore, it is also preferable that one or two members out of $R_{201}$, $R_{202}$ and $R_{203}$ be an optionally substituted aryl group and the remaining groups be linear, branched, or cyclic alkyl groups. Specific examples of the structures include the structures described in paragraphs 0141 to 0153 of JP2004-210670A.

Here, specific examples of the aryl group include the same aryl groups as $R_{201}$, $R_{202}$ and $R_{203}$. It is preferable for the aryl group to have any one of a hydroxyl group, an alkoxy group, and an alkyl group as a substituent. The substituent is more preferably an alkoxy group having 1 to 12 carbon atoms, and still more preferably an alkoxy group having 1 to 6 carbon atoms.

The linear, branched, or cyclic alkyl groups of the remaining groups are preferably alkyl groups having 1 to 6 carbon atoms. These groups may further have substituents. When two remaining groups exist, they may be bonded to each other to form a ring structure.

The compound (ZI-1) is, for example, a compound represented by the following general formula (ZI-1A).

[Chem. 112]

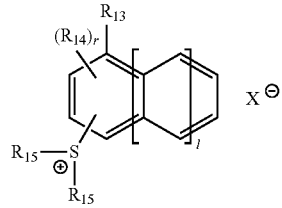

(ZI-1A)

In the general formula (ZI-1A), $R_{13}$ represents a hydrogen atom, fluorine atom, a hydroxyl group, an alkyl group, a cycloalkyl group, an alkoxy group, a cycloalkyloxy group, or an alkoxycarbonyl group.

In the case of a plurality of $R_{14}$'s being present, they each independently represent an alkyl group, a cycloalkyl group, an alkoxy group, an alkylsulfonyl group, or a cycloalkylsulfonyl group.

$R_{15}$'s each independently represent an alkyl group or a cycloalkyl group. Two $R_{15}$'s may be bonded to each other to form a ring structure.

l represents an integer of 0 to 2.

r represents an integer of 0 to 8.

$X^-$ represents a non-nucleophilic anion and examples thereof include the same $X^-$'s in the general formula (ZI).

The alkyl group of $R_{13}$, $R_{14}$ or $R_{15}$ may be either a linear alkyl group or a branched alkyl group. The alkyl group preferably has 1 to 10 carbon atoms, and examples thereof include a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, and an n-decyl group. Among these, a methyl group, an ethyl group, an n-butyl group and a t-butyl group are particularly preferred.

Examples of the cycloalkyl group of $R_{13}$, $R_{14}$ or $R_{15}$ include a cyclopropyl group, a cyclobutyl group, a cyclopentyl group, a cyclohexyl group, a cycloheptyl group, a cyclooctyl group, a cyclododecanyl group, a cyclopentenyl group, a cyclohexenyl and a cyclooctadienyl group. Among these, a cyclopropyl group, a cyclopentyl group, a cyclohexyl group, and a cyclooctyl group are particularly preferred.

Examples of the alkyl group moiety in the alkoxy group of $R_{13}$ or $R_{14}$ include those exemplified above as the alkyl group of $R_{13}$, $R_{14}$ or $R_{15}$. As the alkoxy group, a methoxy group, an ethoxy group, an n-propoxy group, and an n-butoxy group are particularly preferred.

Examples of the cycloalkyl group moiety in the cycloalkyloxy group of $R_{13}$ include those exemplified above as the cycloalkyl group of $R_{13}$, $R_{14}$ or $R_{15}$. As the cycloalkyloxy group, a cyclopentyloxy group and a cyclohexyloxy group are particularly preferred.

Examples of the alkoxy group moiety in the alkoxycarbonyl group of $R_{13}$ include those exemplified above as the alkoxy group of $R_{13}$ or $R_{14}$. As the alkoxycarbonyl group, a methoxycarbonyl group, an ethoxycarbonyl group, and an n-butoxycarbonyl group are particularly preferred.

Examples of the alkyl group moiety in the alkylsulfonyl group of $R_{14}$ include those exemplified above as the alkyl group of $R_{13}$, $R_{14}$ or $R_{15}$. Further, examples of the cycloalkyl group moiety in the cycloalkylsulfonyl group of $R_{14}$ include those exemplified above as the cycloalkyl group of $R_{13}$, $R_{14}$ or $R_{15}$. As the alkylsulfonyl group or cycloalkylsulfonyl group, a methanesulfonyl group, an ethanesulfonyl group, an n-propanesulfonyl group, an n-butanesulfonyl group, a cyclopentanesulfonyl group and a cyclohexanesulfonyl group are particularly preferred.

l is preferably 0 or 1, and more preferably 1. r is preferably 0 to 2.

Each of the groups of $R_{13}$, $R_{14}$ and $R_{15}$ may further have a substituent. Examples of the substituent include halogen atoms such as a fluorine atom, a hydroxy group, a carboxy group, a cyano group, a nitro group, an alkoxy group, a cycloalkyloxy group, an alkoxyalkyl group, a cycloalkyloxyalkyl group, an alkoxycarbonyl group, a cycloalkyloxycarbonyl group, an alkoxycarbonyloxy group, and a cycloalkyloxycarbonyloxy group.

The alkoxy group may be linear or branched. Examples of the alkoxy group include those having 1 to 20 carbon atoms, such as a methoxy group, an ethoxy group, an n-propoxy group, an i-propoxy group, an n-butoxy group, a 2-methylpropoxy group, a 1-methylpropoxy group and a t-butoxy group.

Examples of the cycloalkyloxy group include those having 3 to 20 carbon atoms, such as a cyclopentyloxy group and a cyclohexyloxy group.

The alkoxyalkyl group may be linear or branched. Examples of the alkoxyalkyl group include those having 2 to 21 carbon atoms, such as a methoxymethyl group, an ethoxymethyl group, a 1-methoxyethyl group, a 2-methoxyethyl group, a 1-ethoxyethyl group, and 2-ethoxyethyl group.

Examples of the cycloalkyloxyalkyl group include those having 4 to 21 carbon atoms, such as a cyclohexyloxymethyl group, a cyclopentyloxymethyl group, and a cyclohexyloxyethyl group.

The alkoxycarbonyl group may be linear or branched. Examples of the alkoxycarbonyl group include those having 2 to 21 carbon atoms, such as a methoxycarbonyl group, an ethoxycarbonyl, n-propoxycarbonyl group, an i-propoxycarbonyl group, an n-butoxycarbonyl group, a 2-methylpropoxycarbonyl group, a 1-methylpropoxycarbonyl group, and a t-butoxycarbonyl group.

Examples of the cycloalkyloxycarbonyl group include those having 4 to 21 carbon atoms, such as a cyclopentyloxycarbonyl group and a cyclohexyloxycarbonyl group.

The alkoxycarbonyloxy group may be linear or branched. Examples of the alkoxycarbonyloxy group include those having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, and a t-butoxycarbonyloxy group.

Examples of the cycloalkyloxycarbonyloxy group include those having 4 to 21 carbon atoms, such as a cyclopentyloxycarbonyloxy group and a cyclohexyloxycarbonyloxy group.

As the ring structure which may be formed by the mutual bonding of two $R_{15}$'s, structures that form a 5- or 6-membered ring together with the S atom in the formula (ZI-1A) are preferred, and structures that form a 5-membered ring (that is, a tetrahydrothiophene ring) are particularly preferred.

The ring structure may further have a substituent. Examples of the substituent include a hydroxy group, a carboxy group, a cyano group, a nitro group, an alkoxy group, an alkoxyalkyl group, an alkoxycarbonyl group, and an alkoxycarbonyloxy group.

As $R_{15}$, a methyl group, an ethyl group, and a divalent group that forms a tetrahydrothiophene ring structure by the mutual bonding of two $R_{15}$'s together with a sulfur atom are particularly preferred.

The alkyl group, the cycloalkyl group, the alkoxy group and the alkoxycarbonyl group of $R_{13}$, and the alkyl group, the cycloalkyl group, the alkoxy group, the alkylsulfonyl group and the cycloalkylsulfonyl group of $R_{14}$ may further have a substituent. As the substituent, a hydroxy group, an alkoxy group, an alkoxycarbonyl group, and a halogen atom (particularly a fluorine atom) are preferred.

Preferred specific examples of the cation in the compound represented by the general formula (ZI-1A) are shown below.

[Chem. 113]

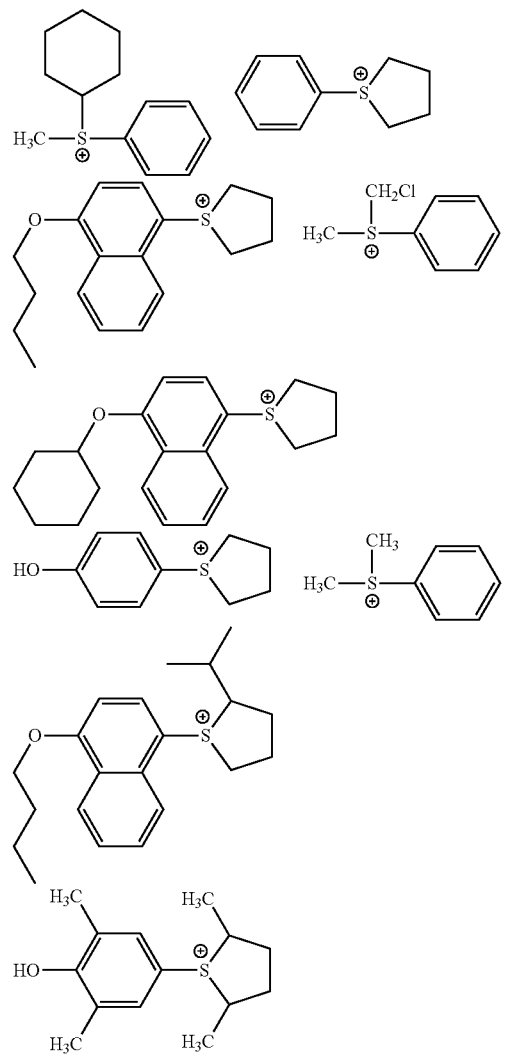

-continued

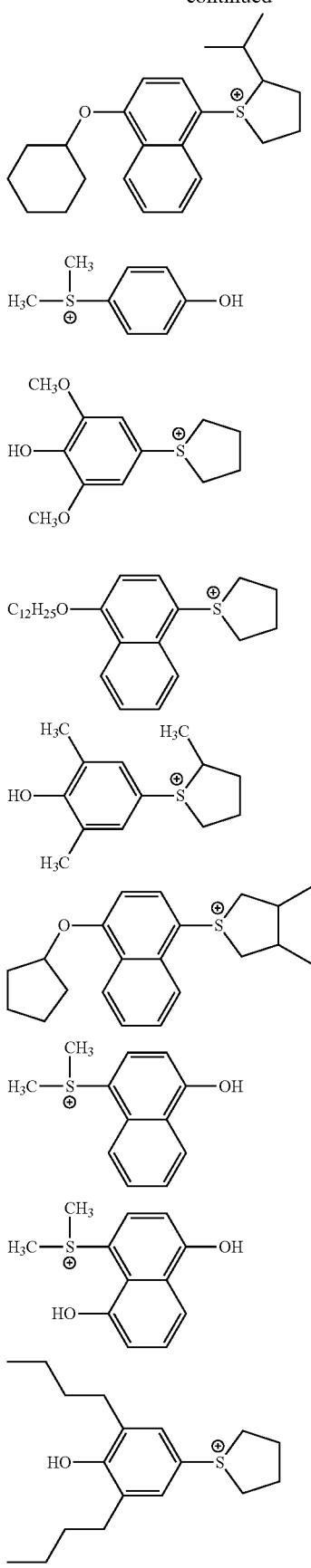

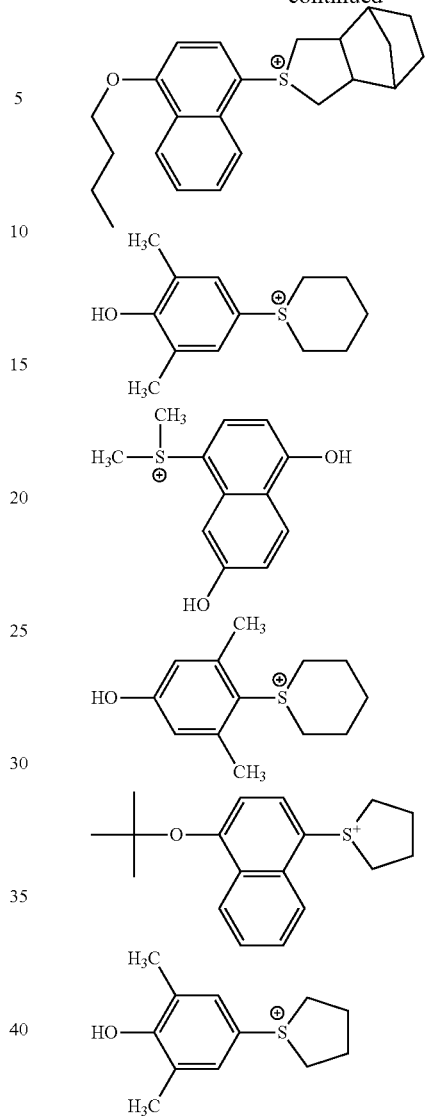

Next, the compound (ZI-2) will be described.

The compound (ZI-2) is a compound in which $R_{201}$ to $R_{203}$ in the formula (ZI) each independently represent an aromatic ring-free organic group. The aromatic ring as used herein includes an aromatic ring containing a heteroatom.

The aromatic ring-free organic group as $R_{201}$ to $R_{203}$ has 1 to 30 carbon atoms, and preferably 1 to 20 carbon atoms.

$R_{201}$ to $R_{203}$ are each independently preferably an alkyl group, a 2-oxoalkyl group, an alkoxycarbonylmethyl group, an allyl group, or a vinyl group, more preferably a linear, branched, or cyclic 2-oxoalkyl group or an alkoxycarbonylmethyl group, and particularly preferably a linear or branched 2-oxoalkyl group.

The alkyl group as $R_{201}$ to $R_{203}$ may be linear, branched, or cyclic, and preferred examples thereof include linear or branched alkyl groups having 1 to 10 carbon atoms (for example, a methyl group, an ethyl group, a propyl group, a butyl group, and a pentyl group) and cycloalkyl groups having 3 to 10 carbon atoms (a cyclopentyl group, a cyclohexyl group, or a norbornyl group).

The 2-oxoalkyl group as $R_{201}$ to $R_{203}$ may be linear, branched or cyclic, and preferred examples thereof include a group having >C=O at the 2-position of the above-described alkyl group.

Preferred examples of the alkoxy group in the alkoxycarbonylmethyl group as $R_{201}$ to $R_{203}$ include an alkoxy group having 1 to 5 carbon atoms (a methoxy group, an ethoxy group, a propoxy group, a butoxy group, and a pentoxy group).

$R_{201}$ to $R_{203}$ may be further substituted with, for example, a halogen atom, an alkoxyl group (for example, having 1 to 5 carbon atoms), a hydroxyl group, a cyano group, and/or a nitro group.

Two members out of $R_{201}$ to $R_{203}$ may be bonded to each other to form a ring structure, and the ring structure may contain an oxygen atom, a sulfur atom, an ester bond, an amide bond, and/or a carbonyl group in the ring. Examples of the group formed by the mutual bonding of two members out of $R_{201}$ to $R_{203}$ include alkylene groups (for example, a butylene group and a pentylene group).

Next, the compound (ZI-3) will be described.

The compound (ZI-3) is a compound represented by the following general formula (ZI-3), which is a compound having a phenacylsulfonium structure.

[Chem. 114]

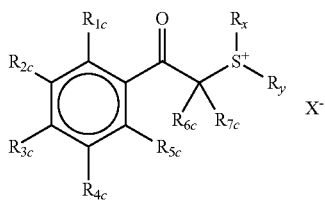

(ZI-3)

In the formula, $R_{1c}$ to $R_{5c}$ each independently represent a hydrogen atom, an alkyl group, an alkoxy group, or a halogen atom. The number of carbon atoms of the alkyl group and the alkoxy group is preferably from 1 to 6.

$R_{6c}$ and $R_7$ represent a hydrogen atom or an alkyl group. The number of carbon atoms of the alkyl group is preferably from 1 to 6.

$R_x$ and $R_y$ each independently represent an alkyl group, a 2-oxoalkyl group, an alkoxycarbonylmethyl group, an allyl group, or a vinyl group. The number of carbon atoms of the atomic group is preferably from 1 to 6.

Any two or more members out of $R_{1c}$ to $R_{7c}$ may be bonded to each other to form a ring structure, and the ring structure may contain an oxygen atom, a sulfur atom, an ester bond, and/or an amide bond.

$X^-$ in the general formula (ZI-3) has the same definition as X in the general formula (ZI).

Specific examples of the compound (ZI-3) include the compounds as the compounds exemplified in paragraphs 0047 and 0048 of JP2004-233661A and paragraphs 0040 to 0046 of JP2003-35948A.

Next, the compound (ZI-4) will be described.

The compound (ZI-4) is a compound having a cation represented by the following general formula (ZI-4). This compound (ZI-4) is effective to suppress outgassing.

[Chem. 115]

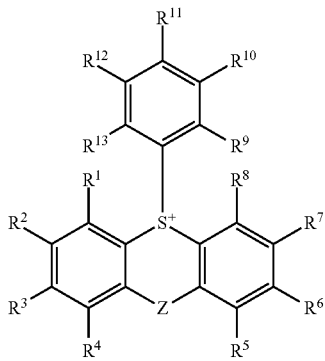

(ZI-4)

In the general formula (ZI-4), $R^1$ to $R^{13}$ each independently represent a hydrogen atom or a substituent. At least one of $R^1$ to $R^{13}$ is preferably a substituent containing an alcoholic hydroxyl group. Further, the term "alcoholic hydroxyl group" as used herein means a hydroxyl group bonded to a carbon atom of an alkyl group.

Z represents a single bond or a divalent connecting group.

In the case where $R^1$ to $R^{13}$ are each a substituent containing an alcoholic hydroxyl group, $R^1$ to $R^{13}$ are each preferably a group represented by —(W—Y), wherein Y is an alkyl group substituted with a hydroxyl group and W is a single bond or a divalent connecting group.

Preferred examples of the alkyl group represented by Y include an ethyl group, a propyl group and an isopropyl group. Y particularly preferably contains a structure represented by —$CH_2CH_2OH$.

The divalent connecting group represented by W is not particularly limited, but is preferably a single bond or a divalent group formed by substituting a single bond for an arbitrary hydrogen atom of an alkoxy group, an acyloxy group, an acylamino group, an alkyl- or aryl-sulfonylamino group, an alkylthio group, an alkylsulfonyl group, an acyl group, an alkoxycarbonyl group or a carbamoyl group, and more preferably a single bond or a divalent group formed by substituting a single bond for an arbitrary hydrogen atom of an acyloxy group, an alkylsulfonyl group, an acyl group or an alkoxycarbonyl group.

In the case where $R^1$ to $R^{13}$ are a substituent containing an alcoholic hydroxyl group, the number of carbons contained therein is preferably from 2 to 10, more preferably from 2 to 6, and particularly preferably from 2 to 4.

The alcoholic hydroxyl group-containing substituent as $R^1$ to $R^{13}$ may have two or more alcoholic hydroxyl groups. The number of alcoholic hydroxyl groups in the alcoholic hydroxyl group-containing substituent as $R^1$ to $R^{13}$ is from 1 to 6, preferably from 1 to 3, and more preferably 1.

The number of alcoholic hydroxyl groups contained in the compound represented by the general formula (ZI-4) is, in total of all of $R^1$ to $R^{13}$, from 1 to 10, preferably from 1 to 6, and more preferably from 1 to 3.

In the case where $R^1$ to $R^{13}$ contain no alcoholic hydroxyl group, examples of the substituent as $R^1$ to $R^{13}$ include a halogen atom, an alkyl group, a cycloalkyl group, an alkenyl group, a cycloalkenyl group, an alkynyl group, an aryl group, heterocycle group, a cyano group, a nitro group, a carboxy group, an alkoxy group, an aryloxy group, a silyloxy group, heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—OPO(OH)$_2$), a sulfato group (—OSO$_3$H), and other known substituents.

In the case where $R^1$ to $R^{13}$ contain no alcoholic hydroxyl group, $R^1$ to $R^{13}$ are each preferably a hydrogen atom, a halogen atom, an alkyl group, a cycloalkyl group, an alkenyl group, a cycloalkenyl group, an alkynyl group, an aryl group, a cyano group, a carboxy group, an alkoxy group, an aryloxy group, an acyloxy group, a carbamoyloxy group, an acylamino group, an aminocarbonylamino group, an alkoxycarbonylamino group, an aryloxycarbonylamino group, a sulfamoylamino group, an alkyl- or aryl-sulfonylamino group, an alkylthio group, an arylthio group, a sulfamoyl group, an alkyl- or aryl-sulfonyl group, an aryloxycarbonyl group, an alkoxycarbonyl group, a carbamoyl group, an imide group, a silyl group, or a ureido group.

In the case where $R^1$ to $R^{13}$ contain no alcoholic hydroxyl group, $R^1$ to $R^{13}$ are each more preferably a hydrogen atom, a halogen atom, an alkyl group, a cycloalkyl group, a cyano group, an alkoxy group, an acyloxy group, an acylamino group, an aminocarbonylamino group, an alkoxycarbonylamino group, an alkyl- or aryl-sulfonylamino group, an alkylthio group, a sulfamoyl group, an alkyl- or aryl-sulfonyl group, an alkoxycarbonyl group, or a carbamoyl group.

In the case where $R^1$ to $R^{13}$ contain no alcoholic hydroxyl group, $R^1$ to $R^{13}$ are each particularly preferably a hydrogen atom, an alkyl group, a cycloalkyl group, a halogen atom, or an alkoxy group.

Two adjacent members out of $R^1$ to $R^{13}$ may be bonded to each other to form a ring structure. This ring structure includes an aromatic or non-aromatic hydrocarbon ring and a heterocycle. These ring structures may be further combined with each other to form a condensed ring.

The compound (ZI-4) preferably has a structure where at least one of $R^1$ to $R^{13}$ contains an alcoholic hydroxyl group, and more preferably a structure where at least one of $R^9$ to $R^{13}$ contains an alcoholic hydroxyl group.

Z represents, as described above, a single bond or a divalent connecting group. Examples of the divalent connecting group include an alkylene group, an arylene group, a carbonyl group, a sulfonyl group, a carbonyloxy group, a carbonylamino group, a sulfonylamide group, an ether group, a thioether group, an amino group, a disulfide group, an acyl group, an alkylsulfonyl group, —CH═CH—, an aminocarbonylamino group, and an aminosulfonylamino group.

The divalent connecting group may have a substituent. Examples of the substituent thereof are the same as those enumerated above with respect to $R^1$ to $R^{13}$ Z is preferably a non-electron-withdrawing bond or group such as a single bond, an alkylene group, an arylene group, an ether group, a thioether group, an amino group, —CH═CH—, an aminocarbonylamino group, and an aminosulfonylamino group, more preferably a single bond, an ether group, or a thioether group, and particularly preferably a single bond.

The general formulae (ZII) and (ZIII) will be described below.

In the general formulae (ZII) and (ZIII), $R_{204}$ to $R_{207}$ each independently represent an aryl group, an alkyl group, or a cycloalkyl group. The aryl group, the alkyl group, and the cycloalkyl group may have a substituent.

Preferred examples of the aryl group as $R_{204}$ to $R_{207}$ include the groups enumerated above with respect to $R_{201}$ to $R_{203}$ in the compound (ZI-1).

Preferred examples of the alkyl group and the cycloalkyl group as $R_{204}$ to $R_{207}$ include the linear, branched or cycloalkyl groups enumerated above with respect to $R_{201}$ to $R_{203}$ in the compound (ZI-2).

Further, $X^-$'s in the general formulae (ZII) and (ZIII) have the same definitions as $X^-$ in the general formula (ZI).

Other preferred examples of the photo-acid generator include the compounds represented by the following general formula (ZIV), (ZV), or (ZVI).

[Chem. 116]

$$Ar_3-SO_2-SO_2-Ar_4 \quad \text{ZIV}$$

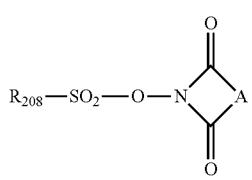

ZV

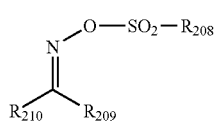

ZVI

In the general formulae (ZIV) to (ZVI), $Ar_3$ and $Ar_4$ each independently represent a substituted or unsubstituted aryl group.

$R_{208}$'s of the general formulae (ZV) and (ZVI) each independently represent an alkyl group, a cycloalkyl group or an aryl group. These alkyl groups, cycloalkyl groups, and aryl groups may or may not be substituted.

These groups are preferably substituted with a fluorine atom. This can increase the strength of the acid generated from the photo-acid generator.

$R_{209}$ and $R_{210}$ each independently represent an alkyl group, a cycloalkyl group, an aryl group, or an electron-withdrawing group. The alkyl group, the cycloalkyl group, the aryl group, and the electron-withdrawing group may or may not be substituted.

Preferred examples of $R_{209}$ include a substituted or unsubstituted aryl group.

Preferred examples of $R_{210}$ include an electron-withdrawing group. Examples of this electron-withdrawing group include a cyano group and a fluoroalkyl group.

A represents an alkylene group, an alkenylene group, or an arylene group. The alkylene group, the alkenylene group, and the arylene group may have a substituent.

Moreover, as the photo-acid generator, a compound having a plurality of structures represented by the general formula (ZVI) is also preferred. Examples of the compound include a compound having a structure where $R_{209}$ or $R_{210}$ in a compound represented by the general formula (ZVI) is bonded to $R_{209}$ or $R_{210}$ in another compound represented by the general formula (ZVI).

The photo-acid generator is more preferably a compound represented by any of the general formulae (ZI) to (ZIII), still more preferably a compound represented by the general formula (ZI), and particularly preferably the compounds (ZI-1) to (ZI-3).

As the acid generator used in the present invention, a compound having a group capable of decomposing by the action of an acid to increase the solubility in an alkali developer can also be preferably used. Examples of such an acid generator include the compounds described in JP2005-97254A and JP2007-199692A, and the like.

Specific examples of the photo-acid generator are shown below, but the present invention is not limited thereto.

[Chem. 117]

B-1
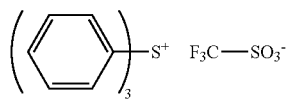

B-2
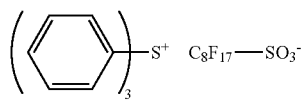

B-3

B-4

B-5

B-6

B-7
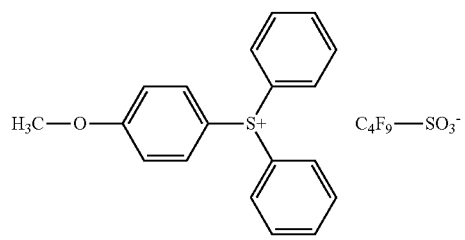

B-8

B-9

B-10

B-11
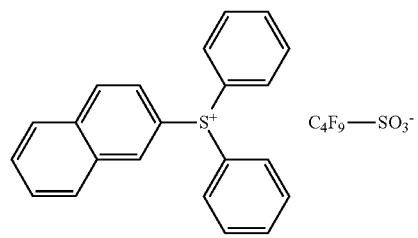

B-12

B-13
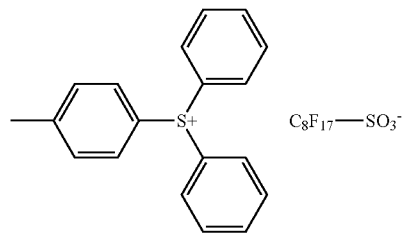

B-14

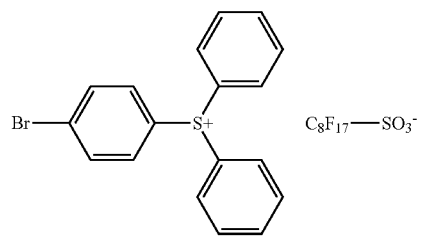

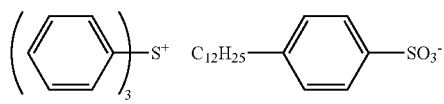
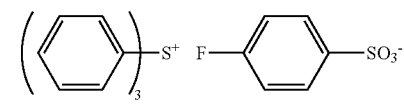

-continued
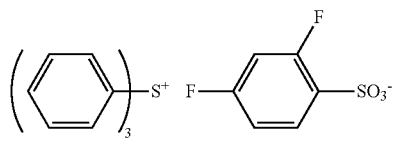
B-15
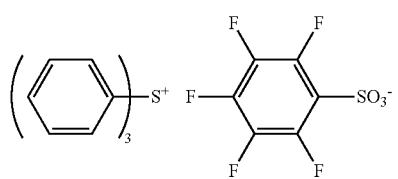
B-16
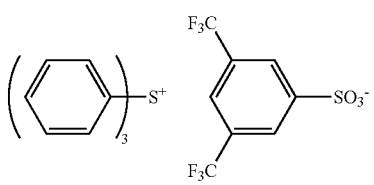
B-17
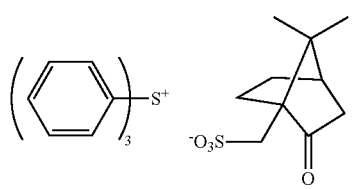
B-18
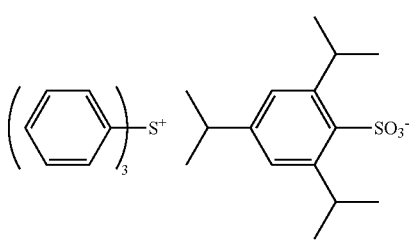
B-19
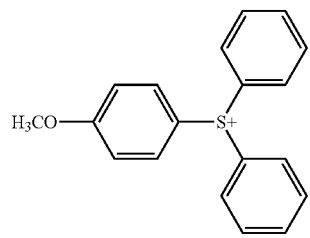
B-20
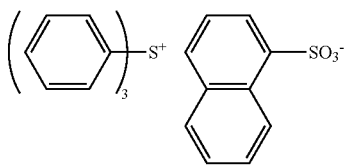
B-21
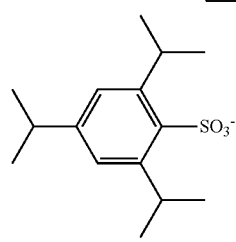
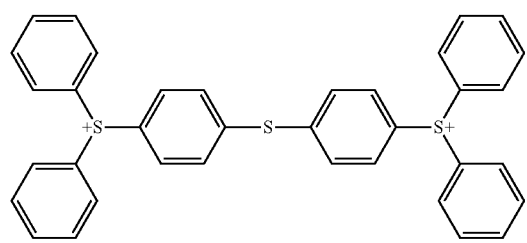
B-22
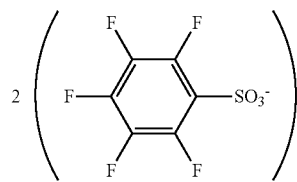
B-23

-continued
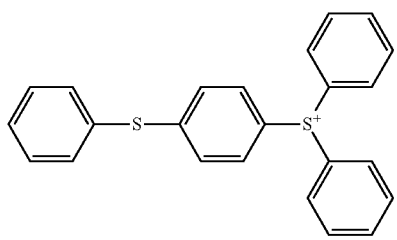 B-24
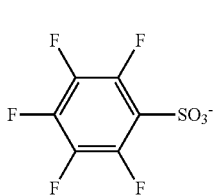
B-25 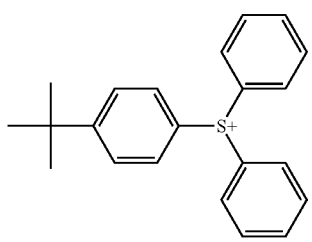
B-26 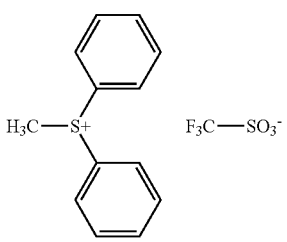
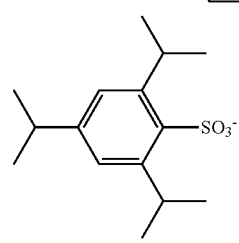
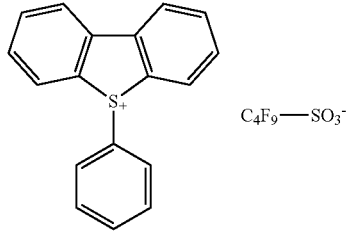
[Chem. 119]
B-28 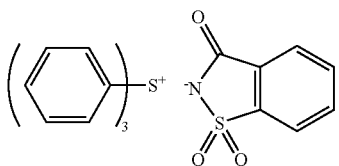
B-29 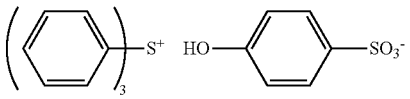
B-30
B-31 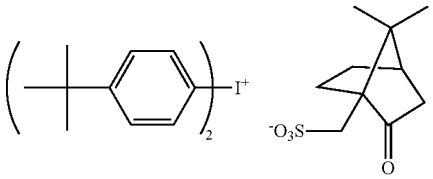
B-32
B-33 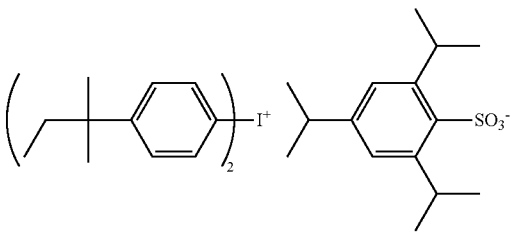

-continued
[Chem. 120]
B-34
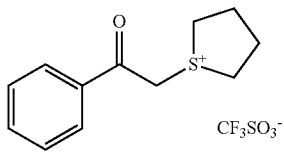
CF$_3$SO$_3^-$
B-35
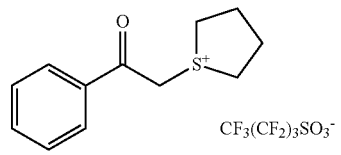
CF$_3$(CF$_2$)$_3$SO$_3^-$
B-36
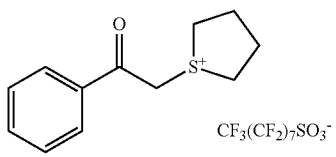
CF$_3$(CF$_2$)$_7$SO$_3^-$
B-37
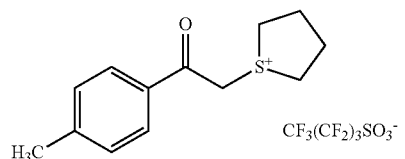
CF$_3$(CF$_2$)$_3$SO$_3^-$
B-38
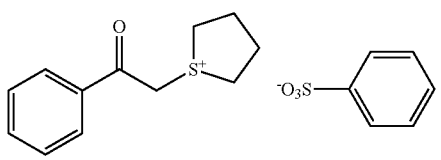
B-39
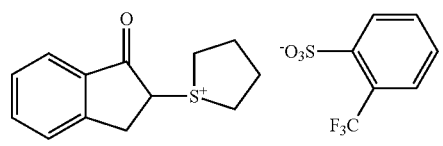
B-40
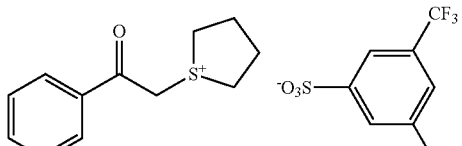
B-41
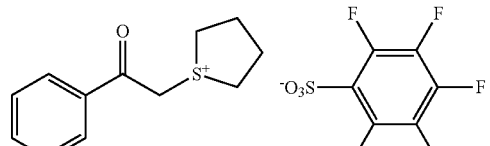
B-42
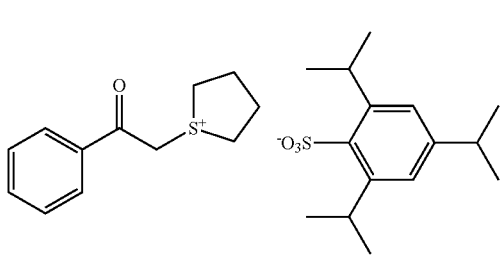
B-43
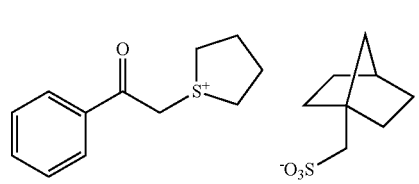
B-44
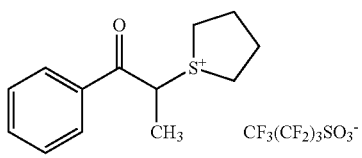
CF$_3$(CF$_2$)$_3$SO$_3^-$
B-45
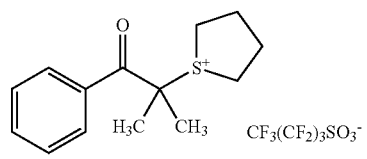
CF$_3$(CF$_2$)$_3$SO$_3^-$
B-46
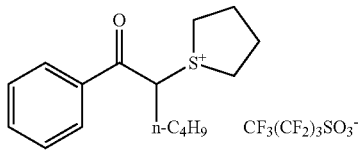
CF$_3$(CF$_2$)$_3$SO$_3^-$
[Chem. 121]
B-47
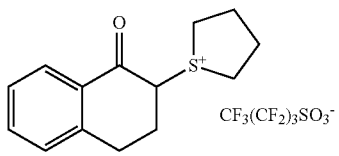
CF$_3$(CF$_2$)$_3$SO$_3^-$
B-48
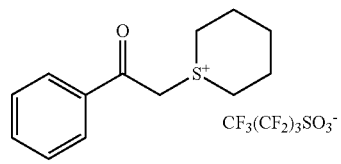
CF$_3$(CF$_2$)$_3$SO$_3^-$ -continued
B-49 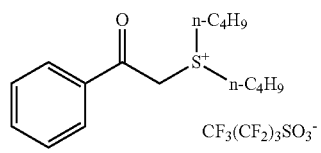
B-50 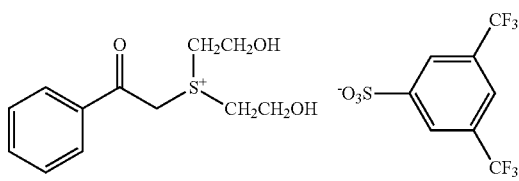
B-51 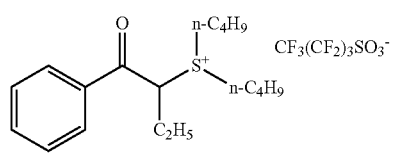
B-52 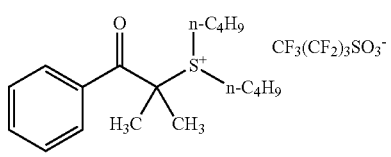
B-53 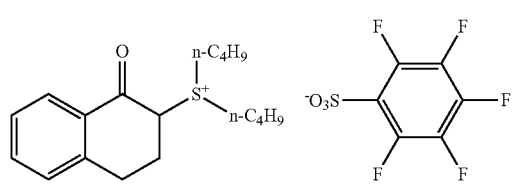
B-54 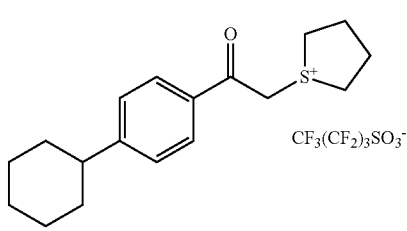
B-55 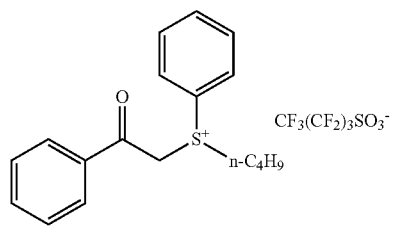
B-56 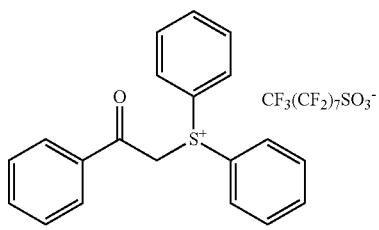
[Chem. 122]
B-57 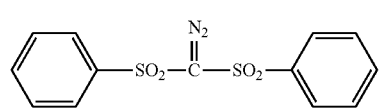
B-58 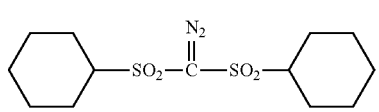
B-59 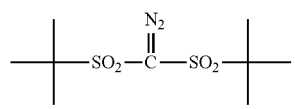
B-60 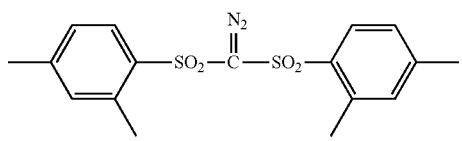
B-61 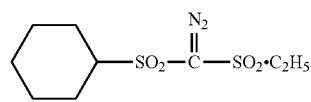
B-62 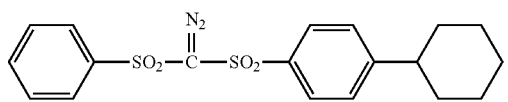
B-63 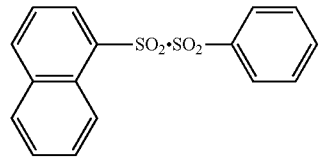
B-64 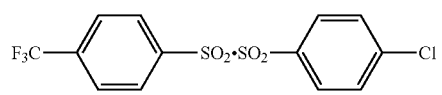
B-65 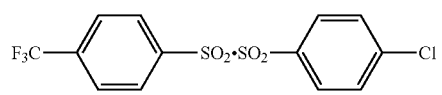
B-66 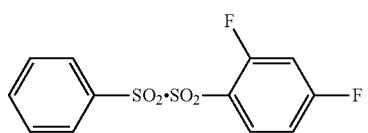

[Chem. 123]
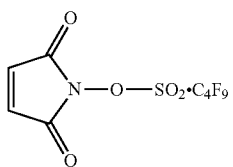
B-67
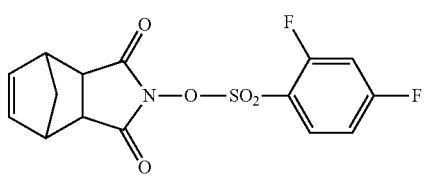
B-68
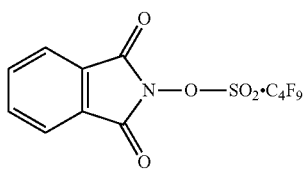
B-69
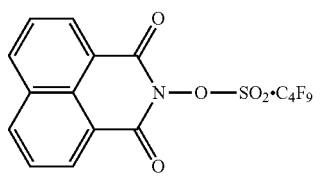
B-70
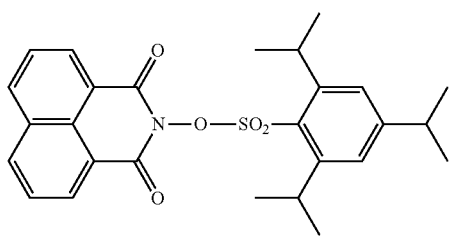
B-71
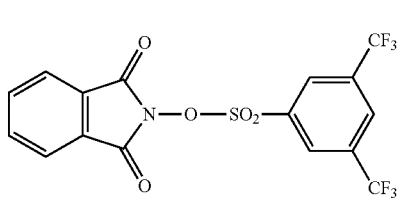
B-72
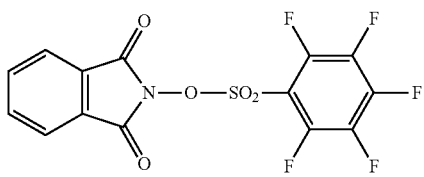
B-73
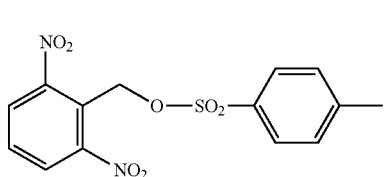
B-74
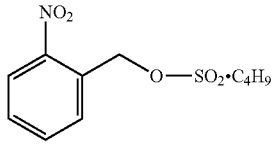
B-75
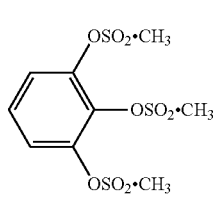
B-76
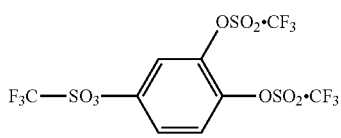
B-77
[Chem. 124]
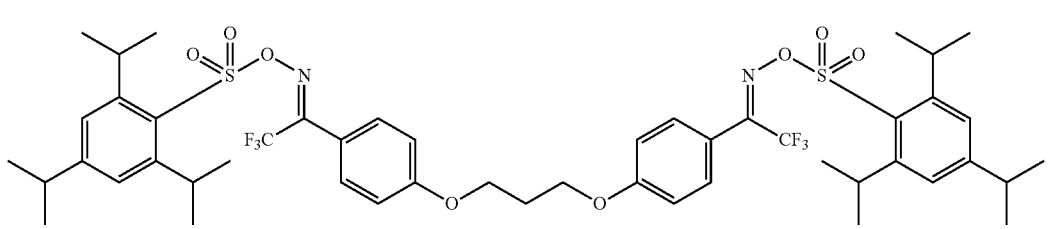
B-78
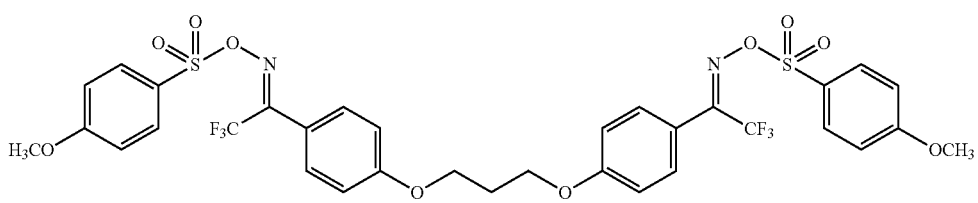
B-79

-continued
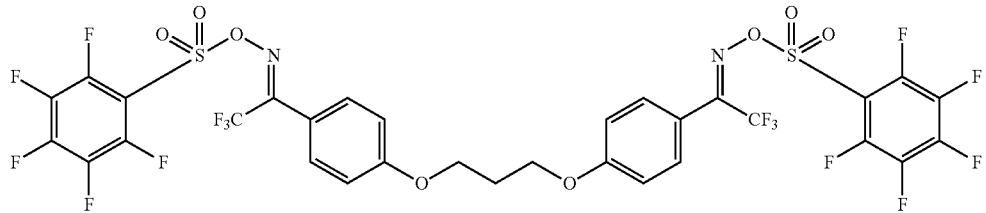
B-80
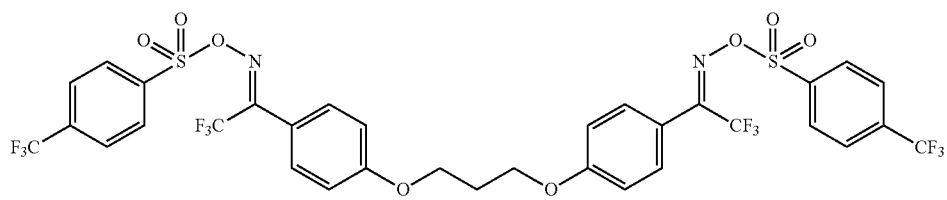
B-81
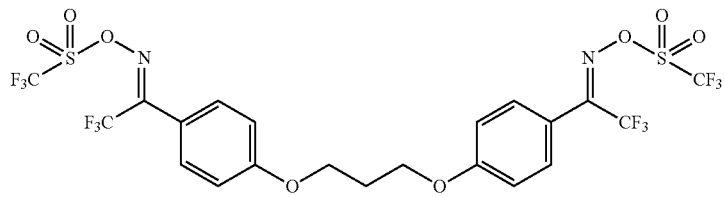
B-82
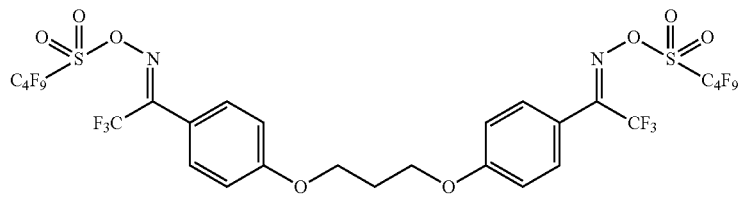
B-83
[Chem. 125]
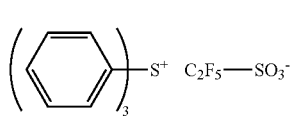
B-84
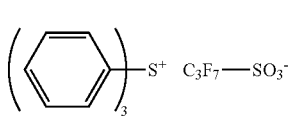
B-85
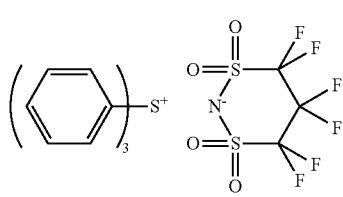
B-86
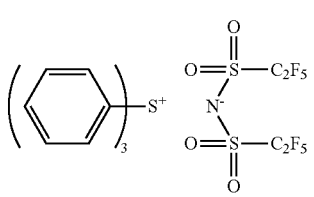
B-87
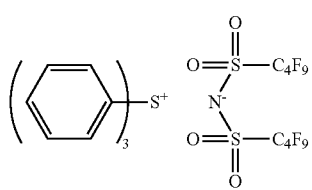
B-88
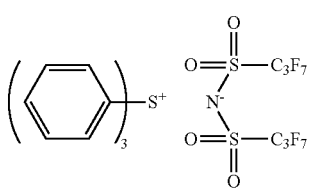
B-89
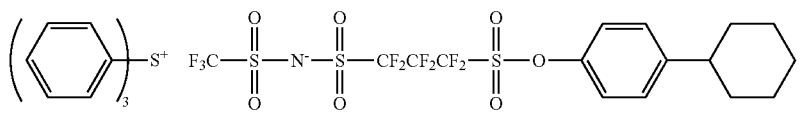
B-90
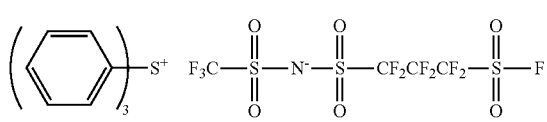
B-91

-continued
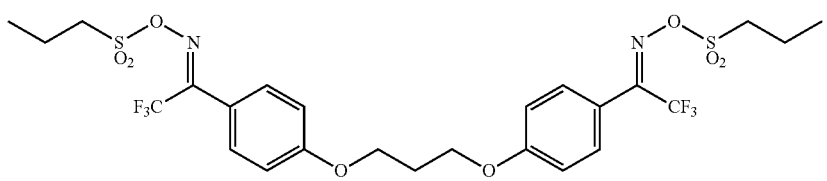
B-92
[Chem. 126]
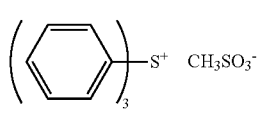 B-93
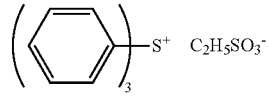 B-94
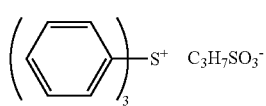 B-95
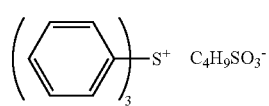 B-96
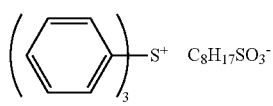 B-97
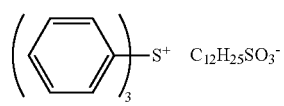 B-98
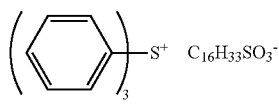 B-99
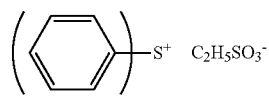 B-100
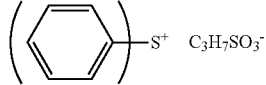 B-101
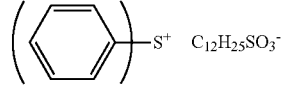 B-102
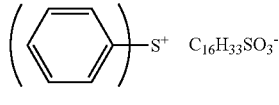 B-103
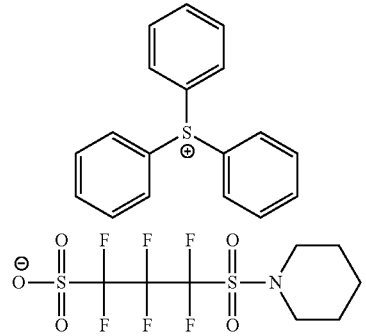 B-104
[Chem. 127]
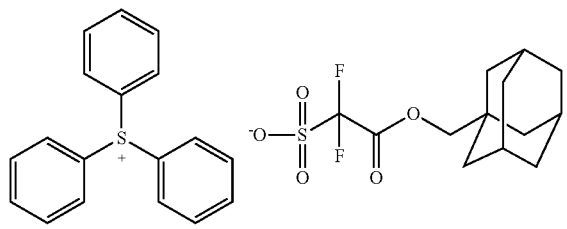 B-105
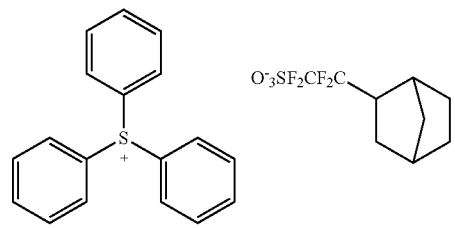 B-106

-continued
B-107
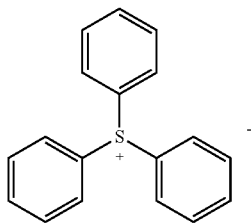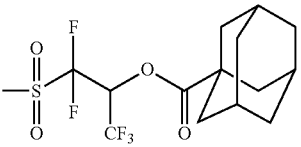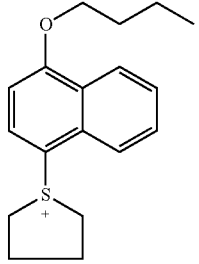
B-108
B-109
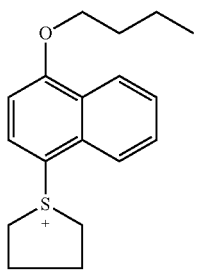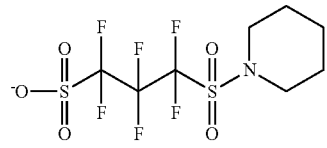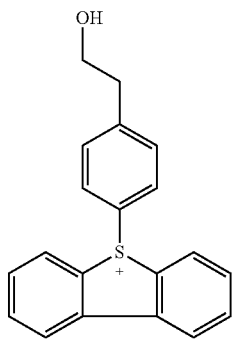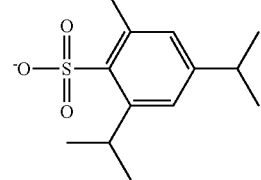
B-110
B-111
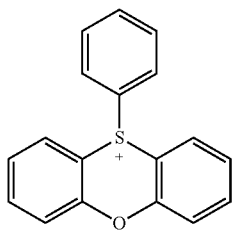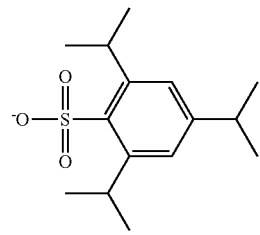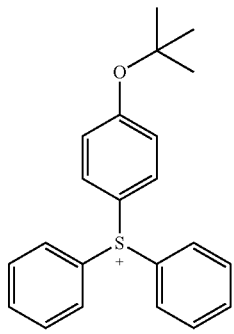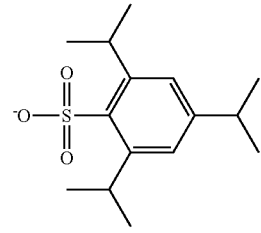
B-112
B-113
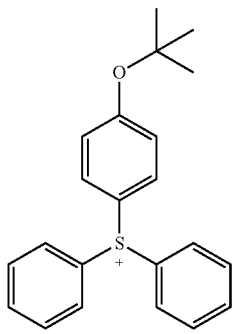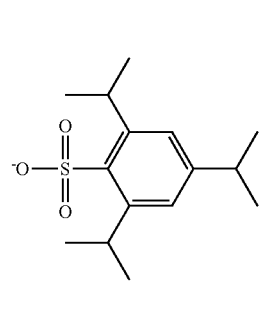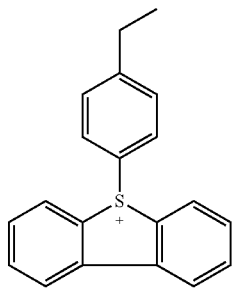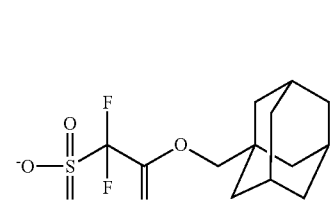
B-114

-continued
B-115
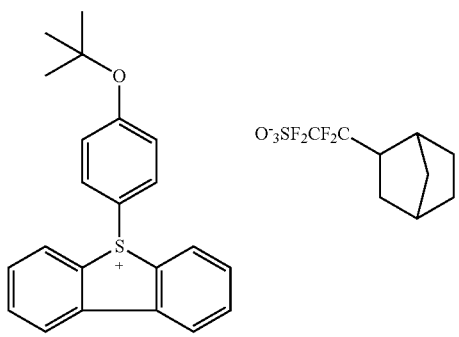
B-116
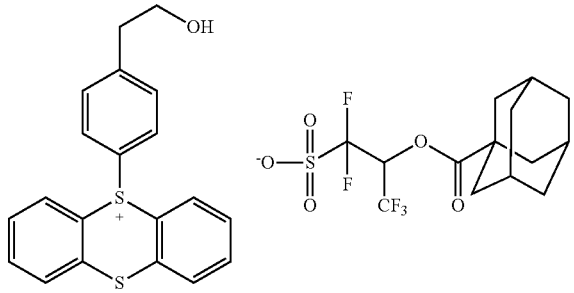
B-117 B-118
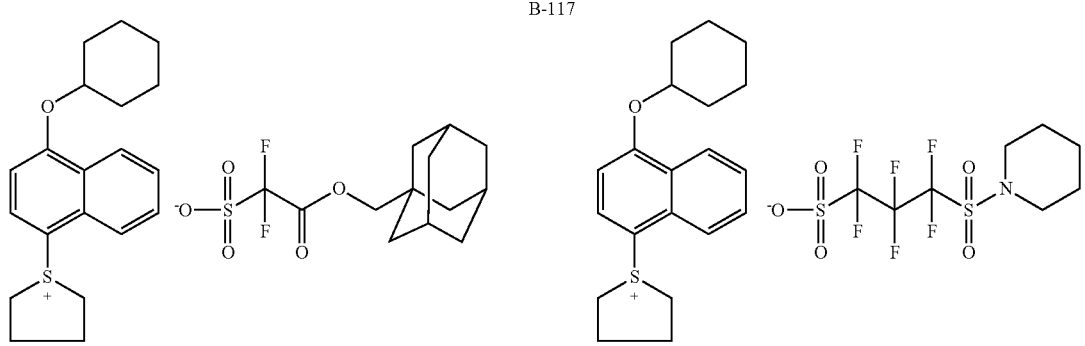
B-119 B-120
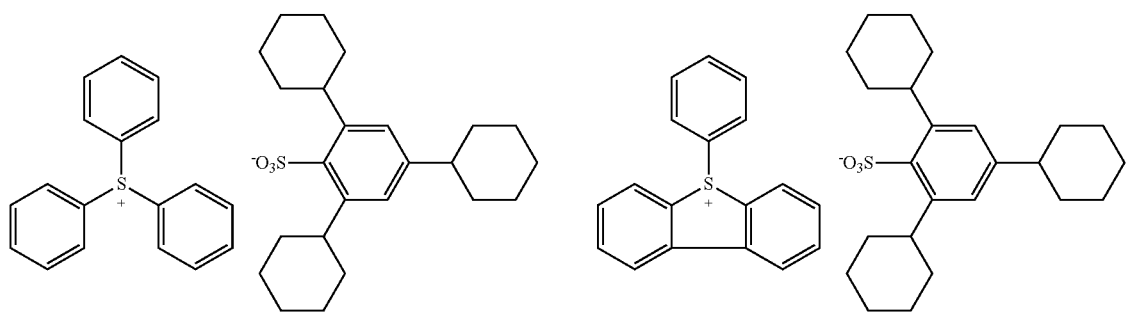
[Chem. 128]
B-121
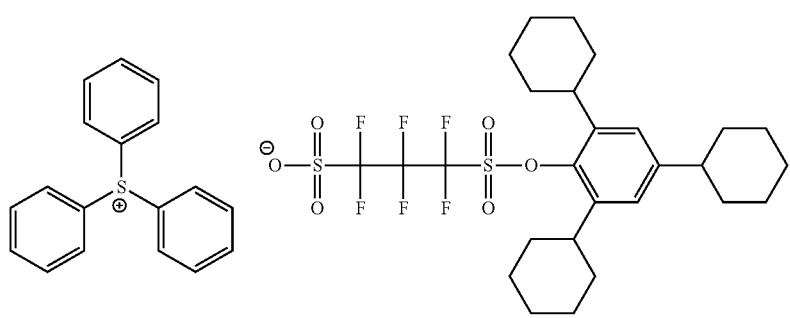

-continued
B-122
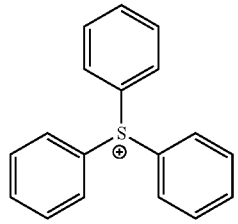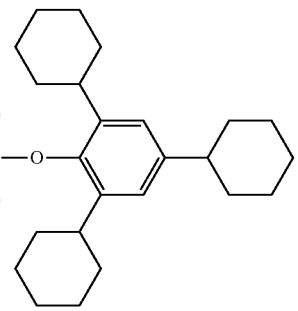
B-123
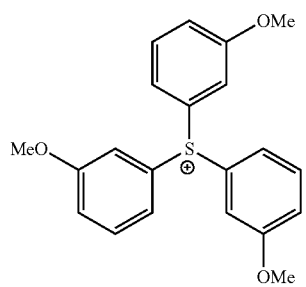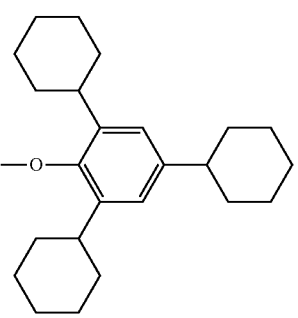
B-124
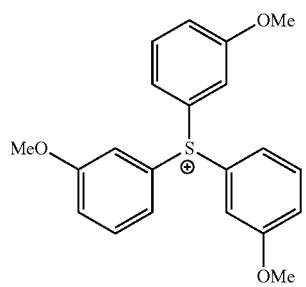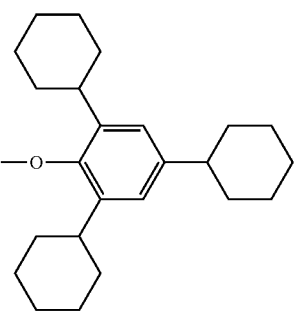
B-125
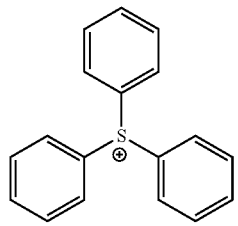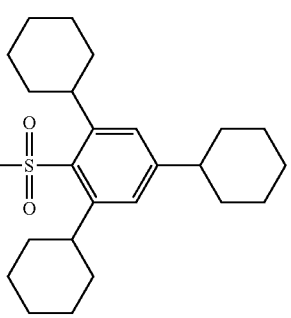
B-126
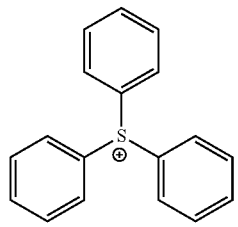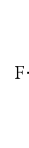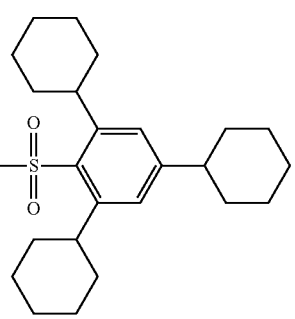

-continued
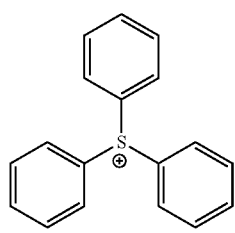 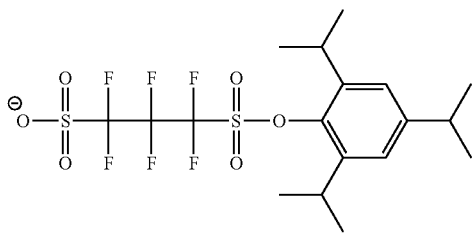
B-127
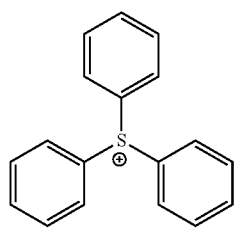 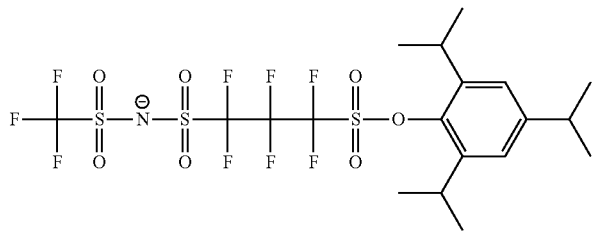
B-128
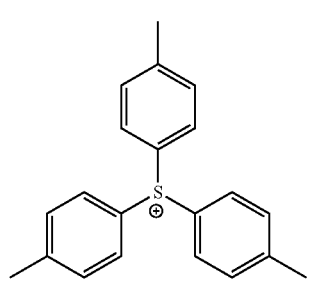 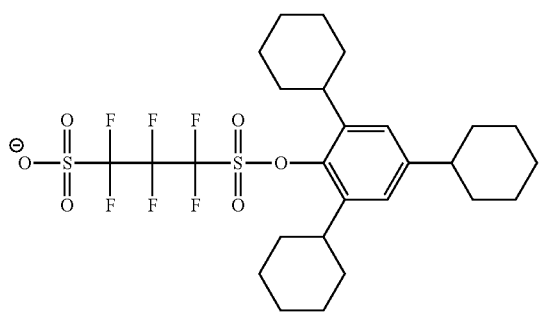
B-129
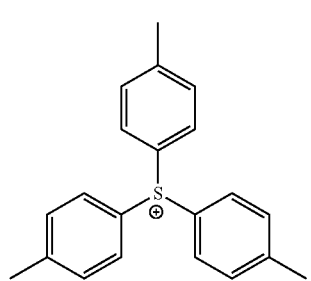 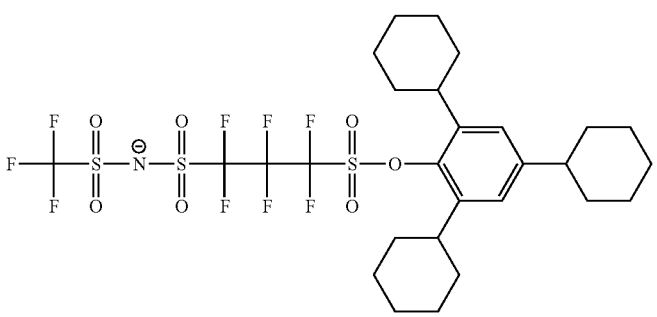
B-130
[Chem. 129]
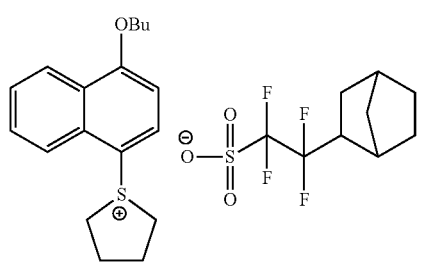
B-131
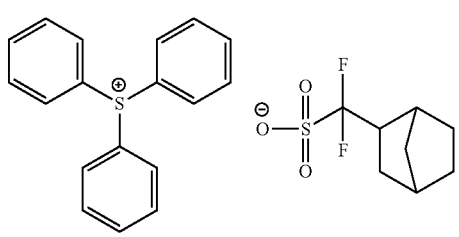
B-132

-continued
B-133 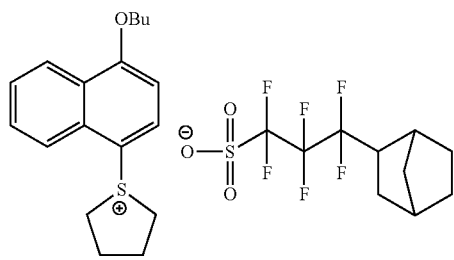
B-134 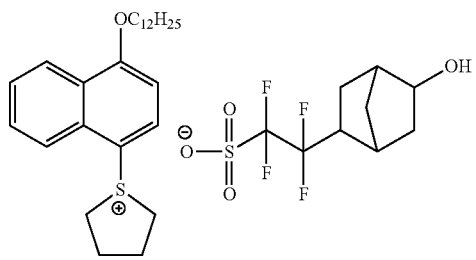
B-135 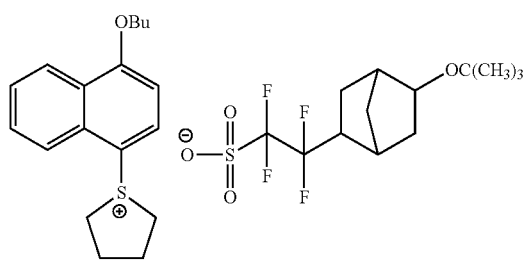
B-136 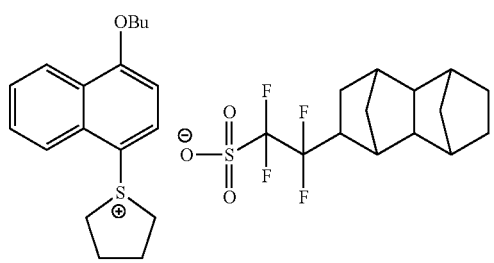
B-137 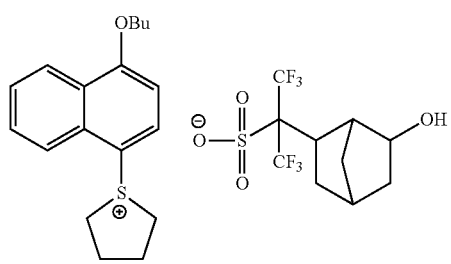
B-138 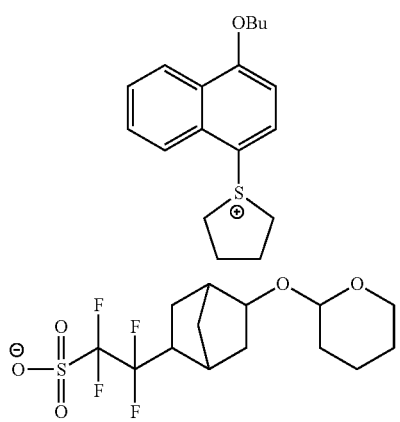
B-139 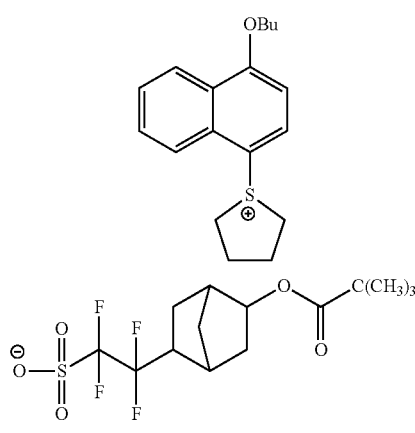
B-140 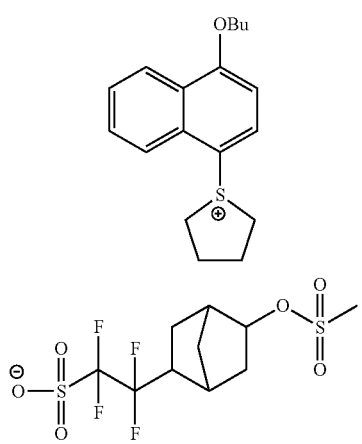

B-141
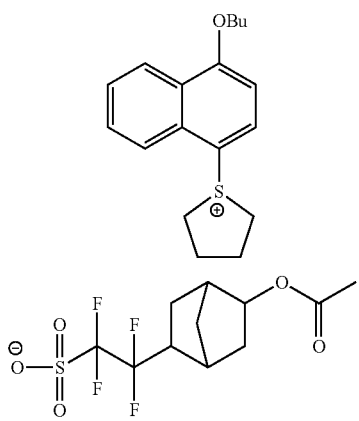
B-142
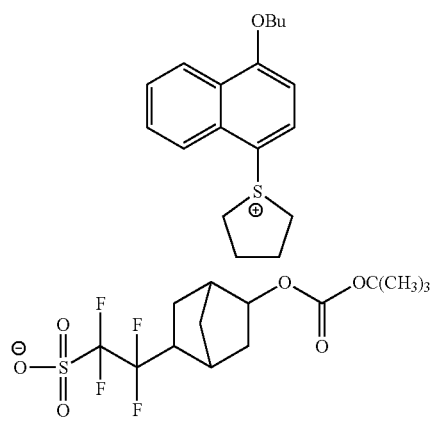
B-143
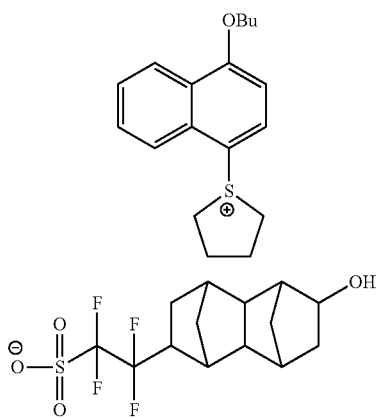
B-144
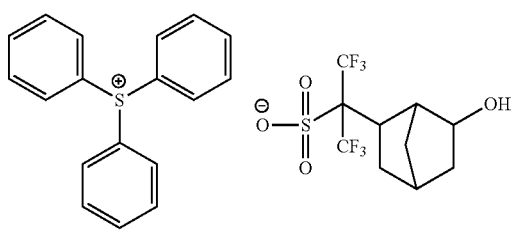
B-145
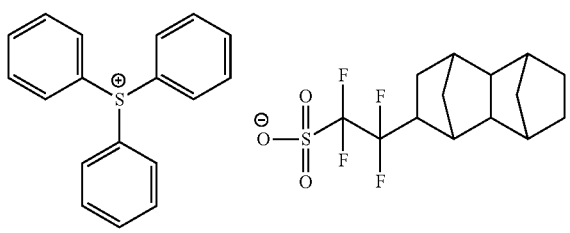
[Chem. 130]
B-146
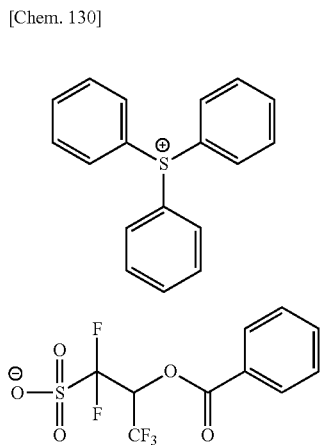
B-147
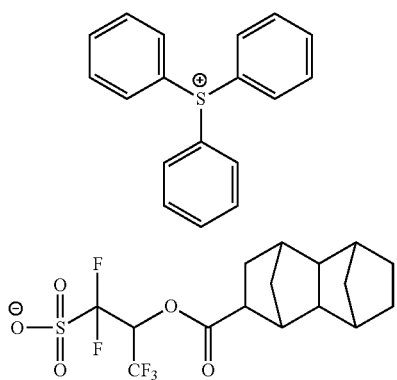

B-148
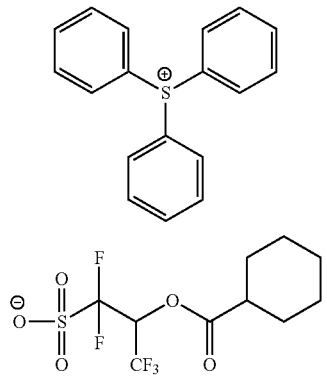
B-149
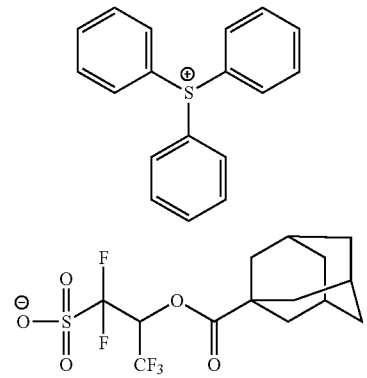
B-150
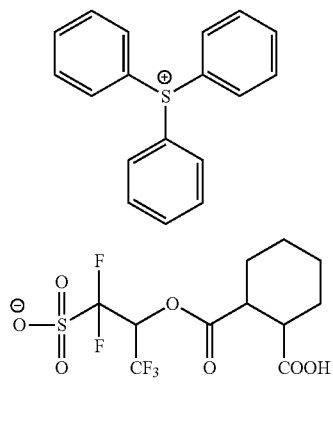
B-151
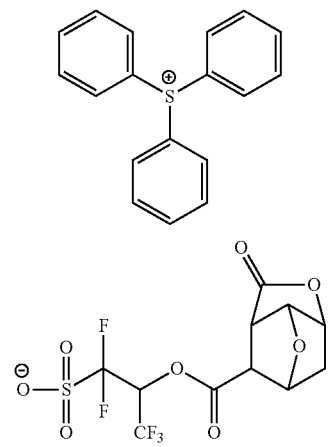
B-152
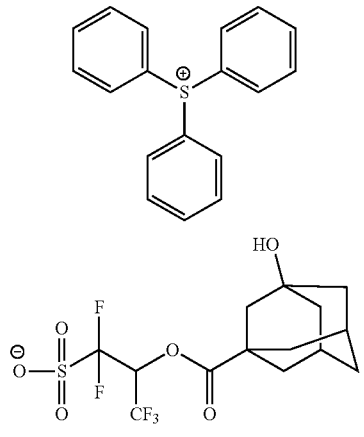
B-153
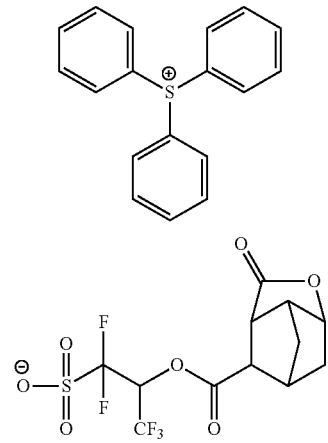

-continued
B-154
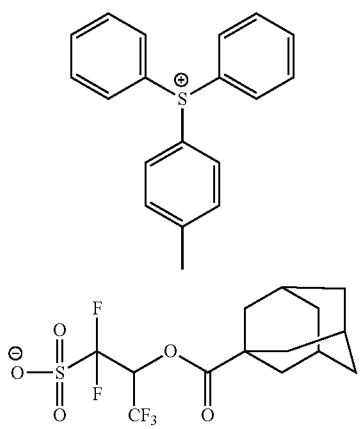
B-155
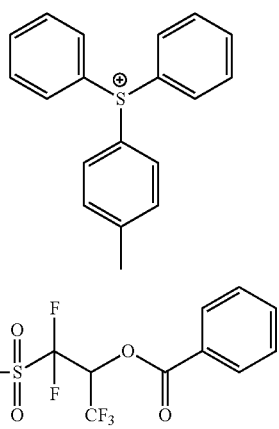
B-156
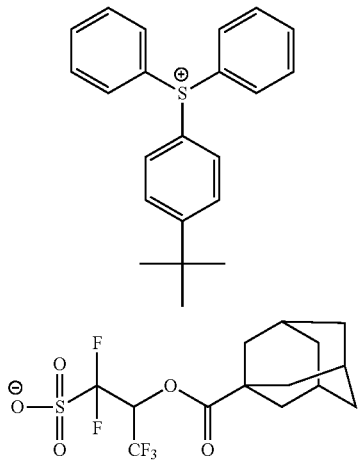
B-157
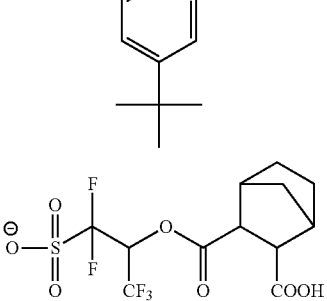
[Chem. 131]
B-158
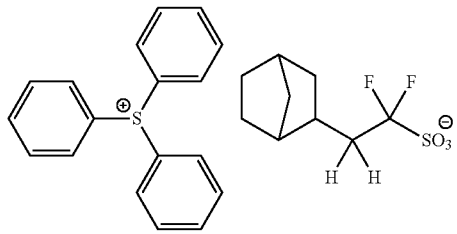
B-159
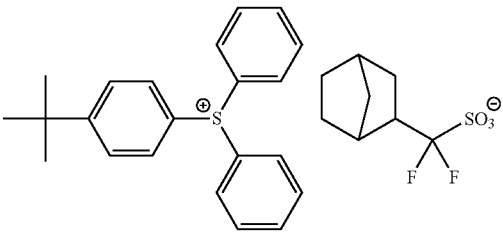
B-160
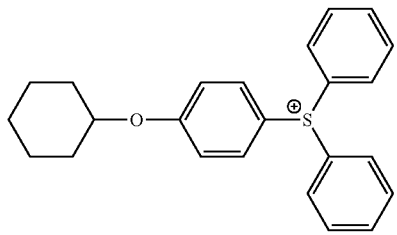
B-161
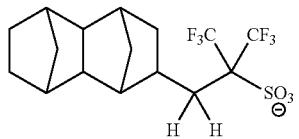

-continued
B-162
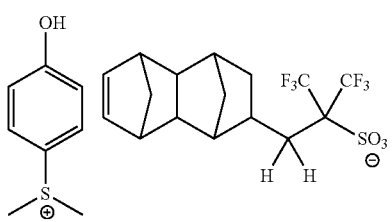
B-163
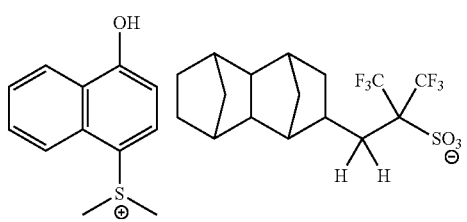
B-164
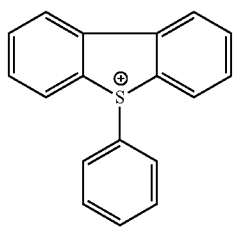
B-165
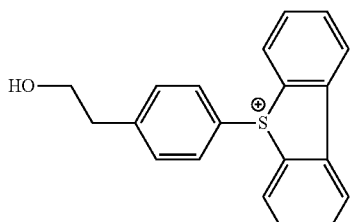
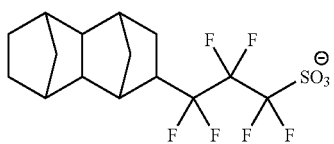
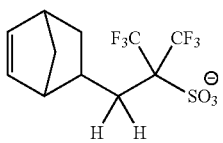
[Chem. 132]
B-166
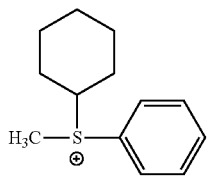
B-167
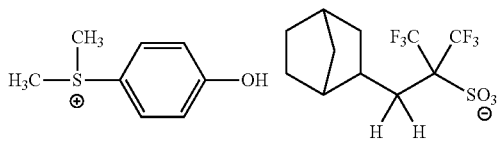
B-168
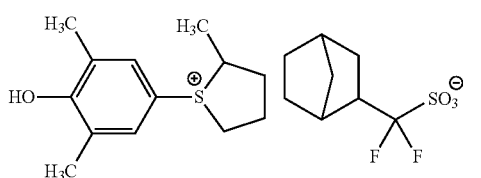
B-169
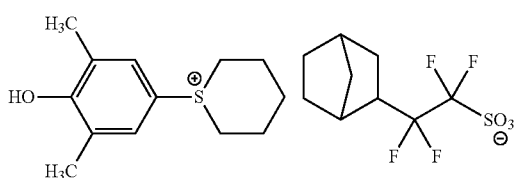
B-170
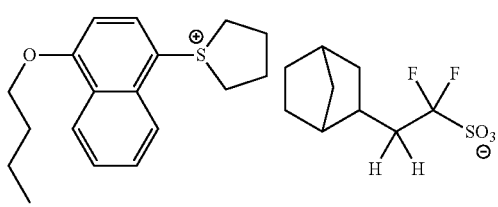
B-171
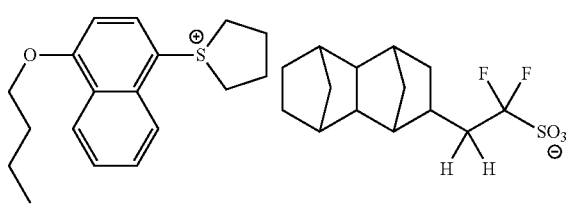
B-172
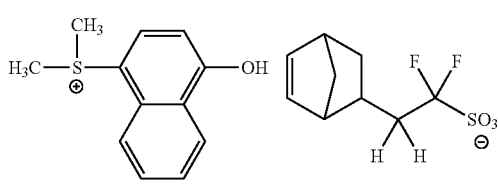
B-173
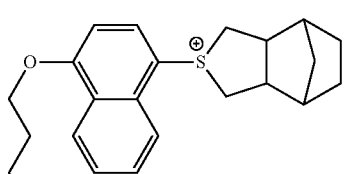
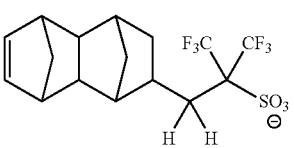

-continued
B-174 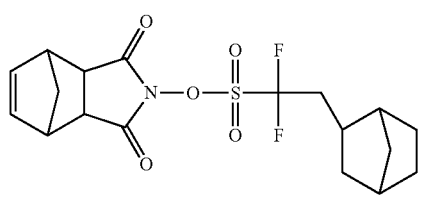
B-175 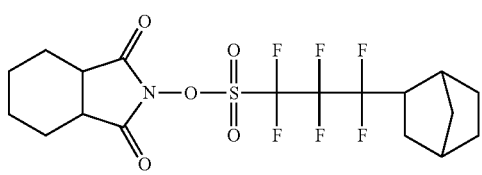
B-176 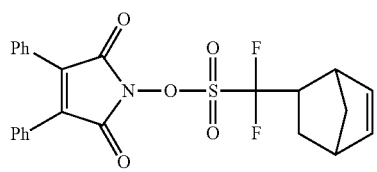
B-177 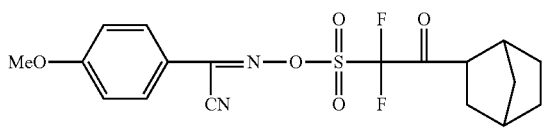
B-178 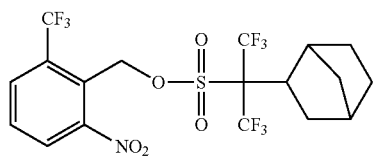
B-179 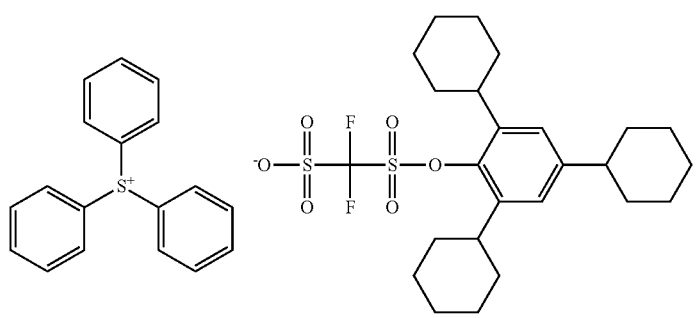
B-180 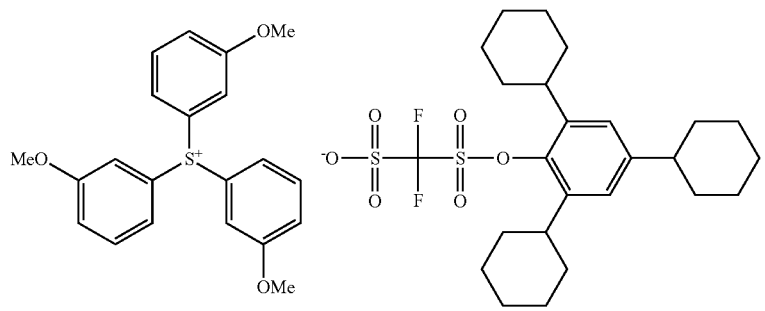
B-181 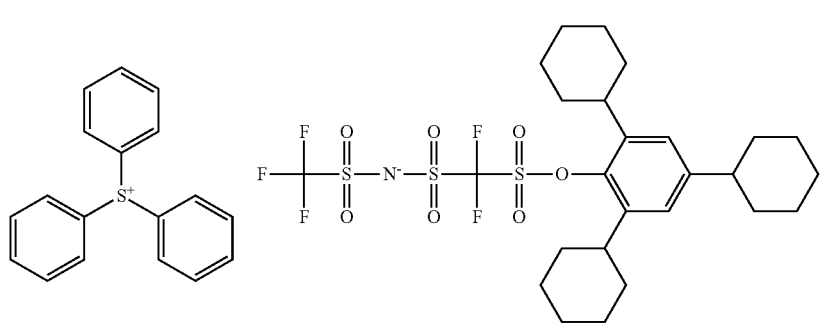

-continued
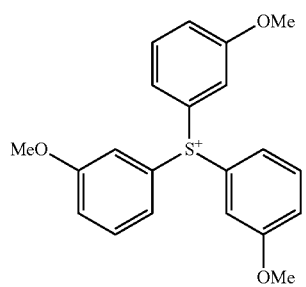
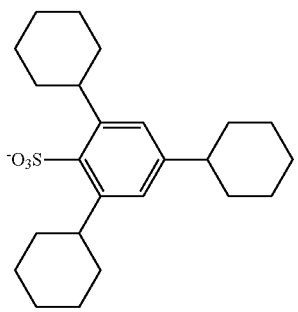
B-182
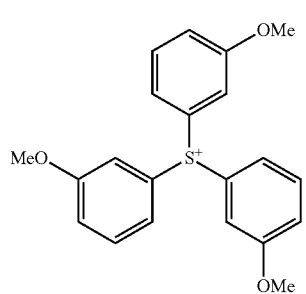
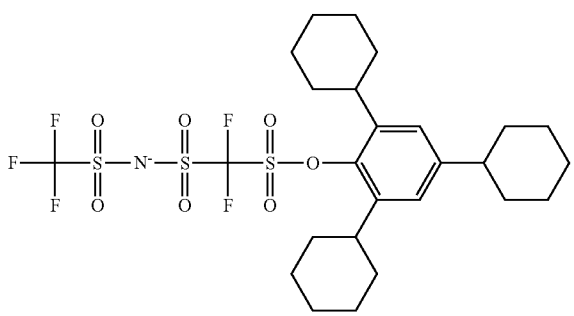
B-183
[Chem. 135]
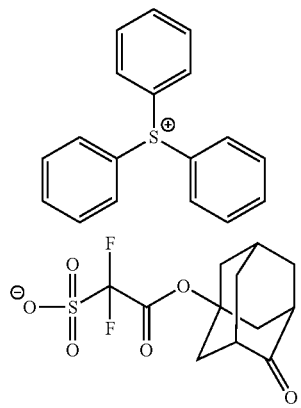
(Y-1)
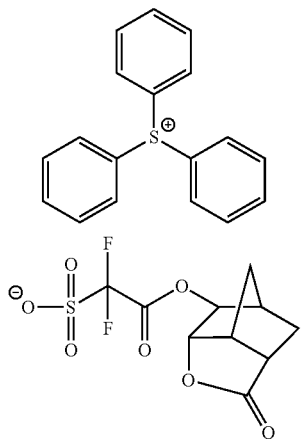
(Y-2)
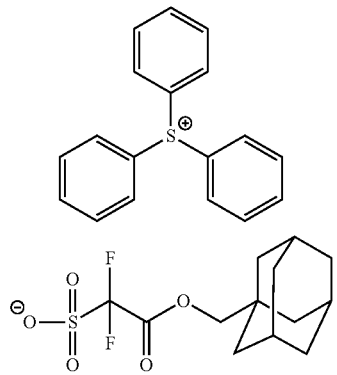
(Y-3)
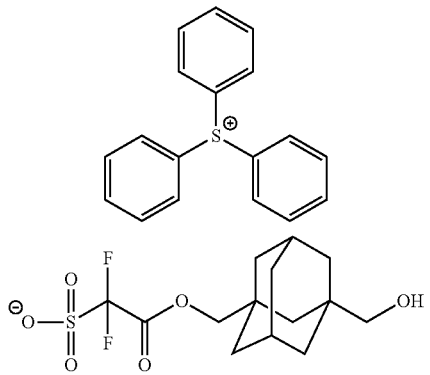
(Y-4)

-continued
(Y-5)
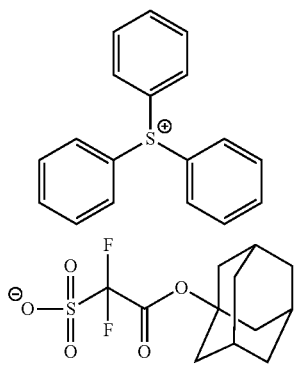
(Y-6)
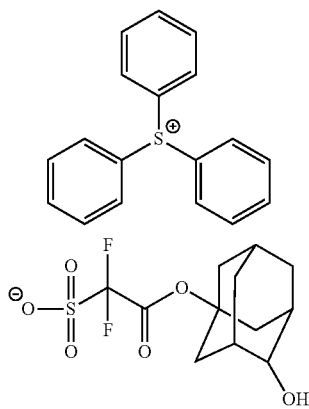
(Y-7)
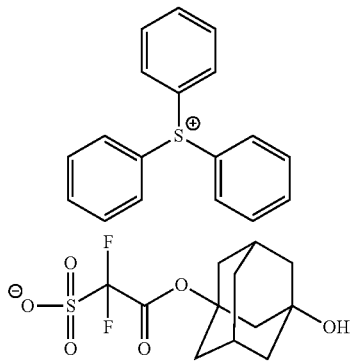
(Y-8)
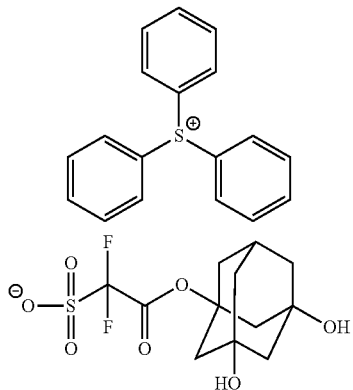
(Y-9)
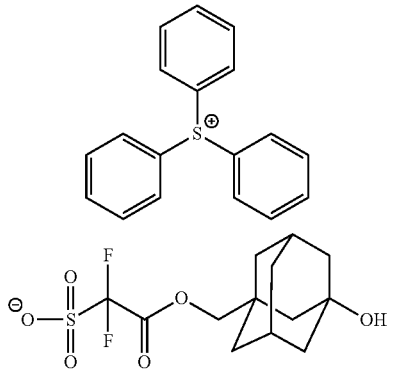
(Y-10)
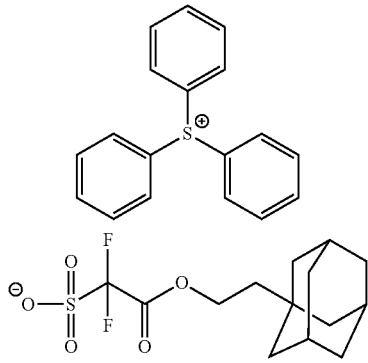
(Y-11)
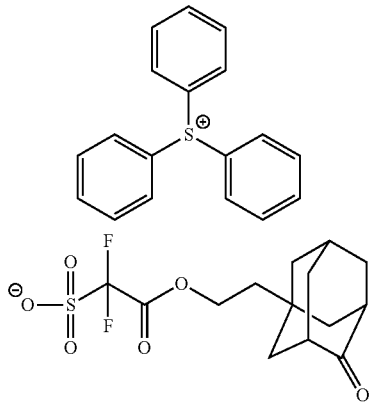
(Y-12)
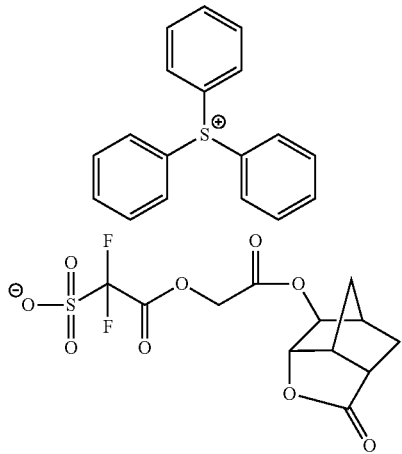

-continued
(Y-13)
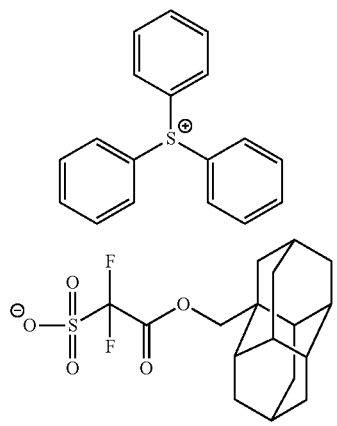
(Y-14)
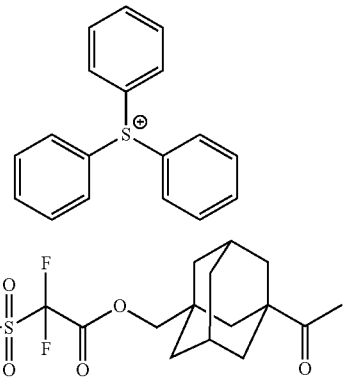
(Y-15)
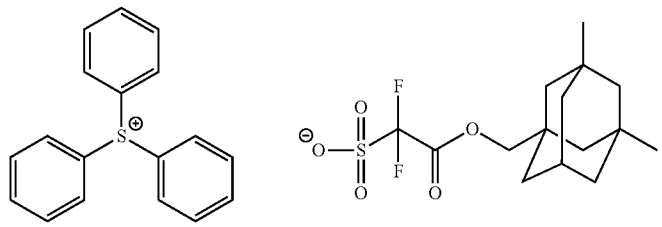
[Chem. 136]
(Y-16)
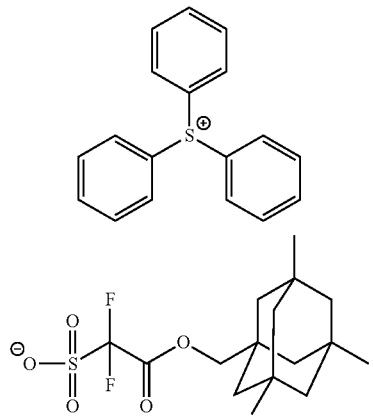
(Y-17)
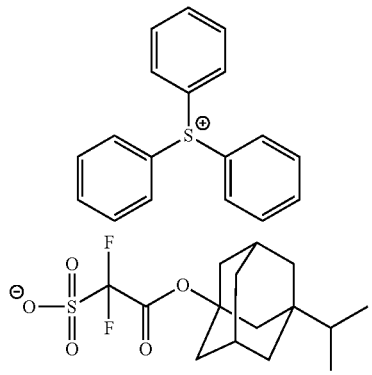
(Y-18)
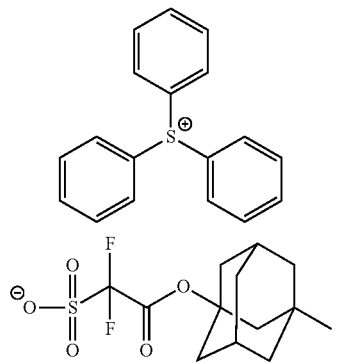
(Y-19)
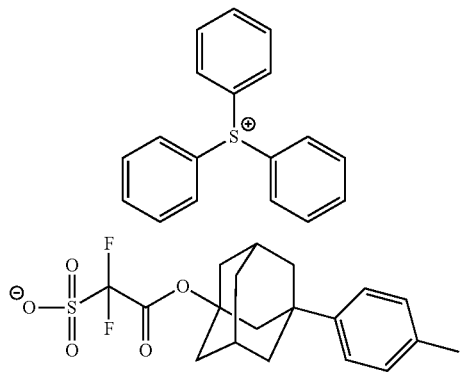

-continued
(Y-20)
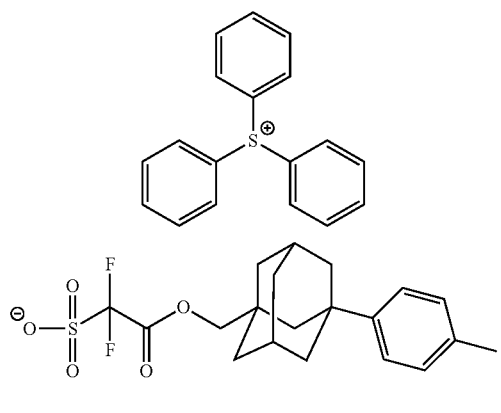
(Y-21)
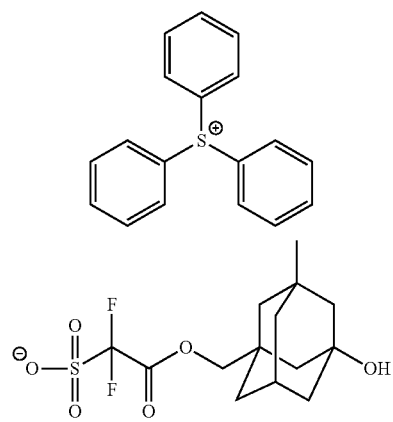
(Y-22)
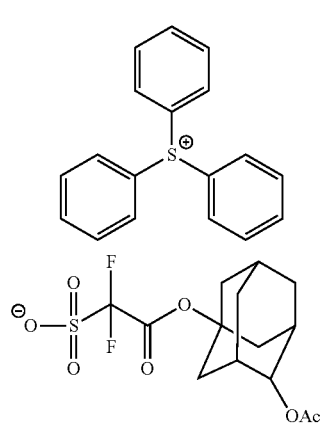
(Y-23)
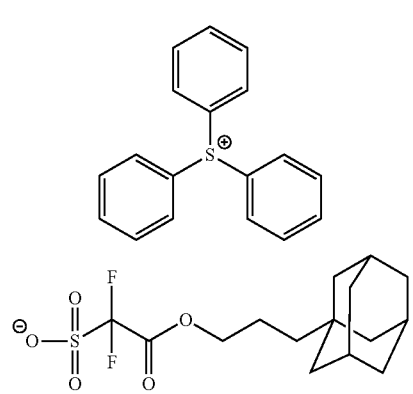
[Chem. 137]
(Y-24)
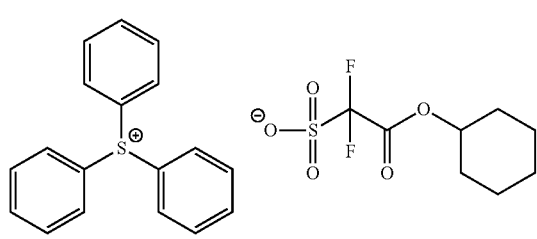
(Y-25)
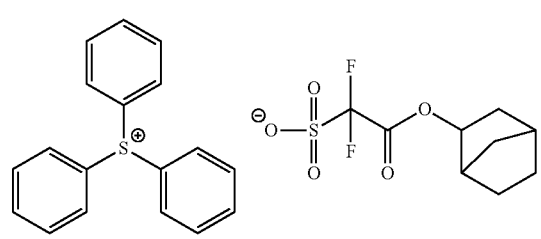
(Y-26)
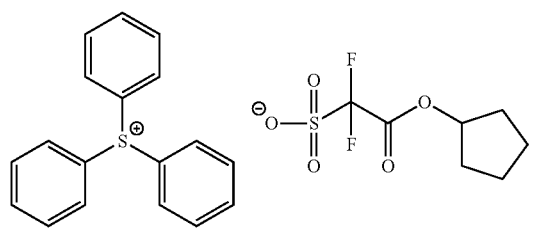
(Y-27)
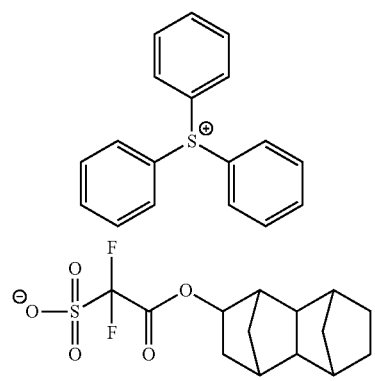

-continued
(Y-28)
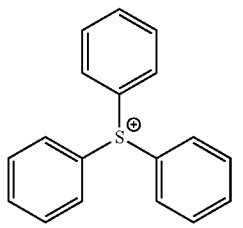 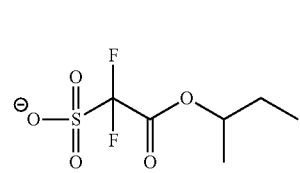
(Y-29)
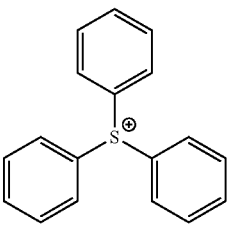 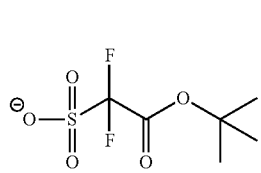
(Y-30)
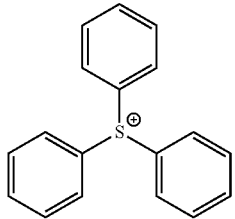 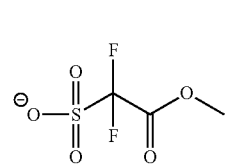
(Y-31)
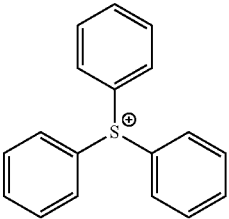 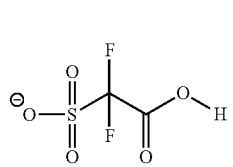
(Y-32)
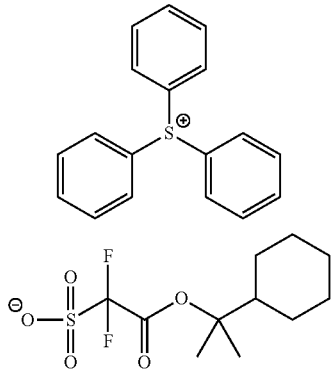
(Y-33)
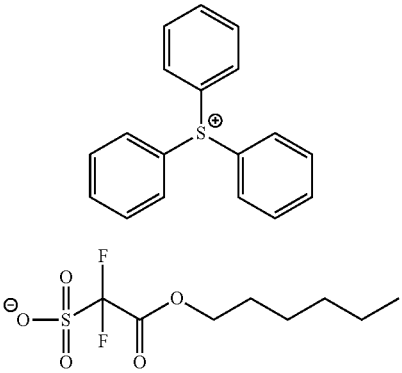
(Y-34)
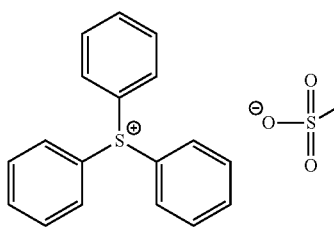
(Y-35)
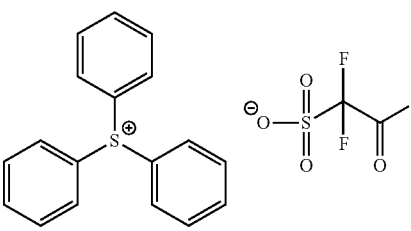
(Y-36)
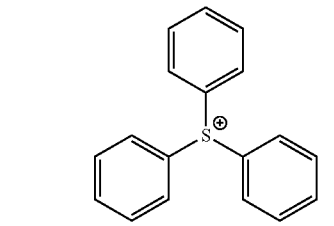
(Y-37)
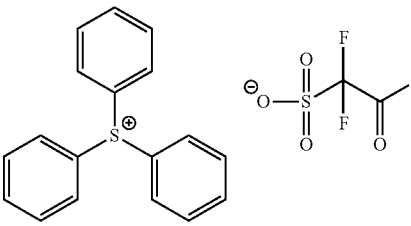
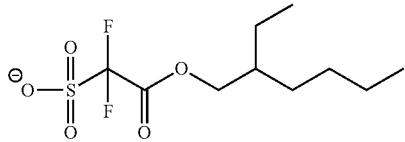

-continued
(Y-38)
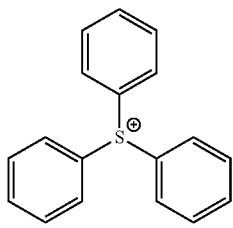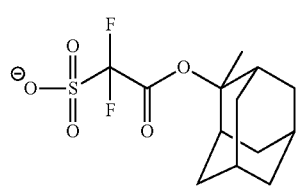
(Y-39)
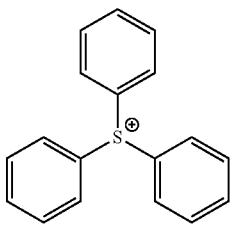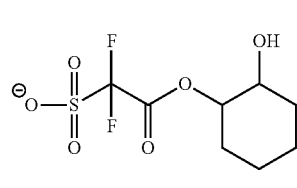
(Y-40)
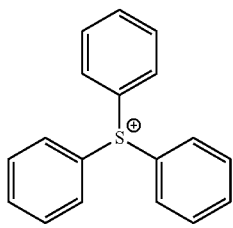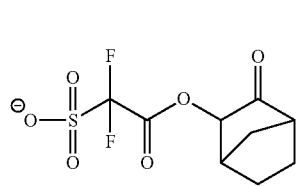
(Y-41)
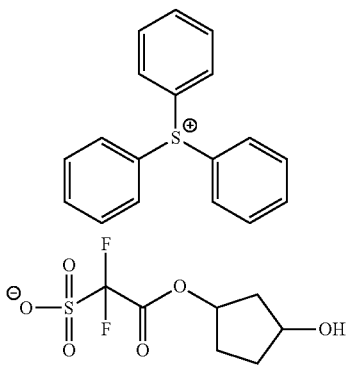
(Y-42)
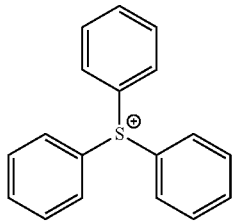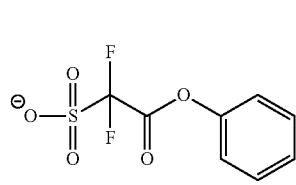
(Y-43)
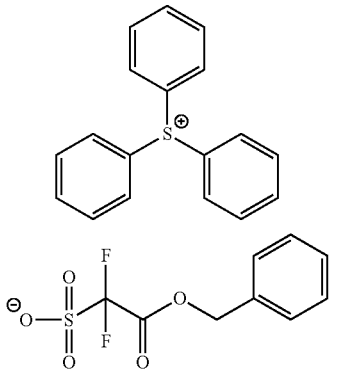
(Y-44)
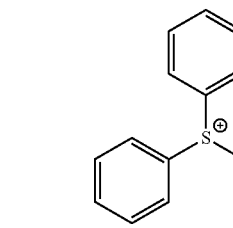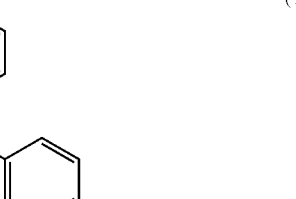
(Y-45)
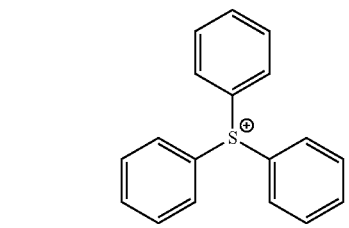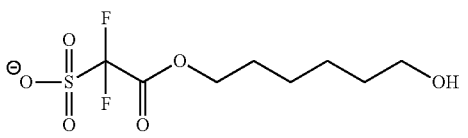

-continued
(Y-46)
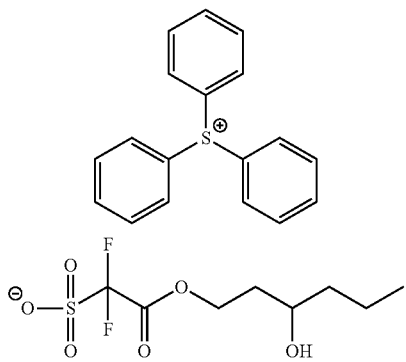
(Y-47)
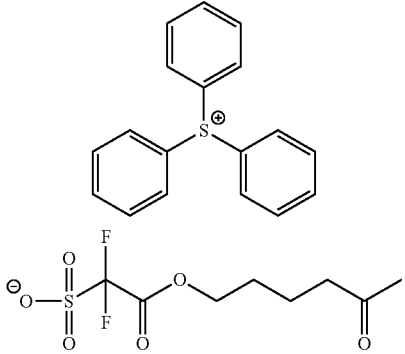
(Y-48)
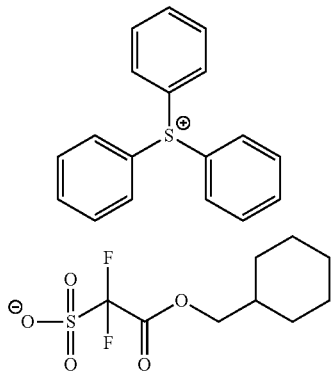
(Y-49)
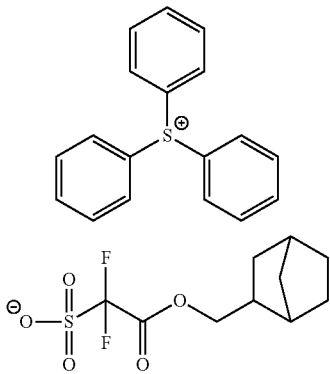
(Y-50)
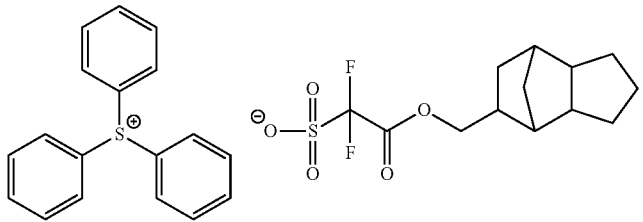
[Chem. 138]
(Y-51)
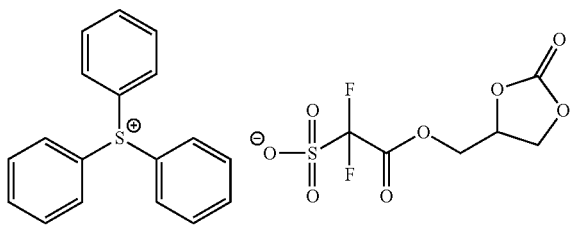
(Y-52)
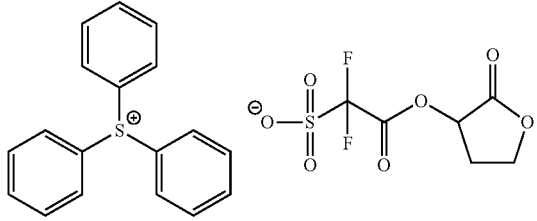
(Y-53)

-continued
(Y-54)
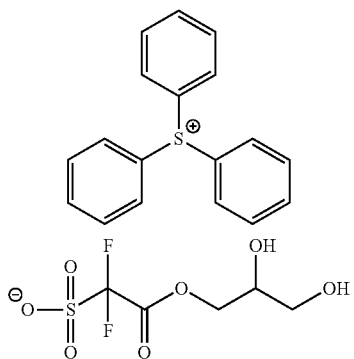
(Y-55)
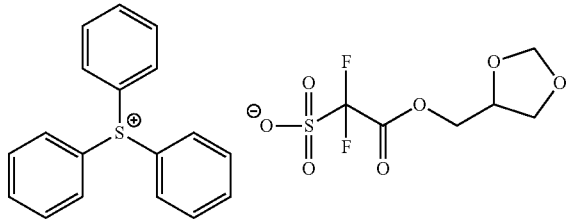
(Y-56)
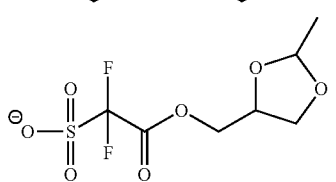
(Y-57)
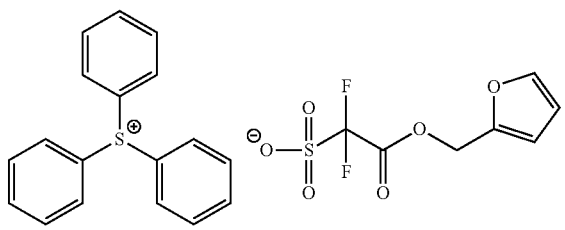
(Y-58)
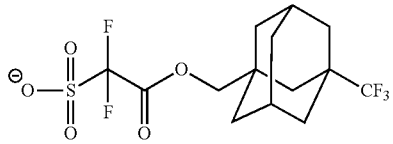
(Y-59)
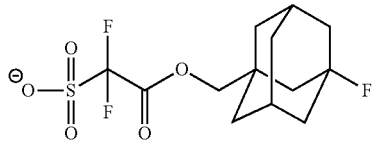
(Y-60)
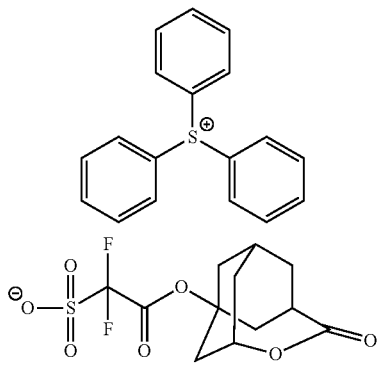
(Y-61)
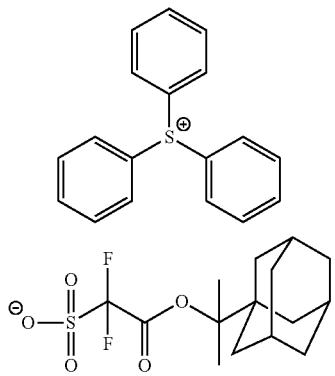

[Chem. 139]
(Y-62)
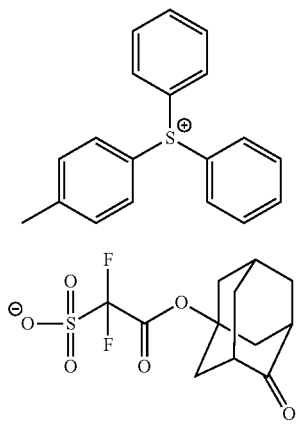
(Y-63)
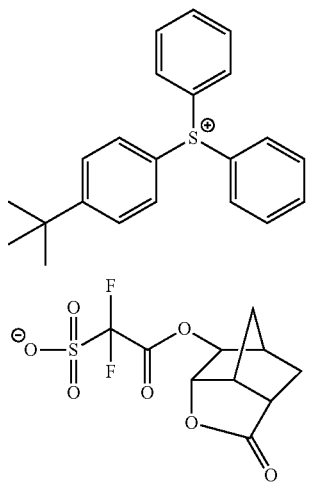
(Y-64)
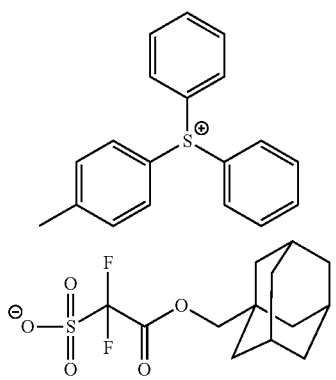
(Y-65)
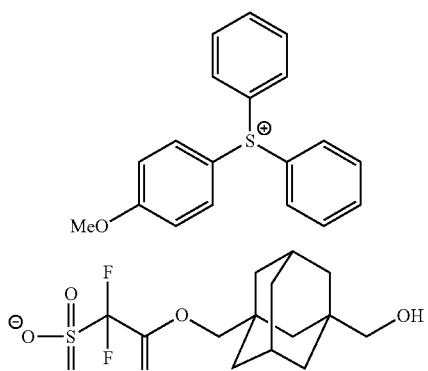
(Y-66)
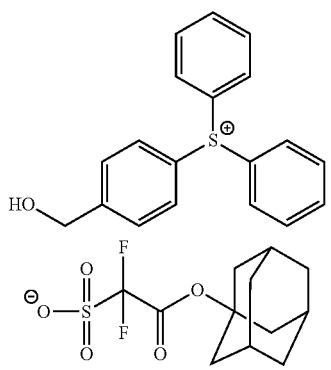
(Y-67)
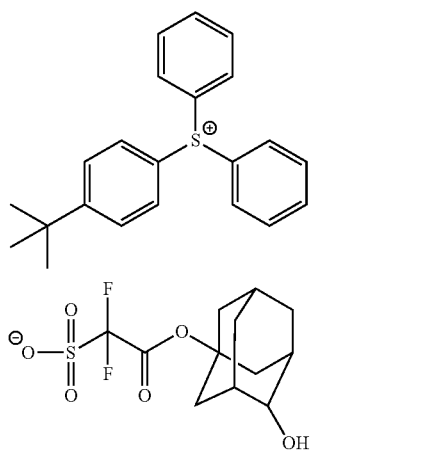
(Y-68)
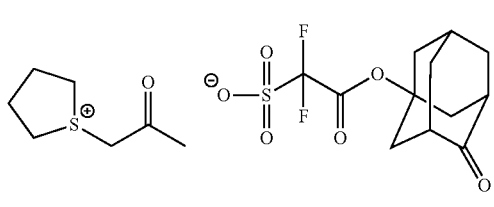
(Y-69)
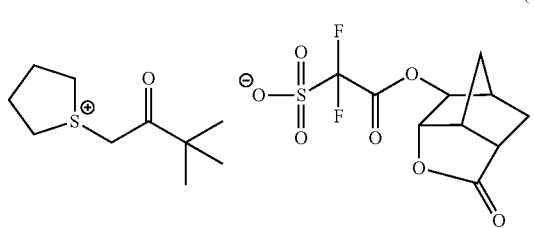

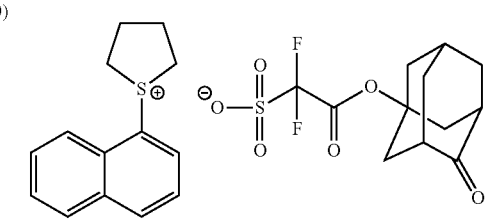
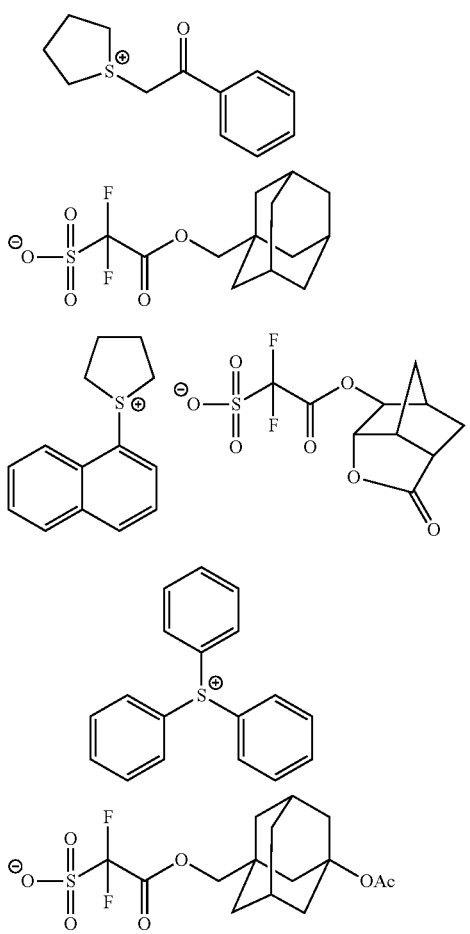
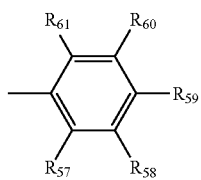

Furthermore, the photo-acid generator may be used alone or in combination of two or more kinds thereof. In the latter case, compounds capable of generating two kinds of organic acids differing in the number of all atoms excluding hydrogen atom by 2 or more are preferably combined.

Furthermore, the content of the photo-acid generator is preferably from 0.1 to 50% by mass, more preferably from 0.5 to 40% by mass, and still more preferably from 1 to 30% by mass, based on the total solid contents of the composition.

(4) Resin (Aa)

The composition according to the present invention may further contain a resin (Aa) containing at least either one of a fluorine atom and a silicon atom.

In the resin (Aa), at least either one of a fluorine atom and a silicon atom may be contained in the main chain or the side chain of the resin.

In the case where the resin (Aa) contains fluorine atoms, the resin preferably contains, as the fluorine atom-containing partial structure, a fluorine atom-containing alkyl group, a fluorine atom-containing cycloalkyl group or a fluorine atom-containing aryl group.

The fluorine atom-containing alkyl group, preferably having 1 to 10 carbon atoms, and more preferably 1 to 4 carbon atoms, is a linear or branched alkyl group with at least one hydrogen atom substituted with a fluorine atom, and may further have another substituent.

The fluorine atom-containing cycloalkyl group is a monocyclic or polycyclic cycloalkyl group with at least one hydrogen atom being substituted by a fluorine atom. This fluorine atom-containing cycloalkyl group may further have another substituent other than fluorine atoms.

The fluorine atom-containing aryl group is an aryl group with at least one hydrogen atom being substituted by a fluorine atom. Examples of this aryl group include a phenyl group and a naphthyl group. The fluorine atom-containing aryl group may further have a substituent other than fluorine atoms.

Examples of the fluorine atom-containing alkyl group, the fluorine atom-containing cycloalkyl group, and the fluorine atom-containing aryl group include a group represented by any one of the following general formulae (F2) to (F4), but the present invention is not limited thereto.

[Chem. 140]

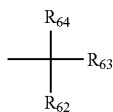

(F3)

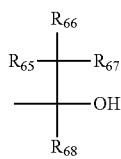

(F4)

In the general formulae (F2) to (F4), $R_{57}$ to $R_{68}$ each independently represent a hydrogen atom, a fluorine atom, or an (linear or branched) alkyl group, provided that at least one of $R_{57}$ to $R_{61}$, at least one of $R_{62}$ to $R_{64}$, and at least one of $R_{65}$ to $R_{68}$ represent a fluorine atom or an alkyl group (preferably 1 to 4 carbon atoms) with at least one hydrogen atom substituted with a fluorine atom.

It is preferable that all of $R_{57}$ to $R_{61}$ and $R_{65}$ to $R_{67}$ be fluorine atoms. $R_{62}$, $R_{63}$, and $R_{68}$ are each preferably a fluoroalkyl group (preferably having 1 to 4 carbon atoms), and more preferably a perfluoroalkyl group having 1 to 4 carbon atoms. When $R_{62}$ and $R_{63}$ are each a perfluoroalkyl group, $R_{64}$ is preferably a hydrogen atom. Further, $R_{62}$ and $R_{63}$ may be connected to each other to form a ring.

Specific examples of the group represented by the general formula (F2) include a p-fluorophenyl group, a pentafluorophenyl group, and a 3,5-di(trifluoromethyl)phenyl group.

Specific examples of the group represented by the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, and a perfluorocyclohexyl group, with a hexafluoroisopropyl group, a heptafluoroisopropyl group, a hexafluoro(2-methyl)isopropyl group, an octafluoroisobutyl group, a nonafluoro-t-butyl group, and a perfluoroisopentyl group being preferred, and a hexafluoroisopropyl group and a heptafluoroisopropyl group being more preferred.

Specific examples of the group represented by the general formula (F4) include —C(CF$_3$)$_2$OH, —C(C$_2$F$_5$)$_2$OH, —C(CF$_3$)(CH$_3$)OH, and —CH(CF$_3$)OH, and among these, —C(CF$_3$)$_2$OH is preferred.

The fluorine atom-containing partial structure may be bonded directly to the main chain or may be bonded to the main chain through a group selected from the group consisting of an alkylene group, a phenylene group, an ether bond, a thioether bond, a carbonyl group, an ester bond, an amide bond, a urethane bond, and a ureylene bond, or a group formed by a combination of two or more thereof.

Preferred examples of the repeating units having a fluorine atom are those shown below.

[Chem. 141]

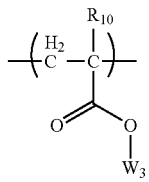

(C-Ia)

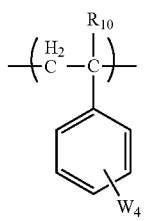

(C-Ib)

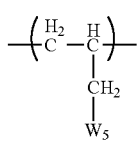

(C-Ic)

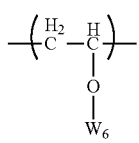

(C-Id)

In the formulae, $R_{10}$ and $R_{11}$ each independently represent a hydrogen atom, a fluorine atom, or an alkyl group. The alkyl group is preferably a linear or branched alkyl group having 1 to 4 carbon atoms and may have a substituent, and the alkyl group having a substituent may include, in particular, a fluorinated alkyl group.

$W_3$ to $W_6$ each independently represent an organic group having at least one or more fluorine atoms, and specific examples thereof include the atomic groups of (F2) to (F4) above.

Furthermore, other than these, the hydrophobic resin (Aa) may contain a unit as shown below as the repeating units having a fluorine atom.

[Chem. 142]

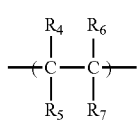

(C-II)

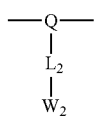

(C-III)

In the formulae, $R_4$ to $R_7$ each independently represent a hydrogen atom, a fluorine atom or an alkyl group. The alkyl group is preferably a linear or branched alkyl group having 1 to 4 carbon atoms and may have a substituent, and the alkyl group having a substituent may include, in particular, a fluorinated alkyl group.

Incidentally, at least one of $R_4$ to $R_7$ represents a fluorine atom. $R_4$ and $R_5$, or $R_6$ and $R_7$ may form a ring.

$W_2$ represents an organic group having at least one fluorine atom and specific examples thereof include the atomic groups of (F2) to (F4) above.

$L_2$ represents a single bond or a divalent connecting group. The divalent connecting group is a substituted or unsubstituted arylene group, a substituted or unsubstituted alkylene group, a substituted or unsubstituted cycloalkylene group, —O—, —SO$_2$—, —CO—, —N(R)— (wherein R represents a hydrogen atom or an alkyl group), —NHSO$_2$—, or a divalent connecting group formed by a combination of a plurality of these groups.

Q represents an alicyclic structure. The alicyclic structure may have a substituent and may be monocyclic or polycyclic, and in the case of a polycyclic structure, the structure may be a crosslinked structure. The monocyclic structure is preferably a cycloalkyl group having 3 to 8 carbon atoms, and examples thereof include a cyclopentyl group, a cyclohexyl group, a cyclobutyl group, and a cyclooctyl group. Examples of the polycyclic structure include a group containing a bicyclo, tricyclo or tetracyclo structure having 5 or more carbon atoms. A cycloalkyl group having 6 to 20 carbon atoms is preferred, and examples thereof include an adamantyl group, a norbornyl group, a dicyclopentyl group, a tricyclodecanyl group, and a tetracyclododecyl group. Parts of carbon atoms in the cycloalkyl group may be substituted with heteroatoms such as an oxygen atom. In particular, preferred examples of Q include a norbornyl group, a tricyclodecanyl group, and a tetracyclododecyl group.

The resin (Aa) may contain a silicon atom.

An alkylsilyl structure (preferably a trialkylsilyl group) or a cyclosiloxane structure is preferred as a partial structure having a silicon atom.

Specific examples of the alkylsilyl structure and the cyclosiloxane structure include groups represented by the following formulae (CS-1) to (CS-3).

[Chem. 143]

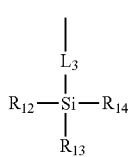

(CS-1)

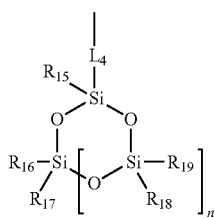

(CS-2)

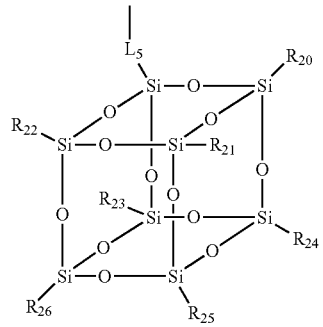

(CS-3)

In the general formulae (CS-1) to (CS-3), $R_{12}$ to $R_{26}$ each independently represent a linear or branched alkyl group (preferably having 1 to 20 carbon atoms) or a cycloalkyl group (preferably having 3 to 20 carbon atoms).

$L_3$ to $L_5$ each represent a single bond or a divalent connecting group. The divalent connecting group is a single group or a combination of two or more groups selected from the group consisting of an alkylene group, a phenylene group, an ether bond, a thioether bond, a carbonyl group, an ester bond, an amide bond, a urethane bond, and a ureylene bond.

n represents an integer of 1 to 5, and is preferably an integer of 2 to 4.

The repeating units having at least either fluorine atoms or silicon atoms are preferably (meth)acrylate-based repeating units.

Specific examples of the repeating units having at least either fluorine atoms or silicon atoms are shown below, but the present invention is not limited thereto. In the specific examples, $X_1$ represents a hydrogen atom, —CH$_3$, —F, or —CF$_3$, and $X_2$ represents —F or —CF$_3$.

[Chem. 144]

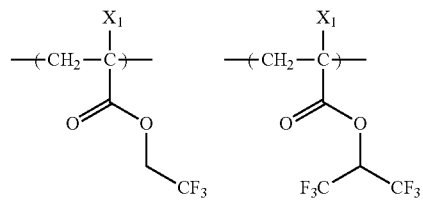

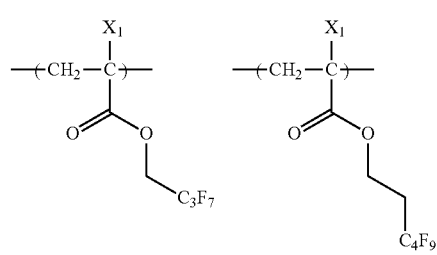

309
-continued
310
-continued
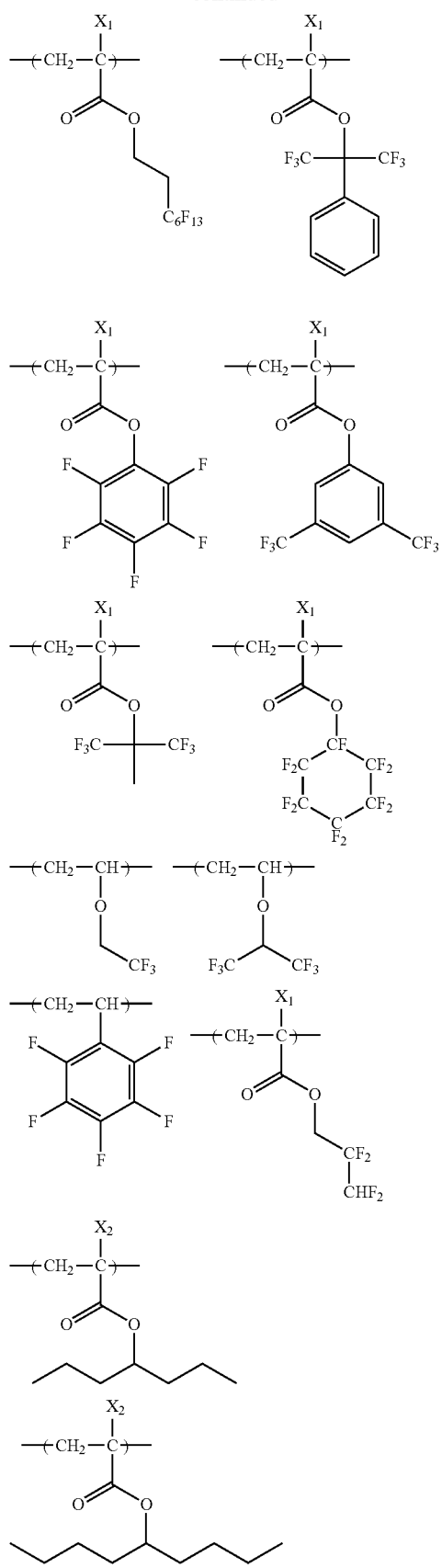
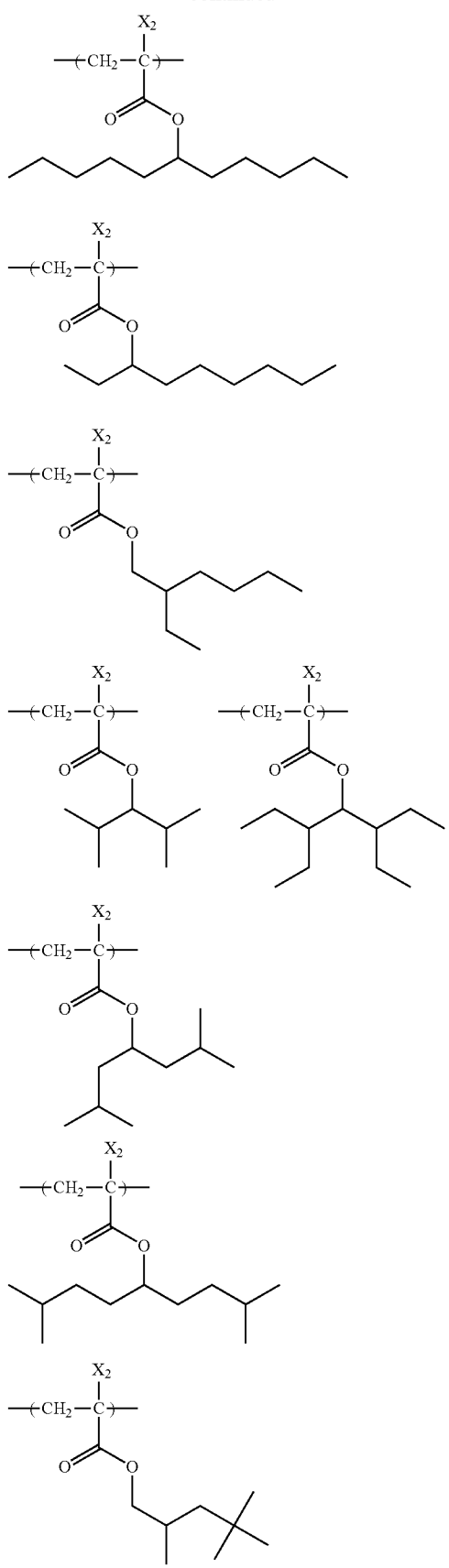

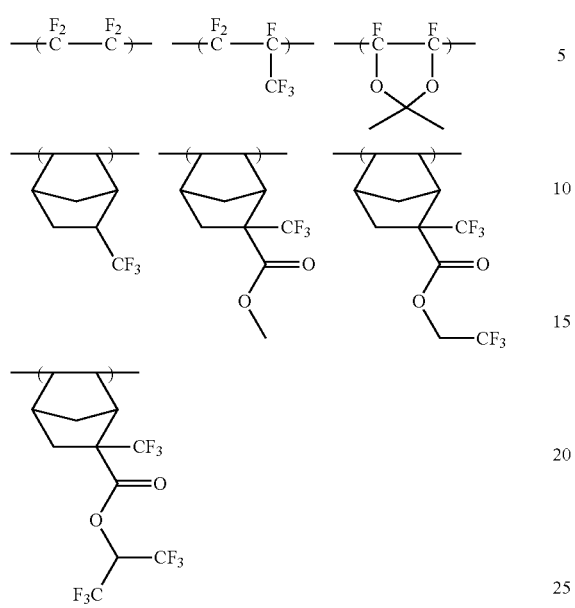
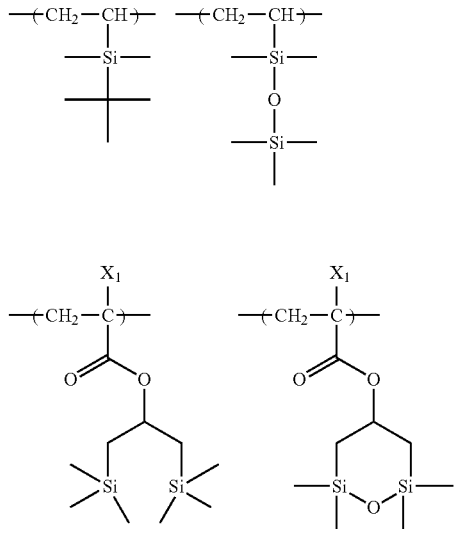
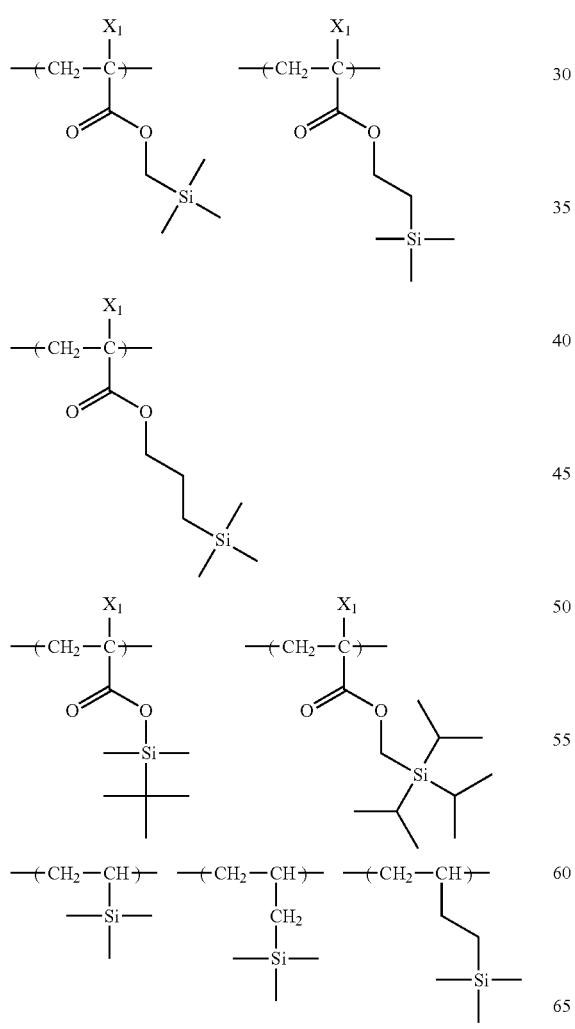
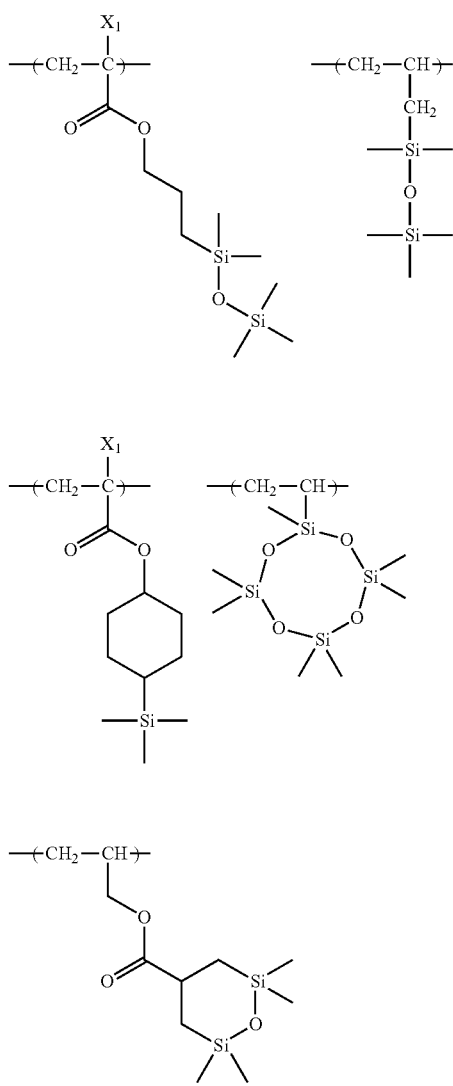

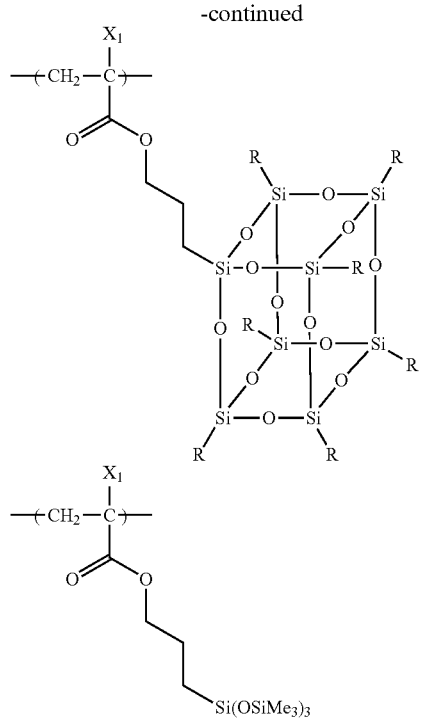

R = CH₃, C₂H₅, C₃H₇, C₄H₉

The resin (Aa) preferably has a repeating unit (b) having at least one group selected from the group consisting of the following (x) to (z).

(x) an alkali-soluble group, (y) a group capable of decomposing by the action of an alkali developer to increase the solubility in an alkali developer, and (z) a group capable of decomposing by the action of an acid to increase the solubility in an alkali developer.

The repeating unit (b) includes the following types.

(b') repeating units having at least either fluorine atoms or silicon atoms and at least one group selected from the group consisting of (x) to (z) on one side chain, (b*) repeating units having at least one group selected from the group consisting of (x) to (z) and having neither a fluorine atom nor a silicon atom, and (b'') repeating units having at least one group selected from the group consisting of (x) to (z) on one side chain and having at least either fluorine atoms or silicon atoms on a side chain different from the side chain above in the same repeating unit.

The resin (Aa) more preferably contains the repeating unit (b') as the repeating unit (b). That is, the repeating unit (b) having at least one group selected from the group consisting of (x) to (z) more preferably contains at least either fluorine atoms or silicon atoms.

Furthermore, in the case where the resin (Aa) contains the repeating unit (b*), the resin is preferably a copolymer with repeating units having at least either fluorine atoms or silicon atoms (a repeating unit different from the repeating units (b') and (b'')). Further, in the repeating unit (b''), the side chain having at least one group selected from the group consisting of (x) to (z) and the side chain having at least either fluorine atoms or silicon atoms are preferably bonded to the same carbon atom in the main chain, that is, have the same positional relationship as in the following formula (K1).

In the formula, B1 represents a partial structure having at least one group selected from the group consisting of (x) to (z), and B2 represents a partial structure having at least either fluorine atoms or silicon atoms.

[Chem. 147]

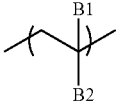

(K1)

The group selected from the group consisting of (x) to (z) is preferably (x) an alkali-soluble group or (y) a polarity converting group, and more preferably (y) a polarity converting group.

Examples of the alkali-soluble group (x) include a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris(alkylsulfonyl)methylene group.

Preferred alkali-soluble groups include a fluorinated alcohol group (preferably, a hexafluoroisopropanol group), a sulfonimide group, and a bis(carbonyl)methylene group.

Examples of the repeating unit (bx) having an alkali-soluble group (x) include a repeating unit where an alkali-soluble group is directly bonded to the main chain of the resin, such as repeating unit from an acrylic acid or a methacrylic acid, and a repeating unit where an alkali-soluble group is bonded to the main chain of the resin through a connecting group. Furthermore, an alkali-soluble group may be introduced into the polymer chain terminal by using an alkali-soluble group-containing polymerization initiator or chain transfer agent at the polymerization. Any of these cases are preferred.

In the case where the repeating unit (bx) is repeating units having at least either fluorine atoms or silicon atoms (that is, a repeating unit corresponding to the repeating unit (b') or (b'')), examples of the fluorine atom-containing partial structure in the repeating unit (bx) are the same as those described with respect to the repeating units having at least either fluorine atoms or silicon atoms and preferably include the groups represented by the general formulae (F2) to (F4). Also in this case, examples of the silicon atom-containing partial structure in the repeating unit (bx) are the same as those described with respect to the repeating units having at least either fluorine atoms or silicon atoms and preferably include the groups represented by the general formulae (CS-1) to (CS-3).

The content of the repeating unit (bx) having an alkali-soluble group (x) is preferably from 1 to 50% by mole, more preferably from 3 to 35% by mole, and still more preferably from 5 to 20% by mole, based on all repeating units in the hydrophobic resin (Aa).

Specific examples of the repeating unit (bx) having an alkali-soluble group (x) are shown below. Further, in specific examples, $X_1$ represents a hydrogen atom, —CH₃, —F, or —CF₃.

[Chem. 148]
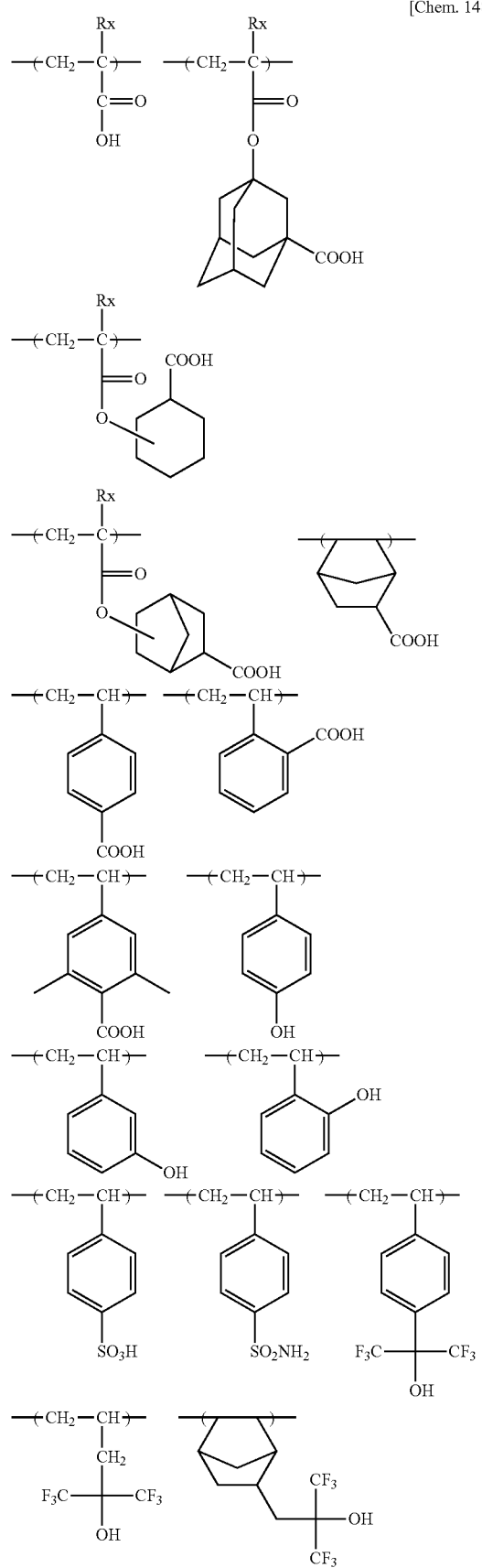
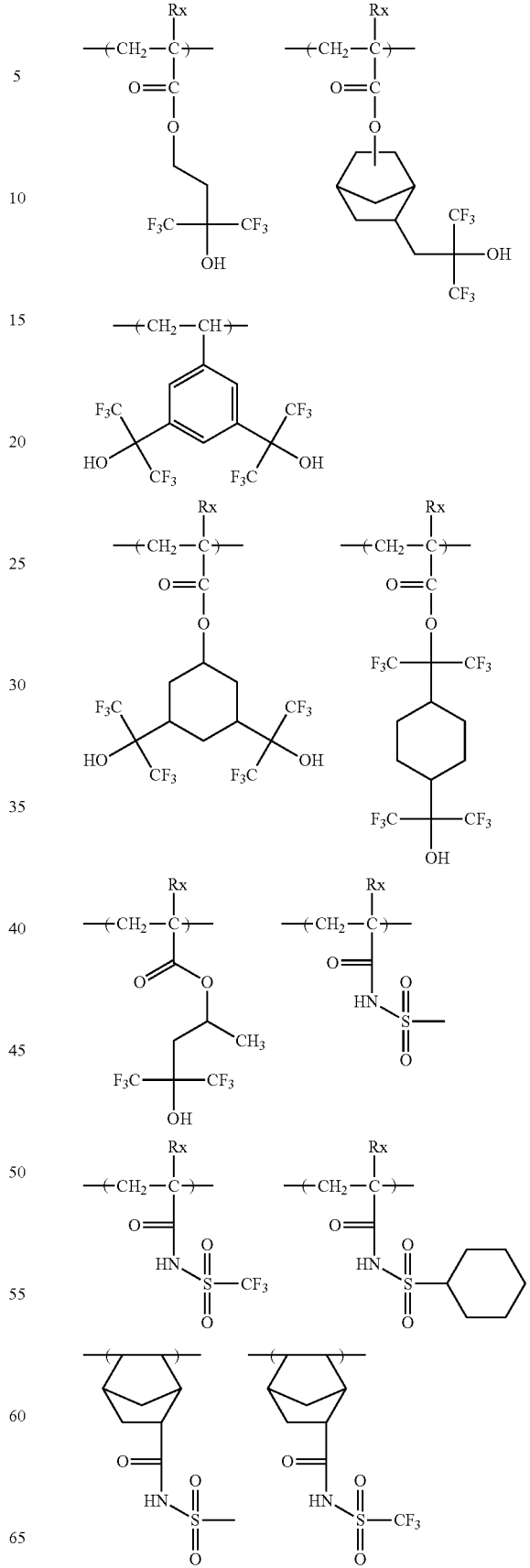

-continued

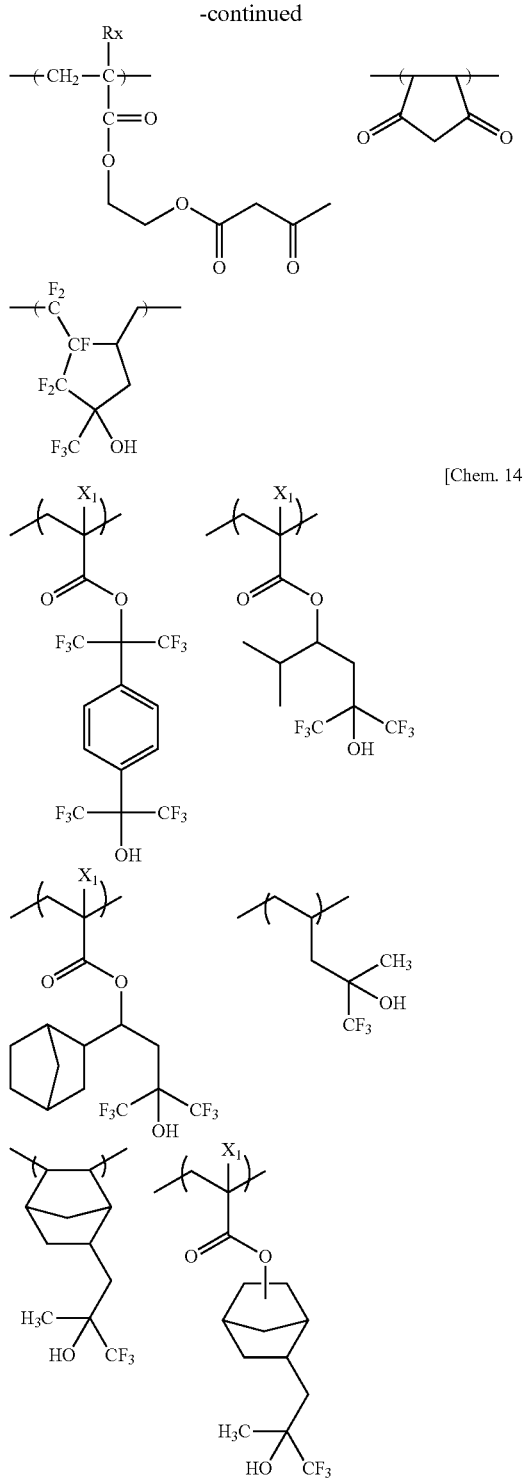

wherein Rx represents H, CH₃, CF₃, or CH₂OH.

Examples of the polarity converting group (y) include a lactone group, a carboxylic acid ester group (—COO—), an acid anhydride group (—C(O)OC(O)—), an acid imide group (—NHCONH—), a carboxylic acid thioester group (—COS—), a carbonic acid ester group (—OC(O)O—), a sulfuric acid ester group (—OSO₂O—), and a sulfonic acid ester group (—SO₂O—), with a lactone group being preferred.

As for the polarity converting group (y), both a configuration where the polarity converting group is included in a repeating unit composed of an acrylic acid ester or a methacrylic acid ester and thereby is introduced into the side chain of the resin, and a configuration where the polarity converting group is introduced into the polymer chain terminal by using a polymerization initiator or chain transfer agent containing the polarity converging group (y) during the polymerization are preferred.

Specific examples of the repeating unit (by) having a polarity converting group (y) include repeating units having a lactone structure represented by the formulae (KA-1-1) to (KA-1-17) as described later.

Furthermore, the repeating unit (by) having a polarity converting group (y) is preferably a repeating unit having at least either a fluorine atom and a silicon atom (that is, a repeating unit corresponding to the repeating unit (b') or (b")). The repeating unit (by)-containing resin has hydrophobicity, and addition thereof is preferred, in particular, from the viewpoint of reducing the development defect.

Examples of the repeating unit (by) include a repeating unit represented by the formula (K0).

[Chem. 150]

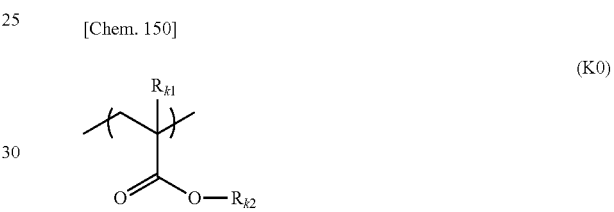

(K0)

In the formula, $R_{k1}$ represents a hydrogen atom, a halogen atom, a hydroxyl group, an alkyl group, a cycloalkyl group, an aryl group, or a polarity converting group-containing group.

$R_{k2}$ represents an alkyl group, a cycloalkyl group, an aryl group, or a polarity converting group-containing group.

However, at least either one of $R_{k1}$ and $R_{k2}$ represents a polarity converting group-containing group.

The polarity converting group is, as described above, a group that decomposes by the action of an alkali developer to increase the solubility in an alkali developer. The polarity converting group is preferably a group X in a partial structure represented by the general formula (KA-1) or (KB-1).

[Chem. 151]

In the general formulae (KA-1) and (KB-1), X represents a carboxylic acid ester group: —COO—, an acid anhydride group: —C(O)OC(O)—, an acid imide group: —NHCONH—, a carboxylic acid thioester group: —COS—, a carbonic acid ester group: —OC(O)O—, a sulfuric acid ester group: —OSO₂O—, or a sulfonic acid ester group: —SO₂O—.

Each of $Y^1$ and $Y^2$, which may be the same as or different from each other, represents an electron-withdrawing group.

Incidentally, the repeating unit (by) has a preferred group that increases the solubility in an alkali developer by containing a group having a partial structure represented by the general formula (KA-1) or (KB-1), but as in the case of the partial structure represented by the general formula (KA-1) or the partial structure represented by the general formula (KB-1) wherein $Y^1$ and $Y^2$ are monovalent, when the partial structure does not have a bond, the group having the partial structure is a group having a monovalent or higher valent group formed by removing at least one arbitrary hydrogen atom in the partial structure.

The partial structure represented by the general formula (KA-1) or (KB-1) is connected to the main chain of the hydrophobic resin (Aa) at an arbitrary position through a substituent.

The partial structure represented by the general formula (KA-1) is a structure forming a ring structure together with the group as X.

In the general formula (KA-1), X is preferably a carboxylic acid ester group (that is, a case of forming a lactone ring structure as KA-1), an acid anhydride group or a carbonic acid ester group, more preferably a carboxylic acid ester group.

The ring structure represented by the general formula (KA-1) may have a substituent and, for example, may have nka substituents $Z_{ka1}$.

When a plurality of $Z_{ka1}$'s are present, they each independently represent a halogen atom, an alkyl group, a cycloalkyl group, an ether group, a hydroxyl group, an amido group, an aryl group, a lactone ring group, or an electron-withdrawing group.

$Z_{ka1}$'s may be bonded to each other to form a ring. Examples of the ring formed by the connecting of $Z_{ka1}$'s with each other include a cycloalkyl ring and a heterocycle (a cyclic ether ring, a lactone ring, and the like).

nka represents an integer of 0 to 10 and is preferably an integer of 0 to 8, more preferably an integer of 0 to 5, still more preferably an integer of 1 to 4, and most preferably an integer of 1 to 3.

The electron-withdrawing group as $Z_{ka1}$ has the same meaning as the electron-withdrawing group of $Y^1$ and $Y^2$ to be described hereinafter. Incidentally, the electron-withdrawing group above may be substituted with another electron-withdrawing group.

$Z_{ka1}$ is preferably an alkyl group, a cycloalkyl group, an ether group, a hydroxyl group or an electron-withdrawing group, more preferably an alkyl group, a cycloalkyl group or an electron-withdrawing group. The ether group is preferably an ether group substituted, for example, with an alkyl group or a cycloalkyl group, that is, an alkyl ether group. The electron-withdrawing group has the same meaning as above.

Examples of the halogen atom as $Z_{ka1}$ include a fluorine atom, a chlorine atom, a bromine atom and an iodine atom, with a fluorine atom being preferred.

The alkyl group as $Z_{ka1}$ may have a substituent and may be either linear or branched. The linear alkyl group is preferably an alkyl group having 1 to 30 carbon atoms, more preferably 1 to 20 carbon atoms, and examples thereof include a methyl group, an ethyl group, an n-propyl group, an n-butyl group, a sec-butyl group, a t-butyl group, an n-pentyl group, an n-hexyl group, an n-heptyl group, an n-octyl group, an n-nonyl group and an n-decanyl group. The branched alkyl group is preferably an alkyl group having 3 to 30 carbon atoms, more preferably 3 to 20, and examples thereof include an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group and a t-decanoyl group. An alkyl group having 1 to 4 carbon atoms is preferred, such as a methyl group, an ethyl group, an n-propyl group, an i-propyl group, an n-butyl group, an i-butyl group and a t-butyl group.

The cycloalkyl group as $Z_{ka1}$ may have a substituent and may be monocyclic or polycyclic. The polycyclic cycloalkyl group may be crosslinked. That is, in this case, the cycloalkyl group may have a bridged structure. The monocyclic type is preferably a cycloalkyl group having 3 to 8 carbon atoms, and examples thereof include a cyclopropyl group, a cyclopentyl group, a cyclohexyl group, a cyclobutyl group and a cyclooctyl group. The polycyclic type includes a group having a bicyclo, tricyclo or tetracyclo structure or the like and having 5 or more carbon atoms. A cycloalkyl group having 6 to 20 carbon atoms is preferred, and examples thereof include an adamantyl group, a norbornyl group, an isobornyl group, a camphanyl group, a dicyclopentyl group, an α-pinel group, a tricyclodecanyl group, a tetracyclododecyl group and an androstanyl group. The following structures are also preferred as the cycloalkyl group. Incidentally, parts of carbon atoms in the cycloalkyl group may be substituted with heteroatoms such as an oxygen atom.

[Chem. 152]

 (1)

 (2)

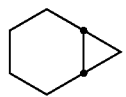 (3)

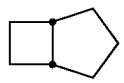 (4)

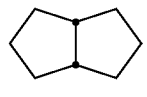 (5)

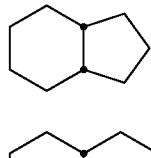 (6)

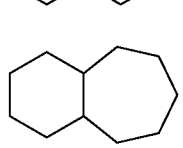 (7)

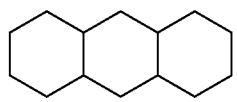 (8)

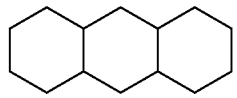 (9)

321
-continued
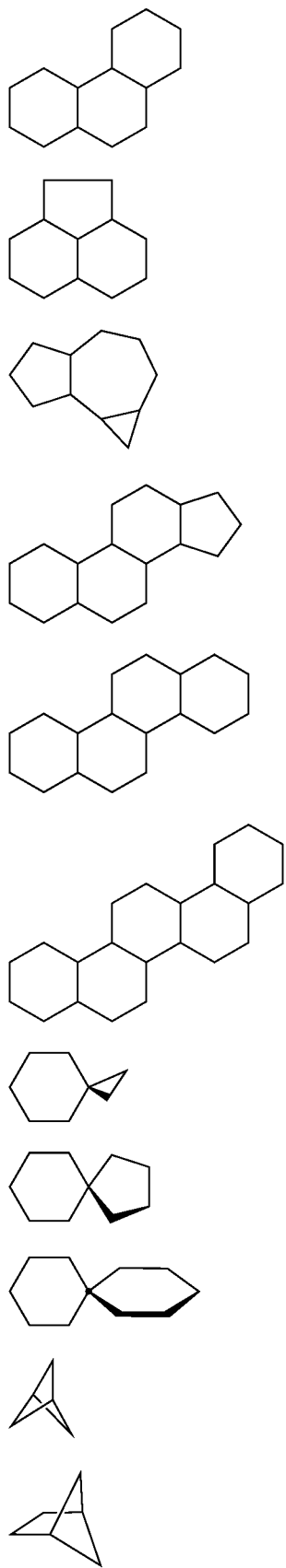
322
-continued
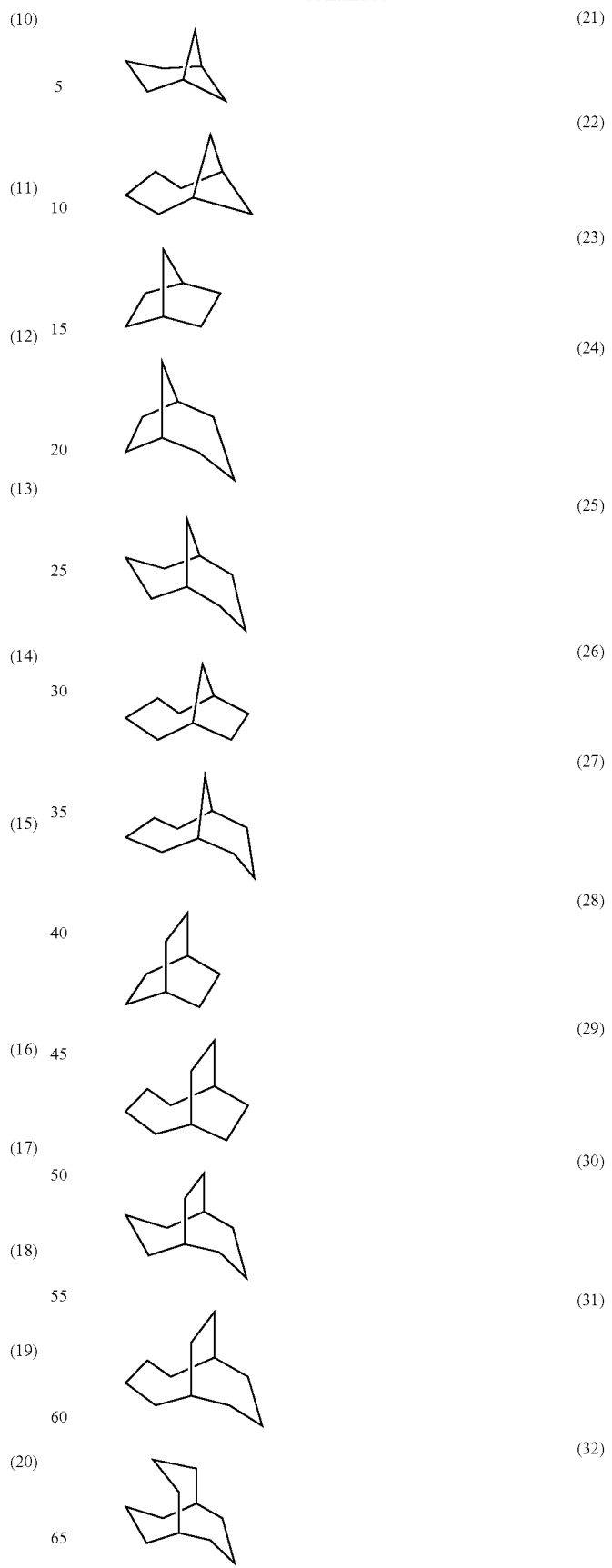

-continued

(33) 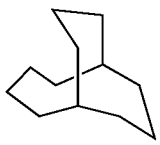

(34) 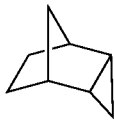

(35) 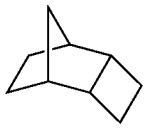

(36) 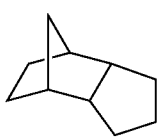

(37) 

(38) 

(39) 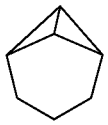

(40) 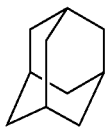

(41) 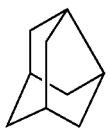

(42) 

(43) 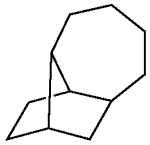

(44) 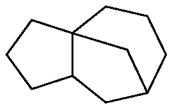

-continued

(45) 

(46) 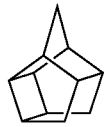

(47) 

(48) 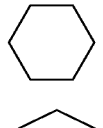

(49) 

(50)

Preferred examples of the alicyclic structure include an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group, more preferably an adamantyl group, a decalin residue, a norbornyl group, a cedrol group, a cyclohexyl group, a cycloheptyl group, a cyclooctyl group, a cyclodecanyl group, a cyclododecanyl group, and a tricyclodecanyl group.

Examples of the substituent in these alicyclic groups include an alkyl group, a halogen atom, a hydroxyl group, an alkoxy group, a carboxyl group, and an alkoxycarbonyl group. The alkyl group is preferably a lower alkyl group such as a methyl group, an ethyl group, a propyl group, an isopropyl group, and a butyl group, and more preferably, it represents a methyl group, an ethyl group, a propyl group, or an isopropyl group. Examples of the alkoxy group include an alkoxy group having 1 to 4 carbon atoms, such as a methoxy group, an ethoxy group, a propoxy group and a butoxy group. Examples of the substituent which the alkyl group and alkoxy group each may further have include a hydroxyl group, a halogen atom, and an alkoxy group (preferably having 1 to 4 carbon atoms).

Furthermore, the groups above may further have a substituent, and examples of the further substituent include a hydroxyl group, a halogen atom (for example, fluorine, chlorine, bromine, and iodine), a nitro group, a cyano group, the above-described alkyl group, an alkoxy group such as a methoxy group, an ethoxy group, a hydroxyethoxy group, a propoxy group, a hydroxypropoxy group, an n-butoxy group, an isobutoxy group, a sec-butoxy group, and a t-butoxy group, an alkoxycarbonyl group such as a methoxycarbonyl group and an ethoxycarbonyl group, an aralkyl group such as a benzyl group, a phenethyl group, and a cumyl group, an acyl group such as an aralkyloxy group, a formyl group, an acetyl group, a butyryl group, a benzoyl group, a cinnamoyl group, and a valeryl group, an acyloxy group such as a butyryloxy group, the above-described alkenyl group, an alkenyloxy group such as a vinyloxy group, a propenyloxy group, an allyloxy group, and a butenyloxy group, the above-described aryl group, an aryloxy group such as a phenoxy group, and an aryloxycarbonyl group such as a benzoyloxy group.

It is preferable that X in the general formula (KA-1) be a carboxylic ester group and the partial structure represented by the general formula (KA-1) be a lactone ring, and preferably a 5- to 7-membered lactone ring.

Incidentally, it is preferable that as in (KA-1-1) to (KA-1-17) shown below, another ring structure is condensed to a 5- to 7-membered lactone ring as the partial structure represented by the general formula (KA-1) in the form of forming a bicyclo or spiro structure.

Examples of the peripheral ring structure with which the ring structure represented by the general formula (KA-1) may be combined include those in (KA-1-1) to (KA-1-17) shown below and structures based on these structures.

The structure containing a lactone ring structure represented by the general formula (KA-1) is more preferably a structure represented by any one of the following (KA-1-1) to (KA-1-17). Further, the lactone structure may be bonded directly to the main chain. Preferred structures are (KA-1-1), (KA-1-4), (KA-1-5), (KA-1-6), (KA-1-13), (KA-1-14), and (KA-1-17).

[Chem. 153]

KA-1-1

KA-1-2

KA-1-3

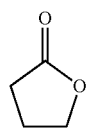

KA-1-4

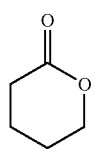

KA-1-5

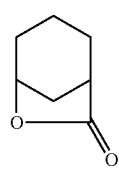

KA-1-6

KA-1-7

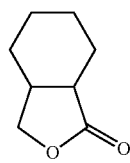

KA-1-8

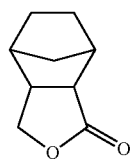

KA-1-9

KA-1-10

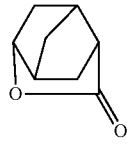

KA-1-11

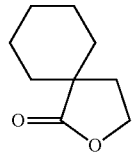

KA-1-12

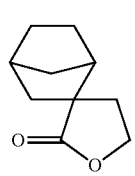

KA-1-13

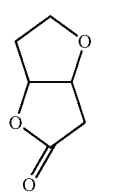

KA-1-14

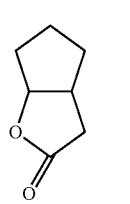

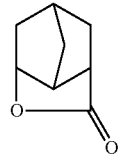

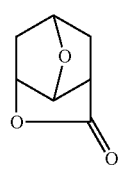

KA-1-15

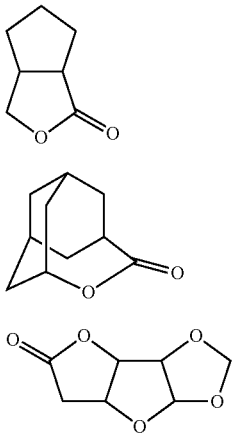

KA-1-16

KA-1-17

The structure containing the above-described lactone ring structure may or may not have a substituent. Preferable examples of the substituent are the same as those of the substituent $Z_{ka1}$ which may be contained in the ring structure represented by the general formula (KA-1).

In the general formula (KB-1), X preferably includes a carboxylic ester group (—COO—).

In the general formula (KB-1), $Y^1$ and $Y^2$ each independently represent an electron-withdrawing group.

The electron-withdrawing group is a partial structure represented by the following formula (EW). In the formula (EW), * represents a bonding directly bonded to (KA-1) or a bonding directly bonded to X in (KB-1).

[Chem. 154]

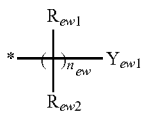
(EW)

In the formula (EW), $n_{ew}$ is a repetition number of the connecting group represented by —$C(R_{ew1})(R_{ew2})$—, and represents an integer of 0 or 1. In the case where $n_{ew}$ is 0, this indicates a single bond and direct bonding of $Y_{ew}1$.

$Y_{ew1}$ is a halogen atom, a cyano group, a nitrile group, a nitro group, a halo(cyclo)alkyl, a haloaryl group represented by —$C(R_{f1})(R_{f2})$—$R_{f3}$, an oxy group, a carbonyl group, a sulfonyl group, a sulfinyl group, or a combination thereof. Further, the electron-withdrawing group may be, for example, a structure shown below. The "halo(cyclo)alkyl group" indicates an alkyl or cycloalkyl group that is at least partially halogenated. The term "haloaryl group" indicates an aryl group that is at least partially halogenated. In the structural formulae below, $R_{ew3}$ and $R_{ew4}$ each independently represent an arbitrary structure. The partial structure represented by the general formula (EW) has an electron-withdrawing property irrespective of structures of $R_{ew3}$ and $R_{ew4}$ and may be combined with, for example, the main chain of the resin, but is preferably an alkyl group, a cycloalkyl group, or an alkyl fluoride group.

[Chem. 155]

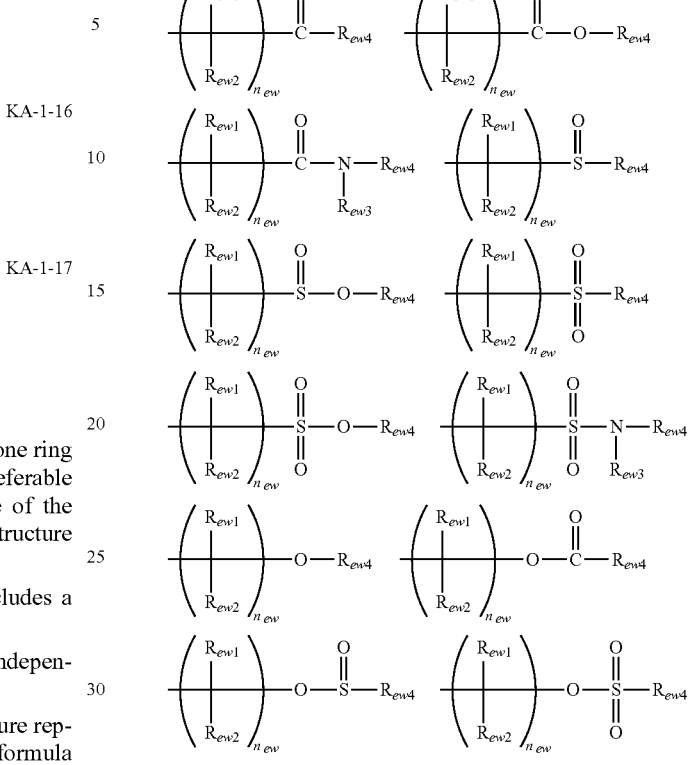

In the case where $Y_{ew1}$ is a divalent or higher-valent group, the remaining bond forms bonding to an arbitrary atom or substituent. At least any one group of $Y_{ew1}$, $R_{ew1}$, and $R_{ew2}$ may be combined with the main chain of a resin (C) through a further substituent.

$Y_{ew1}$ is preferably a halogen atom, or a halo(cyclo)alkyl or haloaryl group represented by —$C(R_{f1})(R_{f2})$—$R_{f3}$.

$R_{ew1}$ and $R_{ew2}$ each independently represent an arbitrary substituent, and represent, for example, a hydrogen atom, an alkyl group, a cycloalkyl group, or an aryl group.

At least two members out of $R_{ew1}$, $R_{ew2}$, and $Y_{ew1}$ may be combined with each other to form a ring.

Here, $R_{f1}$ represents a halogen atom, a perhaloalkyl group, a perhalocycloalkyl group or a perhaloaryl group and is preferably a fluorine atom, a perfluoroalkyl group, or a perfluorocycloalkyl group, and more preferably a fluorine atom or a trifluoromethyl group.

$R_{f2}$ and $R_{f3}$ each independently represent a hydrogen atom, a halogen atom or an organic group, and $R_{f2}$ and $R_{f3}$ may be combined with each other to form a ring. Examples of the organic group include an alkyl group, a cycloalkyl group, an alkoxy group, and the like. $R_{f2}$ more preferably represents the same group as $R_{f1}$ or is combined with $R_{f3}$ to form a ring.

$R_{f1}$ to $R_{f3}$ may be combined with each other to form a ring, and examples of the ring formed include a (halo)cycloalkyl ring and a (halo)aryl ring.

Examples of the (halo)alkyl group in $R_{f1}$ to $R_{f3}$ include the alkyl groups in $Z_{ka1}$ and halogenated structures thereof.

Examples of the (per)halocycloalkyl group and the (per) haloaryl group in $R_{f1}$ to $R_{f3}$ or in the ring formed by combination of $R_{f2}$ and $R_{f3}$ include the above-described structures resulting from halogenation of cycloalkyl groups in $Z_{ka1}$, and a fluoroalkyl group represented by —$C_{(n)}F_{(2n-2)}H$ and a perfluoroaryl group represented by —$C_{(n)}F_{(n-1)}$ are preferable, where the number of carbon atoms n is not particularly limited but is preferably from 5 to 13, and more preferably 6.

The ring which may be formed by combination of at least two members out of $R_{ew1}$, $R_{ew2}$, and $Y_{ew1}$ with each other is preferably a cycloalkyl group or a heterocyclic group, and the heterocyclic group is preferably a lactone ring group. Examples of the lactone ring include structures represented by the formulae (KA-1-1) to (KA-1-17).

Incidentally, the repeating unit (by) may have a plurality of partial structures represented by the general formula (KA-1), a plurality of partial structures represented by the general formula (KB-1), or both a partial structure represented by the general formula (KA-1) and a partial structure represented by the general formula (KB-1).

Furthermore, the partial structure of the general formula (KA-1) may partially or entirely serve also as the electron-withdrawing group of $Y^1$ or $Y^2$ in the general formula (KB-1). For example, in the case where X in the general formula (KA-1) is a carboxylic ester group, the carboxylic ester group may function as the electron-withdrawing group of $Y^1$ or $Y^2$ in the general formula (KB-1).

Moreover, in the case where the repeating unit (by) corresponds to the repeating unit (b*) or the repeating unit (b") and has a partial structure represented by the general formula (KA-1), the partial structure represented by the general formula (KA-1) is more preferably a partial structure where the polarity converting group is —COO— in the structure represented by the general formula (KA-1).

The repeating unit (by) may be a repeating unit having a partial structure represented by the general formula (KY-0).

[Chem. 156]

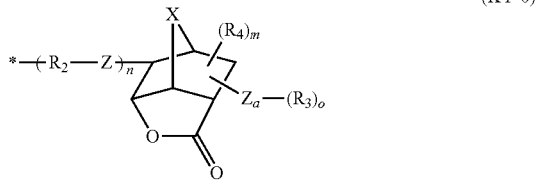

(KY-0)

In the general formula (KY-0), $R_2$ represents a chained or cyclic alkylene group and when a plurality of $R_2$'s are present, they may be the same as or different from each other.

$R_3$ represents a linear, branched, or cyclic hydrocarbon group where a part or all of hydrogen atoms on the constituent carbons are substituted with a fluorine atom.

$R_4$ represents a halogen atom, a cyano group, a hydroxyl group, an amido group, an alkyl group, a cycloalkyl group, an alkoxy group, a phenyl group, an acyl group, an alkoxycarbonyl group, or a group represented by R—C(=O)— or R—C(=O)O— (wherein R represents an alkyl group or a cycloalkyl group), and when a plurality of $R_4$'s are present, they may be the same as or different from each other, and two or more $R_4$'s may be bonded to each other to form a ring.

X represents an alkylene group, an oxygen atom, or a sulfur atom.

Each of Z and Za represents a single bond, an ether bond, an ester bond, an amide bond, a urethane bond, or a urea bond, and when a plurality of Z's or Za's are present, they may be the same as or different from each other.

* represents a bonding to the main chain or side chain of the resin.

s the number of substituents and represents an integer of 1 to 7.

m is the number of substituents and represents an integer of 0 to 7.

n is a repetition number and represents an integer of 0 to 5.

The structure of —$R_2$—Z— is preferably a structure represented by —$(CH_2)_l$—COO— (wherein l represents an integer of 1 to 5).

The preferable range of number of carbon atoms and specific examples of the chained or cyclic alkylene group as $R_2$ are the same as those described with respect to the chained alkylene group and a cyclic alkylene group in $Z_2$ of the general formula (bb).

The number of carbon atoms of the linear, branched, or cyclic hydrocarbon group as $R_3$ is, in the case of a linear hydrocarbon group, preferably from 1 to 30, and more preferably from 1 to 20, in the case of a branched hydrocarbon group, preferably from 3 to 30, and more preferably from 3 to 20, and in the case of a cyclic hydrocarbon group, from 6 to 20. Specific examples of $R_3$ include the specific examples of the alkyl group and a cycloalkyl group as $Z_{ka1}$.

The preferable number of carbon atoms and specific examples of the alkyl group and a cycloalkyl group as $R_4$ and R are the same as those described with respect to the alkyl group and the cycloalkyl group as $Z_{ka1}$.

The acyl group as $R_4$ is preferably an acyl group having 1 to 6 carbon atoms, and examples thereof include a formyl group, an acetyl group, a propionyl group, a butyryl group, an isobutyryl group, a valeryl group, and a pivaloyl group.

The alkyl moiety in the alkoxy group and the alkoxycarbonyl group as $R_4$ include a linear, branched, or cyclic alkyl moiety, and the preferable number of carbon atoms and specific examples of the alkyl moiety are the same as those described with respect to the alkyl group and the cycloalkyl group of $Z_{ka1}$.

The alkylene group as X includes a chained or cyclic alkylene group, and the preferable number of carbon atoms and specific examples thereof are the same as those described with respect to the chained alkylene group and the cyclic alkylene group as $R_2$.

Furthermore, the specific structure of the repeating unit (by) also contains a repeating unit having a partial structure shown below.

[Chem. 157]

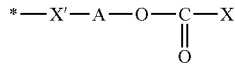

(rf-1)

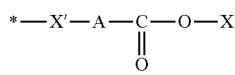

(rf-2)

In the general formulae (rf-1) and (rf-2),

X' represents an electron-withdrawing substituent and is preferably a carbonyloxy group, an oxycarbonyl group, a fluorine atom-substituted alkylene group, or a fluorine atom-substituted cycloalkylene group.

A represents a single bond, a divalent connecting group represented by —C(Rx)(Ry)-, wherein Rx and Ry independently represent a hydrogen atom, a fluorine atom, an alkyl group (preferably having 1 to 6 carbon atoms, which may be substituted with a fluorine atom or the like), or a cycloalkyl group (preferably having 5 to 12 carbon atoms, which may be substituted with a fluorine atom or the like), and each of Rx and Ry is preferably a hydrogen atom, an alkyl group, or a fluorine atom-substituted alkyl group.

X represents an electron-withdrawing group and specific examples thereof include the electron-withdrawing groups as $Y^1$ and $Y^2$, and X is preferably an alkyl fluoride group, a cycloalkyl fluoride group, an aryl group substituted with fluorine or an alkyl fluoride group, an aralkyl group substituted with fluorine or an alkyl fluoride group, a cyano group, or a nitro group.

* represents a bonding to the main chain or side chain of the resin, that is, a bonding which is bonded to the main chain of the resin through a single bond or a connecting group.

Incidentally, when X' is a carbonyloxy group or an oxycarbonyl group, A is not a single bond.

The polarity converting group decomposes by the action of an alkali developer to effect polarity conversion, whereby the receding contact angle with water of the resin composition film after alkaline development can be decreased. Decrease in the receding contact angle with water of the film after alkaline development is preferable from the viewpoint of suppressing the development defect.

The receding contact angle with water of the resin composition film after alkaline development is preferably 50° or less, more preferably 40° or less, still more preferably 35° or less, and most preferably 30° or less, at a temperature of 23±3° C. and a humidity of 45±5%.

The receding contact angle is a contact angle measured when a contact line recedes on the liquid droplet-substrate interface, and this is generally known to be useful in simulating the mobility of a liquid droplet in the dynamic state. In a simple manner, the receding contact angle can be defined as a contact angle at the time of the liquid droplet interface receding when a liquid droplet ejected from a needle tip is landed on a substrate and then the liquid droplet is again suctioned into the needle. In general, the receding contact angle can be measured by a contact angle measuring method called an expansion/contraction method.

The receding contact angle of the film after alkaline development is a contact angle when a film shown below is measured by the expansion/contraction method described in Examples as described later. That is, it is a contact angle of a film obtained as follows by measurement by an expansion/contraction method: ARC29A (manufactured by Nissan Chemical Industries, Ltd.) for forming an organic antireflection film was applied onto a silicon wafer (8-inch opening diameter) and baked at 205° C. for 60 seconds, thereby forming an antireflection film having a film thickness of 98 nm. The actinic ray-sensitive or radiation-sensitive resin composition of the present invention was applied thereonto and baked at 120° C. for 60 seconds, thereby forming a film having a film thickness of 120 nm. This film was developed in an aqueous tetramethylammonium hydroxide solution (2.38% by mass) for 30 seconds, rinsed with pure water, and then spin-dried, thereby obtaining a film.

The hydrolysis rate of the resin (Aa) for an alkali developer is preferably 0.001 nm/sec or more, more preferably 0.01 nm/sec or more, still more preferably 0.1 nm/sec or more, and most preferably 1 nm/sec or more.

The hydrolysis rate of the resin (Aa) for an alkali developer as used herein is the rate at which the thickness of a resin film formed only of the resin (Aa) decreases when treated with TMAH (an aqueous tetramethylammonium hydroxide solution) (2.38% by mass) at 23° C.

The repeating unit (by) is more preferably a repeating unit having at least two or more polarity converting groups.

In the case where the repeating unit (by) has at least two polarity converting groups, the repeating unit preferably has a group containing a partial structure having two polarity converting groups represented by the following general formula (KY-1). Incidentally, when the structure represented by the general formula (KY-1) does not have a bond, this is a group containing a monovalent or higher valent group formed by removing at least one arbitrary hydrogen atom in the structure.

[Chem. 158]

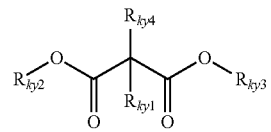

(KY-1)

In the general formula (KY-1), $R_{ky1}$ and $R_{ky4}$ each independently represent a hydrogen atom, a halogen atom, an alkyl group, a cycloalkyl group, a carbonyl group, a carbonyloxy group, an oxycarbonyl group, an ether group, a hydroxyl group, a cyano group, an amido group, or an aryl group. Alternatively, $R_{ky1}$ and $R_{ky4}$ may be bonded to the same atom to form a double bond. For example, $R_{ky1}$ and $R_{ky4}$ may be bonded to the same oxygen atom to form a part (=O) of a carbonyl group.

$R_{ky2}$ and $R_{ky3}$ each independently represent an electron-withdrawing group, or while $R_{ky1}$ and $R_{ky2}$ are combined to form a lactone ring, $R_{ky3}$ is an electron-withdrawing group. The lactone ring formed is preferably a structure of (KA-1-1) to (KA-1-17). Examples of the electron-withdrawing group are the same as set forth with respect to $Y_1$ and $Y_2$ in the general formula (KB-1), and a halogen atom and a halo(cyclo)alkyl or haloaryl group represented by —C($R_{f1}$)($R_{f2}$)—$R_{f3}$ are preferable. Preferably, $R_{ky3}$ is a halogen atom or a halo(cyclo)alkyl or haloaryl group represented by —C($R_{f1}$)($R_{f2}$)—$R_{f3}$, and $R_{ky2}$ is combined with $R_{ky1}$ to form a lactone ring or is an electron-withdrawing group containing no halogen atom.

$R_{ky1}$, $R_{ky2}$, and $R_{ky4}$ may be combined with each other to form a monocyclic or polycyclic structure.

Specific examples of $R_{ky1}$ and $R_{ky4}$ include the same groups as set forth with respect to $Z_{ka1}$ in the formula (KA-1).

The lactone ring formed by combination of $R_{ky1}$ and $R_{ky2}$ is preferably the structures of (KA-1-1) to (KA-1-17). Examples of the electron-withdrawing group are the same as set forth with respect to $Y_1$ and $Y_2$ in the general formula (KB-1).

The structure represented by the general formula (KY-1) is preferably a structure represented by the following general formula (KY-2). Here, the structure represented by the general formula (KY-2) is a group having a monovalent or higher valent group formed by removing at least one arbitrary hydrogen atom in the structure.

[Chem. 159]

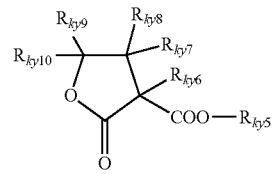

(KY-2)

In the formula (KY-2), $R_{ky6}$ to $R_{ky10}$ each independently represent a hydrogen atom, a halogen atom, an alkyl group, a cycloalkyl group, a carbonyl group, a carbonyloxy group, an oxycarbonyl group, an ether group, a hydroxyl group, a cyano group, an amido group, or an aryl group.

Two or more members out of $R_{ky6}$ to $R_{ky10}$ may be combined with each other to form a monocyclic or polycyclic structure.

$R_{ky5}$ represents an electron-withdrawing group, and examples of the electron-withdrawing group are the same as set forth with respect to $Y_1$ and $Y_2$, with a halogen atom, or a halo(cyclo)alkyl or haloaryl group represented by —C($R_1$)($R_{f2}$)—$R_{3f}$ being preferred.

Specific examples of $R_{ky5}$ to $R_{ky10}$ include the same groups as $Z_{ka1}$ in the formula (KA-1).

The structure represented by the formula (KY-2) is more preferably a partial structure represented by the following general formula (KY-3).

[Chem. 160]

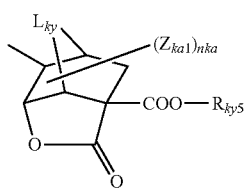

(KY-3)

In the formula (KY-3), $Z_{ka1}$ and $n_{ka}$ have the same meanings as in the general formula (KA-1). $R_{ky5}$ has the same meaning as in the formula (KY-2).

$L_{ky}$ represents an alkylene group, an oxygen atom, or a sulfur atom. Examples of the alkylene group of $L_{ky}$ include a methylene group, an ethylene group, and the like. $L_{ky}$ is preferably an oxygen atom or a methylene group, and more preferably a methylene group.

The repeating unit (b) is not limited as long as it is a repeating unit obtained by polymerization such as addition polymerization, condensation polymerization and addition condensation, but a repeating unit obtained by addition polymerization of a carbon-carbon double bond is preferable. Examples thereof include an acrylate-based repeating unit (including a system having a substituent at the α- or β-position), a styrene-based repeating unit (including a system having a substituent at the α- or β-position), a vinyl ether-based repeating unit, a norbornene-based repeating unit, a maleic acid derivative (such as maleic anhydride or a derivative thereof, maleimide, and the like) repeating unit, and the like. An acrylate-based repeating unit, a styrene-based repeating unit, a vinyl ether-based repeating unit and a norbornene-based repeating unit are preferable, an acrylate-based repeating unit, a vinyl ether-based repeating unit and a norbornene-based repeating unit are more preferable, and an acrylate-based repeating unit is most preferable.

In the case where the repeating unit (by) is a repeating unit having at least either fluorine atoms or silicon atoms (that is, a repeating unit corresponding to the repeating unit (b') or (b'')), examples of the fluorine atom-containing partial structure in the repeating unit (by) are the same as those in the above-described repeating unit having at least either fluorine atoms or silicon atoms, and the groups represented by the general formulae (F2) to (F4) are preferable. Further, examples of the silicon atom-containing partial structure in the repeating unit (by) are the same as those in the above-described repeating unit having at least either fluorine atoms or silicon atoms, and the groups represented by the general formulae (CS-1) to (CS-3) are preferable.

The content of the repeating units (by) in the resin (Aa) is preferably from 10 to 100% by mole, more preferably from 20 to 99% by mole, still more preferably from 30 to 97% by mole, and most preferably from 40 to 95% by mole, based on all the repeating units in the resin (Aa).

Specific examples of the repeating unit (by) having a group capable of increasing the solubility in an alkali developer are illustrated below, but the present invention is not limited thereto. Specific examples of the repeating unit (by) also include those described as specific examples of the repeating unit (a3) of the resin (A).

Ra represents a hydrogen atom, a fluorine atom, a methyl group, or a trifluoromethyl group.

[Chem. 161]

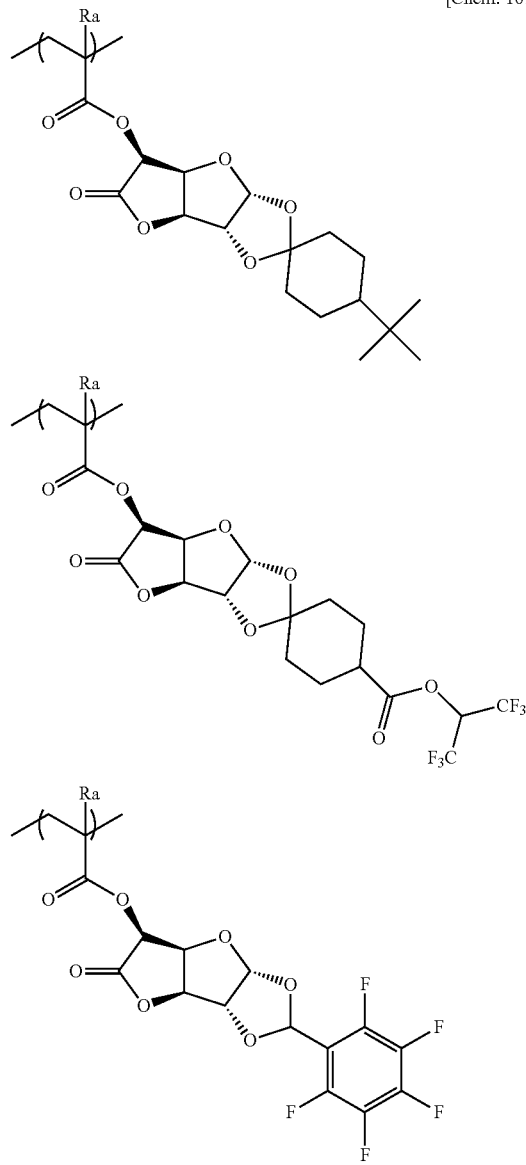

335
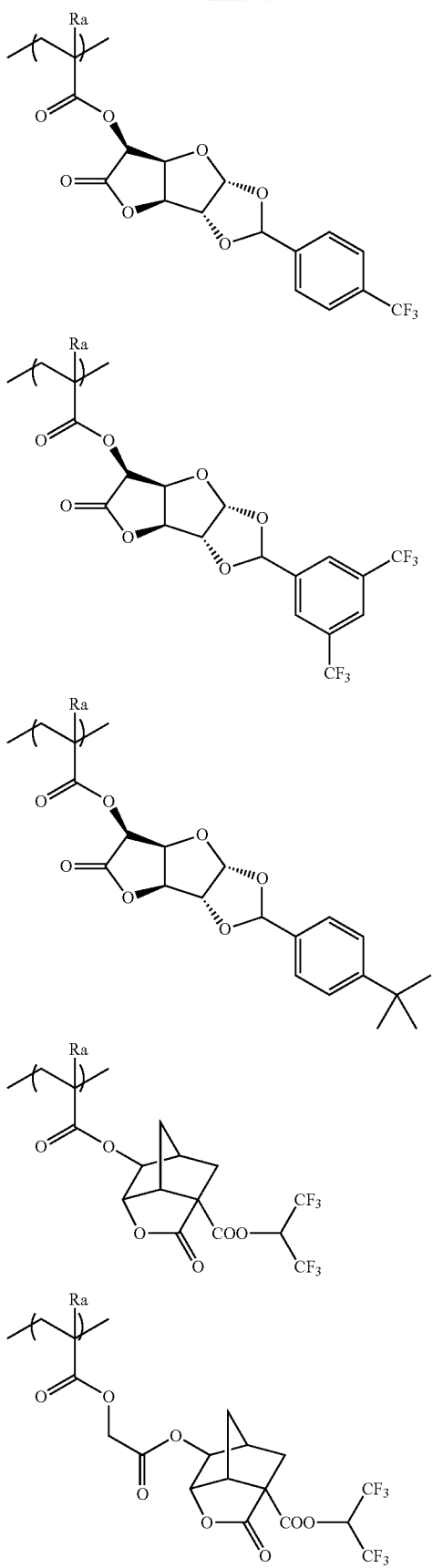
336
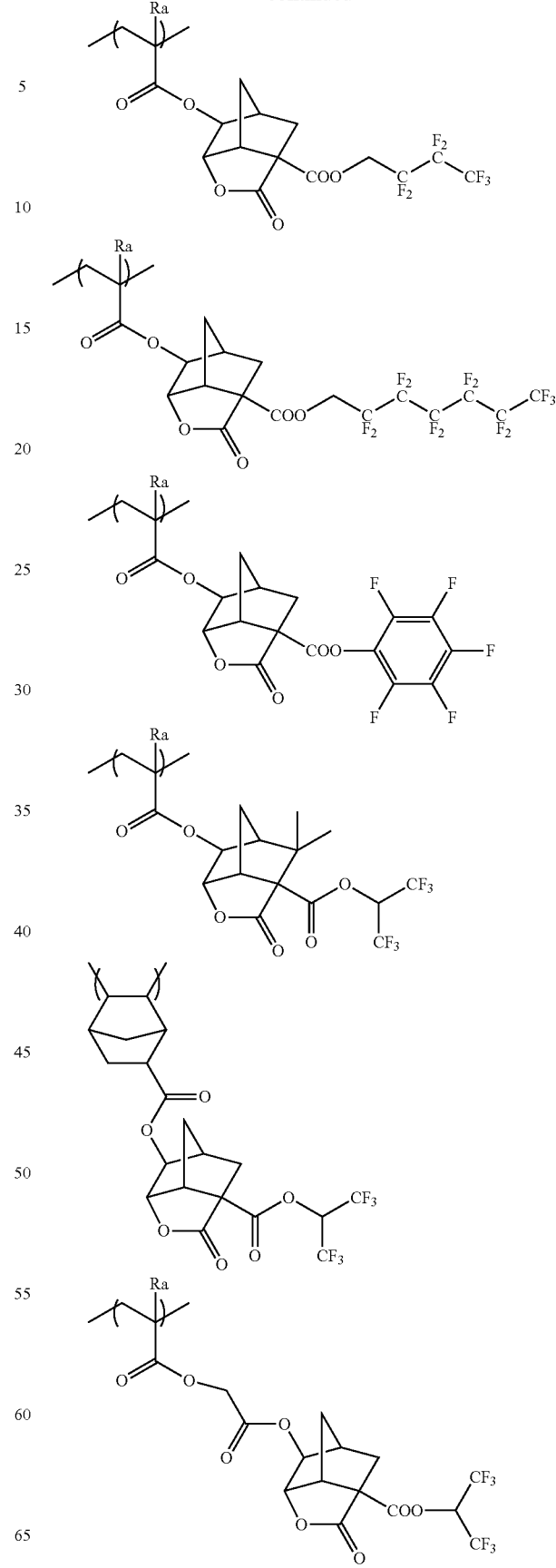

337
-continued
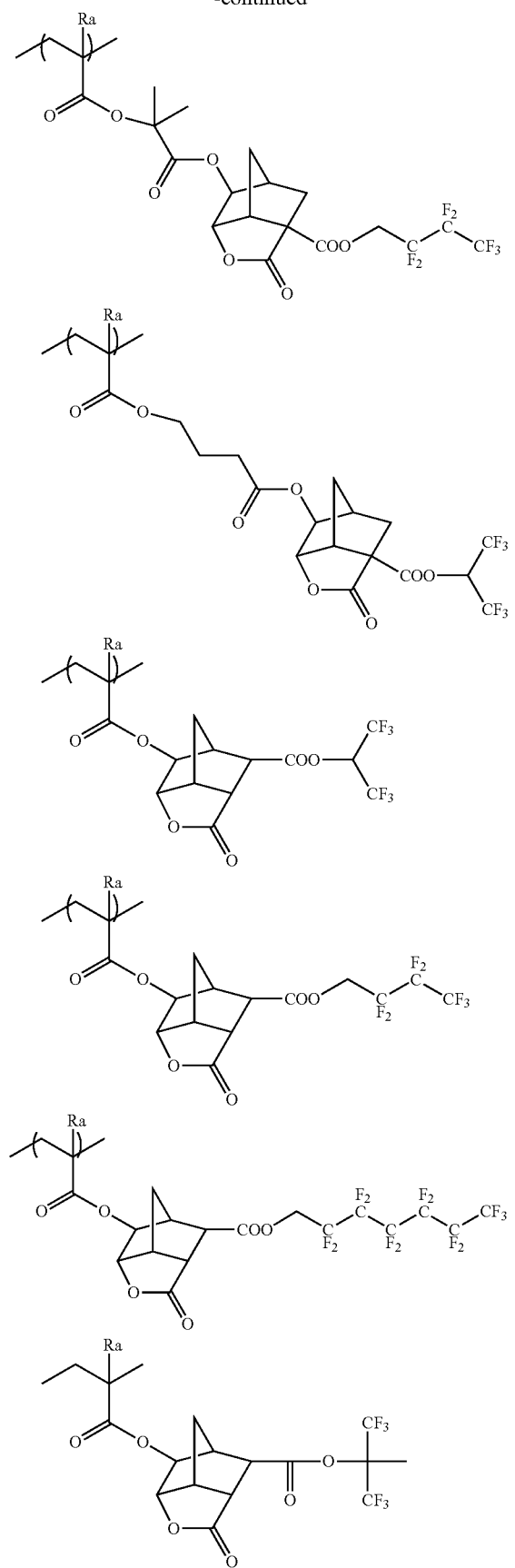
338
-continued
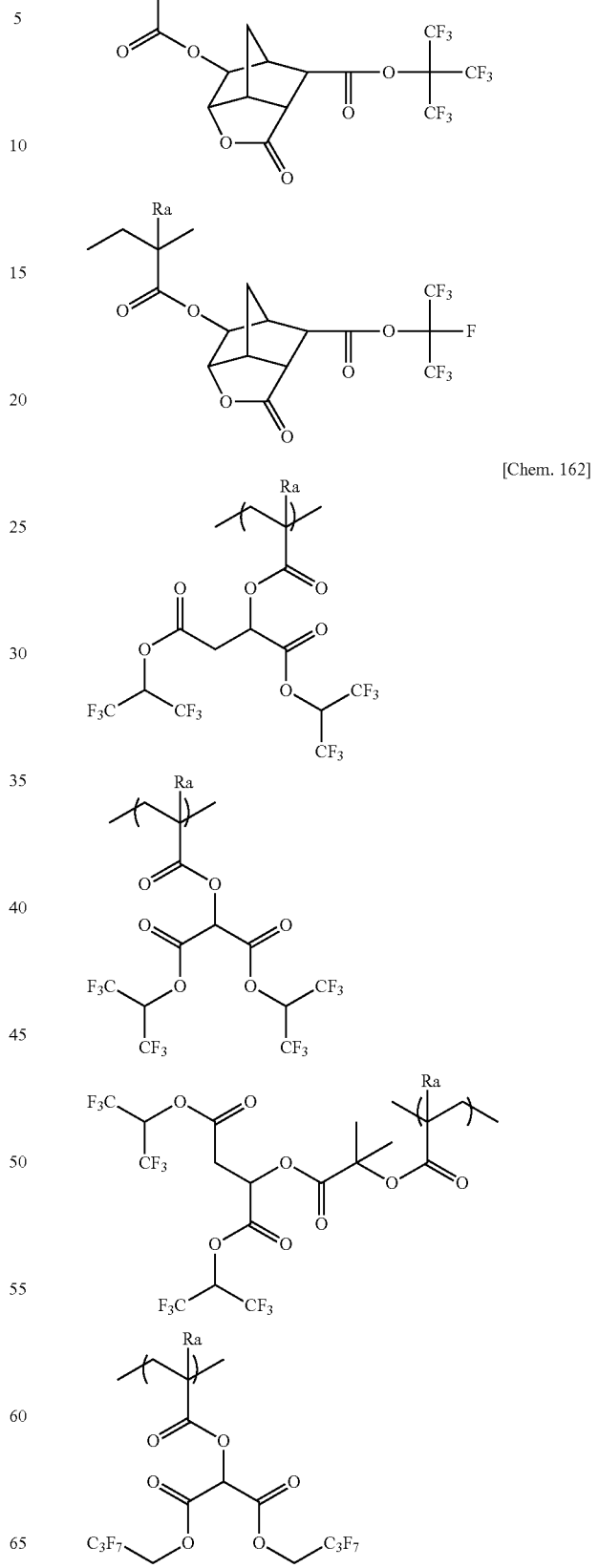
[Chem. 162]

-continued

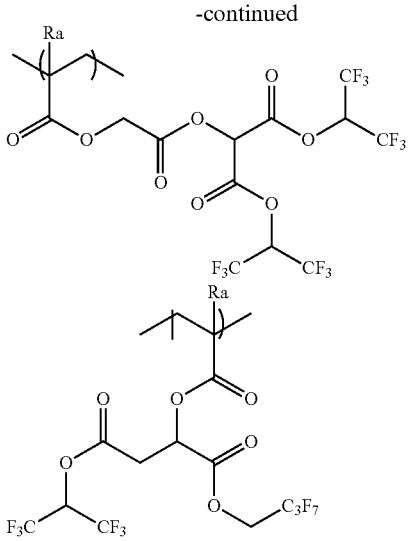

In the resin (Aa), examples of the repeating unit (bz) having a group capable of decomposing by the action of an acid (z) include those described above for the repeating unit having an acid-decomposable group in the resin (A).

In the case where the repeating unit (bz) is a repeating unit having at least either fluorine atoms or silicon atoms (that is, a repeating unit corresponding to the repeating unit (b') or (b″)), examples of the fluorine atom-containing partial structure in the repeating unit (bz) are the same as those described with respect to the repeating units having at least either fluorine atoms or silicon atoms and preferably include the groups represented by the general formulae (F2) to (F4). Also in this case, examples of the silicon atom-containing partial structure in the repeating unit (by) are the same as those described with respect to the repeating units having at least either fluorine atoms or silicon atoms and preferably include the groups represented by the general formulae (CS-1) to (CS-3).

In the resin (Aa), the content of the repeating units (bz) having a group (z) that decomposes by the action of an acid is preferably from 1 to 80% by mole, more preferably from 10 to 80% by mole, and still more preferably from 20 to 60% by mole, based on all repeating units in the resin (Aa).

The repeating unit (b) having at least one group selected from the group consisting of (x) to (z) above was described as above, but the content of the repeating units (b) in the resin (Aa) is preferably from 1 to 98% by mole, more preferably from 3 to 98% by mole, still more preferably from 5 to 97% by mole, and most preferably from 10 to 95% by mole, based on all repeating units in the resin (Aa).

The content of the repeating units (b') is preferably from 1 to 100% by mole, more preferably from 3 to 99% by mole, still more preferably from 5 to 97% by mole, and most preferably from 10 to 95% by mole, based on all repeating units in the resin (Aa).

The content of the repeating units (b*) is preferably from 1 to 90% by mole, more preferably from 3 to 80% by mole, still more preferably 5 to 70% by mole, and most preferably 10 to 60% by mole, based on all repeating units in the resin (Aa). The content of the repeating units having at least either fluorine atoms or silicon atoms, which is used together with the repeating unit (b*) is preferably from 10 to 99% by mole, more preferably from 20 to 97% by mole, still more preferably from 30 to 95% by mole, and most preferably from 40 to 90% by mole, based on all repeating units in the resin (Aa).

The content of the repeating units (b″) is preferably from 1 to 100% by mole, more preferably from 3 to 99% by mole, more preferably from 5 to 97% by mole, and most preferably from 10 to 95% by mole, based on all repeating units in the resin (Aa).

The resin (Aa) may further contain a repeating unit represented by the following general formula (III).

[Chem. 163]

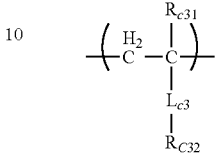

(III)

In the general formula (III), $R_{c31}$ represents a hydrogen atom, an alkyl group which may be substituted with an alkyl group or a fluorine atom, a cyano group or a —$CH_2$—O—$R_{ac2}$ group wherein $R_{ac2}$ represents a hydrogen atom, an alkyl group, or an acyl group. $R_{31}$ is preferably a hydrogen atom, a methyl group, a hydroxymethyl group or a trifluoromethyl group, and more preferably a hydrogen atom or a methyl group.

$R_{c32}$ represents a group containing an alkyl group, a cycloalkyl group, an alkenyl group, a cycloalkenyl group or an aryl group. Each of these groups may be substituted with a fluorine atom- or silicon atom-containing group or the like.

$L_{c3}$ represents a single bond or a divalent connecting group.

In the general formula (III), the alkyl group of $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably a phenyl group having 6 to 20 carbon atoms or a naphthyl group, which may have a substituent.

$R_{c32}$ is preferably an unsubstituted alkyl group or an alkyl group substituted with a fluorine atom.

The divalent connecting group of $Lc_3$ is preferably an alkylene group (preferably having 1 to 5 carbon atoms), an oxy group, a phenylene group, or an ester bond (a group represented by —COO—).

It is also preferable that the resin (Aa) further contain a repeating unit represented by the following general formula (BII-AB).

[Chem. 164]

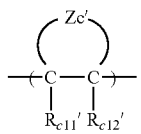

(BII-AB)

In the formula (BII-AB), $R_{c11'}$ and $R_{c12'}$ each independently represent a hydrogen atom, a cyano group, a halogen atom, or an alkyl group.

$Z_{c'}$ represents an atomic group for forming an alicyclic structure containing two carbon atoms (C—C) to which $Z_{c'}$ is bonded.

In the case where each group in the repeating units represented by the general formulae (III) and (BII-AB) is substituted with a fluorine atom- or silicon atom-containing group, the repeating unit corresponds also to the repeating units having at least either fluorine atoms or silicon atoms.

Specific examples of the repeating units represented by the general formulae (III) and (BII-AB) are shown below, but the present invention is not limited thereto. In the formulae, Ra represents H, CH₃, CH₂OH, CF₃, or CN. Incidentally, the repeating unit where Ra is CF₃ corresponds also to the repeating units having at least either fluorine atoms or silicon atoms.

[Chem. 165]

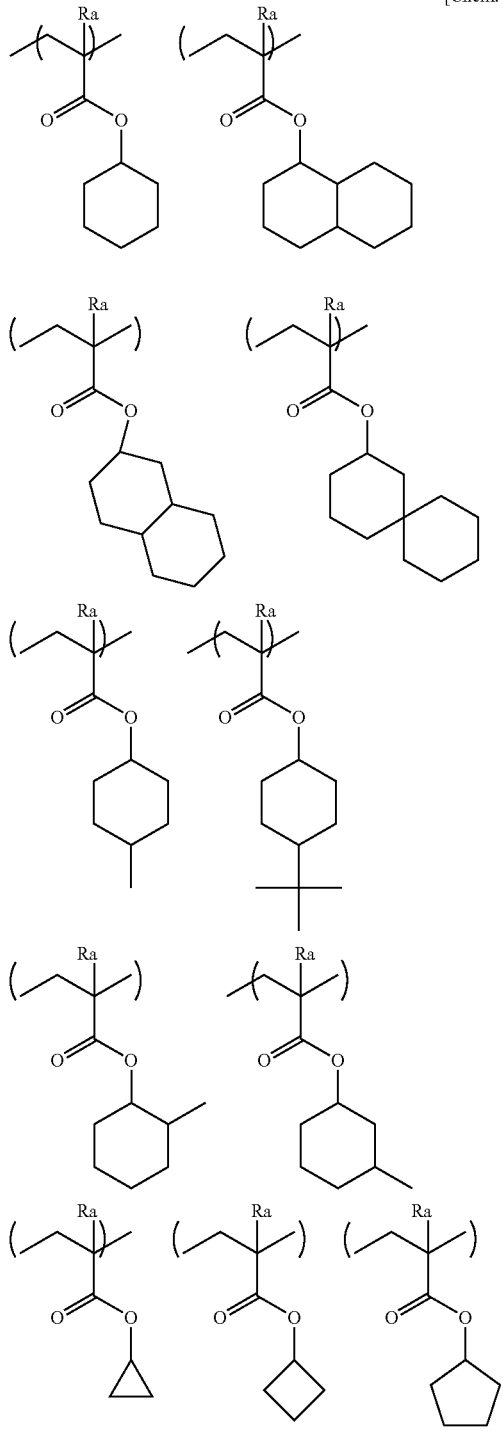

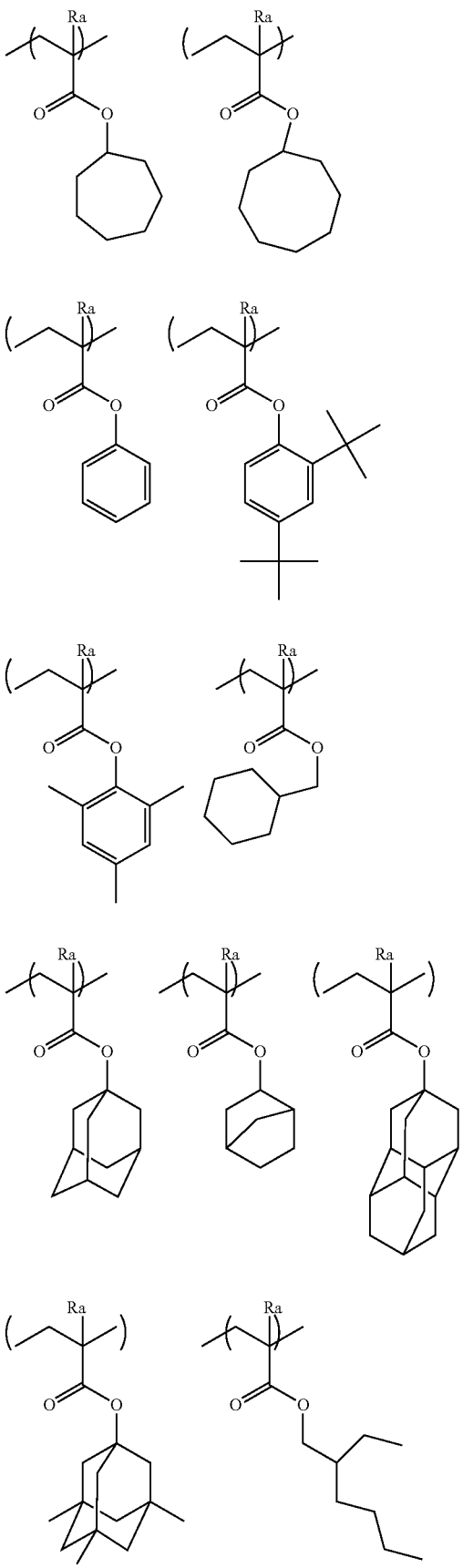

-continued

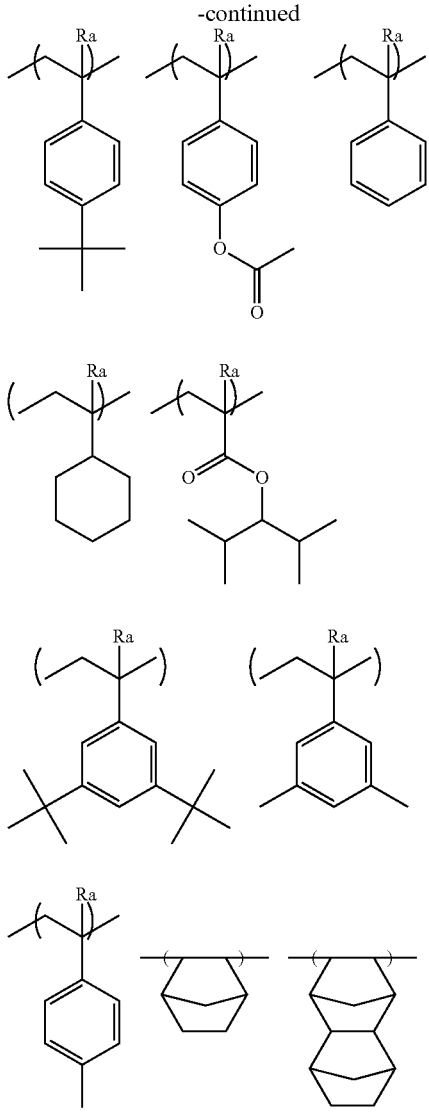

-continued

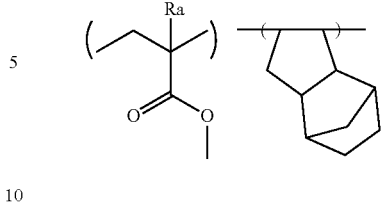

In the resin (Aa), similarly to the resin (A), it is of course preferable that the content of impurities such as metals be low, but also, the content of residual monomers or oligomer components is preferably from 0 to 10% by mole, more preferably from 0 to 5% by mole, and still more preferably from 0 to 1% by mole. When these conditions are satisfied, a resist composition free from foreign substances in a liquid or change with aging of sensitivity or the like can be obtained. Furthermore, in view of the resolution, the resist profile, the side wall of a resist pattern, the roughness, or the like, the molecular weight distribution (Mw/Mn, also referred to as "dispersity") is preferably in a range of 1 to 3, more preferably 1 to 2, still more preferably 1 to 1.8, and most preferably 1 to 1.5.

As for the resin (Aa), various commercially available products may be also used, or the resin may be synthesized by an ordinary method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferable.

The reaction solvent, the polymerization initiator, the reaction conditions (for example, temperature, concentration) and the purification method after reaction are the same as those described with respect to the resin (A).

Specific examples of the resin (Aa) are shown below. Further, the molar ratio of the repeating units (corresponding to the respective repeating units starting from the left), the weight average molecular weight, and the dispersity in the respective resins are shown in the table below.

TABLE 1

[Chem. 166]

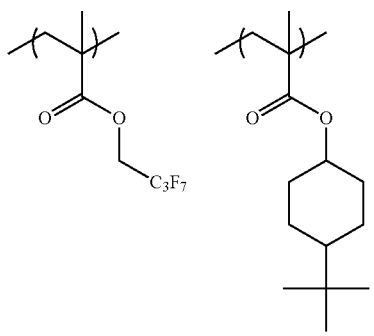

(Aa-1)

TABLE 1-continued
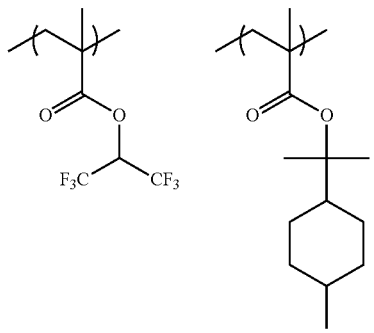
(Aa-2)
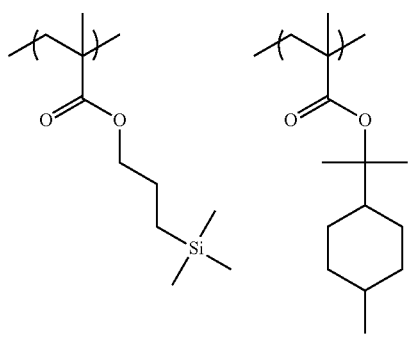
(Aa-3)
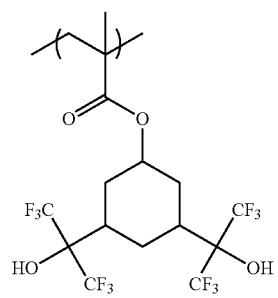
(Aa-4)
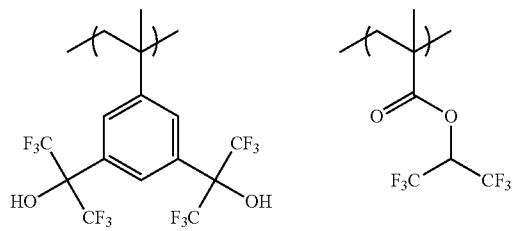
(Aa-5)

TABLE 1-continued
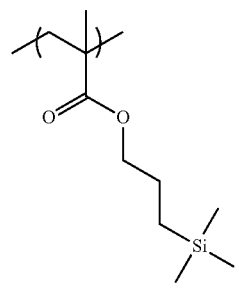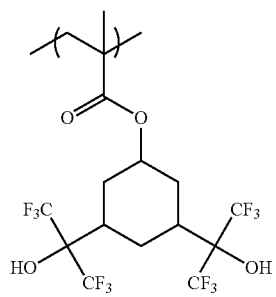
(Aa-6)
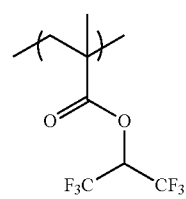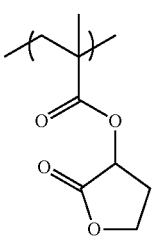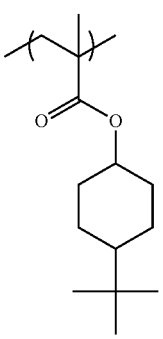
(Aa-7)
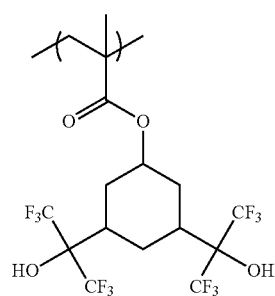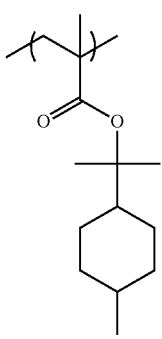
(Aa-8)
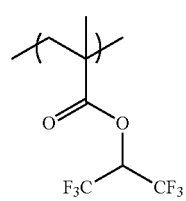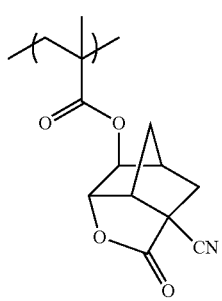
(Aa-9)

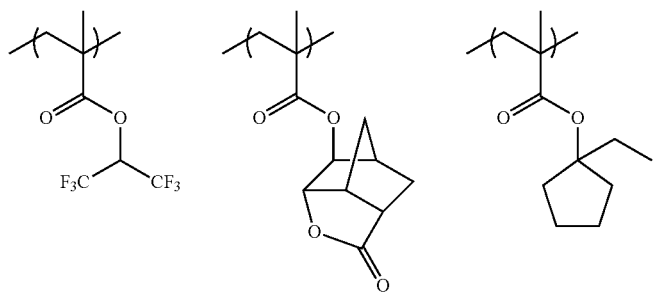
(Aa-10)
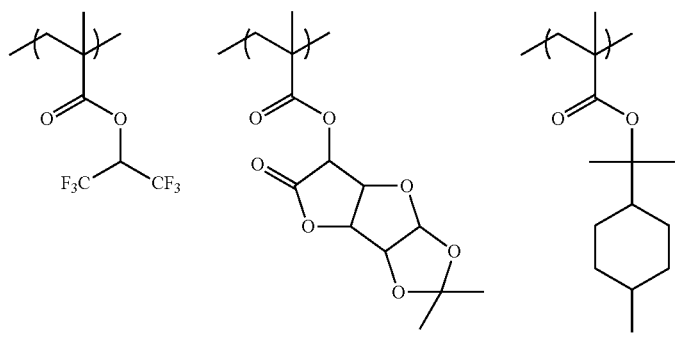
(Aa-11)
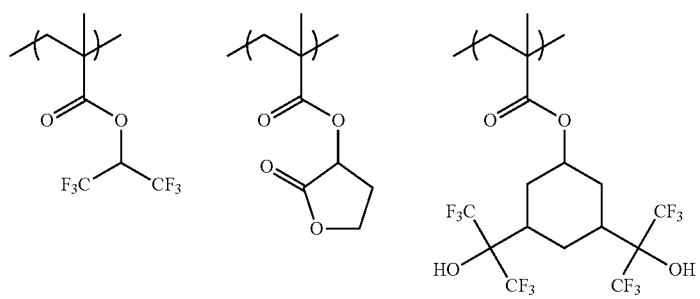
(Aa-12)
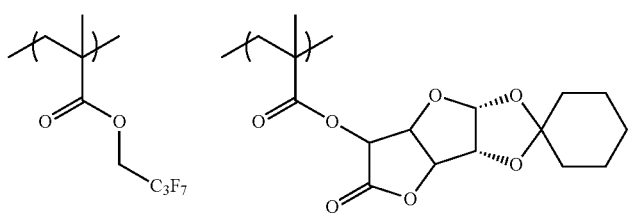
(Aa-13)

TABLE 1-continued
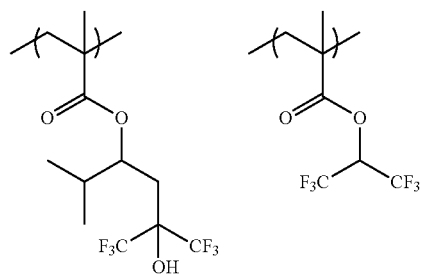
(Aa-14)
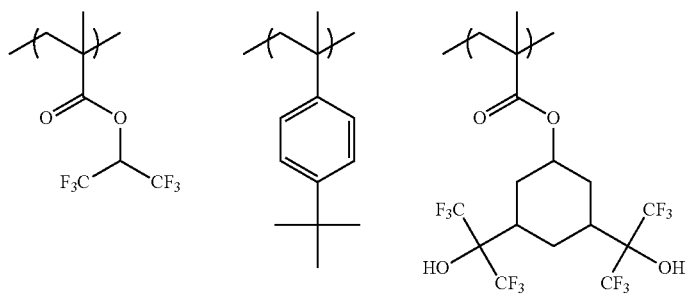
(Aa-15)
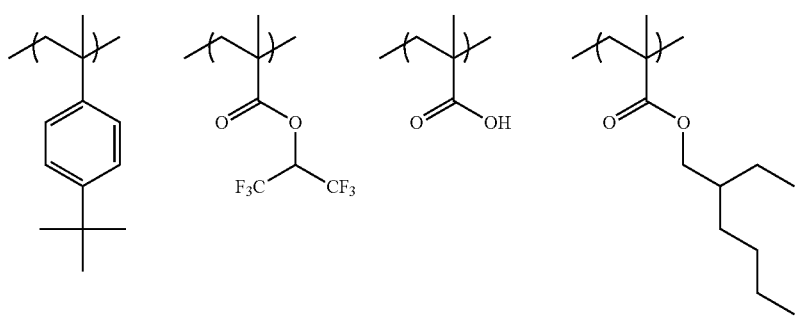
(Aa-16)
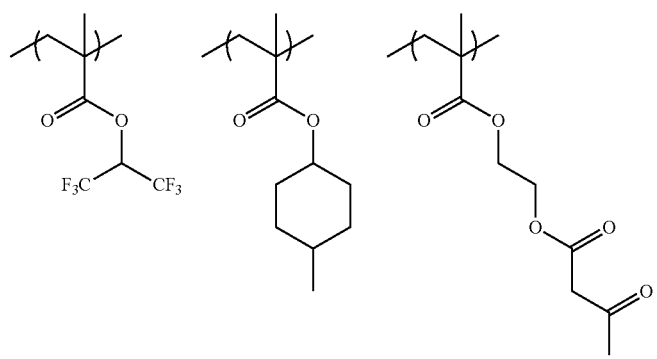
(Aa-17)

TABLE 1-continued
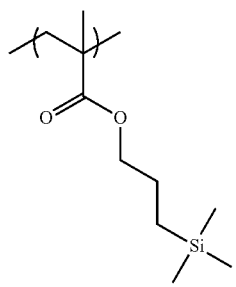
(Aa-18)
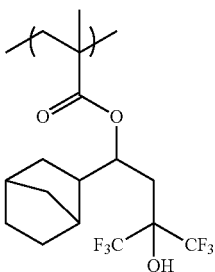
(Aa-19)
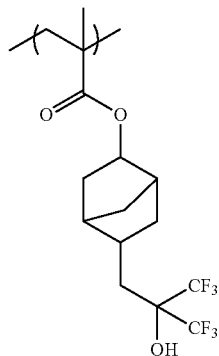
(Aa-20)
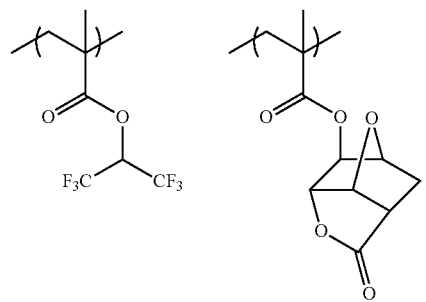
(Aa-21)

TABLE 1-continued
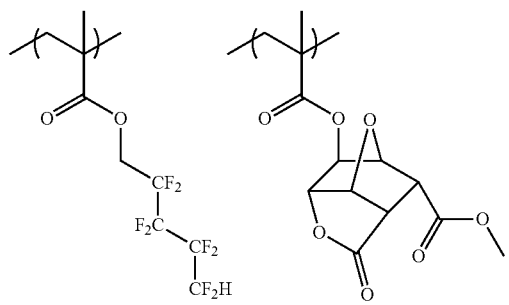
(Aa-22)
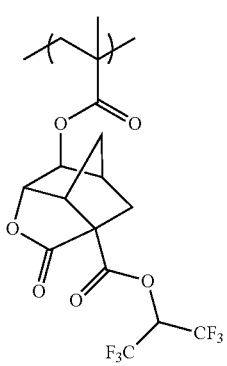
(Aa-23)
[Chem. 167]
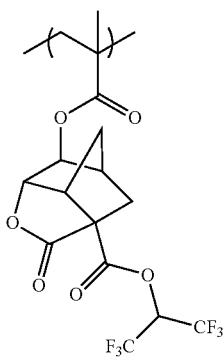
(Aa-24)
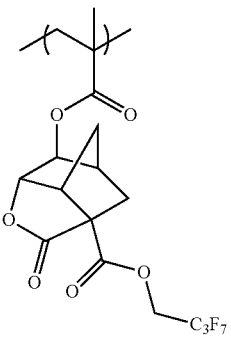
(Aa-25)

TABLE 1-continued
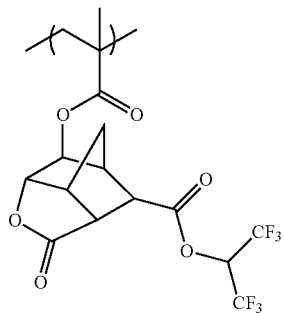
(Aa-26)
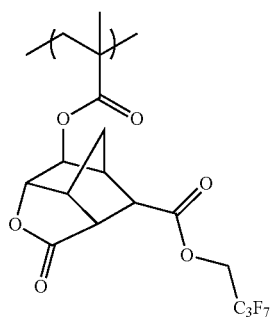
(Aa-27)
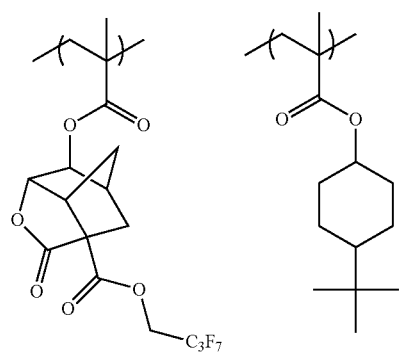
(Aa-28)
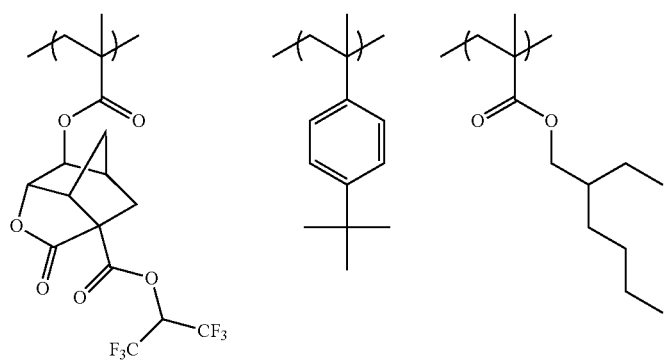
(Aa-29)

TABLE 1-continued
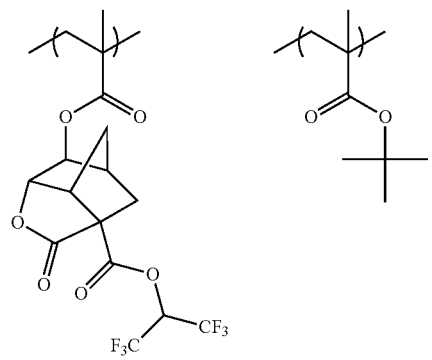
(Aa-30)
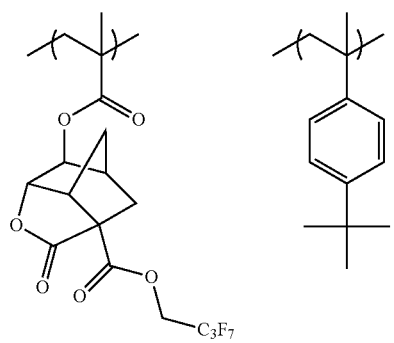
(Aa-31)
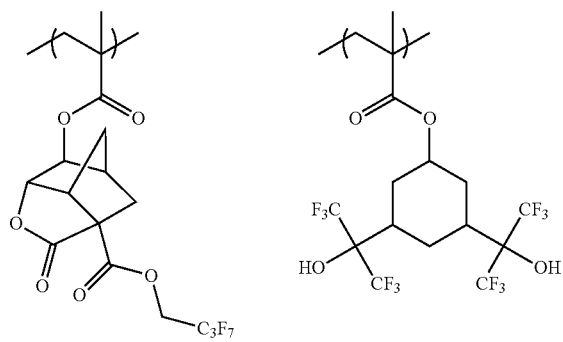
(Aa-32)
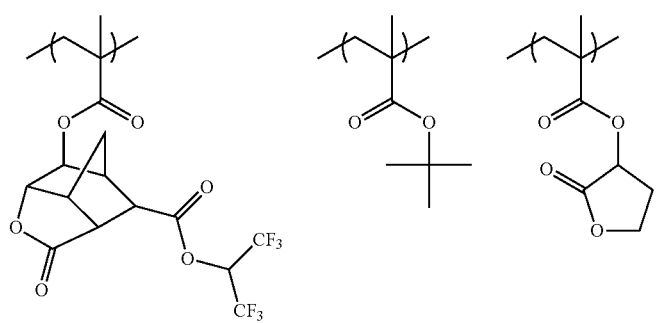
(Aa-33)

TABLE 1-continued
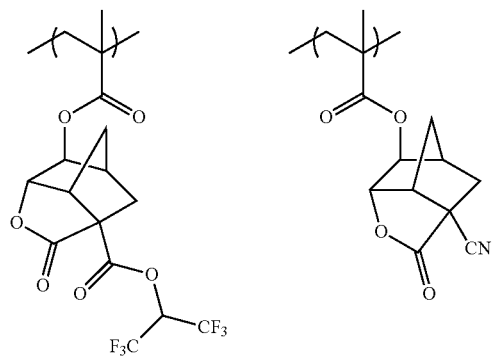
(Aa-34)
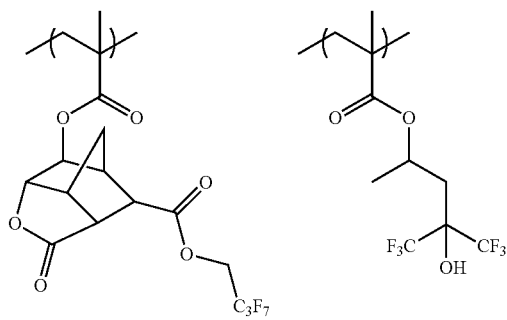
(Aa-35)
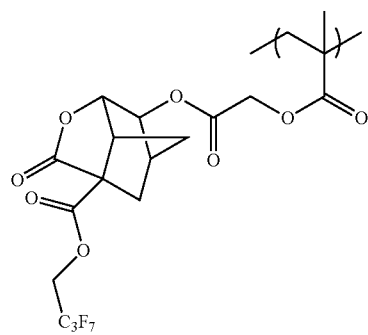
(Aa-36)
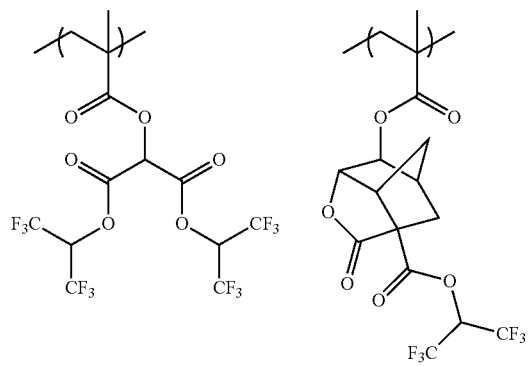
(Aa-37)

TABLE 1-continued
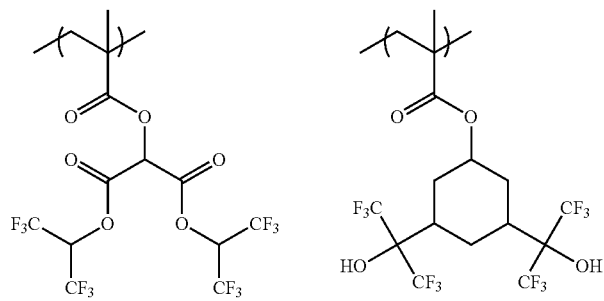
(Aa-38)
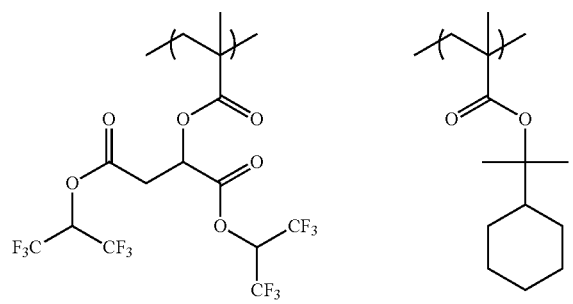
(Aa-39)
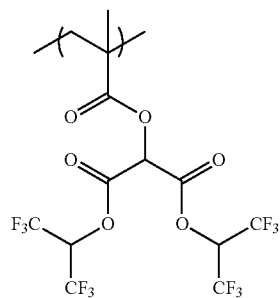
(Aa-40)
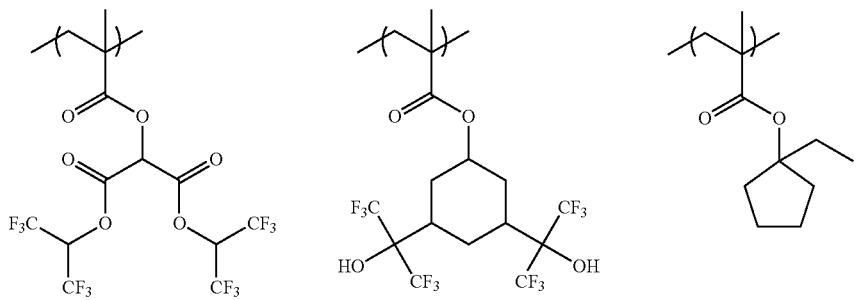
(Aa-41)

TABLE 1-continued
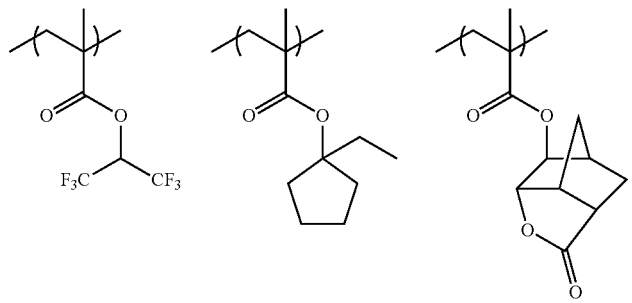
(Aa-42)
[Chem. 168]
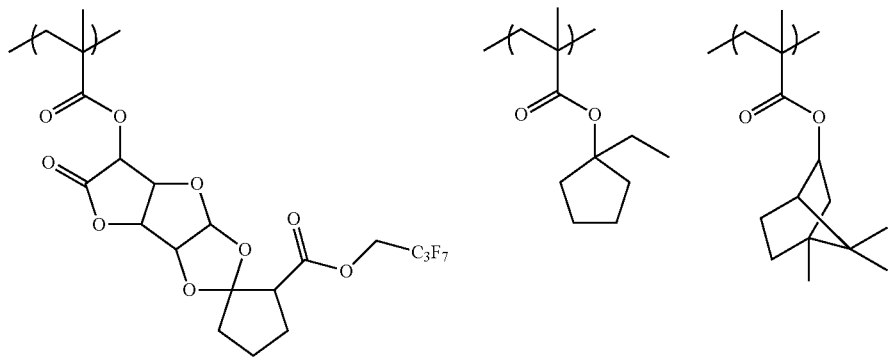
(Aa-43)
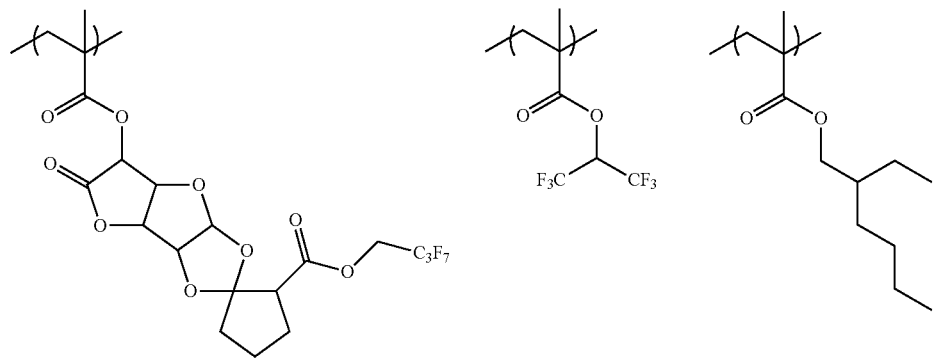
(Aa-44)

TABLE 1-continued
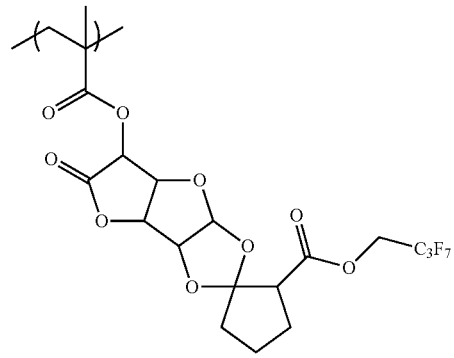
(Aa-45)
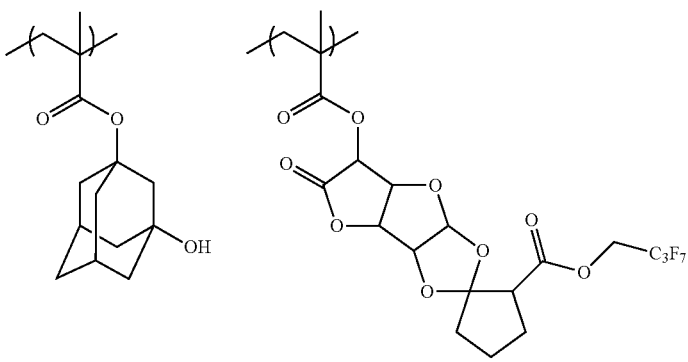
(Aa-46)
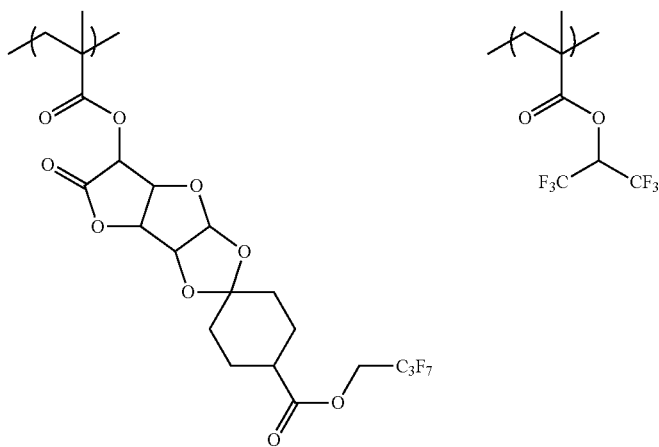
(Aa-47)

TABLE 1-continued
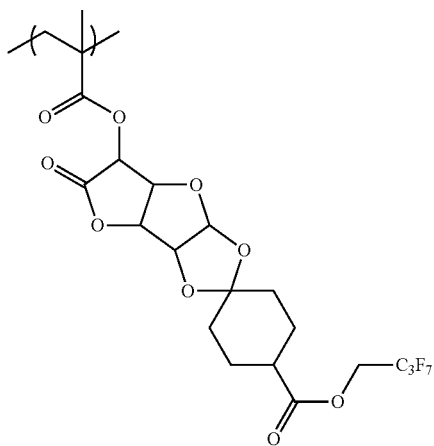
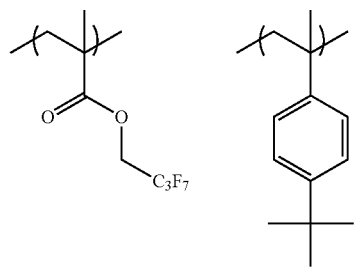
(Aa-48)
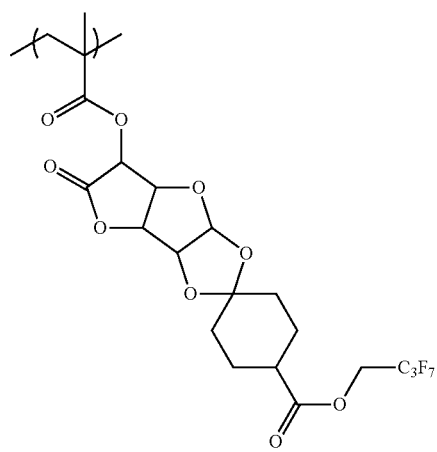
(Aa-49)
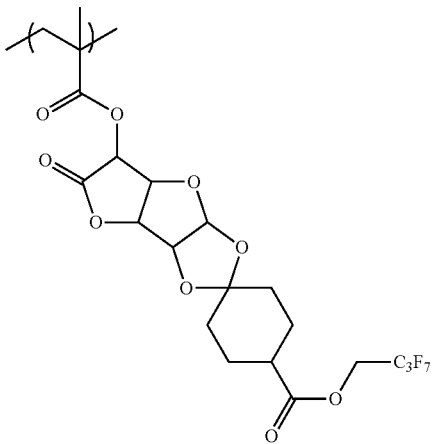
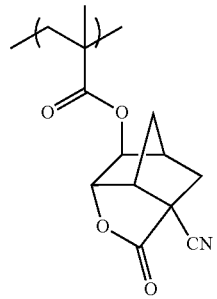
(Aa-50)

TABLE 1-continued
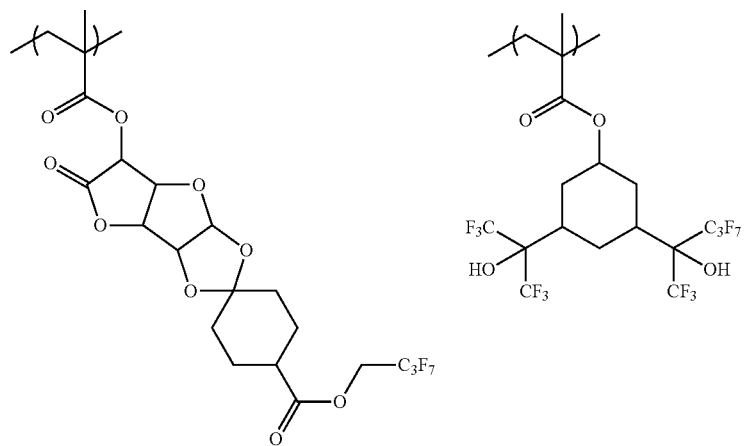
(Aa-51)
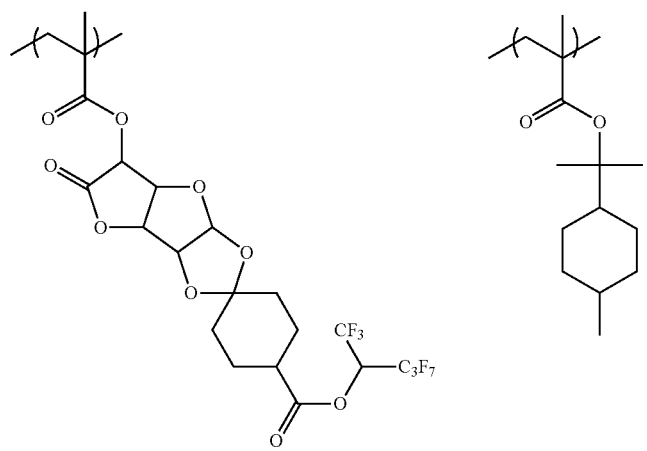
(Aa-52)
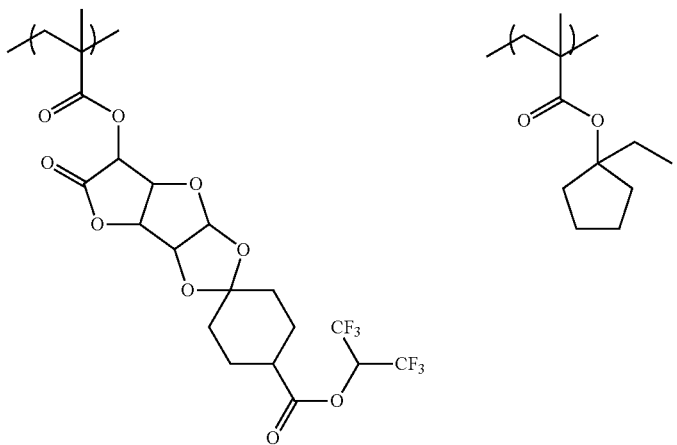
(Aa-53)

TABLE 1-continued
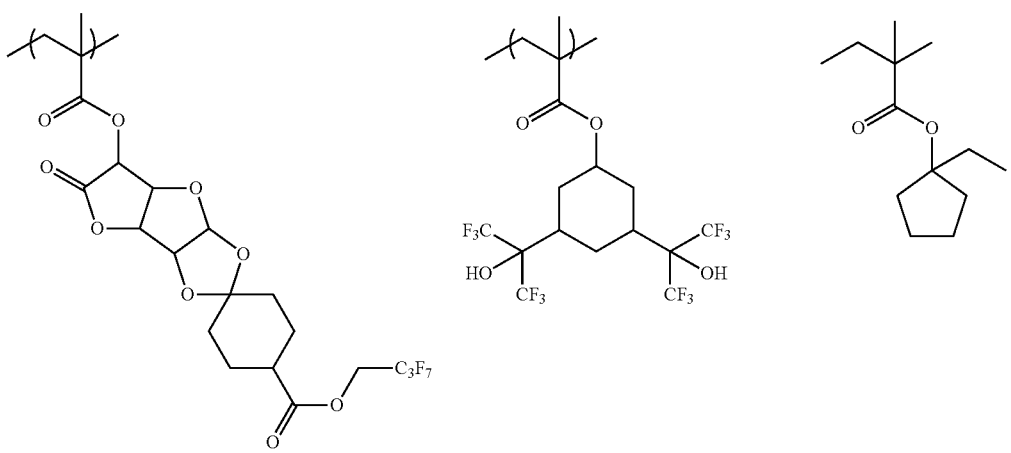
(Aa-54)
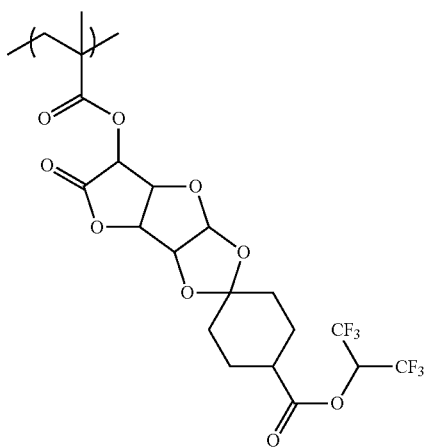
(Aa-55)
| Polymer | Compositional ratio (% by mole) | Mw | Mw/Mn |
|---|---|---|---|
| Aa-1 | 50/50 | 6000 | 1.5 |
| Aa-2 | 30/70 | 6500 | 1.4 |
| Aa-3 | 45/55 | 8000 | 1.4 |
| Aa-4 | 100 | 15000 | 1.7 |
| Aa-5 | 60/40 | 6000 | 1.4 |
| Aa-6 | 40/60 | 8000 | 1.4 |
| Aa-7 | 30/40/30 | 8000 | 1.4 |
| Aa-8 | 60/40 | 8000 | 1.3 |
| Aa-9 | 50/50 | 6000 | 1.4 |
| Aa-10 | 40/40/20 | 7000 | 1.4 |
| Aa-11 | 40/30/30 | 9000 | 1.6 |
| Aa-12 | 30/30/40 | 6000 | 1.4 |
| Aa-13 | 60/40 | 9500 | 1.4 |
| Aa-14 | 60/40 | 8000 | 1.4 |
| Aa-15 | 35/35/30 | 7000 | 1.4 |
| Aa-16 | 50/40/5/5 | 6800 | 1.3 |
| Aa-17 | 20/30/50 | 8000 | 1.4 |
| Aa-18 | 25/25/50 | 6000 | 1.4 |
| Aa-19 | 100 | 9500 | 1.5 |
| Aa-20 | 100 | 7000 | 1.5 |
| Aa-21 | 50/50 | 6000 | 1.6 |
| Aa-22 | 40/60 | 9600 | 1.3 |
| Aa-23 | 100 | 20,000 | 1.7 |
| Aa-24 | 100 | 25,000 | 1.4 |
| Aa-25 | 100 | 15,000 | 1.7 |

TABLE 1-continued

| | | | |
|---|---|---|---|
| Aa-26 | 100 | 12,000 | 1.8 |
| Aa-27 | 100 | 18,000 | 1.3 |
| Aa-28 | 70/30 | 15,000 | 2.0 |
| Aa-29 | 80/15/5 | 18,000 | 1.8 |
| Aa-30 | 60/40 | 25,000 | 1.8 |
| Aa-31 | 90/10 | 19,000 | 1.6 |
| Aa-32 | 60/40 | 20,000 | 1.8 |
| Aa-33 | 50/30/20 | 11,000 | 1.6 |
| Aa-34 | 60/40 | 12,000 | 1.8 |
| Aa-35 | 60/40 | 15,000 | 1.6 |
| Aa-36 | 100 | 22,000 | 1.8 |
| Aa-37 | 20/80 | 35,000 | 1.6 |
| Aa-38 | 30/70 | 12,000 | 1.7 |
| Aa-39 | 30/70 | 9,000 | 1.5 |
| Aa-40 | 100 | 9,000 | 1.5 |
| Aa-41 | 40/15/45 | 12,000 | 1.9 |
| Aa-42 | 30/30/40 | 13,000 | 2.0 |
| Aa-43 | 40/40/20 | 23,000 | 2.1 |
| Aa-44 | 65/30/5 | 25,000 | 1.6 |
| Aa-45 | 100 | 15,000 | 1.7 |
| Aa-46 | 20/80 | 9,000 | 1.7 |
| Aa-47 | 70/30 | 18,000 | 1.5 |
| Aa-48 | 60/20/20 | 18,000 | 1.8 |
| Aa-49 | 100 | 12,000 | 1.4 |
| Aa-50 | 60/40 | 20,000 | 1.6 |
| Aa-51 | 70/30 | 33,000 | 2.0 |
| Aa-52 | 60/40 | 19,000 | 1.8 |
| Aa-53 | 50/50 | 15,000 | 1.5 |
| Aa-54 | 40/20/40 | 35,000 | 1.9 |
| Aa-55 | 100 | 16,000 | 1.4 |

Since the hydrophobic resin (Aa) containing at least either fluorine atoms or silicon atoms is included in the actinic ray-sensitive or radiation-sensitive resin composition of the present invention, the resin (Aa) is unevenly distributed at a surface layer of the film formed from the actinic ray-sensitive or radiation-sensitive resin composition and when the liquid immersion medium is water, the receding contact angle of the film surface with water can be increased, thereby enhancing the followability of the liquid for liquid immersion.

The receding contact angle of the film including the actinic ray-sensitive or radiation-sensitive resin composition of the present invention that has been baked but is not yet exposed, as measured at the exposure temperature, generally room temperature of 23±3° C. and a humidity of 45±5%, is preferably in the range of 60° to 90°, more preferably 65° or more, still more preferably 70° or more and most preferably 75° or more.

The resin (Aa) is, as described above, unevenly distributed at the interface but unlike a surfactant, need not necessarily have a hydrophilic group in the molecule and may not contribute to uniform mixing of polar/nonpolar substances.

In the liquid immersion exposure step, the liquid for liquid immersion needs to move on a wafer following the movement of an exposure head that is scanning the wafer at a high speed and forming an exposure pattern. Therefore, the contact angle of the liquid for liquid immersion with the resist film in a dynamic state is important, and the resist is required to have a performance of allowing liquid droplets to follow the high-speed scanning of an exposure head without leaving any liquid droplets.

As the resin (Aa) is hydrophobic, the problems of development residue (scum) and BLOB defect after alkaline development are likely to become serious. However, improvement of performance in terms of the development residue (scum) and BLOB defect can be attained due to an increase in alkali dissolution rate by containing three or more polymer chains combined together through at least one branch point, as compared with linear chain resins.

When the resin (Aa) contains fluorine atoms, the content of the fluorine atoms is preferably from 5 to 80% by mole, and more preferably from 10 to 80% by mole, based on the molecular weight of the resin (Aa). The proportion of the repeating units containing a fluorine atom is preferably from 10 to 100% by mole, and more preferably 30 to 100% by mole, based on all repeating units in the resin (Aa).

When the resin (Aa) contains silicon atoms, the content of the silicon atoms is preferably from 2 to 50% by mole, and more preferably from 2 to 30% by mole, based on the molecular weight of the resin (Aa). The proportion of the repeating units containing a silicon atom is preferably from 10 to 90% by mole, and more preferably 20 to 80% by mole, based on all the repeating units of the resin (Aa).

The weight average molecular weight of the resin (Aa) is preferably 1,000 to 100,000, more preferably 2,000 to 50,000, and still more preferably 3,000 to 30,000. Here, the weight average molecular weight of the resin indicates a molecular weight in terms of polystyrene as measured by GPC (carrier: tetrahydrofuran (THF)). Specifically, the weight average molecular weight (Mw) of the resin (Aa) may be determined by using, for example, HLC-8120 (manufactured by Tosoh Corporation) using TSK gel Multipore HXL-M (manufactured by Tosoh Corporation, 7.8 mm ID×30.0 cm) as a column and THF as an eluent.

The content of the resin (Aa) in the actinic ray-sensitive or radiation-sensitive resin composition may be adjusted prior to use so that the receding contact angle of the film formed of the actinic ray-sensitive or radiation-sensitive resin composition falls within the above-specified range. The content of the resin (Aa) is preferably 0.01 to 20% by mass, more preferably 0.1 to 15% by mass, still more preferably 0.1 to 10% by mass, and particularly preferably 0.5 to 8% by mass, based on the total solid contents of the actinic ray-sensitive or radiation-sensitive resin composition.

The resins (Aa) may be used alone or in combination of two or more thereof.

(5) Basic Compound

The composition according to the present invention may further contain a basic compound (except for nitrogen-containing compounds represented by the general formulae (N1) and (N2)). The basic compound is preferably a compound having higher basicity than phenol. Further, this basic compound is preferably an organic basic compound, and more preferably a nitrogen-containing basic compound.

The usable nitrogen-containing basic compound is not particularly limited, but, for example, the compounds classified into (1) to (7) below can be used.

(1) Compound Represented by General Formula (BS-1)

[Chem. 169]

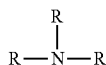

(BS-1)

In the general formula (BS-1),

R's each independently represent any a hydrogen atom or an organic group, provided that at least one of three R's is an organic group. This organic group is a linear or branched alkyl group, a monocyclic or polycyclic cycloalkyl group, an aryl group, or an aralkyl group.

The number of carbon atoms of the alkyl group as R is not particularly limited, but, it is usually 1 to 20, and preferably 1 to 12.

The number of carbon atoms of the cycloalkyl group as R is not particularly limited, but it is usually 3 to 20, and preferably 5 to 15.

The number of carbon atoms of the aryl group as R is not particularly limited, but it is usually 6 to 20, and preferably 6 to 10. In particular, examples of the aryl group include a phenyl group and a naphthyl group.

The number of carbon atoms of the aralkyl group as R is not particularly limited, but it is usually 7 to 20, and preferably 7 to 11. In particular, examples of the aralkyl group include a benzyl group.

In the alkyl group, the cycloalkyl group, the aryl group, and the aralkyl group as R, a hydrogen atom may be substituted with a substituent. Examples of the substituent include an alkyl group, a cycloalkyl group, an aryl group, an aralkyl group, a hydroxy group, a carboxy group, an alkoxy group, an aryloxy group, an alkylcarbonyloxy group, and an alkyloxycarbonyl group.

Moreover, in the compounds represented by the general formula (BS-1), it is preferable that at least two members out of R's be an organic group.

Specific examples of the compound represented by the general formula (BS-1) include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, dodecylamine, methyloctadecylamine, dimethylundecylamine, N,N-dimethyldodecylamine, methyldioctadecylamine, N,N-dibutylaniline, N,N-dihexylaniline, 2,6-diisopropylaniline, and 2,4,6-tri(t-butyl)aniline.

Furthermore, preferred examples of the basic compound represented by the general formula (BS-1) include those in which at least one of the R's is an alkyl group substituted with a hydroxyl group can be mentioned. Specific examples of the compound include triethanolamine and N,N-dihydroxyethylaniline.

In addition, with respect to the alkyl group as R, an oxygen atom may be present in the alkyl chain so as to form an oxyalkylene chain. The oxyalkylene chain is preferably —$CH_2CH_2O$—. Specific examples thereof include tris(methoxyethoxyethyl)amine, and the compounds exemplified in column 3 line 60 et seq. of U.S. Pat. No. 6,040,112A.

Examples of the basic compound represented by the general formula (BS-1) include the following.

[Chem. 170]

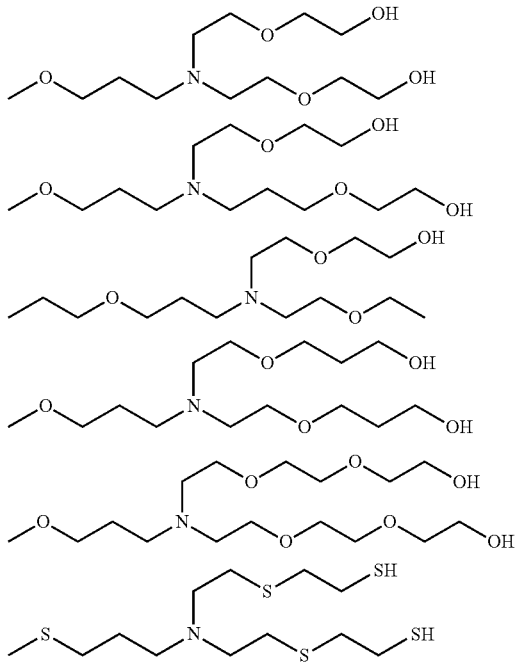

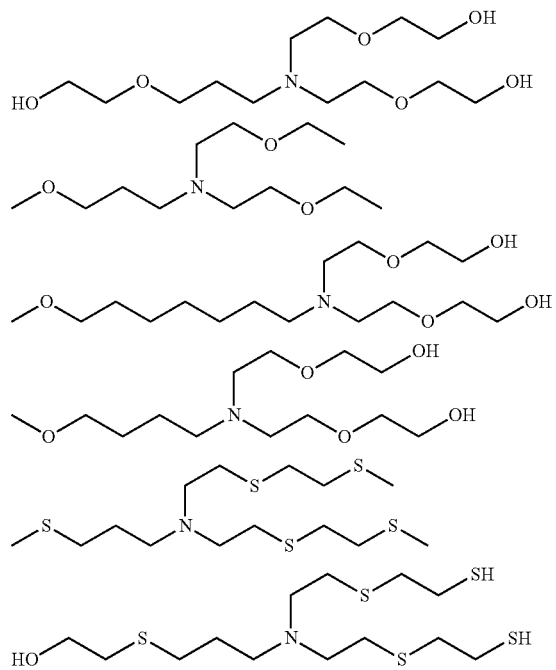

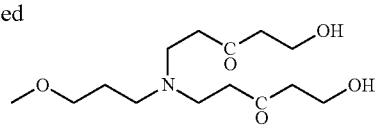
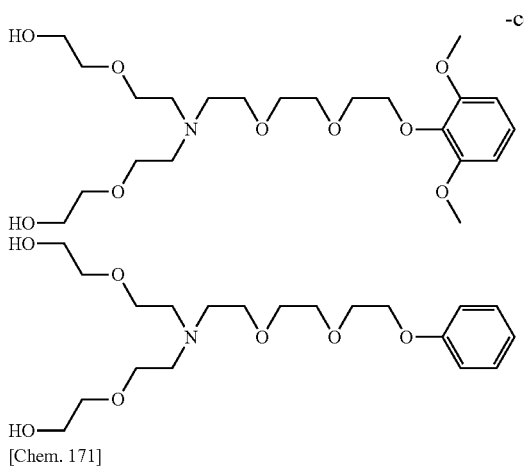

[Chem. 171]

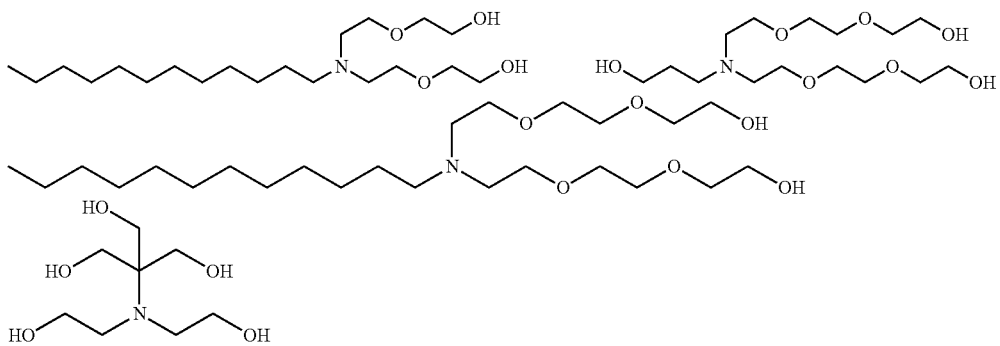

(2) Compound Having Nitrogen-containing Heterocyclic Structure

The nitrogen-containing heterocyclic structure may or may not have aromaticity. Further, it may have a plurality of nitrogen atoms, and also may have a heteroatom other than nitrogen. Examples thereof include compounds having an imidazole structure (2-phenylbenzoimidazole, 2,4,5-triphenylimidazole, and the like), compounds having a piperidine structure (N-hydroxyethylpiperidine, bis(1,2,2,6,6-pentamethyl-4-piperidyl) sebacate, and the like), compounds having a pyridine structure (4-dimethylaminopyridine and the like), and compounds having an antipyrine structure (antipyrine, hydroxyantipyrine, and the like).

In addition, compounds with two or more ring structures can be appropriately used. Specific examples thereof include 1,5-diazabicyclo[4.3.0]non-5-ene and 1,8-diazabicyclo[5.4.0]-undec-7-ene.

(3) Amine Compound Containing Phenoxy Group

The amine compounds containing a phenoxy group are those having a phenoxy group at the end of the alkyl group of each of the amine compounds opposite to the nitrogen atom. The phenoxy group may have a substituent, such as an alkyl group, an alkoxy group, a halogen atom, a cyano group, a nitro group, a carboxyl group, a carboxylic ester group, a sulfonic ester group, an aryl group, an aralkyl group, an acyloxy group, and an aryloxy group.

Compounds having at least one oxyalkylene chain between the phenoxy group and the nitrogen atom are more preferred. The number of oxyalkylene chains in each molecule is preferably in the range of 3 to 9, and more preferably 4 to 6. Among the oxyalkylene chains, —$CH_2CH_2O$— is preferable.

Specific examples thereof include 2-[2-{2-(2,2-dimethoxy-phenoxyethoxy)ethyl}-bis-(2-methoxyethyl)]-amine, compounds (C1-1) to ($C_{3-3}$) exemplified in the paragraph 0066 of US2007/0224539A1, and the like.

The amine compound having a phenoxy group can be obtained by, for example, first heating a primary or secondary amine having a phenoxy group and a haloalkyl ether so as to effect a reaction therebetween, subsequently adding an aqueous solution of a strong base such as sodium hydroxide, potassium hydroxide, and tetraalkylammonium, and thereafter carrying out an extraction with an organic solvent such as ethyl acetate and chloroform. Alternatively, the amine compound having a phenoxy group can be obtained by first heating a primary or secondary amine and a haloalkyl ether having a phenoxy group at its terminus so as to effect a reaction therebetween, subsequently adding an aqueous solution of a strong base such as sodium hydroxide, potassium hydroxide, and a tetraalkylammonium, and thereafter carrying out an extraction with an organic solvent such as ethyl acetate and chloroform.

(4) Ammonium Salt

As the basic compound, an ammonium salt may also be suitably used. Examples of the anion of the ammonium salt include halide, sulfonate, borate, and phosphate. Among these, halide and sulfonate are particularly preferred.

The halide is particularly preferably chloride, bromide or iodide.

The sulfonate is particularly preferably organic sulfonate having 1 to 20 carbon atoms. Examples of the organic sulfonate include an alkyl sulfonate and an aryl sulfonate each having 1 to 20 carbon atoms.

The alkyl group contained in the alkyl sulfonate may have a substituent, and examples of the substituent include a fluorine atom, a chlorine atom, a bromine atom, an alkoxy group, an acyl group, and an aryl group. Specific examples of the alkyl sulfonate include methane sulfonate, ethane sulfonate, butane sulfonate, hexane sulfonate, octane sulfonate, benzyl sulfonate, trifluoromethane sulfonate, pentafluoroethane sulfonate and nonafluorobutane sulfonate.

Examples of the aryl group contained in aryl sulfonate include a phenyl group, a naphthyl group and an anthryl group. These aryl groups may have a substituent. Preferred examples of the substituent include a linear or branched alkyl group having 1 to 6 carbon atoms and a cycloalkyl group having 3 to 6 carbon atoms. Specific preferred examples thereof include a methyl group, an ethyl group, an n-propyl group, an isopropyl group, an n-butyl group, an i-butyl group, a t-butyl group, an n-hexyl group, and a cyclohexyl group, and other examples of the substituent include an alkoxy group having 1 to 6 carbon atoms, a halogen atom, cyano, nitro, an acyl group and an acyloxy group.

The ammonium salt may be hydroxide or carboxylate. In this case, the ammonium salt is particularly preferably tetraalkylammonium hydroxide having 1 to 8 carbon atoms, such as tetramethylammonium hydroxide, tetraethylammonium hydroxide and tetra-(n-butyl)ammonium hydroxide.

Preferred examples of the basic compound include guanidine, aminopyridine, aminoalkylpyridine, aminopyrrolidine, indazole, imidazole, pyrazole, pyrazine, pyrimidine, purine, imidazoline, pyrazoline, piperazine, aminomorpholine, and aminoalkylmorpholine. These may further have a substituent.

Preferred examples of the substituent include an amino group, an aminoalkyl group, an alkylamino group, an aminoaryl group, an arylamino group, an alkyl group, an alkoxy group, an acyl group, an acyloxy group, an aryl group, an aryloxy group, a nitro group, a hydroxyl group, and a cyano group.

Particularly preferred examples of the basic compound include guanidine, 1,1-dimethylguanidine, 1,1,3,3,-tetramethylguanidine, imidazole, 2-methylimidazole, 4-methylimidazole, N-methylimidazole, 2-phenylimidazole, 4,5-diphenylimidazole, 2,4,5-triphenylimidazole, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoethylpyridine, 4-aminoethylpyridine, 3-aminopyrrolidine, piperazine, N-(2-aminoethyl)piperazine, N-(2-aminoethyl)piperidine, 4-amino-2,2,6,6 tetramethylpiperidine, 4-piperidinopiperidine, 2-iminopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5 methylpyrazine, pyrimidine, 2,4-diaminopyrimidine, 4,6-dihydroxypyrimidine, 2-pyrazoline, 3-pyrazoline, and N-aminomorpholine, and N-(2-aminoethyl)morpholine.

(5) Compound (PA) Containing Functional Group which has Proton Acceptor Properties and is Decomposed by Irradiation of Actinic Rays or Radiation to Produce Compound Exhibiting Lower Proton Acceptor Properties, or No Proton Acceptor Properties, or Exhibiting Acid Properties Derived from Proton Acceptor Properties The composition according to the present invention may further contain, as a basic compound, a compound containing a functional group with proton acceptor properties, which is decomposed by the irradiation of actinic rays or radiation to produce a compound exhibiting lower proton acceptor properties lower, or no proton acceptor properties, or exhibiting acid properties derived from the proton acceptor properties (hereinafter also referred to as a compound (PA)).

The functional group with proton acceptor properties refers to a functional group having a group, or an electron, capable of electrostatic interaction with a proton, and, for example, means a functional group with a macrocyclic structure, such as a cyclopolyether, or a functional group containing a nitrogen atom with an unshared electron pair not contributing to π-conjugation. The nitrogen atom with an unshared electron pair not contributing to π-conjugation is, for example, a nitrogen atom with any of the partial structures of the following general formula.

[Chem. 172]

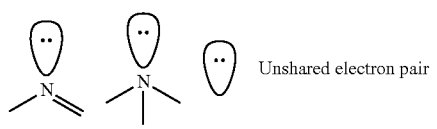

Examples of the partial structures of the functional groups with proton acceptor properties include crown ether, azacrown ether, primary to tertiary amine, pyridine, imidazole and pyrazine structures.

The compound (PA) is decomposed by irradiation of actinic rays or radiation to produce a compound exhibiting lower proton acceptor properties lower, or no proton acceptor properties, or exhibiting acid properties derived from the proton acceptor properties of the compound (PA). The expression "exhibiting lower proton acceptor properties lower, or no proton acceptor properties, or exhibiting acid properties derived from the proton acceptor properties of the compound (PA)" refers to a change of proton acceptor properties caused by the addition of a proton to the functional group with proton acceptor properties. In particular, the expression means that when a proton adduct is formed from the compound (PA) containing a functional group with proton acceptor properties and a proton, the equilibrium constant of the chemical equilibrium thereof is decreased.

The proton acceptor properties can be ascertained by performing pH measurement. In the present invention, it is preferable for the acid dissociation constant pKa of the compound produced by the decomposition of the compound (PA) by irradiation of actinic rays or radiation to satisfy the relationship pKa←1. Satisfying the relationship −13<pKa←1 is more preferred, and satisfying the relationship −13<pKa←3 is further more preferred.

In the present invention, the acid dissociation constant pKa refers to the acid dissociation constant pKa in an aqueous solution, for example, any of those listed in Chemical Handbook (II) (Revised 4$^{th}$ Edition, 1993, edited by The Chemical Society of Japan, published by Maruzen Co., Ltd.). The lower the value of acid dissociation constant, the greater the acid strength. For example, the acid dissociation constant pKa in an aqueous solution can be actually measured through the determination of the acid dissociation constant at 25° C. using an infinitely diluted aqueous solution. Alternatively, the values based on a database of heretofore known literature values and Hammett's substituent constants can be determined by calculation by means of the following software package 1. All the pKa values appearing in this description are those determined by calculation by means of this software package.

Software package 1: Advanced Chemistry Development (ACD/Labs) Software V 8.14 for Solaris (1994-2007 ACD/Labs).

The compound (PA) produces, for example, any of the compounds of the general formula (PA-1) below as the above proton adduct produced by the decomposition by irradiation of actinic rays or radiation. Each of the compounds of the general formula (PA-1) contains not only a functional group with proton acceptor properties but also an acidic group, thereby being a compound exhibiting lower proton acceptor properties lower, or no proton acceptor properties, or exhibiting acid properties derived from the proton acceptor properties of the compound (PA).

[Chem. 173]

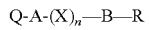

$$Q\text{-}A\text{-}(X)_n\text{—}B\text{—}R \qquad (PA\text{-}1)$$

In the general formula (PA-1),

Q represents —$SO_3H$, —$CO_2H$, or —$X_1NHX_2Rf$, in which Rf represents an alkyl group, a cycloalkyl group, or an aryl group, and $X_1$ and $X_2$ each independently represent —$SO_2$— or —CO—.

A represents a single bond or a divalent connecting group.

X represents —$SO_2$— or —CO—.

n represents 0 or 1.

B represents a single bond, an oxygen atom, or —N(Rx)Ry-, in which Rx represents a hydrogen atom or a monovalent organic group, and Ry represents a single bond or a divalent organic group, provided that Rx may be bonded to Ry to form a ring or may be bonded to R to form a ring.

R represents a monovalent organic group containing a functional group with proton acceptor properties.

The general formula (PA-1) will be described in greater detail.

The divalent connecting group in A is preferably a divalent connecting group having 2 to 12 carbon atoms, and examples thereof include an alkylene group and a phenylene group. The divalent connecting group is more preferably an alkylene group having at least one fluorine atom, preferably having 2 to 6 carbon atoms, and more preferably 2 to 4 carbon atoms. The alkylene chain may contain a connecting group such as an oxygen atom and a sulfur atom. The alkylene group is particularly preferably an alkylene group where from 30 to 100% by number of the hydrogen atoms are substituted with fluorine atoms, more preferably an alkylene group where the carbon atoms bonded to the Q site has fluorine atoms, still more preferably a perfluoroalkylene group, and even still more preferably a perfluoroethylene group, a perfluoropropylene group, or a perfluorobutylene group.

The monovalent organic group in $R_x$ is preferably a monovalent organic group having 1 to 30 carbon atoms, and examples thereof include an alkyl group, a cycloalkyl group, an aryl group, an aralkyl group, and an alkenyl group. These groups may further have a substituent.

The alkyl group in Rx may have a substituent and is preferably a linear or branched alkyl group having 1 to 20 carbon atoms, and the alkyl chain may contain an oxygen atom, a sulfur atom, or a nitrogen atom.

The divalent organic group in Ry is preferably an alkylene group.

As the ring structure that may be formed by the mutual bonding of Rx and Ry, there can be mentioned a 5- to 10-membered, especially preferably 6-membered, ring containing a nitrogen atom.

Furthermore, the alkyl group having a substituent includes a group where a cycloalkyl group is substituted particularly on a linear or branched alkyl group (for example, an adamantylmethyl group, an adamantylethyl group, a cyclohexylethyl group, and a camphor residue).

The cycloalkyl group in $R_x$ may have a substituent and is preferably a cycloalkyl group having 3 to 20 carbon atoms, and the cycloalkyl group may contain an oxygen atom in the ring.

The aryl group in $R_x$ may have a substituent and is preferably an aryl group having 6 to 14 carbon atoms.

The aralkyl group in $R_x$ may have a substituent and is preferably an aralkyl group having 7 to 20 carbon atoms.

The alkenyl group in $R_x$ may have a substituent and includes, for example, a group having a double bond at an arbitrary position of the alkyl group described as Rx.

The functional group with proton acceptor properties in R is as set forth above. There can be mentioned groups with, for example, a nitrogen atom-containing heterocyclic aromatic structure, such as an azacrown ether, a primary to tertiary amine, pyridine or imidazole.

As the organic group containing any of these structures, the organic group preferably has 4 to 30 carbon atoms, and examples thereof include an alkyl group, a cycloalkyl group, an aryl group, an aralkyl group, and an alkenyl group.

The alkyl group, cycloalkyl group, aryl group, aralkyl group and alkenyl group in the functional group with proton accepting properties or ammonium group-containing alkyl, cycloalkyl, aryl, aralkyl and alkenyl groups in R are the same as the alkyl group, the cycloalkyl group, the aryl group, the aralkyl group, and the alkenyl group described with respect to $R_x$ above.

Examples of the substituent which the respective groups above may have include a halogen atom, a hydroxyl group, a nitro group, a cyano group, a carboxy group, a carbonyl group, a cycloalkyl group (preferably having 3 to 10 carbon atoms), an aryl group (preferably having 6 to 14 carbon atoms), an alkoxy group (preferably having 1 to 10 carbon atoms), an acyl group (preferably having 2 to 20 carbon atoms), an acyloxy group (preferably having 2 to 10 carbon atoms), an alkoxycarbonyl group (preferably having 2 to 20 carbon atoms), and an aminoacyl group (preferably having 2 to 20 carbon atoms). As for the cyclic structure in the aryl group, the cycloalkyl group, or the like, as well as the aminoacyl group, other examples of the substituent include an alkyl group (preferably having 1 to 20 carbon atoms).

When B is —N(Rx)Ry-, it is preferable that R and Rx be bonded to each other to form a ring. By virtue of forming a ring structure, the stability is enhanced and the composition using this compound is also enhanced in the storage stability. The number of carbon atoms constituting the ring is preferably from 4 to 20, and the ring may be monocyclic or polycyclic and may contain an oxygen atom, a sulfur atom, or a nitrogen atom in the ring.

Examples of the monocyclic structure include a 4-, 5-, 6-, 7-, or 8-membered ring containing a nitrogen atom. Examples of the polycyclic structure include a structure composed of a combination of two monocyclic structures or three or more monocyclic structures. The monocyclic structure and polycyclic structure may have a substituent, and preferred examples of the substituent include a halogen atom, a hydroxyl group, a cyano group, a carboxy group, a carbonyl group, a cycloalkyl group (preferably having 3 to 10 carbon atoms), an aryl group (preferably having 6 to 14 carbon atoms), an alkoxy group (preferably having 1 to 10 carbon atoms), an acyl group (preferably having 2 to 15 carbon atoms), an acyloxy group (preferably having 2 to 15 carbon atoms), an alkoxycarbonyl group (preferably having 2 to 15 carbon atoms), and an aminoacyl group (preferably having 2 to 20 carbon atoms). As for the cyclic structure in the aryl group, a cycloalkyl group and the like, examples of the substituent further include an alkyl group (preferably having 1 to 15 carbon atoms). As for the aminoacyl group, examples of the substituent further include an alkyl group (preferably having 1 to 15 carbon atoms).

Rf of —X$_1$NHX$_2$Rf represented by Q is preferably an alkyl group having 1 to 6 carbon atoms in which fluorine atoms are optionally contained, and more preferably a perfluoroalkyl group having 1 to 6 carbon atoms. Preferably, at least one of X$_1$ and X$_2$ is —SO$_2$—, and more preferably, both of X$_1$ and X$_2$ are —SO$_2$—.

Among the compounds represented by the general formula (PA-I), a compound where the Q site is a sulfonic acid can be synthesized using a general sulfonamidation reaction. For example, this compound can be obtained by a method of selectively reacting one sulfonyl halide moiety of a bis-sulfonyl halide compound with an amine compound to form a sulfonamide bond and then hydrolyzing the other sulfonyl halide moiety, or a method of ring-opening a cyclic sulfonic anhydride through reaction with an amine compound.

It is preferable for the compound (PA) to be an ionic compound. The functional group with proton acceptor properties may be contained in either moiety, of an anion moiety or a cation moiety. Preferably, the functional group is contained in an anion moiety.

The compound (PA) is preferably any of the compounds of the following general formulae (4) to (6).

[Chem. 174]

  (4)

  (5)

  (6)

In the general formulae (4) to (6), A, X, n, B, R, Rf, X$_1$ and X$_2$ have the same definitions as in the general formula (PA-1), respectively.

C$^+$ represents a counter cation.

The counter cation is preferably an onium cation. More particularly, as preferred examples thereof, there can be mentioned a sulfonium cation described above as being expressed by S$^+$(R$_{201'}$)(R$_{202'}$)(R$_{203'}$) of the general formula (ZI) and an iodonium cation described above as being expressed by I$^+$(R$_{204'}$)(R$_{205'}$) of the general formula (ZII) in the photo-acid generators.

Specific examples of the compounds (PA) are shown below, but the present invention is not limited thereto.

[Chem. 175]

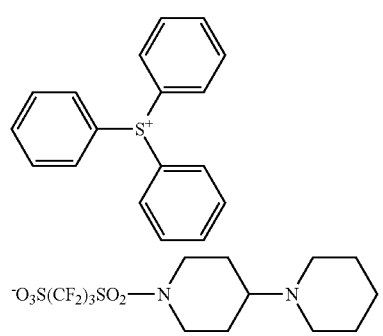 (PA-1)

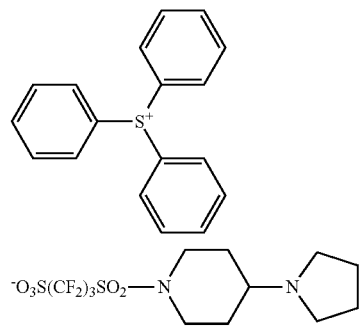 (PA-2)

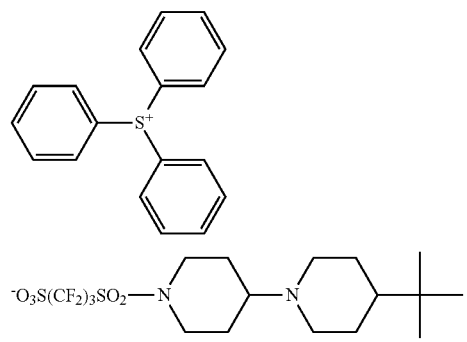 (PA-3)

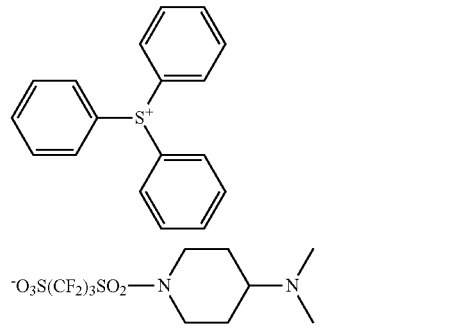 (PA-4)

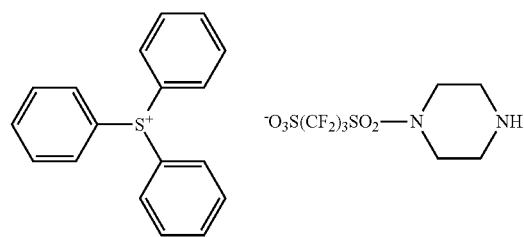 (PA-5)

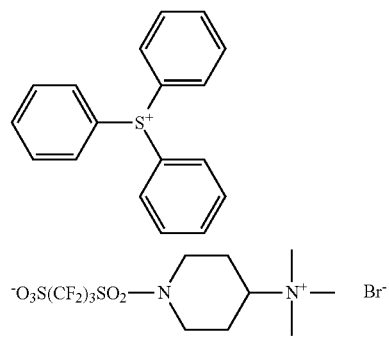 (PA-6)

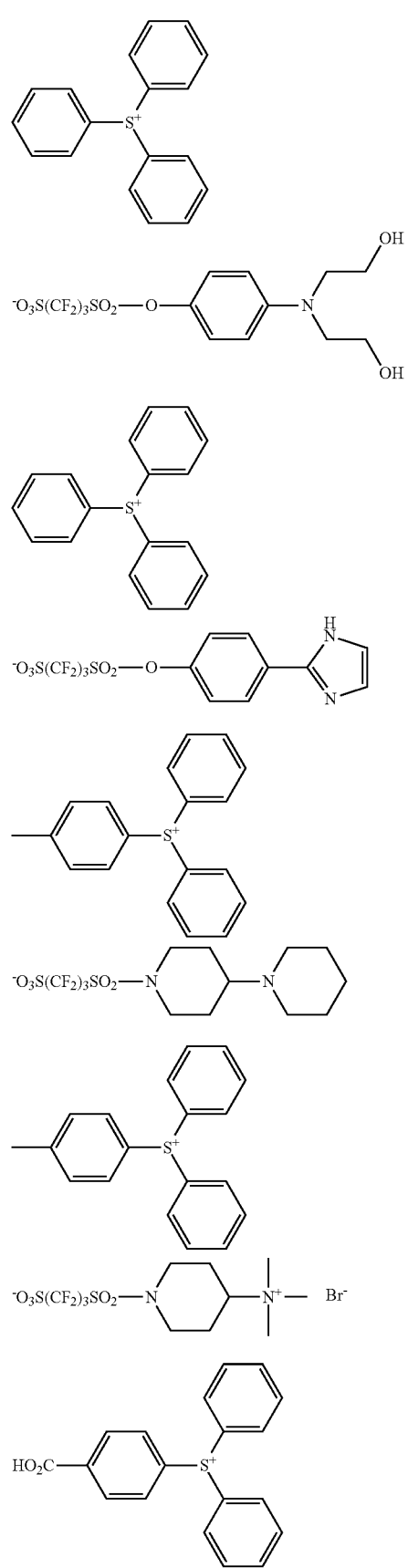
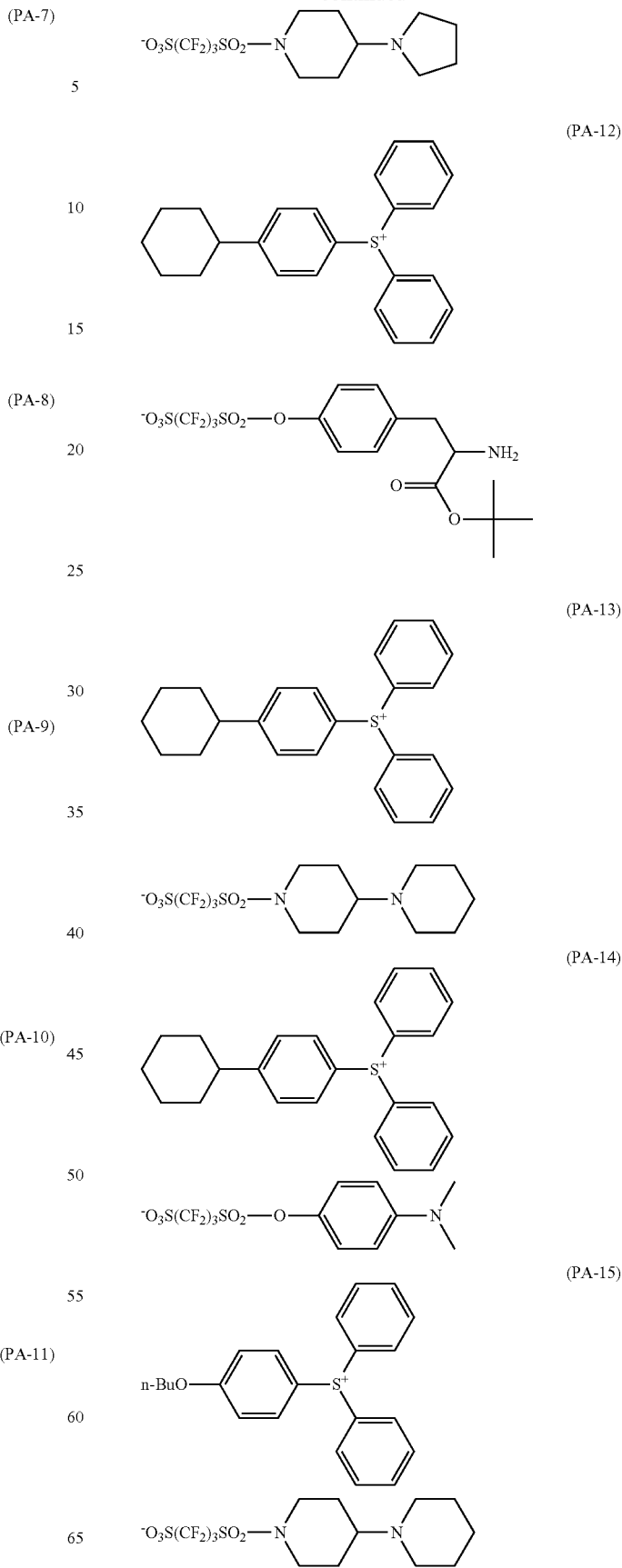

(PA-16)
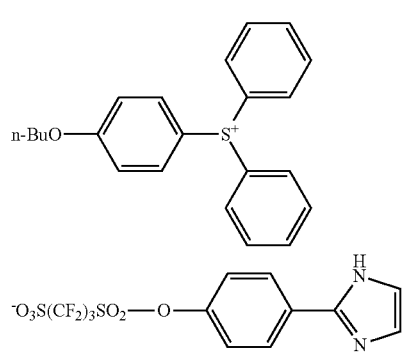
[Chem. 176]
(PA-17)
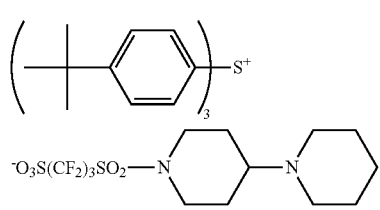
(PA-18)
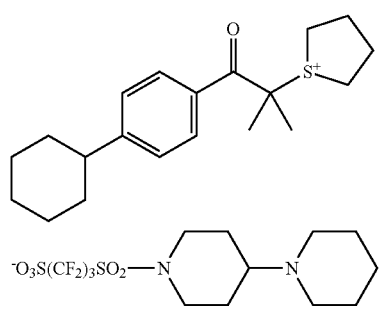
(PA-19)
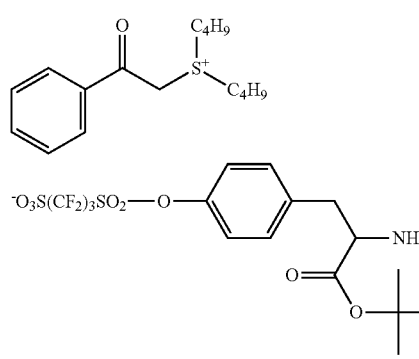
(PA-20)
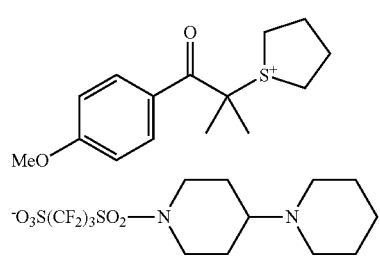
(PA-21)
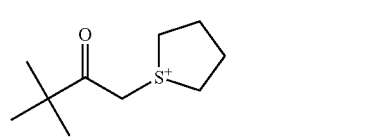
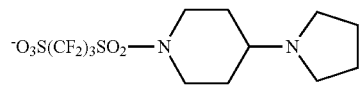
(PA-22)
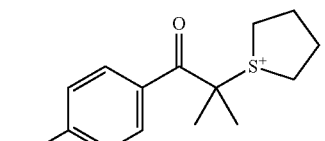
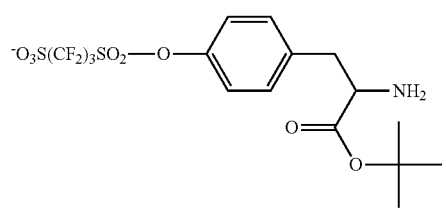
(PA-23)
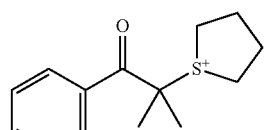
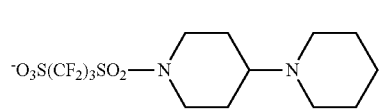
(PA-24)
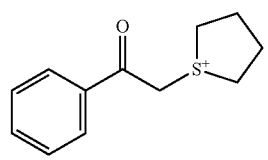
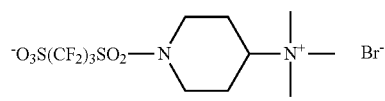
(PA-25)
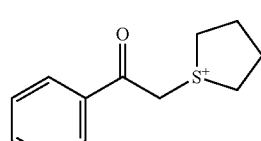
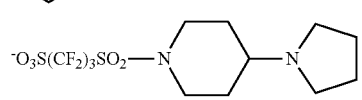
(PA-26)
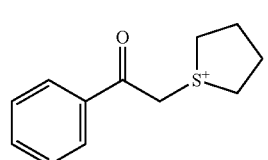
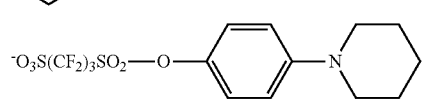

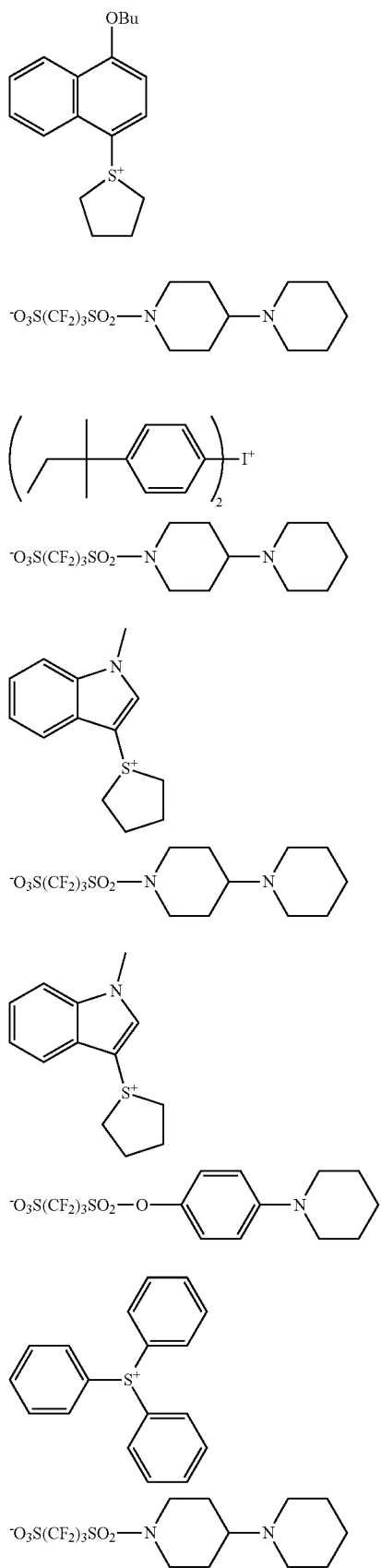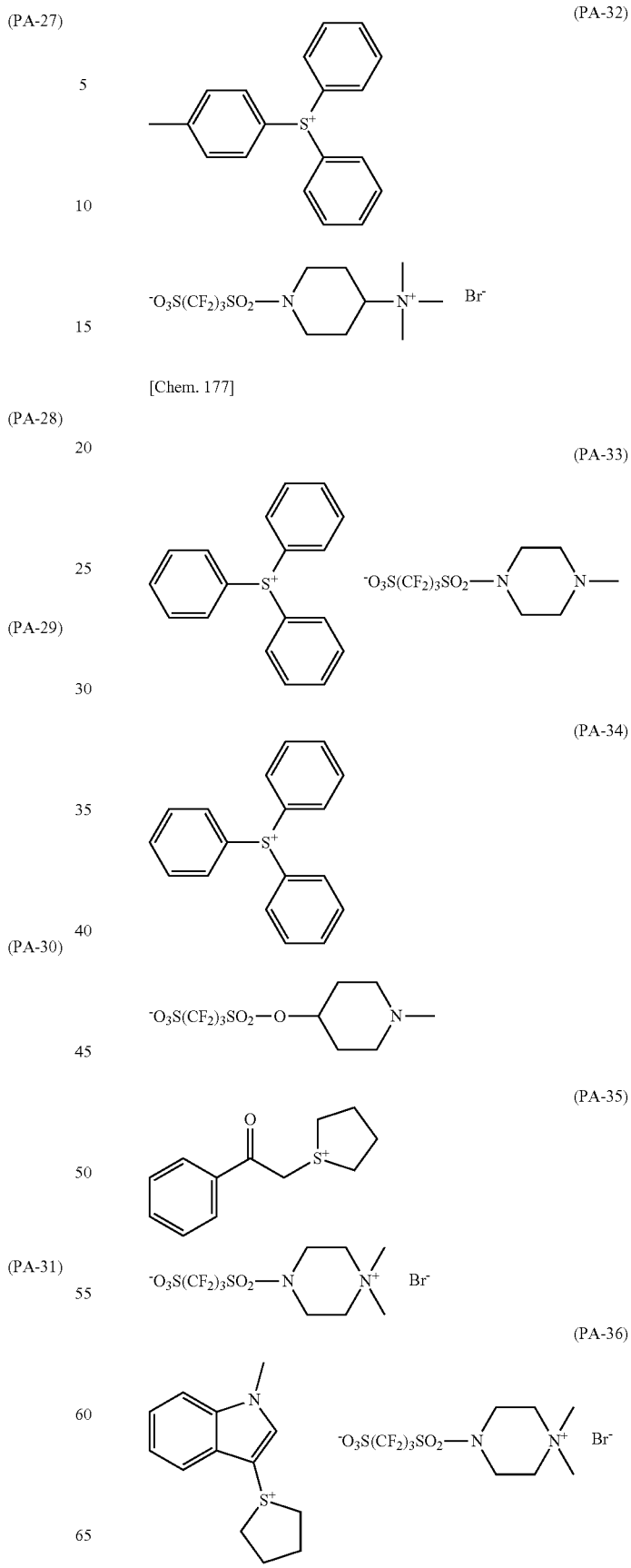

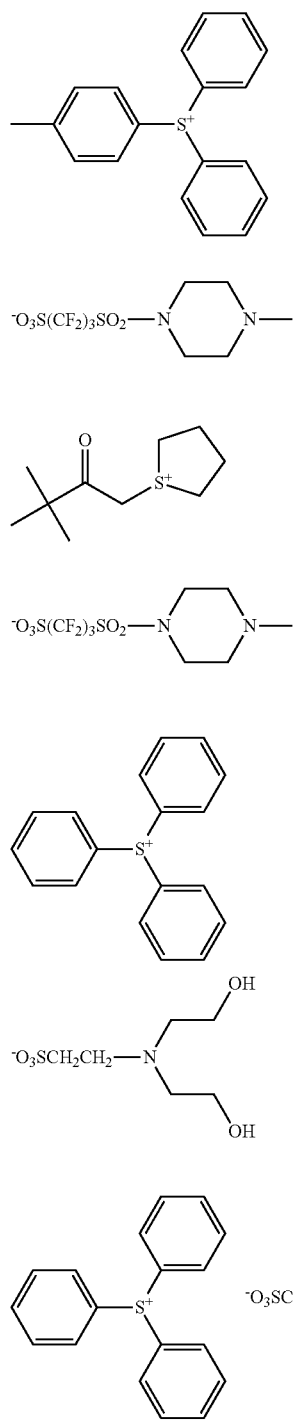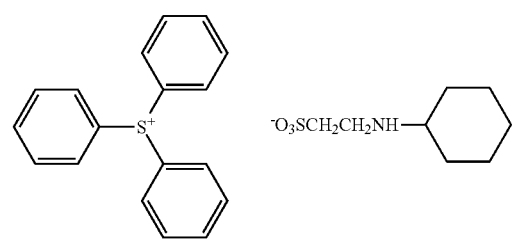

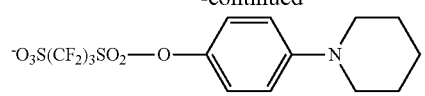
(PA-48)
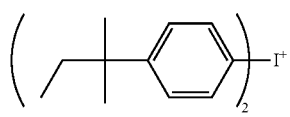
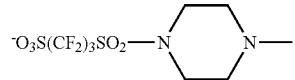
[Chem. 178]
(PA-49)
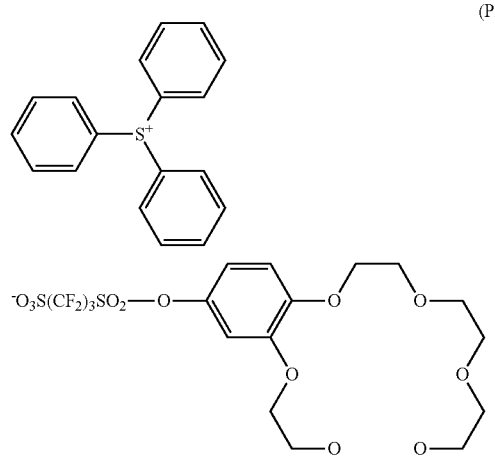
(PA-50)
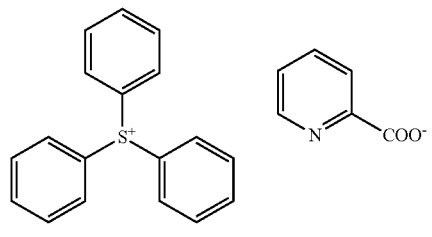
(PA-51)
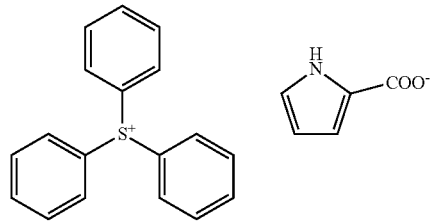
(PA-52)
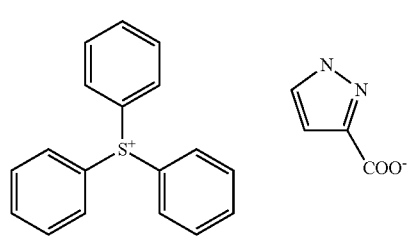
(PA-53)
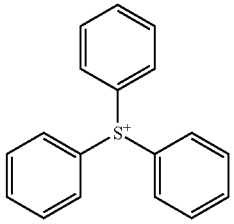 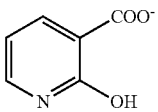
(PA-54)
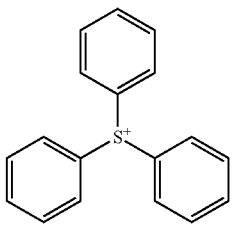 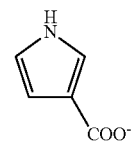
(PA-55)
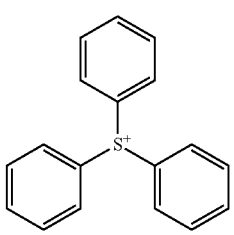 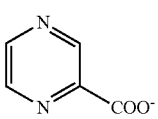
(PA-56)
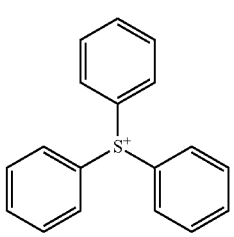 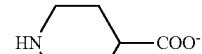
(PA-57)
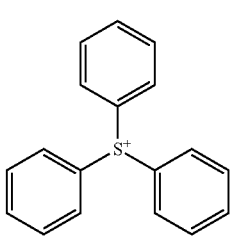 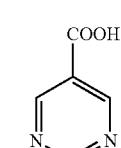
(PA-58)
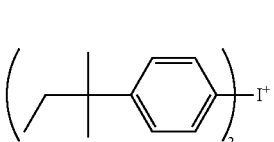
[Chem. 179]
(PA-59)
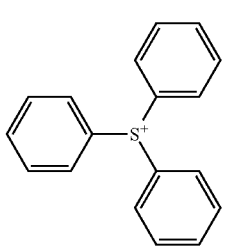

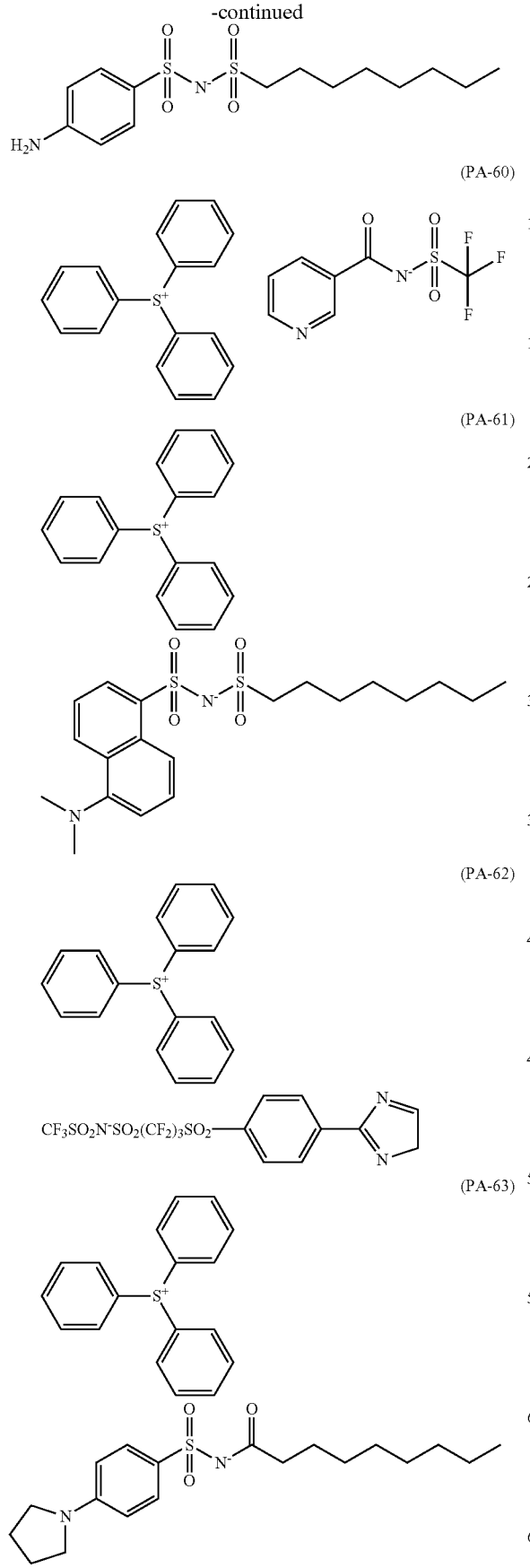
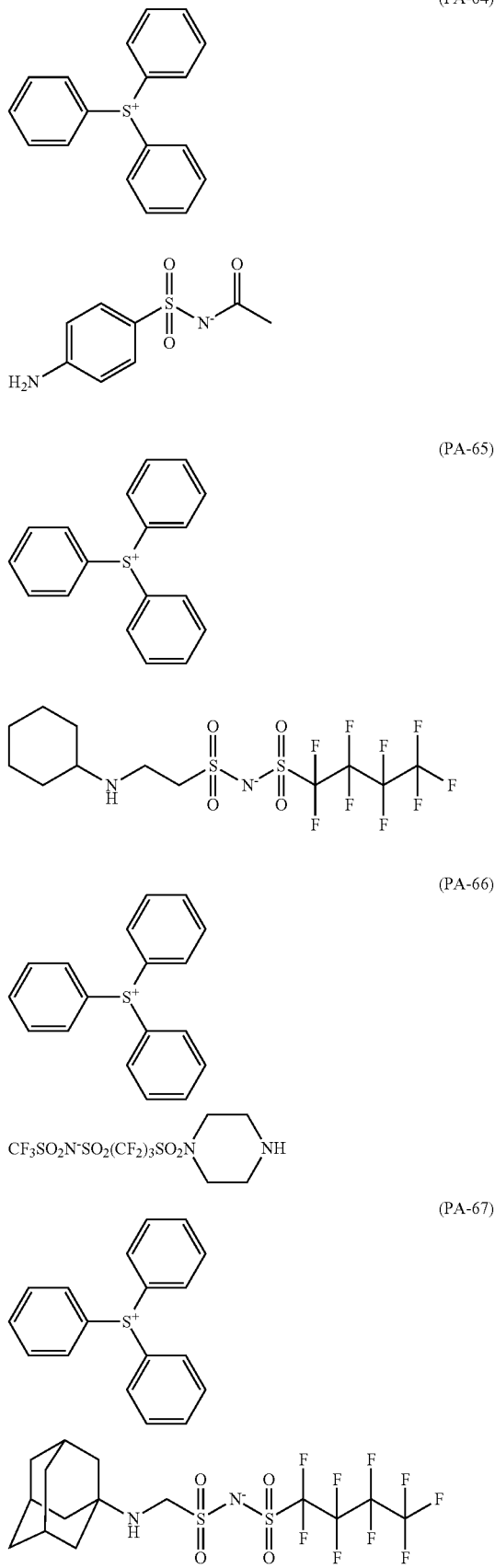

(PA-68)
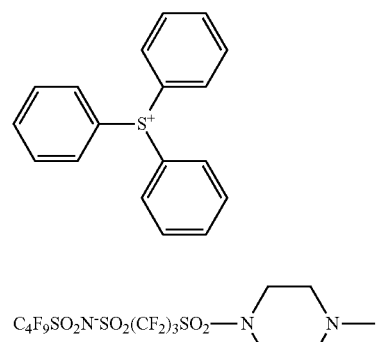
(PA-69)
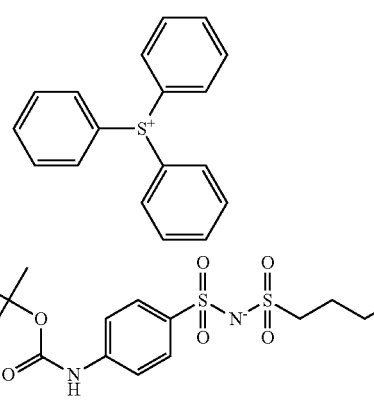
(PA-70)
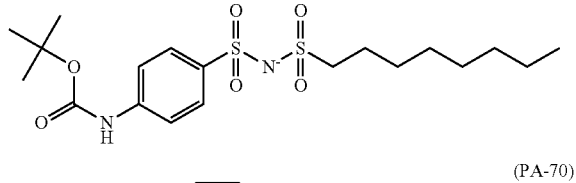
[Chem. 180]
(PA-71)
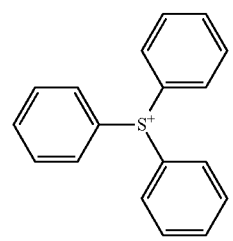
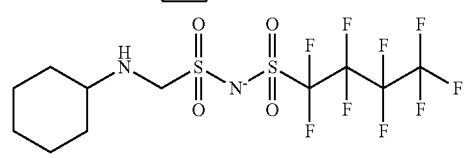
(PA-72)
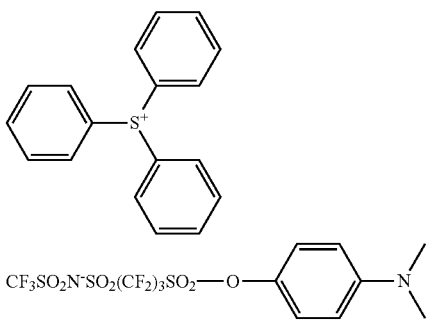
(PA-73)
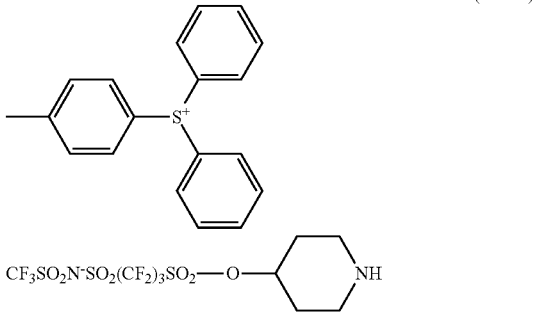
(PA-74)
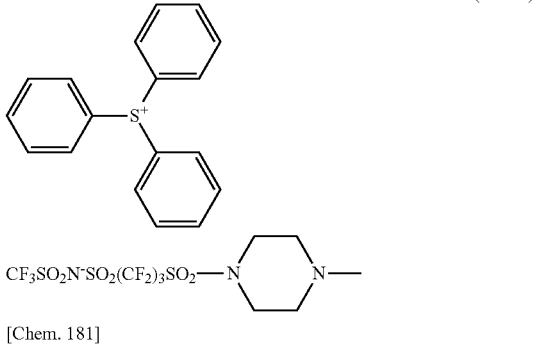
[Chem. 181]
(PA-75)
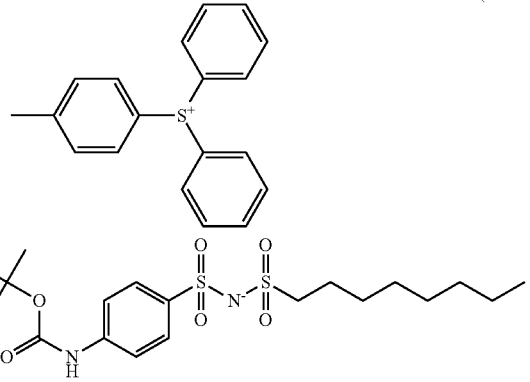
(PA-76)
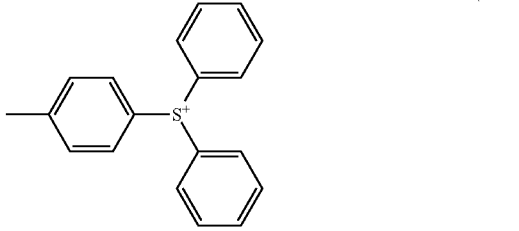

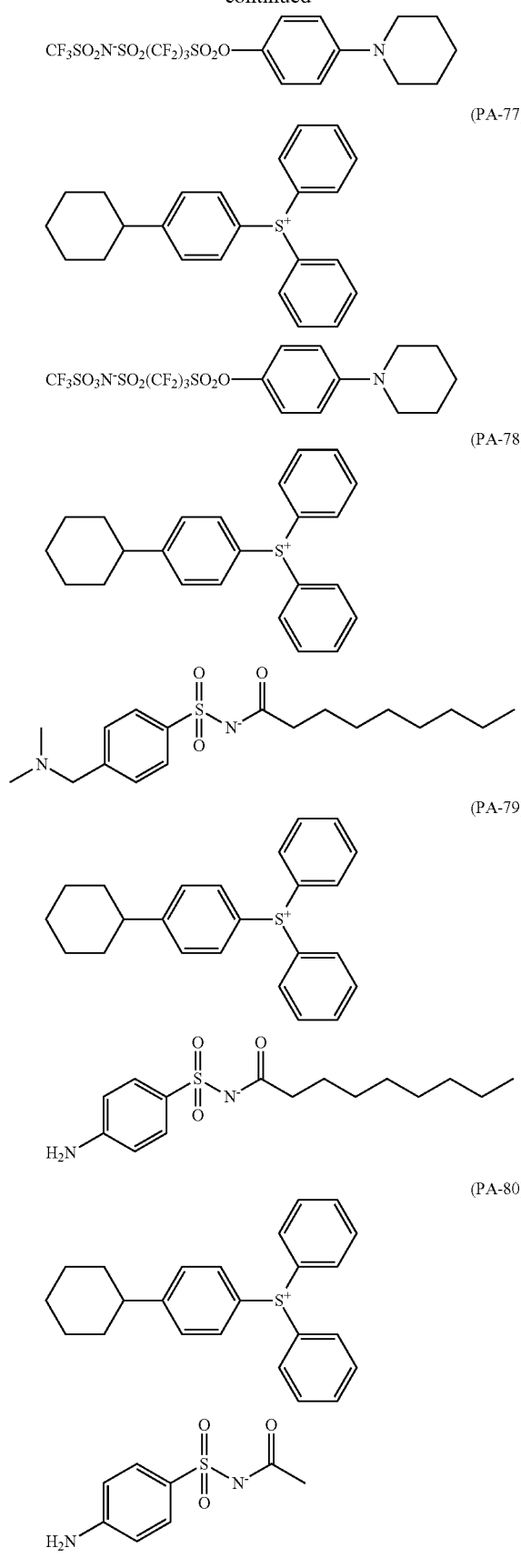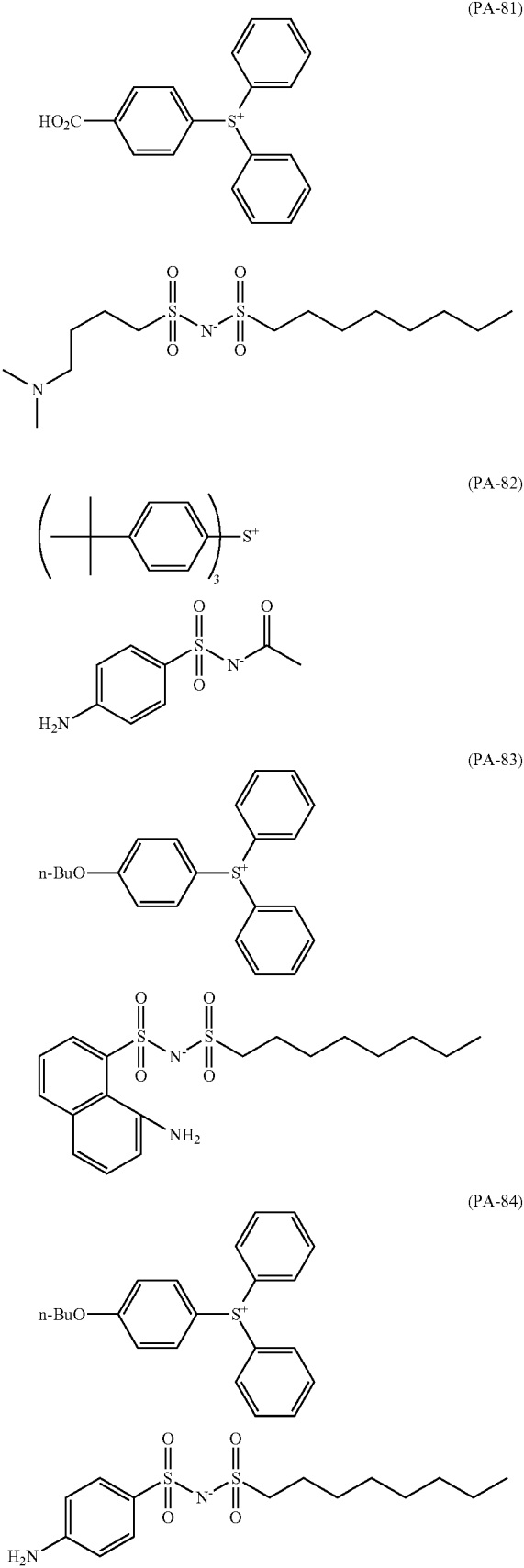

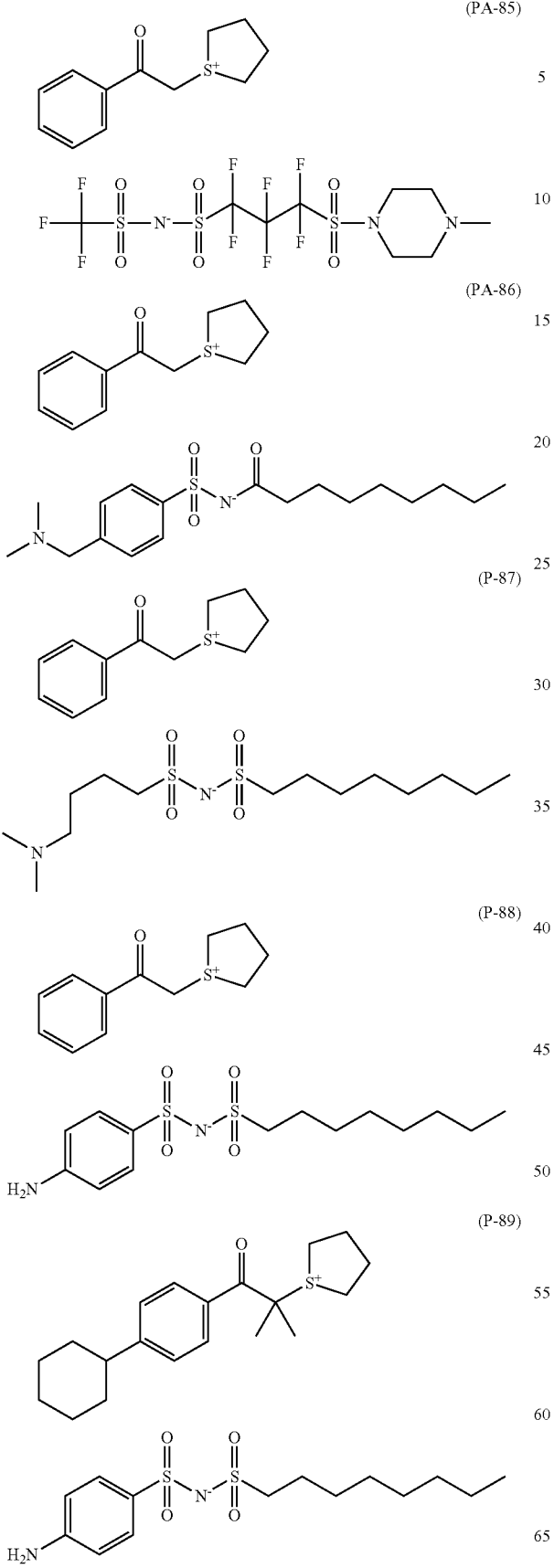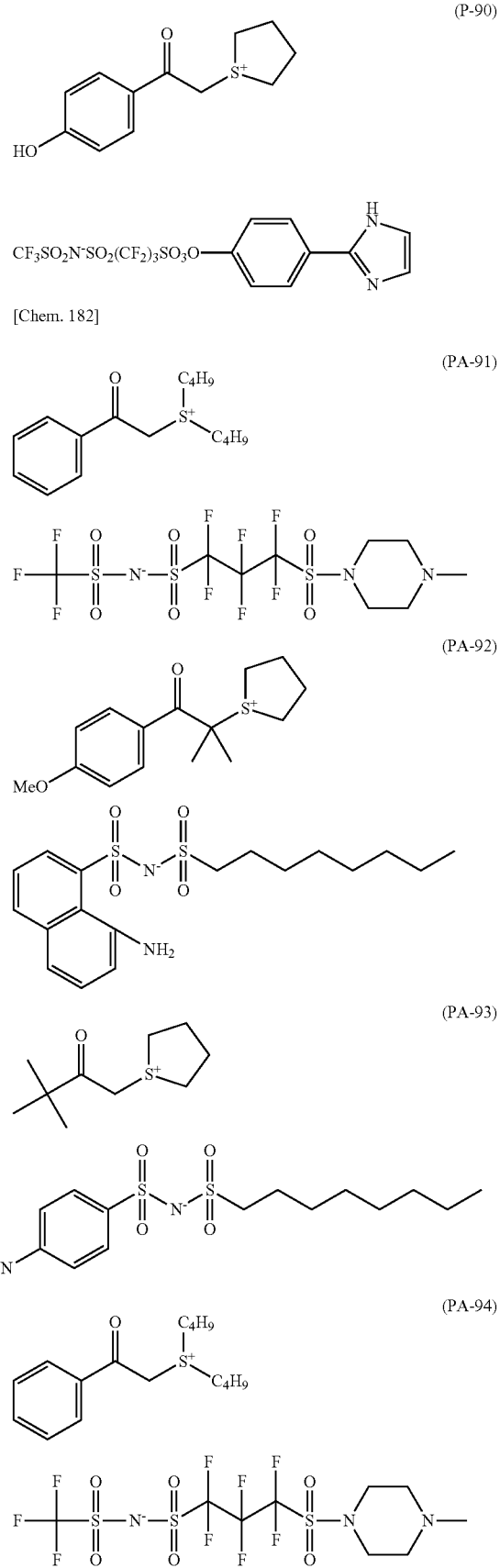

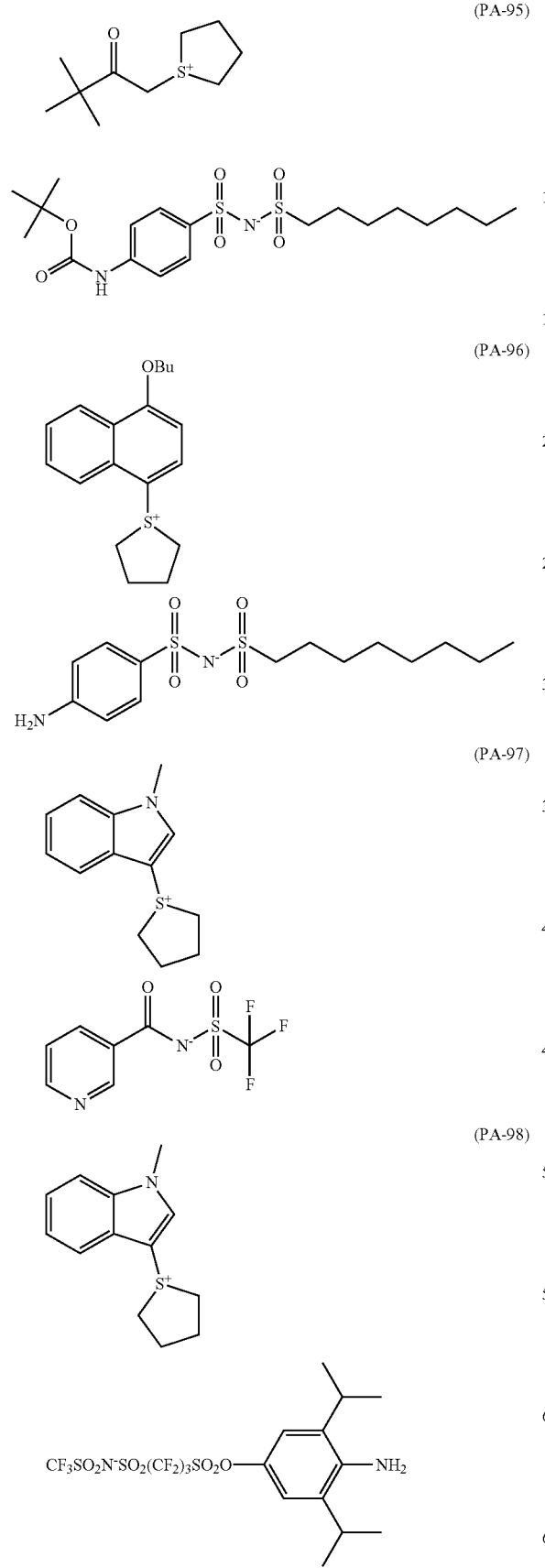

Furthermore, in the present invention, the compounds (PA) other than those producing the compounds represented by the general formula (PA-1) can be appropriately selected. For example, compounds which are the ionic compounds and each contain a proton acceptor moiety at their cation parts may be used. More specific examples of the compound include compounds represented by the following general formula (7).

[Chem. 183]

(7)

In the formula, A represents a sulfur atom or an iodine atom.

m is 1 or 2, and n is 1 or 2, provided that when A is a sulfur atom, m+n=3, and that when A is an iodine atom, m+n=2.

R represents an aryl group.

$R_N$ represents an aryl group substituted with a functional group with proton acceptor properties.

$X^-$ represents a counter anion.

Specific examples of $X^-$ include the same groups as $X^-$ in the general formula (ZI).

A preferred specific example of the aryl groups of R and $R_N$ is a phenyl group.

Specific examples of the functional groups with proton acceptor properties introduced in $R_N$ are the same functional group with proton accepting properties as set forth above with respect to the formula (PA-1).

In the composition of the present invention, the content of the compound (PA) in the entire composition is preferably in the range of 0.1 to 10% by mass, and more preferably 1 to 8% by mass, based on the total solid contents.

(6) Guanidine Compound

The composition of the present invention may further contain a guanidine compound having a structure represented by the following formula.

[Chem. 184]

The guanidine compound exhibits strong basicity because dispersion of positive electric charges of a conjugate acid is stabilized by three nitrogen atoms.

As for the basicity of the guanidine compound (A) for use in the present invention, the pKa of the conjugate acid is preferably 6.0 or more, and more preferably from 7.0 to 20.0 in view of high neutralization reactivity with an acid and excellent roughness performance, and still more preferably from 8.0 to 16.0.

Due to such strong basicity, the compound can suppress the diffusion of an acid and contribute to the formation of an excellent pattern profile.

Furthermore, the "pKa" as used herein is pKa in an aqueous solution and described, for example, in Chemical Handbook (II), 4$^{th}$ ed., 1993, compiled by The Chemical Society of Japan, Maruzen, and a lower value indicates higher acid strength. Specifically, the pKa in an aqueous solution can be measured in practice by using an infinite-dilution aqueous solution and measuring the acid dissociation constant at 25° C., or a value based on the Hammett substituent constants and the database of known publications can be determined by computation using the following software package 1. All values of pKa cited in the specification of the present invention are a value determined by computation using this software package.

Software Package 1: Advanced Chemistry Development (ACD/Labs) Software V 8.14 for Solaris (1994-2007 ACD/Labs)

In the present invention, the log P is a logarithmic value of the n-octanol/water partition coefficient (P) and is an effective parameter capable of characterizing the hydrophilicity/hydrophobicity for compounds over a wide range. The partition coefficient is usually determined by computation but not from experiments and in the present invention, a value computed using CS ChemDraw Ultra Ver. 8.0 software package (Crippen's fragmentation method) is employed.

Furthermore, the log P of the guanidine compound (A) is preferably 10 or less. When the value is in this range, the compound can be uniformly contained in the resist film.

The log P of the guanidine compound (A) in the present invention is preferably in a range of 2 to 10, more preferably in a range of 3 to 8, and still more preferably in a range of 4 to 8.

Furthermore, the guanidine compound (A) in the present invention preferably contains no nitrogen atoms except for in the guanidine structure.

Specific examples of the guanidine compound are shown below, but the present invention is not limited thereto.

[Chem. 185]

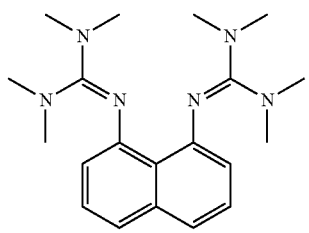
Log P: 4.29

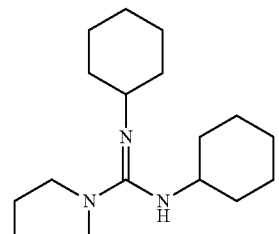
Log P: 3.32

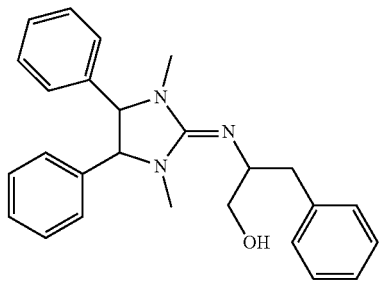
Log P: 5.66

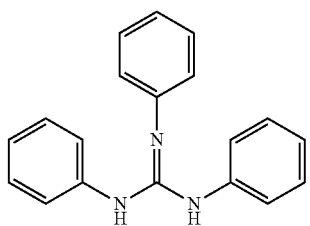
Log P: 5.24

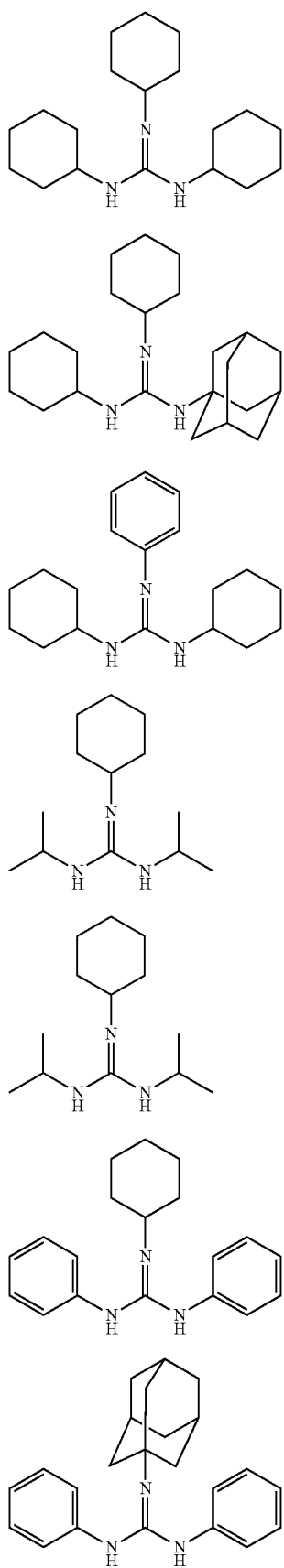
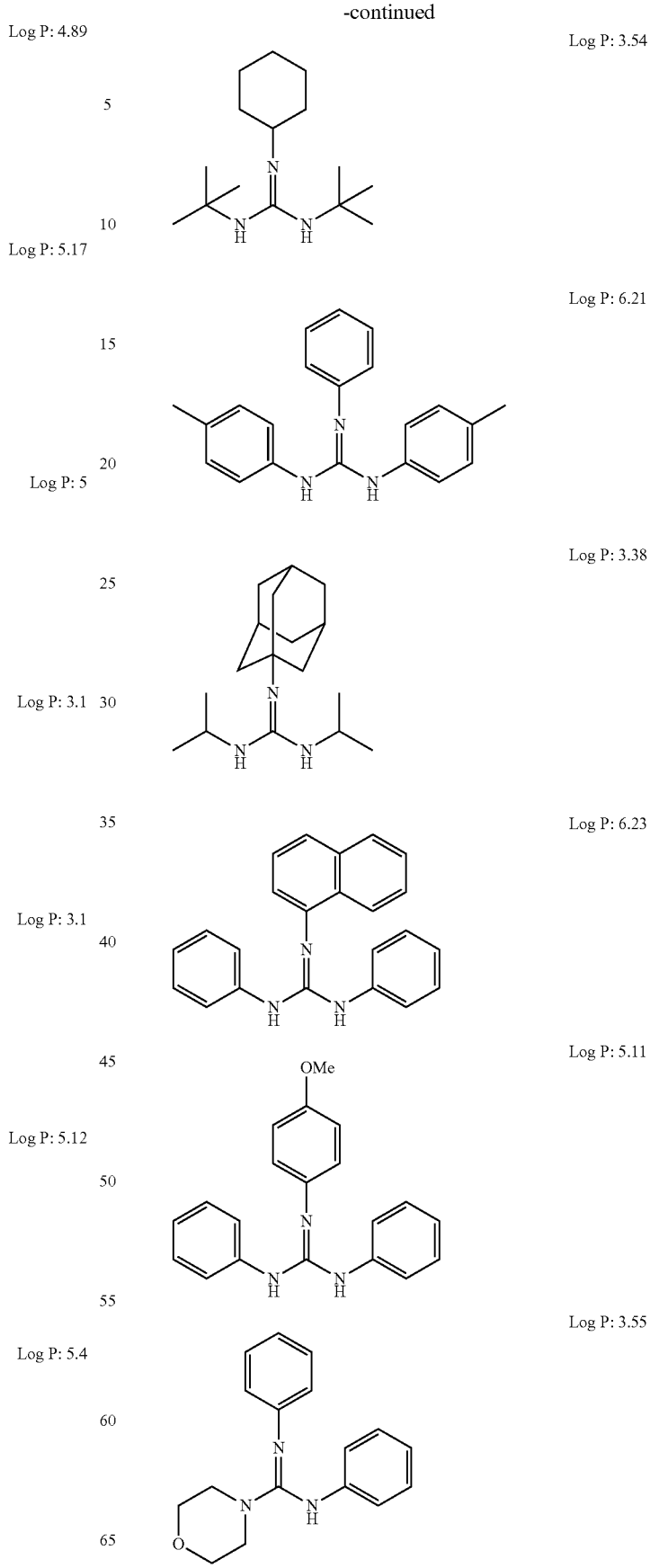
Log P: 4.89
Log P: 5.17
Log P: 5
Log P: 3.1
Log P: 3.1
Log P: 5.12
Log P: 5.4
Log P: 3.54
Log P: 6.21
Log P: 3.38
Log P: 6.23
Log P: 5.11
Log P: 3.55

411
-continued
412
-continued
[Chem. 186]
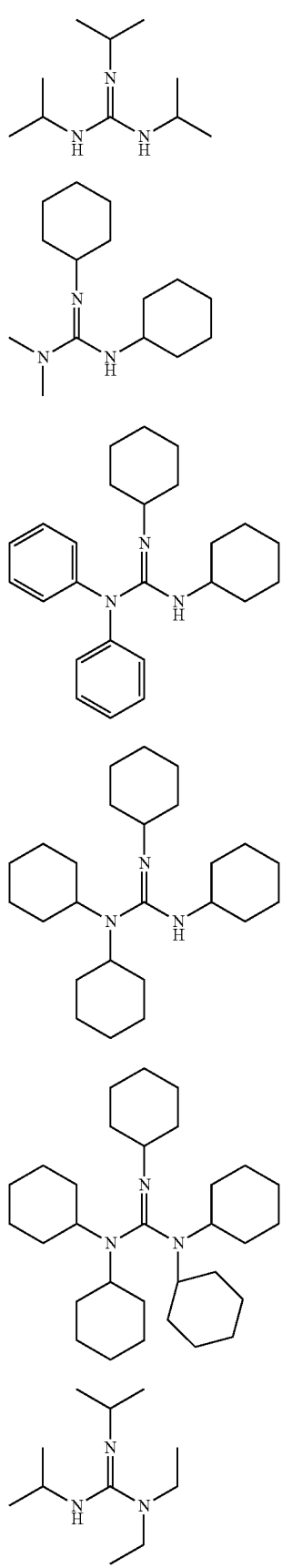
Log P: 2.21
Log P: 3.72
Log P: 7.21
Log P: 6.81
Log P: 8.74
Log P: 2.61
Log P: 3.34
Log P: 3.1
Log P: 3.34
Log P: 5.42
Log P: 4.05
Log P: 5.19

413
-continued
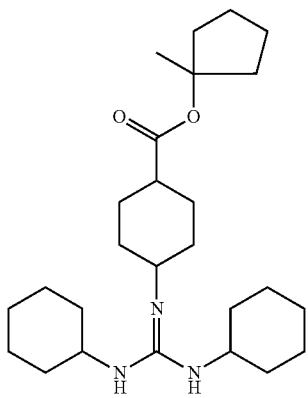
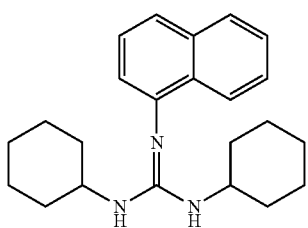
Log P: 4.61
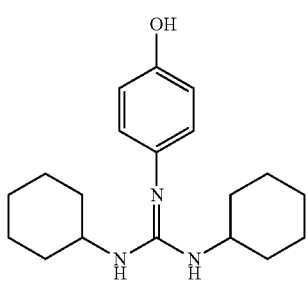
Log P: 5.83
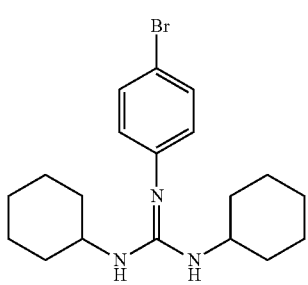
Log P: 6.53
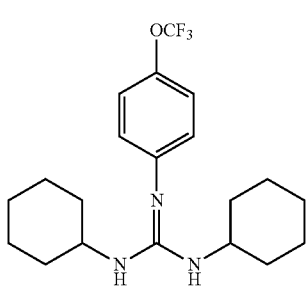
414
-continued
Log P: 5.66
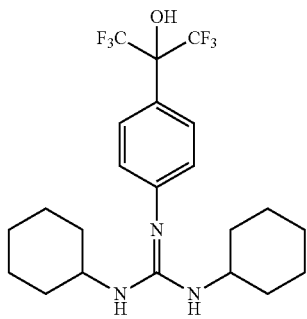
Log P: 6.25
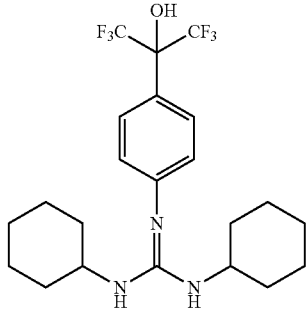
Log P: 6.25
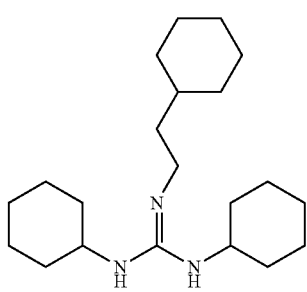
Log P: 5.66
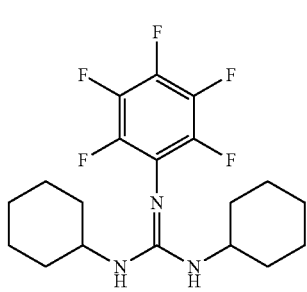
Log P: 5.79
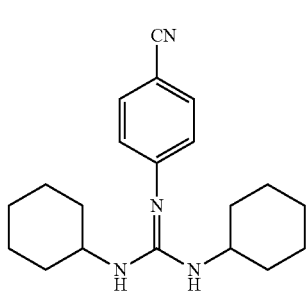
Log P: 5.04

415
-continued
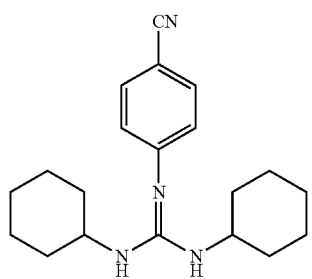
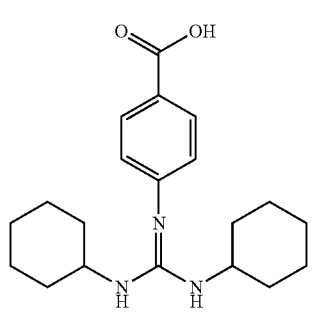
[Chem. 187]
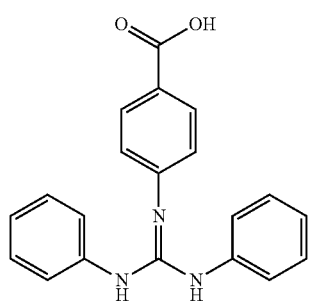
416
-continued
Log P: 5.04
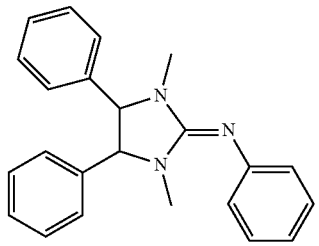
Log P: 4.56
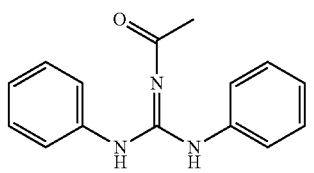
Log P: 4.79
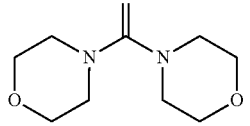
Log P: 3.66
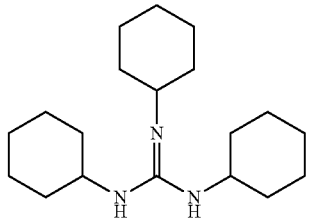
Log P: 1.56
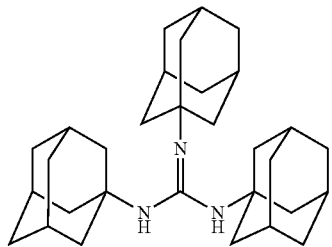
Log P: 5.84
Log P: 3.28
Log P: 1.75
Log P: 4.89
Log P: 5.73
Log P: 5
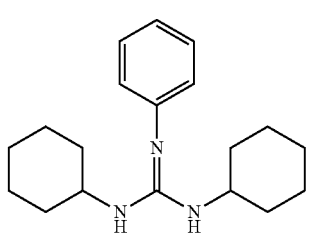

Log P: 5.26
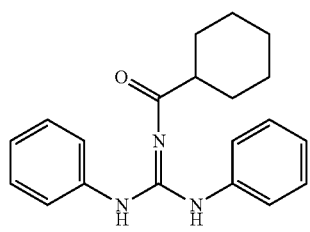
Log P: 4.95
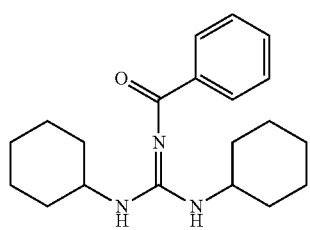
Log P: 4.51
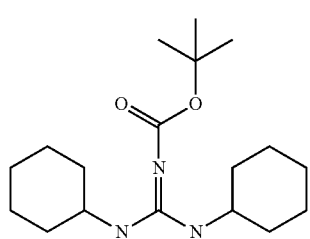
Log P: 3.83
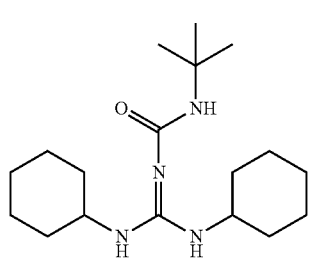
Log P: 2.31
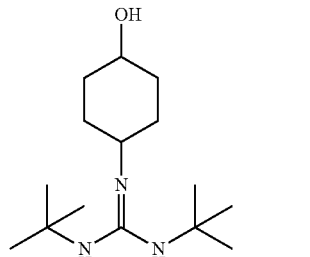
Log P: 4.46
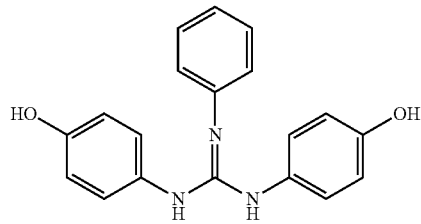
Log P: 3.38
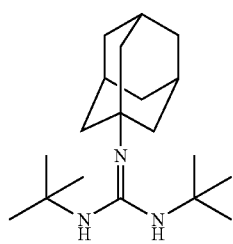
Log P: 7.23
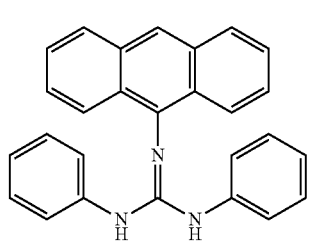
[Chem. 188]
Log P: 4.55
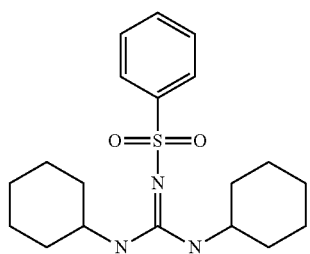
Log P: 5.04
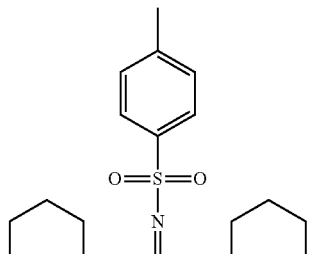
Log P: 2.36
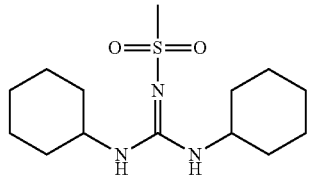
Log P: 4.54
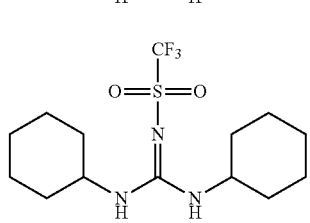

419
-continued
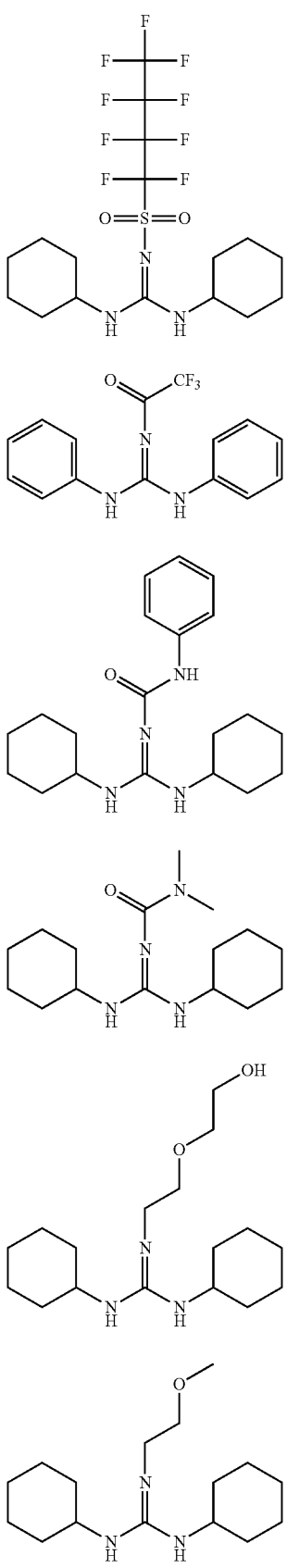
Log P: 6.08
Log P: 4.43
Log P: 4.62
Log P: 3.19
Log P: 2.67
Log P: 3.18
420
-continued
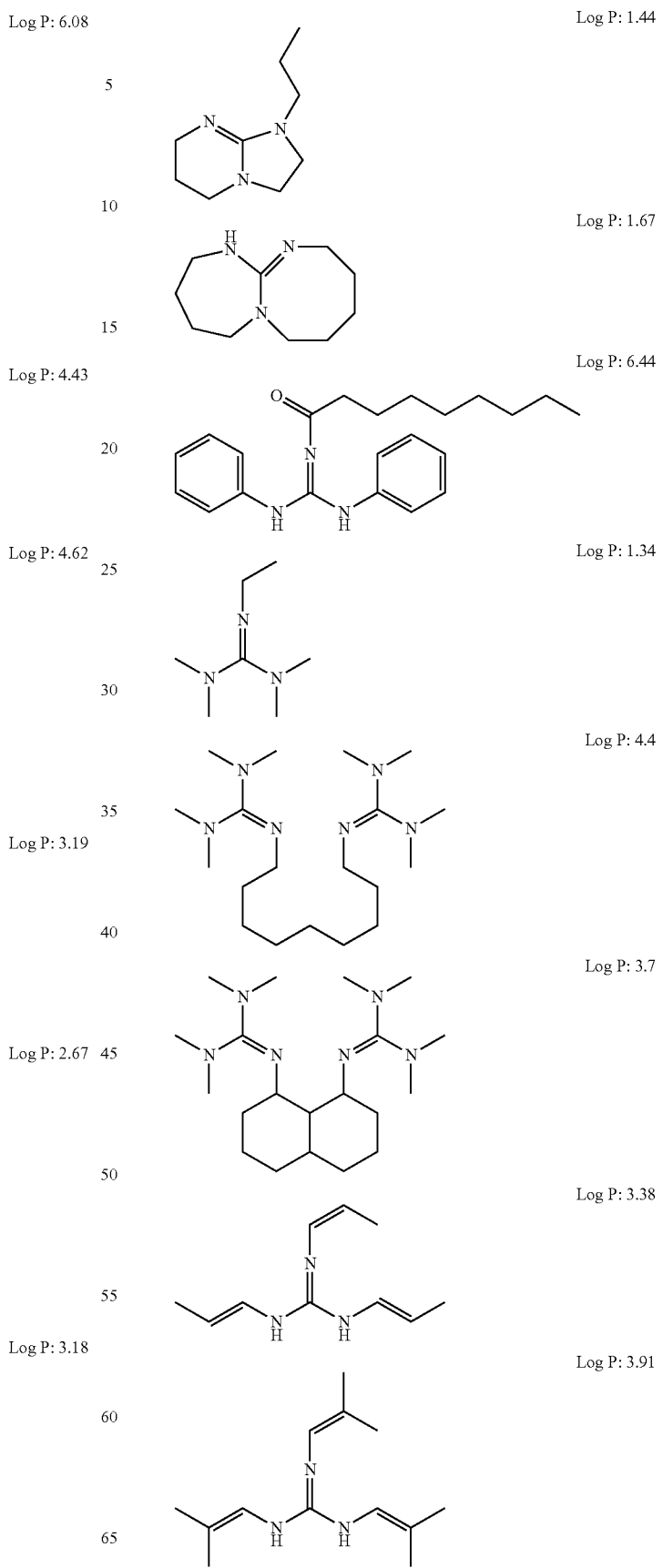
Log P: 1.44
Log P: 1.67
Log P: 6.44
Log P: 1.34
Log P: 4.4
Log P: 3.7
Log P: 3.38
Log P: 3.91

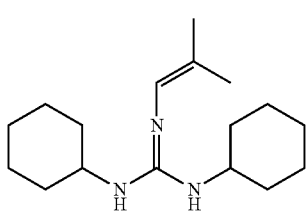

Log P: 4.47

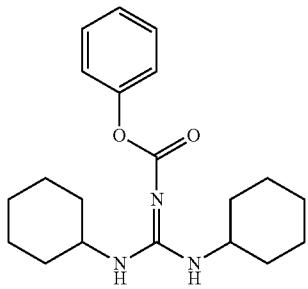

Log P: 5.3

(7) Low Molecular Compound Containing Nitrogen Atom and Containing Group that Leaves by Action of Acid The composition of the present invention may contain a low molecular compound containing a nitrogen atom and a group capable of leaving by the action of an acid (also referred to as a "low molecular compound (D)" or a "compound (D)"). The low molecular compound (D) preferably has basicity after the group capable of leaving by the action of an acid leaves.

The group capable of leaving by the action of an acid is not particularly limited, but an acetal group, a carbonate group, a carbamate group, a tertiary ester group, a tertiary hydroxyl group, and a hemiaminal ether group are preferred, and a carbamate group and a hemiaminal ether group are particularly preferred.

The molecular weight of the low molecular compound (D) containing a group capable of leaving by the action of an acid is preferably from 100 to 1,000, more preferably from 100 to 700, and particularly preferably from 100 to 500.

As the compound (D), an amine derivative containing group capable of leaving by the action of an acid on a nitrogen atom is preferred.

The compound (D) may contain a carbamate group having a protecting group on a nitrogen atom. The protecting group constituting the carbamate group can be represented by the following general formula (d-1).

[Chem. 189]

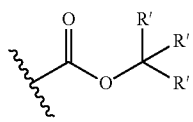

(d-1)

In the general formula (d-1), each R' independently represents a hydrogen atom, a linear or branched alkyl group, a cycloalkyl group, an aryl group, an aralkyl group, or an alkoxyalkyl group. R's may be bonded to each other to form a ring.

R' is preferably a linear or branched alkyl group, cycloalkyl group, or aryl group, and more preferably a linear or branched alkyl group or a cycloalkyl group.

Specific structures of these groups are shown below.

[Chem. 190]

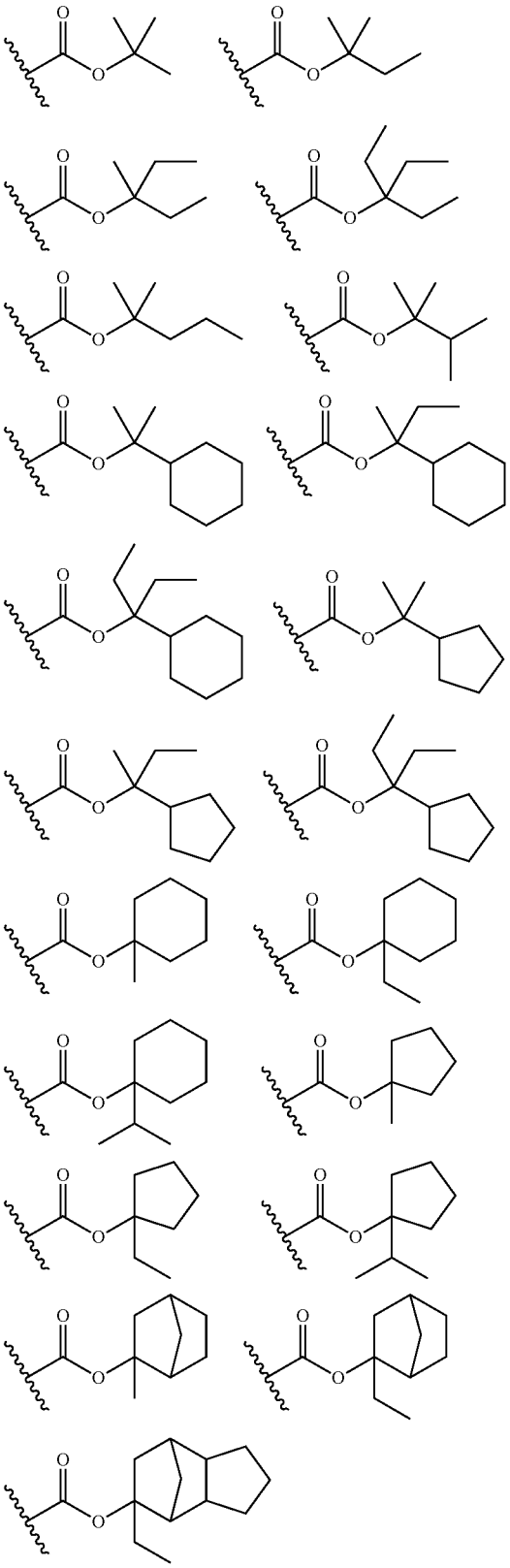

-continued

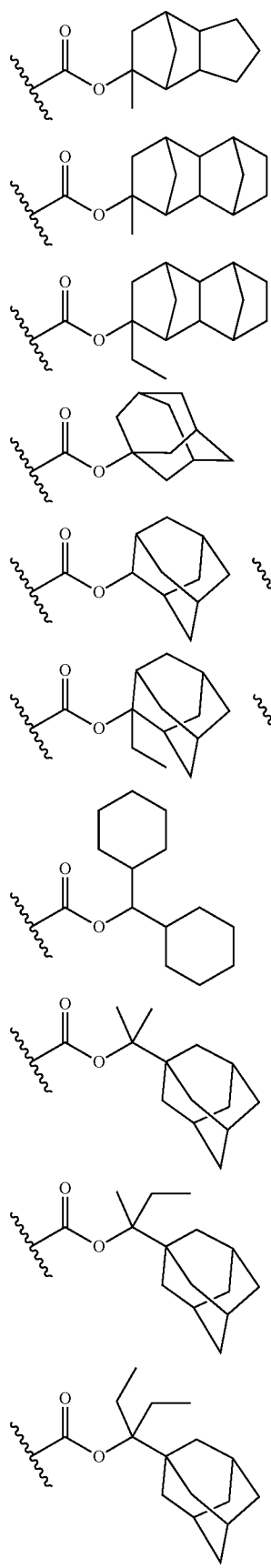

-continued

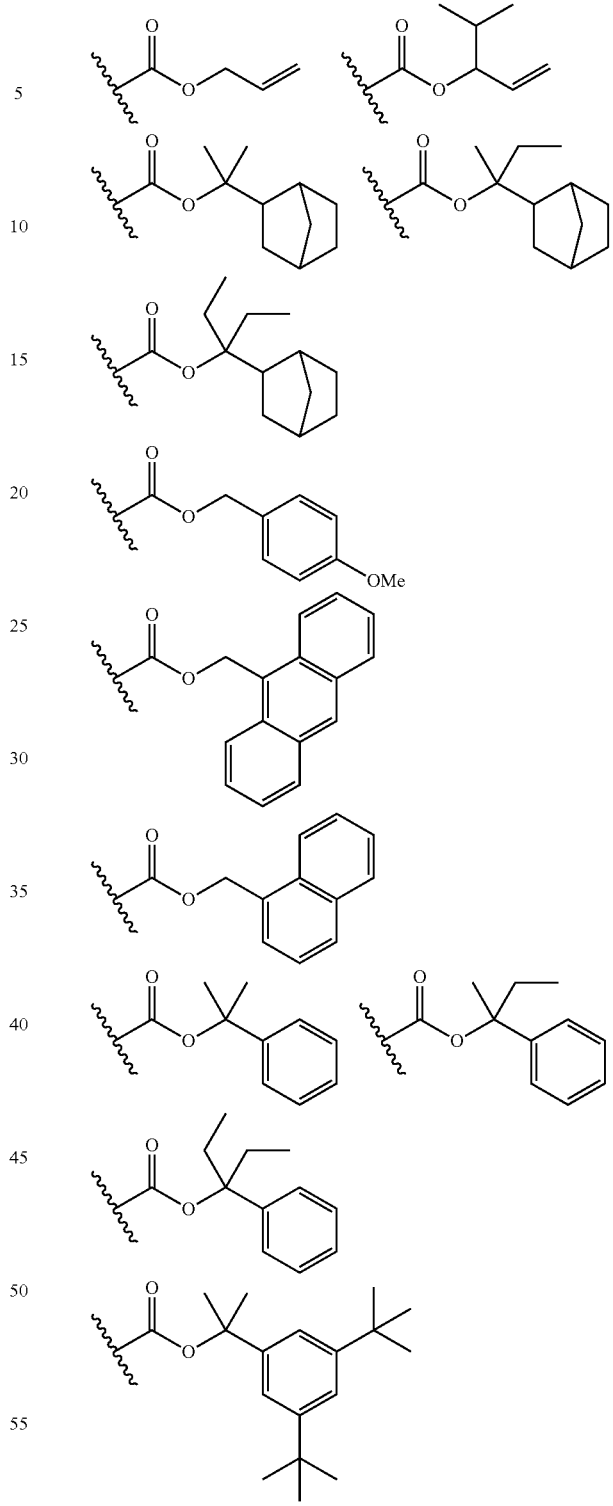

The compound (D) can be formed by any combination of the basic compound as described later and a structure represented by the general formula (d-1).

The compound (D) is particularly preferably one having a structure represented by the following general formula (A).

Furthermore, the compound (D) may correspond to the basic compound as long as it is a low molecular compound containing group capable of leaving by the action of an acid.

[Chem. 191]

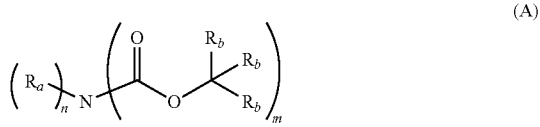

(A)

In the general formula (A), $R_a$ represents a hydrogen atom, an alkyl group, a cycloalkyl group, an aryl group, or an aralkyl group. Further, with n=2, two $R_a$'s may be the same as or different from each other, or the two $R_a$'s may be bonded to each other to form a divalent heterocyclic hydrocarbon group (preferably having 20 or less carbon atoms) or a derivative thereof.

$R_b$'s each independently represent a hydrogen atom, an alkyl group, a cycloalkyl group, an aryl group, or an alkoxyalkyl group. However, in —C($R_b$)($R_b$)($R_b$), when one or more $R_b$'s are hydrogen atoms, at least one of the remaining $R_b$'s is a cyclopropyl group, a 1-alkoxyalkyl group, or an aryl group.

At least two $R_b$'s may be bonded to form an aliphatic hydrocarbon group, an aromatic hydrocarbon group, a heterocyclic hydrocarbon group, or a derivative thereof.

n represents an integer of 0 to 2 and m represents an integer of 1 to 3, with n+m=3.

In the general formula (A), each of the alkyl group, the cycloalkyl group, the aryl group, and the aralkyl group represented by $R_a$ and $R_b$ may be substituted with a functional group such as a hydroxyl group, a cyano group, an amino group, a pyrrolidino group, a piperidino group, a morpholino group, and an oxo group, an alkoxy group, or a halogen atom. The alkoxyalkyl group represented by $R_b$ is also the same.

Examples of the alkyl group, cycloalkyl group, aryl group and aralkyl group (each of the alkyl group, the cycloalkyl group, the aryl group, and the aralkyl group may be substituted with the above-described functional group, an alkoxy group, or a halogen atom) of $R_a$ and/or $R_b$ include:

a group derived from a linear or branched alkane such as methane, ethane, propane, butane, pentane, hexane, heptane, octane, nonane, decane, undecane, and dodecane, or a group where the group derived from an alkane is substituted with one or more kinds of or one or more groups of cycloalkyl groups such as a cyclobutyl group, a cyclopentyl group, and a cyclohexyl group;

a group derived from a cycloalkane such as cyclobutane, cyclopentane, cyclohexane, cycloheptane, cyclooctane, norbornane, adamantane, and noradamantane, or a group where the group derived from a cycloalkane is substituted with one or more kinds of or one or more groups of linear or branched alkyl groups such as a methyl group, an ethyl group, an n-propyl group, an i-propyl group, an n-butyl group, a 2-methylpropyl group, a 1-methylpropyl group, and a t-butyl group;

a group derived from an aromatic compound such as benzene, naphthalene or anthracene, or a group where the group derived from an aromatic compound is substituted with one or more kinds of or one or more groups of linear or branched alkyl groups such as a methyl group, an ethyl group, an n-propyl group, an i-propyl group, an n-butyl group, a 2-methylpropyl group, a 1-methylpropyl group, and a t-butyl group;

a group derived from a heterocyclic compound such as pyrrolidine, piperidine, morpholine, tetrahydrofuran, tetrahydropyran, indole, indoline, quinoline, perhydroquinoline, indazole, and benzimidazole, or a group where the group derived from a heterocyclic compound is substituted with one or more kinds of or one or more groups of linear or branched alkyl groups or aromatic compound-derived groups; a group where the group derived from a linear or branched alkane or the group derived from a cycloalkane is substituted with one or more kinds of or one or more groups of aromatic compound-derived groups such as a phenyl group, a naphthyl group and an anthracenyl group; and a group where the substituent above is substituted with a functional group such as a hydroxyl group, a cyano group, an amino group, a pyrrolidino group, a piperidino group, a morpholino group, and an oxo group.

Incidentally, examples of the divalent heterocyclic hydrocarbon group (preferably having 1 to 20 carbon atoms) formed by the mutual bonding of $R_a$'s or a derivative thereof include a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline and 1,5,9-triazacyclododecane, and a group where the group derived from a heterocyclic compound is substituted with one or more kinds of or one or more groups of a linear or branched alkane-derived group, a cycloalkane-derived group, an aromatic compound-derived group, a heterocyclic compound-derived group, and a functional group such as a hydroxyl group, a cyano group, an amino group, a pyrrolidino group, a piperidino group, a morpholino group and an oxo group.

Specific examples of the particularly preferable compound (D) in the present invention are shown below, but the present invention is not limited thereto.

[Chem. 192]

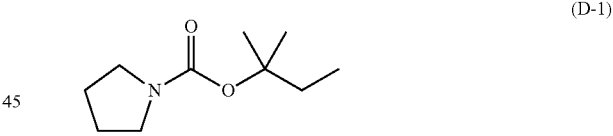

(D-1)

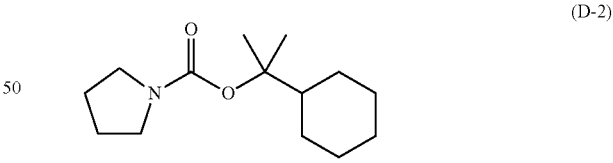

(D-2)

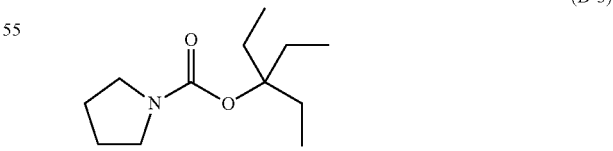

(D-3)

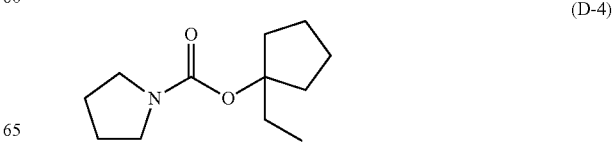

(D-4)

-continued
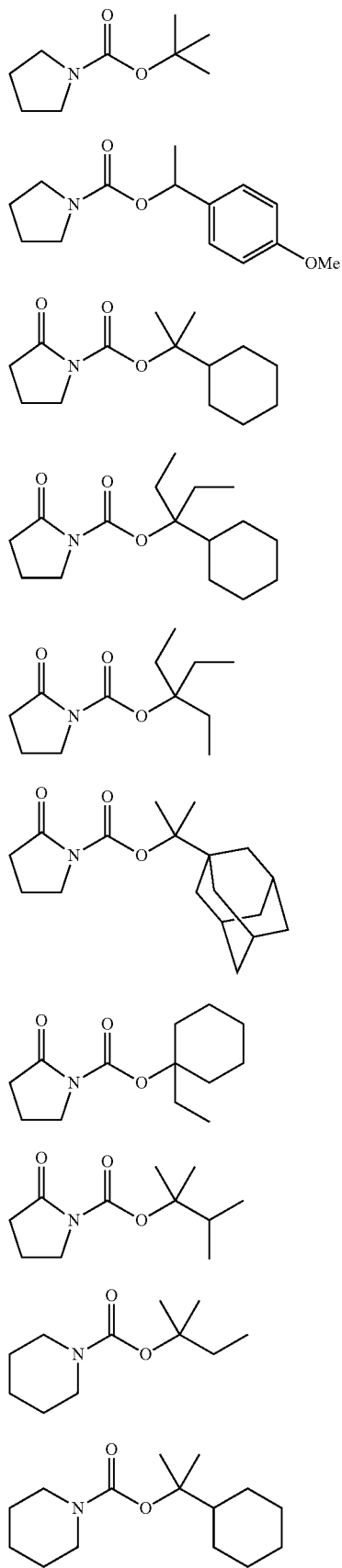
(D-5)
(D-6)
(D-7)
(D-8)
(D-9)
(D-10)
(D-11)
(D-12)
(D-13)
(D-14)
-continued
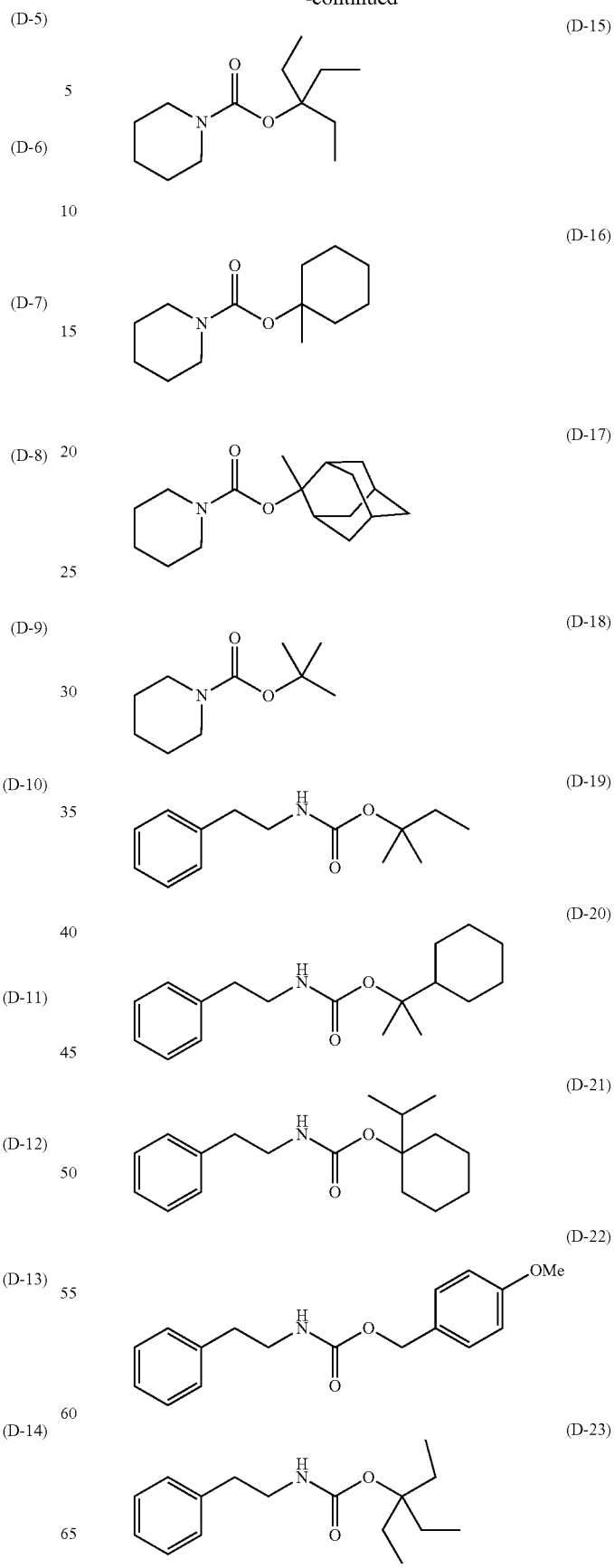
(D-15)
(D-16)
(D-17)
(D-18)
(D-19)
(D-20)
(D-21)
(D-22)
(D-23)

(D-24)
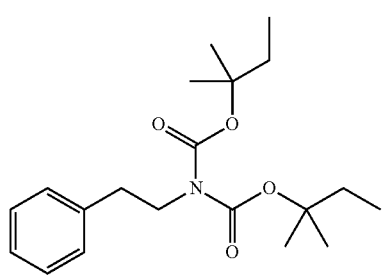
(D-25)
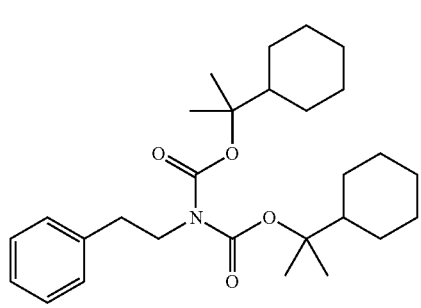
(D-26)
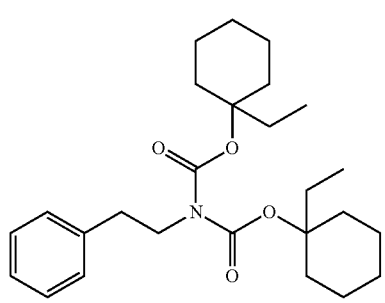
(D-27)
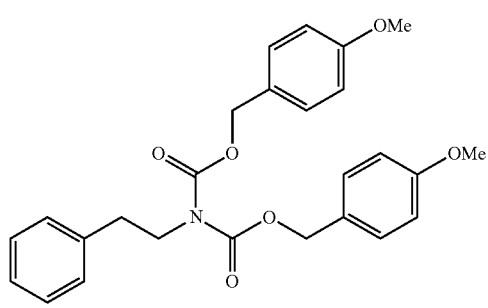
(D-28)
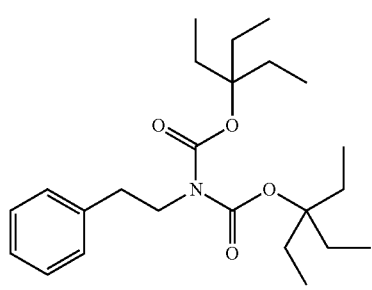
(D-29)
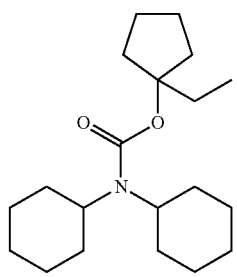
(D-30)
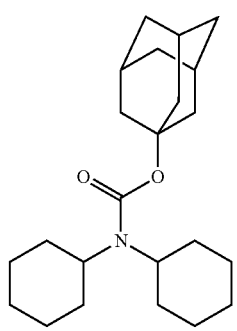
(D-31)
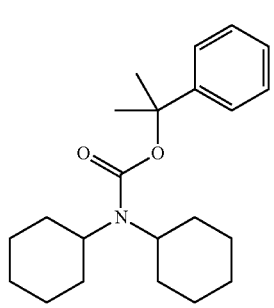
(D-32)
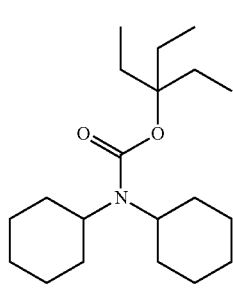
(D-33)
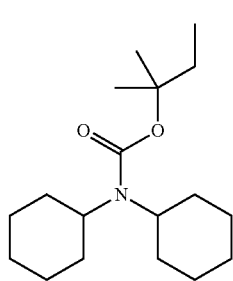

[Chem. 193]
(D-34)
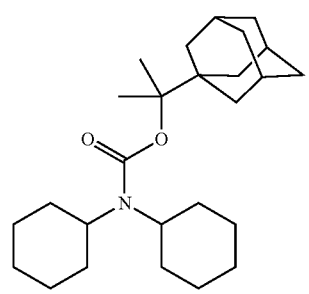
(D-35)
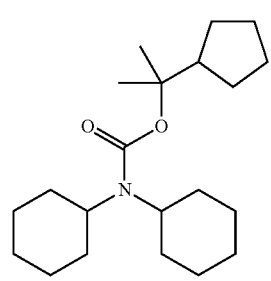
(D-36)
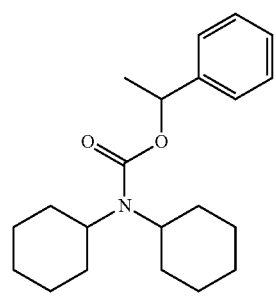
(D-37)
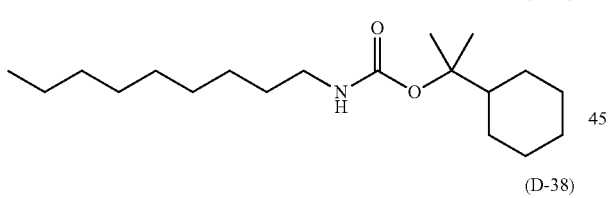
(D-38)
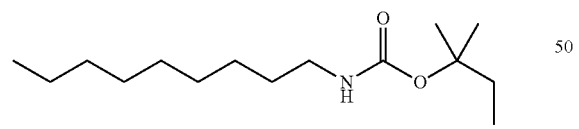
(D-39)
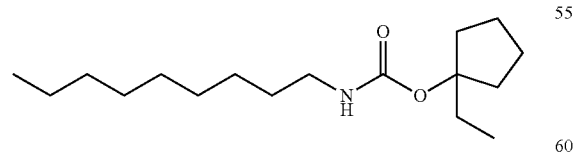
(D-40)
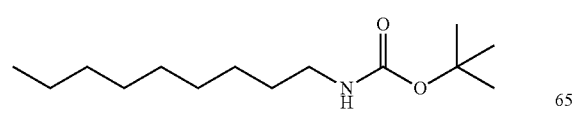
(D-41)
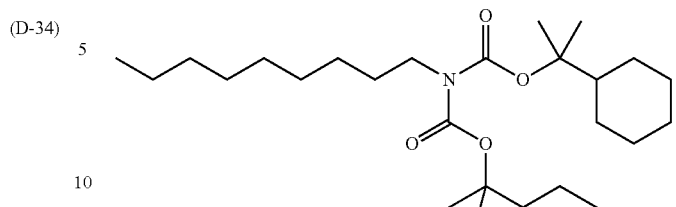
(D-42)
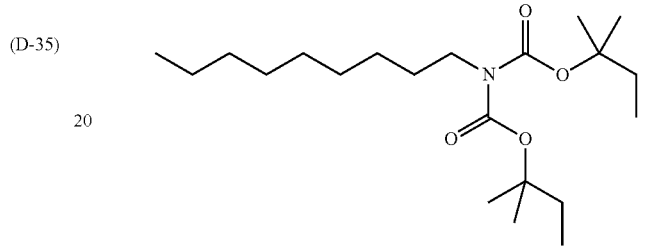
(D-43)
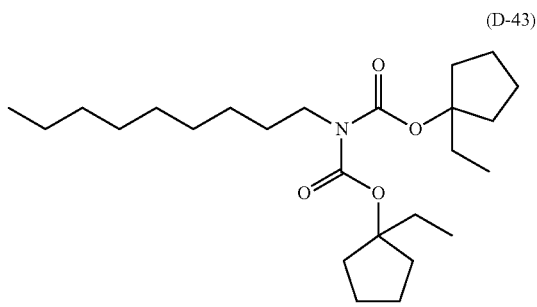
(D-44)
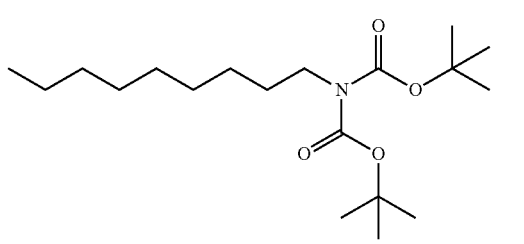
(D-45)
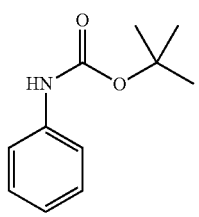
(D-46)
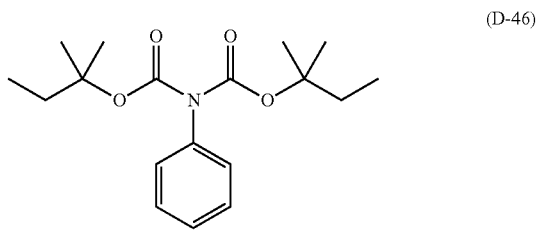

(D-47) 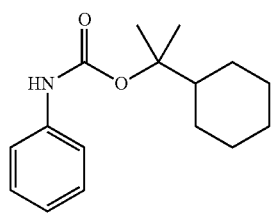
(D-48) 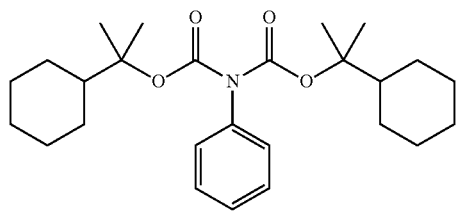
(D-49) 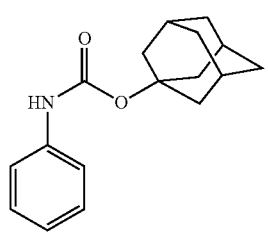
(D-50) 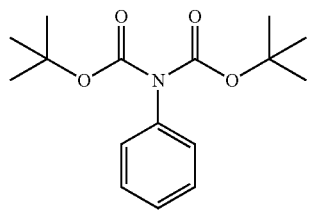
(D-51) 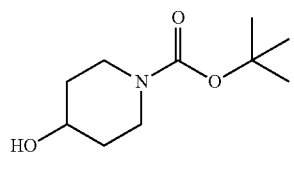
(D-52) 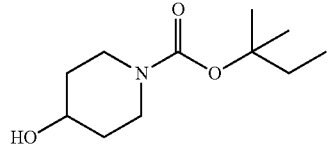
(D-53) 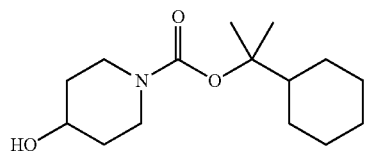
(D-54) 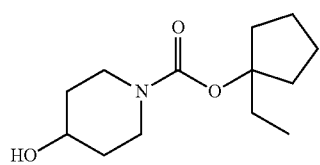
(D-55) 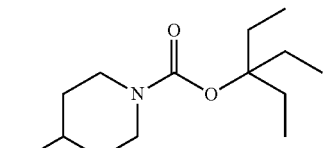
[Chem. 194]
(D-56) 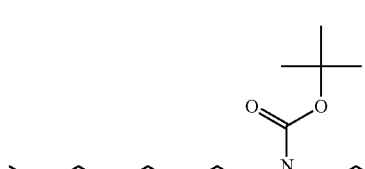
(D-57) 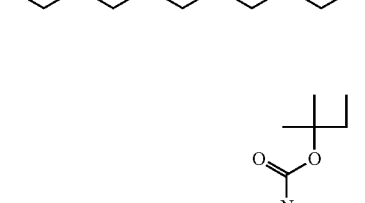
(D-58) 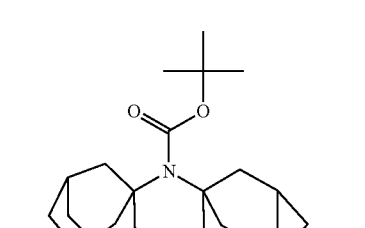
(D-59) 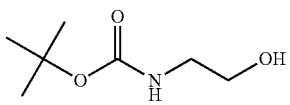
(D-60) 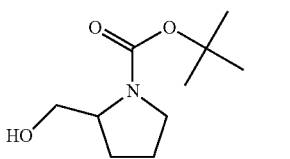
(D-61) 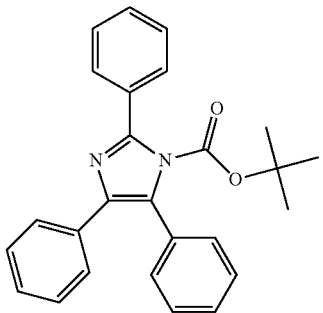

(D-62)
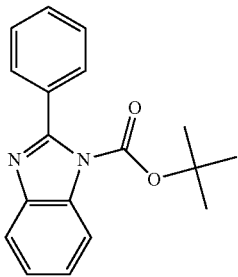

(D-63)
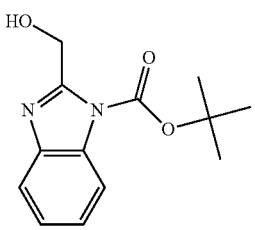

(D-64)
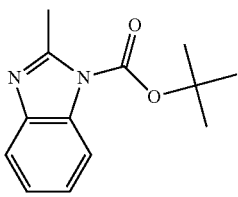

(D-65)
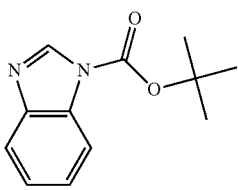

The compound represented by the general formula (A) can be synthesized, based on JP2007-298569A and JP2009-199021A, and the like.

In the present invention, the low molecular compound (D) may be used alone or in mixture of two or more kinds thereof.

The composition of the present invention may not contain the low molecular compound (D), but in the case where it contains the low molecular compound (D), the content of the compound (D) is usually from 0.001 to 20% by mole, preferably from 0.001 to 10% by mole, more preferably from 0.01 to 5% by mole, based on the total solid contents of the composition combined with the basic compound.

Furthermore, in the case where the composition of the present invention contains an acid generator, the ratio between the acid generator and the compound (D) used in the composition is preferably acid generator/[compound (D)+the following basic compound](molar ratio)=from 2.5 to 300. That is, the molar ratio is preferably 2.5 or more from the viewpoint of sensitivity and resolution, and preferably 300 or less from the viewpoint of suppressing the reduction in resolution due to thickening of the resist pattern with aging after exposure until heat treatment. The acid generator/[compound (D)+the basic compound above](molar ratio) is more preferably from 5.0 to 200, and still more preferably from 7.0 to 150.

Other examples of the compounds usable in the composition according to the present invention include the compounds synthesized in Examples of JP2002-363146A, and the compounds described in paragraph 0108 of JP2007-298569A.

Furthermore, photosensitive basic compounds may be used as the basic compound. As photosensitive basic compounds, use can be made of, for example, the compounds described in JP2003-524799A, J. Photopolym. Sci&Tech. Vol. 8, p. 543-553 (1995), etc.

The molecular weight of the basic compound is usually from 100 to 1,500, preferably from 150 to 1,300, and more preferably from 200 to 1,000.

This basic compound may be used alone or in combination of two or more kinds thereof.

In the case where the composition according to the present invention contains a basic compound the content of the basic compound is preferably 0.01 to 8.0% by mass, more preferably 0.1 to 5.0% by mass, and particularly preferably 0.2 to 4.0% by mass, based on the total solid contents of the composition.

The molar ratio of the basic compound to the photo-acid generator is preferably from 0.01 to 10, more preferably from 0.05 to 5, and still more preferably from 0.1 to 3. When this molar ratio is excessively high, the sensitivity and/or resolution may decrease in some cases. When this molar ratio is excessively small, there is a possibility that reduction in the pattern occurs between the exposure and the heating (post-bask). The molar ratio is more preferably from 0.05 to 5, and still more preferably from 0.1 to 3. The photo-acid generator as used in the molar ratio is based on the total amount of the repeating unit (B) of the resin and the photo-acid generator which the resin may further contain.

(6) Acid Proliferator

The actinic ray-sensitive or radiation-sensitive composition of the present invention may further one or two or more kinds of compounds capable of decomposing by the action of an acid to generate an acid (hereinafter also referred to as an acid proliferator). The acid that the acid proliferator generates is preferably a sulfonic acid, a methide acid, an imide acid, or the like. The content of the acid proliferator is preferably 0.1 to 50% by mass, more preferably 0.5 to 30% by mass, and still more preferably 1.0 to 20% by mass, based on the total solid contents of the composition.

The amount ratio of the acid proliferator to the acid generator (the solid fraction of the acid proliferator based on the total solid contents of the composition/the solid fraction of the acid generator based on the total solid contents of the composition) is not particularly limited, but is preferably 0.01 to 50, more preferably 0.1 to 20, and particularly preferably 0.2 to 1.0.

Examples of the compound that can be used in the present invention are shown below, but the present invention is not limited thereto.

[Chem. 195]

(PA-1)
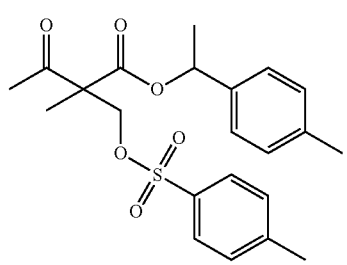

(PA-2) 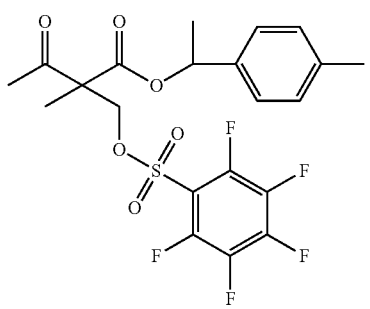
(PA-3) 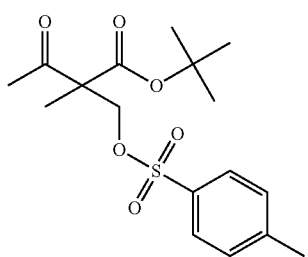
(PA-4) 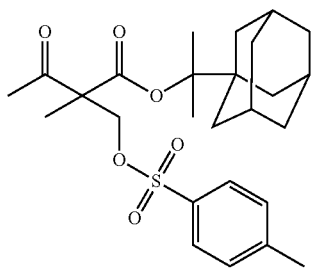
(PA-5) 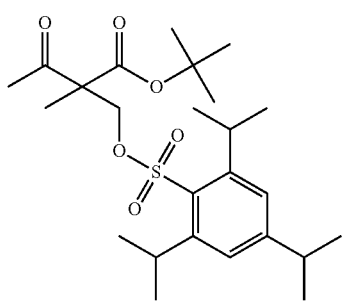
(PA-6) 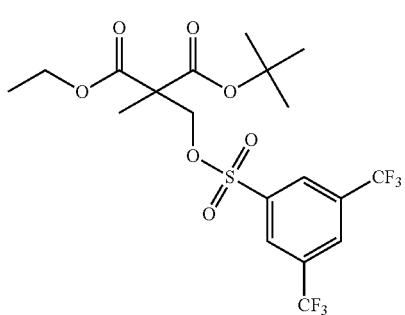
(PA-7) 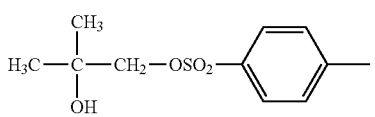
(PA-8) 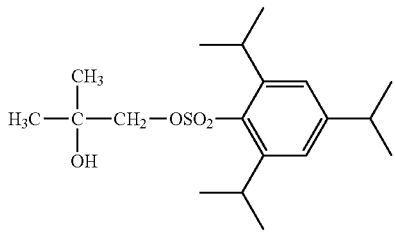
(PA-9) 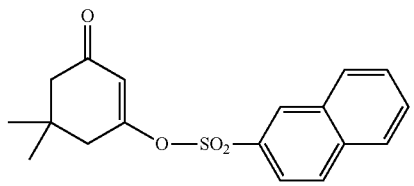
(PA-10) 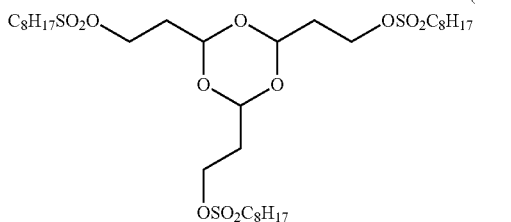
(PA-11) 
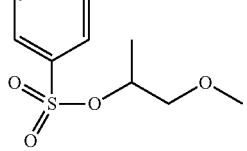
(PA-12) 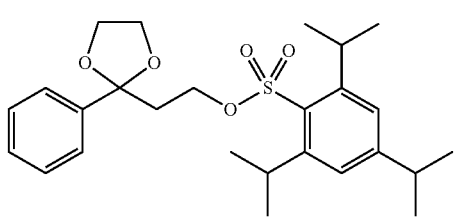
(PA-13) 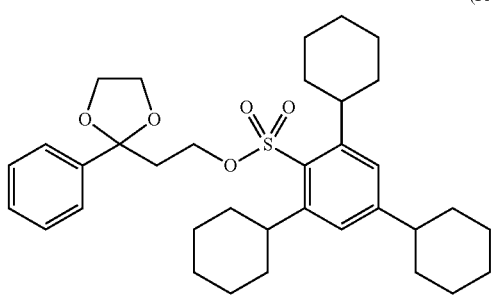
(PA-14) 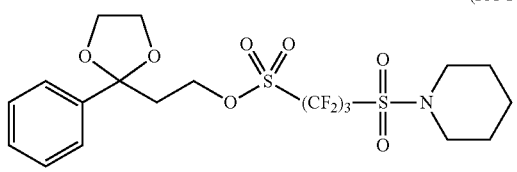

(PA-15)
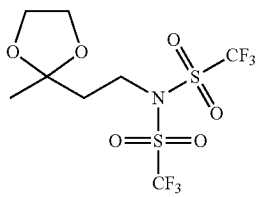

(PA-16)
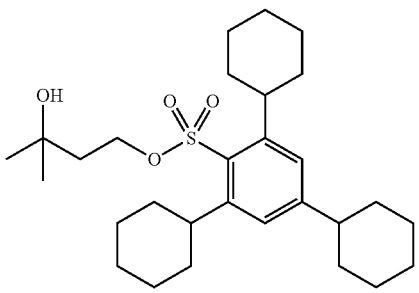

(PA-17)
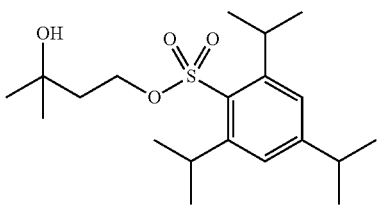

(PA-18)
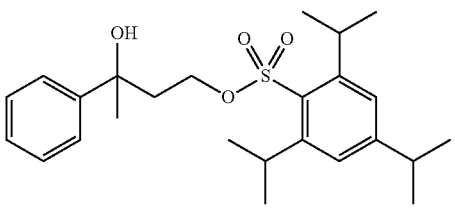

(7) Surfactant

The composition of the present invention may further contain a surfactant. The surfactant is particularly preferably a fluorine-based and/or silicon-based surfactant.

Examples of the fluorine-based and/or silicone-based surfactant include Megaface F176 or Megaface R08 manufactured by DIC Corporation, PF656 and PF6320 manufactured by OMNOVA SOLUTIONS, INC., Troy Sol S-366 manufactured by Troy Chemical Co., Ltd., Fluorad FC430 manufactured by Sumitomo 3M Ltd., and polysiloxane polymer KP-341 manufactured by Shin-Etsu Chemical Co., Ltd.

Surfactants other than these fluorine-based and/or silicone-based surfactants may also be used. Examples of such other surfactants include nonionic surfactants such as polyoxyethylene alkyl ethers and polyoxyethylene alkylaryl ethers.

Moreover, other generally known surfactants may also be appropriately used. Examples of the useful surfactants include those described in 0273 et seq. of US 2008/0248425 A1.

These surfactants may be used alone or in combination of two or more kinds thereof.

In the case where the composition according to the present invention further contains a surfactant, the amount of surfactant used is preferably in the range of 0.0001 to 2% by mass, and more preferably 0.001 to 1% by mass, based on the total solid contents of the composition.

(8) Dye

The composition according to the present invention may further include a dye. Examples of suitable dyes include oil dyes and basic dyes. Specific examples thereof include Oil Yellow #101, Oil Yellow #103, Oil Pink #312, Oil Green BG Oil Blue BOS, Oil Blue #603, Oil Black BY, Oil Black BS and Oil Black T-505 (all manufactured by Orient Chemical Industries, Ltd.), Crystal Violet (CI42555), Methyl Violet (CI42535), Rhodamine B (CI45170B), Malachite Green (CI42000), and Methylene Blue (CI52015).

(9) Photo-Base Generator

The composition according to the present invention may further contain a photo-base generator. When a photo-base generator is contained, a more excellent pattern can be formed.

Examples of the photo-base generator include compounds described in JP1992-151156A (JP-H04-151156A), JP1992-162040A (JP-H04-162040A), JP1993-197148A (JP-H05-197148A), JP1993-5995A (JP-H05-5995), JP1994-194834A (JP-H06-194834), JP1996-146608A (JP-H08-146608A), and JP1998-83079 (JP-H10-83079A), and EP622,682B.

Specific preferred examples of the photo-base generator include 2-nitrobenzylcarbamate, 2,5-dinitrobenzylcyclohexylcarbamate, N-cyclohexyl-4-methylphenylsulfonamide, and 1,1-dimethyl-2-phenylethyl-N-isopropylcarbamate.

(10) Antioxidant

The composition according to the present invention may further contain an antioxidant. When an antioxidant is contained, the organic material can be prevented from oxidation in the presence of oxygen.

Examples of the antioxidant include a phenol-based antioxidant, an antioxidant composed of an organic acid derivative, a sulfur-containing antioxidant, a phosphorus-based antioxidant, an amine-based antioxidant, an antioxidant composed of an amine-aldehyde condensate, and an antioxidant composed of an amine-ketone condensate. Among these antioxidants, a phenol-based antioxidant or an antioxidant composed of an organic acid derivative is particularly preferably used. When such an antioxidant is used, the function as an antioxidant can be brought out without deteriorating the performance of the composition.

As the phenol-based antioxidant, for example, substituted phenols, and bis-, tris-, and poly-phenols may be used.

Examples of the substituted phenols include 1-oxy-3-methyl-4-isopropylbenzene, 2,6-di-tert-butylphenol, 2,6-di-tert-butyl-4-ethylphenol, 2,6-di-tert-butyl-4-methylphenol, 4-hydroxymethyl-2,6-di-tert-butylphenol, butylhydroxyanisole, 2-(1-methylcyclohexyl)-4,6-dimethylphenol, 2,4-dimethyl6-tert-butylphenol, 2-methyl-4,6-dinonylphenol, 2,6-di-tert-butyl-α-dimethylamino-p-cresol, 6-(4-hydroxy-3,5-di-tert-butylanilino)2,4-bis-octyl-thio-1,3,5 triazine, n-octadecyl-3-(4'-hydroxy-3',5'-di-tertbutylphenyl)propionate, octylated phenol, aralkyl-substituted phenols, alkylated p-cresol, and hindered phenol.

Examples of the bis-, tris-, and poly-phenols include 4,4'-dihydroxydiphenyl, methylenebis(dimethyl-4,6-phenol), 2,2'-methylene-bis-(4-methyl-6-tert-butylphenol), 2,2'-methylene-bis-(4-methyl-6-cyclohexylphenol), 2,2'-methylene-bis-(4-ethyl-6-tert-butylphenol), 4,4'-methylene-bis-(2,6-di-tert-butylphenol), 2,2'-methylene-bis-(6-alphamethylbenzyl-p-cresol), methylene-crosslinked polyhydric alkylphenol, 4,4'-butylidenebis-(3-methyl-6-tertert-butylphenol), 1,1-bis-(4-hydroxyphenyl)cyclohexane, 2,2'-dihydroxy-3,3'-di-(α-methylcyclohexyl)-5,5'-dimethyldiphenylmethane, alkylated bisphenol, hindered bisphenol, 1,3,5-trimethyl-2,4,6-tris(3,5-di-tertert-butyl-4-hydroxybenzyl)

benzene, tris(2-methyl-4-hydroxy-5-tertert-butylphenyl)butane, tetrakis-[methylene-3-(3',5'-di-tertert-butyl-4'-hydroxyphenyl)propionate]methane.

Preferred examples of the antioxidants include 2,6-di-t-butyl-4-methylphenol, 4-hydroxymethyl-2,6-di-t-butylphenol, 2,2'-methylenebis(4-methyl-6-t-butylphenol), butylhydroxyanisole, t-butylhydroquinone, 2,4,5-trihydroxybutyrophenone, nordihydroguaiaretic acid, propyl gallate, octyl gallate, lauryl gallate, and isopropyl citrate. Among these, 2,6-di-t-butyl-4-methylphenol, 4-hydroxymethyl-2,6-di-t-butylphenol, butylhydroxyanisole and t-butylhydroquinone are preferred, and 2,6-di-t-butyl-4-methylphenol and 4-hydroxymethyl-2,6-di-t-butylphenol are more preferred.

These antioxidants may be used alone or in combination of two or more kinds thereof.

In the case where the composition according to the present invention contains an antioxidant, the addition amount of antioxidant is preferably 1 ppm or more, more preferably 5 ppm or more, still more preferably 10 ppm or more, even still more preferably 50 ppm or more, particularly preferably 100 ppm or more, and most preferably 100 to 1,000 ppm.

(11) Solvent

The composition according to the present invention may further contain a solvent. As the solvent, an organic solvent is typically used. Examples of the organic solvent include alkylene glycol monoalkyl ether carboxylate, alkylene glycol monoalkyl ether, alkyl lactate, alkyl alkoxypropionate, cyclic lactone (preferably having 4 to 10 carbon atoms), a monoketone compound (preferably having 4 to 10 carbon atoms) which may contain a ring, alkylene carbonate, alkyl alkoxyacetate, and alkyl pyruvate.

Preferred examples of the alkylene glycol monoalkyl ether carboxylate include propylene glycol monomethyl ether acetate (PGMEA; also called 1-methoxy-2-acetoxypropane), propylene glycol monoethyl ether acetate, propylene glycol monopropyl ether acetate, propylene glycol monobutyl ether acetate, propylene glycol monomethyl etherpropionate, propylene glycol monoethyl etherpropionate, ethylene glycol monomethyl ether acetate, and ethylene glycol monoethyl ether acetate.

Examples of the alkylene glycol monoalkyl ether include propylene glycol monomethyl ether (PGME; also called 1-methoxy-2-propanol), propylene glycol monoethyl ether, propylene glycol monopropyl ether, propylene glycol monobutyl ether, ethylene glycol monomethyl ether, and ethylene glycol monoethyl ether.

Examples of the alkyl lactate include methyl lactate, ethyl lactate, propyl lactate, and butyl lactate.

Examples of the alkyl alkoxypropionate include ethyl 3-ethoxypropionate, methyl 3-methoxypropionate, methyl 3-ethoxypropionate, and ethyl 3-methoxypropionate.

Examples of the cyclic lactone include β-propiolactone, β-butyrolactone, γ-butyrolactone, α-methyl-γ-butyrolactone, β-methyl-γ-butyrolactone, γ-valerolactone, γ-caprolactone, γ-octanoic lactone, and α-hydroxy-γ-butyrolactone.

Examples of the monoketone compound which may contain a ring include 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

Examples of the alkylene carbonate include propylene carbonate, vinylene carbonate, ethylene carbonate, and butylene carbonate.

Examples of the alkyl alkoxyacetate include 2-methoxyethyl acetate, 2-ethoxyethyl acetate, 2-(2-ethoxyethoxy)ethyl acetate, 3-methoxy-3-methylbutyl acetate, and 1-methoxy-2-propyl acetate.

Examples of the alkyl pyruvate include methyl pyruvate, ethyl pyruvate, and propyl pyruvate.

As the solvent, a solvent having a boiling point of 130° C. or higher at ordinary temperature under atmospheric pressure is preferably used. Specific examples thereof include cyclopentanone, γ-butyrolactone, cyclohexanone, ethyl lactate, ethylene glycol monoethyl ether acetate, PGMEA, ethyl 3-ethoxypropionate, ethyl pyruvate, 2-ethoxyethyl acetate, 2-(2-ethoxyethoxy)ethyl acetate, and propylene carbonate.

These solvents may be used alone or in a mixture of two or more kinds thereof. In the latter case, a mixed solvent of a solvent containing a hydroxyl group and a solvent not containing a hydroxyl group are preferably used.

Examples of the solvent containing a hydroxyl group include ethylene glycol, ethylene glycol monomethyl ether, ethylene glycol monoethyl ether, propylene glycol, PGME, propylene glycol monoethyl ether, and ethyl lactate. Among these, PGME and ethyl lactate are particularly preferred.

Examples of the solvent not containing a hydroxyl group include PGMEA, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone and butyl acetate are preferred. Among these, PGMEA, ethyl ethoxypropionate and 2-heptanone are more preferred.

In the case of using a mixed solvent of a solvent containing a hydroxyl group and a solvent not containing a hydroxyl group, the mass ratio therebetween is preferably from 1/99 to 99/1, more preferably from 10/90 to 90/10, and still more preferably from 20/80 to 60/40.

Incidentally, when a mixed solvent containing 50% by mass or more of a hydroxyl group-free solvent is used, particularly excellent coating uniformity can be achieved. Incidentally, the solvent is particularly preferably a mixed solvent of PGMEA and one or more kinds of other solvents.

The content of the solvent in the composition of the present invention may be appropriately adjusted according to the desired film thickness or the like, but the composition is usually prepared such that the entire solid content concentration of the composition becomes from 0.5 to 30% by mass, preferably from 1.0 to 20% by mass, and more preferably from 1.5 to 10% by mass.

<Pattern Forming Method>

The present invention relates to an actinic ray-sensitive or radiation-sensitive film formed using the above-described composition of the present invention. Further, the pattern forming method of the present invention includes a step of exposing and developing the actinic ray-sensitive or radiation-sensitive film.

The composition according to the present invention is typically used as follows. That is, the composition according to the present invention is typically coated on a support such as substrate to form a film. The thickness of the film is preferably from 0.02 to 0.1 μm. The method for coating the composition on a substrate is preferably spin coating, and the spinning speed is preferably from 1,000 to 3,000 rpm.

For example, the composition is coated on such a substrate (for example, a silicon/silicon dioxide-coated substrate, and a silicon nitride and chromium-deposited quartz substrate) as used in the production of a precision integrated circuit device, an imprint mold or the like, by using a spinner, a coater, or the like. Thereafter, the coating is dried to obtain actinic ray-sensitive or radiation-sensitive film (hereinafter also referred to as a resist film). Incidentally, a known antireflection film may also be previously provided by coating.

Subsequently, the actinic ray-sensitive or radiation-sensitive film is irradiated with actinic rays or radiation, then preferably baked (usually at 80 to 150° C., and preferably 90 to 130° C.), and developed. By performing baking, a more excellent pattern can be obtained.

Examples of the actinic ray or radiation include infrared light, visible light, ultraviolet light, far ultraviolet light, X ray and electron beam. An actinic ray or radiation having, for example, a wavelength of 250 nm or less, particularly 220 nm or less, is preferred. Examples of such actinic rays or radiation include KrF excimer laser (248 nm), ArF excimer laser (193 nm), $F_2$ excimer laser (157 nm), X ray, and electron beam. Preferred examples of the actinic ray or radiation include KrF excimer laser, electron beam, X ray, and EUV light, and more preferably electron beam, X ray, and EUV light.

That is, the present invention also relates to actinic ray-sensitive or radiation-sensitive resin composition for KrF excimer laser, electron beam, X ray or EUV light (preferably electron beam, X ray, or EUV light).

In the development step, an alkali developer is usually used.

Examples of the alkali developer include an alkaline aqueous solution containing inorganic alkalis such as sodium hydroxide, potassium hydroxide, sodium carbonate, sodium silicate, sodium metasilicate, and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, or cyclic amines such as pyrrole and piperidine.

Furthermore, an appropriate amount of an alcohol and/or a surfactant may be added to the alkali developer.

The concentration of the alkali developer is usually from 0.1 to 20% by mass. The pH of the alkali developer is usually from 10.0 to 15.0.

Moreover, an imprint mold may be produced using the composition according to the present invention. For details, reference may be made to, for example, JP4109085B, JP2008-162101A, and "Basic and Technology Expansion•Application Development of Nanoimprint-Substrate Technology of Nanoimprint and Latest Technology Expansion, edited by Yoshihiko Hirai (published by Frontier Publishing)".

The composition of the present invention may also be used in the process, in which after coating, forming a film, and exposing the film, development using a developer having an organic solvent as a main component is performed to obtain a negative tone pattern. For such as process, for example, a process described in JP2010-217884A may be used.

The vapor pressure of the developer having an organic solvent as a main component (the overall vapor pressure in the case of a mixed solvent) is preferably 5 kPa or less, more preferably 3 kPa or less, and particularly preferably 2 kPa at 20° C. By setting the vapor pressure of the organic solvent at 5 kPa or less, the evaporation of the developer on a substrate or in a developing cup is suppressed, and thus, the temperature uniformity in the wafer surface is improved. As a result, the dimension uniformity in the wafer surface becomes good.

As the organic solvent used in the developer, various organic solvents are used widely, but, for example, solvents such as an ester-based solvent, a ketone-based solvent, an alcohol-based solvent, an amide-based solvent, an ether-based solvent, and a hydrocarbon-based solvent may be used.

In the present invention, the ester-based solvent is a solvent having an ester group in the molecule, the ketone-based solvent is a solvent having a ketone group in the molecule, the alcohol-based solvent is a solvent having an alcoholic hydroxyl group in the molecule, the amide-based solvent is a solvent having an amide group in the molecule, and the ether-based solvent is a solvent having an ether bond in the molecule. Among these, there exists a solvent having a plurality of types of the above-described functional groups in one molecule, and in such as case, it is assumed that the solvent corresponds to any of the solvent species containing a functional group contained by the solvent. For example, it is assumed that diethylene glycol monomethyl ether corresponds to any of the alcohol-based solvents and the ether-based solvents among the classes above. Further, the hydrocarbon-based solvent is a hydrocarbon solvent having no substituent.

In particular, preferred is the developer containing at least one solvent selected from the ketone-based solvent, the ester-based solvent, the alcohol-based solvent, and the ether-based solvent.

A plurality of the solvents above may be mixed or a mixture of a solvent and a solvent other than the solvents above or water may be used. However, in order to sufficiently exhibit the effects of the present invention, the water content of the entire developer is preferably less than 10% by mass, and more preferably substantially does not contain water.

The concentration of the organic solvent in the developer (the sum in the case of a mixture of the plurality of the organic solvents) is preferably 50% by mass or more, more preferably 70% by mass or more, and still more preferably 90% by mass or more. A case where the developer contains substantially only the organic solvent is particularly preferred. Further, the case where the developer contains substantially only the organic solvent means that the developer contains trace amounts of a surfactant, an antioxidant, a stabilizer, an antifoaming agent, or the like.

It is more preferable that the developer contain at least one selected from the group consisting of butyl acetate, pentyl acetate, isopentyl acetate, propylene glycol monomethyl ether acetate, 2-heptanone, and anisole, among the solvents above.

EXAMPLES

The present invention is described in greater detail below, but the contents of the present invention are not limited thereto.

Synthesis Example 1

Synthesis of Compound (AM-21)

The compound (AM-21) was synthesized according to the following scheme.

10.00 g of the following compound (1) was dissolved in 100.00 g of methylene chloride, and 51.29 g of triethylamine was added thereto, followed by cooling to 0° C. 14.26 g of the following compound (2) and 90.00 g of a methylene chloride solution were added dropwise thereto. After stirring for 3 hours, a saturated aqueous sodium hydrogen carbonate solution was added to the mixture. Subsequently, 300 g of methylene chloride was added thereto, and an operation for extracting a product from the aqueous layer was carried out three times. The obtained organic layer was dried over anhydrous magnesium sulfate, and the solvent was evaporated. The residue was isolated and purified by column chromatography to obtain 11.00 g of a compound (AM-21).

$^1$H-NMR (ppm, CDCl$_3$): 1.22 (9H, s), 4.05 (2H, d), 4.30 (2H, d), 7.25-7.33 (10H, m)

$^1$H-NMR (ppm, toluene-d$_8$): 1.34 (3H, t), 2.4-2.7 (2H, m), 5.59 (1H, d), 6.75 (1H, q), 7.0-7.2 (3H, m), 7.88 (1H, d), 8.29 (1H, d)

[Chem. 197]

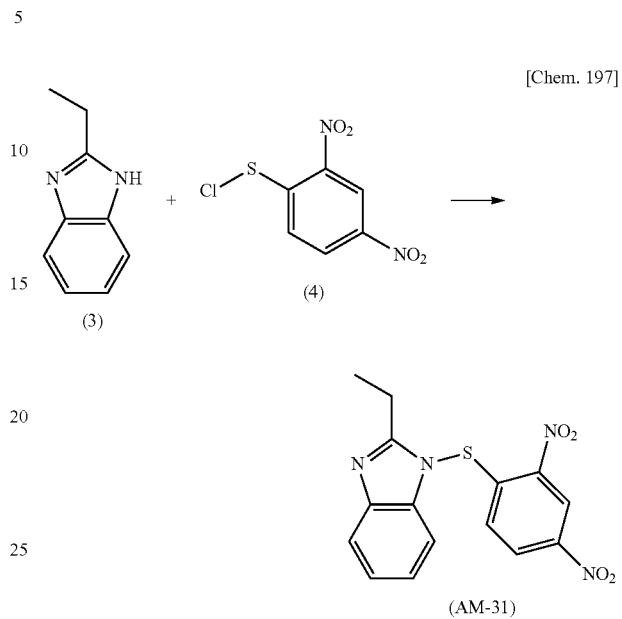

[Chem. 196]

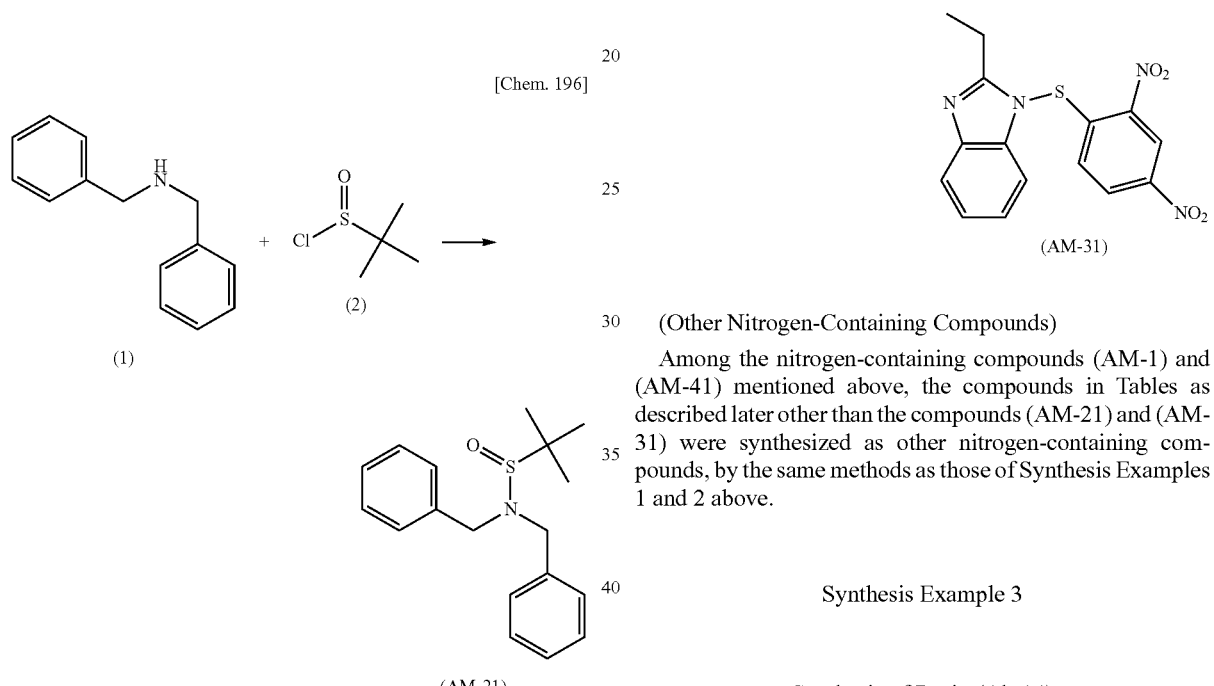

(Other Nitrogen-Containing Compounds)

Among the nitrogen-containing compounds (AM-1) and (AM-41) mentioned above, the compounds in Tables as described later other than the compounds (AM-21) and (AM-31) were synthesized as other nitrogen-containing compounds, by the same methods as those of Synthesis Examples 1 and 2 above.

Synthesis Example 2

Synthesis of Compound (AM-31)

The compound (AM-31) was synthesized according to the following scheme.

10.00 g of the following compound (3) was dissolved in 300.00 g of dehydrated tetrahydrofuran, and 8.31 g of triethylamine was added thereto, followed by cooling to 0° C. 16.05 g of the following compound (4) was added thereto, and the mixture was stirred at room temperature for 30 minutes, and then heated and refluxed for 5 hours. Subsequently, the mixture was left to be cooled to room temperature, and then 1,000 g of ethyl acetate was added thereto. Thereafter, the organic layer was washed with 300 g of ion exchange water three times, and then dried over anhydrous magnesium sulfate, and the solvent was removed by distillation. The residue was isolated and purified by column chromatography to obtain 12.95 g of a compound (AM-31).

Synthesis Example 3

Synthesis of Resin (Ab-14)

The resin (Ab-14) was synthesized by the same method as the synthesis method for the polymer (B-2) described in paragraph 0153 of JP2007-052193A.

Synthesis Example 4

Synthesis of Resin (Ab-97)

The resin (Ab-97) was synthesized by the same method as the synthesis method for the polymer (A-1) described in paragraph 0357 of JP2009-86358A.

Synthesis Example 5

Synthesis of Resin (Ab-245)

The resin (Ab-245) was synthesized in accordance with the following scheme.

[Chem. 198]

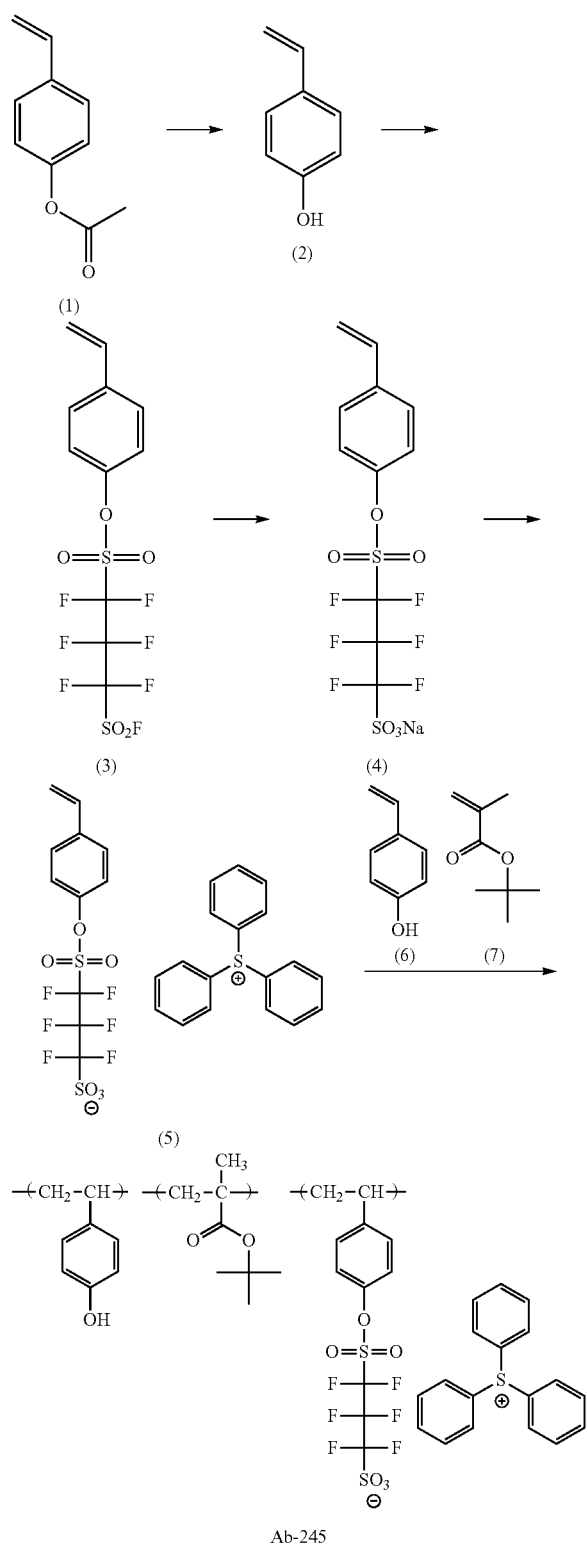

Ab-245

<Synthesis of Compound (5)>

100.00 g of the compound (1) was dissolved in 400 g of ethyl acetate. The obtained solution was cooled to 0° C., and 47.60 g of sodium methoxide (28%-by-mass methanol solution) was added dropwise thereto over 30 minutes. Thereafter, the mixture was stirred at room temperature over 5 hours. Ethyl acetate was added to the reaction solution, and subsequently, the organic layer was washed with distilled water three times and then dried over anhydrous sodium sulfate. The solvent was removed by distillation. In this way, 131.70 g of a compound (2) (54%-by-mass ethyl acetate solution) was obtained.

56.00 g of ethyl acetate was added to 18.52 g of the compound (2) (54%-by-mass ethyl acetate solution) was added. 31.58 g of 1,1,2,2,3,3-hexafluoropropane-1,3-disulfonyl difluoride was added thereto, followed by cooling to 0° C. A solution formed by dissolving 12.63 g of triethylamine in 25.00 g of ethyl acetate was added dropwise to the cooled solution over 30 minutes, and the mixture was stirred over 4 hours while maintaining the temperature of the liquid at 0° C. Ethyl acetate was added to the obtained solution, and then the organic layer was washed with saturated brine three times and dried over anhydrous sodium sulfate. The solvent was removed by distillation. In this way, 32.90 g of a compound (3) was obtained.

35.00 g of the compound (3) was dissolved in 315 g of methanol, followed by cooling to 0° C. 245 g of a 1 N aqueous sodium hydroxide solution was added thereto, and the mixture was stirred at room temperature for 2 hours. The solvent was removed by distillation, and then ethyl acetate was added thereto. The organic layer was washed with saturated brine three times, followed by drying over anhydrous sodium sulfate, and the solvent was removed by distillation. In this way, 34.46 g of a compound (4) was obtained.

28.25 g of the compound (4) was dissolved in 254.25 g of methanol, 23.34 g of triphenylsulfonium bromide was added thereto and the mixture was stirred at room temperature for 3 hours. The solvent was removed by distillation, distilled water was added thereto, and the product was extracted with chloroform three times. The obtained organic layer was washed with distilled water three times, and then the solvent was removed by distillation. In this way, 42.07 g of a compound (5) was obtained.

<Synthesis of Resin (Ab-245)>

8.15 g of the compound (6) (53.1%-by-mass propylene glycol monomethyl ether solution), 6.14 g of the compound (7), 7.31 g of the compound (5), and 2.07 g of a polymerization initiator V-601 (manufactured by Wako Pure Chemical Industries, Ltd.) were dissolved in 30.13 g of propylene glycol monomethyl ether (PGME). Under a nitrogen gas atmosphere, the obtained solution was added dropwise to 7.53 g of PGME that had been heated to 85° C. over 2 hours. The reaction solution was heated and stirred over 4 hours, and then left to be cooed to room temperature.

The reaction solution was diluted by the addition of 30 g of acetone. The diluted solution was added dropwise to 1,000 g of hexane/ethyl acetate=8/2, and the polymer was precipitated and filtered. 250 g of hexane/ethyl acetate=8/2 was used and poured into the filtered solid for washing. The obtained solid was dissolved in 70 g of acetone, and the solution was added dropwise to 700 g of methanol/distilled water=1/9 to precipitate a polymer, followed by filtration. 150 g of methanol/distilled water=1/9 was used and poured into the filtered solid for washing. Thereafter, the washed solid was provided to be dried under reduced pressure to obtain 13.87 g of a resin Ab-245.

(Other Resins (Ab))

Among the resins (Ab-1) to (Ab-283) mentioned above, the respective resins shown in Table 2 were synthesized as the resins (Ab) other than the resins (Ab-14), (Ab-97), and (Ab-245) by the same methods as those mentioned in Synthesis Examples 3 to 5.

With respect to the resins (Ab) synthesized above, the weight average molecular weight and the dispersity were measured using GPC (manufactured by Tosoh Corp., HLC-8120; Tsk gel Multipore HXL-M). The results obtained are shown in Tables below together with the compositional ratios. Further, in this GPC measurement, THF was used as the solvent.

TABLE 2

|  | Weight average molecular weight | Compositional ratio | | | | | Dispersity |
|---|---|---|---|---|---|---|---|
| Ab-14 | 3,000 | 70 | 30 | — | — | — | 1.10 |
| Ab-17 | 12,000 | 10 | 65 | 25 | — | — | 1.12 |
| Ab-97 | 18,000 | 50 | 40 | 10 | — | — | 1.61 |
| Ab-120 | 7,000 | 60 | 40 | — | — | — | 1.45 |
| Ab-143 | 8,500 | 40 | 15 | 20 | 25 | — | 1.69 |
| Ab-167 | 3,500 | 55 | 45 | — | — | — | 1.12 |
| Ab-173 | 4,000 | 60 | 40 | — | — | — | 1.15 |
| Ab-178 | 24,000 | 50 | 35 | 15 | — | — | 1.65 |
| Ab-232 | 10,000 | 45 | 10 | 35 | 10 | — | 1.55 |
| Ab-233 | 11,000 | 10 | 35 | 10 | 35 | 10 | 1.53 |
| Ab-234 | 10,000 | 10 | 35 | 10 | 35 | 10 | 1.56 |
| Ab-238 | 5,000 | 45 | 25 | 5 | 25 | — | 1.73 |
| Ab-240 | 20,000 | 55 | 40 | 5 | — | — | 1.50 |
| Ab-245 | 9,000 | 40 | 48 | 12 | — | — | 1.38 |
| Ab-269 | 10,000 | 50 | 50 | — | — | — | 1.13 |
| Ab-273 | 17,000 | 70 | 30 | — | — | — | 1.15 |
| Ab-275 | 5,000 | 60 | 40 | — | — | — | 1.16 |
| Ab-277 | 7,000 | 75 | 25 | — | — | — | 1.16 |
| Ab-281 | 12,000 | 30 | 10 | 60 | — | — | 1.55 |
| Ab-282 | 15,000 | 45 | 55 | — | — | — | 1.58 |
| Ab-283 | 9,000 | 20 | 5 | 75 | — | — | 1.60 |

<Resin (Aa)>

Among the resins (Aa-1) to (Aa-55) mentioned above, (Aa-1), (Aa-16), (Aa-29), and (Aa-52) shown in Tables 3 and 6 were used as the resin (Aa).

<Photo-Acid Generator>

Among the compounds (B-1) to (B-183), (Y-1) to (Y-75) mentioned above, the compounds shown in Tables 3 and 4 were used as the photo-acid generator.

<Basic Compound>

Any one of the following N-1 to N-4 was used as the basic compound other than the nitrogen-containing compound of the present invention.

[Chem. 199]

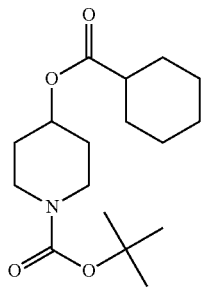

N-1

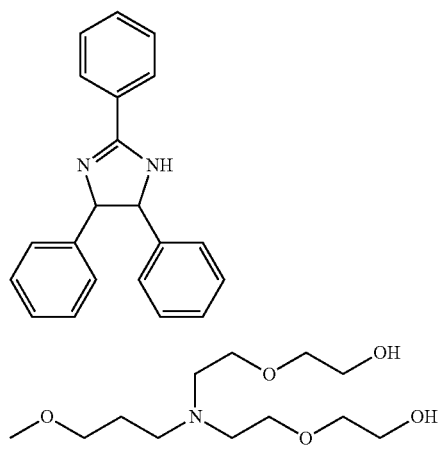

N-2

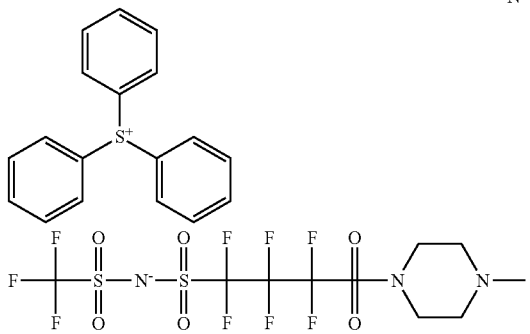

N-3

N-4

<Surfactant>

Any one of the following W-1 to W-4 was used as the surfactant.

W-1: Megaface R08 (manufactured by Dainippon Ink & Chemicals, Inc.; fluorine- and silicon-based)

W-2: Polysiloxane Polymer KP-341 (manufactured by Shin-Etsu Chemical Co., Ltd.; silicon-based)

W-3: Troysol S-366 (manufactured by Troy Chemical; fluorine-based)

W-4: PF6320 (manufactured by OMNOVA; fluorine-based)

<Solvent>

Any one of the following S-1 to S-4 was appropriately mixed and used as the solvent.

S-1: PGMEA (b.p.=146° C.)
S-2: PGME (b.p.=120° C.)
S-3: Methyl lactate (b.p.=145° C.)
S-4: Cyclohexanone (b.p.=157° C.)

<Developer>

G-1: Butyl acetate
G-2: Methyl amyl ketone (2-heptanone)
G-3: Anisole

<Rinsing Liquid>

G-4: 4-Methyl-2-pentanol
G-5: 1-Hexanol
G-6: Decane

<Evaluation of Resist: EB Exposure, Alkali Development/Positive Tone Pattern>

The components shown in Table 3 below were dissolved in the solvent shown in the same Tables to prepare a solution having a solid content concentration of 3.0% by mass. This solution was finely filtered through a membrane filter having a pore size of 0.1 μm to obtain a resist solution.

The numerical value of "% by mass" shown in Table 3 is a value based on the entire solid content excluding the surfactant of the composition. Incidentally, the content of the surfactant is 0.01% by mass based on the entire solid content excluding the surfactant of the composition.

The positive tone resist solution above was coated on a hexamethyldisilazane-treated silicon substrate by using a spin coater and dried by heating on a hot plate at 100° C. for 60 seconds to obtain a resist film having an average thickness of 100 nm.

This resist film was irradiated with electron beam using an electron beam irradiation apparatus (HL750, manufactured by Hitachi, Ltd., accelerating voltage: 50 keV). Immediately after the irradiation, the film was baked on a hot plate at 100° C. for 90 seconds, then developed with an aqueous tetramethylammonium hydroxide solution having a concentration of 2.38% by mass at 23° C. for 60 seconds, rinsed with pure water for 30 seconds, and dried by heating at 95° C. for 60 seconds. In this way, a line-and-space pattern (line:space=1:1) was formed.

<Evaluation of Resist: EB Exposure, Organic Solvent Development/Negative Tone Pattern>

The components shown in Table 4 below were dissolved in the solvent shown in the same Tables to prepare a solution having a solid content concentration of 3.0% by mass. This solution was finely filtered through a membrane filter having a pore size of 0.1 μm to obtain a resist solution.

The numerical value of "% by mass" shown in Table 4 is a value based on the entire solid content excluding the surfactant of the composition. Incidentally, the content of the surfactant is 0.01% by mass based on the entire solid content excluding the surfactant of the composition.

A pattern formation was carried out in the same manner as for the alkali development/positive pattern except that the development was carried out by means of an organic developer instead of the alkali developer while irradiating the inverted drawing area with an electron beam, the development was carried out for 30 seconds instead of 60 seconds, and an organic rinsing liquid was used instead of pure water as the rinsing liquid.

For each of the obtained positive tone pattern and the negative tone pattern, the sensitivity, the pattern profiles, and the resolution were evaluated by the evaluation methods described below.

(Sensitivity)

The cross-sectional profile of the obtained line-and-space pattern was observed using a scanning electron microscope (S-4800, manufactured by Hitachi, Ltd.), and the minimum irradiation energy when resolving a line having a line width of 100 nm was determined. This value was shown as "Sensitivity (μC/cm$^2$)". The evaluation results are shown in Table 3.

(Pattern Profile)

The cross-sectional profile of the 100-nm line pattern (line:space=1:1) at the irradiation dose giving the sensitivity above was observed using a scanning electron microscope (S-4800, manufactured by Hitachi, Ltd.), and the profile was evaluated on a 3-stage scale, that is, "Rectangular", "Tapered", and "Reversely tapered".

(Resolution)

In the sensitivity obtained above, a minimum nm at which resolution could be made with line:space=1:1 was observed using a scanning electron microscope.

The evaluation results are shown in Tables 3 and

TABLE 3

(EB Exposure, Alkali Development)

| | Resist composition | | | | | | Evaluation results | | |
|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | Surfactant (0.01% by mass) | Sensitivity (μC/cm$^2$) | Pattern profile | Resolution (nm) |
| Ex. 1 | — | Ab-17 (63) | S-4/S-3 (80/20) | B-110 (35) | AM-10/N-2 (80/20) | W-3 | 20 | Rectangular | 62.5 |
| Ex. 2 | — | Ab-178 (88) | S-2 | B-122 (10) | AM-13 | W-3 | 12 | Rectangular | 50.0 |
| Ex. 3 | — | Ab-178 (88) | S-2 | B-122 (10) | AM-12 | W-3 | 17 | Rectangular | 62.5 |
| Ex. 4 | Aa-16 (5) | Ab-240 (93) | S-2/S-3 (80/20) | — | AM-31 | W-4 | 10 | Rectangular | 37.5 |
| Ex. 5 | Aa-29 (5) | Ab-173 (58) | S-1/S-2 (70/30) | B-123 (35) | AM-21 | W-4 | 15 | Rectangular | 50.0 |
| Ex. 6 | — | Ab-14 (63) | S-1/S-2 (80/20) | B-119 (35) | AM-38 | W-4 | 14 | Rectangular | 50.0 |
| Ex. 7 | — | Ab-14 (63) | S-1/S-2 (80/20) | B-119 (35) | AM-12 | W-4 | 21 | Rectangular | 62.5 |
| Ex. 8 | — | Ab-232 (98) | S-2/S-4 (70/30) | — | AM-15 | W-2 | 26 | Rectangular | 87.5 |
| Ex. 9 | — | Ab-233 (98) | S-2/S-4 (70/30) | — | AM-15 | W-2 | 22 | Rectangular | 75.0 |
| Ex. 10 | — | Ab-234 (98) | S-2/S-4 (70-30) | — | AM-15 | W-2 | 18 | Rectangular | 62.5 |
| Ex. 11 | — | Ab-245 (98) | S-2/S-1 (90/10) | — | AM-34 | W-1 | 12 | Rectangular | 50.0 |
| Ex. 12 | — | Ab-143 (63) | S-4/S-1 (90/10) | B-118 (35) | AM-40 | W-3 | 14 | Rectangular | 50.0 |
| Ex. 13 | — | Ab-143 (63) | S-4/S-1 (90/10) | B-118 (35) | AM-38 | W-3 | 18 | Rectangular | 62.5 |
| Ex. 14 | — | Ab-143 (63) | S-4/S-1 (90/10) | B-118 (35) | AM-39 | W-3 | 22 | Rectangular | 75.0 |
| Ex. 15 | — | Ab-143 (63) | S-4/S-1 (90/10) | B-118 (35) | AM-30 | W-3 | 26 | Rectangular | 87.5 |
| Ex. 16 | Aa-52 (5) | Ab-120 (58) | S-3/S-2 (90/10) | Y-70 (35) | AM-4 | W-2 | 13 | Rectangular | 50.0 |
| Ex. 17 | — | Ab-97 (63) | S-1/S-2 (90/10) | B-149 (35) | AM-18 | W-4 | 19 | Rectangular | 62.5 |

TABLE 3-continued (EB Exposure, Alkali Development)

| | Resist composition | | | | | Surfactant | Evaluation results | | |
|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | (0.01% by mass) | Sensitivity ($\mu C/cm^2$) | Pattern profile | Resolution (nm) |
| Ex. 18 | — | Ab-167 (63) | S-1/S-4 (80/20) | Y-61 (35) | AM-38 | W-3 | 11 | Rectangular | 37.5 |
| Ex. 19 | — | Ab-167 (63) | S-1/S-4 (80/20) | Y-61 (35) | AM-41 | W-3 | 15 | Rectangular | 50.0 |
| Ex. 20 | — | Ab-238 (98) | S-3/S-4 (80/20) | — | AM-1/N-4 (50/50) | W-3 | 18 | Rectangular | 62.5 |
| Ex. 21 | — | Ab-269 (78) | S-1/S-2 (90/10) | B-104 (20) | AM-31 | W-2 | 20 | Rectangular | 75.0 |
| Ex. 22 | — | Ab-273 (58) | S-1/S-2 (70/30) | Y-3 (40) | AM-16 | W-1 | 12 | Rectangular | 62.5 |
| Ex. 23 | — | Ab-275 (68) | S-1/S-2 (70/30) | B-182 (30) | AM-38 | W-4 | 14 | Rectangular | 37.5 |
| Ex. 24 | — | Ab-277 (73) | S-1/S-2 (60/40) | B-182 (25) | AM-30 | W-3 | 16 | Rectangular | 50.0 |
| Ex. 25 | — | Ab-281 (83) | S-1/S-2 (80/20) | B-121 (15) | AM-38 | W-4 | 18 | Rectangular | 62.5 |
| Ex. 26 | — | Ab-282 (63) | S-1/S-2 (50/50) | B-181 (35) | AM-5 | W-3 | 15 | Rectangular | 50.0 |
| Ex. 27 | — | Ab-283 (78) | S-1/S-2 (60/40) | B-180 (20) | AM-11 | W-4 | 15 | Rectangular | 62.5 |
| Comp. Ex. 1 | — | Ab-97 (63) | S-1/S-2 (90/10) | B-149 (35) | N-3 | W-4 | 32 | Reversely tapered | 125.0 |
| Comp. Ex. 2 | — | Ab-245 (98) | S-2/S-1 (90/10) | — | N-1 | W-1 | 33 | Reversely tapered | 112.5 |
| Comp. Ex. 3 | — | Ab-17 (63) | S-4/S-3 (80/20) | B-110 (35) | N-2 | W-3 | 35 | Reversely tapered | 125.0 |

TABLE 4

(EB Exposure, Organic Solvent Development)

| | Resist composition | | | | | Surfactant | | | Evaluation results | | |
|---|---|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | (0.01% by mass) | Developer | Rinsing liquid | Sensitivity ($\mu C/cm^2$) | Pattern profile | Resolution (nm) |
| Ex. 28 | — | Ab-178 (88) | S-2 | B-122 (10) | AM-12 | W-3 | G-1 | G-6 | 14 | Rectangular | 75.0 |
| Ex. 29 | — | Ab-245 (98) | S-2/S-1 (90/10) | — | AM-34 | W-1 | G-1 | — | 15 | Rectangular | 62.5 |
| Ex. 30 | — | Ab-143 (63) | S-4/S-1 (90/10) | B-118 (35) | AM-30 | W-3 | G-1 | G-5 | 27 | Rectangular | 87.5 |
| Ex. 31 | — | Ab-97 (63) | S-1/S-2 (90/10) | B-149 (35) | AM-18 | W-4 | G-3 | — | 20 | Rectangular | 75.0 |
| Ex. 32 | — | Ab-281 (83) | S-1/S-2 (80/20) | B-121 (15) | AM-38 | W-4 | G-1 | — | 21 | Rectangular | 62.5 |
| Ex. 33 | — | Ab-282 (63) | S-1/S-2 (50/50) | B-181 (35) | AM-5 | W-3 | G-1 | G-4 | 16 | Rectangular | 62.5 |
| Ex. 34 | Aa-1 (10) | Ab-283 (68) | S-1/S-2 (60/40) | B-180 (20) | AM-15 | W-2 | G-2 | — | 18 | Rectangular | 62.5 |
| Comp. Ex. 4 | — | Ab-97 (63) | S-1/S-2 (90/10) | B-149 (35) | N-3 | W-4 | G-3 | — | 34 | Tapered | 125.0 |
| Comp. Ex. 5 | — | Ab-245 (98) | S-2/S-1 (90/10) | — | N-1 | W-1 | G-1 | — | 35 | Tapered | 125.0 |

<Evaluation of Resist: EUV Exposure, Alkali Development/Positive Tone Pattern>

The components shown in Table 4 below were dissolved in the solvent shown in the same Tables to prepare a solution having a solid content concentration of 1.5% by mass, and the solution was filtered through a membrane filter having a pore size of 0.05 μm to obtain a resist solution.

The numerical value of "% by mass" shown in Table 5 is a value based on the entire solid content excluding the surfactant of the composition. Incidentally, the content of the surfactant is 0.01% by mass based on the entire solid content excluding the surfactant of the composition.

The positive tone resist solution above was coated on a hexamethyldisilazane-treated silicon substrate by using a spin coater and dried by heating on a hot plate at 100° C. over 60 seconds to obtain a resist film having an average thickness of 50 nm.

This resist film was irradiated with EUV light using an EUV exposure apparatus (Micro Exposure Tool, NA0.3, X-dipole manufactured by Exitech, Outer Sigma 0.68, Inner Sigma 0.36). Immediately after the irradiation, the film was baked on a hot plate at 100° C. over 90 seconds, then developed with an aqueous tetramethylammonium hydroxide solution having a concentration of 2.38% by mass at 23° C. for 60 seconds, rinsed with pure water for 30 seconds, and dried by heating at 95° C. for 60 seconds. In this way, a line-and-space pattern (line:space=1:1) was formed.

<Evaluation of Resist: EUV Exposure, Organic Solvent Development/Negative Tone Pattern>

The components shown in Table 6 below were dissolved in the solvent shown in the same Tables to prepare a solution having a solid content concentration of 1.5% by mass. This solution was finely filtered through a membrane filter having a pore size of 0.05 μm to obtain a resist solution.

The numerical value of "% by mass" shown in Table 6 is a value based on the entire solid content excluding the surfactant of the composition. Incidentally, the content of the surfactant is 0.01% by mass based on the entire solid content excluding the surfactant of the composition.

A pattern formation was carried out in the same manner as for the alkali development/positive pattern except that the development was carried out by means of an organic developer instead of the alkali developer using an exposing mask that inverted the pattern of the exposed mask, the development was carried out for 30 seconds instead of 60 seconds, and an organic rinsing liquid was used instead of pure water as the rinsing liquid.

For each of the obtained positive tone pattern and the negative tone pattern, the sensitivity, the pattern profiles, the resolution, and DOF were evaluated by the evaluation methods described below.

(Sensitivity)

First, the cross-sectional profile of the obtained line-and-space pattern was observed using a scanning electron microscope (S-4800, manufactured by Hitachi, Ltd.), and the minimum irradiation energy when resolving a line having a line width of 50 nm was determined. This value was shown as "Sensitivity (mJ/cm$^2$)".

(Pattern Profile)

The cross-sectional profile of the 100-nm line pattern (line:space=1:1) at the irradiation dose giving the sensitivity above was observed using a scanning electron microscope (S-4800, manufactured by Hitachi, Ltd.), and the profile was evaluated on a 2-stage scale, that is, "Rectangular" and "Reversely tapered".

(Resolution)

In the sensitivity obtained above, a minimum nm at which resolution could be made with line:space=1:1 was observed using a scanning electron microscope.

(DOF)

For a 50-nm line pattern (line:space=1:1), a 50-nm isolated line (line:space=1:10), and a 50-nm isolated trench pattern, an acceptable range of focus variation was determined and a common focus variation width (μm) acceptable in all was determined.

These evaluation results are shown in Tables 5 and 6.

TABLE 5

(EUV Exposure, Alkali Development)

| | Resist composition | | | | | Evaluation results | | | |
|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | Surfactant (0.01% by mass) | Sensitivity (mJ/cm$^2$) | Pattern profile | Resolution (nm) | DOF (μm) |
| Ex. 35 | — | Ab-17 (63) | S-4/S-3 (80/20) | B-110 (35) | AM-10/N-2 (80/20) | W-3 | 18 | Rectangular | 34.0 | 0.20 |
| Ex. 36 | — | Ab-178 (88) | S-2 | B-122 (10) | AM-13 | W-3 | 11 | Rectangular | 32.0 | 0.25 |
| Ex. 37 | — | Ab-178 (88) | S-2 | B-122 (10) | AM-12 | W-3 | 16 | Rectangular | 34.0 | 0.20 |
| Ex. 38 | Aa-16 (5) | Ab-240 (93) | S-2/S-3 (80/20) | — | AM-31 | W-4 | 9 | Rectangular | 30.0 | 0.30 |
| Ex. 39 | Aa-29 (5) | Ab-173 (58) | S-1/S-2 (70/30) | B-123 (35) | AM-21 | W-4 | 15 | Rectangular | 32.0 | 0.25 |
| Ex. 40 | — | Ab-14 (63) | S-1/S-2 (80/20) | B-119 (35) | AM-38 | W-4 | 11 | Rectangular | 32.0 | 0.25 |
| Ex. 41 | — | Ab-14 (63) | S-1/S-2 (80/20) | B-119 (35) | AM-12 | W-4 | 19 | Rectangular | 34.0 | 0.20 |
| Ex. 42 | — | Ab-232 (98) | S-2/S-4 (70/30) | — | AM-15 | W-2 | 26 | Rectangular | 38.0 | 0.10 |
| Ex. 43 | — | Ab-233 (98) | S-2/S-4 (70/30) | — | AM-15 | W-2 | 22 | Rectangular | 36.0 | 0.15 |
| Ex. 44 | — | Ab-234 (98) | S-2/S-4 (70/30) | — | AM-15 | W-2 | 17 | Rectangular | 34.0 | 0.20 |
| Ex. 45 | — | Ab-245 (98) | S-2/S-1 (90/10) | — | AM-34 | W-1 | 12 | Rectangular | 32.0 | 0.25 |
| Ex. 46 | — | Ab-143 (63) | S-4/S-1 (90/10) | B-118 (35) | AM-40 | W-3 | 18 | Rectangular | 30.0 | 0.25 |
| Ex. 47 | — | Ab-143 (63) | S-4/S-1 (90/10) | B-118 (35) | AM-38 | W-3 | 20 | Rectangular | 32.0 | 0.20 |
| Ex. 48 | — | Ab-143 (63) | S-4/S-1 (90/10) | B-118 (35) | AM-39 | W-3 | 23 | Rectangular | 34.0 | 0.15 |
| Ex. 49 | — | Ab-143 (63) | S-4/S-1 (90/10) | B-118 (35) | AM-30 | W-3 | 26 | Rectangular | 36.0 | 0.10 |

TABLE 5-continued (EUV Exposure, Alkali Development)

| | Resist composition | | | | | | Evaluation results | | | |
|---|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | Surfactant (0.01% by mass) | Sensitivity (mJ/cm$^2$) | Pattern profile | Resolution (nm) | DOF (μm) |
| Ex. 50 | Aa-52 (5) | Ab-120 (58) | S-3/S-2 (90/10) | Y-70 (35) | AM-4 | W-2 | 13 | Rectangular | 32.0 | 0.25 |
| Ex. 51 | — | Ab-97 (63) | S-1/S-2 (90/10) | B-149 (35) | AM-18 | W-4 | 18 | Rectangular | 34.0 | 0.20 |
| Ex. 52 | — | Ab-167 (63) | S-1/S-4 (80/20) | Y-61 (35) | AM-38 | W-3 | 10 | Rectangular | 32.0 | 0.25 |
| Ex. 53 | — | Ab-167 (63) | S-1/S-4 (80/20) | Y-61 (35) | AM-41 | W-3 | 14 | Rectangular | 34.0 | 0.20 |
| Ex. 54 | — | Ab-238 (98) | S-3/S-4 (80/20) | — | AM-1/N-4 (50/50) | W-3 | 17 | Rectangular | 34.0 | 0.20 |
| Ex. 55 | — | Ab-269 (78) | S-1/S-2 (90/10) | B-104 (20) | AM-31 | W-2 | 18 | Rectangular | 38.0 | 0.15 |
| Ex. 56 | — | Ab-273 (58) | S-1/S-2 (70/30) | Y-3 (40) | AM-16 | W-1 | 11 | Rectangular | 36.0 | 0.15 |
| Ex. 57 | — | Ab-275 (68) | S-1/S-2 (70/30) | B-182 (30) | AM-38 | W-4 | 14 | Rectangular | 32.0 | 0.25 |
| Ex. 58 | — | Ab-277 (73) | S-1/S-2 (60/40) | B-182 (25) | AM-30 | W-3 | 15 | Rectangular | 34.0 | 0.25 |
| Ex. 59 | — | Ab-281 (83) | S-1/S-2 (80/20) | B-121 (15) | AM-38 | W-4 | 22 | Rectangular | 36.0 | 0.20 |
| Ex. 60 | — | Ab-282 (63) | S-1/S-2 (50/50) | B-181 (35) | AM-5 | W-3 | 13 | Rectangular | 34.0 | 0.20 |
| Ex. 61 | — | Ab-283 (78) | S-1/S-2 (60/40) | B-180 (20) | AM-11 | W-4 | 19 | Rectangular | 38.0 | 0.15 |
| Comp. Ex. 6 | — | Ab-97 (63) | S-1/S-2 (90/10) | B-149 (35) | N-3 | W-4 | 34 | Reversely tapered | 50.0 | 0.05 |
| Comp. Ex. 7 | — | Ab-245 (98) | S-2/S-1 (90/10) | — | N-1 | W-1 | 33 | Reversely tapered | 50.0 | 0.05 |
| Comp. Ex. 8 | — | Ab-17 (63) | S-4/S-3 (80/20) | B-110 (35) | N-2 | W-3 | 35 | Reversely tapered | 50.0 | 0.05 |

TABLE 6

(EUV Exposure, Organic Solvent Development)

| | Resist composition | | | | | | | | Evaluation results | | | |
|---|---|---|---|---|---|---|---|---|---|---|---|---|
| | Resin (Aa) (% by mass) | Resin (Ab) (% by mass) | Solvent (mass ratio) | Photo-acid generator (% by mass) | Basic compound (2% by mass) | Surfactant (0.01% by mass) | Developer | Rinsing liquid | Sensitivity (mJ/cm$^2$) | Pattern profile | Resolution (nm) | DOF (μm) |
| Ex. 62 | — | Ab-178 (88) | S-2 | B-122 (10) | AM-12 | W-3 | G-1 | G-6 | 14 | Rectangular | 34.0 | 0.20 |
| Ex. 63 | — | Ab-245 (98) | S-2/S-1 (90/10) | — | AM-34 | W-1 | G-1 | — | 16 | Rectangular | 34.0 | 0.20 |
| Ex. 64 | — | Ab-143 (63) | S-4/S-1 (90/10) | B-118 (35) | AM-30 | W-3 | G-1 | G-5 | 28 | Rectangular | 36.0 | 0.10 |
| Ex. 65 | — | Ab-97 (63) | S-1/S-2 (90/10) | B-149 (35) | AM-18 | W-4 | G-3 | — | 20 | Rectangular | 36.0 | 0.15 |
| Ex. 66 | — | Ab-281 (83) | S-1/S-2 (80/20) | B-121 (15) | AM-38 | W-4 | G-1 | — | 23 | Rectangular | 36.0 | 0.20 |
| Ex. 67 | — | Ab-282 (63) | S-1/S-2 (50/50) | B-181 (35) | AM-5 | W-3 | G-1 | G-4 | 15 | Rectangular | 36.0 | 0.20 |
| Ex. 68 | Aa-1 (10) | Ab-283 (68) | S-1/S-2 (60/40) | B-180 (20) | AM-15 | W-2 | G-2 | — | 20 | Rectangular | 38.0 | 0.15 |
| Comp. Ex. 9 | — | Ab-97 (63) | S-1/S-2 (90/10) | B-149 (35) | N-3 | W-4 | G-3 | — | 35 | Tapered | 52.0 | 0.05 |
| Comp. Ex. 10 | — | Ab-245 (98) | S-2/S-1 (90/10) | — | N-1 | W-1 | G-1 | — | 35 | Tapered | 54.0 | 0.05 |

What is claimed is:

1. An actinic ray-sensitive or radiation-sensitive resin composition comprising:
   a nitrogen-containing compound, and
   a resin (Ab) capable of varying a polarity thereof by the action of an acid,
   wherein the nitrogen-containing compound is a compound having at least one amino group formed by bonding one or two hydrogen atoms to a nitrogen atom, and
   at least one hydrogen atom of the one or two hydrogen atoms is substituted by an —S—$R_3$ group or an —S(O)$R_3$ group,
   wherein $R_3$ is selected from the group consisting of an alkyl group, a cycloalkyl group, an alkoxy group, an acyl group, an acyloxy group, a halogen atom, a cyano group, a silicon atom-containing organic group, an aryl group, an aryloxy group, an aralkyl group, an aralkyloxy group, a hydroxy group, a nitro group, a sulfonylamino group, an alkylthio group, an arylthio group, and an aralkylthio group.

2. The composition according to claim 1,
   wherein the resin (Ab) capable of varying an alkali solubility thereof by the action of an acid.

3. The composition according to claim 1,
   wherein the nitrogen-containing compound is represented by either the general formula (N1) or (N2),

[Chem. 1]

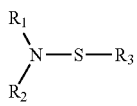

(N1)

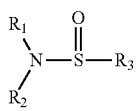

(N2)

wherein in the general formulae (N1) and (N2),
$R_1$ and $R_2$ each independently represents a hydrogen atom or a substituent, provided that a case where $R_1$ and $R_2$ are hydrogen atoms at the same time is excluded; further, $R_1$ and $R_2$ may be bonded to each other to form a ring together with a nitrogen atom in the formula, and
$R_3$ is selected from the group consisting of an alkyl group, a cycloalkyl group, an alkoxy group, an acyl group, an acyloxy group, a halogen atom, a cyano group, a silicon atom-containing organic group, an aryl group, an aryloxy group, an aralkyl group, an aralkyloxy group, a hydroxy group, a nitro group, a sulfonylamino group, an alkylthio group, an arylthio group, and an aralkylthio group.

4. The composition according to claim 3,
   wherein $R_1$ and $R_2$ in the general formula (N1) and (N2) are bonded to each other to form a ring together with a nitrogen atom in the formula.

5. The composition according to claim 1,
   wherein $R_3$ comprises an acid-decomposable group.

6. The composition according to claim 1,
   further comprising a compound capable of generating an acid by irradiation with actinic rays or radiation.

7. The composition according to claim 1,
   wherein the resin (Ab) contains a repeating unit (B) comprising a structural portion capable of generating an acid by irradiation with actinic rays or radiation.

8. The composition according to claim 1,
   further comprising a resin (Aa) containing at least any one of fluorine atoms and silicon atoms.

9. The composition according to claim 1,
   wherein the resin (Ab) contains at least one kind of repeating unit represented by the general formula (A),

[Chem. 2]

wherein the general formula (A),
n represents an integer of 1 to 5 and m represents an integer of 0 to 4, satisfying the relationship of 1≤m+n≤5,
$S_1$ represents a substituent,
in the case where m is 2 or more, a plurality of $S_1$'s may be the same as or different from each other.

10. The composition according to claim 9,
    wherein the resin (Ab) at least contains a repeating unit represented by the following formula as the repeating unit represented by the general formula (A):

[Chem. 3]

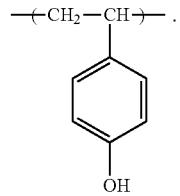

11. The composition according to claim 1,
    wherein the resin (Ab) contains at least one kind of the repeating units represented by the general formulae (A1) and (A2),

[Chem. 4]

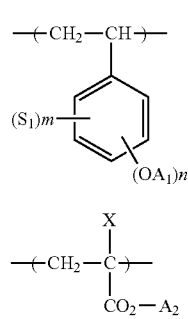

wherein the general formula (A1),
n represents an integer of 1 to 5 and m represents an integer of 0 to 4, satisfying the relationship of 1≤m+n≤5,
$S_1$ represents a substituent, and in the case where m is 2 or more, a plurality of $S_1$'s may be the same as or different from each other, $A_1$ represents a hydrogen atom or a group capable of leaving by the action of an acid; however, at least one $A_1$ represents a group capable of leaving by the action of an acid, in the case of n≥2, a plurality of $A_1$'s may be the same as or different from each other; and wherein the general formula (A2), X represents a hydrogen atom, an alkyl group, a hydroxyl group, an alkoxy group, a halogen atom, a cyano group, a nitro group, an acyl group, an acyloxy group, a cycloalkyl group, a cycloalkyloxy group, an aryl group, a carboxy group, an alkyloxycarbonyl group, an alkylcarbonyloxy group, or an aralkyl group, $A_2$ represents a group capable of leaving by the action of an acid.

12. The composition according to claim 3, wherein the resin (Ab) contains at least one kind of the repeating units represented by the general formulae (A1) and (A2),

[Chem. 5]

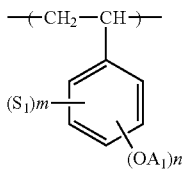

(A1)

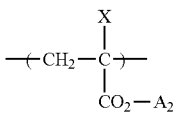

(A2)

wherein the general formula (A1), n represents an integer of 1 to 5 and m represents an integer of 0 to 4, satisfying the relationship of 1≤m+n≤5, $S_1$ represents a substituent, and in the case where m is 2 or more, a plurality of $S_1$'s may be the same as or different from each other, $A_1$ represents a hydrogen atom or a group capable of leaving by the action of an acid; however, at least one $A_1$ represents a group capable of leaving by the action of an acid, in the case of n≢2, a plurality of $A_1$'s may be the same as or different from each other; and wherein the general formula (A2), X represents a hydrogen atom, an alkyl group, a hydroxyl group, an alkoxy group, a halogen atom, a cyano group, a nitro group, an acyl group, an acyloxy group, a cycloalkyl group, a cycloalkyloxy group, an aryl group, a carboxy group, an alkyloxycarbonyl group, an alkylcarbonyloxy group, or an aralkyl group, $A_2$ represents a group capable of leaving by the action of an acid.

13. The composition according to claim 1, which is used for EUV exposure.

14. An actinic ray-sensitive or radiation-sensitive film formed using the composition according to claim 1.

15. A pattern forming method comprising:
a step of forming a film using the composition according to claim 1;
a step of exposing the formed film; and
a step of developing the exposed film.

16. The pattern forming method according to claim 15, wherein exposure is carried out using EUV.

17. The composition according to claim 1, wherein $R_3$ is an alkyl group, a cycloalkyl group, or an aryl group.

18. The composition according to claim 1, wherein $R_3$ is an alkyl group or an aryl group.

* * * * *